US012760033B2

(12) United States Patent
Shin et al.

(10) Patent No.: US 12,760,033 B2
(45) Date of Patent: Oct. 13, 2026

(54) COMPOUNDS HAVING INHIBITORY ACTIVITY ON PROSTAGLANDIN E2 RECEPTOR AND USES THEREOF

(71) Applicants: KANAPH THERAPEUTICS INC., Seoul (KR); KOREA RESEARCH INSTITUTE OF CHEMICAL TECHNOLOGY, Daejeon (KR)

(72) Inventors: Young Sook Shin, Seoul (KR); Sang Kyun Lim, Seoul (KR); Yeri Lee, Seoul (KR); Donggeon Kim, Seoul (KR); Soo Bong Han, Daejeon (KR); Chang Soo Yun, Daejeon (KR); Hyun Jin Kim, Daejeon (KR); Joo Youn Lee, Daejeon (KR); Hyuk Lee, Daejeon (KR); Sikwang Seong, Daejeon (KR)

(73) Assignees: Kanaph Therapeutics Inc., Seoul (KR); Korea Research Institute of Chemical Technology, Daejeon (KR)

( * ) Notice: Subject to any disclaimer, the term of this patent is extended or adjusted under 35 U.S.C. 154(b) by 756 days.

(21) Appl. No.: 18/042,352

(22) PCT Filed: Aug. 20, 2021

(86) PCT No.: PCT/KR2021/011143
§ 371 (c)(1),
(2) Date: Feb. 21, 2023

(87) PCT Pub. No.: WO2022/039563
PCT Pub. Date: Feb. 24, 2022

(65) Prior Publication Data

US 2023/0365582 A1 Nov. 16, 2023

(30) Foreign Application Priority Data

Aug. 21, 2020 (KR) ........................ 10-2020-0105545

(51) Int. Cl.

| | |
|---|---|
| ***C07D 333/24*** | (2006.01) |
| ***A61K 31/451*** | (2006.01) |
| ***A61K 31/4709*** | (2006.01) |
| ***A61K 31/497*** | (2006.01) |
| ***A61P 9/00*** | (2006.01) |
| ***A61P 35/00*** | (2006.01) |
| ***C07D 209/34*** | (2006.01) |
| ***C07D 215/48*** | (2006.01) |
| ***C07D 237/32*** | (2006.01) |
| ***C07D 333/38*** | (2006.01) |
| ***C07D 409/06*** | (2006.01) |
| ***C07D 409/10*** | (2006.01) |
| ***C07D 471/12*** | (2006.01) |
| ***C07D 487/10*** | (2006.01) |
| ***C07D 495/04*** | (2006.01) |

(52) U.S. Cl.
CPC ......... *C07D 495/04* (2013.01); *C07D 333/24* (2013.01); *C07D 333/38* (2013.01); *C07D 409/06* (2013.01); *C07D 409/10* (2013.01)

(58) Field of Classification Search
CPC .. C07D 333/24; C07D 209/34; C07D 215/48; C07D 237/32; C07D 471/12; C07D 487/10; A61K 31/451; A61K 31/4709; A61K 31/497; A61P 35/00; A61P 9/00
See application file for complete search history.

(56) References Cited

U.S. PATENT DOCUMENTS

| | | | |
|---|---|---|---|
| 8,653,118 | B2 | 2/2014 | Martos et al. |
| 2004/0054003 | A1 | 3/2004 | Tanimoto et al. |
| 2004/0072871 | A1 | 4/2004 | Dublanchet et al. |
| 2011/0178101 | A1 | 7/2011 | Fatheree et al. |
| 2015/0099731 | A1 | 4/2015 | Crooks et al. |
| 2015/0099734 | A1 | 4/2015 | Hunziker et al. |
| 2016/0016914 | A1 | 1/2016 | Ladziata et al. |
| 2018/0250282 | A1 | 9/2018 | Fisher et al. |

FOREIGN PATENT DOCUMENTS

| | | | |
|---|---|---|---|
| JP | 2006504674 | A | 2/2006 |
| JP | 2013517295 | A | 5/2013 |
| KR | 19990028261 | A | 4/1999 |
| KR | 20080047581 | A | 5/2008 |
| KR | 20150015031 | A | 2/2015 |
| WO | 0053573 | A1 | 9/2000 |
| WO | WO 0236583 | A1 | 5/2002 |
| WO | WO 2010019796 | A1 | 2/2010 |
| WO | WO 2012024559 | A1 | 2/2012 |
| WO | WO 2013146969 | A1 | 10/2013 |
| WO | WO 2013161871 | A1 | 10/2013 |
| WO | WO 2018151678 | A1 | 8/2018 |

(Continued)

OTHER PUBLICATIONS

Blouin et al., "The Discovery of 4-{1-[({2,5-Dimethyl-4-[4-(trifluoromethyl)benzyl]-3-thienyl}carbonyl)amino]cyclopropyl}benzoic Acid (MK-2894), A Potent and Selective Prostaglandin E2 Subtype 4 Receptor Antagonist," *Journal of Medicinal Chemistry* 53(5):2227-2238, Feb. 17, 2010. (12 pages).
RN Registry No. 1938281-08-3, Jun. 24, 2016. (1 page).
RN Registry No. 1938965-54-8, Jun. 24, 2016. (1 page).
RN Registry No. 2026969-84-4, Nov. 8, 2016. (1 page).
CAS Registry No. 1575065-63-2; 3-[[(3-Phenyl-2-thienyl)carbonyl]amino]cyclopentanecarboxylic acid, Mar. 28, 2014.
CAS Registry No. 2026980-52-7; (1R,3S)-3-[[(3-Phenyl-2-thienyl)carbonyl]amino]cyclopentanecarboxylic acid, Nov. 8, 2016.
CAS Registry No. 1821870-54-5; (1S,3R)-3-[[(3-Phenyl-2-thienyl)carbonyl]amino]cyclopentanecarboxylic acid, Dec. 3, 2015.

(Continued)

*Primary Examiner* — Bruck Kifle
(74) *Attorney, Agent, or Firm* — Seed IP Law Group LLP

(57) ABSTRACT

The present application relates to a novel compound having inhibitory activity on prostaglandin $E_2$ receptor and uses thereof, and provides a compound represented by formula I, a solvate, stereoisomer or pharmaceutically acceptable salt thereof, a pharmaceutical composition comprising the same, and a method of using the same.

11 Claims, No Drawings

(56) References Cited

FOREIGN PATENT DOCUMENTS

| | | | |
|---|---|---|---|
| WO | WO 2018195123 | A1 | 10/2018 |
| WO | 2019087028 | A1 | 5/2019 |

OTHER PUBLICATIONS

CAS Registry No. 1568868-86-9; 4-[[(3-Phenyl-2-thienyl)carbonyl]amino]cyclohexanecarboxylic acid, Mar. 14, 2014.
CAS Registry No. 2027140-66-3; cis-3-[[[3-(4-Methylphenyl)-2-thienyl]carbonyl]amino]cyclobutanecarboxylic acid, Nov. 8, 2016.
CAS Registry No. 1939011-46-7; (1R,3S)-3-[[[3-(4-Methylphenyl)-2-thienyl]carbonyl]aminocyclopentanecarboxylicacid, Jun. 24, 2016.
CAS Registry No. 1822172-50-8; (1S,3R)-3-[[[3-(4-Methylphenyl)-2-thienyl]carbonyl]amino]cyclopentanecarboxylic acid, Dec. 3, 2015.
CAS Registry No. 1575047-55-0; 4-[[[3-(4-Methylphenyl)-2-thienyl]carbonyl]amino]cyclohexanecarboxylic acid, Mar. 28, 2014.
CAS Registry No. 1575584-06-3; 3-[[[3-(4-Fluorophenyl)-2-thienyl]carbonyl]amino]cyclopentanecarboxylic acid, Mar. 28, 2014.
CAS Registry No. 1572564-88-5; 4-[[[3-(4-Fluorophenyl)-2-thienyl]carbonyl]amino]cyclohexanecarboxylic acid, Mar. 24, 2014.
CAS Registry No. 1489627-76-0; 3-[[[3-(1H-Pyrrol-1-yl)-2-thienyl]carbonyl]amino]cyclopentanecarboxylic acid, Dec. 8, 2013.
CAS Registry No. 1960914-37-7; rel-(1R,3S)-3-[[[3-(1H-Pyrrol-1-yl)-2-thienyl]carbonyl]amino]cyclopentanecarboxylic acid, Jul. 27, 2016.
CAS Registry No. 1822026-44-7; (1S,3R)-3-[[[3-(1H-Pyrrol-1-yl)-2-thienyl]carbonyl]amino]cyclopentanecarboxylic acid, Dec. 3, 2015.
CAS Registry No. 1827057-88-4; 4-[[[3-(1H-Pyrrol-1-yl)-2-thienyl]carbonyl]amino]cyclohexanecarboxylic acid, Dec. 11, 2015.
CAS Registry No. 1478091-02-9; 3-[[[3-(1H-Tetrazol-1-yl)-2-thienyl]carbonyl]amino]cyclopentanecarboxylic acid, Nov. 21, 2013.
CAS Registry No. 1938411-43-8; (1S,3R)-3-[[[3-(1H-Tetrazol-1-yl)-2-thienyl]carbonylaminocyclopentanecarboxylic acid, Jun. 24, 2016.
CAS Registry No. 1939058-74-8; (1R,3S)-3-[[[3-(1H-Tetrazol-1-yl)-2-thienyl]carbonyl]aminocyclopentanecarboxylic acid, Jun. 24, 2016.
CAS Registry No. 1573246-53-3; 4-[[[3-(1H-Tetrazol-1-yl)-2-thienyl]carbonyl]amino]cyclohexanecarboxylic acid, Mar. 25, 2014.
CAS Registry No. 1825266-15-6; (1S,3R)-3-[[(3-Cyclopropyl-2-thienyl)carbonyl]amino]cyclopentanecarboxylic acid, Dec. 8, 2015.
CAS Registry No. 1837147-86-0; 4-[[(3-Cyclopropyl-2-thienyl)carbonyl]amino]cyclohexanecarboxylic acid, Dec. 27, 2015.
Office Action, dated Mar. 19, 2025, for New Zealand Patent Application No. 796802. (5 pages).
CAS Registry No. 1575643-00-3; 3-[[[3-(4-Methylphenyl)-2-thienyl]carbonyl]amino]cyclopentanecarboxylic acid, Mar. 28, 2014.
International Search Report, mailed Dec. 10, 2021, for International Application No. PCT/KR2021/011143. (5 pages).

COMPOUNDS HAVING INHIBITORY ACTIVITY ON PROSTAGLANDIN E2 RECEPTOR AND USES THEREOF

TECHNICAL FIELD

The present application relates to a novel compound having inhibitory activity on prostaglandin $E_2$ receptor and uses thereof, a pharmaceutical composition comprising the same, and a method for treating or preventing a disease using the same.

BACKGROUND ART

Prostaglandin (PG), as well as thromboxane, is a physiologically active substance known as prostanoid, and it is a lipid having a prostanoic acid skeleton. Prostanoid such as prostaglandin is biosynthesized from arachidonic acid that is released from a membrane phospholipid by the action of phospholipase A2. Prostaglandin is classified into groups A to J, based on differences in the types of an oxygen atom attached to the 5-membered ring thereof and a double bond. In addition, prostaglandin is classified into groups 1 to 3, based on the number of double bonds on the side chain of the prostanoic acid skeleton. For example, prostaglandin E (PGE) includes $PGE_1$, $PGE_2$ and $PGE_3$, which are different from one another in terms of the number of double bonds on the side chain of the prostanoic acid skeleton.

Regarding prostaglandin, $PGH_2$ is generated from $PGG_2$ that is biosynthesized from arachidonic acid by the action of cyclooxygenase I (COX-I) or cyclooxygenase II (COX-II), and then, $PGD_2$, $PGE_2$, $PGF_{2\alpha}$ and the like are generated based on a difference in the cleavage of the bond between oxygen atoms. The generation reaction of each prostaglandin occurs by the action of a specific enzyme, and it is known that these enzymes have tissue specificity. On the other hand, among prostaglandins, it is considered that PGE plays a role in various important biological activities and that, through the mediation of its specific receptor, PGE is involved in regulation of the immune system, as well as vasodilatation, a decrease in blood pressure and uterine contraction. The $PGE_2$ receptor is a seven transmembrane G protein-conjugated receptor, as with other PG receptors. The $PGE_2$ receptor is abbreviated as EP, and it was revealed that EP has 4 subtypes ($EP_1$, $EP_2$, $EP_3$, and $EP_4$). Each subtype is involved in various phenomena in vivo. That is, $EP_1$ is involved in an increase in intracellular $Ca^{2+}$ concentration, $EP_2$ and $EP_4$ are involved in an increase in cAMP level, and $EP_3$ is involved in a decrease in cAMP level.

On the other hand, cancer is one of the leading causes of death worldwide. Tumor consists of abnormally proliferating malignant cancer cells, as well as a functionally supporting microenvironment. This tumor microenvironment consists of a complex array of cells, extracellular matrix components and signaling molecules, and is established by altered communication between stromal cells and tumor cells. As tumors grow in size, they lead to the production of a variety of factors, such as angiogenesis factors (promoting the growth of blood vessels) that can aid in tumor growth or help evade attack of the host immune response. Under this microenvironment, $PGE_2$ functions as such an immune-modulatory factor produced in tumors. The EP receptors of $PGE_2$, particularly $EP_2$ and $EP_4$, are abnormally overexpressed in several types of cancer, specifically in gastrointestinal (GI) cancer and pancreatic cancer. In addition, overexpression of $PGE_2$ and/or $EP_2$ and/or $EP_4$ is closely correlated with cancers such as esophageal squamous cell carcinoma, squamous cell carcinoma of the lung, prostate cancer, and head and neck squamous cell carcinoma. In addition, it is known that epidemiologically, $PGE_2$ signaling is mainly involved in the communication between tumor cells and stromal cells, creating a microenvironment favorable for tumor growth. It is noteworthy that some tumor cells overexpress EP2 and/or EP4, by which PGE2 signaling can directly induce the proliferation of tumor cells.

In addition, it has been reported that $PGE_2$ antagonists, such as $EP_2$ and/or $EP_4$ antagonist, are effective in a chronic inflammatory disease, and effective in a neurodegenerative disease such as epilepsy, Alzheimer's disease, Parkinson's disease, amyotrophic lateral sclerosis and traumatic brain injury.

Under this technical background, a study on antagonists of the prostaglandin $E_2$ receptor that can be utilized clinically in various ways is in progress (Korean Patent Application Publication No. 10-2013-0092579), but it is still incomplete.

DISCLOSURE OF INVENTION

Technical Problem

In one aspect, there is provided a novel compound, solvate, stereoisomer or pharmaceutically acceptable salt thereof that exhibits inhibitory activity on prostaglandin $E_2$ receptor.

In another aspect, there is provided a pharmaceutical composition comprising the compound, solvate, stereoisomer or pharmaceutically acceptable salt thereof as an active ingredient, or medicinal uses thereof.

Solution to Problem

Each description and embodiment disclosed in the present application may also be applied to each other description and embodiment. That is, all combinations of the various elements disclosed in the present application fall within the scope of the present application. In addition, the scope of the present application is not intended to be limited to the particular descriptions described below.

In one aspect of the present invention, there is provided a compound represented by formula I, a solvate, stereoisomer or pharmaceutically acceptable salt thereof:

[Formula I]

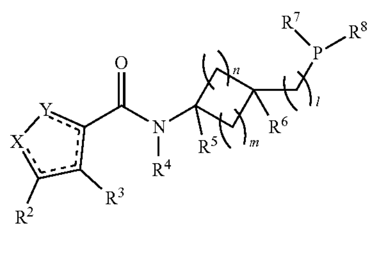

in which, one of X and Y is S and the other is $CR^1$, and ---- is a single bond or a double bond, two of which are double bonds;

$R^1$ and $R^2$ are selected from the group consisting of hydrogen, halogen, hydroxy, cyano, amino, $C_1$-$C_6$ alkyl, $C_1$-$C_6$ alkoxy, —NH—($C_1$-$C_6$ alkyl), —N($C_1$-$C_6$ alkyl)$_2$, $C_3$-$C_8$ cycloalkyl, and $C_6$-$C_{10}$ aryl, wherein said $C_1$-$C_6$ alkyl and $C_1$-$C_6$ alkoxy may be each independently optionally substituted with one or more halogen, hydroxy, cyano or amino, and said $C_3$-$C_8$ cycloalkyl and $C_6$-$C_{10}$ aryl may be each independently optionally substituted with one or more halogen, hydroxy, cyano, amino, oxo, $C_1$-$C_6$ alkyl, $C_1$-$C_6$ haloalkyl, $C_1$-$C_6$ alkoxy or $C_1$-$C_6$ haloalkoxy; and $R^3$ is

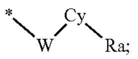

or $R^1$ is selected from the group consisting of hydrogen, halogen, hydroxy, cyano, amino, $C_1$-$C_6$ alkyl, $C_1$-$C_6$ alkoxy, —NH—($C_1$-$C_6$ alkyl), —N($C_1$-$C_6$ alkyl)$_2$, $C_3$-$C_8$ cycloalkyl, and $C_6$-$C_{10}$ aryl, wherein said $C_1$-$C_6$ alkyl and $C_1$-$C_6$ alkoxy may be each independently optionally substituted with one or more halogen, hydroxy, cyano or amino, and said $C_3$-$C_8$ cycloalkyl and $C_6$-$C_{10}$ aryl may be each independently optionally substituted with one or more halogen, hydroxy, cyano, amino, oxo, $C_1$-$C_6$ alkyl, $C_1$-$C_6$ haloalkyl, $C_1$-$C_6$ alkoxy or $C_1$-$C_6$ haloalkoxy; and $R^2$ and $R^3$ together with the carbon atom to which they are attached form

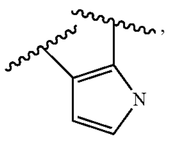 [SMILES: *c1cc[nH]c1*]

wherein

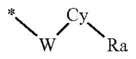

is bonded to the nitrogen atom of

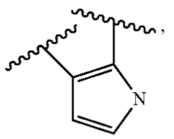 [SMILES: *c1cc[nH]c1*]

and either or both of the carbon atoms of

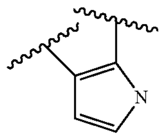 [SMILES: *c1cc[nH]c1*]

may be optionally substituted with halogen, hydroxy, cyano, $C_1$-$C_6$ alkyl, $C_1$-$C_6$ alkoxy, $C_1$-$C_6$ haloalkyl or $C_1$-$C_6$ haloalkoxy;

W is —$(CH_2)_o$—, —$(CH_2)_o$—C≡C—, —C(O)—, —O—, —S—, —NH—, or —N($C_1$-$C_6$ alkyl)-, wherein H of said $CH_2$ may be optionally substituted with one or more halogen, hydroxy, cyano, $C_1$-$C_6$ alkyl, $C_1$-$C_6$ alkoxy, $C_1$-$C_6$ haloalkyl or $C_1$-$C_6$ haloalkoxy;

Cy is selected from the group consisting of $C_6$-$C_{14}$ aryl, 4- to 14-membered heteroaryl, 4- to 14-membered heterocycloalkyl, $C_3$-$C_8$ cycloalkyl and $C_3$-$C_8$ cycloalkenyl, and may be optionally substituted with one or more R';

$R_a$ is hydrogen, halogen, hydroxy, cyano, amino, $C_1$-$C_6$ alkyl, $C_1$-$C_6$ alkoxy, —NH—($C_1$-$C_6$ alkyl), —N($C_1$-$C_6$ alkyl)$_2$, oxo, or —V-$Cy_2$, wherein said $C_1$-$C_6$ alkyl and $C_1$-$C_6$ alkoxy may be optionally substituted with one or more halogen, hydroxy, cyano or amino, wherein V is absent or —NH—, —$NHCH_2$—, —$NHCH_3$—, —CONH—, —NHCO—, —$NHSO_2$—, —S—, —$SO_2$—, —$CH_2$—, —$OCH_2$— or —O—, $Cy_2$ is selected from the group consisting of $C_6$-$C_{14}$ aryl, 4- to 14-membered heteroaryl, 4- to 14-membered heterocycloalkyl, $C_3$-$C_8$ cycloalkyl and $C_3$-$C_8$ cycloalkenyl, and may be optionally substituted with one or more R";

R' is each independently selected from the group consisting of halogen, hydroxy, cyano, amino, oxo, $C_1$-$C_6$ alkyl, $C_1$-$C_6$ alkoxy, —NH—($C_1$-$C_6$ alkyl) and —N($C_1$-$C_6$ alkyl)$_2$, wherein said $C_1$-$C_6$ alkyl and $C_1$-$C_6$ alkoxy may be optionally substituted with one or more halogen, hydroxy, cyano or amino;

R" is selected from the group consisting of halogen, hydroxy, cyano, amino, oxo, $C_1$-$C_6$ alkyl, $C_1$-$C_6$ alkoxy, —S—($C_1$-$C_6$ alkyl), —$SO_2$—($C_1$-$C_6$ alkyl), —CO—($C_1$-$C_6$ alkyl), —C(O)H, —COO—($C_1$-$C_6$ alkyl), —COOH, —$CONH_2$, —CONH—($C_1$-$C_6$ alkyl), —CON($C_1$-$C_6$ alkyl)$_2$, —$(CH_2)_p$—$NH_2$, —$(CH_2)_p$—NH—($C_1$-$C_6$ alkyl), —$(CH_2)_p$—N($C_1$-$C_6$ alkyl)$_2$, —$(CH_2)_p$—NH—CO—($C_1$-$C_6$ alkyl), —$(CH_2)_p$—NH—COO—($C_1$-$C_6$ alkyl), —$(CH_2)_p$—OH, 3- to 7-membered heterocycloalkyl, $C_3$-$C_8$ cycloalkyl, and —$(CH_2)_p$—($C_3$-$C_8$ cycloalkyl), wherein said $C_1$-$C_6$ alkyl and $C_1$-$C_6$ alkoxy may be optionally substituted with one or more halogen, hydroxy, cyano or amino, and said 3- to 7-membered heterocycloalkyl and $C_3$-$C_8$ cycloalkyl may be optionally substituted with one or more halogen, hydroxy, cyano, oxo or amino;

$R^4$ is hydrogen, or $C_1$-$C_6$ alkyl;

$R^5$, $R^6$ and $R^7$ each have the following definitions:

(i) $R^5$ and $R^6$ are H, and $R^7$ is absent, (ii) $R^5$ and $R^6$ together represent —$(CH_2)_q$—, and $R^7$ is absent, or (iii) $R^5$ is H, and $R^6$ and $R^7$ together represent —$(CH_2)_r$—; and P is absent or —$CH_2$—, provided that if $R^7$ is absent, then P is also absent;

$R^8$ is

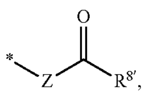

wherein Z is —$(CH_2)_s$, and $R^{8'}$ is hydrogen, hydroxy, $C_1$-$C_6$ alkyl or $C_1$-$C_6$ alkoxy;

l, m and n are each independently an integer of 0 to 2, wherein at least one of m and n is not 0, and if P and $R^7$ are absent, then l is 0;

o and p are each independently an integer of 0 to 3;

q and r are each independently an integer of 1 or 2; and s is an integer of 0 to 3.

In some embodiments, X is S and Y is $CR^1$, or X is $CR^1$ and Y is S. In one embodiment,  is a single bond or a double bond, two of which are double bonds, such that the 5-membered ring containing X and Y forms a thiophenyl ring.

In some embodiments, $R^1$ may be hydrogen, halogen, hydroxy, cyano, amino, $C_1$-$C_3$ alkyl, $C_1$-$C_3$ alkoxy, —NH—($C_1$-$C_3$ alkyl) or —N($C_1$-$C_3$ alkyl)$_2$, wherein said $C_1$-$C_3$ alkyl and $C_1$-$C_3$ alkoxy may be each independently optionally substituted with one or more halogen, hydroxy, cyano or amino. In one embodiment, $R^1$ may be hydrogen, halogen, hydroxy, $C_1$-$C_3$ alkyl, $C_1$-$C_3$ alkoxy, $C_1$-$C_3$ haloalkyl, or $C_1$-$C_3$ haloalkoxy. In one embodiment, $R^1$ may be hydrogen, halogen, $C_1$-$C_3$ alkyl, or $C_1$-$C_3$ haloalkyl.

In some embodiments, $R^2$ may be hydrogen, halogen, hydroxy, $C_1$-$C_3$ alkyl, $C_1$-$C_3$ alkoxy, $C_1$-$C_3$ haloalkyl, $C_1$-$C_3$ haloalkoxy, $C_3$-$C_6$ cycloalkyl or phenyl, wherein said $C_1$-$C_3$ alkyl and $C_1$-$C_3$ alkoxy may be each independently optionally substituted with one or more halogen, hydroxy, cyano or amino. In one embodiment, $R^2$ may be hydrogen, halogen, $C_1$-$C_3$ alkyl, $C_1$-$C_3$ haloalkyl, cyclopropyl, cyclobutyl or phenyl. In one embodiment, $R^2$ may be hydrogen, fluoro, chloro, bromo, methyl, ethyl, trifluoromethyl, difluoromethyl, cyclopropyl, cyclobutyl or phenyl or the like.

In some embodiments, $R^3$ may be

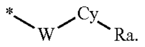

In another embodiment, $R^2$ and $R^3$ together with the carbon atom to which they are attached may form

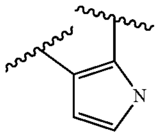 [SMILES: *c1cc[nH]c1*]

to form a 4H-thieno[3,2-b]pyrrole fused ring, in which case

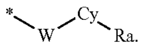

may be bonded to the nitrogen atom of

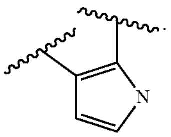 [SMILES: *c1cc[nH]c1*]

In one embodiment, either or both of the carbon atoms of

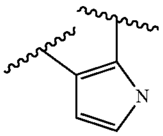

may be optionally substituted with halogen, $C_1$-$C_3$ alkyl, or $C_1$-$C_3$ haloalkyl. In one embodiment, either or both of the carbon atoms of

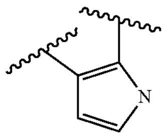 [SMILES: *c1cc[nH]c1*]

may be optionally substituted with fluoro, chloro, bromo, methyl, ethyl, trifluoromethyl, difluoromethyl or the like. In one embodiment, either or both of the carbon atoms of

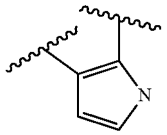

may be optionally substituted with $C_1$-$C_3$ alkyl.

In some embodiments, W may be —$(CH_2)_o$—, —$(CH_2)_o$—C≡C—, —C(O)—, —O—, —NH— or —N($C_1$-$C_3$ alkyl)-, wherein H of said $CH_2$ may be optionally substituted with one or more halogen, hydroxy, $C_1$-$C_3$ alkoxy or $C_1$-$C_3$ haloalkoxy.

In one embodiment, W may be —$(CH_2)_o$—, —C(O)—, —O—, —NH—, or —N($C_1$-$C_6$ alkyl)-. In another embodiment, W may be —$(CH_2)_o$— or —$(CH_2)_o$—C≡C—.

In one embodiment, H of said $CH_2$ may be optionally substituted with one or more halogen, hydroxy, or $C_1$-$C_3$ alkoxy. In one embodiment, H of said $CH_2$ may be optionally substituted with hydroxy, methoxy, ethoxy, trifluoromethoxy, difluoromethoxy, or the like. In one embodiment, o may be an integer of 0, 1 or 2. In one embodiment, o may be an integer of 0 or 1.

In some embodiments, Cy may be $C_6$-$C_{10}$ aryl, 5- to 10-membered heteroaryl containing 1 to 3 heteroatoms selected from N, O and S, or 4- to 10-membered heterocycloalkyl containing 1 to 3 heteroatoms selected from N, O and S. In one embodiment, Cy may be phenyl, naphthyl; heteroaryl selected from pyrrolyl, furanyl, thiophenyl, pyrazolyl, imidazolyl, oxazolyl, isoxazolyl, thiazolyl, isothiazolyl, triazolyl, oxadiazolyl, thiadiazolyl, pyridinyl, pyrimidinyl, pyridazinyl, pyrazinyl, indolyl, benzimidazolyl, benzofuranyl, benzothiazolyl, quinolinyl and isoquinolinyl; or heterocycloalkyl selected from azetidinyl, oxetanyl, pyrrolidinyl, tetrahydrofuranyl, pyrazolidinyl, imidazolidinyl, thiazolidinyl, oxazolidinyl, isoxazolidinyl, piperidinyl, piperazinyl and morpholinyl.

In one embodiment, Cy may be phenyl, 5- to 10-membered heteroaryl containing 1 or 2 nitrogen atoms, or 4- to 7-membered heterocycloalkyl containing 1 or 2 nitrogen atoms. In one embodiment, Cy may be phenyl, pyrrolyl, pyrazolyl, imidazolyl, pyridinyl, pyrimidinyl, pyridazinyl, pyrazinyl, indolyl, isoindolyl, benzimidazolyl, indazolyl, pyrrolidinyl, piperidinyl, piperazinyl or morpholinyl. In one embodiment, Cy may be phenyl, pyrazolyl, pyridinyl, pyrimidinyl, indolyl or piperazinyl.

Said Cy may be optionally substituted with one or more R'. In one embodiment, R' may be halogen, hydroxy, cyano, amino, oxo, $C_1$-$C_3$ alkyl, $C_1$-$C_3$ haloalkyl, $C_1$-$C_3$ alkoxy, $C_1$-$C_3$ haloalkoxy, —NH—($C_1$-$C_3$ alkyl) or —N($C_1$-$C_3$ alkyl)$_2$. In one embodiment, R' may be halogen, amino, $C_1$-$C_3$ alkyl, or $C_1$-$C_3$ haloalkyl. In one embodiment, R' may be one or more fluoro, chloro, bromo, amino, methylamino, dimethylamino, ethylamino, or diethylamino, or the like.

In some embodiments, $R_a$ may be hydrogen, halogen, amino, $C_1$-$C_3$ alkyl, $C_1$-$C_3$ haloalkyl, —NH—($C_1$-$C_3$ alkyl), or —N($C_1$-$C_3$ alkyl)$_2$, or —V-$Cy_2$. In one embodiment, $R_a$ may be hydrogen, halogen, $C_1$-$C_3$ alkyl, $C_1$-$C_3$ haloalkyl or —V-$Cy_2$. In one embodiment, $R_a$ may be hydrogen, fluoro, chloro, bromo, methyl, ethyl, trifluoromethyl, difluoromethyl, or —V-$Cy_2$. In one embodiment, $R_a$ may be —V-$Cy_2$.

In some embodiments, V may be absent or —NH—, —$NHCH_2$—, —$NHCH_3$—, —S—, —$SO_2$—, —$CH_2$—, —$OCH_2$— or —O—. In one embodiment, V may be absent or —$CH_2$— or —O—. In one embodiment, V may be absent or —$CH_2$—.

In some embodiments, $Cy_2$ may be selected from the group consisting of $C_6$-$C_{10}$ aryl, 5- to 10-membered heteroaryl containing 1 to 3 heteroatoms selected from N, O and S, 4- to 10-membered heterocycloalkyl containing 1 to 3 heteroatoms selected from N, O and S, $C_3$-$C_8$ cycloalkyl and $C_3$-$C_8$ cycloalkenyl. In one embodiment, $Cy_2$ may be phenyl; heteroaryl selected from pyrrolyl, furanyl, thiophenyl, pyrazolyl, imidazolyl, oxazolyl, isoxazolyl, thiazolyl, isothiazolyl, triazolyl, oxadiazolyl, thiadiazolyl, pyridinyl, pyrimidinyl, pyridazinyl, pyrazinyl, indolyl, benzimidazolyl, benzofuranyl, benzothiazolyl, quinolinyl and isoquinolinyl; heterocycloalkyl selected from azetidinyl, oxetanyl, pyrrolidinyl, tetrahydrofuranyl, pyrazolidinyl, imidazolidinyl, thiazolidinyl, oxazolidinyl, isoxazolidinyl, piperidinyl, piperazinyl and morpholinyl; cyclobutyl, cyclopentyl, cyclohexyl or cycloheptyl; or cyclobutenyl, cyclopentenyl, cyclohexenyl or cycloheptenyl.

In one embodiment, $Cy_2$ may be selected from the group consisting of phenyl, 5- to 10-membered heteroaryl containing 1 or 2 heteroatoms selected from N or O, 4- or 7-membered heterocycloalkyl containing 1 or 2 heteroatoms selected from N or O, $C_4$-$C_7$ cycloalkyl and $C_4$-$C_7$ cycloalkenyl. In one embodiment, $Cy_2$ may be phenyl, pyrrolyl, furanyl, pyrazolyl, imidazolyl, pyridinyl, pyrimidinyl, pyridazinyl, pyrazinyl, pyrrolidinyl, tetrahydrofuranyl, piperidinyl, piperazinyl, morpholine, cyclopentyl, cyclohexyl, cyclopentenyl, or cyclohexenyl. In one embodiment, $Cy_2$ may be phenyl, furanyl, pyrazolyl, pyridinyl, pyrimidinyl, piperidinyl, morpholinyl, cyclohexyl, or cyclohexenyl.

Said $Cy_2$ may be optionally substituted with R". In some embodiments, R" is selected from the group consisting of halogen, hydroxy, cyano, amino, oxo, $C_1$-$C_6$ alkyl, $C_1$-$C_6$ alkoxy, —S—($C_1$-$C_6$ alkyl), —$SO_2$—($C_1$-$C_6$ alkyl), —COO—($C_1$-$C_6$ alkyl), —COOH, —$CONH_2$, —$(CH_2)_p$—$NH_2$, —$(CH_2)_p$—NH—($C_1$-$C_6$ alkyl), —$(CH_2)_p$—N($C_1$-$C_6$ alkyl)$_2$, —$(CH_2)_p$—NH—COO—($C_1$-$C_6$ alkyl), —$(CH_2)_p$—OH, 3- to 5-membered heterocycloalkyl containing 1 heteroatom selected from N, O and S, $C_3$-$C_5$ cycloalkyl, and —($CH_2$)—($C_3$-$C_5$ cycloalkyl), wherein said $C_1$-$C_6$ alkyl and $C_1$-$C_6$ alkoxy may be optionally substituted with one or more halogen, hydroxy, cyano or amino, and said 3- to 5-membered heterocycloalkyl and $C_3$-$C_5$ cycloalkyl may be optionally substituted with one or more halogen, hydroxy, cyano, oxo or amino. In one embodiment, said 3- to 5-membered heterocycloalkyl may be aziridinyl, oxiranyl, azetidinyl, oxetanyl, pyrrolidinyl and tetrahydrofuranyl or $C_3$-$C_5$ cycloalkyl. In one embodiment, p may be an integer of 0, 1 or 2. In one embodiment, p may be an integer of 0 or 1.

In one embodiment, R" may be halogen, hydroxy, cyano, amino, oxo, $C_1$-$C_6$ alkyl, $C_1$-$C_6$ haloalkyl, $C_1$-$C_6$ alkoxy, $C_1$-$C_6$ haloalkoxy, —S—($C_1$-$C_6$ alkyl), —$SO_2$—($C_1$-$C_6$ alkyl), —COO—($C_1$-$C_6$ alkyl), —COOH, —$CONH_2$, —$(CH_2)_p$—$NH_2$, —$(CH_2)_p$—NH—($C_1$-$C_6$ alkyl), —$(CH_2)_p$—N($C_1$-$C_6$ alkyl)$_2$, —$(CH_2)_p$—NH—COO—($C_1$-$C_6$ alkyl), —$(CH_2)_p$—OH; azetidinyl or oxetanyl, optionally substituted with hydroxy or oxo; cyclopropyl or cyclopropylmethyl, optionally substituted with hydroxy or oxo.

In another embodiment, R" may be halogen, hydroxy, cyano, amino, oxo, $C_1$-$C_6$ alkyl, $C_1$-$C_6$ haloalkyl, $C_1$-$C_6$ alkoxy, $C_1$-$C_6$ haloalkoxy, —$(CH_2)_p$—$NH_2$, —$(CH_2)_p$—NH—($C_1$-$C_6$ alkyl), —$(CH_2)_p$—N($C_1$-$C_6$ alkyl)$_2$; azetidinyl or oxetanyl, optionally substituted with hydroxy or oxo; cyclopropyl or cyclopropylmethyl, optionally substituted with hydroxy or oxo.

In one embodiment, R" may be halogen, hydroxy, methyl, ethyl, hydroxymethyl, hydroxyethyl, aminomethyl, aminoethyl, trifluoromethyl, difluoromethyl, trifluoroethyl, difluoroethyl, methoxy, ethoxy, isopropoxy, trifluoromethoxy, difluoromethoxy, cyano, amino, oxo, —S—$CH_3$, —S—$CH_2CH_3$, —$SO_2$—$CH_3$, —$SO_2$—$CH_2CH_3$, —$COOCH_3$, —$COOCH_2CH_3$, —$COOCH_2CH_2CH_3$, —$COOCH(CH_3)_2$, —$COOCH_2CH(CH_3)_2$, —$COOC(CH_3)_4$, —COOH, —$CONH_2$, —$CH_2NH_2$, —$CH_2CH_2NH_2$, —$CH_2NHCOOCH_3$, —$CH_2NHCOOCH_2CH_3$, —$CH_2NHCOOCH_2CH_2CH_3$, —$CH_2NHCOOCH(CH_3)_2$, —$CH_2NHCOOCH_2CH(CH_3)_2$, —$CH_2NHCOOC(CH_3)_3$, —$CH_2OH$, —$CH_2CH_2OH$, azetidinyl, oxetanyl, cyclopropyl, or cyclobutylmethyl.

In one embodiment, $R_a$ is —V-$Cy_2$, and

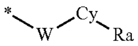

has a structure selected from the following group, wherein Cy and $Cy_2$ may be each optionally substituted with R' and R":

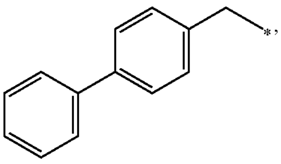
,

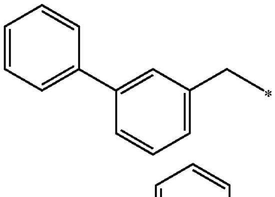
,

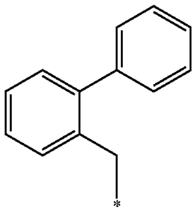
,

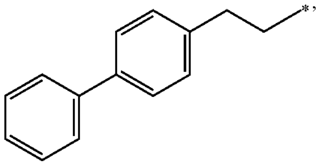
,

-continued
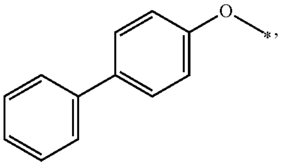
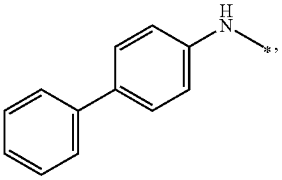
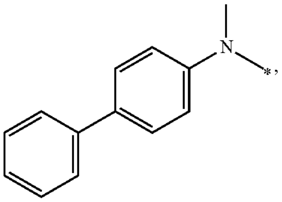
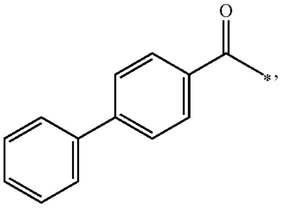
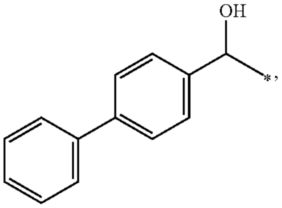
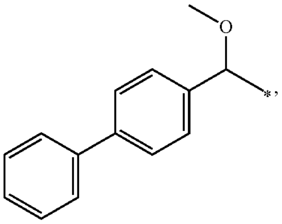
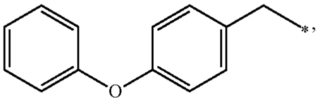
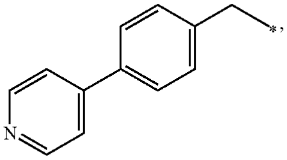
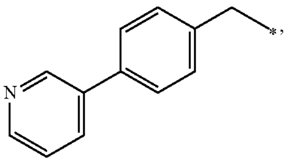
-continued
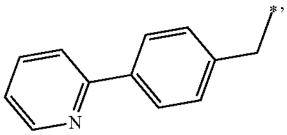
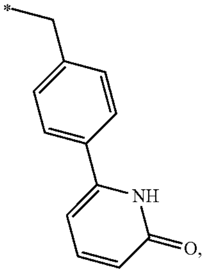
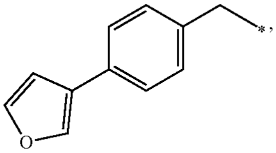
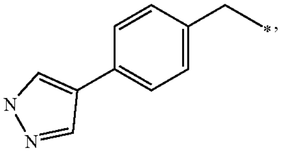
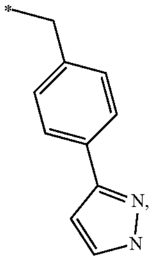
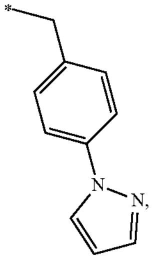
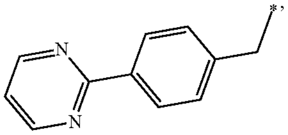
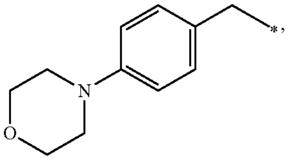
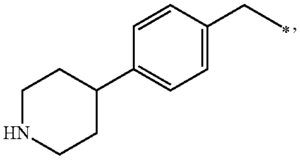

-continued

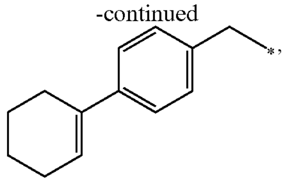,

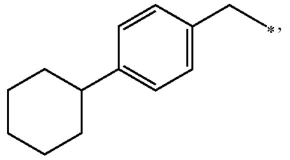,

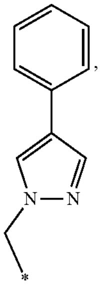,

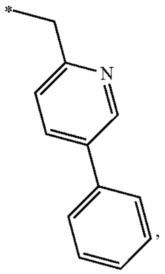,

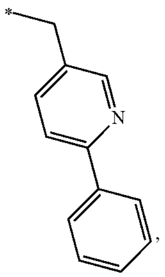,

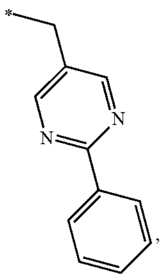,

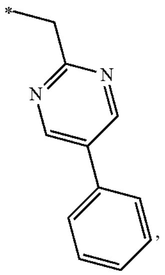,

-continued

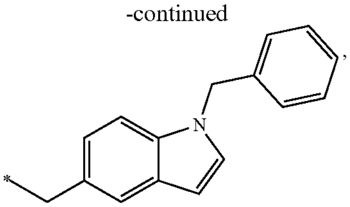,

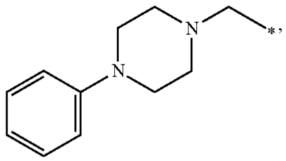,

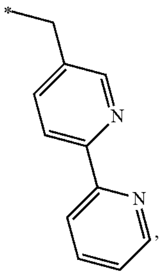, and

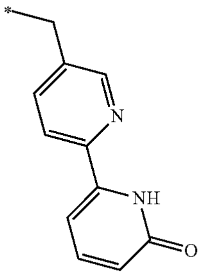

In some embodiments, $R_4$ may be hydrogen or $C_1$-$C_3$ alkyl.

In some embodiments, $R^5$ and $R^6$ may be H and $R^7$ may be absent, and the structure attached to the amide bond in formula I may be the following structure:

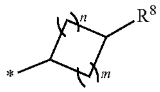

(in which, n and m may be each an integer of 1 or 2.)

In another embodiment, $R^5$ and $R^6$ may together represent $—(CH_2)_q—$, and $R^7$ may be absent, in which case the structure attached to the amide bond in formula I may be the following structure:

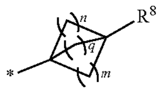

(in which, n, m and q may be each an integer of 1 or 2.)

In another embodiment, $R^5$ may be H, and $R^6$ and $R^7$ may together represent $—(CH_2)_r—$, in which case the structure attached to the amide bond in formula I may be the following structure:

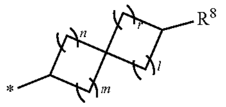

(in which, n, m, r and l may be each an integer of 1 or 2.)

In one embodiment, the structure attached to the amide bond in formula I includes isomers of that structure, and for example, may be the following structure, but is not limited thereto:

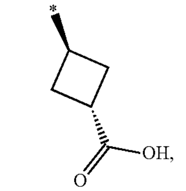

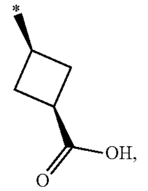

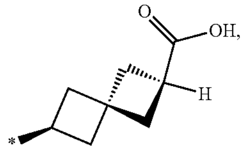

or

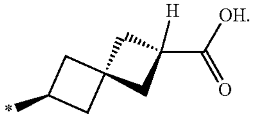

In some embodiments, $R^8$ may be

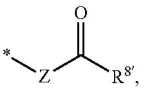

wherein Z may be —$(CH_2)_s$, and $R^{8'}$ may be hydroxy or $C_1$-$C_6$ alkoxy, and s may be an integer of 0 or 1. In one embodiment, s may be 0, and $R^{8'}$ may be hydroxy.

In another aspect of the present invention, there is provided a compound of formula IA-1 or IA-2 or a solvate, stereoisomer or pharmaceutically acceptable salt thereof:

[Formula IA-1]

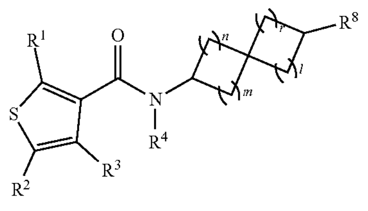

[Formula IA-2]

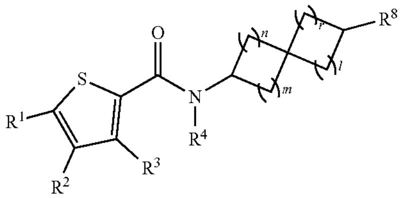

in which, $R^1$ and $R^2$ are selected from the group consisting of hydrogen, halogen, hydroxy, cyano, amino, $C_1$-$C_6$ alkyl, $C_1$-$C_6$ alkoxy, —NH—($C_1$-$C_6$ alkyl), —N($C_1$-$C_6$ alkyl$)_2$, $C_3$-$C_8$ cycloalkyl, and $C_6$-$C_{10}$ aryl, wherein said $C_1$-$C_6$ alkyl and $C_1$-$C_6$ alkoxy may be each independently optionally substituted with one or more halogen, hydroxy, cyano or amino, and said $C_3$-$C_8$ cycloalkyl and $C_6$-$C_{10}$ aryl may be each independently optionally substituted with one or more halogen, hydroxy, cyano, amino, oxo, $C_1$-$C_6$ alkyl, $C_1$-$C_6$ haloalkyl, $C_1$-$C_6$ alkoxy or $C_1$-$C_6$ haloalkoxy;

$R^3$ is

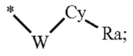

and

W, Cy, Ra, $R^4$, $R^8$, n, m, r and l are as defined in formula I above. The specific examples and embodiments described with respect to $R^1$, $R^2$, W, Cy, $R_a$, $R^4$, $R^8$, n, m, r and l in formula I may be also equally applied to formulae IA-1 and IA-2 as long as they are structurally acceptable.

In some embodiments of formulae IA-1 and IA-2, $R^1$ may be hydrogen, halogen, hydroxy, cyano, amino, $C_1$-$C_6$ alkyl, $C_1$-$C_6$ alkoxy, —NH—($C_1$-$C_6$ alkyl) or —N($C_1$-$C_6$ alkyl$)_2$, wherein said $C_1$-$C_6$ alkyl and $C_1$-$C_6$ alkoxy may be each independently optionally substituted with one or more halogen, hydroxy, cyano or amino. In one embodiment, $R^1$ may be hydrogen, halogen, hydroxy, $C_1$-$C_3$ alkyl, $C_1$-$C_3$ alkoxy, $C_1$-$C_3$ haloalkyl, or $C_1$-$C_3$ haloalkoxy. In one embodiment, $R^1$ may be hydrogen, halogen, $C_1$-$C_3$ alkyl, or $C_1$-$C_3$ haloalkyl.

In some embodiments, $R^2$ may be hydrogen, halogen, hydroxy, $C_1$-$C_3$ alkyl, $C_1$-$C_3$ alkoxy, $C_1$-$C_3$ haloalkyl, $C_1$-$C_3$ haloalkoxy, $C_3$-$C_6$ cycloalkyl or phenyl, wherein said $C_1$-$C_3$ alkyl and $C_1$-$C_3$ alkoxy may be each independently optionally substituted with one or more halogen, hydroxy, cyano or amino. In one embodiment, said $C_3$-$C_6$ cycloalkyl and phenyl may be optionally substituted with one or more halogen, $C_1$-$C_3$ alkyl or $C_1$-$C_3$ haloalkyl. In one embodiment, $R^2$ may be hydrogen, halogen, $C_1$-$C_3$ alkyl, $C_1$-$C_3$ haloalkyl, cyclopropyl, cyclobutyl, or phenyl.

In some embodiments, W may be —$(CH_2)_o$—, —$(CH_2)_o$—C≡C—, —C(O)—, —O—, —NH— or —N($C_1$-$C_3$ alkyl)-. In one embodiment, W may be —$(CH_2)_o$—, —C(O)—, —O—, —NH—, or —N($C_1$-$C_6$ alkyl)-. In this case, H of said $CH_2$ of W may be optionally substituted with one or more halogen, hydroxy, or $C_1$-$C_6$ alkoxy.

In some embodiments, Cy may be $C_6$-$C_{10}$ aryl, 5- to 10-membered heteroaryl containing 1 to 3 heteroatoms selected from N, O and S, or 4- to 10-membered heterocycloalkyl containing 1 to 3 heteroatoms selected from N, O and S. In one embodiment, Cy may be phenyl, 5- to 10-membered heteroaryl containing 1 or 2 nitrogen atoms, or 4- to 7-membered heterocycloalkyl containing 1 or 2 nitrogen atoms. For example, Cy may be phenyl, pyrrolyl, pyrazolyl, imidazolyl, pyridinyl, pyrimidinyl, pyridazinyl, pyrazinyl, indolyl, isoindolyl, benzimidazolyl, indazolyl, pyrrolidinyl, piperidinyl, piperazinyl or morpholinyl. In one embodiment, Cy may be phenyl, pyrazolyl, pyridinyl, pyrimidinyl, indolyl or piperazinyl. In one embodiment, Cy may be phenyl, pyrazolyl, or piperazinyl.

Said Cy may be optionally substituted with one or more R'. In some embodiments, R' may be halogen, hydroxy, cyano, amino, oxo, $C_1$-$C_3$ alkyl, $C_1$-$C_3$ haloalkyl, $C_1$-$C_3$ alkoxy, $C_1$-$C_3$ haloalkoxy, —NH—($C_1$-$C_3$ alkyl), or —$N(C_1$-$C_3$ alkyl$)_2$. In one embodiment, R' may be halogen, amino, $C_1$-$C_3$ alkyl, or $C_1$-$C_3$ haloalkyl.

In some embodiments, $R_a$ may be hydrogen, halogen, $C_1$-$C_3$ alkyl, $C_1$-$C_3$ haloalkyl or —V-$Cy_2$. In one embodiment, $R_a$ may be —V-$Cy_2$.

In some embodiments, V may be absent or —NH—, —$NHCH_2$—, —$NHCH_3$—, —S—, —$SO_2$—, —$CH_2$—, —$OCH_2$— or —O—. In one embodiment, V may be absent or —$CH_2$— or —O—.

In some embodiments, $Cy_2$ may be selected from the group consisting of $C_6$-$C_{10}$ aryl, 5- to 10-membered heteroaryl containing 1 to 3 heteroatoms selected from N, O and S, 4- to 10-membered heterocycloalkyl containing 1 to 3 heteroatoms selected from N, O and S, $C_3$-$C_8$ cycloalkyl and $C_3$-$C_8$ cycloalkenyl. In one embodiment, $Cy_2$ may be selected from the group consisting of phenyl, 5- to 10-membered heteroaryl containing 1 or 2 heteroatoms selected from N or O, 4- or 7-membered heterocycloalkyl containing 1 or 2 heteroatoms selected from N or O, $C_4$-$C_7$ cycloalkyl and $C_4$-$C_7$ cycloalkenyl.

In one embodiment, $Cy_2$ may be phenyl, furanyl, pyrazolyl, pyridinyl, pyrimidinyl, piperidinyl, morpholinyl, cyclohexyl, or cyclohexenyl. In one embodiment, $Cy_2$ may be phenyl, furanyl, pyrazolyl, pyridinyl, morpholinyl, piperidinyl, cyclohexyl, or cyclohexenyl.

Said $Cy_2$ may be optionally substituted with one or more R". In some embodiments, R" may be selected from the group consisting of halogen, hydroxy, cyano, amino, oxo, $C_1$-$C_6$ alkyl, $C_1$-$C_6$ alkoxy, —S—($C_1$-$C_6$ alkyl), —$SO_2$—($C_1$-$C_6$ alkyl), —COO—($C_1$-$C_6$ alkyl), —COOH, —$CONH_2$, —$(CH_2)_p$—$NH_2$, —$(CH_2)_p$—NH—($C_1$-$C_6$ alkyl), —$(CH_2)_p$—$N(C_1$-$C_6$ alkyl$)_2$, —$(CH_2)_p$—NH—COO—($C_1$-$C_6$ alkyl), —$(CH_2)_p$—OH, 3- to 5-membered heterocycloalkyl containing 1 heteroatom selected from N, O and S, $C_3$-$C_5$ cycloalkyl, and —$(CH_2)_p$—($C_3$-$C_5$ cycloalkyl). In this case, said $C_1$-$C_6$ alkyl and $C_1$-$C_6$ alkoxy may be optionally substituted with one or more halogen, hydroxy, cyano or amino, and said 3- to 5-membered heterocycloalkyl and $C_3$-$C_8$ cycloalkyl may be optionally substituted with one or more halogen, hydroxy, cyano, oxo or amino.

In one embodiment, R" may be selected from the group consisting of halogen, hydroxy, cyano, amino, oxo, $C_1$-$C_6$ alkyl, $C_1$-$C_6$ haloalkyl, $C_1$-$C_6$ alkoxy, $C_1$-$C_6$ haloalkoxy, —S—($C_1$-$C_6$ alkyl), —$SO_2$—($C_1$-$C_6$ alkyl), —COO—($C_1$-$C_6$ alkyl), —COOH, —$CONH_2$, —$(CH_2)_p$—$NH_2$, —$(CH_2)_p$—NH—($C_1$-$C_6$ alkyl), —$(CH_2)_p$—$N(C_1$-$C_6$ alkyl$)_2$, —$(CH_2)_p$—NH—COO—($C_1$-$C_6$ alkyl), —$(CH_2)_p$—OH; azetidinyl or oxetanyl, optionally substituted with hydroxy or oxo; and cyclopropyl or cyclopropylmethyl, optionally substituted with hydroxy or oxo.

In some embodiments, $R^4$ may be hydrogen or $C_1$-$C_3$ alkyl.

In some embodiments, the compound having formula IA-1 or IA-2 above may be represented by formula IA-3 or IA-4:

[Formula IA-3]

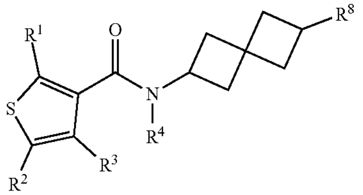

-continued

[Formula IA-4]

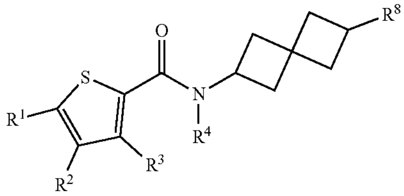

in which, $R^1$, $R^2$, $R^3$, $R^4$ and $R^8$ are as defined in formulae IA-1 and IA-2 above.

In another aspect, there is provided a compound of formula IB-1 or a solvate, stereoisomer or pharmaceutically acceptable salt thereof:

[Formula IB-1]

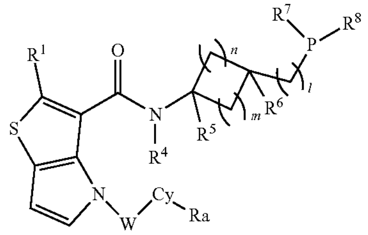

in which, $R^1$ is selected from the group consisting of hydrogen, halogen, hydroxy, cyano, amino, $C_1$-$C_6$ alkyl, $C_1$-$C_6$ alkoxy, —NH—($C_1$-$C_6$ alkyl), —$N(C_1$-$C_6$ alkyl$)_2$, $C_3$-$C_8$ cycloalkyl, and $C_6$-$C_{10}$ aryl, wherein said $C_1$-$C_6$ alkyl and $C_1$-$C_6$ alkoxy may be each independently optionally substituted with one or more halogen, hydroxy, cyano or amino, and said $C_3$-$C_8$ cycloalkyl and $C_6$-$C_{10}$ aryl may be each independently optionally substituted with one or more halogen, hydroxy, cyano, amino, oxo, $C_1$-$C_6$ alkyl, $C_1$-$C_6$ haloalkyl, $C_1$-$C_6$ alkoxy or $C_1$-$C_6$ haloalkoxy;

either or both of the carbon atoms of

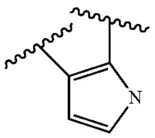 [SMILES: *c1cc[nH]c1*]

may be optionally substituted with halogen, hydroxy, cyano, $C_1$-$C_6$ alkyl, $C_1$-$C_6$ alkoxy, $C_1$-$C_6$ haloalkyl or $C_1$-$C_6$ haloalkoxy; and W, Cy, $R_a$, $R^4$, $R^5$, $R^6$, $R^7$, $R^8$, P, n, m and l are as defined in formula I above.

The specific examples and embodiments described with respect to W, Cy, $R_a$, $R^4$, $R^8$, $R^6$, $R^7$, $R^8$, P, n, m and l in formula I may be also equally applied to formula IB-1 as long as they are structurally acceptable.

In some embodiments, the compound having formula IB-1 may be represented by formula IB-2, IB-3 or IB-4:

[Formula IB-2]

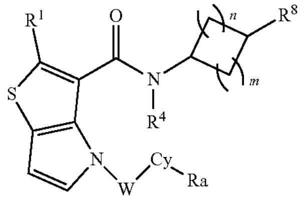

[Formula IB-3]

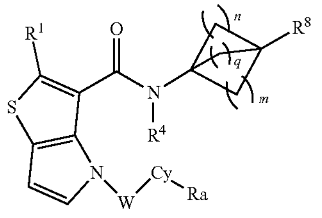

[Formula IB-4]

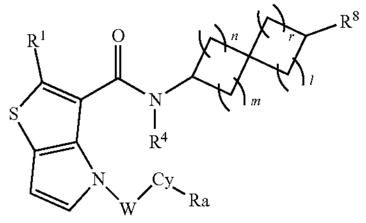

In some embodiments of formula IB-2, IB-3 and IB-4, $R^1$ may be hydrogen, halogen, hydroxy, cyano, amino, $C_1$-$C_6$ alkyl, $C_1$-$C_6$ alkoxy, —NH—($C_1$-$C_6$ alkyl) or —N($C_1$-$C_6$ alkyl)$_2$, wherein said $C_1$-$C_6$ alkyl and $C_1$-$C_6$ alkoxy may be each independently optionally substituted with one or more halogen, hydroxy, cyano or amino. In one embodiment, $R^1$ may be hydrogen, halogen, hydroxy, $C_1$-$C_3$ alkyl, $C_1$-$C_3$ alkoxy, $C_1$-$C_3$ haloalkyl, or $C_1$-$C_3$ haloalkoxy.

In some embodiments, either or both of the carbon atoms of

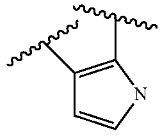 [SMILES: *c1cc[nH]c1*]

may be optionally substituted with halogen, $C_1$-$C_3$ alkyl, or $C_1$-$C_3$ haloalkyl. In one embodiment, either or both of the carbon atoms of

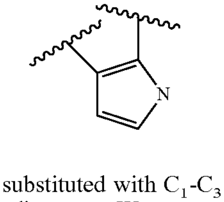

may be optionally substituted with $C_1$-$C_3$ alkyl.

In some embodiments, W may be —$(CH_2)_o$—, —$(CH_2)_o$—C≡C—, —C(O)—, —O—, —NH— or —N($C_1$-$C_3$ alkyl)-. In one embodiment, W may be —$(CH_2)_o$— or —$(CH_2)_o$—C≡C—. In this case, H of said $CH_2$ may be optionally substituted with one or more halogen, hydroxy or $C_1$-$C_6$ alkoxy.

In some embodiments, Cy may be selected from the group consisting of $C_6$-$C_{10}$ aryl, 5- to 10-membered heteroaryl containing 1 to 3 heteroatoms selected from N, O and S, and 4- to 10-membered heterocycloalkyl containing 1 to 3 heteroatoms selected from N, O and S. In one embodiment, Cy may be phenyl, or 5- to 10-membered heteroaryl containing 1 or 2 nitrogen atoms. In one embodiment, Cy may be phenyl, pyrrolyl, pyrazolyl, imidazolyl, pyridinyl, pyrimidinyl, pyridazinyl, pyrazinyl, indolyl, isoindolyl, benzimidazolyl or indazolyl. In one embodiment, Cy may be phenyl, pyridinyl, pyrimidinyl or indolyl.

Said Cy may be optionally substituted with one or more R'. In some embodiments, R' may be halogen, hydroxy, cyano, amino, oxo, $C_1$-$C_3$ alkyl, $C_1$-$C_3$ haloalkyl, $C_1$-$C_3$ alkoxy, $C_1$-$C_3$ haloalkoxy, —NH—($C_1$-$C_3$ alkyl) or —N($C_1$-$C_3$ alkyl)$_2$. In one embodiment, R' may be halogen, amino, $C_1$-$C_3$ alkyl, or $C_1$-$C_3$ haloalkyl.

In some embodiments, $R_a$ may be hydrogen, halogen, $C_1$-$C_3$ alkyl, $C_1$-$C_3$ haloalkyl or —V-$Cy_2$. In this case, V may be absent or —NH—, —$NHCH_2$—, —$NHCH_3$—, —S—, —$SO_2$—, —$CH_2$—, —$OCH_2$— or —O—. In one embodiment, V may be absent or —$CH_2$— or —O—. In one embodiment, V may be absent or —$CH_2$—.

In some embodiments, $Cy_2$ may be selected from the group consisting of $C_6$-$C_{10}$ aryl, 5- to 10-membered heteroaryl containing 1 to 3 heteroatoms selected from N, O and S, 4- to 10-membered heterocycloalkyl containing 1 to 3 heteroatoms selected from N, O and S, $C_3$-$C_8$ cycloalkyl and $C_3$-$C_8$ cycloalkenyl. In one embodiment, $Cy_2$ may be phenyl, or 5- to 10-membered heteroaryl containing 1 or 2 nitrogen atoms. In one embodiment, $Cy_2$ may be phenyl, pyrrolyl, furanyl, pyrazolyl, imidazolyl, pyridinyl, pyrimidinyl, pyridazinyl, pyrazinyl, pyrrolidinyl, tetrahydrofuranyl, piperidinyl, piperazinyl, morpholine, cyclopentyl, cyclohexyl, cyclopentenyl, or cyclohexenyl. In one embodiment, $Cy_2$ may be phenyl, pyrazolyl, pyridinyl, or pyrimidinyl.

Said $Cy_2$ may be optionally substituted with one or more R". In some embodiments, R" may be selected from the group consisting of halogen, hydroxy, cyano, amino, oxo, $C_1$-$C_6$ alkyl, $C_1$-$C_6$ alkoxy, —S—($C_1$-$C_6$ alkyl), —$SO_2$—($C_1$-$C_6$ alkyl), —COO—($C_1$-$C_6$ alkyl), —COOH, —$CONH_2$, —$(CH_2)_p$—$NH_2$, —$(CH_2)_p$—NH—($C_1$-$C_6$ alkyl), —$(CH_2)_p$—N($C_1$-$C_6$ alkyl)$_2$, —$(CH_2)_p$—NH—COO—($C_1$-$C_6$ alkyl), —$(CH_2)_p$—OH, 3- to 5-membered heterocycloalkyl containing 1 heteroatom selected from N, O and S, $C_3$-$C_5$ cycloalkyl, and —$(CH_2)_p$—($C_3$-$C_5$ cycloalkyl). Said $C_1$-$C_6$ alkyl and $C_1$-$C_6$ alkoxy may be optionally substituted with one or more halogen, hydroxy, cyano or amino, and said 3- to 5-membered heterocycloalkyl and $C_3$-$C_8$ cycloalkyl may be optionally substituted with one or more halogen, hydroxy, cyano, oxo or amino.

In one embodiment, R" may be selected from the group consisting of halogen, hydroxy, cyano, amino, oxo, $C_1$-$C_6$ alkyl, $C_1$-$C_6$ haloalkyl, $C_1$-$C_6$ alkoxy, $C_1$-$C_6$ haloalkoxy, —$(CH_2)_p$—$NH_2$, —$(CH_2)_p$—NH—($C_1$-$C_6$ alkyl), —$(CH_2)_p$—N($C_1$-$C_6$ alkyl)$_2$; azetidinyl or oxetanyl, optionally substituted with hydroxy or oxo; and cyclopropyl or cyclopropylmethyl, optionally substituted with hydroxy or oxo.

In some embodiments, $R^4$ may be hydrogen or $C_1$-$C_3$ alkyl.

In some embodiments, $R^8$ may be

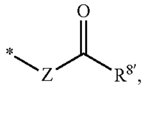

wherein Z may be —$(CH_2)_s$, and $R^{8'}$ may be hydroxy or $C_1$-$C_6$ alkoxy. In this case, s may be an integer of 0 or 1.

In one embodiment, l, m and n may be each independently an integer of 1 or 2. In one embodiment, o and p may be each independently an integer of 0 to 2. In one embodiment, q and r may be each independently an integer of 1 or 2. In one embodiment, s may be an integer of 0 or 1.

In some embodiments, the compound having formula IB-1 above may be represented by formula IB-5, IB-6, IB-7 or IB-8:

[Formula IB-5]

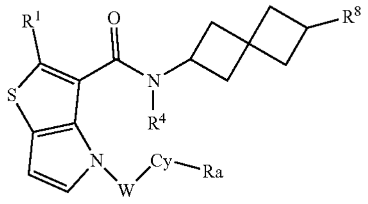

[Formula IB-6]

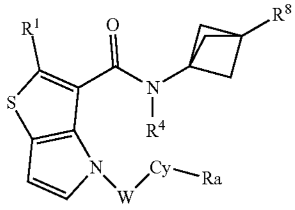

[Formula IB-7]

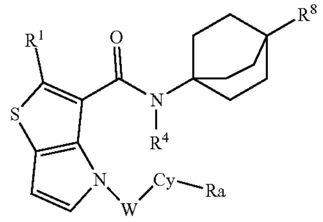

[Formula IB-8]

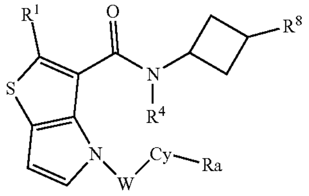

in which, $R^1$, W, Cy, $R_a$, $R^4$ and $R^8$ are as defined in formula IB-1.

In one embodiment, the compound of formula I of the present invention may be a compound selected from the group consisting of the following compounds:

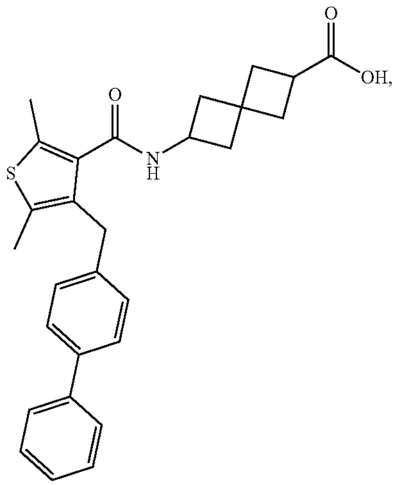

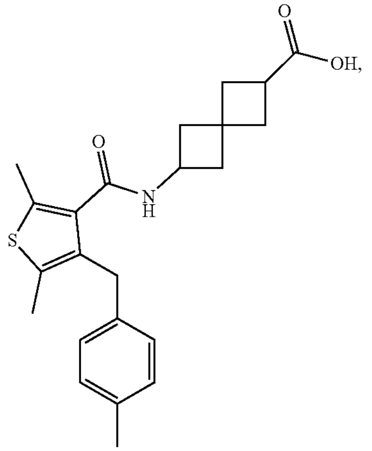

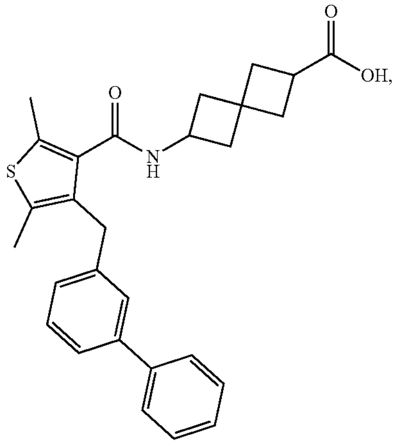

-continued
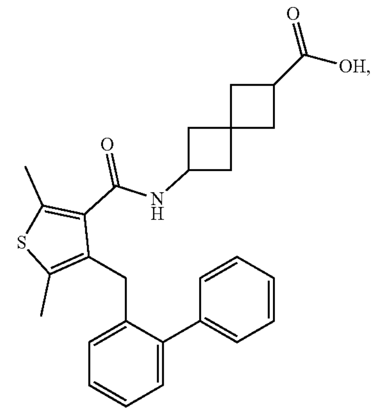
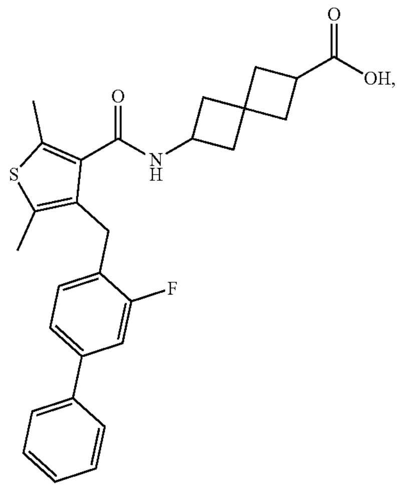
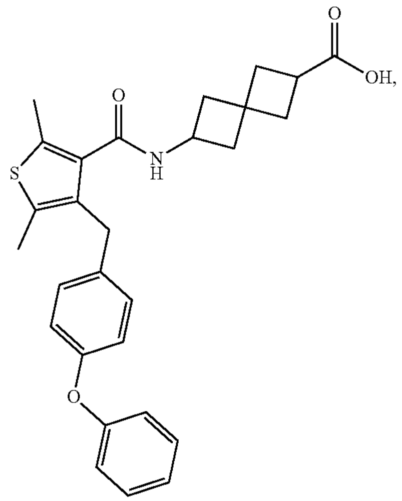
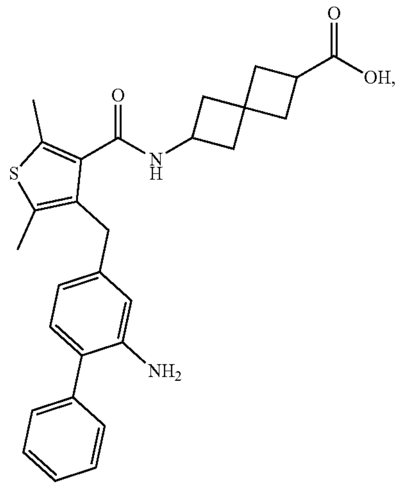
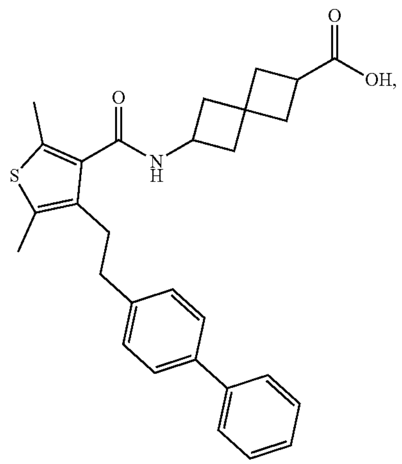
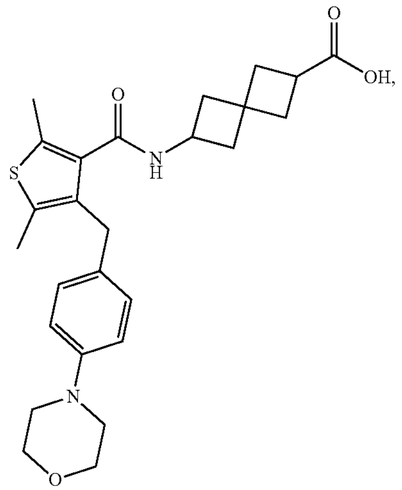

-continued
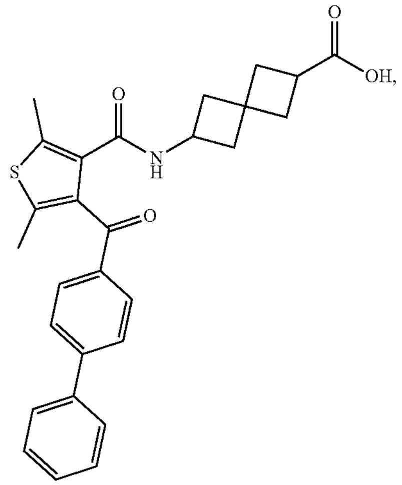
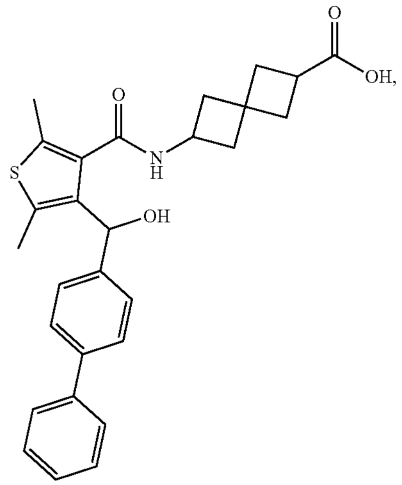
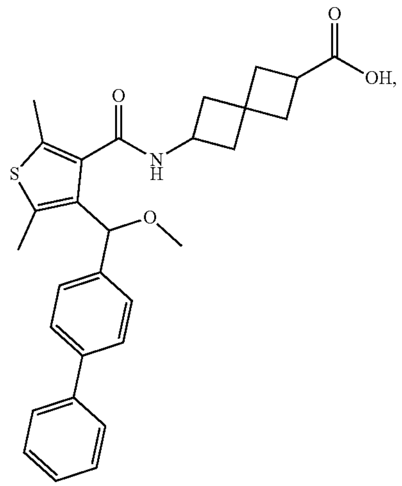
-continued
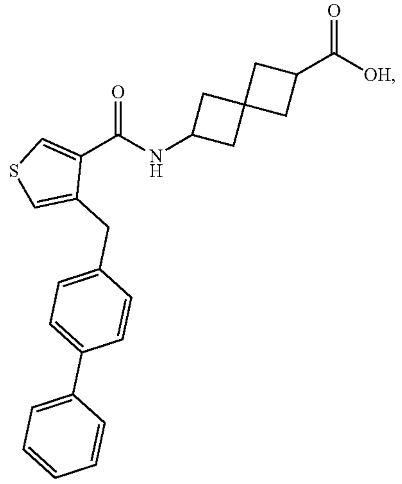
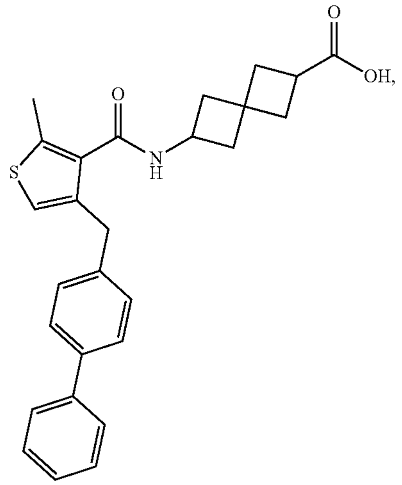
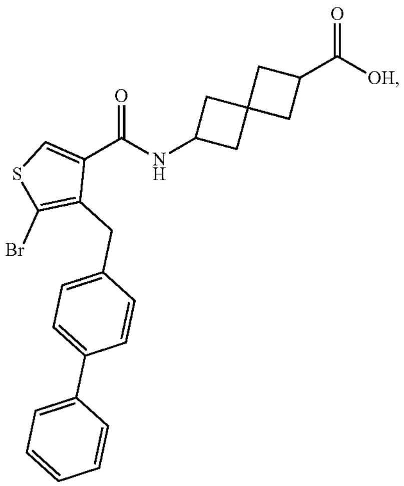

-continued
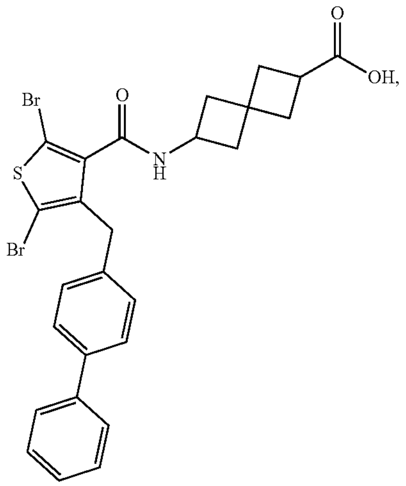
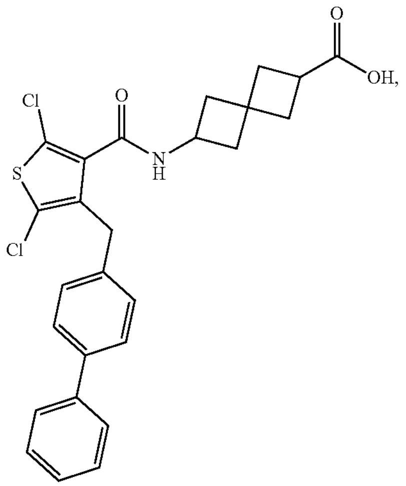
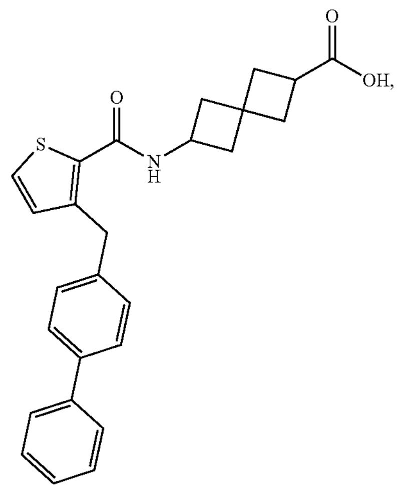
-continued
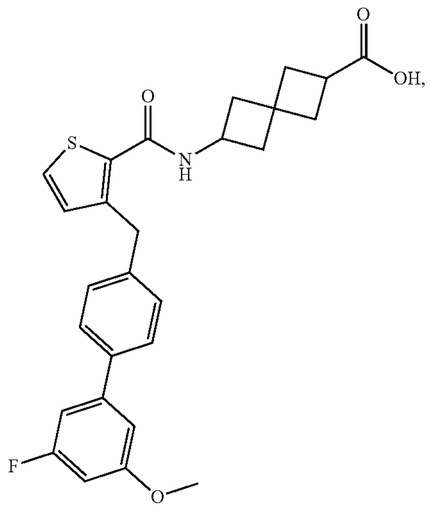
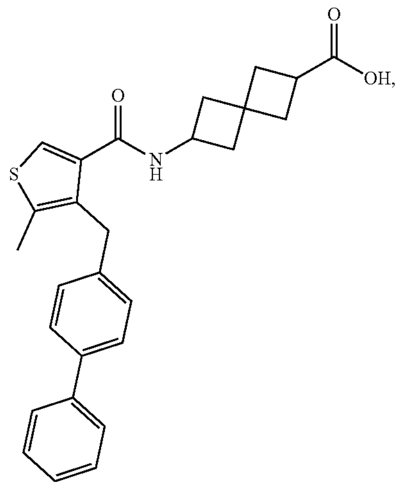
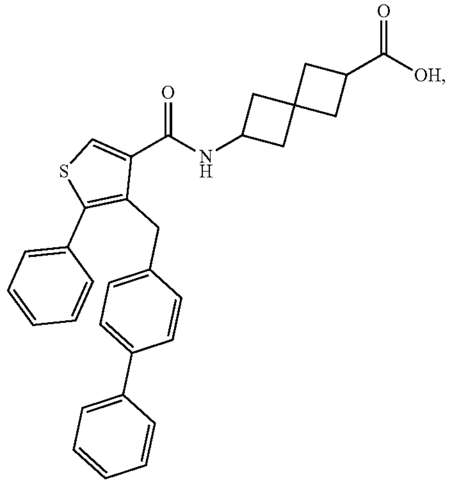

-continued
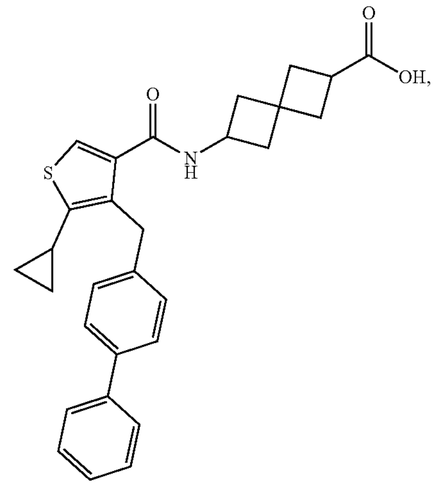
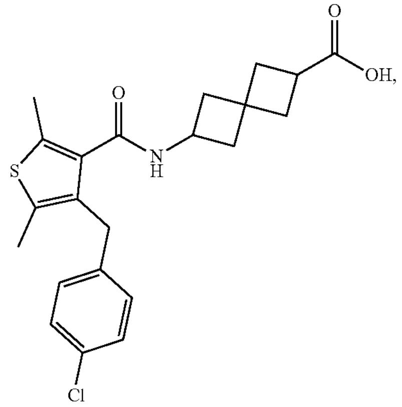
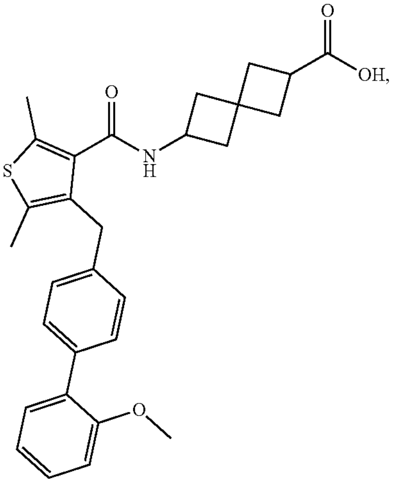
-continued
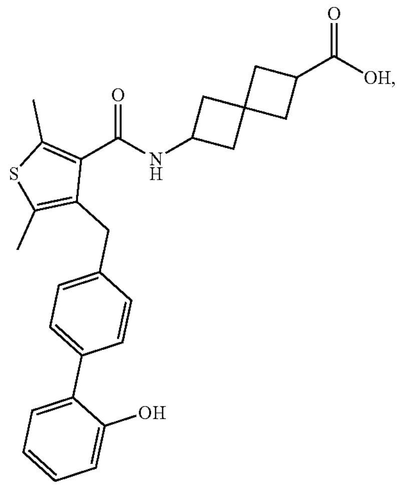
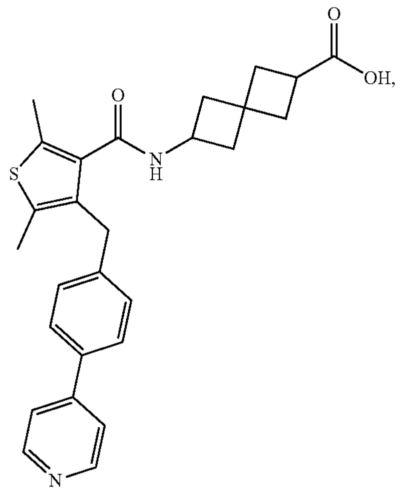
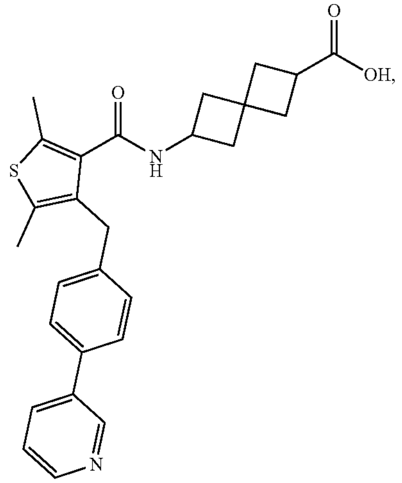

-continued
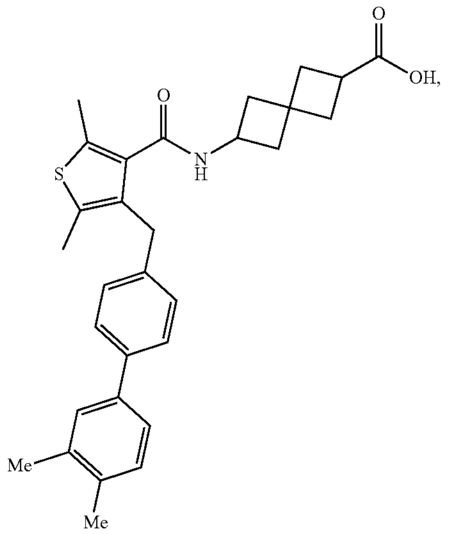
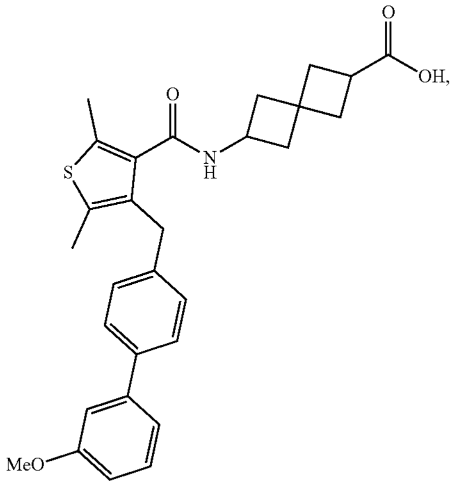
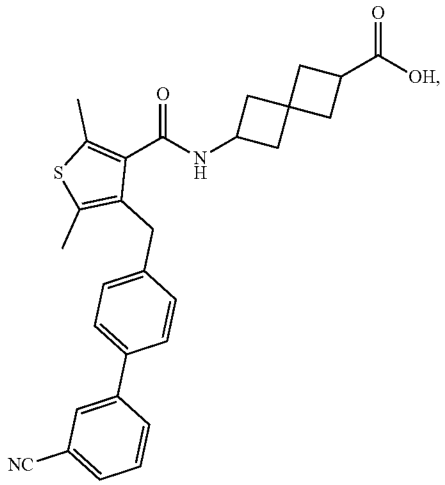
-continued
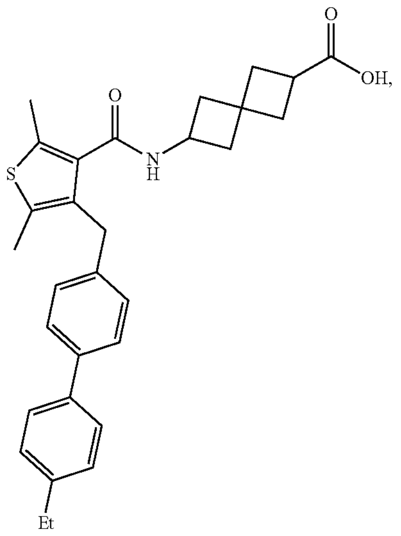
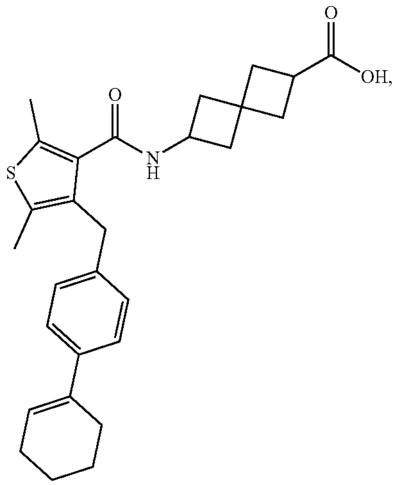
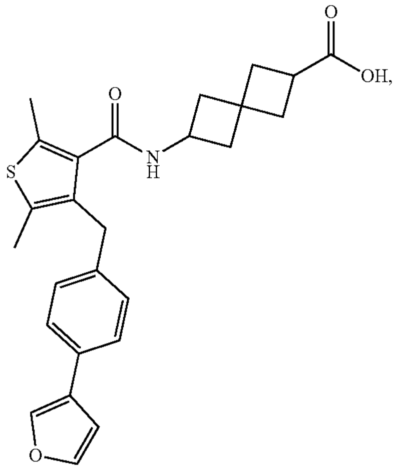

-continued
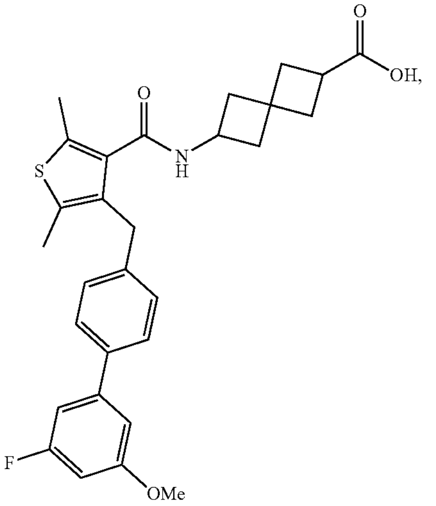
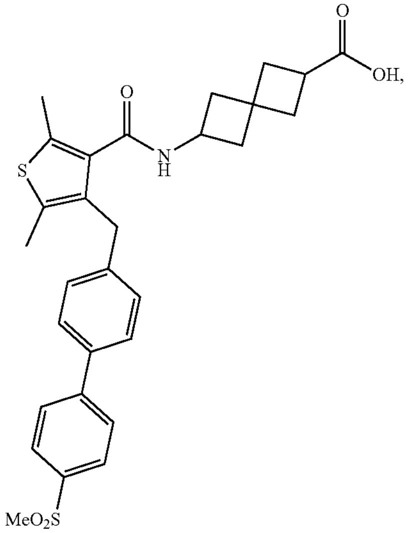
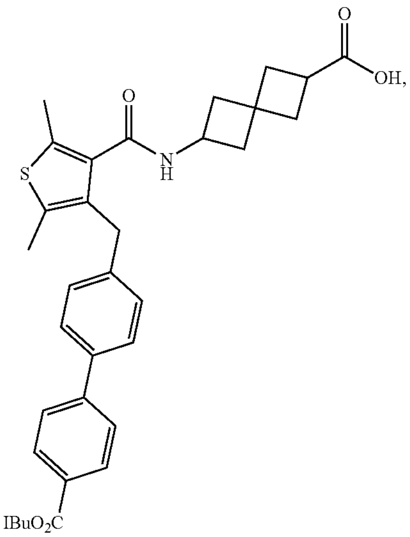
-continued
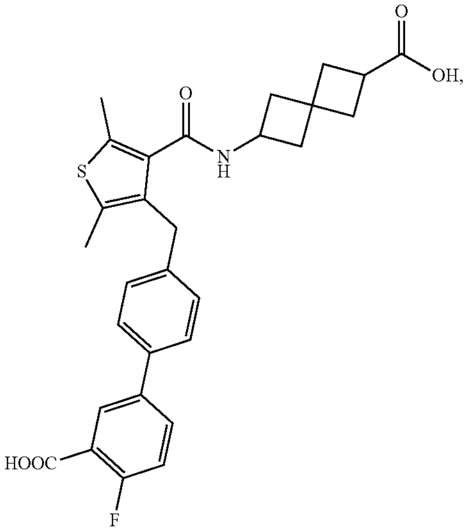
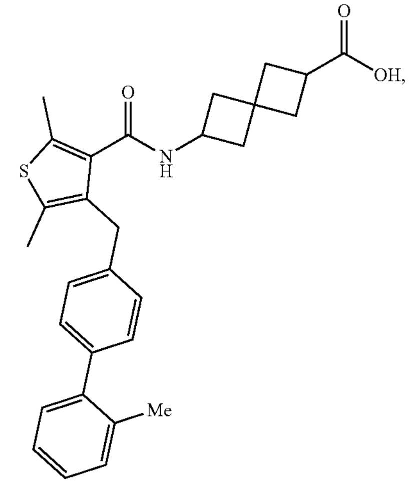
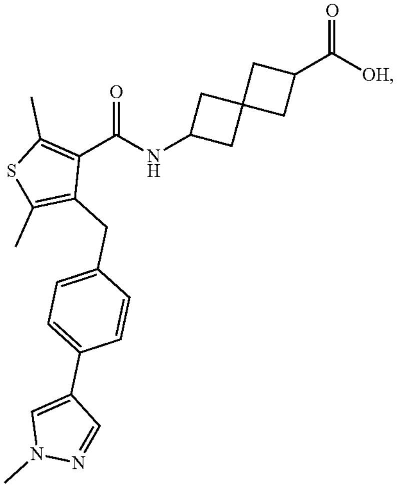

-continued
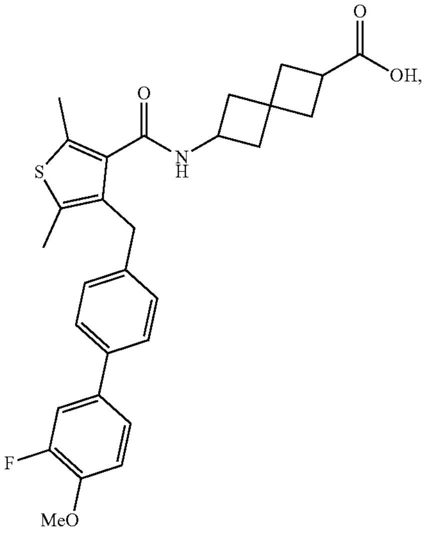
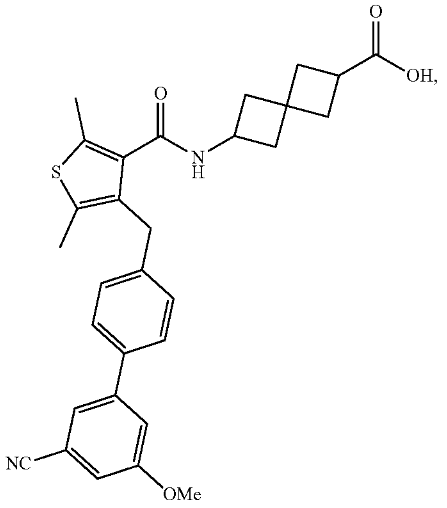
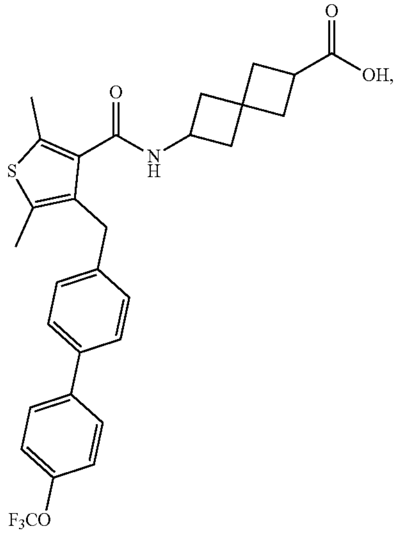
-continued
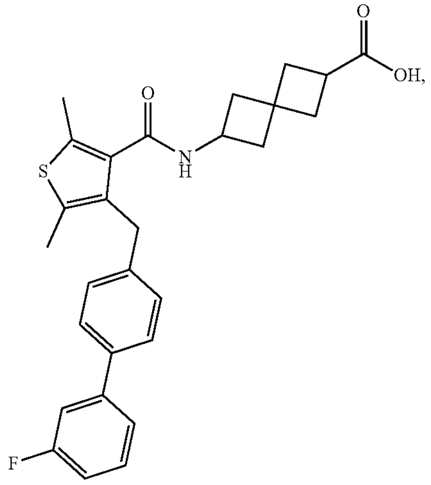
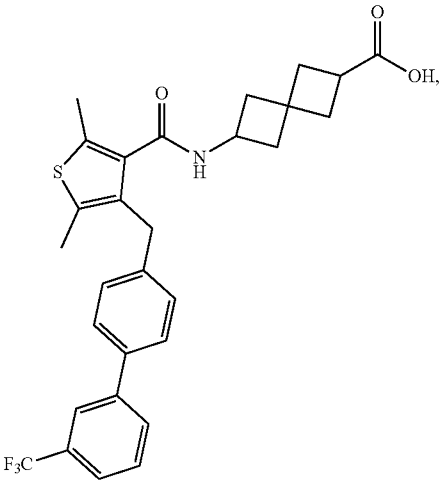
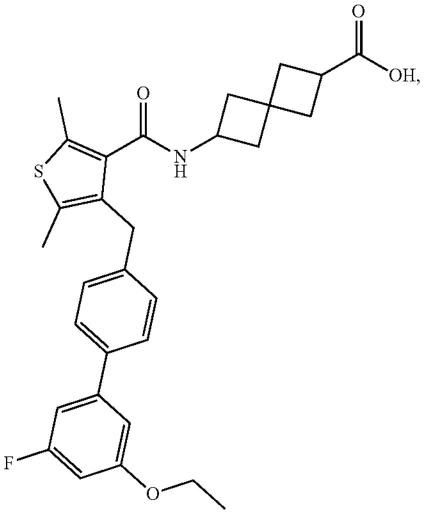

-continued
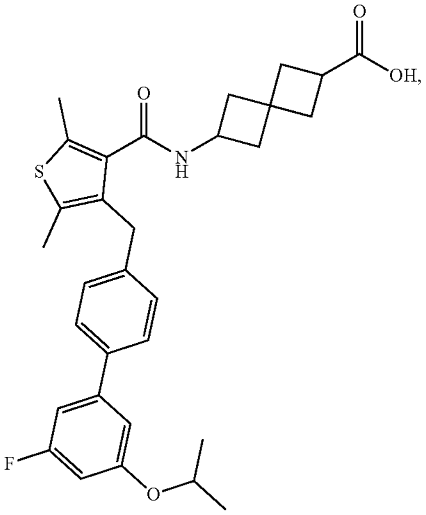
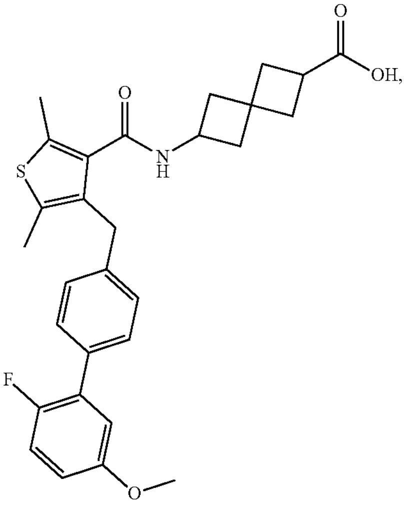
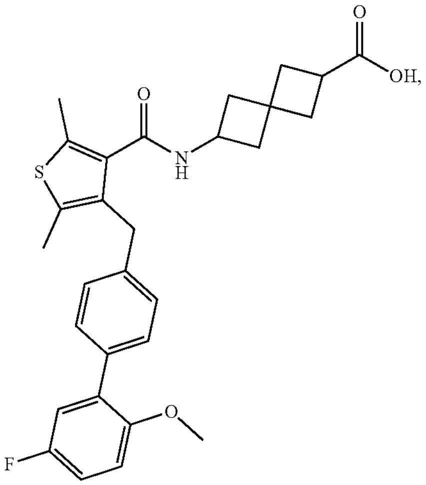
-continued
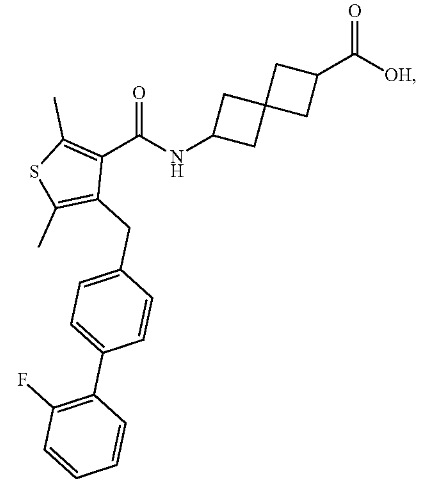
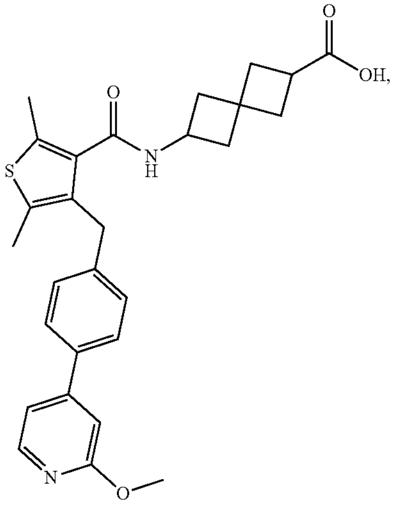
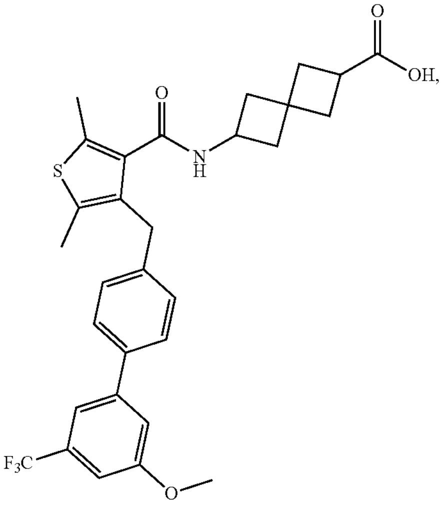

-continued
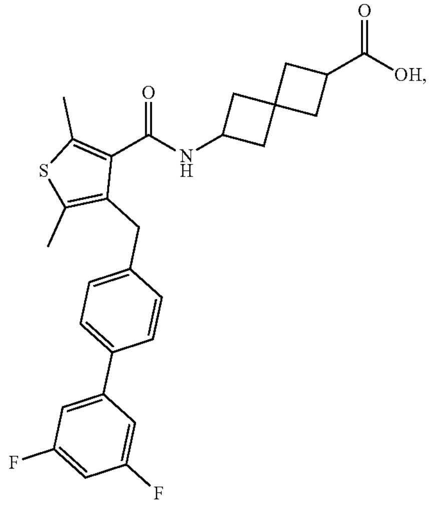
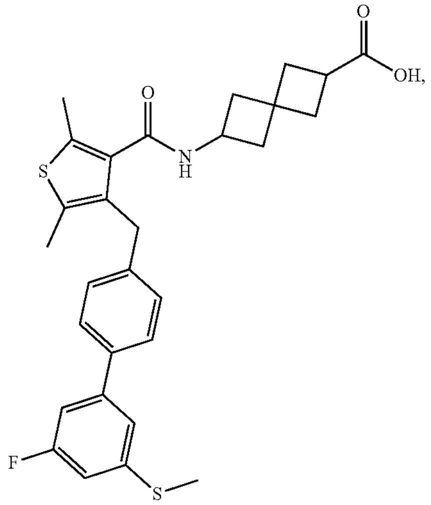
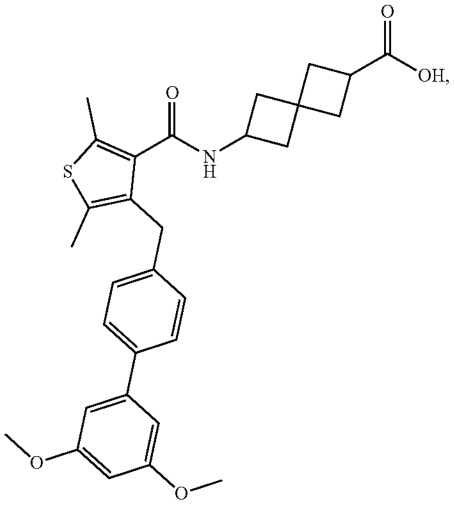
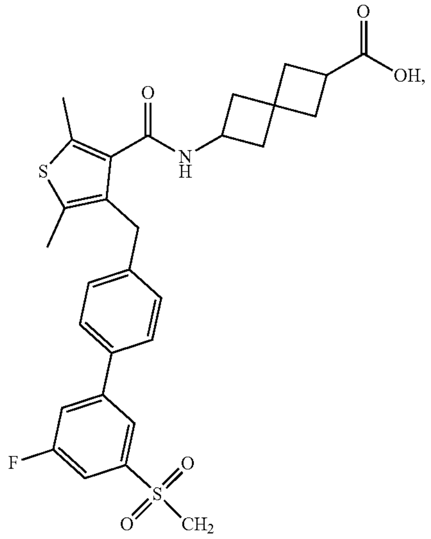
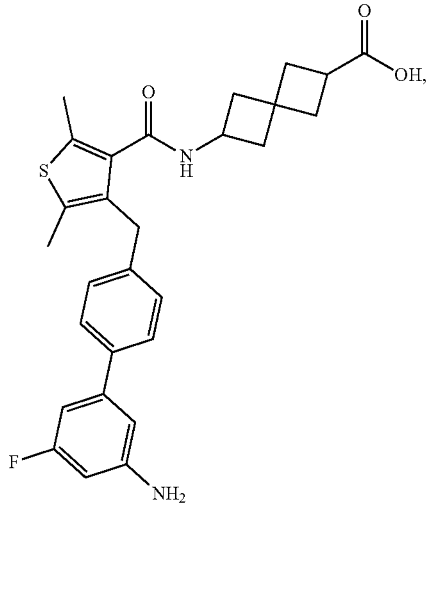
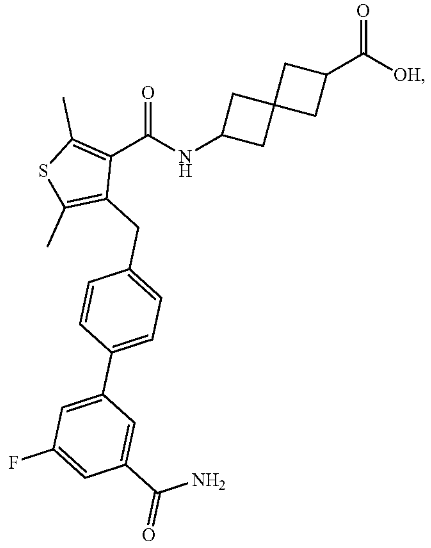

-continued
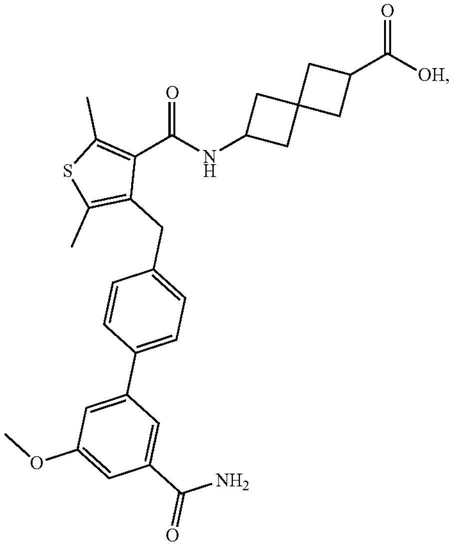
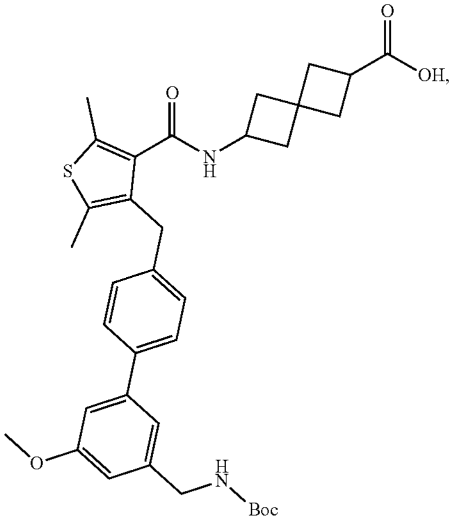
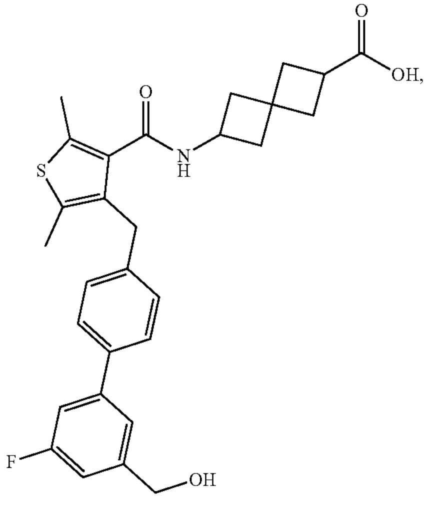
-continued
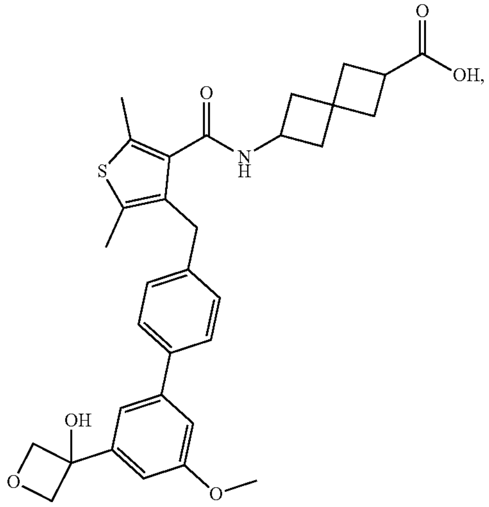
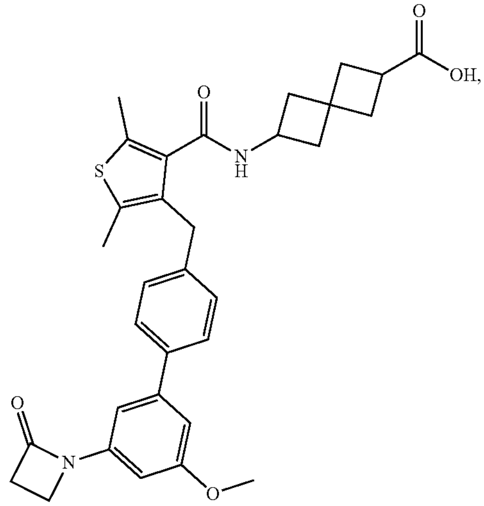
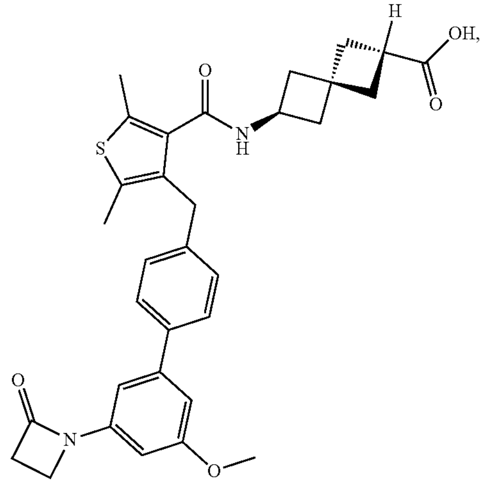

-continued
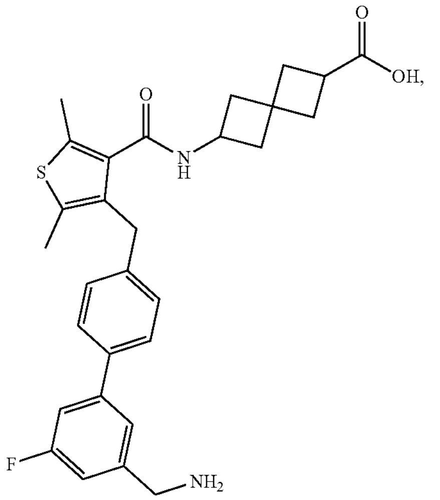 [SMILES: Cc1sc(C)c(C(=O)NC2CC3(C2)CC(C(=O)O)C3)c1Cc1ccc(-c2cc(F)cc(CN)c2)cc1]
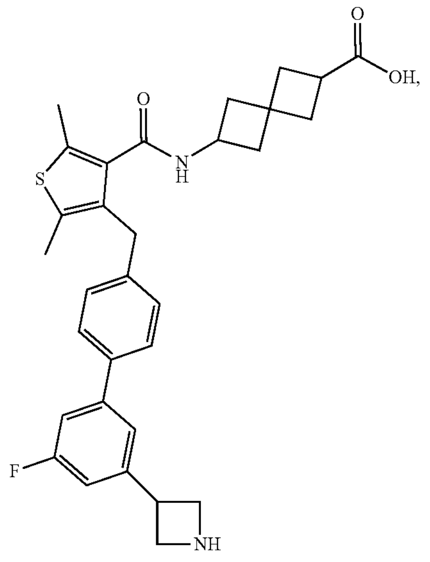
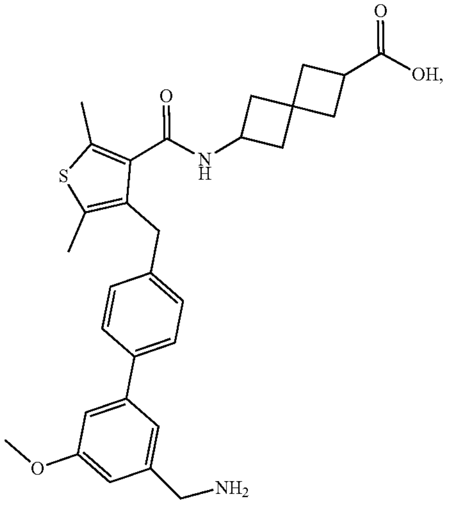
-continued
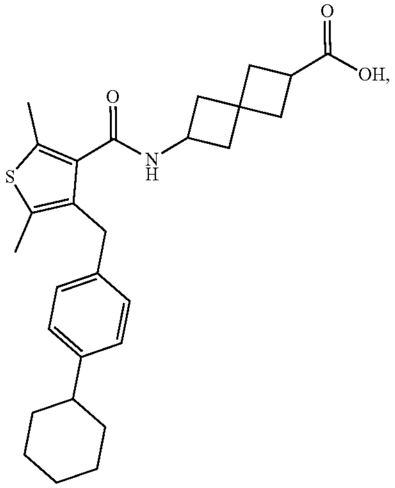
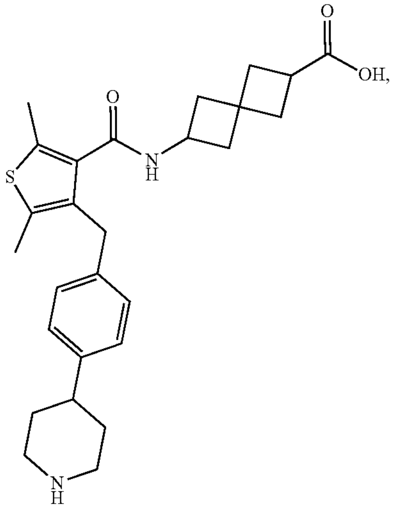
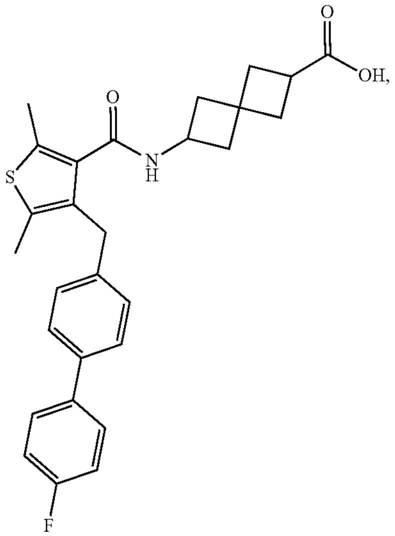

-continued
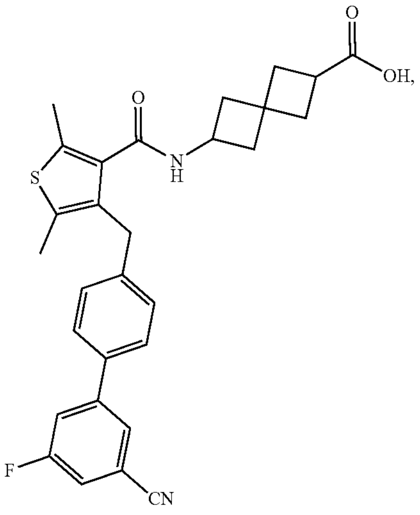
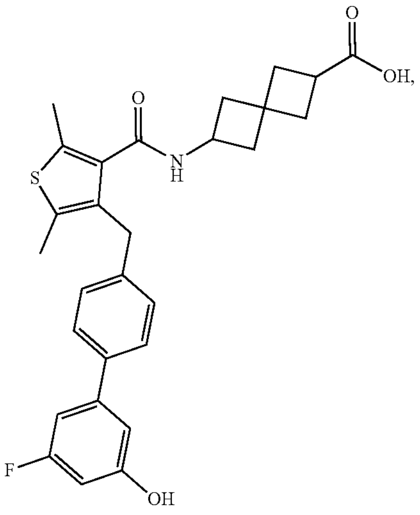
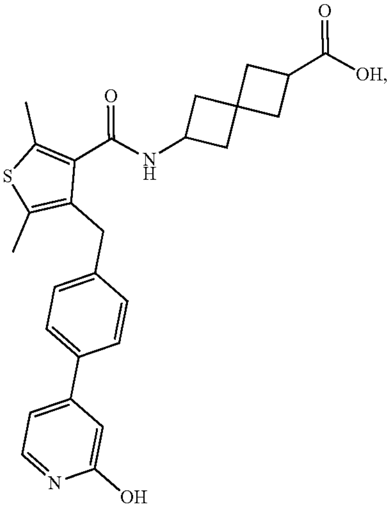
-continued
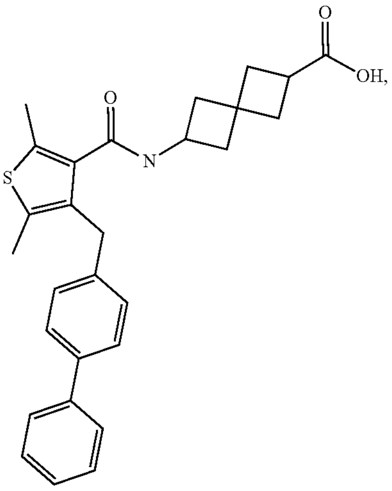
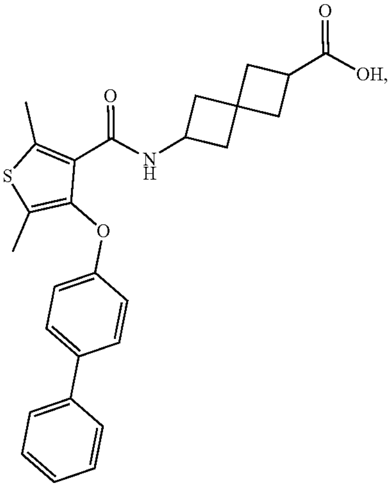
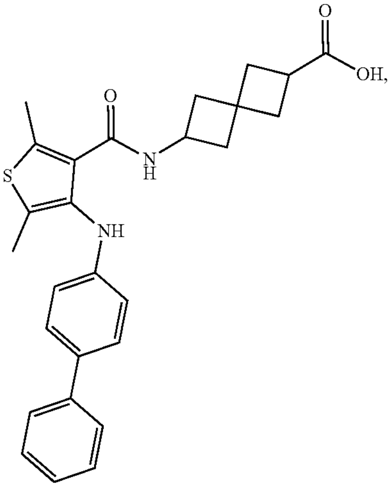

-continued
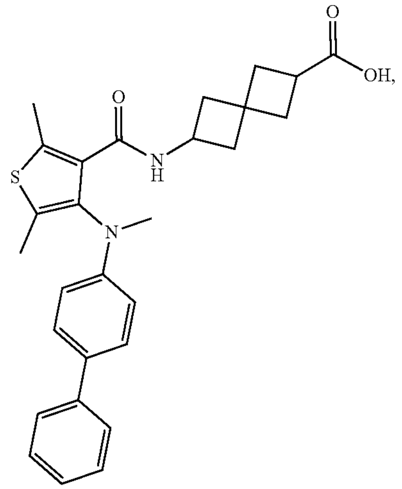
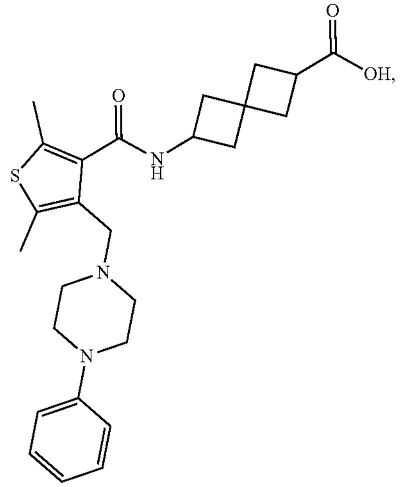
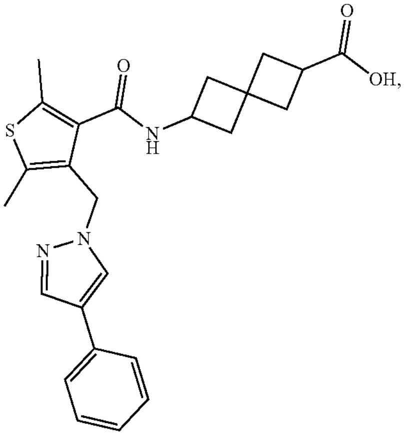
-continued
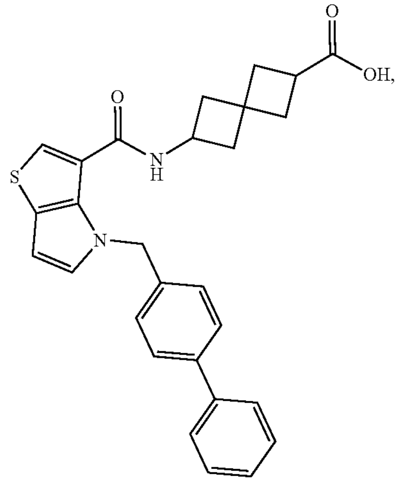
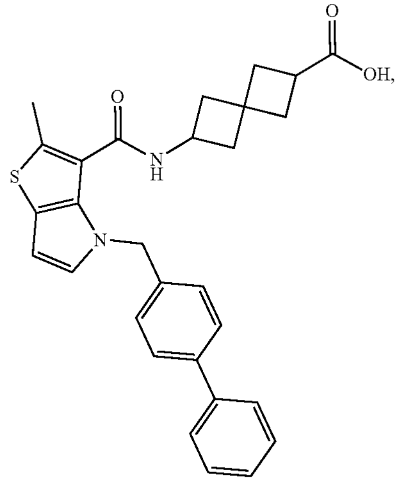
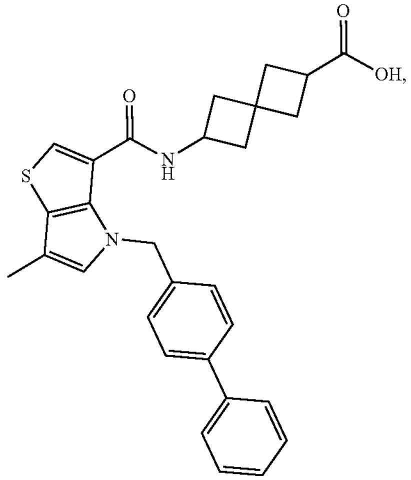

-continued
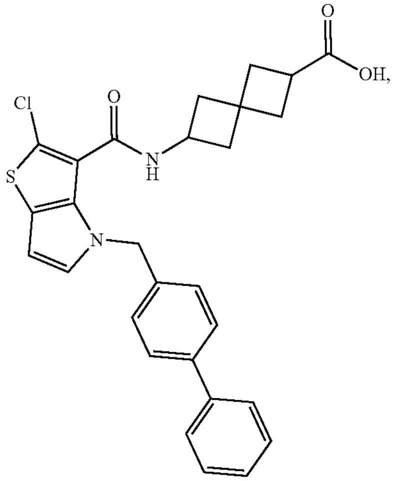
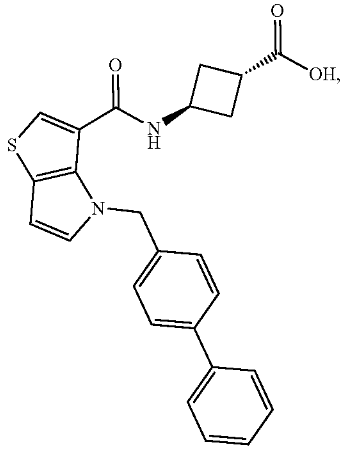
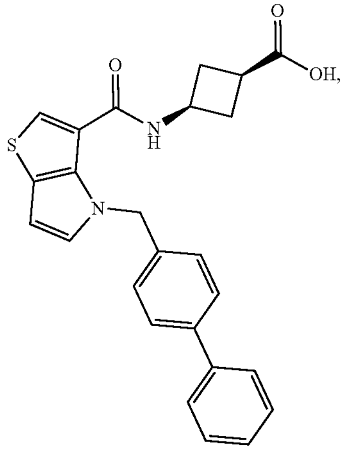
-continued
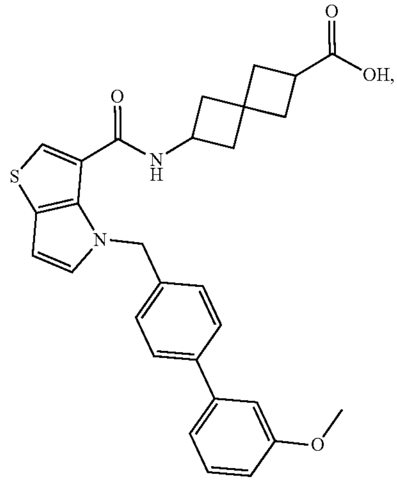
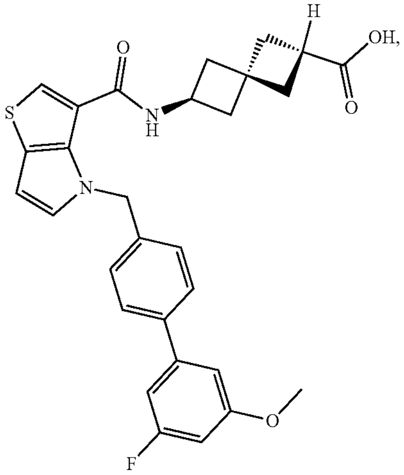
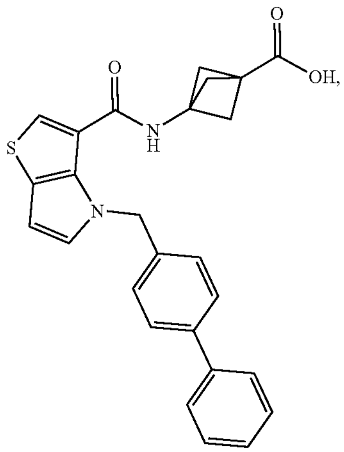

-continued
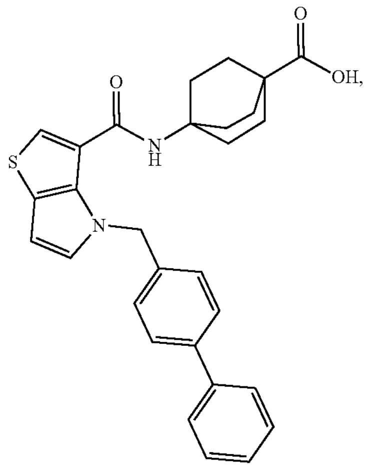
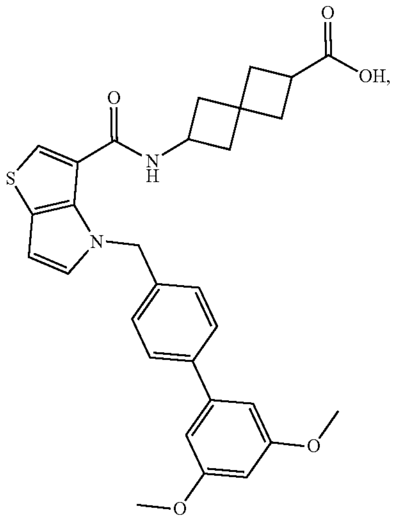
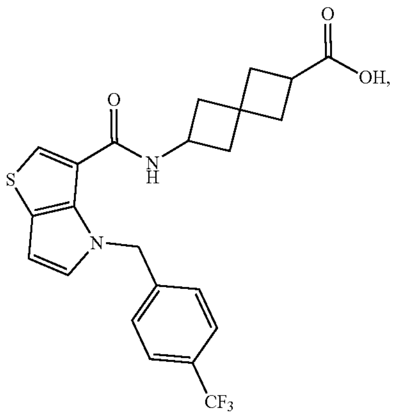
-continued
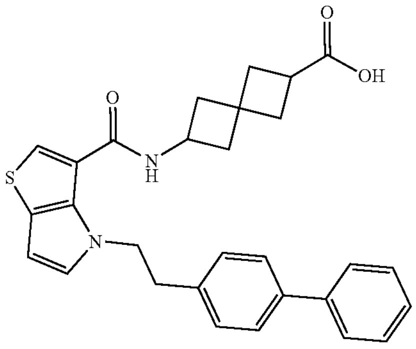
,
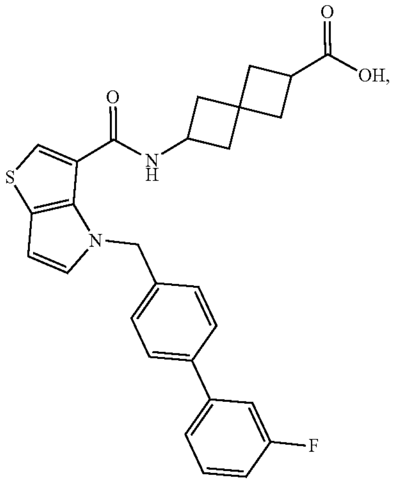
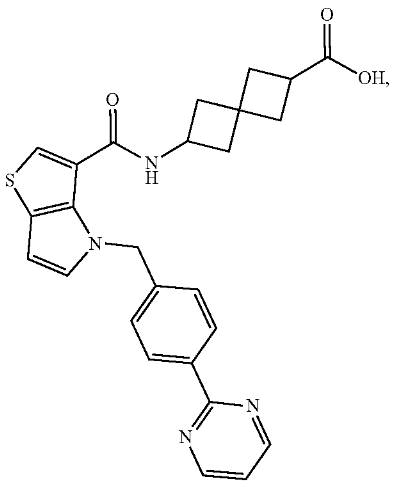

-continued
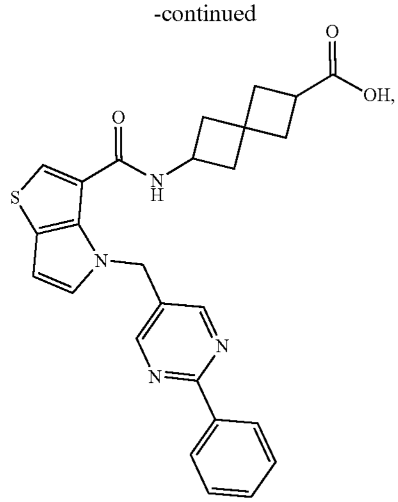
,
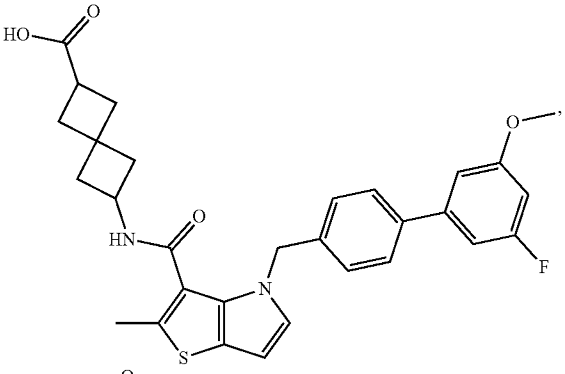
,
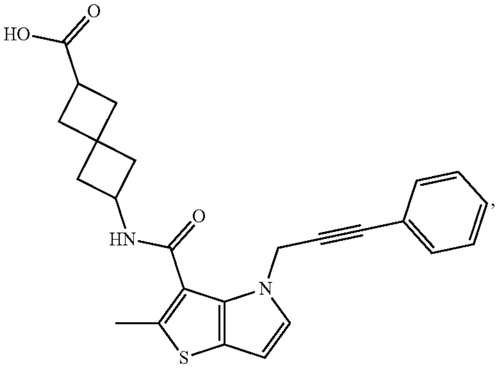
,
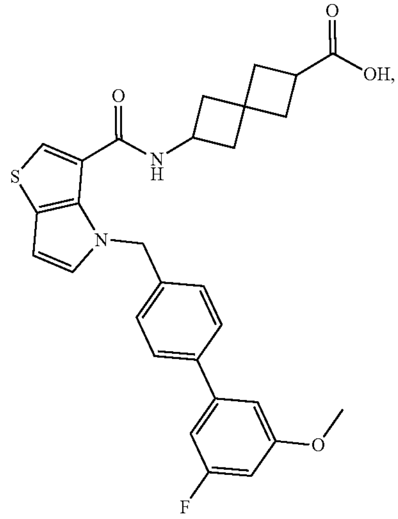
,
-continued
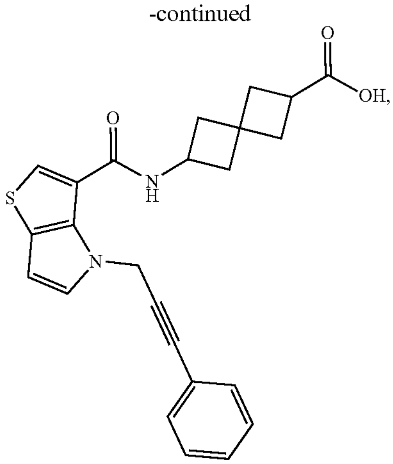
,
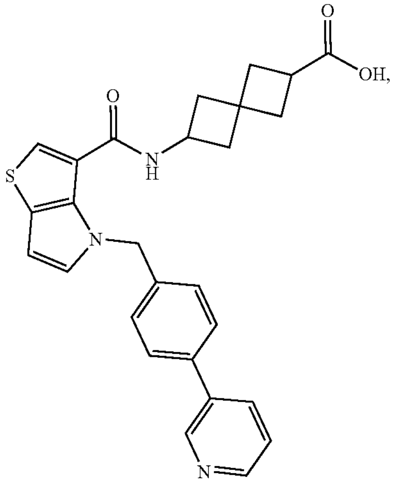
,
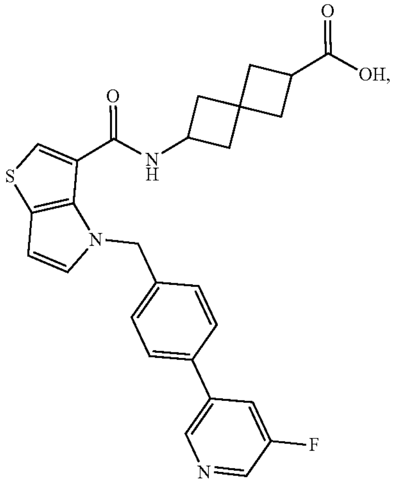
, -continued
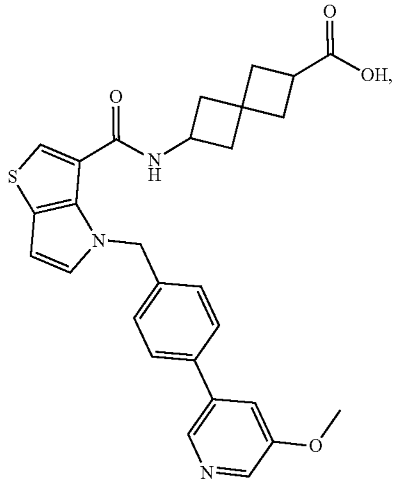
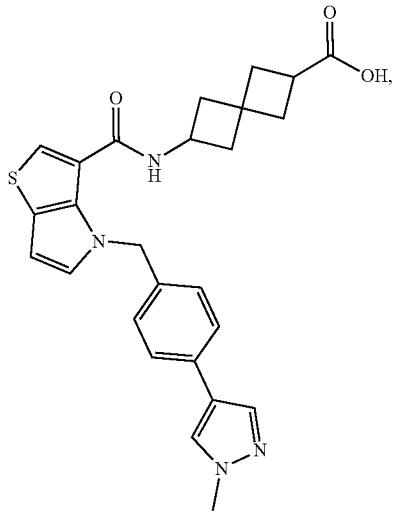
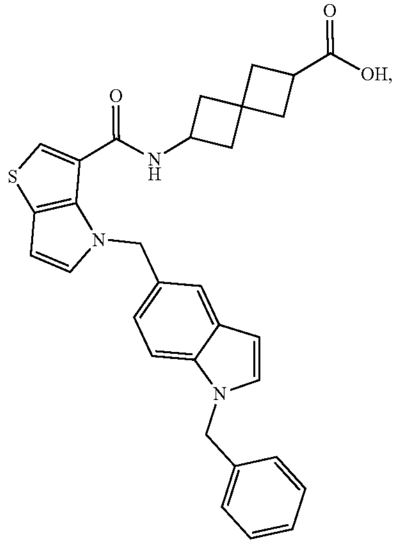
-continued
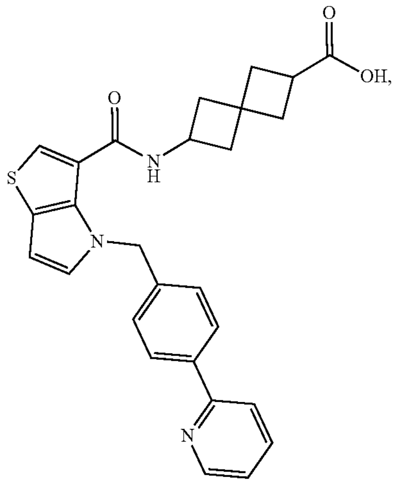
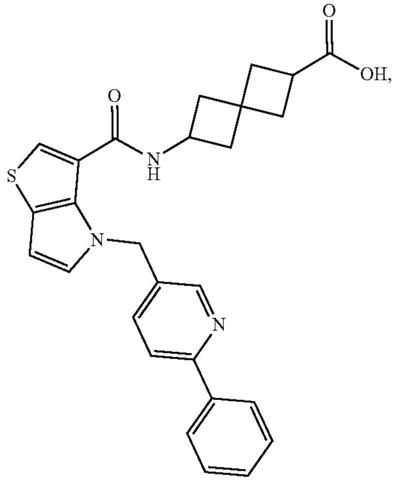
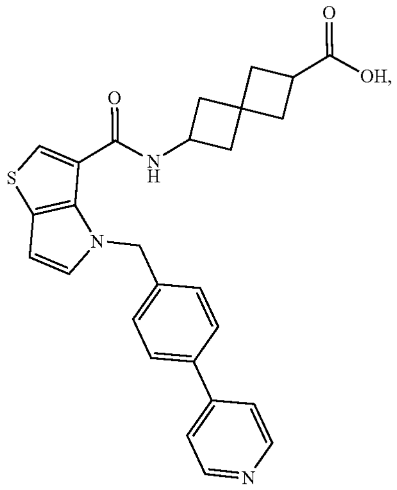

-continued
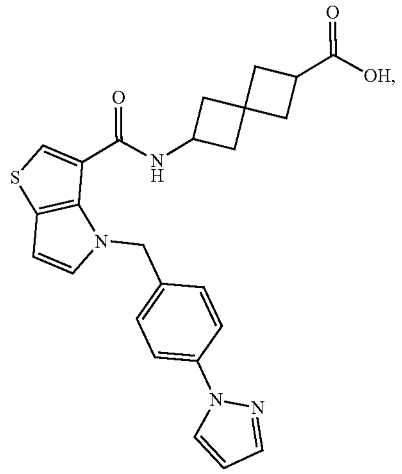
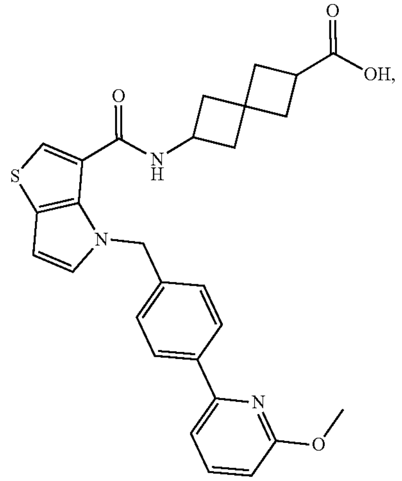
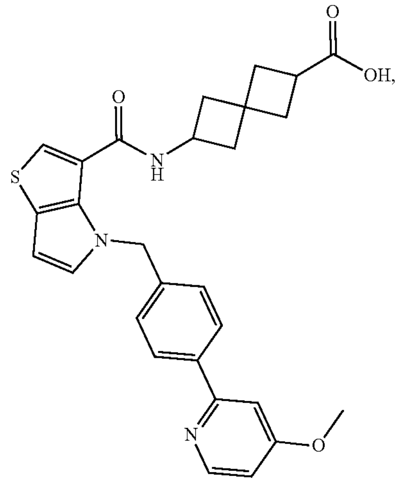
-continued
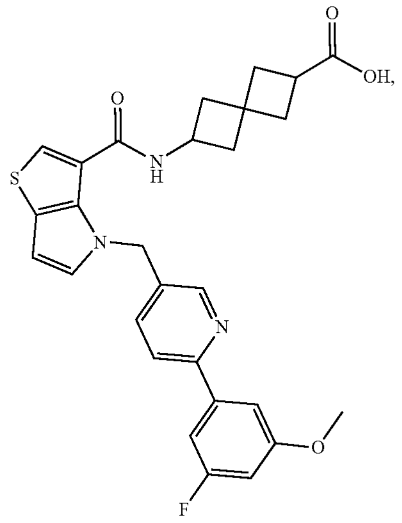
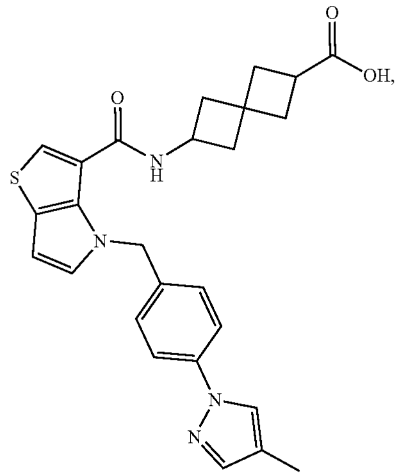
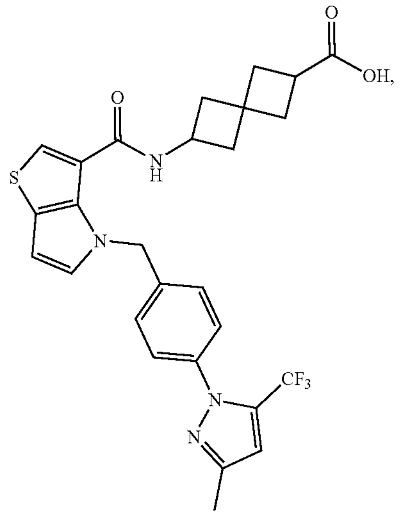
and -continued
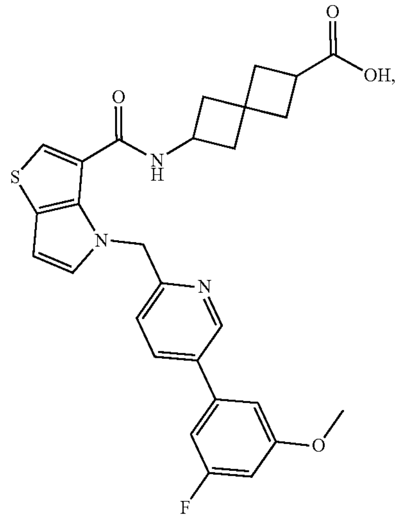
In one embodiment, the compound of formula I of the present invention may be a compound selected from the group consisting of the following compounds:
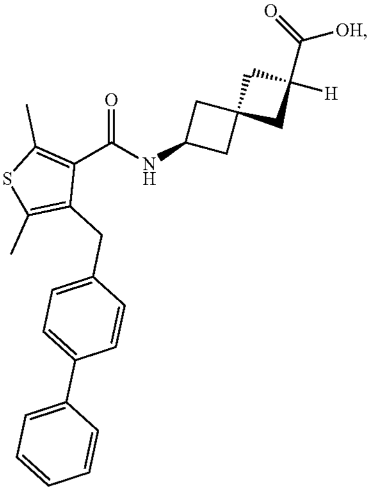
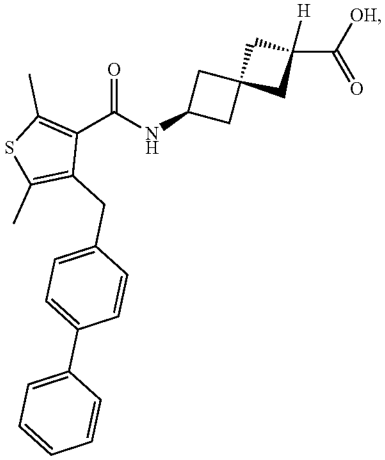
-continued
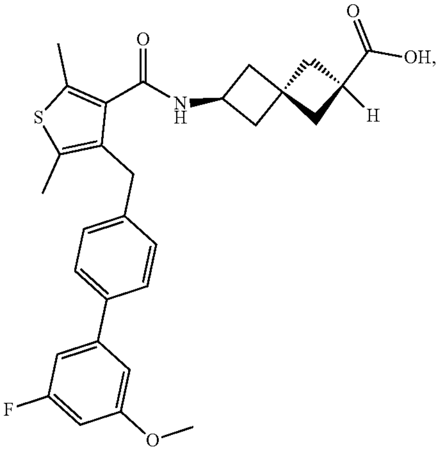
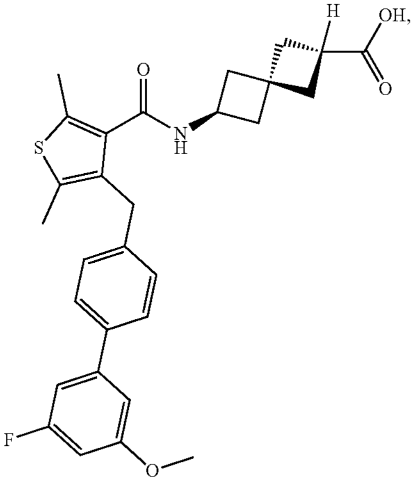
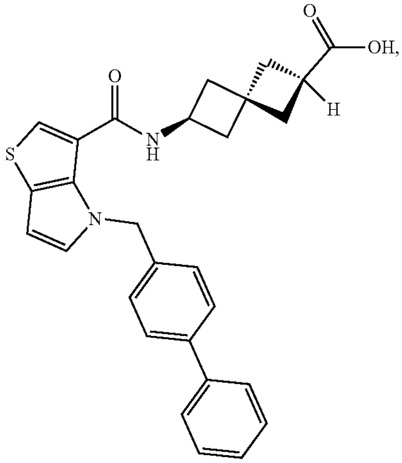

-continued

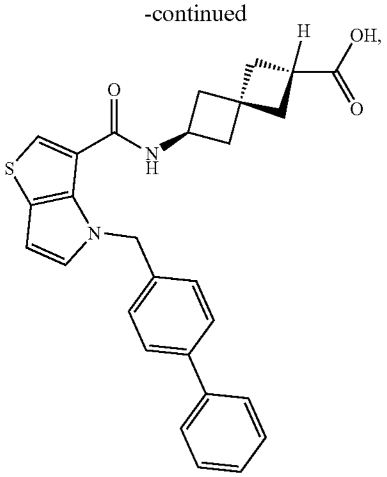

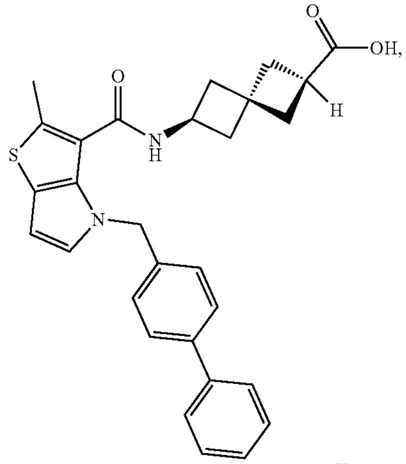

and

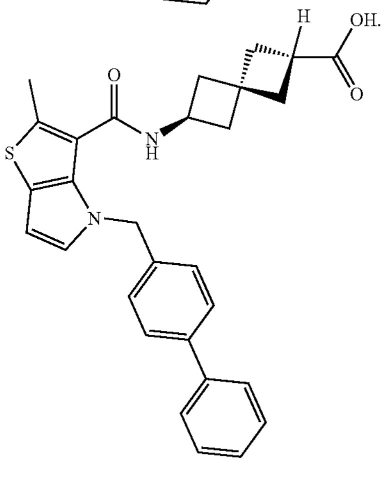

Definition

All technical and scientific terms used herein have the meanings commonly understood by one of ordinary skill in the art, and unless otherwise stated, conventional methods of measurement, methods of manufacture, conventional ingredients or substances are used based on conventional techniques such as pharmacology, pharmaceutical manufacturing chemistry, mass spectrometry, NMR, HPLC, biochemistry, and the like.

Unless otherwise indicated, in the present disclosure and the appended claims, "or" and "and" mean "and/or". The term "include" and "included" are open-ended, and mean that a compound, composition, or method may include additional features or ingredients in addition to the listed features or ingredients.

The "*" indicated at the end of the linking group of a residue herein indicates the position at which it binds to the remainder of the compound.

In the present disclosure, the term "halogen" may be F, Cl, Br, or I.

In the present disclosure, unless otherwise stated, the term "alkyl" refers to a straight chain or branched chain hydrocarbon residue, which may be unsubstituted or substituted. The alkyl may be $C_1$-$C_{15}$ alkyl, $C_1$-$C_{12}$ alkyl, $C_1$-$C_9$ alkyl, $C_1$-$C_6$ alkyl, or $C_1$-$C_3$ alkyl. Examples of alkyl may include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl and n-octyl and all possible isomers thereof.

In the present disclosure, unless otherwise stated, the term "alkoxy" refers to a straight chain or branched chain hydrocarbon residue, which may be unsubstituted or substituted, linked by oxygen. The alkoxy may include, without limitation, methoxy, ethoxy, propoxy, and butoxy, or all possible isomers thereof, for example, such as isopropoxy, isobutoxy, and t-butoxy.

In the present disclosure, the term "cycloalkyl" refers to a saturated hydrocarbon ring having the specified number of carbon atoms as ring elements (that is, $C_3$-$C_8$ cycloalkyl refers to a cycloalkyl group having 3, 4, 5, 6, 7 or 8 carbon atoms as ring elements). The cycloalkyl may be $C_3$-$C_{15}$ cycloalkyl, $C_3$-$C_{13}$ cycloalkyl, $C_3$-$C_{11}$ cycloalkyl, $C_3$-$C_8$ cycloalkyl, $C_3$-$C_6$ cycloalkyl, or $C_3$-$C_8$ cycloalkyl, and a cycloalkyl having a polycyclic hydrocarbon ring may have two or more cycloalkyls bridged or fused.

In the present disclosure, the term "cycloalkenyl" refers to a non-aromatic unsaturated monocyclic or polycyclic hydrocarbon ring having at least one carbon-carbon double bond and containing the specified number of carbon atoms. For example, cycloalkenyl includes cyclopent-1-en-1-yl, cyclohex-1-en-1-yl, cyclohex-1,3-dien-1-yl, and the like, but is not limited thereto.

In the present disclosure, the term "hydroxyl" refers to an —OH group.

In the present disclosure, the term "oxo" refers to a substituent having the structure =O, in which there is a double bond between the atom and oxygen atom.

In the present disclosure, the term "haloalkyl" refers to an alkyl group in which at least one hydrogen atom is replaced with a halogen atom. In some embodiments, 1, 2 or 3 hydrogen atoms of the hydrogen atoms of the alkyl may be replaced with a halogen atom. In one embodiment, a hydrogen atom may be replaced with the same halogen atom (for example, fluoro), or may be replaced with a combination of different halogen atoms (for example, fluoro and chloro).

In the present disclosure, the term "haloalkoxy" refers to an alkoxy group in which at least one hydrogen atom is replaced with a halogen atom, and the description of "haloalkyl" above is also applied to "haloalkoxy."

In the present disclosure, the term "aryl" refers to a monocyclic or polycyclic aromatic hydrocarbon group. The aryl has an alternating (resonance) double bond between adjacent carbon atoms, and may also include a form in which two or more rings are simply attached to each other (pendant) or condensed. The aryl may be, for example, $C_6$-$C_{14}$ aryl, $C_6$-$C_{10}$ aryl, or $C_6$-$C_9$ aryl, and may include, without limitation, for example, phenyl, biphenyl, naphthyl, toluyl, naphthalenyl, anthracenyl, or all possible isomers thereof.

In the present disclosure, the term "heteroaryl" refers to a heterocyclic aromatic group containing at least one heteroatom selected from B, N, O, S, P(=O), Si and P as a ring-forming atom. The heteroaryl may also include a form in which two or more rings are simply attached to each other (pendant) or condensed.

In some embodiments, heteroaryl may contain 1 to 4 heteroatoms, 1 to 3 heteroatoms, 1 or 2 heteroatoms, or 1 heteroatom selected from N, O and S. In one embodiment, heteroaryl may contain 1 to 3 N, 1 or 2 N, or 1 N. In some embodiments, heteroaryl may contain 4 to 14, 5 to 10, or 5 to 6 ring atoms.

Examples of monocyclic heteroaryl may include thiophenyl, furanyl, pyrrolyl, pyrazolyl, thiazolyl, isothiazolyl, oxazolyl, isoxazolyl, imidazolyl, triazolyl, oxadiazolyl, thiadiazolyl, tetrazolyl, pyridinyl, pyridazinyl, pyrimidinyl, pyrazinyl, triazinyl and similar groups thereto, but are not limited thereto. Examples of bicyclic heteroaryl may include indolyl, isoindolyl, indazolyl, indolizinyl, benzothiophenyl, benzofuranyl, benzimidazolyl, benzopyrazolyl, benzoxazolyl, benzisoxazolyl, benzthiazolyl, benzisothiazolyl, benzthiadiazolyl, benztriazolyl, quinolinyl, isoquinolinyl, quinoxalinyl, quinazolinyl, purinyl, phthalazinyl, pteridinyl, furopyridinyl, oxochromene, dioxoisoindoline, imidazopyridinyl, pyrrolopyridinyl, pyrrolopyrimidinyl, pyrazolopyridinyl and similar groups thereto, but are not limited thereto.

In the present disclosure, unless otherwise stated, the term "heterocycloalkyl" refers to a monocyclic or polycyclic, saturated or partially unsaturated ring system containing at least one heteroatom selected from B, N, O, S, P(=O), Si and P and having the specified number of ring elements (that is, 3- to 7-membered heterocycloalkyl refers to a heterocycloalkyl group having 3, 4, 5, 6 or 7 ring elements, including heteroatoms). The polycyclic heterocycloalkyl may have two or more heterocycloalkyls bridged or fused.

In some embodiments, heterocycloalkyl may contain 1 to 4 heteroatoms, 1 to 3 heteroatoms, 1 or 2 heteroatoms, or 1 heteroatom selected from N, O and S. In one embodiment, heterocycloalkyl may contain 1 to 3 N, 1 or 2 N, or 1 N. In some embodiments, heterocycloalkyl may contain 3 to 7, 3 to 6, 4 to 6, 4 to 10, or 4 to 14 ring atoms.

For example, the heterocycloalkyl group includes aziridinyl, oxiranyl, azetidinyl, oxetanyl, thietanyl, pyrrolidinyl, pyrrolinyl, dihydrofuranyl, tetrahydrofuranyl, dihydrothiophenyl, tetrahydrothiophenyl, sulfolanyl, dioxolanyl, imidazolinyl, imidazolidinyl, pyrazolinyl, pyrazolidinyl, thiazolinyl, thiazolidinyl, isothiazolinyl, isothiazolidinyl, oxazolinyl, oxazolidinyl, isoxazolinyl, isoxazolidinyl, triazolinyl, triazolidinyl, tetrazolinyl, tetrazolidinyl, pyranyl, dihydropyranyl, tetrahydropyranyl, thiopyranyl, tetrahydrothiopyranyl, dihydrothiopyranyl, dioxanyl, tetrahydrotriazinyl, hexahydrotriazinyl, morpholinyl, thiomorpholinyl, piperidinyl, dihydropyridinyl, tetrahydropyridinyl, piperazinyl, tetrahydropyrimidinyl, dihydropyrimidinyl, dihydropyridazinyl, tetrahydropyridazinyl, tetrahydrooxazinyl, hexahydroazepinyl, perhydroazepinyl, perhydrooxepinyl, indolinyl, isoindolinyl, dihydrobenzimidazolyl, dihydrobenzofuranyl, dihydrobenzoxazolyl, dihydrobenzothiazolyl, chromanyl, isochromanyl, azabicyclo[2.2.1]heptanyl, 3-azabicyclo[3.2.1]heptanyl, 7-azabicyclo[4.1.0]-heptanyl, 2,5-diazabicyclo[2.2.1]heptanyl, 2-oxa-5-azabicyclo[2.2.1]heptanyl, tropanyl, 2-oxa-6-azaspiro[3.3]heptanyl, and N-oxide, sulfone or sulfoxide thereof, but is not limited thereto.

In some embodiments, heterocycloalkyl includes aziridinyl, oxiranyl, azetidinyl, oxetanyl, pyrrolidinyl, tetrahydrofuranyl, pyrazolidinyl, imidazolidinyl, thiazolidinyl, oxazolidinyl, isoxazolidinyl, piperidinyl, piperazinyl, thiomorpholinyl or morpholinyl.

In the present disclosure, the term "substituted" group refers to one in which one or more hydrogen atoms are replaced with one or more non-hydrogen atom groups, provided that valence requirements should be met and a chemically stable compound should occur from the substitution. In the present disclosure, unless explicitly stated as "unsubstituted," all substituents should be construed as being capable of being unsubstituted or substituted. The "optionally substituted" moiety mentioned herein without limitation of a particular substituent encompasses a moiety unsubstituted or substituted with any substituent, and for example, includes a moiety substituted with halogen, hydroxy, cyano, amino, $C_1$-$C_6$ alkyl, $C_1$-$C_6$ alkoxy, —NH—($C_1$-$C_6$ alkyl), —N($C_1$-$C_6$ alkyl)$_2$, $C_3$-$C_8$cycloalkyl, $C_6$-$C_{14}$ aryl, 4- to 14-membered heteroaryl, or 4- to 14-membered heterocycloalkyl. In one embodiment, the "optionally substituted" moiety includes a moiety substituted with halogen, hydroxy, cyano, amino, $C_1$-$C_6$ alkyl, $C_1$-$C_6$ alkoxy, —NH—($C_1$-$C_6$ alkyl), or —N($C_1$-$C_6$ alkyl)$_2$.

In the present disclosure, when a combination of substituents is mentioned such as one group, for example, arylalkyl, cycloalkylalkyl, or the like, the last-mentioned group contains the atom attached to the end of the molecule.

In the present disclosure, the numerical range indicated using the term "to" refers to a range including the numerical values described before and after the term "to" as the lower limit and the upper limit, respectively.

In the present disclosure, the term "solvate" may refer to a compound of the present invention or a salt thereof comprising a stoichiometric or non-stoichiometric amount of a solvent bound by non-covalent intermolecular forces. Preferred solvents therefor may be any solvent that is volatile, non-toxic, and/or suitable for administration to humans.

In the present disclosure, the term "stereoisomer" may refer to a compound of the present invention or a salt thereof that has the same chemical formula or molecular formula but is optically or sterically different, and may be specifically a diastereomer, an enantiomer or a geometric isomer.

In some embodiments, the compound of the present invention may be in the form of a racemate, a single enantiomer, a mixture of enantiomers, a single diastereomer, a mixture of diastereomers, and the like, containing one or more asymmetric centers. In one embodiment, due to the limited rotation or nature of the asymmetric center, the compound of the present invention may be in the form of an enantiomer or a diastereomer.

When two or more asymmetric centers are present in the compound of the present invention, several diastereomers and enantiomers of the chemical structures disclosed herein may exist, and pure isomers, separated isomers, partially pure isomers, racemic mixtures or the like are all intended to fall within the scope of the present invention.

Purification of the isomers and separation of a mixture of the isomers may be achieved by standard techniques known in the art. For example, a diastereomeric mixture may be separated into its respective diastereomers by a chromatographic process or crystallization, and a racemate may be separated into its respective enantiomers by resolution or a chromatographic process on a chiral phase.

In addition, when the compound of the present invention contains a group capable of tautomerism, all tautomeric forms are included within the scope of the present invention. For example, 2-hydroxy pyridine may include 2-pyridone, and all such isomeric forms are included in the present invention.

As used herein, "pharmaceutically acceptable salt" may include acid or base salts of the parent compound, and may include mineral acid or organic acid salts of basic residues such as amines, alkali or organic salts of acid residues such as carboxylic acids, and the like, but is not limited thereto.

For example, a pharmaceutically acceptable salt of the compound of the present invention may be formed from pharmaceutically acceptable non-toxic bases, including inorganic bases and organic bases. In one embodiment, the pharmaceutically acceptable salt of the present invention includes an inorganic base addition salt, such as, lithium salt, sodium salt, potassium salt, magnesium salt, calcium salt, aluminum salt, ammonium salt, copper salt, ferric salt, ferrous salt, manganese salt, zinc salt, and the like. In one embodiment, the pharmaceutically acceptable salt of the present invention may include an organic base addition salt, such as, a salt derived from arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resin, procaine, purine, theobromine, triethylamine, trimethylamine, tripropylamine, dicyclohexylamine, tris (hydroxymethyl)methylamine, and the like.

In addition, the compound of the present invention may be used in the form of a pharmaceutically acceptable salt derived from an inorganic acid or organic acid, and for example, the salt may be a salt derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, toluenesulfonic acid, or the like.

A pharmaceutically acceptable salt of the compound may be prepared by, for example, dissolving the compound of formula I in a water-miscible organic solvent, such as acetone, methanol, ethanol, acetonitrile, or the like, and adding an excess of an organic acid or adding an aqueous acid solution of an inorganic acid, and then precipitating or crystallizing. Subsequently, after evaporating the solvent or an excess of acid from this mixture, it may be prepared by drying to obtain an addition salt or by suction filtration of the precipitated salt.

On the other hand, the acid addition salt form of the present invention may be easily converted to the free base form by treatment with an appropriate base, and the base addition salt form may be easily converted to the free acid form by treatment with a suitable acid.

General Preparation Method of Compound

On the other hand, the compound can be prepared through chemical modifications well known to one of ordinary skill in the art of organic/pharmaceutical chemistry according to the method representatively shown below.

The following general reaction scheme is a general illustration of a representative preparation method of the compound of formula I. One of ordinary skill in the art will be able to easily prepare the compound of formula I by appropriately selecting a starting material, a reaction temperature, a reaction condition, a catalyst, a solvent, a treatment method, and the like suitable for the desired compound, based on the preparation method specifically disclosed in the Examples herein.

For example, a compound of formula I having a thiophene ring can be prepared according to Reaction Schemes 1 to 5 below:

[Reaction Scheme 1]

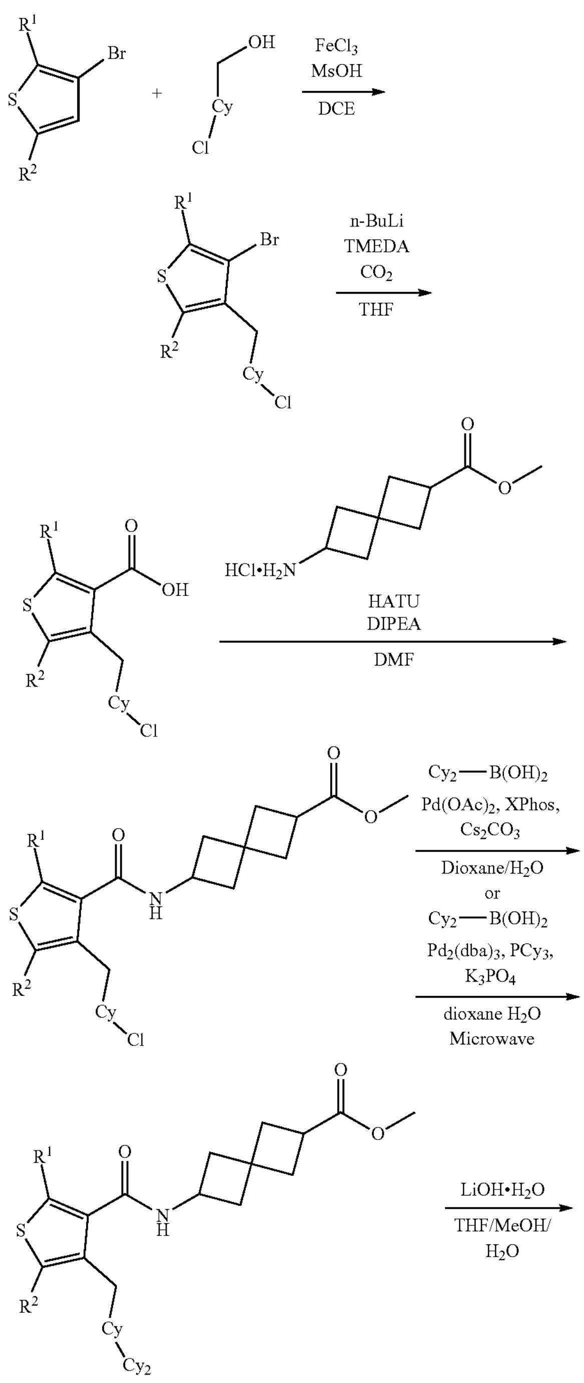

-continued
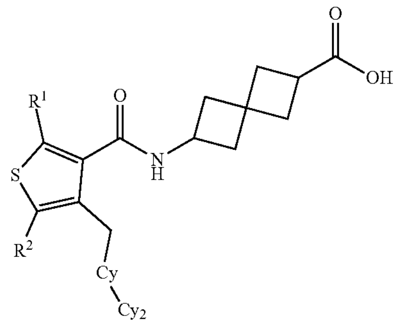
[Reaction Scheme 2]
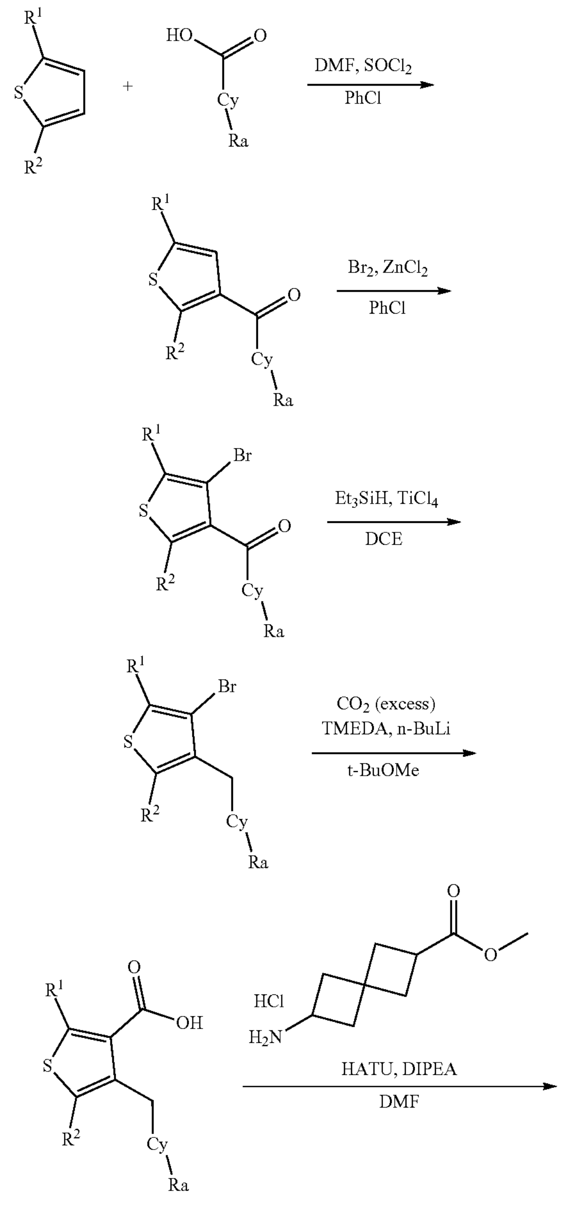
-continued
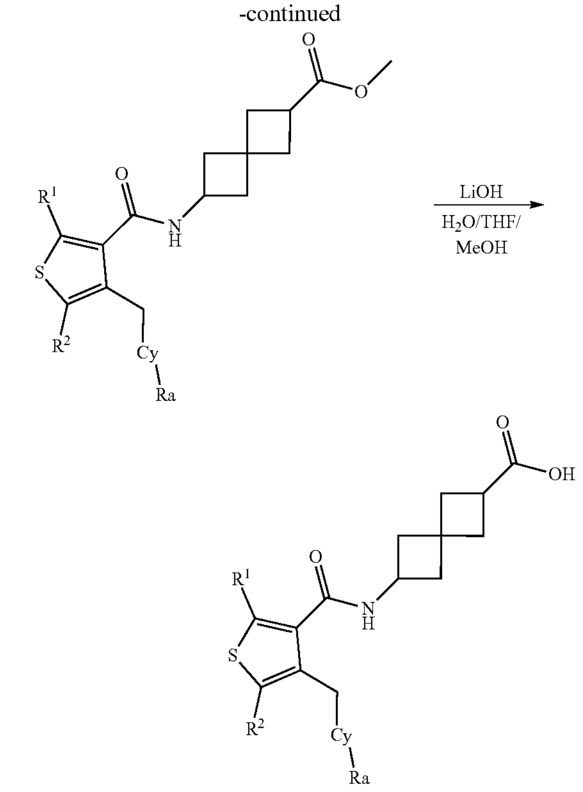
[Reaction Scheme 3]
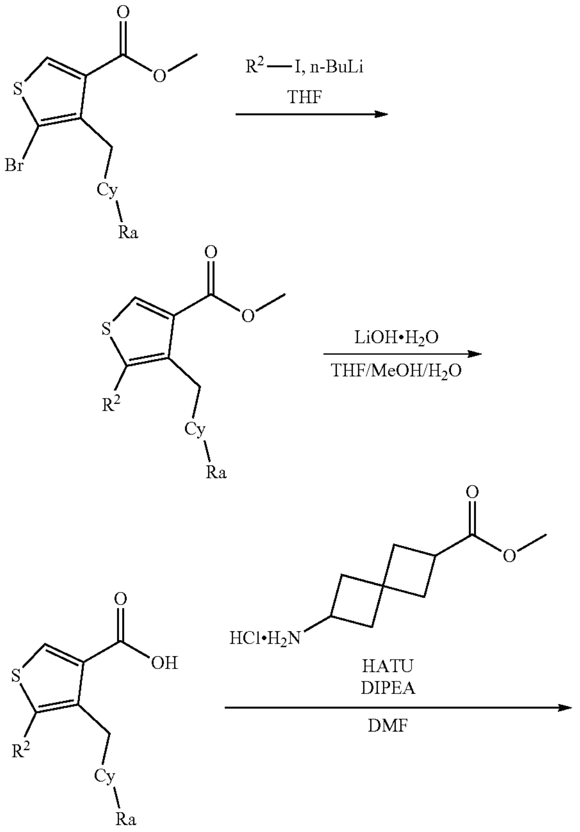

-continued
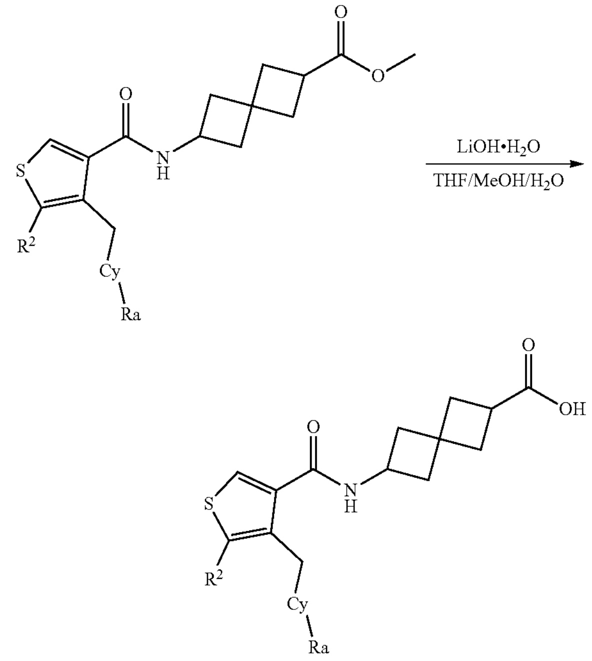
[Reaction Scheme 4]
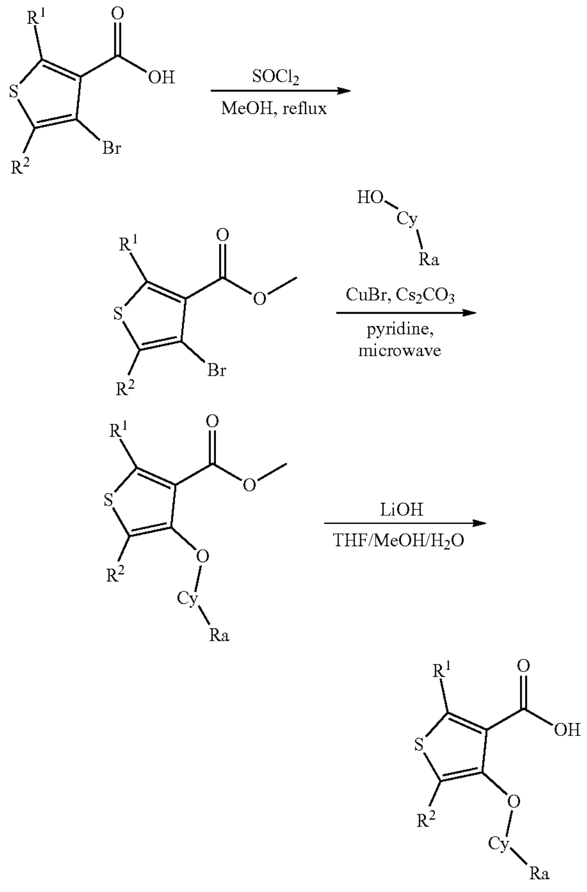
-continued
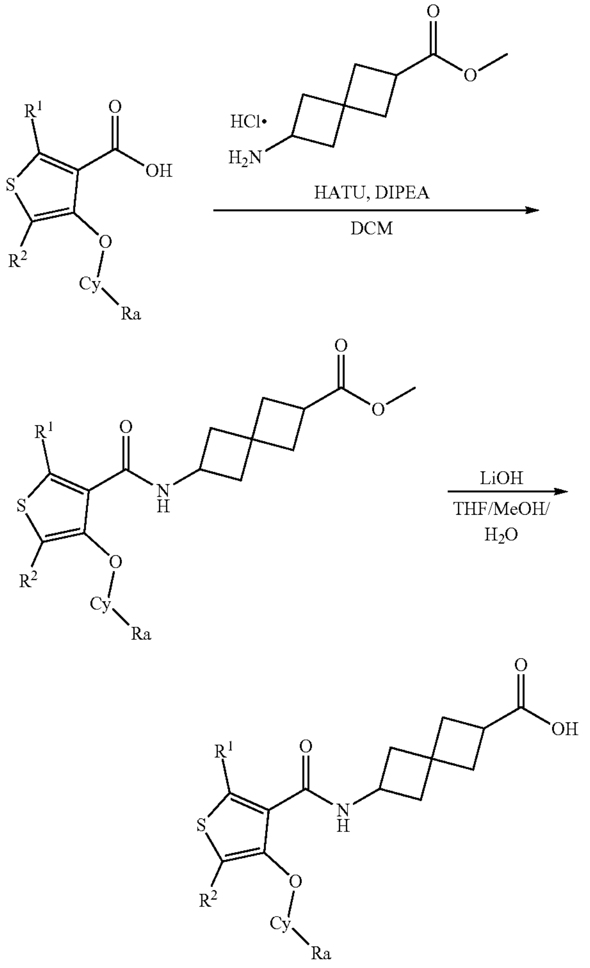
[Reaction Scheme 5]
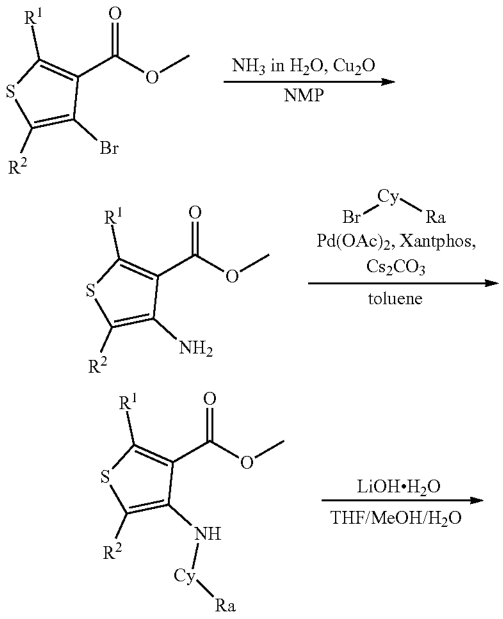

-continued
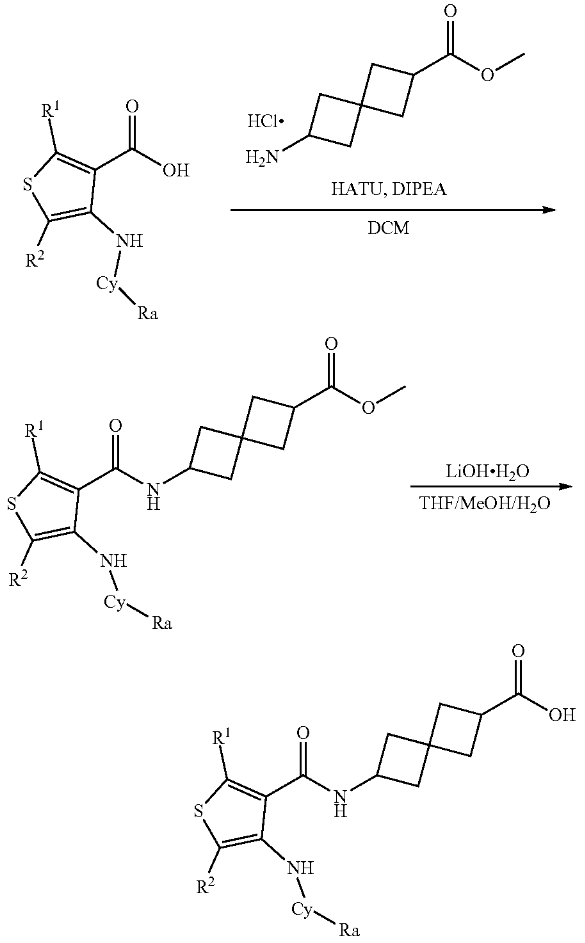
For example, a compound of formula I having a 4H-thieno[3,2-b]pyrrole fused ring can be prepared according to Reaction Scheme 6 below:
[Reaction Scheme 6]
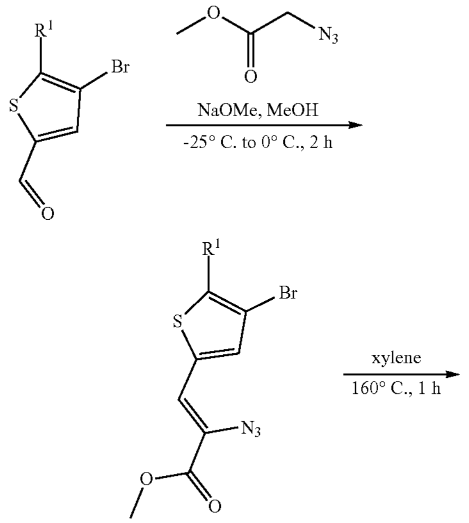
-continued
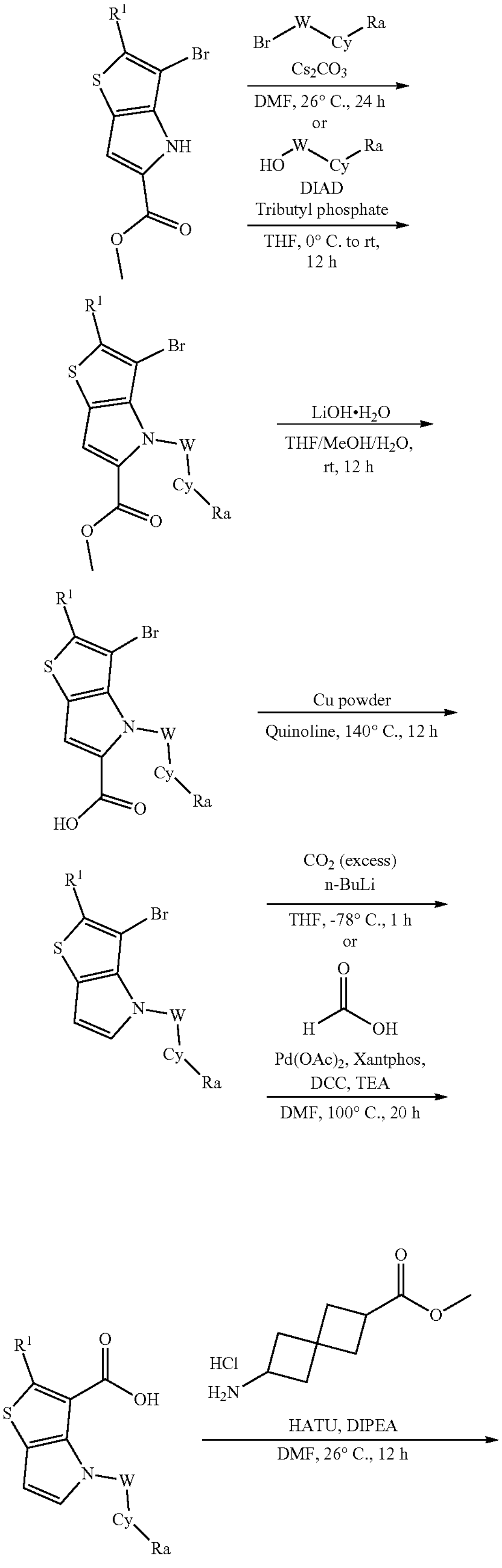

-continued

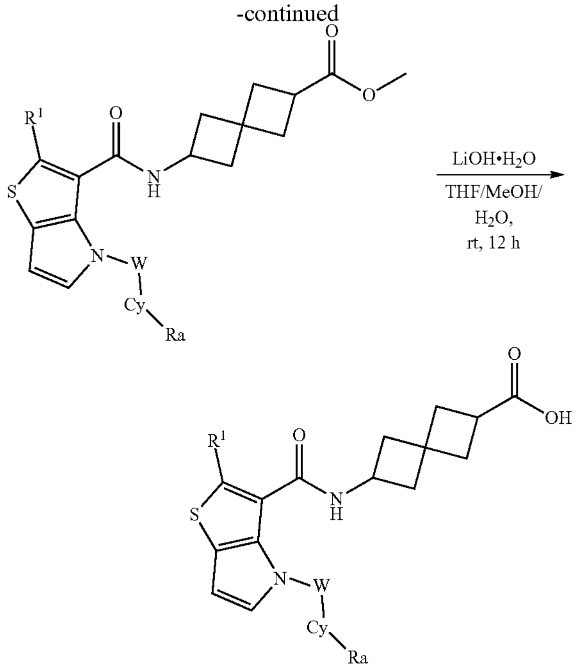

In the preparation of the compounds according to Reaction Schemes 1 to 6 above, compounds in which various ring structures are bonded to an amide bond can be prepared using an appropriate amino-cycloalkyl-carboxylate compound, such as methyl 3-aminocyclobutane-1-carboxylate, methyl 3-aminobicyclo[1.1.1]pentane-1-carboxylate, methyl 4-aminobicyclo[1.1.1]octane-1-carboxylate, and the like instead of methyl 3-aminobicyclo[1.1.1]pentane-1-carboxylate hydrochloride.

Medicinal Use, Pharmaceutical Composition, Administration Method

In another aspect, there is provided a pharmaceutical composition for the prevention or treatment of a disease associated with prostaglandin $E_2$ overexpression and/or prostaglandin $E_2$ receptor overexpression, comprising a compound represented by formula I, IA-1, IA-2, IA-3, IA-4, IB-1, IB-2, IB-3, IB-4, IB-5, IB-6, IB-7 or IB-8 above, a solvate, stereoisomer or pharmaceutically acceptable salt thereof as an active ingredient.

In the present disclosure, the term "preventing" or "prevention" refers to preventing a disease, for example, preventing a disease, condition or disorder in a subject who may be predisposed to the disease, condition or disorder but has not yet experienced or exhibited the pathology or signs of the disease.

In the present disclosure, the term "treating" or "treatment" refers to inhibiting a disease, for example, inhibiting a disease, condition or disorder in a subject who experiences or exhibits the pathology or signs of the disease, condition or disorder, i.e., preventing further development of the pathology and/or signs, or ameliorating the disease, for example, ameliorating the disease, condition or disorder in a subject who experiences or exhibits the pathology or signs of the disease, condition or disorder, i.e., reversing the pathology and/or signs, for example, reducing the severity of the disease.

The "disease associated with prostaglandin $E_2$ overexpression and/or prostaglandin $E_2$ receptor overexpression," which is a disease to be prevented or treated by the pharmaceutical composition, is a disease closely associated with the activity of prostaglandin $E_2$, and may refer to a disease in which an effective therapeutic effect can be achieved through an antagonistic action on prostaglandin $E_2$ or the prostaglandin $E_2$ receptor. The disease associated with prostaglandin $E_2$ overexpression and/or prostaglandin $E_2$ receptor overexpression may be a disease caused by overexpression or overactivation of prostaglandin $E_2$ and/or prostaglandin $E_2$ receptor. The disease associated with prostaglandin $E_2$ overexpression and/or prostaglandin $E_2$ receptor overexpression may be, for example, cancer, a neurodegenerative disease, or an inflammatory disease, or the like. The cancer may be, for example, squamous cell cancer, basal cell cancer, glioblastoma, bone cancer, stomach cancer, kidney cancer, lung cancer, bladder cancer, prostate cancer, breast cancer, prostate cancer, ovarian cancer, endometrial cancer, cervical cancer, bladder cancer, head and neck cancer, renal cell carcinoma, esophageal cancer, pancreatic cancer, brain cancer, gastrointestinal cancer, liver cancer, leukemia, lymphoma, melanoma, multiple myeloma, osteosarcoma, colorectal cancer, cholangiocarcinoma, choriocarcinoma, oral cancer, neuroblastoma, skin cancer, testis cancer, stromal tumor, germ cell tumor, or thyroid cancer, but is not limited thereto. The neurodegenerative disease may be epilepsy, Alzheimer's disease, Parkinson's disease, amyotrophic lateral sclerosis or traumatic brain injury, but is not limited thereto. The inflammatory disease may be edema, allergy, asthma, conjunctivitis, periodontitis, rhinitis, otitis media, pharyngolaryngitis, tonsillitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatoid arthritis, periarthritis of shoulder, tendinitis, tenosynovitis, myositis, hepatitis, cystitis, nephritis, Sjogren's syndrome or multiple sclerosis, but is not limited thereto.

When used in the treatment of cancer, the compound of the present invention may be used alone or in combination with other anticancer therapies, for example, radiation therapy, anti-CTLA4 antibodies (for example, ipilimumab), anti-PD-L1 antibodies (for example, atezolizumab, avelumab), anti-PD-1 antibodies (for example, nivolumab, pembrolizumab) or cytotoxic agents (for example, alkylating agents such as cisplatin, dacarbazine, and chlorambucil; antimetabolites such as methotrexate, fludarabine, and gemcitabine; antimicrotubule agents such as vinblastine and paclitaxel; topoisomerase inhibitors such as topotecan and doxorubicin), and the like.

According to one embodiment, the compound represented by represented by formula I, IA-1, IA-2, IA-3, IA-4, IB-1, IB-2, IB-3, IB-4, IB-5, IB-6, IB-7 or IB-8 exhibits effective inhibitory activity on prostaglandin $E_2$ receptor, for example, $EP_2$ and/or $EP_4$, and may exert a therapeutic effect by regulating the activity of prostaglandin $E_2$ through antagonistic action against prostaglandin $E_2$ receptor as described above. Therefore, the compound represented by formula I, IA-1, IA-2, IA-3, IA-4, IB-1, IB-2, IB-3, IB-4, IB-5, IB-6, IB-7 or IB-8, solvate, stereoisomer or pharmaceutically acceptable salt thereof may be used to treat a disease associated with prostaglandin $E_2$ overexpression and/or prostaglandin $E_2$ receptor overexpression.

In one embodiment, the pharmaceutical composition may comprise conventional pharmaceutically acceptable carriers, excipients or additives. The pharmaceutical composition may be formulated according to a conventional method, and may be prepared as various oral dosage forms such as tablets, pills, powders, capsules, syrups, emulsions, microemulsions, or parenteral dosage forms such as intramuscular, intravenous or subcutaneous dosage form.

When the pharmaceutical composition is prepared in the form of an oral formulation, examples of additives or carriers used may include cellulose, calcium silicate, corn starch, lactose, sucrose, dextrose, calcium phosphate, stearic acid, magnesium stearate, calcium stearate, gelatin, talc, surfactant, suspending agent, emulsifying agent, diluent, and the like. When the pharmaceutical composition of the present invention is prepared in the form of an injection, the additive or carrier may include water, saline, aqueous glucose solution, similar aqueous sugar solution, alcohol, glycol, ether (for example, polyethylene glycol 400), oil, fatty acid, fatty acid ester, glyceride, surfactant, suspending agent, emulsifying agent, and the like.

The dosage of the pharmaceutical composition is an amount effective for treatment or prevention of a subject or patient, and may be administered orally or parenterally as desired. It may be administered in one to several divided doses to be administered in an amount of 0.01 to 1000 mg, more specifically 0.1 to 300 mg per kg of body weight daily based on the active ingredient when administered orally, or in an amount of 0.01 to 100 mg, more specifically 0.1 to 50 mg per kg of body weight daily based on the active ingredient when administered parenterally. The dose to be administered to a specific subject or patient should be determined in light of several related factors such as body weight, age, sex, health condition of the patient, diet, administration time, administration method, the severity of the disease, and the like, and it should be understood that it may be appropriately increased or decreased by a specialist. The above dosage is not intended to limit the scope of the present invention in any way. A physician or veterinarian of ordinary skill in the art may readily determine and prescribe the required effective amount of the pharmaceutical composition. For example, by a physician or veterinarian, a dose of the compound of the present invention used in a pharmaceutical composition may start at a level lower than that required to achieve the desired therapeutic effect, and may gradually increase until the desired effect is achieved.

In one embodiment, the pharmaceutical composition includes within its scope a pharmaceutical composition comprising, as an active ingredient, a therapeutically effective amount of at least one of the compounds according to one embodiment, alone or in combination with a pharmaceutical carrier. The term “therapeutically effective amount” or “effective amount” refers to an amount sufficient to produce a beneficial or desired clinical result, for example, an amount sufficient to alleviate, ameliorate, stabilize, reverse, slow or delay the progression of a disease.

Optionally, the compound according to one embodiment may be administered alone, in combination with the compound according to another embodiment, or simultaneously, separately, or sequentially in combination with one or more other therapeutic agents, for example, an anticancer agent or other pharmaceutically active substances. The anticancer agent includes, for example, an anticancer agent, an antiangiogenesis agent, an anti-inflammatory agent, an immunosuppressant, and the like, and may be, for example, an immune anticancer agent including a known immune checkpoint inhibitor such as CTLA-4, PD-1, PD-L1, and the like.

In another aspect, there is provided a method for preventing or treating a disease associated with prostaglandin $E_2$ overexpression and/or prostaglandin $E_2$ receptor overexpression, comprising administering to a subject the compound represented by formula I, IA-1, IA-2, IA-3, IA-4, IB-1, IB-2, IB-3, IB-4, IB-5, IB-6, IB-7 or IB-8, solvate, stereoisomer or pharmaceutically acceptable salt thereof, or the pharmaceutical composition comprising the same.

Among the terms or elements mentioned in the description of the method, the same as those already mentioned are as described above.

The administration may be oral or parenteral administration. It may be administered in one to several divided doses to be administered in an amount of 0.01 to 1000 mg, more specifically 0.1 to 300 mg per kg of body weight daily based on the active ingredient when administered orally, or in an amount of 0.01 to 100 mg, more specifically 0.1 to 50 mg per kg of body weight daily based on the active ingredient when administered parenterally. The dose to be administered to a specific subject or patient should be determined in light of several related factors such as body weight, age, sex, health condition of the patient, diet, administration time, administration method, the severity of the disease, and the like, and it may be appropriately increased or decreased by a specialist.

In the present disclosure, the term “subject” refers to a subject in need of treatment or prevention for a disease, and more specifically means a mammal such as a human or non-human primate, a mouse, a dog, a cat, a horse, and a cow.

In another aspect, there is provided a medicinal use of the compound represented by formula I, IA-1, IA-2, IA-3, IA-4, IB-1, IB-2, IB-3, IB-4, IB-5, IB-6, IB-7 or IB-8, solvate, stereoisomer or pharmaceutically acceptable salt thereof for the prevention or treatment of a disease associated with prostaglandin $E_2$ overexpression and/or prostaglandin $E_2$ receptor overexpression; or a use of the compound represented by formula I, IA-1, IA-2, IA-3, IA-4, IB-1, IB-2, IB-3, IB-4, IB-5, IB-6, IB-7 or IB-8, solvate, stereoisomer or pharmaceutically acceptable salt thereof for the manufacture of a therapeutic agent for a disease associated with prostaglandin $E_2$ overexpression and/or prostaglandin $E_2$ receptor overexpression. Among the terms or elements mentioned in the description of the method or use, the same as those already mentioned are as described above.

Advantageous Effects of Invention

The compound, solvate, stereoisomer or pharmaceutically acceptable salt thereof according to one aspect has effective inhibitory activity on prostaglandin $E_2$ receptor, for example, $EP_2$ and/or $EP_4$.

Therefore, the compound, solvate, stereoisomer or pharmaceutically acceptable salt thereof according to one aspect can be utilized as an active ingredient of a pharmaceutical composition for the prevention or treatment of a disease associated with prostaglandin $E_2$ overexpression and/or prostaglandin $E_2$ receptor overexpression, for example, cancer, a neurodegenerative disease, or an inflammatory disease.

MODE FOR THE INVENTION

Hereinafter, the present invention will be described in detail by way of the examples. However, the following examples are merely illustrative of the present invention, and the content of the present invention is not limited by the following examples.

PREPARATION EXAMPLE

Preparation Example 1: methyl 6-aminospiro[3.3]heptane-2-carboxylate hydrochloride

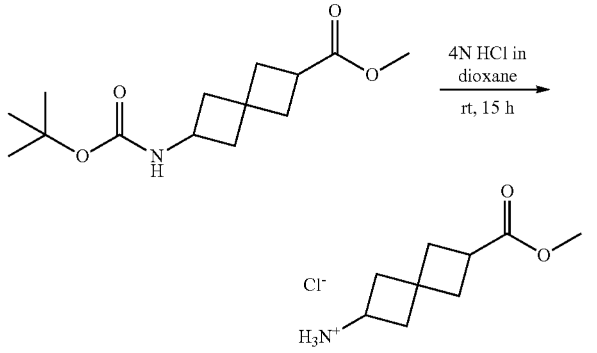

Intermediate A

Methyl 6-((t-butoxycarbonyl)amino)spiro[3.3]heptane-2-carboxylate (10 g, 37.1 mmol) was added to a solution of 4 N HCl in dioxane, stirred for 15 hours, and then concentrated under reduced pressure. The resulting crude product was washed with diethyl ether (100 mL) and dried to obtain Intermediate A (7.32 g, yield 96%) as a white solid. $^1H$ NMR (300 Hz, DMSO-$d_6$) δ 8.09 (bs, 2H), 3.58 (s, 3H), 3.03 (p, J=8.4 Hz, 1H), 2.43-2.31 (m, 1H), 2.28-1.95 (m, 6H).

Preparation Example 2: methyl 2-azido acetate

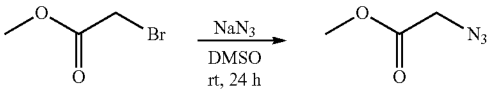

Intermediate B

To a solution of methyl 2-bromoacetate (7.65 g, 50.0 mmol) in DMSO (0.5 M), $NaN_3$ (4.88 g, 75.0 mmol) was added and stirred for 24 hours. The reaction mixture was diluted with EtOAc (100 mL) and washed with distilled water. The organic layer was dried over $Na_2SO_4$ and then concentrated under reduced pressure to obtain Intermediate B (4.09 g, yield 75%) as a colorless liquid. $^1H$ NMR (300 MHz, chloroform-d) δ 3.91 (s, 2H), 3.83 (s, 3H).

Preparation Example 3: 3-bromo-2,5-dimethylthiophene

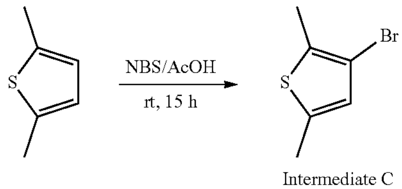

Intermediate C

To a solution of 2,5-dimethylthiophene (11.2 g, 100 mmol) in acetic acid (0.2 M), NBS (17.8 g, 100 mmol) was added and stirred for 15 hours. The reaction mixture was concentrated, diluted with diethyl ether, and then washed with distilled water and sodium bicarbonate solution and brine. The organic layer was dried over $Na_2SO_4$ and then concentrated under reduced pressure. The crude product was purified by column chromatography to obtain Intermediate C (8.80 g, yield 46%) as a colorless liquid. $^1H$ NMR (300 MHz, chloroform-d) δ 6.60-6.56 (m, 1H), 2.42 (s, 3H), 2.35 (s, 3H).

Preparation Example 4: methyl 4-bromo-2,5 dimethylthiophene-3-carboxylate

Step 1: Synthesis of 3,4-dibromo-2,5-dimethylthiophene

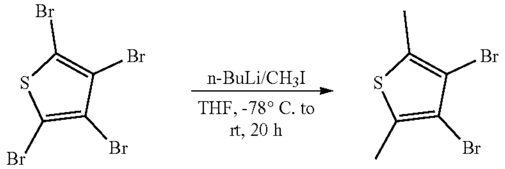

To a solution of tetrabromothiophene (8.0 g, 20.0 mmol, 1.0 equiv) in THF (60 mL, 0.3 M), n-BuLi (2.0 M in cyclohexane, 25.0 mL, 50.0 mmol, 2.5 equiv) was added at −78° C. and stirred at −78° C. for 1 hour. Iodomethane (3.8 mL, 60.0 mmol, 3.0 equiv) was added and then stirred for 20 hours at ambient temperature. The reaction mixture was added to saturated $NH_4Cl$ and extracted with EtOAc. The organic layer was dried over $MgSO_4$ and then concentrated under reduced pressure. The crude product was purified by column chromatography to obtain 3,4-dibromo-2,5-dimethylthiophene (4.9 g, yield 90%).

Step 2: Synthesis of 4-bromo-2,5-dimethylthiophene-3-carboxylic acid

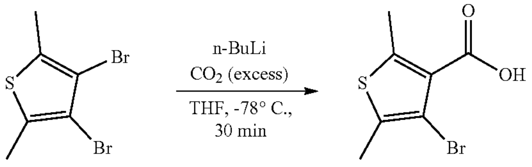

To a solution of 3,4-dibromo-2,5-dimethylthiophene (4.9 g, 18.1 mmol, 1.0 equiv) in THF (60 mL), n-BuLi (2.0 M in cyclohexane, 8.2 mL, 0.9 equiv) was added at −78° C. and stirred at −78° C. for 30 minutes. An excess of dry ice was added and then stirred for 30 minutes at ambient temperature. The reaction mixture was added to 1 N NaOH and extracted with $Et_2O$, and the aqueous layer was acidified with 1 N HCl solution. The resulting precipitate was removed by filtration, washed with distilled water, and then dried to obtain 4-bromo-2,5-dimethylthiophene-3-carboxylic acid (3.3 g, yield 77%).

Step 3: Synthesis of methyl 4-bromo-2.5 dimethylthiophene-3-carboxylate

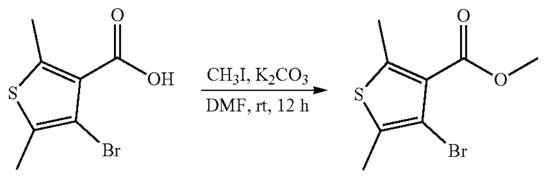

Intermediate D

To a solution of 4-bromo-2,5-dimethylthiophene-3-carboxylic acid (2.64 g, 11.2 mmol, 1.0 equiv) and $K_2CO_3$ (3.1 g, 22.4 mmol, 2.0 equiv) in DMF (15 mL), iodomethane (1.4 mL, 22.4 mmol, 2.0 equiv) was added and stirred for 12 hours. The reaction mixture was added to distilled water and extracted with DCM. The organic layer was dried over $MgSO_4$ and then concentrated under reduced pressure. The crude product was purified by column chromatography to obtain Intermediate D (2.55 g, yield 91%).

Preparation Example 5: 3-fluoro-[1,1'-biphenyl]-4-carboxylic acid

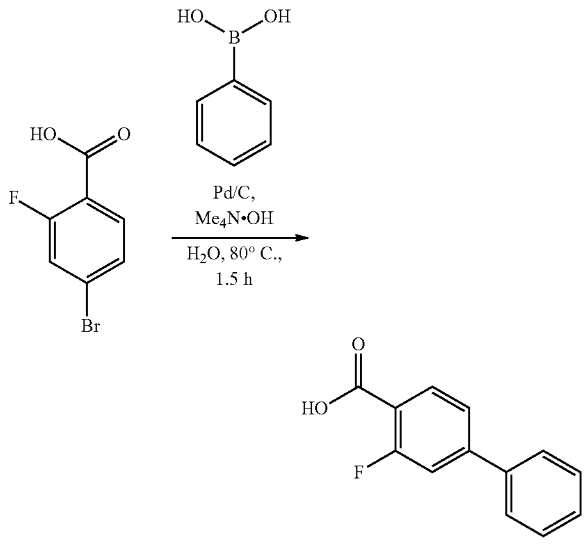

Intermediate E

To 1.0 g of phenylboronic acid (8.20 mmol, 1.0 equiv) and 1.80 g of 4-bromo-2-fluoro-benzoic acid (8.20 mmol, 1.0 equiv), 6.47 g of 26% $Me_4N{\cdot}OH$ aqueous solution (18.45 mmol, 2.25 equiv) was added and stirred at 50° C. 25 mL of distilled water and 25 mg of 5% Pd/C (0.025 w/w) were added under Ar substitution and stirred at 80° C. for 1.5 hours. The reaction mixture was cooled to ambient temperature, and Pd/C was removed by filtration through Celite. After neutralization and crystallization by adding 2.2 mL of 6 M HCl aqueous solution (13.12 mmol, 1.6 equiv) to the reaction mixture, 10 mL of distilled water was added and stirred for 30 minutes. The precipitated crystal was washed with distilled water and then dried under reduced pressure to obtain Intermediate E (1.5 g, yield 85%). $^1H$ NMR (500 MHz, Chloroform-d) S 8.14 (t, J=7.9 Hz, 1H), 7.65 (d, J=7.2 Hz, 2H), 7.54-7.49 (m, 3H), 7.48-7.41 (m, 2H). LC/MS (ESI) m/z: 217.2 $[M+H]^+$.

Preparation Example 6: 2-amino-[1,1'-biphenyl]-4-carbonyl chloride

Step 1: Synthesis of 2-amino-[1,1'-biphenyl]-4-carboxylic acid

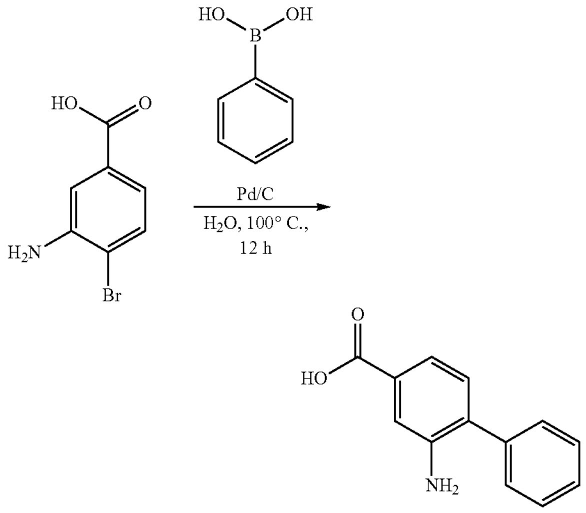

3-amino-4-bromobenzoic acid (5.0 g, 23.2 mmol), 5% Pd/C (255 mg, 0.45 mmol), $K_2CO_3$ (12.8 g, 92.6 mmol) and phenylboronic acid (3.2 g, 25.5 mmol) were added to a sealed tube. Distilled water (46 mL, 0.5 M) was added and stirred at 100° C. for 12 hours. The reaction mixture was cooled to ambient temperature, filtered through a Celite plug, and then washed with distilled water (2×20 mL). The solution was acidified slowly with 1 N citric acid solution, and the precipitate was filtered and then dried to obtain Intermediate F (3.5 g, yield 71%). $^1H$ NMR (300 MHz, DMSO-$d_6$) δ 12.69 (s, 1H), 7.47 (d, J=6.5 Hz, 4H), 7.41-7.34 (m, 2H), 7.21 (dd, J=7.9, 1.6 Hz, 1H), 7.08 (d, J=7.8 Hz, 1H), 5.04 (s, 2H).

Step 2: Synthesis of 2-amino-[1,1'-biphenyl]-4-carbonyl chloride

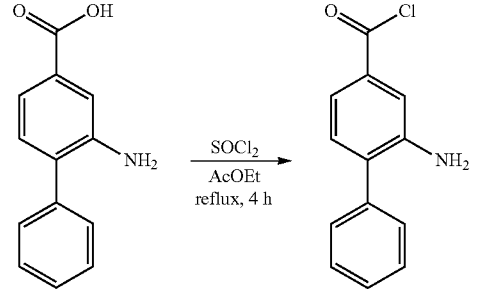

Intermediate F

To a solution of 2-amino-[1,1'-biphenyl]-4-carboxylic acid (2.5 g, 11.73 mmol) in ethyl acetate (39 mL, 0.3 M), thionyl chloride (3.5 mL, 48.1 mmol) was added while stirring. The reaction mixture was stirred under reflux for 4 hours, and then cooled to ambient temperature, and concentrated under reduced pressure to obtain Intermediate F (2.95 g).

Preparation Example 7: (2'-methoxy-[1,1'-biphenyl]-4-yl)methanol

Step 1: Synthesis of methyl 2'-methoxy-[1,1'-biphenyl]-4-carboxylate

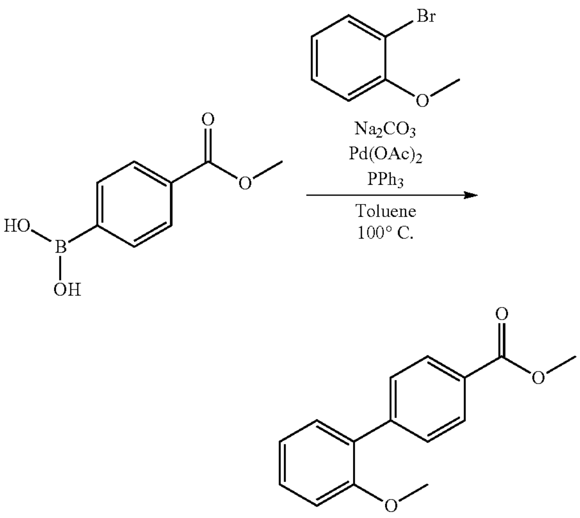

A solution of 4-(methoxycarbonylphenyl)boronic acid (1.08 g, 6 mmol), $Na_2CO_3$ (1.91 g, 18 mmol), $Pd(OAc)_2$ (0.269 g, 1.2 mmol), and $PPh_3$ (0.63 g, 2.4 mmol) in a stirred solution of 2-bromoanisole (0.75 mL, 6 mmol) in toluene (0.6 M) was stirred at 100° C. for 6 hours. The reaction mixture was extracted with ethyl acetate (20 mL×3), and the organic layer was washed with brine solution, and then dried over $Na_2SO_4$, and concentrated under reduced pressure. The crude product was purified by column chromatography (hexane:ethyl acetate=97:3 to 95:5) to obtain methyl 2'-methoxy-[1,1'-biphenyl]-4-carboxylate (507 mg, yield 35%). $^1H$ NMR (500 MHz, $CDCl_3$) δ 8.08 (d, J=8.4 Hz, 2H), 7.61 (d, J=8.4 Hz, 2H), 7.39-7.30 (m, 2H), 7.04 (s, 1H), 6.99 (d, J=8.2 Hz, 1H), 3.93 (d, J=1.9 Hz, 3H), 3.81 (s, 3H).

Step 2: Synthesis of (2'-methoxy-[1,1'-biphenyl]-4-ylmethanol

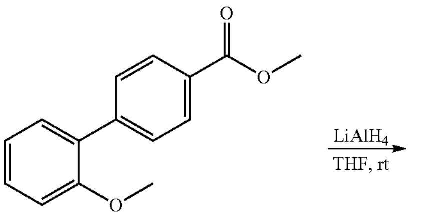

-continued

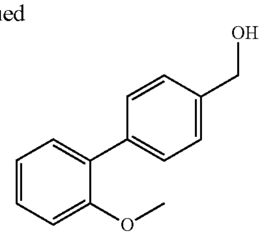

Methyl 2'-methoxy-[1,1'-biphenyl]-4-carboxylate (507 mg, 2.09 mmol) was dissolved in THF (0.2 M), and $LiAlH_4$ (397 mg, 10.5 mmol) was added and stirred for 3 hours. The reaction mixture was cooled to 0° C., and then distilled water (1.6 mL) and NaOH aqueous solution were added, dried over $Na_2SO_4$, and concentrated under reduced pressure. The crude product was purified by column chromatography (hexane:ethyl acetate=7:3) to obtain Intermediate G (340 mg). $^1H$ NMR (500 MHz, $CDCl_3$) δ 7.55 (d, J=8.1 Hz, 2H), 7.41 (d, J=7.9 Hz, 2H), 7.34 (d, J=7.5 Hz, 2H), 7.05 (s, 1H), 7.01 (d, J=8.0 Hz, 1H), 4.70 (s, 2H), 3.81 (s, 3H), 2.23 (s, 1H).

Preparation Example 8: 3-fluoro-5-(4,4,5,5-tetramethyl-1,3,2-dioxaborolan-2-yl)aniline

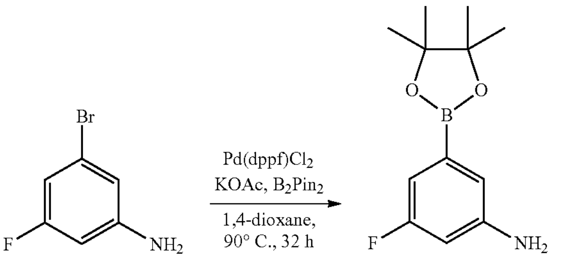

Intermediate H

To a solution of 3-fluoro-5-bromoaniline (380 mg, 2.0 mmol) in 1,4-dioxane (20.0 mL), bis(pinacolato)diboron (1.1 g, 4.4 mmol), KOAc (1.18 g, 12 mmol), and Pd(dppf)$Cl_2$ (146.0 mg, 0.2 mmol) were added under $N_2$ atmosphere and stirred at 90° C. for 32 hours. The reaction mixture was cooled to ambient temperature, filtered through Celite, and washed with EtOAc. The organic layer was concentrated under reduced pressure to obtain Intermediate H (1.4 g).

Preparation Example 9: 2-(3-fluoro-5-(methylthio)phenyl)-4,4,5,5-tetramethyl-1,3,2-dioxaborolane Step 1: Synthesis of (3-bromo-5-fluorophenyl)(methyl)sulfane

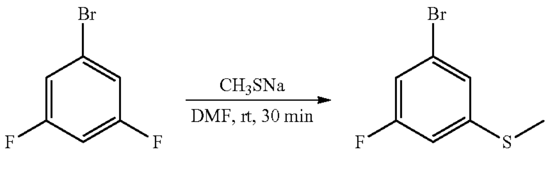

A solution of 3,5-difluorobromobenzene (3 g, 15.54 mmol) in N,N-dimethylformamide (30 mL) was cooled to 0°

C., and sodium thiomethoxide solution (7.1 mL, 15.54 mmol) was added and stirred for 30 minutes. The reaction mixture was diluted with distilled water, extracted with hexane, then washed with brine, and dried over $Na_2SO_4$. The organic layer was concentrated under reduced pressure to obtain (3-bromo-5-fluorophenyl)(methyl)sulfane (2.6 g, yield 75%) as a clear liquid.

Step 2: Synthesis of 2-(3-fluoro-5-(methylthio)phenyl)-4,4,5,5-tetramethyl-1,3,2-dioxaborolane

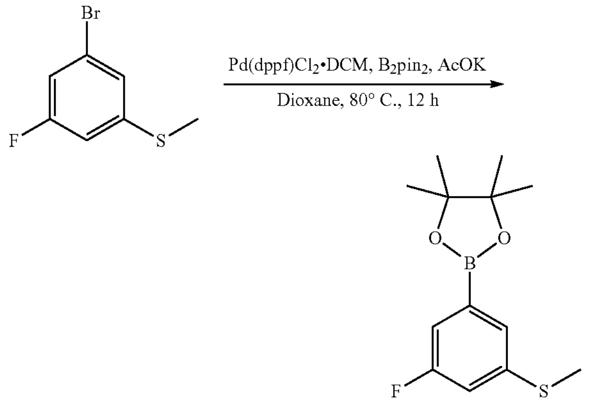

Intermediate I

A sealed tube to which (3-bromo-5-fluorophenyl)(methyl) sulfane (1 g, 4.523 mmol), potassium acetate (2.2 g, 22.615 mmol), (pinacolato)diboron (1.7 g, 6.784 mmol), and $Pd(dppf)Cl_2$ (complex with DCM; 369 mg, 0.452 mmol) were added was purged under $N_2$ atmosphere, and 1,4-dioxane was added and then stirred at 80° C. for 12 hours. The reaction mixture was cooled to ambient temperature, and then ethyl acetate was added, and the precipitate was removed by Celite filtration. The organic layer was concentrated under reduced pressure, and the crude product was purified by flash column chromatography (hexane/ethyl acetate at a concentration from 0% to 100%) to obtain Intermediate I (932 mg, yield 70%) as a yellow liquid.

Preparation Example 10: 3-fluoro-5-(4,4,5,5-tetramethyl-1,3,2-dioxaborolan-2-yl)benzamide Step 1: Synthesis of 3-bromo-5-fluorobenzamide

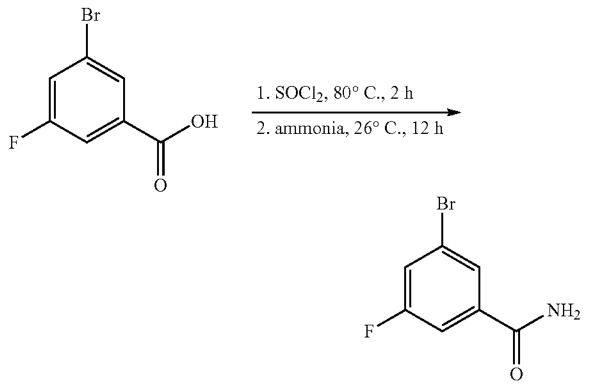

A solution of 3-bromo-5-fluorobenzoic acid (1 g, 4.566 mmol) in thionyl chloride (4 mL) was stirred in reflux condition for 2 hours. The reaction mixture solution was concentrated under reduced pressure, and 28% aqueous ammonia (1.5 mL) was added and then stirred for 12 hours. The reaction mixture was washed three times with distilled water to obtain 3-bromo-5-fluorobenzamide (533 mg, yield 54%) as a white solid. $^1H$ NMR (300 MHz, Chloroform-d) δ 7.74-7.72 (m, 1H), 7.49-7.45 (m, 1H), 7.44-7.40 (m, 1H), 5.83 (s, 2H).

Step 2: Synthesis of 3-fluoro-5-(4,4,5,5-tetramethyl-1,3,2-dioxaborolan-2-yl)benzamide

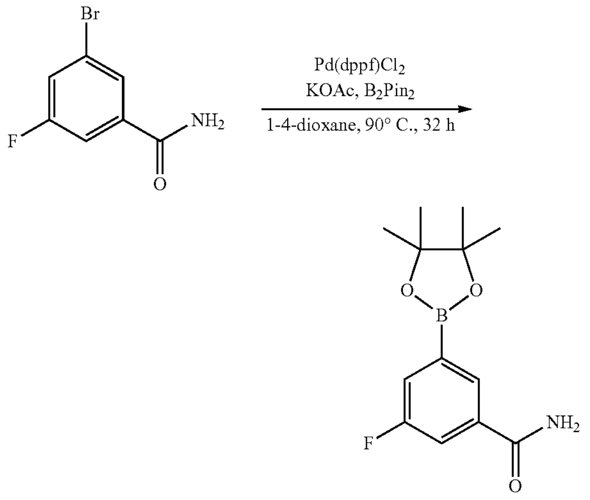

Intermediate J

Intermediate J was obtained by reacting 3-bromo-5-fluorobenzamide in the same manner as in Preparation Example 8.

Preparation Example 11: 3-methoxy-5-(4,4,5,5-tetramethyl-1,3,2-dioxaborolan-2-yl)benzamide

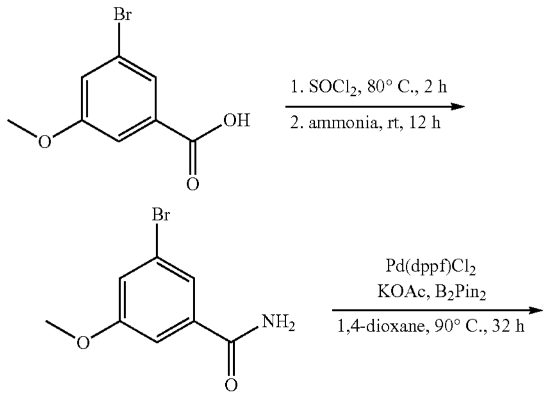

-continued

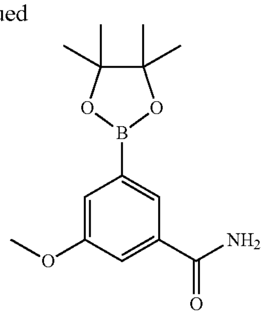

Intermediate K

Intermediate K was obtained in the same manner as in Preparation Example 10, except that 3-bromo-5-methoxybenzoic acid was used instead of 3-bromo-5-fluorobenzoic acid in Step 1. $^1$H NMR (300 MHz, DMSO-$d_6$) δ 8.03 (s, 1H), 7.77 (dd, J=1.6, 0.9 Hz, 1H), 7.53 (dd, J=2.7, 1.6 Hz, 1H), 7.33 (s, 1H), 7.27 (dd, J=2.7, 0.9 Hz, 1H), 3.81 (s, 3H), 1.16 (d, J=2.6 Hz, 12H).

Preparation Example 12: tert-butyl (3-methoxy-5-(4,4,5,5-tetramethyl-1,3,2-dioxaborolan-2-yl)benzyl) carbamate

Step 1: Synthesis of (3-bromo-5-methoxyphenyl)methanamine

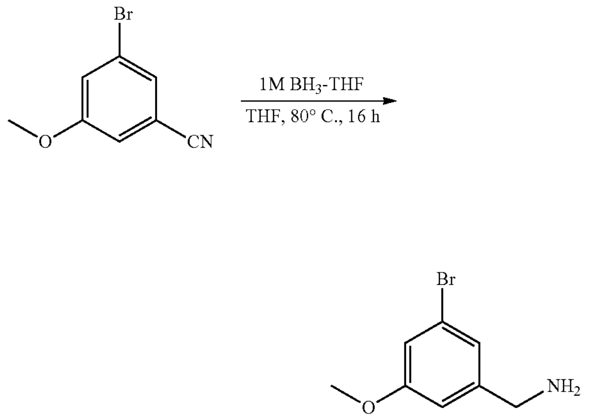

3-bromo-5-methoxybenzonitrile (1 g, 4.716 mmol) was dissolved in THF (9 mL), and then $BH_3$-THF (1 M in THF, 6 mL, 5.895 mmol) was added slowly at 0'° C. The reaction mixture was stirred at 80° C. for 16 hours, and then the solvent was concentrated under reduced pressure and acidified by addition of 1 N HCl. The reaction mixture was stirred at ambient temperature for 2 hours, and then EA and distilled water were added, and the aqueous layer was extracted. The aqueous layer was neutralized with 2 N NaOH (pH 10) and then extracted with EA and brine. The organic layer was concentrated under reduced pressure to obtain (3-bromo-5-methoxyphenyl)methanamine (741 mg, yield 72%). $^1$H NMR (300 MHz, Chloroform-d) δ 7.08-7.03 (m, 1H), 6.92 (t, J=2.0 Hz, 1H), 6.83-6.79 (m, 1H), 3.81 (s, 2H), 3.78 (s, 3H).

Step 2: Synthesis of tert-butyl (3-bromo-5-methoxybenzyl)carbamate

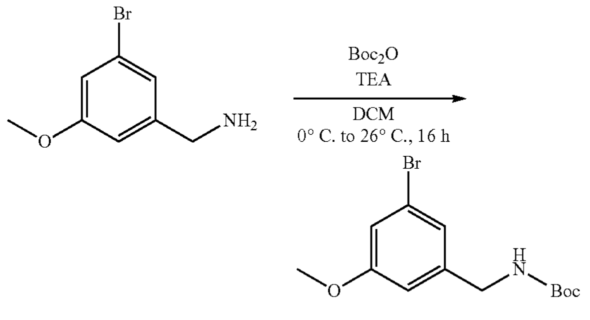

(3-bromo-5-methoxyphenyl)methanamine (741 mg, 3.429 mmol) and $Boc_2O$ (749 mg, 3.429 mmol) were dissolved in DCM. TEA (0.53 mL, 3.772 mmol) was added at 0° C. and then stirred for 16 hours. DCM was partially concentrated and extracted with EA and brine. The organic layer was dried over $MgSO_4$, and then concentrated under reduced pressure, and purified by silica column (EA: hexane=1:3) to obtain tert-butyl (3-bromo-5-methoxybenzyl)carbamate (766 mg, yield 70%). $^1$H NMR (300 MHz, Chloroform-d) δ 7.00 (s, 1H), 6.94 (t, J=2.1 Hz, 1H), 6.75 (s, 1H), 4.84 (s, 1H), 4.25 (s, 2H), 3.78 (s, 3H), 1.46 (s, 9H).

Step 3: Synthesis of tert-butyl (3-methoxy-5-(4,4,5,5-tetramethyl-1,3,2-dioxaborolan-2-yl)benzyl)carbamate

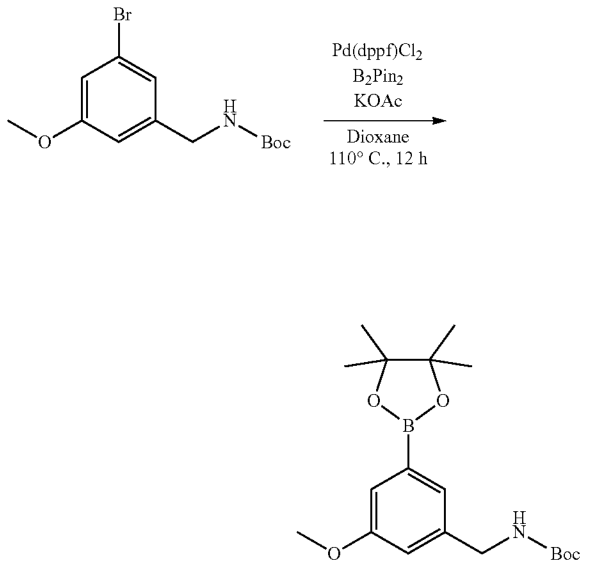

Intermediate L

Intermediate L was obtained by reacting tert-butyl (3-bromo-5-methoxybenzyl)carbamate in the same manner as in Preparation Example 8. $^1$H NMR (300 MHz, Chloroform-d) δ 7.30 (s, 1H), 7.22 (s, 1H), 6.95 (s, 1H), 4.79 (s, 1H), 4.29 (s, 2H), 3.82 (s, 3H), 1.46 (s, 9H), 1.34 (s, 12H).

Preparation Example 13: 3-fluoro-5-(4,4,5,5-tetramethyl-1,3,2-dioxaborolan-2-yl)phenyl)methanol Step 1: Synthesis of (3-bromo-5-fluorophenyl)methanol

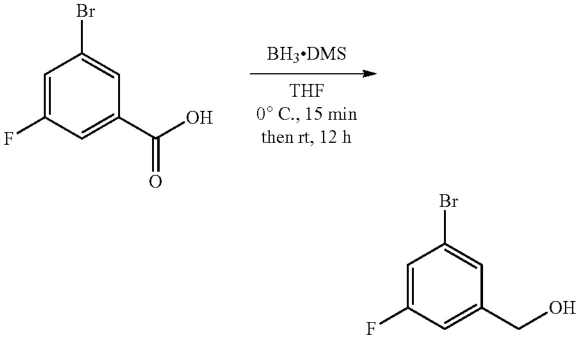

3-bromo-5-fluorobenzoic acid (657.0 mg, 3.0 mmol) was added to THF (15.0 mL) and was cooled to 0° C., and $BH_3$-DMS (5 M, 1.2 mL, 6.0 mmol) was added over 15 minutes and then stirred for 12 hours. The reaction mixture was cooled to 0° C., and an excess of methanol was added. The solution diluted with ethyl acetate was washed with 1 N sodium hydroxide aqueous solution and brine, dried over $Na_2SO_4$, and then concentrated under reduced pressure. The crude product was purified by column chromatography (0 to 30% EtOAc/Hexane) to obtain (3-bromo-5-fluorophenyl) methanol (400 mg, yield 65%). $^1$H NMR (300 MHz, $CDCl_3$) δ 7.33-7.28 (m, 1H), 7.17 (dt, J=8.1, 2.1 Hz, 1H), 7.04 (ddd, J=9.1, 2.4, 1.3 Hz, 1H), 4.69 (s, 2H).

Step 2: Synthesis of (3-fluoro-5-(4,4,5,5-tetramethyl-1,3,2-dioxaborolan-2-yl)phenyl)methanol

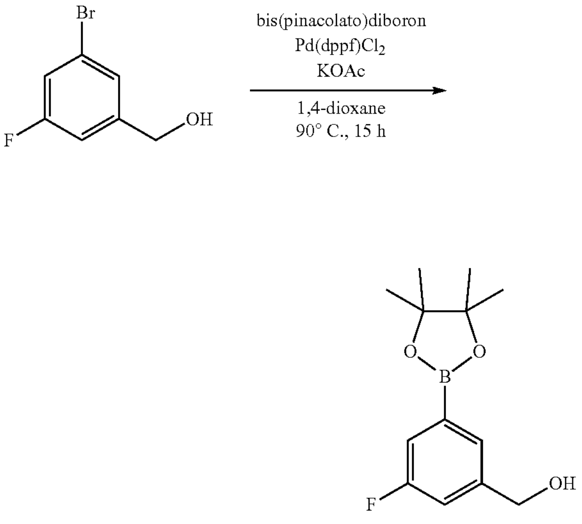

Intermediate M

Intermediate M was obtained by reacting (3-bromo-5-fluorophenyl)methanol in the same manner as in Preparation Example 8.

Preparation Example 14: 3-(3-methoxy-5-(4,4,5,5-tetramethyl-1,3,2-dioxaborolan-2-yl)phenyl)oxetan-3-ol Step 1: Synthesis of 3-(3-bromo-5-methoxyphenyl)oxetan-3-ol

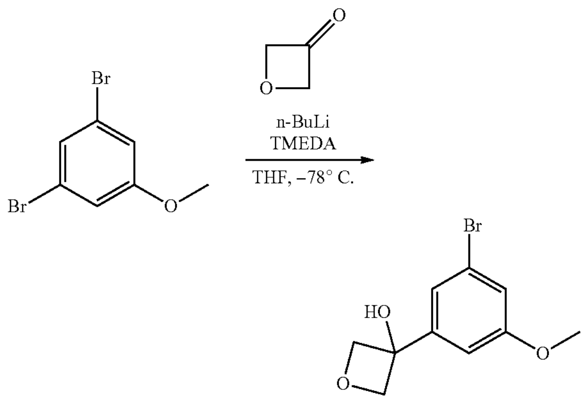

To a solution of 1,3-dibromo-5-methoxybenzene (1.06 g, 4.0 mmol) in THF (0.2 M), TMEDA (923 μL, 6.0 mmol) and n-BuLi (2.5 M in THF, 2.4 mL, 6.0 mmol) were added at −78° C. and stirred for 1 hour. To the reaction mixture, oxetanone (1.02 mL, 4.8 mmol) was added and slowly warmed to ambient temperature. After 4 hours, the resulting mixture was diluted with $NH_4Cl$ aqueous solution (40 mL) and ethyl acetate (40 mL), and the aqueous layer was extracted with ethyl acetate (40 mL). The organic layer was dried over $Na_2SO_4$ and concentrated under reduced pressure. The crude product was purified by column chromatography (hexane:ethyl acetate=1:2) to obtain 3-(3-bromo-5-methoxyphenyl)oxetan-3-ol (443.0 mg as a mixture, about 320.0 mg, yield 31%) as a colorless oil. $^1$H NMR (500 MHz, $CDCl_3$) δ 7.34 (s, 1H), 7.07 (d, J=2.0 Hz, 1H), 7.00 (d, J=2.0 Hz, 1H), 4.86 (d, J=6.8 Hz, 2H), 4.83 (d, J=7.0 Hz, 2H), 3.80 (s, 4H).

Step 2: Synthesis of 3-(3-methoxy-5-(4,4,5,5-tetramethyl-1,3,2-dioxaborolan-2-yl)phenyl)oxetan-3-ol

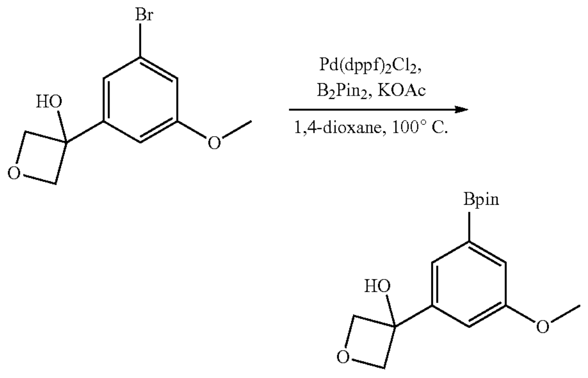

Intermediate N

Intermediate N was obtained by reacting 3-(3-bromo-5-methoxyphenyl)oxetan-3-ol in the same manner as in Preparation Example 8. $^1$H NMR (500 MHz, $CDCl_3$) δ 7.57 (s, 1H), 7.27 (d, J=2.6 Hz, 1H), 7.19 (dd, J=2.6, 1.8 Hz, 1H), 4.94 (d, J=6.9 Hz, 2H), 4.87 (d, J=6.8 Hz, 2H), 3.84 (s, 3H), 1.33 (s, 12H).

Preparation Example 15: 1-(3-methoxy-5-(4,4,5,5-tetramethyl-1,3,2-dioxaborolan-2-yl)phenyl)azetidin-2-one

Step 1: Synthesis of 1-(3-methoxyphenyl)azetidin-2-one

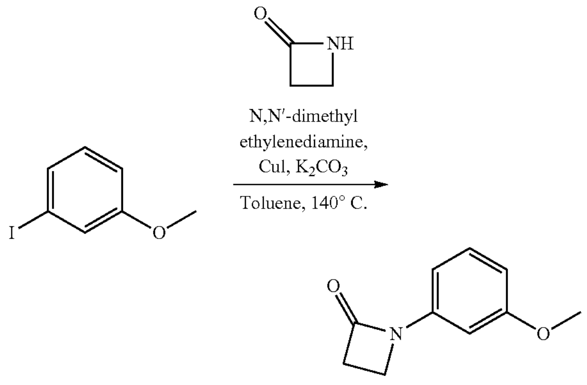

To a solution of 1-iodo-3-methoxybenzene (936.1 mg, 4.0 mmol) in toluene (0.8 M), azetidinone (340.0 mg, 4.8 mmol), CuI (38.1 mg, 0.2 mmol), $K_2CO_3$ (1.1 g, 8.0 mmol) and N,N'-dimethylethylenediamine (43 μL, 0.4 mmol) were added and stirred at 140° C. for 24 hours. The reaction mixture was cooled to ambient temperature and diluted with brine (20 mL) and ethyl acetate (20 mL), and the aqueous layer was extracted with ethyl acetate (20 mL). The organic layer was dried over $Na_2SO_4$ and concentrated under reduced pressure. The crude product was purified by column chromatography (hexane:ethyl acetate=2:1) to obtain 1-(3-methoxyphenyl)azetidin-2-one (436.0 mg, yield 61%) as a colorless oil (436.0 mg, 61%). $^1$H NMR (500 MHz, $CDCl_3$) δ 7.14 (t, J=8.1 Hz, 1H), 6.92 (s, 1H), 6.78 (dd, J=8.1, 1.9 Hz, 1H), 6.56 (dd, J=8.4, 2.5 Hz, 1H), 3.72 (s, 3H), 3.48 (t, J=4.5 Hz, 2H), 2.98 (d, J=4.5 Hz, 2H).

Step 2: 1-(3-methoxy-5-(4,4,5,5-tetramethyl-1,3,2-dioxaborolan-2-yl)phenyl)azetidin-2-one

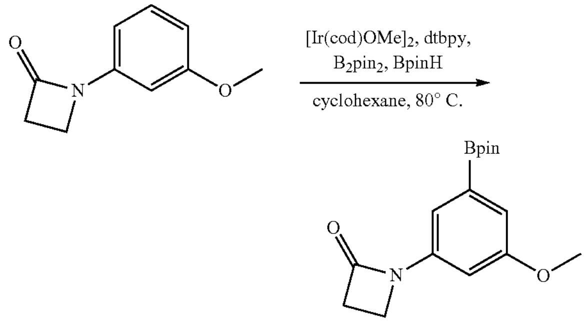

Intermediate O

To a solution of 1-(3-methoxyphenyl)azetidin-2-one (436.0 mg, 2.46 mmol) in cyclohexane (0.1 M), $[Ir(cod)OMe]_2$ (195.7 mg, 0.295 mmol), 4,4'-di-tert-butyl-2'2-bipyridine (dtbpy) (158.5 mg, 0.590 mmol), bis(pinacolato) diboron (1.25 g, 4.90 mmol) and BpinH (42.8 μL, 0.295 mmol) were added and stirred at 80° C. for 24 hours. The reaction mixture was cooled to room temperature and diluted with brine (40 mL) and ethyl acetate (40 mL), and then the aqueous layer was extracted with ethyl acetate (40 mL). The organic layer was dried over $Na_2SO_4$ and concentrated under reduced pressure. The crude product was purified by column chromatography (hexane:ethyl acetate=1:1) to obtain Intermediate O (405.2 mg, yield 54%) as a yellow solid. $^1$H NMR (500 MHz, $CDCl_3$) δ 7.32 (t, J=2.3 Hz, 1H), 7.05 (d, J=2.5 Hz, 1H), 7.04 (d, J=1.9 Hz, 1H), 3.81 (s, 3H), 3.62 (t, J=4.5 Hz, 2H), 3.07 (t, J=4.5 Hz, 2H).

Preparation Example 16: tert-butyl (3-fluoro-5-(4,4,5,5-tetramethyl-1,3,2-dioxaborolan-2-yl)benzyl) carbamate

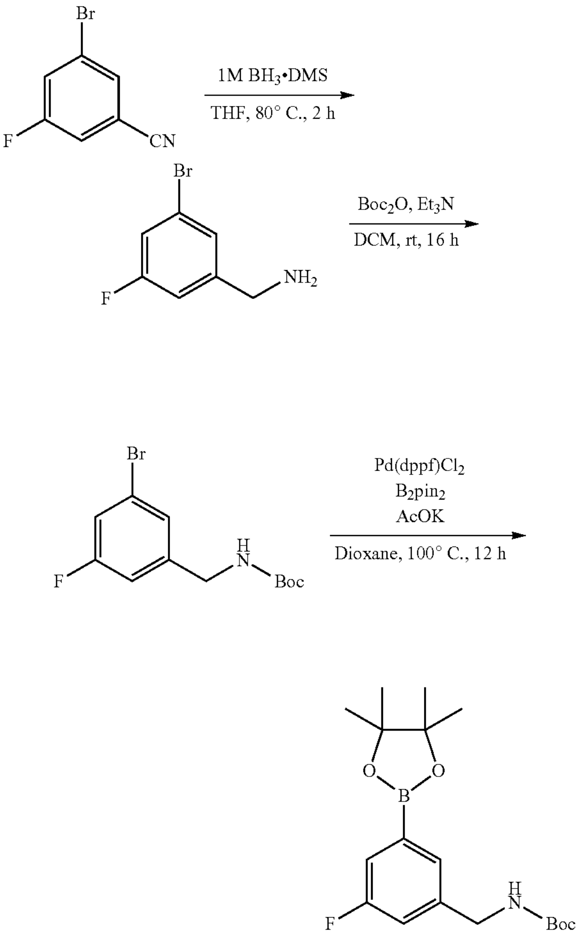

Intermediate P

Intermediate P was obtained in the same manner as in Preparation Example 12, except that 3-bromo-5-fluorobenzonitrile was used instead of 3-bromo-5-methoxybenzonitrile in Step 1 of Preparation Example 12.

Preparation Example 17: tert-butyl 3-(3-fluoro-5-(4,4,5,5-tetramethyl-1,3,2-dioxaborolan-2-yl)phenyl)azetidine-1-carboxylate

Step 1: Synthesis of tert-butyl 3-(3-bromo-5-fluorophenyl)azetidine-1-carboxylate

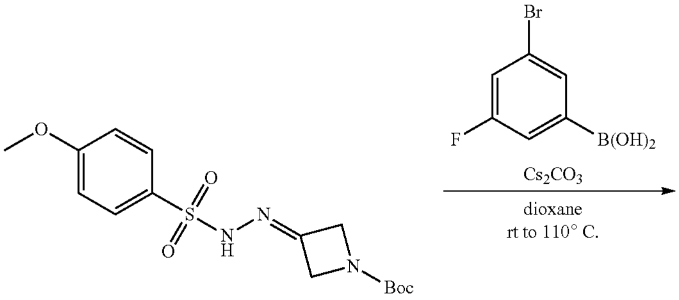

tert-butyl 3-(2-((4-methoxyphenyl)sulfonyl)hydrazinylidene)azetidine-1-carboxylate (1.0 g, 2.8 mmol), 3-bromo-5-fluorophenylboronic acid (1.23 g, 5.6 mmol) and cesium carbonate (1.83 g, 5.6 mmol) were added to 1,4-dioxane (10.0 mL, 0.3 M). The tube was sealed and stirred at 110° C. for 15 hours. The reaction mixture was cooled to ambient temperature, quenched with saturated $NaHCO_3$ aqueous solution (30 mL), and then dried over $MgSO_4$ and concentrated under reduced pressure. The crude product was purified by flash column chromatography (10-30% EtOAc/hexane) to obtain tert-butyl 3-(3-bromo-5-fluorophenyl)azetidine-1-carboxylate (261 mg, 28%). $^1$H NMR (300 MHz, Chloroform-d) δ 7.28 (d, J=3.8 Hz, 1H), 7.16 (dt, J=8.1, 2.0 Hz, 1H), 7.00 (dt, J=9.3, 1.8 Hz, 1H), 4.34 (t, J=8.7 Hz, 2H), 3.93 (dd, J=8.7, 5.8 Hz, 2H), 3.69 (d, J=14.4 Hz, 1H), 1.49 (s, 9H).

Step 2: Synthesis of tert-butyl 3-(3-fluoro-5-(4,4,5,5-tetramethyl-1,3,2-dioxaborolan-2-yl)phenyl)azetidine-1-carboxylate

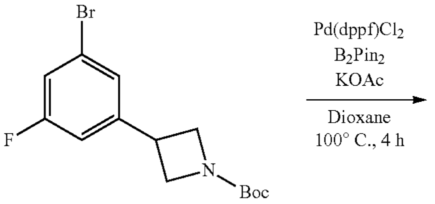

-continued

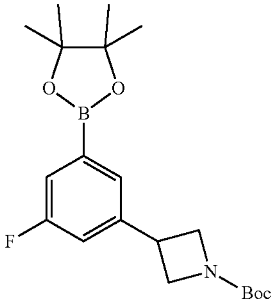

Intermediate Q

Intermediate Q was obtained by reacting tert-butyl 3-(3-bromo-5-fluorophenyl)azetidine-1-carboxylate in the same manner as in Preparation Example 8. $^1$H NMR (300 MHz, Chloroform-d) δ 7.50 (s, 1H), 7.39 (dd, J=8.7, 2.2 Hz, 1H), 7.14 (dt, J=9.8, 2.1 Hz, 1H), 4.34 (t, J=8.7 Hz, 2H), 4.00 (dd, J=8.6, 6.0 Hz, 2H), 3.77 (ddd, J=12.8, 7.8, 5.1 Hz, 1H), 1.49 (s, 9H), 1.37 (s, 12H).

Preparation Example 18: methyl 6-(methylamino)spiro[3.3]heptane-2-carboxylate hydrochloride

Step 1: Synthesis of methyl 6-((tert-butoxycarbonyl)(methyl)amino)spiro[3.3]heptane-2-carboxylate

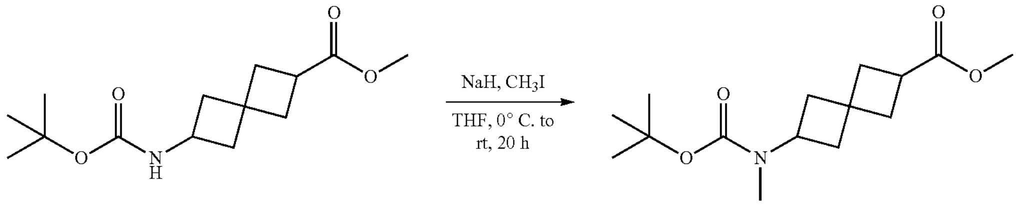 [SMILES: COC(=O)C1CC2(CC(NC(=O)OC(C)(C)C)C2)C1 ; COC(=O)C1CC2(C1)CC(N(C)C(=O)OC(C)(C)C)C2]

To a stirred solution of methyl 6-((tert-butoxycarbonyl)amino)spiro[3.3]heptane-2-carboxylate (269 mg, 1.0 mmol) in THF (0.1 M), 60% NaH (60 mg, 1.50 mmol) was added and stirred at 0° C. for 15 minutes, and iodomethane (0.2 mL, 3.0 mmol) was added to the reaction mixture and stirred for 20 hours. The reaction mixture was quenched with cold distilled water and extracted with ethyl acetate (20 mL). The organic layer was washed with distilled water and brine, dried over $Na_2SO_4$, and then concentrated under reduced pressure to obtain methyl 6-((tert-butoxycarbonyl)(methyl)amino)spiro[3.3]heptane-2-carboxylate (288 mg, crude product) as a yellow liquid. $^1H$ NMR (400 MHz, chloroform-d) δ 4.6-4.14 (m, 1H), 3.69 (s, 3H), 3.05 (p, J=8.5 Hz, 1H), 2.39-2.25 (m, 1H), 2.2-2.00 (m, 1H), 1.47 (s, 9H).

Step 2: Synthesis of methyl 6-(methylamino)spiro[3.3]heptane-2-carboxylate hydrochloride

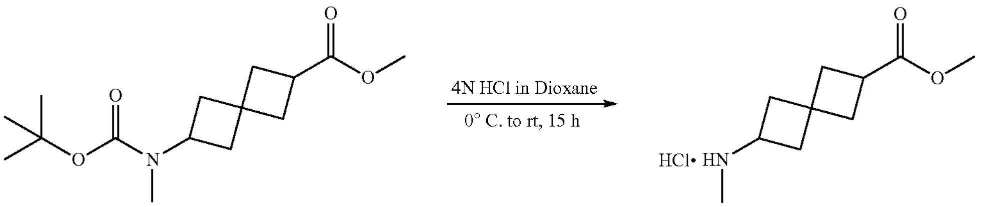

Intermediate R

To methyl 6-((tert-butoxycarbonyl)(methyl)amino)spiro[3.3]heptane-2-carboxylate (288 mg, 1.02 mmol), 4 N HCl in dioxane was added at 0° C. and stirred at ambient temperature for 15 hours. The reaction mixture was concentrated under reduced pressure to obtain the hydrochloride salt of Intermediate R (244 mg) as a yellow solid. $^1H$ NMR (400 MHz, DMSO) δ 9.07 (s, 2H), 3.59 (s, 2H), 3.53-3.39 (m, 1H), 3.22-2.78 (m, 1H), 2.37 (s, 3H), 2.34-2.23 (m, 2H), 2.24-2.01 (m, 6H).

Preparation Example 19: 4-(((tert-butyldimethylsilyl)oxy)methyl)-2,5-dimethylthiophene-3-carboxylic acid Step 1: Synthesis of 4-bromo-2,5-dimethylthiophene-3-carbaldehyde

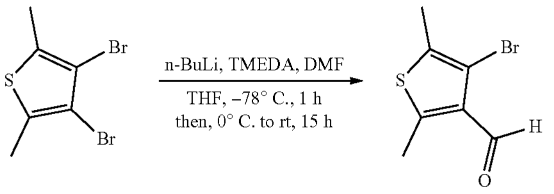

To a solution of 3,4-dibromo-2,5-dimethylthiophene (6.37 g, 23.6 mmol) and TMEDA (3.9 mL, 26 mmol) in THF (0.4 M), n-BuLi (2.5 M in THF, 9.4 mL, 23.6 mmol) was added at −78° C. and stirred for 1 hour. DMF was added to the reaction mixture, and then slowly warmed to ambient temperature, and stirred for 15 hours. The reaction mixture was quenched with distilled water (20 mL), acidified with 1 N HCl solution, and then extracted with ethyl acetate. The organic layer was dried over $Na_2SO_4$, filtered, and concentrated under reduced pressure to obtain 4-bromo-2,5-dimethylthiophene-3-carbaldehyde (3.64 g) as an off-white solid. $^1H$ NMR (300 MHz, $CDCl_3$) δ 10.03 (s, OH), 2.74 (s, 1H), 2.38 (s, 1H).

Step 2: Synthesis of (4-bromo-2,5-dimethylthiophen-3-yl)methanol

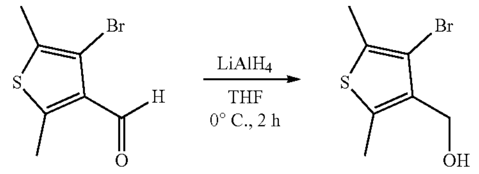

To a solution of 4-bromo-2,5-dimethylthiophene-3-carbaldehyde (1.10 g, 5.02 mmol) in THF (0.2 M), $LiAlH_4$ (191 mg, 5.02 mmol) was added at 0° C. and stirred for 2 hours. The reaction mixture was quenched with EtOAc (1 mL) and ice water (0.3 mL), stirred for 30 minutes, then filtered, and concentrated under reduced pressure. The crude product was purified by column chromatography (20% EtOAc in Hexane) to obtain (4-bromo-2,5-dimethylthiophen-3-yl)methanol (754 mg, yield 68%) as a colorless liquid. $^1H$ NMR (400 MHz, DMSO); S 4.33 (s, 1H), 2.40 (s, 3H), 2.36 (s, 1H), 2.30 (s, 3H).

Step 3: Synthesis of ((4-bromo-2,5-dimethylthiophen-3-yl)methoxy)(tert-butyl)dimethylsilane

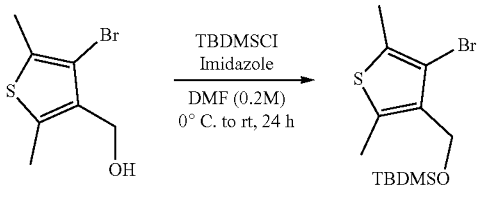

To a solution of (4-bromo-2,5-dimethylthiophen-3-yl)methanol solution (950 mg, 4.30 mmol) in THF (0.2 M, 0° C.), tert-butyldimethylsilyl chloride (777 mg, 5.16 mmol) and imidazole (439 mg, 6.44 mmol) were added and stirred for 24 hours. The reaction mixture was diluted with EtOAc (20 mL) and washed with distilled water (2×20 mL). The organic layer was dried over $Na_2SO_4$, filtered, and then concentrated under reduced pressure. The crude product was purified by column chromatography (5% EtOAc in Hexane) to obtain ((4-bromo-2,5-dimethylthiophen-3-yl)methoxy)

(tert-butyl)dimethylsilane (937 mg, yield 65%) as a colorless liquid. $^{1}H$ NMR (300 MHz, chloroform-d) δ 4.60 (s, 1H), 2.45 (s, 2H), 2.35 (s, 2H), 1.57 (s, 1H), 0.94 (s, 4H), 0.12 (s, 3H).

Step 4: Synthesis of 4-(((tert-butyldimethylsilyl) oxy)methyl)-2,5-dimethylthiophene-3-carboxylic acid

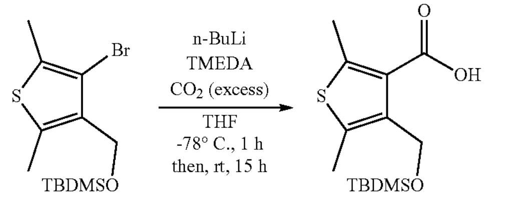

Intermediate S

To a solution of ((4-bromo-2,5-dimethylthiophen-3-yl) methoxy)(tert-butyl)dimethylsilane (335 g, 1.0 mmol) and TMEDA (165 μL, 1.10 mmol) in THF (0.2 M), n-BuLi (2.5 M in THF, 0.44 mL, 1.10 mmol) was added at −78° C. and stirred for 1 hour. The reaction mixture was quenched with $CO_2$ gas at −78° C., and then slowly warmed to ambient temperature, and stirred for 15 hours. The reaction mixture was quenched with distilled water (20 mL), acidified with 1 N HCl solution, and then extracted with ethyl acetate. The organic layer was dried over $Na_2SO_4$, filtered, and then concentrated under reduced pressure. The crude product was purified by column chromatography (20% EtOAc in Hexane) to obtain Intermediate S (300 mg) as a white solid. $^{1}H$ NMR (300 MHz, chloroform-d) δ 4.74 (s, 2H), 2.67 (s, 3H), 2.38 (s, 3H), 0.94 (s, 9H), 0.18 (s, 6H).

Preparation Example 20: methyl 3-bromo-4H-thieno[3,2-b]pyrrole-5-carboxylate

Step 1: Synthesis of methyl (Z)-2-azido-3-(4-bromothiophen-2-yl)acrylate

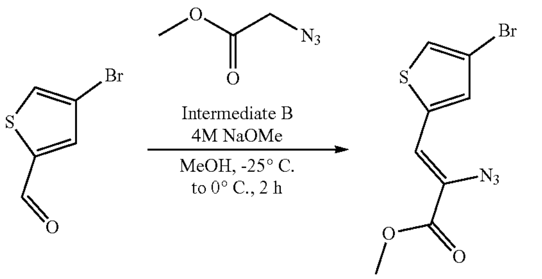

To a solution of 4-bromothiophene-2-carbaldehyde (3.82 g, 20.0 mmol, 1.0 equiv) and Intermediate B (6.91 g, 60.0 mmol, 3.0 equiv) in MeOH (30 mL), 4 M NaOMe (15 mL, 60.0 mmol) was added at −25° C. and stirred at 0° C. for 2 hours. Ice was added to the reaction mixture, washed with distilled water, and filtered, and then the reaction product was dried to obtain methyl (Z)-2-azido-3-(4-bromothiophen-2-yl)acrylate. $^{1}H$ NMR (300 MHz, chloroform-d) δ 7.37 (dd, J=1.4, 0.7 Hz, 1H), 7.22 (dd, J=1.4, 0.6 Hz, 1H), 7.03 (d, J=0.7 Hz, 1H), 3.90 (s, 3H).

Step 2: Synthesis of methyl 3-bromo-4H-thieno[3,2-b]pyrrole-5-carboxylate

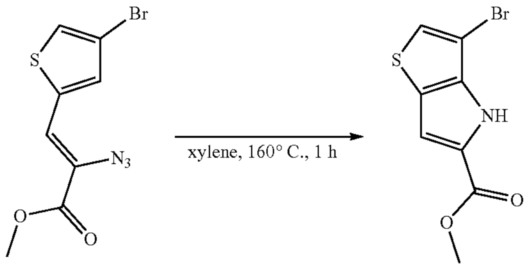

Intermediate T

A solution of methyl (Z)-2-azido-3-(4-bromothiophen-2-yl)acrylate (4.79 g, 16.6 mmol, 1.0 equiv) in o-xylene (60 mL) was stirred at 160° C. for 1 hour. The reaction mixture was partially concentrated, filtered, and then washed with hexane, and dried to obtain Intermediate T. $^{1}H$ NMR (300 MHz, chloroform-d) δ 9.10 (s, 1H), 7.23 (s, 1H), 7.15 (d, J=1.9 Hz, 1H), 3.93 (s, 3H).

Preparation Example 21: methyl 3-bromo-2-methyl-4H-thieno[3,2-b]pyrrole-5-carboxylate

Step 1: Preparation of 4-bromo-5-methylthiophene-2-carbaldehyde

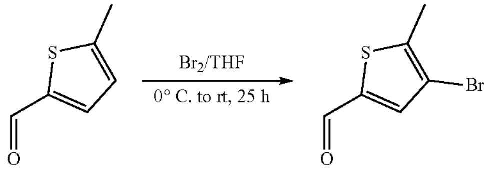

To a solution of 5-methylthiophene-2-carbaldehyde (2.78 g, 22.0 mmol) in THF (0.5 M), bromine (1.7 mL, 33 mmol) was added at 0° C. and stirred for 25 hours. To the reaction mixture, 10% $Na_2S_2O_3$ aqueous solution (30 mL) and 10% $NaHCO_3$ aqueous solution (30 mL) were added and extracted with EtOAc (150 mL). The organic phase was dried over $Na_2SO_4$ and concentrated under reduced pressure. The crude product was purified by column chromatography to obtain 4-bromo-5-methylthiophene-2-carbaldehyde (862 mg, yield 16%) as a colorless solid. $^{1}H$ NMR (300 MHz, chloroform-d) δ 9.80 (s, 1H), 7.62 (s, 1H), 2.51 (s, 3H).

Step 2: Preparation of methyl (Z)-2-azido-3-(4-bromo-5-methylthiophen-2-yl)acrylate

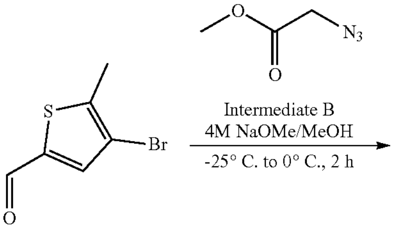

-continued

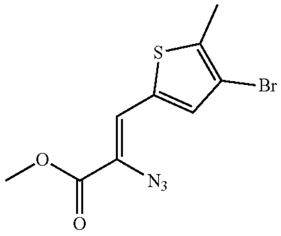

To a solution of 4-bromo-5-methylthiophene-2-carbaldehyde (850 mg, 4.14 mmol) in MeOH (1.5 M), 4 M NaOMe (3 mL, 11.6 mmol) and Intermediate B (1.43 g, 12.4 mmol) were added at −25° C. The reaction mixture was stirred at 0° C. for 2 hours, and then diluted with EtOAc, and washed with brine solution. The organic phase was dried over $Na_2SO_4$ and concentrated under reduced pressure. The crude product was purified by column chromatography to obtain methyl (Z)-2-azido-3-(4-bromo-5-methylthiophen-2-yl) acrylate (813 mg, yield 65%) as a yellow solid. $^1H$ NMR (300 MHz, chloroform-d) δ 7.15 (s, 1H), 6.99 (s, 1H), 3.91 (s, 3H), 2.45 (s, 3H).

Step 3: Preparation of methyl 3-bromo-2-methyl-4H-thieno[3,2-b]pyrrole-5-carboxylate

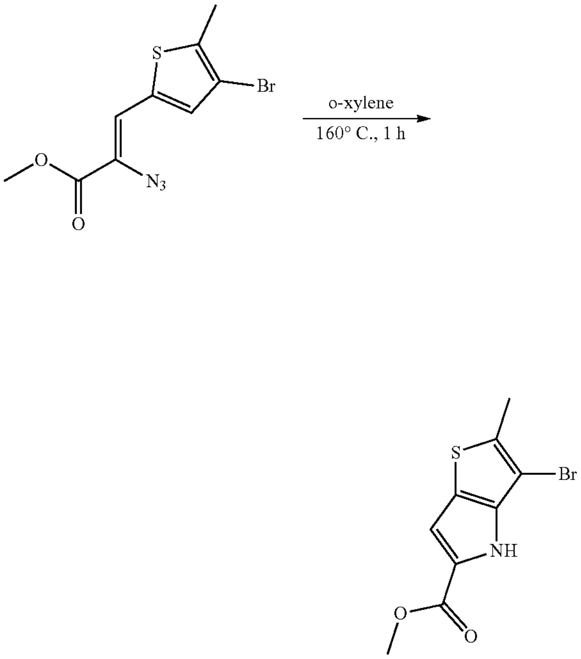

Intermediate U

A solution of methyl (Z)-2-azido-3-(4-bromo-5-methylthiophen-2-yl)acrylate (795 mg, 2.63 mmol) in 4 mL of xylene was added to o-xylene (5 mL) over 10 minutes. After stirring for 1 hour under reflux, the reaction mixture was cooled to ambient temperature and partially concentrated. The solid was filtered to obtain Intermediate U (554 mg, yield 77%) as an off-white solid. $^1H$ NMR (300 MHz, chloroform-d) δ 8.99 (s, 1H), 7.10 (d, J=1.9 Hz, 1H), 3.93 (s, 3H), 2.50 (s, 3H).

Preparation Example 22: ethyl 3-bromo-6-methyl-4H-thieno[3,2-b]pyrrole-5-carboxylate Step 1: Synthesis of 1-(3,4-dibromothiophen-2-yl)ethan-1-one

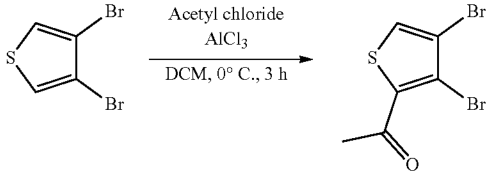

To a solution of $AlCl_3$ (1.33 g, 10.0 mmol, 2.0 equiv) in DCM (20 mL), 3,4-dibromothiophene (1.2 g, 5.0 mmol) was added at 0° C. and stirred for 10 minutes. Acetyl chloride (360 μL, 5.0 mmol, 1.0 equiv) was added and stirred at 0° C. for 3 hours. The reaction mixture was acidified by addition of 6 M HCl and extracted with DCM. The organic layer was dried over $MgSO_4$ and then concentrated under reduced pressure to obtain 1-(3,4-dibromothiophen-2-yl) ethan-1-one. $^1H$ NMR (300 MHz, Chloroform-d) δ 7.63 (s, 1H), 2.72 (s, 3H).

Step 2: Synthesis of ethyl 3-bromo-6-methyl-4H-thieno[3,2-b]pyrrole-5-carboxylate

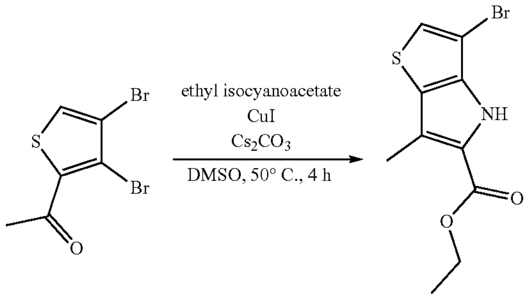

Intermediate V

A solution of 1-(3,4-dibromothiophen-2-yl)ethan-1-one (1.42 g, 5.0 mmol), ethyl isocyanoacetate (600 μL, 5.5 mmol, 1.1 equiv), CuI (95 mg, 0.5 mmol, 0.1 equiv) and $Cs_2CO_3$ (3.26 g, 10.0 mmol, 2.0 equiv) in DMSO (5 mL) was stirred at 50° C. for 4 hours. Distilled water was added to the reaction mixture and extracted with DCM. The organic layer was dried over $MgSO_4$ and then concentrated under reduced pressure. The crude product was purified by flash column chromatography to obtain Intermediate V (806 mg, yield 56%). $^1H$ NMR (300 MHz, Chloroform-d) δ 9.01 (s, 1H), 7.18 (s, 1H), 4.40 (q, J=7.1 Hz, 2H), 1.41 (t, J=7.1 Hz, 3H).

Preparation Example 23: methyl 3-bromo-2-chloro-4H-thieno[3,2-b]pyrrole-5-carboxylate Step 1: Synthesis of 4-bromo-5-chlorothiophene-2-carbaldehyde

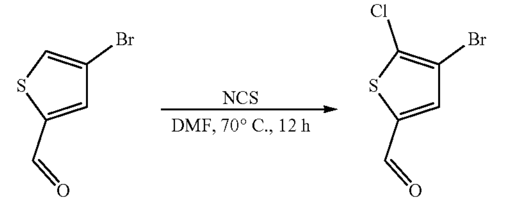 [SMILES: O=Cc1cc(Br)cs1 ; "DMF, 70° C., 12 h" ; "NCS" ; O=Cc1cc(Br)c(Cl)s1]

To a solution of 4-bromothiophene-2-carbaldehyde (500 mg, 2.62 mmol, 1.0 equiv) in DMF (5 mL), N-chlorosuccinimide (699 mg, 5.24 mmol) was added and stirred at 70° C. for 12 hours. Distilled water was added to the reaction mixture, and the solid was filtered, then washed with distilled water, and dried to obtain 4-bromo-5-chlorothiophene-2-carbaldehyde (421 mg, yield 70%). $^1$H NMR (300 MHz, Chloroform-d) δ 9.76 (s, 1H), 7.60 (s, 1H).

Steps 2 and 3: Synthesis of methyl 3-bromo-2-chloro-4H-thieno[3,2-b]pyrrole-5-carboxylate

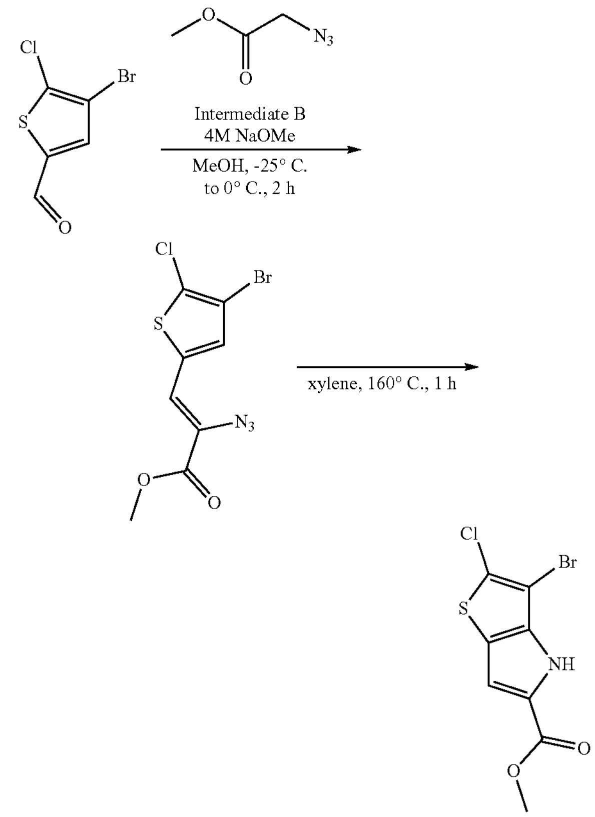

Intermediate W

Intermediate W was obtained by reacting 4-bromo-5-chlorothiophene-2-carbaldehyde in the same manner as in Preparation Example 20. $^1$H NMR (300 MHz, Chloroform-d) δ 9.04 (s, 1H), 7.07 (d, J=1.9 Hz, 1H), 3.92 (s, 3H).

Preparation Example 24: 4'-(bromomethyl)-3-methoxy-1,1'-biphenyl

Step 1: Synthesis of (3'-methoxy-[1,1'-biphenyl]-4-yl)methanol

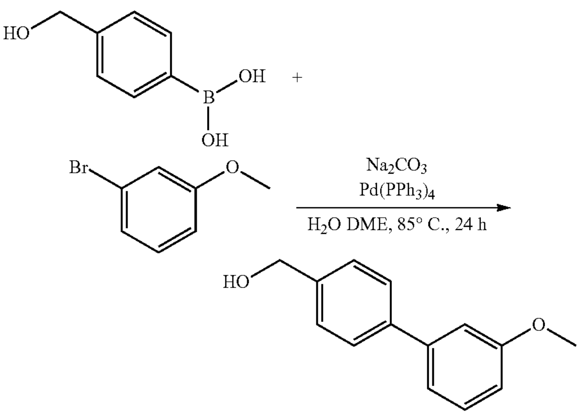

3-bromoanisole (935 mg, 5 mmol), 4-(hydroxymethyl)phenylboronic acid (912 mg, 6 mmol), $Na_2CO_3$ (1.3 g, 12.5 mmol), and $Pd(PPh_3)_4$ (289 mg, 0.25 mmol) were dissolved in a mixture of $H_2O$ and DME and stirred at 85° C. for 24 hours. The reaction mixture was cooled to ambient temperature, then filtered through Celite, and extracted with EA and brine, and the organic layer was dried over $MgSO_4$. The crude product was purified by silica gel column (EtOAc: Hexane=1:2) to obtain (3'-methoxy-[1,1'-biphenyl]-4-yl)methanol (1.00 g, yield 93%) as a yellow oil. $^1$H NMR (300 MHz, Chloroform-d) δ 7.59 (d, J=8.2 Hz, 2H), 7.44 (d, J=8.2 Hz, 2H), 7.36 (t, J=7.9 Hz, 1H), 7.21-7.16 (m, 1H), 7.12 (t, J=2.1 Hz, 1H), 6.90 (ddd, J=8.1, 2.6, 0.9 Hz, 1H), 4.75 (s, 2H), 3.87 (s, 3H).

Step 2: Synthesis of 4'-(bromomethyl)-3-methoxy-1,1'-biphenyl

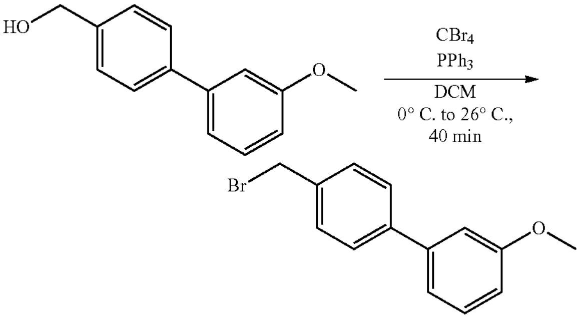

Intermediate X (3'-methoxy-[1,1'-biphenyl]-4-yl)methanol (1.00 g, 4.667 mmol) and $CBr_4$ (1.7 g, 5.134 mmol) were dissolved in DCM (16 mL) and then stirred at 0° C. for 10 minutes. $PPh_3$ (1.35 g, 5.134 mmol) was slowly added and stirred for 40 minutes. The organic layer was concentrated under reduced pressure and purified by silica gel column (EtOAc: Hexane=1:25) to obtain Intermediate X (1.14 g, yield 88%). $^1$H NMR (300 MHz, Chloroform-d) δ 7.57 (d, J=8.3 Hz, 2H), 7.47 (d, J=8.3 Hz, 2H), 7.37 (t, J=7.9 Hz, 1H), 7.20-7.15 (m, 1H), 7.13-7.11 (m, 1H), 6.94-6.89 (m, 1H), 4.56 (s, 2H), 3.87 (s, 3H).

Preparation Example 25: 4'-(bromomethyl)-3-fluoro-5-methoxy-1,1'-biphenyl

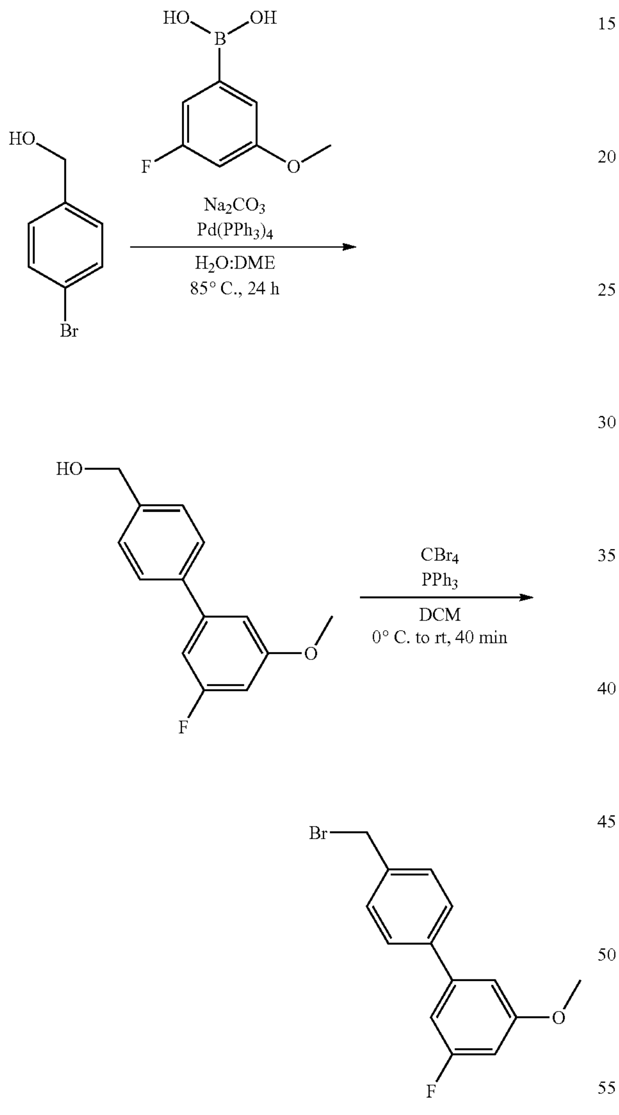

Intermediate Y

Intermediate Y was obtained by using (4-bromophenyl) methanol and (3-fluoro-5-methoxyphenyl)boronic acid as starting materials in the same manner as in Preparation Example 24. $^1$H NMR (300 MHz, Chloroform-d) δ 7.59-7.54 (m, 2H), 7.51-7.46 (m, 2H), 6.90 (dd, J=9.2, 2.2 Hz, 2H), 6.64 (dt, J=10.5, 2.3 Hz, 1H), 4.57 (s, 2H), 3.88 (s, 3H).

Preparation Example 26: methyl (2R,4R,6R)-6-aminospiro[3.3]heptane-2-carboxylate hydrochloride Step 1: Synthesis of methyl 6-(((benzyloxy)carbonyl)amino)spiro[3.3]heptane-2-carboxylate

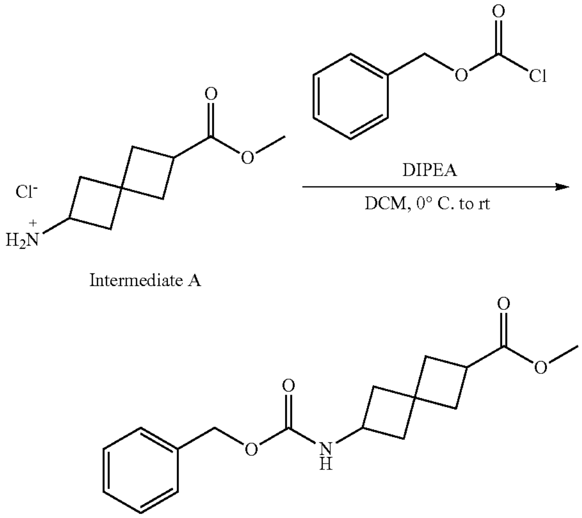

Intermediate A

Intermediate A (3 g, 14.58 mmol) and benzyl chloroformate (3.1 mL, 21.87 mmol) were dissolved in DCM (0.5 M), and DIPEA (7.62 mL, 43.75 mmol) was slowly added at 0° C. and stirred at ambient temperature for 14 hours. The reaction mixture was extracted with $NH_4Cl$ aqueous solution and DCM, and then the organic layer was dried over $MgSO_4$ and concentrated under reduced pressure. The crude product was purified by silica gel column (EtOAc:Hexane=1:1) to obtain methyl 6-(((benzyloxy)carbonyl)amino)spiro[3.3]heptane-2-carboxylate (4.4 g, yield 99%). $^1$H NMR (300 MHz, $CDCl_3$) δ 7.40-7.28 (m, 5H), 5.06 (s, 2H), 4.84 (d, J=8.3 Hz, 1H), 4.11-3.97 (m, 1H), 3.65 (s, 3H), 3.01 (p, J=8.5 Hz, 1H), 2.50 (dt, J=12.0, 6.6 Hz, 1H), 2.43-2.21 (m, 4H), 2.12 (ddd, J=11.7, 8.7, 2.8 Hz, 1H), 1.84 (ddd, J=15.9, 11.3, 8.7 Hz, 2H).

Step 2: Purification of methyl 6-(((benzyloxy)carbonyl)amino)spiro[3.3]heptane-2-carboxylate

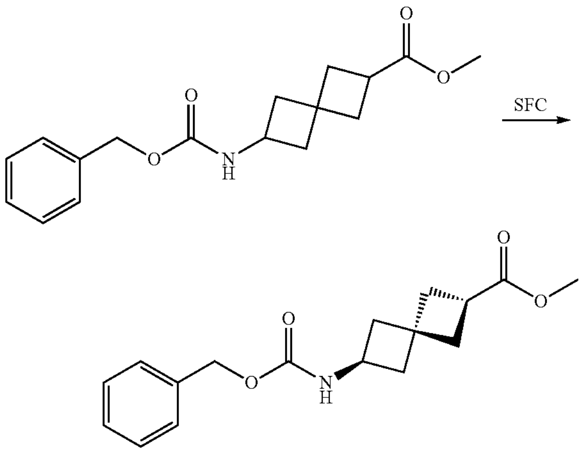

-continued

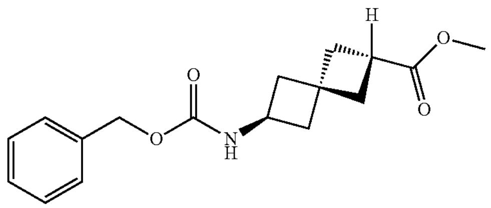

Methyl 6-(((benzyloxy)carbonyl)amino)spiro[3.3]heptane-2-carboxylate (4.34 g) was purified by supercritical fluid chromatography (SFC) under the following conditions to separate the compounds of methyl (2S,4S,6S)-6-(((benzyloxy)carbonyl)amino)spiro[3.3]heptane-2-carboxylate (2.99 g) and methyl (2R,4R,6R)-6-(((benzyloxy)carbonyl)amino)spiro[3.3]heptane-2-carboxylate (0.88 g) as a yellow oil, respectively.

Column: Daicel ChiralPak IG mobile phase (250 mm×4.6 mm, 1 um)

Mobile phase: [Hexane/EtOH]; 80/20 (V/V), 9.4 minutes (2S,4S,6S), 10.7 minutes (2R,4R,6R)

Step 3: Synthesis of methyl (2R,4R,6R)-6-amino-spiro[3.3]heptane-2-carboxylate hydrochloride

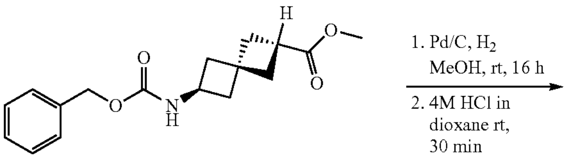

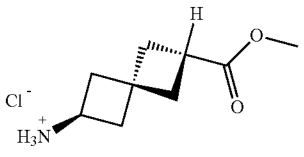

Intermediate Z

Methyl (2R,4R,6R)-6-(((benzyloxy)carbonyl)amino)spiro[3.3]heptane-2-carboxylate (312 mg, 1.03 mmol) was dissolved in MeOH (10.3 mL, 0.1 M), and Pd/C 10% (110 mg, 0.1 equiv) was added. The reaction mixture was purged under $H_2$ atmosphere and stirred for 16 hours. The reaction mixture was filtered through Celite and concentrated under reduced pressure. 1,4-dioxane (10.3 mL, 0.1 M) and 4 N HCl solution (0.8 mL, 3.09 mmol) were added to the concentrated reaction mixture and stirred for an additional 30 minutes. The reaction mixture was concentrated under reduced pressure to obtain Intermediate Z (180 mg).

Preparation Example 27: 4'-(bromomethyl)-3,5-dimethoxy-1,1'-biphenyl

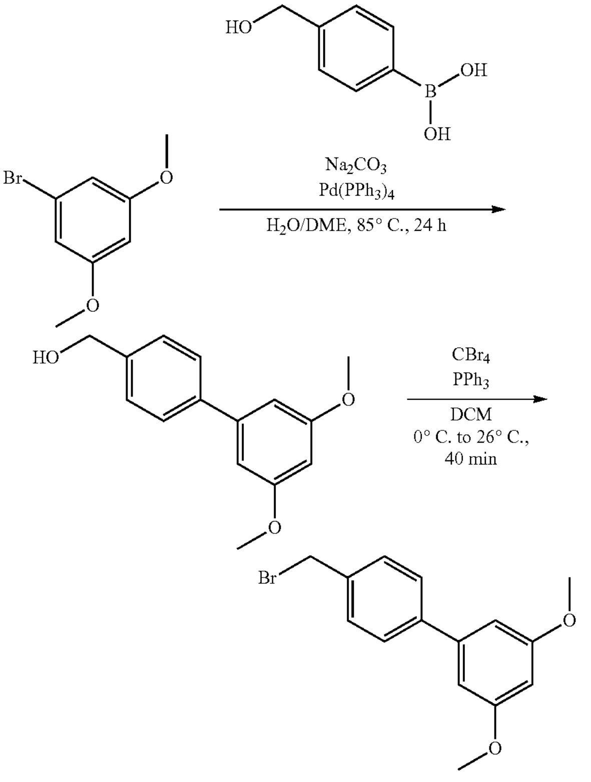

Intermediate AA

Intermediate AA was obtained by using 1-bromo-3,5-dimethoxybenzene and ((4-hydroxy)methylphenyl)boronic acid as starting materials in the same manner as in Preparation Example 24. $^1$H NMR (300 MHz, Chloroform-d) δ 7.55 (d, J=8.3 Hz, 2H), 7.45 (d, J=8.3 Hz, 2H), 6.71 (d, J=2.2 Hz, 2H), 6.48 (t, J=2.2 Hz, 1H), 4.55 (s, 2H), 3.85 (s, 6H).

Preparation Example 28: 4-(2-bromoethyl)-1,1'-biphenyl

Step 1: Synthesis of 2-([1,1'-biphenyl]-4-yl)ethan-1-ol

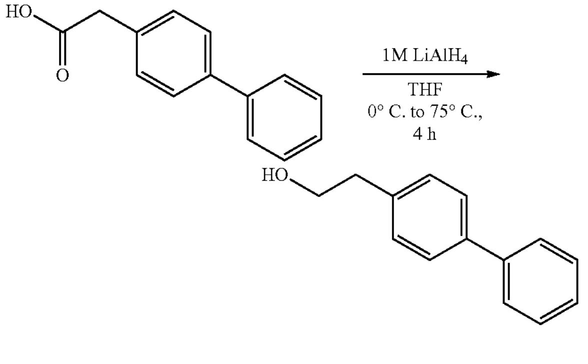

To a solution of 2-([1,1'-biphenyl]-4-yl)acetic acid (559 mg, 3 mmol) in THF (7 mL), $LiAlH_4$ (1 M in THF, 9.0 mL, 3.0 equiv) was added at 0° C. and stirred at 75° C. for 4 hours, and then 1 N NaOH was carefully added to quench it. The reaction mixture was filtered through Celite, and the filtrate was poured into distilled water and extracted with EtOAc. The organic layer was dried over $MgSO_4$ and then concentrated under reduced pressure to obtain 2-([1,1'-biphenyl]-4-yl)ethan-1-ol (522 mg, yield 87%). $^1H$ NMR (300 MHz, Chloroform-d) δ 7.62-7.52 (m, 2H), 7.49-7.40 (m, 1H), 7.39-7.29 (m, 2H), 3.91 (t, J=6.5 Hz, 1H), 2.92 (t, J=6.5 Hz, 1H).

Step 2: Synthesis of 4-(2-bromoethyl)-1,1'-biphenyl

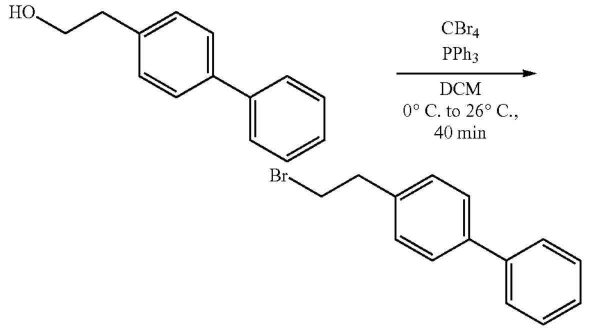

Intermediate BB

To a solution of 2-([1,1'-biphenyl]-4-yl)ethan-1-ol (522 mg, 2.8 mmol, 1.0 equiv) in DCM (12 mL), $CBr_4$ (1.02 g, 3.1 mmol, 1.1 equiv) was added at 0° C. and stirred for 15 minutes, and then $PPh_3$ (813 mg, 3.1 mmol, 1.1 equiv) was added and stirred for 40 minutes. The precipitated solid was filtered to obtain Intermediate BB (639 mg, yield 87%). $^1H$ NMR (300 MHz, Chloroform-d) δ 7.61-7.53 (m, 4H), 7.48-7.40 (m, 2H), 7.38-7.29 (m, 3H), 3.91 (t, J=6.5 Hz, 2H), 2.92 (t, J=6.5 Hz, 2H).

Preparation Example 29: 4'-(bromomethyl)-3-fluoro-1,1'-biphenyl

Step 1: Synthesis of (3'-fluoro-[1,1'-biphenyl]-4-yl) methanol

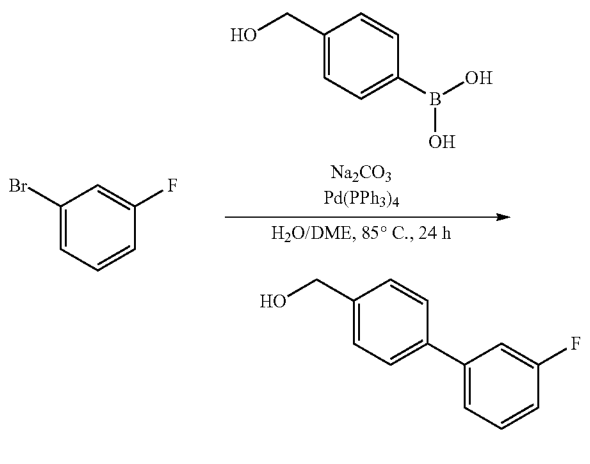

(4-(hydroxymethyl)phenyl)boronic acid (1.04 g, 6.857 mmol), 1-bromo-3-fluorobenzene (1 g, 5.714 mmol), $Na_2CO_3$ (1.51 g, 14.285 mmol) and Pd $(PPh_3)_4$ (330 mg, 0.286 mmol) were dissolved in DME and $H_2O$ (2:1), then heated to 85° C., and stirred for 24 hours. The reaction mixture was extracted with EA and distilled water, and the crude product was purified through flash column chromatography to obtain (3'-fluoro-[1,1'-biphenyl]-4-yl)methanol (1.26 g) as a white solid. $^1H$ NMR (300 MHz, Chloroform-d) δ 7.63-7.56 (m, 2H), 7.50-7.34 (m, 4H), 7.32-7.27 (m, 1H), 7.09-6.99 (m, 1H), 4.76 (s, 2H).

Step 2: Synthesis of 4'-(bromomethyl)-3-fluoro-1,1'-biphenyl

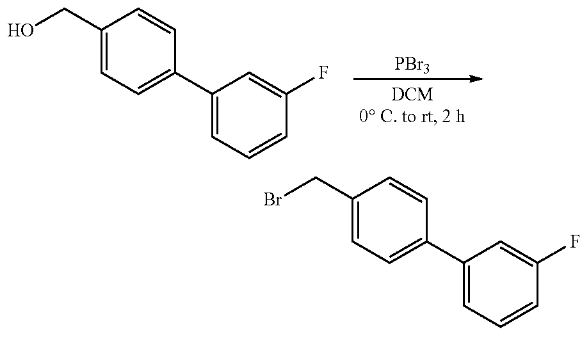

Intermediate CC (3'-Fluoro-[1,1'-biphenyl]-4-yl)methanol (304 mg, 1.641 mmol) was dissolved in DCM, and $PBr_3$ (0.59 mL, 6.231 mmol) was added at 0° C. and stirred for 2 hours, and then additional $PBr_3$ (100 uL) was added and stirred. After 4 hours, 1 mL of MeOH was added at 0° C., and the organic layer was concentrated under reduced pressure to obtain Intermediate CC (1.7 g) as a white solid. $^1H$ NMR (300 MHz, Chloroform-d) δ 7.59-7.53 (m, 2H), 7.51-7.45 (m, 2H), 7.43-7.26 (m, 3H), 7.08-7.02 (m, 1H), 4.55 (s, 2H).

Preparation Example 30: 2-(4-(bromomethyl)phenyl)pyrimidine

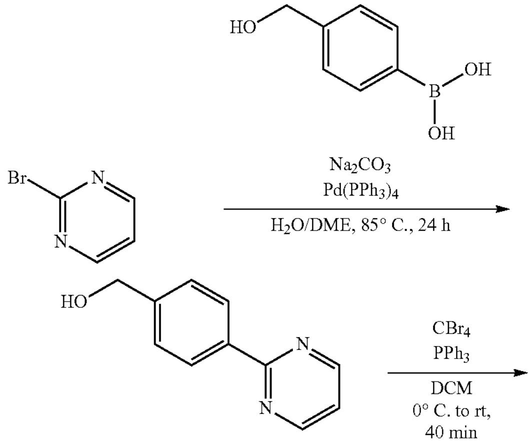

-continued

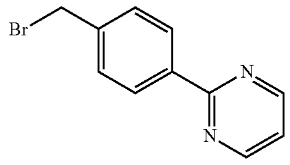

Intermediate DD

Intermediate DD was obtained in the same manner as in Preparation Example 24, except that 2-bromopyridine was used instead of 3-bromoanisole in Step 1 of Preparation Example 24. $^1$H NMR (300 MHz, chloroform-d) δ 8.81 (d, J=4.9 Hz, 2H), 8.43 (d, J=8.4 Hz, 2H), 7.52 (d, J=8.4 Hz, 2H), 7.20 (t, J=4.8 Hz, 1H), 4.56 (s, 2H).

Preparation Example 31: 5-(bromomethyl)-2-phenylpyrimidine

Step 1: Synthesis of (2-phenylpyrimidin-5-yl)methanol

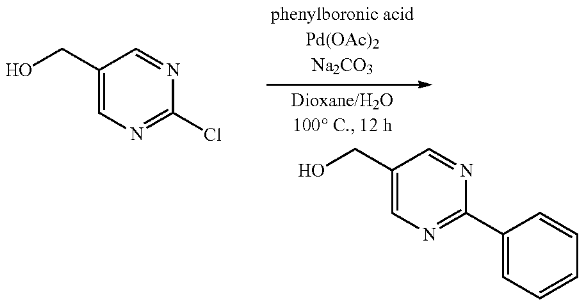

(2-Chloropyrimidin-5-yl)methanol (1.156 g, 8 mmol), phenylboronic acid (1.463 g, 12 mmol), $Pd(OAc)_2$ (179 mg, 0.8 mmol), Xphos (381 mg, 0.8 mmol), and $Na_2CO_3$ (2.199 g, 20 mmol) were dissolved in dioxane/$H_2O$ (4:1, 26 mL), then purged under Ar atmosphere, and then stirred at 100° C. for 12 hours. The reaction mixture was filtered through Celite and then extracted with EA and brine. The organic layer was concentrated under reduced pressure and purified by silica column (EtOAc:Hexane=1:1) to obtain (2-phenylpyrimidin-5-yl)methanol (661 mg, yield 44%). $^1$H NMR (300 MHz, Chloroform-d) δ 8.82 (s, 2H), 8.22-8.52 (m, 2H), 7.58-7.47 (m, 3H), 4.78 (s, 2H).

Step 2: Synthesis of 5-(bromomethyl)-2-phenylpyrimidine

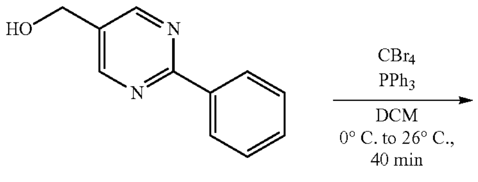

-continued

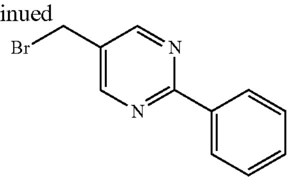

Intermediate EE (2-Phenylpyrimidin-5-yl)methanol (661 mg, 3.549 mmol) was dissolved in DCM (11 mL), and then $CBr_4$ (1.412 g, 4.258 mmol) and $PPh_3$ (1.116 g, 4.258 mmol) were added at 0° C. over 10 minutes and stirred for 40 minutes. The reaction mixture was concentrated under reduced pressure and purified by silica column (EA:hexane=1:9) to obtain Intermediate EE (762 mg, yield 86%). $^1$H NMR (300 MHz, Chloroform-d) δ 8.82 (s, 2H), 8.43-8.46 (m, 2H), 7.49-7.51 (m, 3H), 4.48 (s, 2H).

Preparation Example 32: (3-bromoprop-1-yn-1-yl)benzene

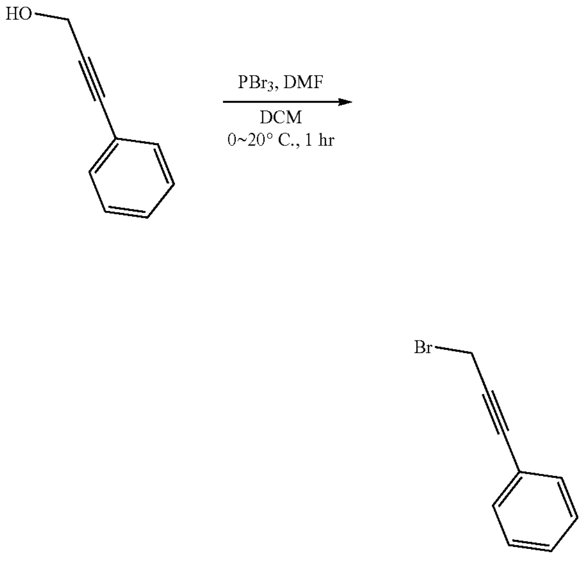

Intermediate FF

To a solution of (3-hydroxyprop-1-yn-1-yl)benzene (10.0 g, 75.6 mmol, 9.43 mL, 1.00 equiv) and DMF (276 mg, 3.78 mmol, 0.05 equiv) in DCM (100 mL), $PBr_3$ (24.5 g, 90.8 mmol, 1.20 equiv) was added at 0° C. and stirred for 1 hour. The reaction mixture was cooled to 0° C., then quenched by addition of distilled water (50 mL), and extracted with DCM (2×50 mL). The organic layer was washed with $NaHCO_3$ aqueous solution (1×100 mL) and brine (1×100 mL), dried over $Na_2SO_4$, filtered, and concentrated under reduced pressure. The crude product was purified by silica gel column chromatography (ether/ethyl acetate=50/1 to 20/1) to obtain Intermediate FF (13.8 g, 70.7 mmol, yield 93.5%) as a colorless oil.

Preparation Example 33: (4-(pyridin-3-yl)phenyl)methanol

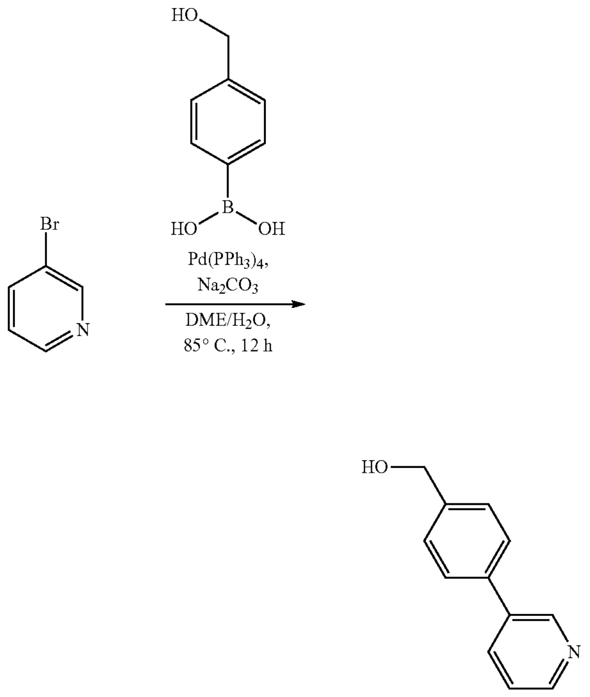

Intermediate GG (4-(Hydroxymethyl)phenyl)boronic acid (1.154 g, 7.595 mmol), 3-bromopyridine (1 g, 6.329 mmol), $Na_2CO_3$ (1.68 g, 15.823 mmol), and $Pd(PPh_3)_4$ (366 mg, 0.316 mmol) were dissolved in DME/$H_2O$ (2:1) and then stirred at 85° C. for 12 hours. The reaction mixture was cooled to ambient temperature and then extracted with EA and distilled water. The crude product was purified through flash column chromatography to obtain Intermediate GG (1.34 g) as a yellow solid. $^1H$ NMR (300 MHz, Chloroform-d) δ 8.82-8.81 (m, 1H), 8.61-8.59 (m, 1H), 8.00 (d, J=8.0 Hz, 1H), 7.61-7.55 (m, 2H), 7.53-7.45 (m, 3H), 4.78 (s, 2H).

Preparation Example 34: (4-(5-fluoropyridin-3-yl)phenyl)methanol

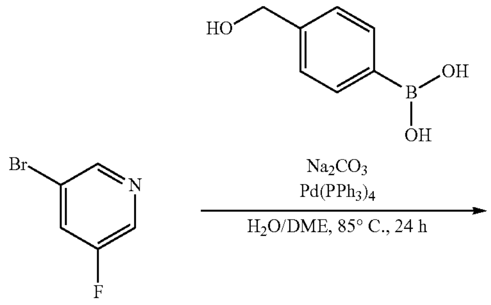

-continued

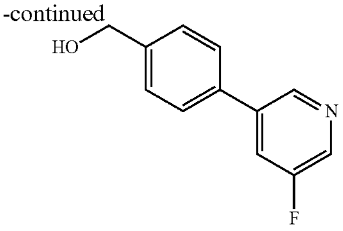

Intermediate HH

Intermediate HH was obtained by using the corresponding starting materials in the same manner as in Preparation Example 33. $^1H$ NMR (300 MHz, Chloroform-d) δ 8.63-8.61 (m, 1H), 8.45-8.44 (m, 1H), 7.65-7.45 (m, 5H), 4.78 (s, 2H).

Preparation Example 35: (4-(5-methoxypyridin-3-yl)phenyl)methanol

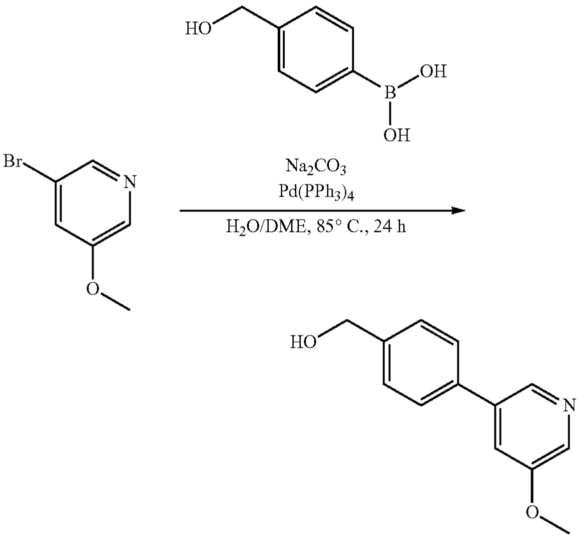

Intermediate II

Intermediate II was obtained by using the corresponding starting materials in the same manner as in Preparation Example 33. $^1H$ NMR (300 MHz, Chloroform-d) δ 8.49-8.48 (m, 1H), 8.30-8.29 (m, 1H), 7.67-7.65 (m, 1H), 7.60-7.50 (m, 4H), 4.79 (s, 2H), 3.99 (s, 3H).

Preparation Example 36: (4-(1-benzyl-1H-pyrazol-4-yl)phenyl)methanol

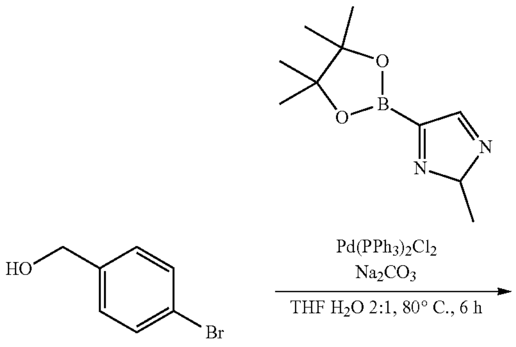

-continued

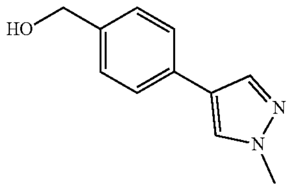

Intermediate JJ (4-Bromophenyl)methanol (1.49 g, 8 mmol), 1-methyl-4-(4,4,5,5-tetramethyl-1,3,2-dioxaborolan-2-yl)-1H-pyrazole (2.5 g, 12 mmol), $Pd(PPh_3)_2Cl_2$ (561 mg, 0.8 mmol), and $Na_2CO_3$ (2.199 g, 20 mmol) were dissolved in THF/$H_2O$ (2:1, 16 mL), purged under Ar atmosphere, and then stirred at 80° C. for 6 hours. The reaction mixture was filtered through Celite, then extracted with EA and brine, and dried over $MgSO_4$. It was purified by silica gel column (EA:hexane=1:3) to obtain Intermediate JJ (948 mg, yield 63%). $^1H$ NMR (300 MHz, Chloroform-d) δ 7.76 (d, J=0.8 Hz, 1H), 7.62 (d, J=0.8 Hz, 1H), 7.43-7.50 (m, 2H), 7.31-7.41 (m, 2H), 4.69 (s, 2H), 3.95 (s, 3H).

Preparation Example 37: (1-benzyl-1H-indol-5-yl)methanol

Step 1: Synthesis of methyl 1-benzyl-1H-indole-5-carboxylate

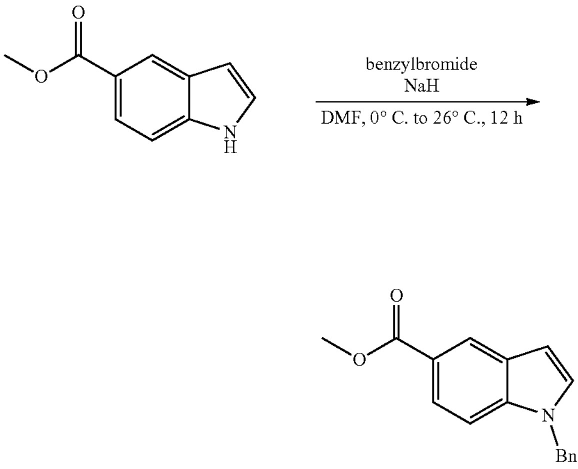 [SMILES: COC(=O)c1ccc2[nH]ccc2c1 ; COC(=O)c1ccc2c(ccn2Cc2ccccc2)c1]

To a solution of methyl 1H-indole-5-carboxylate (2.80 g, 16 mmol) and benzyl bromide (2.1 mL, 17.6 mmol) in DMF (30 mL), NaH (460 mg, 19.2 mmol) was added portionwise at 0° C. and stirred at ambient temperature for 12 hours. The reaction mixture was extracted with EA and brine, and the organic layer was dried over $MgSO_4$ and then concentrated under reduced pressure. The crude product was purified by silica column (EA:hexane=1:9) to obtain methyl 1-benzyl-1H-indole-5-carboxylate (5.083 g, yield 78%). $^1H$ NMR (300 MHz, Chloroform-d) δ 8.42 (dd, J=0.7, 1.7 Hz, 1H), 7.88 (dd, J=1.7, 8.7 Hz, 1H), 7.25-7.35 (m, 4H), 7.19 (d, J=3.2 Hz, 1H), 7.06-7.14 (m, 2H), 6.65 (dd, J=0.9, 3.3 Hz, 1H), 5.35 (s, 2H), 3.93 (s, 3H).

Step 2: Synthesis of (1-benzyl-1H-indol-5-yl)methanol

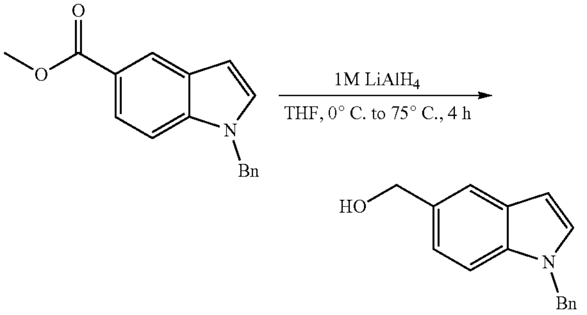

Intermediate KK

Methyl 1-benzyl-1H-indole-5-carboxylate (2.0 g, 7.538 mmol) was dissolved in THF (25 mL), and $LiAlH_4$ (1 M in THF, 22.6 mL, 22.615 mmol) was added at 0° C. and stirred at 75° C. for 4 hours. The organic layer was filtered through Celite, concentrated under reduced pressure, and purified by silica column (EA:hexane=1:2) to obtain Intermediate KK (1.734 g, yield 97%). $^1H$ NMR (300 MHz, Chloroform-d) δ 7.62 (m, 1H), 7.22-7.31 (m, 4H), 7.18 (dd, J=1.7, 8.5 Hz, 1H), 7.04-7.11 (m, 2H), 6.53 (dd, J=0.8, 3.1 Hz, 1H), 5.31 (s, 2H), 4.74 (s, 2H).

Preparation Example 38: (4-(pyridin-2-yl)phenyl)methanol

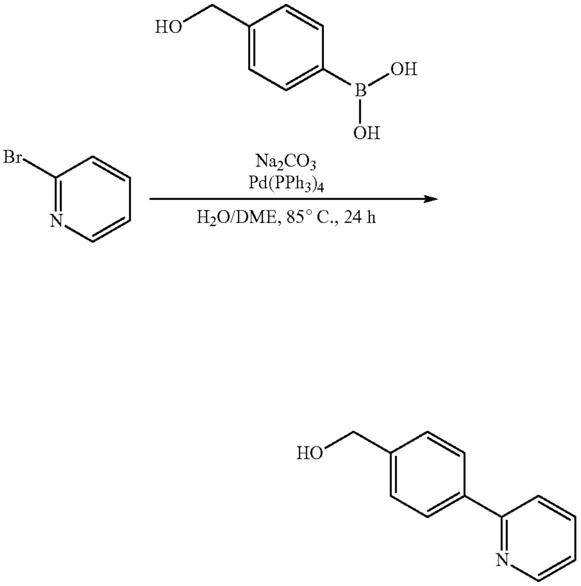

Intermediate LL

Intermediate LL was obtained by using the corresponding starting materials in the same manner as in Preparation Example 33. $^1H$ NMR (300 MHz, chloroform-d) δ 8.73 (d, J=4.9 Hz, 1H), 8.01 (d, J=8.2 Hz, 2H), 7.88-7.73 (m, 2H), 7.49 (d, J=8.2 Hz, 2H), 7.32-7.30 (m, 1H), 4.77 (s, 2H).

Preparation Example 39: (6-phenylpyridin-3-yl)methanol

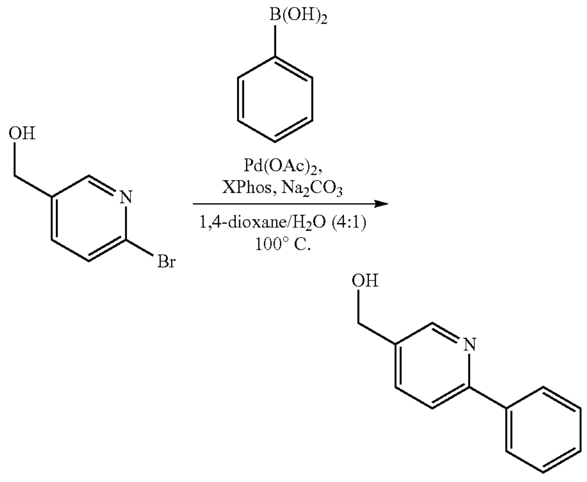

Intermediate MM

To a solution of (6-bromopyridin-3-yl)methanol (940.1 mg, 5.0 mmol) in 1,4-dioxane/$H_2O$ (0.25 M), phenylboronic acid (914.5 mg, 7.5 mmol), $Pd(OAc)_2$ (56.1 mg, 0.25 mmol), Xphos (238.4 mg, 0.5 mmol) and $Na_2CO_3$ (1.59 g, 15.0 mmol) were added and stirred at 100° C. After 18 hours, the reaction mixture was cooled to ambient temperature and diluted with brine (50 mL) and ethyl acetate (50 mL), and the aqueous layer was extracted with ethyl acetate (30 mL). The organic layer was dried over $Na_2SO_4$ and concentrated under reduced pressure. The crude product was purified by column chromatography (hexane:ethyl acetate=3:7) to obtain Intermediate MM (618.6 mg, yield 67%) as a white solid. $^1H$ NMR (500 MHz, $CDCl_3$) δ 8.66-8.62 (m, 1H), 7.99-7.93 (m, 2H), 7.77 (dd, J=8.1, 2.2 Hz, 1H), 7.71 (d, J=8.1 Hz, 1H), 7.46 (t, J=7.5 Hz, 2H), 7.43-7.36 (m, 1H), 4.75 (s, 2H).

Preparation Example 40: (4-pyridin-4-yl)phenyl)methanol

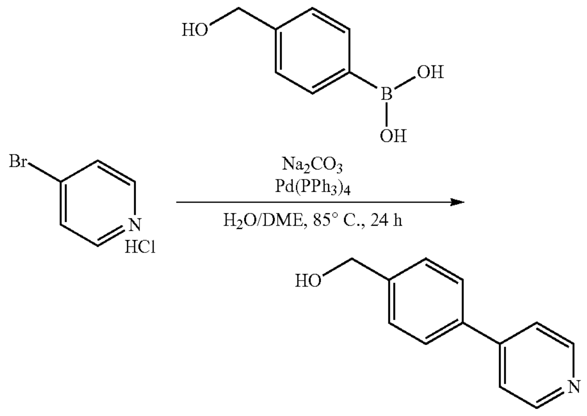

Intermediate NN

Intermediate NN was obtained by using the corresponding starting materials in the same manner as in Preparation Example 33. $^1H$ NMR (300 MHz, Chloroform-d) δ 8.71-8.62 (m, 2H), 7.66 (d, J=8.2 Hz, 2H), 7.60-7.55 (m, 2H), 7.51 (d, J=8.2 Hz, 2H), 4.79 (s, 2H).

Preparation Example 41: (4-(6-methoxypyridin-2-yl)phenyl)methanol

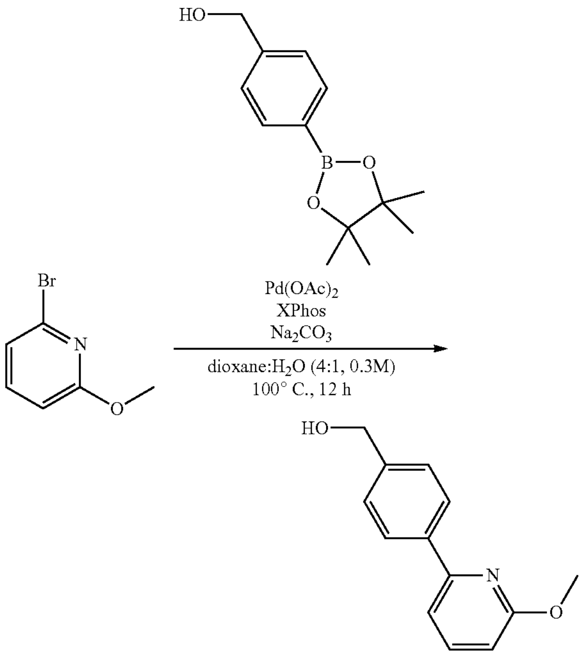

Intermediate OO

Intermediate OO was obtained by using the corresponding starting materials in the same manner as in Preparation Example 39. $^1H$ NMR (300 MHz, Chloroform-d) δ 8.07 (d, J=8.3 Hz, 2H), 7.69-7.62 (m, 1H), 7.48 (d, J=8.4 Hz, 2H), 7.37 (d, J=7.4 Hz, 1H), 6.72 (d, J=8.2 Hz, 1H), 4.78 (s, 2H), 4.06 (s, 3H).

Preparation Example 42: (4-(4-methoxypyridin-2-yl)phenyl)methanol

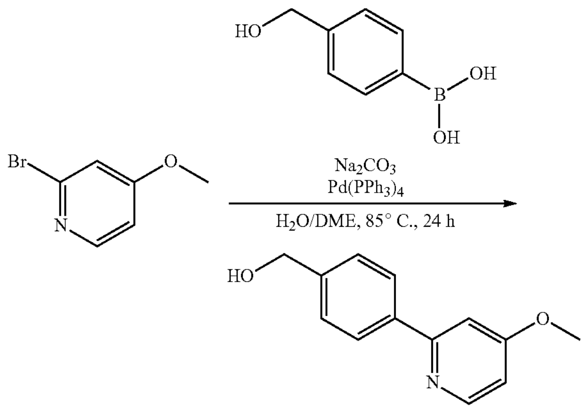

Intermediate PP

Intermediate PP was obtained by using the corresponding starting materials in the same manner as in Preparation Example 33. ${}^{1}H$ NMR (300 MHz, Chloroform-d) δ 8.63 (d, J=6.3 Hz, 1H), 8.02 (d, J=8.2 Hz, 2H), 7.52 (d, J=8.2 Hz, 3H), 7.30 (d, J=2.5 Hz, 1H), 6.97 (dd, J=6.3, 2.5 Hz, 1H), 4.78 (s, 2H), 4.03 (s, 3H).

Preparation Example 43: (6-(3-fluoro-5-methoxyphenyl)pyridin-3-yl)methanol

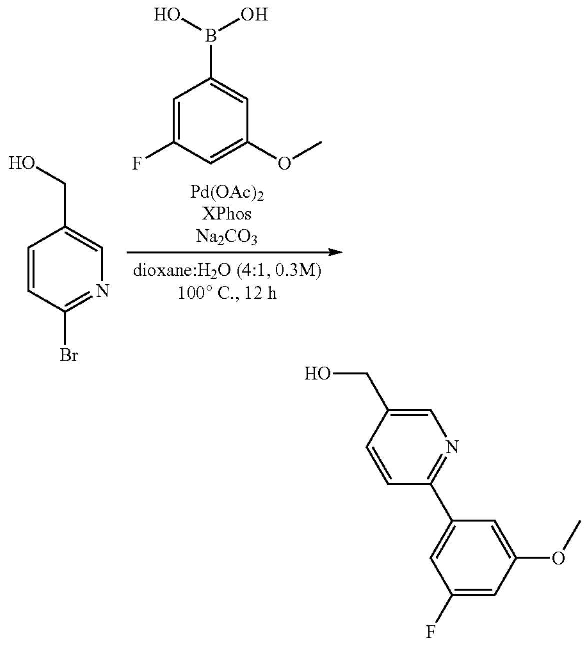

Intermediate QQ

Intermediate QQ was obtained by using the corresponding starting materials in the same manner as in Preparation Example 39. ${}^{1}H$ NMR (300 MHz, DMSO-d6) δ 8.63-8.60 (m, 1H), 8.00 (d, J=8.2 Hz, 1H), 7.82 (dd, J=8.1, 2.0 Hz, 1H), 7.53-7.45 (m, 2H), 6.94-6.86 (m, 1H), 5.39 (s, 1H), 4.58 (d, J=5.6 Hz, 2H), 3.86 (s, 3H).

Preparation Example 44: (4-(4-methyl-1H-pyrazol-1-yl)phenyl)methanol

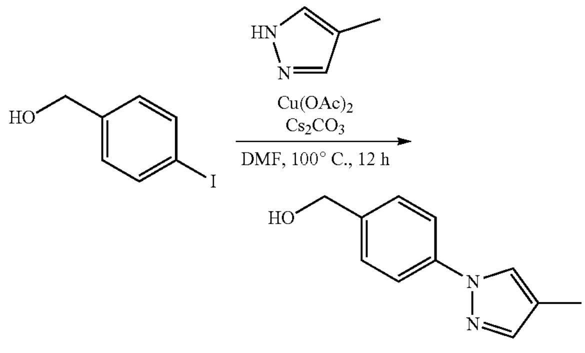

Intermediate RR (4-Iodophenyl)methanol (234 mg, 1 mmol), 4-methyl-1H-pyrazole (121 uL, 1.5 mmol), $Cs_2CO_3$ (651 mg, 2 mmol), and $Cu(OAc)_2$ (18 mg, 0.1 mmol) were dissolved in DMF (5 mL), and then the mixture was purged under Ar atmosphere and then stirred at 100° C. for 12 hours. The reaction mixture was extracted with EA and brine, and then the organic layer was dried over $MgSO_4$ and concentrated under reduced pressure. The mixture was purified by silica chromatography (EA:hexane=1:3) to obtain Intermediate RR (191 mg, mixture). LC/MS (ESI) m/z: 189.1 [M+H].

Preparation Example 45: (4-(3-methyl-5-(trifluoromethyl)-1H-pyrazol-1-yl)phenyl)methanol

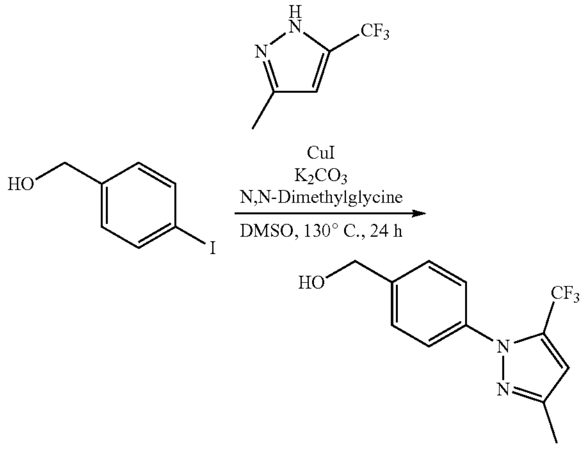

Intermediate SS 3-methyl-5-(trifluoromethyl)-1H-pyrazole (353 mg, 2.35 mmol), (4-iodophenyl)methanol (500 mg, 2.136 mmol), $K_2CO_3$ (590 mg, 4.272 mmol), CuI (41 mg, 0.214 mmol), and N,N-dimethylglycine (44 mg, 0.427 mmol) were dissolved in DMSO, heated to 130° C., and stirred for 24 hours. The reaction mixture was cooled to ambient temperature and extracted with EA and distilled water, and then the crude product was purified by flash column chromatography to obtain Intermediate SS (562 mg, yield 99%) as a clear liquid. ${}^{1}H$ NMR (300 MHz, Chloroform-d) δ 7.54-7.40 (m, 4H), 6.46 (s, 1H), 4.78 (d, J=5.9 Hz, 2H), 2.35 (d, J=0.7 Hz, 3H), 1.87 (t, J=5.9 Hz, 1H).

Preparation Example 46: (5-(3-fluoro-5-methoxyphenyl)pyridin-2-yl)methanol

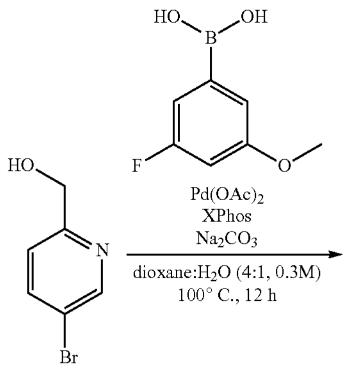

-continued

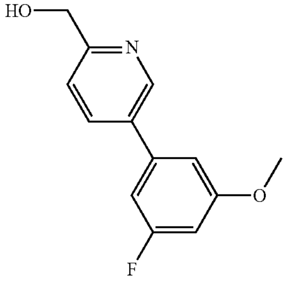

Intermediate TT

Intermediate TT was obtained by using the corresponding starting materials in the same manner as in Preparation Example 39. $^1$H NMR (300 MHz, DMSO-d6) δ 8.83 (d, J=2.1 Hz, 1H), 8.13 (dd, J=8.2, 2.4 Hz, 1H), 7.55 (d, J=8.2 Hz, 1H), 7.22-7.12 (m, 2H), 6.88 (dt, J=11.0, 2.2 Hz, 1H), 5.49 (t, J=5.9 Hz, 1H), 4.62 (d, J=5.9 Hz, 2H), 3.85 (s, 3H).

EXAMPLE

Example 1: 6-(4-([1,1'-biphenyl]-4-ylmethyl)-2,5-dimethylthiophene-3-carboxamido)spiro[3.3]heptane-2-carboxylic acid

Step 1: Synthesis of [1,1'-biphenyl]-4-yl(2,5-dimethylthiophen-3-yl)methanone

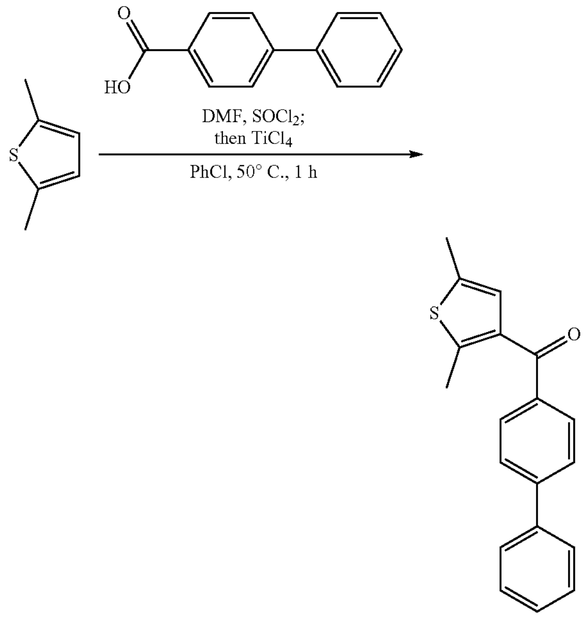

To a solution of [1,1'-biphenyl]-4-carboxylic acid (7.8 g, 39.3 mmol) and DMF (about 0.1 mL) in PhCl (45 mL, 0.8 M), $SOCl_2$ (4.9 g, 41.0 mmol) was added at 0° C., and then the reaction mixture was heated to 50° C. and stirred for 1 hour. After 1 hour, the mixture was cooled to ambient temperature, and dimethylthiophene (4.1 mL, 35.7 mmol) was added. The reaction mixture solution was cooled to 0° C., and 1 M $TiCl_4$ solution (35.7 mL, 35.7 mmol) was added. After 1 hour, the reaction mixture was acidified by addition of 1 N HCl solution and extracted with heptane. The combined extracts were dried over $Na_2SO_4$, then filtered, and concentrated. The crude product was purified by column chromatography to obtain [1,1'-biphenyl]-4-yl(2,5-dimethylthiophen-3-yl)methanone (3.31 g, yield 32%). $^1$H NMR (500 MHz, chloroform-d) δ 7.90 (d, J=8.4 Hz, 2H), 7.71 (d, J=8.4 Hz, 2H), 7.67 (d, J=7.1 Hz, 2H), 7.51 (t, J=7.5 Hz, 2H), 7.43 (t, J=7.4 Hz, 1H), 6.85 (s, 1H), 2.63 (s, 3H), 2.46 (s, 3H). LC/MS (ESI) m/z: 293.7 $[M+H]^+$.

Step 2: Synthesis of [1,1'-biphenyl]-4-yl(4-bromo-2,5-dimethylthiophen-3-yl)methanone

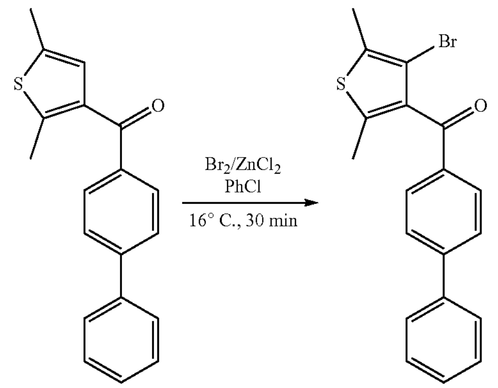 [SMILES: Cc1cc(C(=O)c2ccc(-c3ccccc3)cc2)c(C)s1 ; Cc1sc(C)c(C(=O)c2ccc(-c3ccccc3)cc2)c1Br]

To a solution of [1,1'-biphenyl]-4-yl(2,5-dimethylthiophen-3-yl)methanone (3.29 g 11.25 mol) and PhCl (14.1 mL, 0.8 M), ZnCl, (46.0 mg, 0.34 mmol) was added, and then the reaction mixture was cooled to 16° C. $Br_2$ (1.8 g, 22.5 mmol) was added at 16° C. over 30 minutes. The reaction mixture was stirred at room temperature for 30 minutes, and the reaction mixture was acidified by addition of 1 N HCl solution. The product was extracted with heptane, and then the combined extracts were dried over $Na_2SO_4$, then filtered, and concentrated. The crude product was purified by column chromatography to obtain [1,1'-biphenyl]-4-yl(4-bromo-2,5-dimethylthiophen-3-yl)methanone (2.61 g, yield 63%). $^1$H NMR (500 MHz, chloroform-d) δ 7.94 (d, J=7.5 Hz, 2H), 7.72 (d, J=7.7 Hz, 2H), 7.67 (d, J=7.6 Hz, 2H), 7.50 (t, J=7.3 Hz, 2H), 7.44 (t, J=7.3 Hz, 1H), 2.42 (s, 3H), 2.38 (s, 3H). LC/MS (ESI) m/z: 373.3 $[M+H]^+$.

Step 3: Synthesis of 3-([1,1'-biphenyl]-4-ylmethyl)-4-bromo-2,5-dimethylthiophene

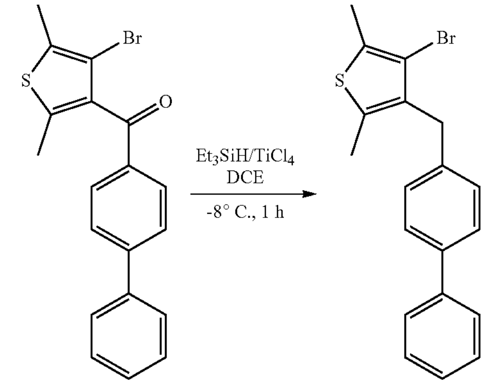 [SMILES: Cc1sc(C)c(C(=O)c2ccc(-c3ccccc3)cc2)c1Br ; Cc1sc(C)c(Cc2ccc(-c3ccccc3)cc2)c1Br]

To a solution of [1,1'-biphenyl]-4-yl(4-bromo-2,5-dimethylthiophen-3-yl)methanone (2.61 g, 7.03 mmol) and DCE (14.1 mL, 0.5 M), $Et_3SiH$ (2.1 g, 17.6 mmol) was added. The reaction mixture was cooled to −8° C., and 1 M $TiCl_4$ solution (7.1 mL, 7.1 mmol) was slowly added. The reaction mixture was stirred at ambient temperature for 1 hour, and then the reaction mixture was acidified by addition of 1 N HCl solution. The product was extracted with heptane, then dried over $Na_2SO_4$, then filtered and concentrated. The crude product was purified by column chromatography to obtain 3-([1,1'-biphenyl]-4-ylmethyl)-4-bromo-2,5-dimethylthiophene (1.45 g, yield 58%). $^1H$ NMR (500 MHz, chloroform-d) δ 7.59 (d, J=7.6 Hz, 2H), 7.52 (d, J=8.0 Hz, 2H), 7.45 (d, J=7.6 Hz, 2H), 7.35 (d, J=7.3 Hz, 1H), 7.24 (d, J=7.9 Hz, 2H), 4.00 (s, 2H), 2.40 (d, J=4.4 Hz, 6H).

Step 4: Synthesis of 4-([1,1'-biphenyl]-4-ylmethyl)-2,5-dimethylthiophene-3-carboxylic acid

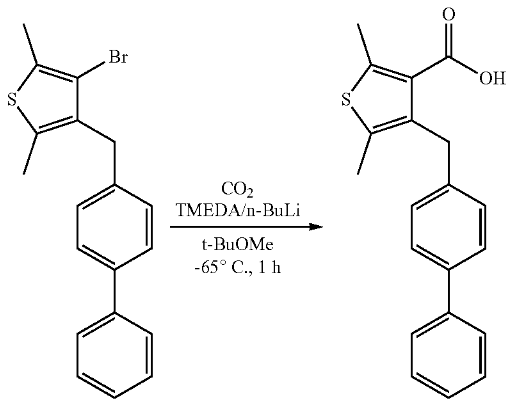 [SMILES: Cc1sc(C)c(Cc2ccc(-c3ccccc3)cc2)c1Br ; Cc1sc(C)c(C(=O)O)c1Cc1ccc(-c2ccccc2)cc1]

To a solution of 3-([1,1'-biphenyl]-4-ylmethyl)-4-bromo-2,5-dimethylthiophene (1.0 g, 2.80 mmol), TMEDA (0.46 mL, 3.08 mmol) and methyl t-butyl ether (14 mL, 0.2 M), n-BuLi (1.5 mL, 2.64 mmol) was gradually added at −65° C. and then stirred. The mixture was stirred for 30 minutes, and then an excess of dry ice was added at −65° C. and stirred for 1 hour. The reaction mixture was acidified by addition of 1 N HCl solution and then extracted with EtOAc and distilled water. The organic layer was dried over $Na_2SO_4$, then filtered, concentrated, and purified to obtain 4-([1,1'-biphenyl]-4-ylmethyl)-2,5-dimethylthiophene-3-carboxylic acid (0.46 g, yield 51%). $^1H$ NMR (500 MHz, DMSO-$d_6$) δ 12.64 (s, 1H), 7.61 (d, J=7.6 Hz, 2H), 7.55-7.52 (m, 2H), 7.44 (t, J=7.2 Hz, 2H), 7.36-7.32 (m, 1H), 7.16-7.12 (m, 2H), 4.17 (s, 2H), 2.55 (s, 3H), 2.31 (s, 3H).

Step 5: Synthesis of methyl 6-(4-([1,1'-biphenyl]-4-ylmethyl)-2,5-dimethylthiophene-3-carboxamido)spiro[3.3]heptane-2-carboxylate

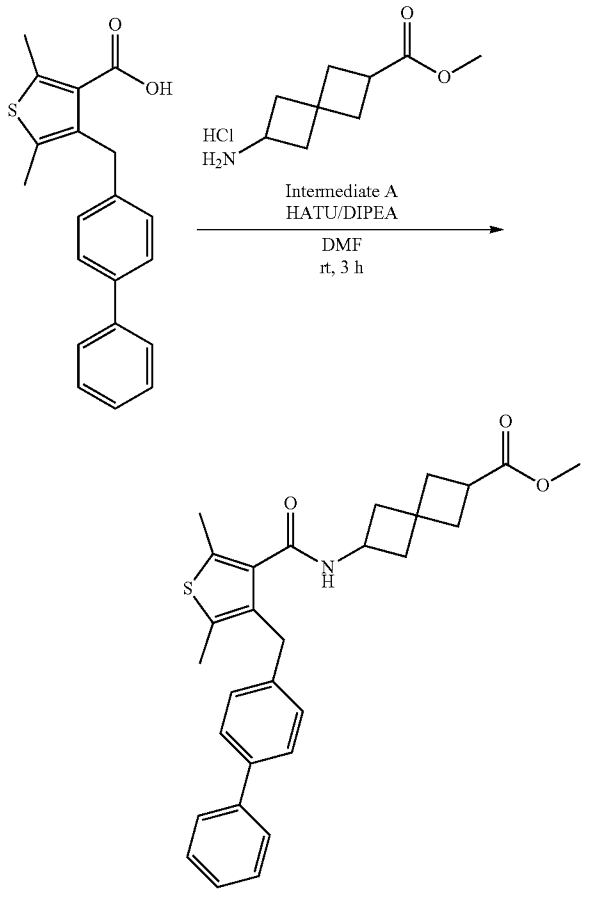 [SMILES: Cc1sc(C)c(C(=O)O)c1Cc1ccc(-c2ccccc2)cc1 ; Cl ; COC(=O)C1CC2(CC(N)C2)C1 ; COC(=O)C1CC2(CC(NC(=O)c3c(C)sc(C)c3Cc3ccc(-c4ccccc4)cc3)C2)C1]

To a solution of 4-([1,1'-biphenyl]-4-ylmethyl)-2,5-dimethylthiophene-3-carboxylic acid (0.1 g, 0.31 mmol) in DMF (1.1 mL, 0.3 M), Intermediate A (70 mg, 0.34 mmol), HATU (0.13 g, 0.34 mmol) and DIPEA (0.16 mL, 0.93 mmol) were added and stirred at ambient temperature for 3 hours. The reaction mixture was basified by addition of 1N NaOH solution and then extracted with EtOAc and distilled water. The organic layer was dried over $Na_2SO_4$, then filtered, concentrated, and purified by column chromatography to obtain methyl 6-(4-([1,1'-biphenyl]-4-ylmethyl)-2,5-dimethylthiophene-3-carboxamido)spiro[3.3]heptane-2-carboxylate (110 mg, yield 75%). $^1H$ NMR (500 MHz, chloroform-d) δ 7.57 (d, J=7.6 Hz, 2H), 7.52 (d, J=7.3 Hz, 2H), 7.46 (t, J=7.3 Hz, 2H), 7.36 (t, J=7.2 Hz, 1H), 7.19 (d, J=7.6 Hz, 2H), 5.39 (d, J=7.1 Hz, 1H), 4.28 (m, 1H), 4.00 (s, 2H), 3.66 (s, 3H), 2.97 (p, J=8.9, 8.4 Hz, 1H), 2.46 (s, 3H), 2.38 (s, 3H), 2.30 (dd, J=14.1, 7.1 Hz, 4H), 2.21-2.14 (m, 1H), 1.99 (d, J=19.5 Hz, 1H), 1.53 (dt, J=19.1, 10.0 Hz, 2H). LC/MS (ESI) m/z: 475.2 $[M+H]^+$.

Step 6: Synthesis of 6-(4-([1,1'-biphenyl]-4-ylmethyl)-2,5-dimethylthiophene-3-carboxamido)spiro[3.3]heptane-2-carboxylic acid

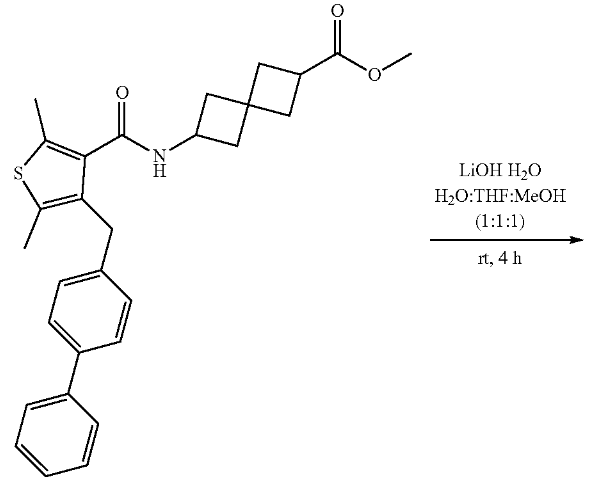

-continued

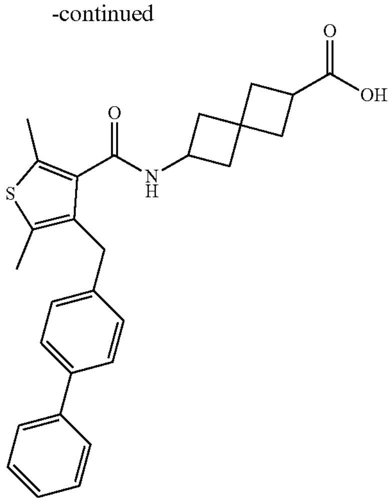

1

To a solution of methyl 6-(4-([1,1'-biphenyl]-4-ylmethyl)-2,5-dimethylthiophene-3-carboxamido)spiro[3.3]heptane-2-carboxylate (110 mg, 0.23 mmol) in $H_2O$:THF:MeOH (1:1:1), LiOH·$H_2O$ (29 mg, 0.69 mmol) was added and stirred for 4 hours. The reaction mixture was acidified by addition of 1 N HCl solution and then extracted with EtOAc and distilled water. The organic layer was dried over $Na_2SO_4$, then filtered, and concentrated to obtain the compound of Example 1 (86 mg, yield 81%) without purification. $^1H$ NMR (500 MHz, DMSO-$d_6$) δ 12.03 (s, 1H), 8.29 (d, J=7.4 Hz, 1H), 7.61 (d, J=7.7 Hz, 2H), 7.51 (d, J=7.6 Hz, 2H), 7.45 (t, J=7.4 Hz, 2H), 7.34 (t, J=7.2 Hz, 1H), 7.19 (d, J=7.7 Hz, 2H), 4.16 (h, J=8.3 Hz, 1H), 3.90 (s, 2H), 2.91 (p, J=8.3 Hz, 1H), 2.34 (s, 3H), 2.32 (s, 3H), 2.29-2.13 (m, 4H), 2.11-2.06 (m, 1H), 2.02 (s, 1H), 1.87 (s, 1H), 1.85 (d, J=9.6 Hz, 1H). LC/MS (ESI) m/z: 460.01 $[M+H]^+$.

The compounds of Examples 2 to 5 were prepared in the same manner as in Example 1 except for the differences in the preparation methods described below.

TABLE 1

| Example No. | Chemical structure | Name | Difference in preparation method |
|---|---|---|---|
| 2 | 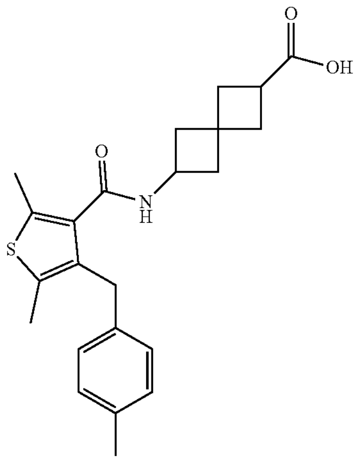 [SMILES: Cc1ccc(Cc2c(C)sc(C)c2C(=O)NC2CC3(C2)CC(C(=O)O)C3)cc1] | 6-(2,5-dimethyl-4-(4-methylbenzyl)thiophene-3-carboxamido)spiro[3.3]heptane-2-carboxylic acid | 4-methylbenzoic acid was used instead of [1,1'-biphenyl]-4-carboxylic acid in Step 1 |

TABLE 1-continued

| Example No. | Chemical structure | Name | Difference in preparation method |
|---|---|---|---|
| 3 | 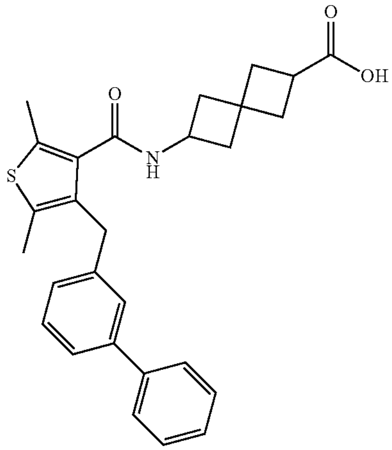 [SMILES: Cc1sc(C)c(C(=O)NC2CC3(C2)CC(C(=O)O)C3)c1Cc1cccc(-c2ccccc2)c1] | 6-(4-([1,1'-biphenyl]-3-ylmethyl)-2,5-dimethylthiophene-3-carboxamido)spiro[3.3]heptane-2-carboxylic acid | [1,1'-biphenyl]-3-carboxylic acid was used instead of [1,1'-biphenyl]-carboxylic acid in Step 1 |
| 4 | 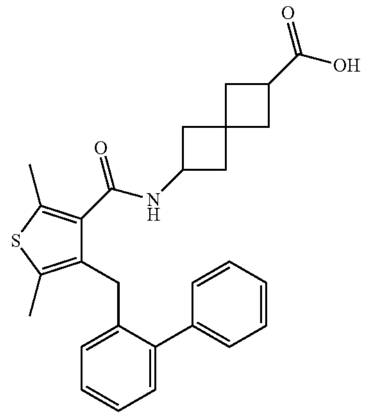 [SMILES: Cc1sc(C)c(C(=O)NC2CC3(C2)CC(C(=O)O)C3)c1Cc1ccccc1-c1ccccc1] | 6-(4-([1,1'-biphenyl]-2-ylmethyl)-2,5-dimethylthiophene-3-carboxamido)spiro[3.3]heptane-2-carboxylic acid | [1,1'-biphenyl]-2-carboxylic acid was used instead of [1,1'-biphenyl-4-carboxylic acid in Step 1 |
| 5 | 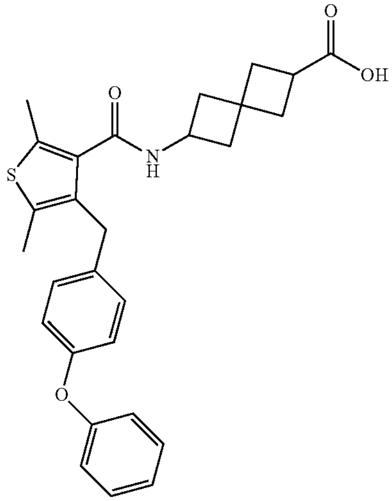 [SMILES: Cc1sc(C)c(C(=O)NC2CC3(C2)CC(C(=O)O)C3)c1Cc1ccc(Oc2ccccc2)cc1] | 6-(2,5-dimethyl-4-(4-phenoxybenzyl)thiophene-3-carboxamido)spiro[3.3]heptane-2-carboxylic acid | 4-phenoxybenzoic acid was used instead of [1,1'-biphenyl-4-carboxylic acid in Step 1 |

TABLE 2

| Example No. | LC/MS (EST) m/z: [M + H]+ | NMR |
|---|---|---|
| 2 | 398.5 | $^1$H NMR (500 MHz, DMSO-$d_6$) δ 12.01 (s, 1H), 8.25 (d. J = 7.5 Hz, 1H), 7.02 (d. J = 7.7 Hz, 2H), 6.97 (d, J = 7.7 Hz, 2H), 4.15 (d. J = 7.9 Hz, 1H), 3.80 (s, 2H), 2.96-2.88 (m, 1H), 2.35 (dd, J = 11.1, 6.3 Hz, 1H), 2.29 (d, J = 7.1 Hz, 6H), 2.25 (s, 1H), 2.23 (s, 3H), 2.18 (t, J = 9.5 Hz, 2H), 2.12-2.00 (m, 2H), 1.93-1.87 (m, 1H), 1.86-1.80 (m, 1H) |
| 3 | 460.2 | $^1$H NMR (500 MHz, Chloroform-d) δ 7.57 (d, J = 7.1 Hz, 2H), 7.46 (t, J = 7.7 Hz, 3H), 7.37 (q, J = 7.4 Hz, 3H), 7.09 (d, J = 7.1 Hz, 1H), 5.36 (d, J = 7.7 Hz, 1H), 4.23 (h, J = 7.8 Hz, 1H), 4.03 (s, 2H), 2.97 (p, J = 8.5 Hz, 1H), 2.44 (s, 3H), 2.40 (s, 3H), 2.37-2.30 (m, 1H), 2.24 (dt, J = 17.2, 6.8 Hz, 3H), 2.17-2.11 (m, 1H), 1.99-1.93 (m, 1H), 1.51-1.43 (m, 2H). |
| 4 | 460.6 | $^1$H NMR (500 MHz, Chloroform-d) δ 7.46 (t. J = 7.4 Hz, 2H), 7.39 (d, J = 7.4 Hz, 1H), 7.37-7.33 (m, 2H). 7.30 (d, J = 5.2 Hz, 1H), 7.29-7.25 (m, 2H), 6.95 (d, J = 7.8 Hz, 1H), 5.34 (d, J = 7.5 Hz, 1H), 4.20 (h, J = 7.9 Hz, 1H), 3.86 (s. 2H), 3.03 (p, J = 8.4 Hz, 1H), 2.45 (s, 3H), 2.41 (dd, J = 7.0, 4.8 Hz, 1H), 2.34-2.26 (m, 3H), 2.23 (dd, J = 11.7, 8.3 Hz, 1H), 2.14 (s, 3H), 2.11-2.05 (m, 1H), 1.45 (ddd, J = 20.5, 11.3, 8.6 Hz, 2H), |
| 5 | 476.4 | $^1$H NMR (500 MHz, Chloroform-d) δ 7.36-7.32 (m, 2H), 7.09 (dd, J = 23.6, 8.0 Hz, (3H), 6.99 (d, J = 8.5 Hz, 2H), 6.94 (d, J = 8.6 Hz, 2H), 5.42 (d, J = 7.8 Hz, 1H), 4.30 (h, J = 8.0 Hz, 1H), 3.93 (s, 2H), 3.05 (p, J = 8.5 Hz, 1H), 2.52-2.46 (m, 1H), 2.45 (s, 3H), 2.36 (d, J = 4.3 Hz, 6H), 2.27 (dd, J = 11.7, 8.2 Hz, 1H), 2.12 (ddd, J = 11.6, 8.7, 2.3 Hz, 1H), 1.66-1.56 (m, 2H). |

Example 6: 6-(4-(2-([1,1'-biphenyl]-4-yl)ethyl)-2,5-dimethylthiophene-3-carboxamido)spiro[3.3]heptane-2-carboxylic acid Step 1: Synthesis of 2-([1,1'-biphenyl]-4-yl)-1-(2,5-dimethylthiophen-3-yl)ethan-1-one

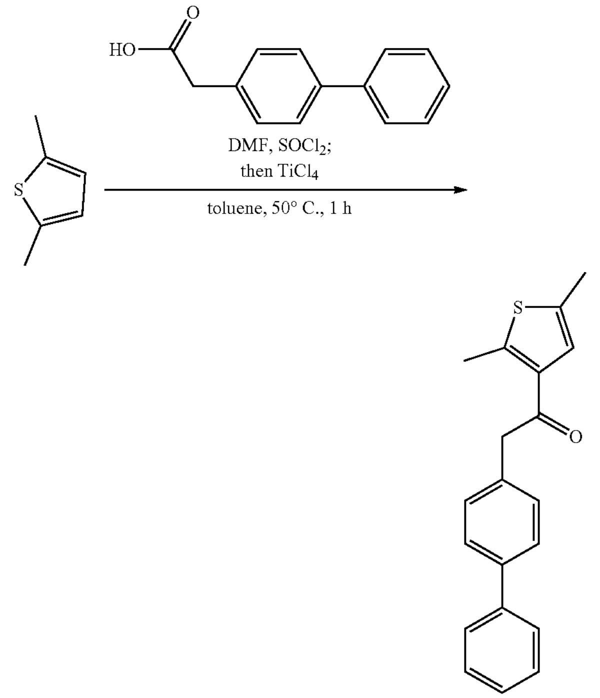

To a solution of 2-([1,1'-biphenyl]-4-yl)acetic acid (10.4 g, 49.1 mmol) and DMF (about 1 mL) in toluene (56 mL, 0.8 M), $SOCl_2$ (6.1 g, 51.3 mmol) was added dropwise at 0° C., and then the reaction mixture was heated to 50° C. for 1 hour. The reaction mixture was cooled to ambient temperature, and dimethylthiophene (5.1 mL, 44.6 mmol) was added and then cooled to 0° C., and 1 M $TiCl_4$ solution (45 mL, 44.6 mmol) was added. The reaction mixture was acidified by addition of 1 N HCl solution and extracted with heptane, and the combined extracts were dried over $Na_2SO_4$, then filtered and concentrated. The crude product was purified by column chromatography to obtain 2-([1,1'-biphenyl]-4-yl)-1-(2,5-dimethylthiophen-3-yl)ethan-1-one (8.8 g, yield 64%). $^1$H NMR (500 MHz, chloroform-d) δ 7.60 (t, J=8.6 Hz, 4H), 7.46 (t, J=7.5 Hz, 2H), 7.36 (dd, J=15.0, 7.5 Hz, 3H), 7.14 (s, 1H), 4.17 (s, 2H), 2.71 (s, 3H), 2.46 (s, 3H).

Step 2: Synthesis of 3-(2-([1,1'-biphenyl]-4-yl)ethyl)-2,5-dimethylthiophene

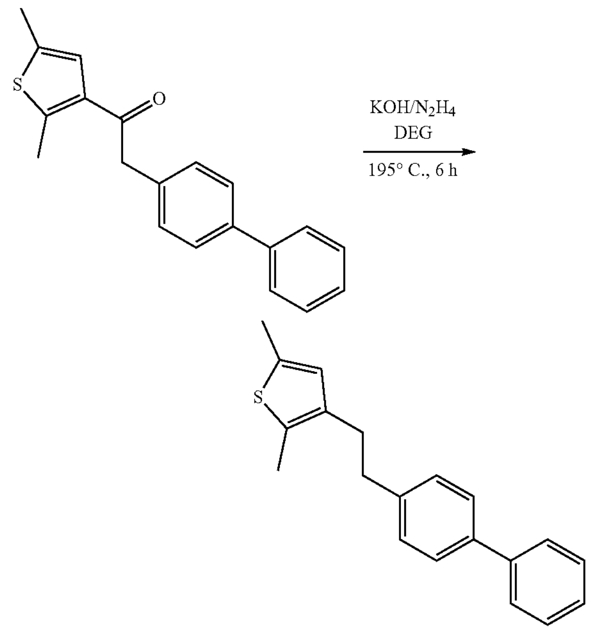

To a solution of 2-([1,1'-biphenyl]-4-yl)-1-(2,5-dimethylthiophen-3-yl)ethan-1-one (4.0 g, 13.1 mmol) in diethyleneglycol (17.7 mL, 0.7 M), 80% hydrazine hydrate (2.0 mL) and KOH (2.5 g, 44.5 mmol) were added. The reaction mixture was stirred under reflux at 195° C. for 6 hours, and then the solution was cooled to ambient temperature, and 18 mL of distilled water was added and then slowly poured into 11 mL of 6 N HCl aqueous solution to induce the formation of a precipitate, thereby obtaining 3-(2-([1,1'-biphenyl]-4-yl)ethyl)-2,5-dimethylthiophene (1.97 g, yield 52%). $^1$H NMR (500 MHz, chloroform-d) δ 7.63 (d, J=7.1 Hz, 2H), 7.55 (d, J=6.5 Hz, 2H), 7.47 (t, J=7.7 Hz, 2H), 7.37 (t, J=7.4 Hz, 1H), 7.27 (d, J=8.1 Hz, 2H), 6.55 (s, 1H), 2.91-2.87 (m, 2H), 2.82-2.77 (m, 2H), 2.44 (s, 3H), 2.22 (s, 3H).

Step 3: Synthesis of 3-(2-([1,1'-biphenyl]-4-yl)ethyl)-4-bromo-2,5-dimethylthiophene

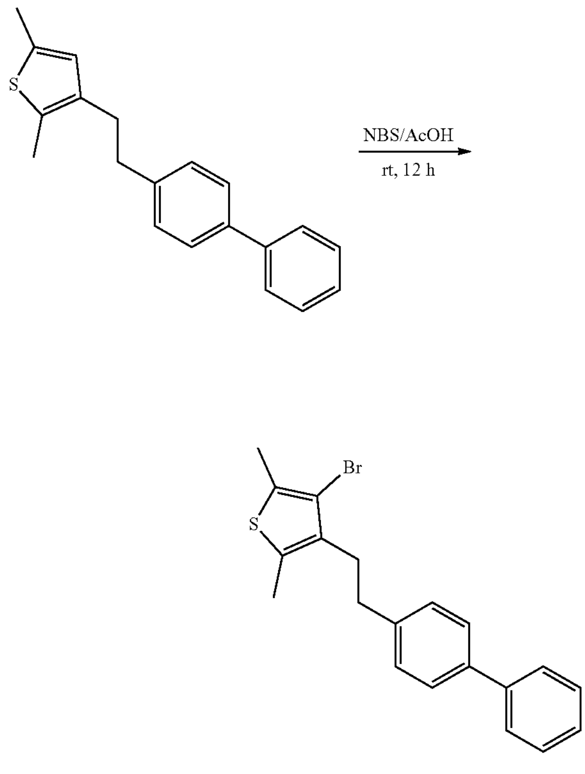

To a solution of 3-(2-([1,1'-biphenyl]-4-yl)ethyl)-2,5-dimethylthiophene (0.21 g, 0.72 mmol) in AcOH (4 mL), N-bromosuccinimide (0.13 g, 0.72 mmol) was added. After stirring for 12 hours, the solution was added to an excess of ice water and extracted with DCM. The DCM solution was washed with sodium carbonate aqueous solution and distilled water. The organic layer was dried over $MgSO_4$, then filtered, and concentrated under reduced pressure. The remaining solution was purified by column chromatography to obtain 3-(2-([1,1'-biphenyl]-4-yl)ethyl)-4-bromo-2,5-dimethylthiophene (159 mg, yield 60%). $^1$H NMR (500 MHz, chloroform-d) δ 7.62 (d, J=8.0 Hz, 2H), 7.55 (d, J=8.2 Hz, 2H), 7.47 (t, J=7.7 Hz, 2H), 7.36 (t, J=7.4 Hz, 1H), 7.27 (d, J=8.1 Hz, 2H), 2.85 (p, J=3.4 Hz, 4H), 2.40 (s, 3H), 2.15 (s, 3H).

Step 4: Synthesis of 4-(2-([1,1'-biphenyl]-4-yl)ethyl)-2,5-dimethylthiophene-3-carboxylic acid

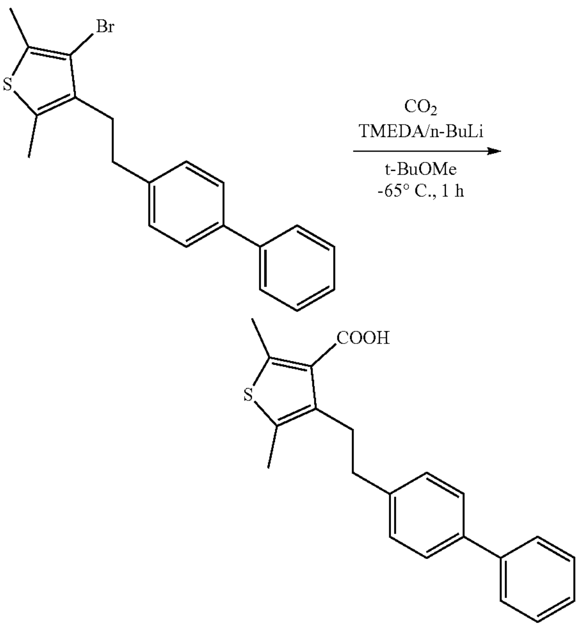

To a solution of 3-(2-([1,1'-biphenyl]-4-yl)ethyl)-4-bromo-2,5-dimethylthiophene (159 mg, 0.43 mmol), THF (2.2 mL, 0.2 M) and TMEDA (70 μL, 0.47 mmol), n-BuLi (2.5 M in THF, 0.22 mL, 0.56 mmol) was added gradually at −65° C. and stirred. After 30 minutes, dry ice was added in excess at −65° C. and stirred at ambient temperature for 1 hour. The reaction mixture was acidified by addition of 1 M HCl solution and then extracted with EtOAc and distilled water. The organic layer was dried over $Na_2SO_4$, then filtered, and concentrated to obtain 4-(2-([1,1'-biphenyl]-4-yl)ethyl)-2,5-dimethylthiophene-3-carboxylic acid (72 mg, yield 51%). $^1$H NMR (500 MHz, DMSO-$d_6$); S 12.69 (s, 1H), 7.65 (d, J=8.0 Hz, 2H), 7.59 (d, J=8.2 Hz, 2H), 7.46 (t, J=7.7 Hz, 2H), 7.35 (t, J=7.4 Hz, 1H), 7.27 (d, J=8.2 Hz, 2H), 2.96 (dd, J=9.4, 6.5 Hz, 2H), 2.75-2.70 (m, 2H), 2.56 (s, 3H), 2.15 (s, 3H).

Step 5: Synthesis of methyl 6-(4-(2-([1,1'-biphenyl]-4-yl)ethyl)-2,5-dimethylthiophene-3-carboxamido)spiro[3.3]heptane-2-carboxylate

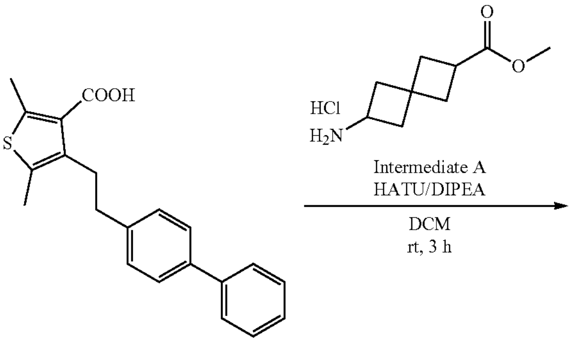

-continued

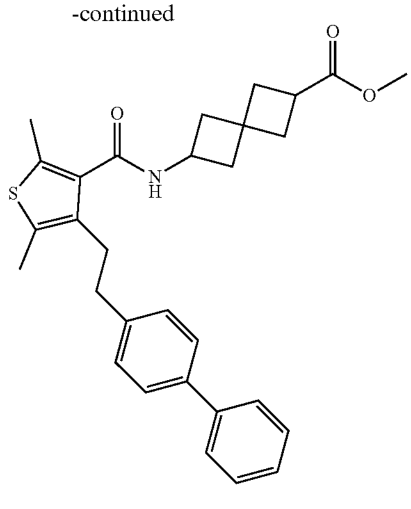

To a solution of 4-(2-([1,1'-biphenyl]-4-yl)ethyl)-2,5-dimethylthiophene-3-carboxylic acid (72 mg, 0.21 mmol), Intermediate A (47 mg, 0.23 mmol), and HATU (87 mg, 0.23 mmol) in DCM (1.1 mL, 0.2 M), DIPEA (0.11 mL, 0.63 mmol) was added and stirred at ambient temperature for 3 hours. The reaction mixture was partially concentrated, and the organic layer was extracted with 1 N NaOH and ethyl acetate, and the aqueous layer was extracted three times with ethyl acetate. The organic layer was washed with brine, dried over $Na_2SO_4$, concentrated, and then purified by column chromatography to obtain methyl 6-(4-(2-([1,1'-biphenyl]-4-yl)ethyl)-2,5-dimethylthiophene-3-carboxamido)spiro[3.3]heptane-2-carboxylate (70 mg, yield 70%). $^1$H NMR (500 MHz, chloroform-d) δ 7.61 (d, J=7.1 Hz, 2H), 7.53 (d, J=8.2 Hz, 2H), 7.46 (t, J=7.7 Hz, 2H), 7.36 (t, J=7.9 Hz, 1H), 7.20 (d, J=8.2 Hz, 2H), 5.55 (d, J=7.7 Hz, 1H), 4.45 (h, J=7.8 Hz, 1H), 3.69 (s, 3H), 3.05 (p, J=8.5 Hz, 1H), 2.86 (dd, J=6.4, 4.0 Hz, 2H), 2.82 (dd, J=9.8, 6.5 Hz, 2H), 2.61 (dt, J=11.8, 5.5 Hz, 1H), 2.48 (dd, J=11.8, 7.1 Hz, 1H), 2.45 (s, 3H), 2.37 (d, J=8.4 Hz, 2H), 2.32-2.27 (m, 1H), 2.19 (s, 3H), 2.16-2.10 (m, 1H), 1.92-1.82 (m, 2H); LC/MS (ESI) m/z: 488.3 [M+H]$^+$.

Step 6: Synthesis of 6-(4-(2-([1,1'-biphenyl]-4-yl)ethyl)-2,5-dimethylthiophene-3-carboxamido)spiro[3.3]heptane-2-carboxylic acid

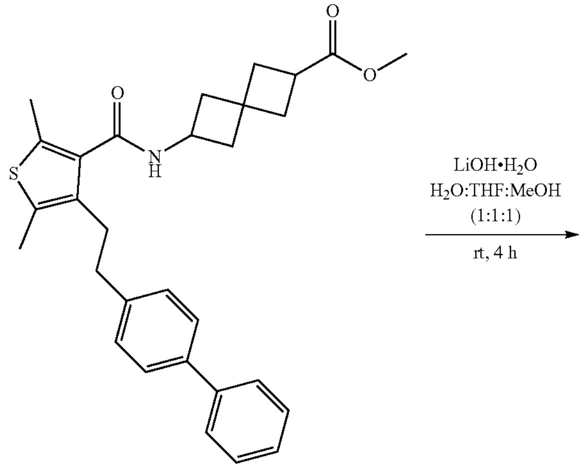

-continued

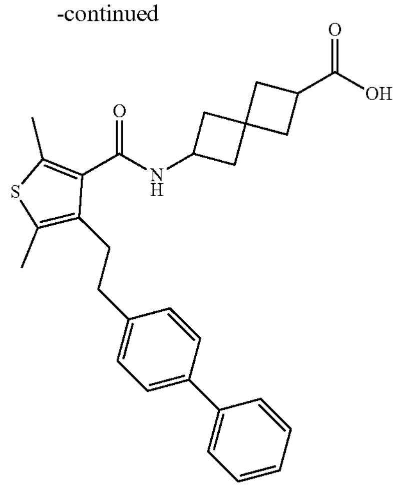

6

To a solution of methyl 6-(4-(2-([1,1'-biphenyl]-4-yl)ethyl)-2,5-dimethylthiophene-3-carboxylamido)spiro[3.3]heptane-2-carboxylate (70 mg, 0.14 mmol) in $H_2O$:THF:MeOH (1:1:1), $LiOH \cdot H_2O$ (18 mg, 0.42 mmol) was added. The reaction mixture was stirred at ambient temperature for 4 hours, then acidified by addition of 1 N HCl solution, and extracted with DCM. The organic layer was dried over $Na_2SO_4$, filtered, and concentrated to obtain the compound of Example 6 (46 mg, 69% yield) without purification. $^1$H NMR (500 MHz, Methanol-d$_4$) δ 8.48 (d, J=7.2 Hz, 1H), 7.61 (d, J=7.2 Hz, 2H), 7.52 (d, J=8.2 Hz, 2H), 7.43 (t, J=7.7 Hz, 2H), 7.32 (t, J=7.4 Hz, 1H), 7.21 (d, J=8.2 Hz, 2H), 4.36 (dt, J=13.2, 6.8 Hz, 1H), 3.04 (p, J=8.5 Hz, 1H), 2.88-2.82 (m, 2H), 2.80-2.75 (m, 2H), 2.61-2.55 (m, 1H), 2.45-2.42 (m, 1H), 2.41 (s, 3H), 2.41-2.34 (m, 2H), 2.29-2.24 (m, 1H), 2.22-2.16 (m, 1H), 2.11 (s, 3H), 2.10-2.01 (m, 2H). LC/MS (ESI) m/z: 474.3 [M+H]$^+$.

Example 7: 6-(4-((3-fluoro-[1,1'-biphenyl]-4-yl)methyl)-2,5-dimethylthiophene-3-carboxamido)spiro[3.3]heptane-2-carboxylic acid Step 1: Synthesis of (4-bromo-2,5-dimethylthiophen-3-yl)(3-fluoro-[1,1'-biphenyl]-4-yl)methanone

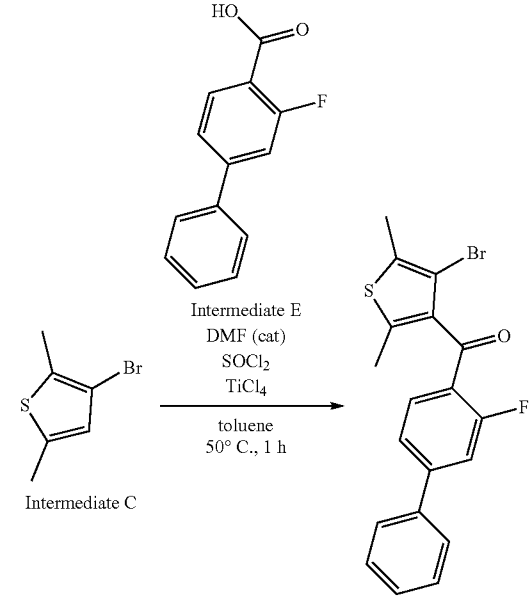

To a solution of Intermediate E (0.50 g, 2.31 mmol) and DMF (about 1 mL) in toluene (2.6 mL, 0.8 M), $SOCl_2$ (0.18 mL, 2.4 mmol) was added at 0° C. The reaction mixture was heated to 50° C. and stirred for 1 hour, and then Intermediate C (0.40 g, 2.1 mmol) was added. The reaction mixture was cooled to 0° C., and $TiCl_4$ (0.23 mL, 2.1 mmol) was added. 1 N HCl aqueous solution (10 mL) was added and stirred for 5 minutes, and then the organic layer was extracted, and the aqueous layer was washed twice with heptane. The organic layer was washed with brine, dried over $MgSO_4$, filtered, and concentrated to obtain (4-bromo-2,5-dimethylthiophen-3-yl)(3-fluoro-[1,1'-biphenyl]-4-yl)methanone (200 mg, yield 25%). $^1$H NMR (500 MHz, Chloroform-d) δ 7.78 (t, J=7.8 Hz, 1H), 7.65 (d, J=7.2 Hz, 2H), 7.53-7.49 (m, 3H), 7.46 (d, J=7.3 Hz, 1H), 7.36 (d, J=11.9 Hz, 1H), 2.48 (s, 3H), 2.39 (s, 3H).

Step 2: Synthesis of 3-bromo-4-((3-fluoro-[1,1'-biphenyl]-4-yl)methyl)-2,5-dimethylthiophene

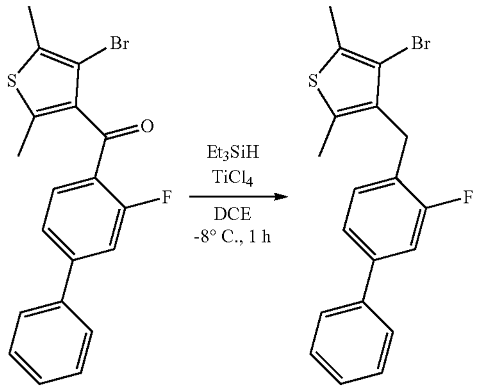 [SMILES: Cc1sc(C)c(C(=O)c2ccc(-c3ccccc3)cc2F)c1Br ; Cc1sc(C)c(Cc2ccc(-c3ccccc3)cc2F)c1Br]

To a solution of (4-bromo-2,5-dimethylthiophen-3-yl)(3-fluoro-[1,1'-biphenyl]-4-yl)methanone (150 mg, 0.39 mmol) in DCE (0.9 mL, 0.5 M), $Et_3SiH$ (0.18 mL, 1.17 mmol) was added. The reaction mixture was cooled to −8° C., $TiCl_4$ (43 μL, 0.39 mmol) was slowly added, and the reaction mixture was stirred for 1 hour. 1 N HCl aqueous solution (10 mL) was added and stirred for 5 minutes, and then the organic layer was extracted, and the aqueous layer was washed twice with heptane. The organic layer was washed with brine, dried over $MgSO_4$, filtered, and concentrated to obtain 3-bromo-4-((3-fluoro-[1,1'-biphenyl]-4-yl)methyl)-2,5-dimethylthiophene (74 mg, yield 53%). $^1$H NMR (500 MHz, Chloroform-d) δ 7.57 (d, J=7.1 Hz, 2H), 7.45 (t, J=7.6 Hz, 2H), 7.37 (t, J=7.4 Hz, 1H), 7.30 (d, J=9.6 Hz, 1H), 7.26 (d, J=6.1 Hz, 1H), 7.00 (t, J=8.0 Hz, 1H), 4.00 (s, 2H), 2.40 (s, 3H), 2.38 (s, 3H).

Step 3: Synthesis of 4-((3-fluoro-[1,1'-biphenyl]-4-yl)methyl)-2,5-dimethylthiophene-3-carboxylic acid

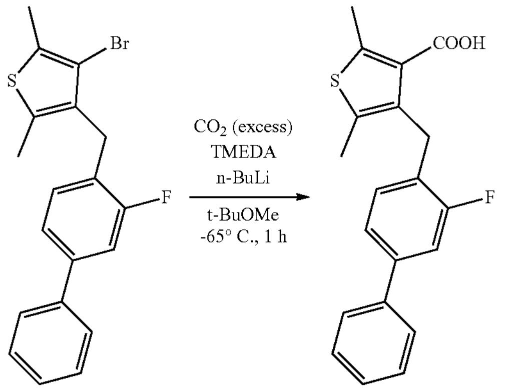 [SMILES: Cc1sc(C)c(Cc2ccc(-c3ccccc3)cc2F)c1Br ; Cc1sc(C)c(C(=O)O)c1Cc1ccc(-c2ccccc2)cc1F]

To a solution of 3-bromo-4-((3-fluoro-[1,1'-biphenyl]-4-yl)methyl)-2,5-dimethylthiophene (74 mg, 0.20 mmol) and tetramethylenediamine (33 μL, 0.22 mmol) in THF (1.0 mL, 0.2 M), n-BuLi (2.5 M in THF, 0.09 mL, 0.22 mmol) was slowly added at −65° C. and then stirred for 45 minutes, and an excess of dry ice was added at −65° C. 1 N HCl aqueous solution (2.0 mL) was added and stirred for 15 minutes, and then the organic layer was extracted, and the aqueous layer was washed twice with EA. The organic layer was washed with brine, dried over $MgSO_4$, filtered, and concentrated to obtain 4-((3-fluoro-[1,1'-biphenyl]-4-yl)methyl)-2,5-dimethylthiophene-3-carboxylic acid (30 mg, yield 45%). $^1$H NMR (500 MHz, Chloroform-d) δ 7.55 (d, J=7.1 Hz, 2H), 7.44 (t, J=7.6 Hz, 2H), 7.36 (d, J=7.3 Hz, 1H), 7.27 (d, J=9.5 Hz, 1H), 7.22 (d, J=7.9 Hz, 1H), 6.91 (t, J=8.0 Hz, 1H), 4.24 (s, 2H), 2.70 (s, 3H), 2.33 (s, 3H).

Step 4: Synthesis of methyl 6-(4-((3-fluoro-[1,1'-biphenyl]-4-yl)methyl)-2,5-dimethylthiophene-3-carboxamido)spiro[3.3] heptane-2-carboxylate

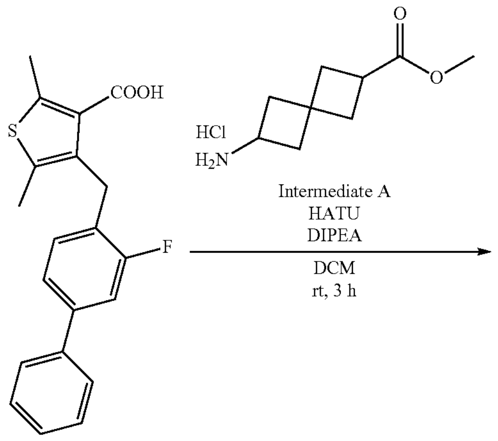

-continued

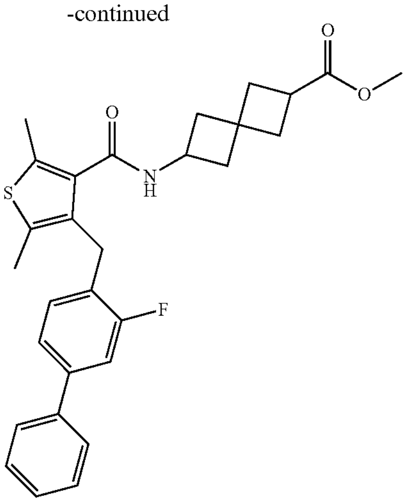

To a solution of 4-((3-fluoro-[1,1'-biphenyl]-4-yl)methyl)-2,5-dimethylthiophene-3-carboxylic acid (30 mg, 0.09 mmol), Intermediate A (21 mg, 0.1 mmol) and HATU (38 mg, 0.1 mmol) in DMF (0.3 mL, 0.3 M), DIPEA (0.05 mL, 0.27 mmol) was added at ambient temperature and stirred for 3 hours. The reaction mixture was concentrated and diluted with 1N NaOH aqueous solution and ethyl acetate, and the aqueous layer was extracted three times with ethyl acetate. The organic layer was washed with brine, dried over $MgSO_4$, concentrated, and purified by silica gel column chromatography (n-hexane and ethyl acetate) to obtain methyl 6-(4-((3-fluoro-[1,1'-biphenyl]-4-yl)methyl)-2,5-dimethylthiophene-3-carboxamido)spiro[3.3] heptane-2-carboxylate (12 mg, yield 30%). $^1$H NMR (500 MHz, Chloroform-d) δ 7.57-7.53 (m, 2H), 7.46 (t, J=7.6 Hz, 2H), 7.38 (t, J=7.9 Hz, 1H), 7.29 (s, 1H), 7.26 (s, 1H), 7.08 (t, J=7.8 Hz, 1H), 5.49 (d, J=7.8 Hz, 1H), 4.34 (h, J=8.0 Hz, 1H), 3.98 (s, 2H), 3.67 (s, 3H), 2.99 (p, J=8.5 Hz, 1H), 2.53-2.47 (m, 1H), 2.46 (s, 3H), 2.39-2.36 (m, 1H), 2.35 (s, 3H), 2.33-2.29 (m, 2H), 2.21 (dd, J=11.6, 8.4 Hz, 1H), 2.06-2.00 (m, 1H), 1.69-1.65 (m, 1H), 1.61 (dd, J=11.6, 8.7 Hz, 1H). LC/MS (ESI) m/z: 492.4 $[M+H]^+$.

Step 5: Synthesis of 6-(4-((3-fluoro-[1,1'-biphenyl]-4-yl)methyl)-2,5-dimethylthiophene-3-carboxamido) spiro[3.3] heptane-2-carboxylic acid

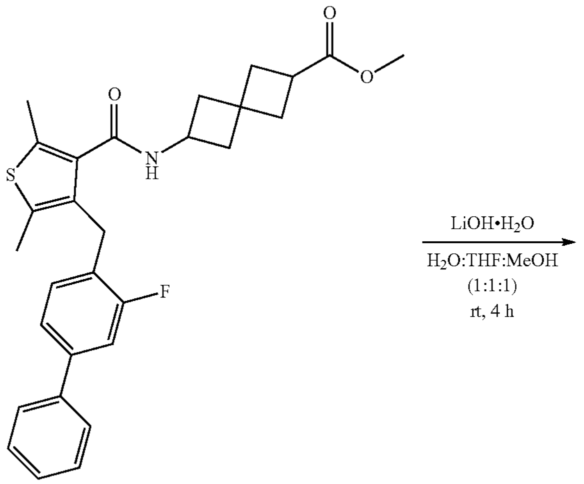

-continued

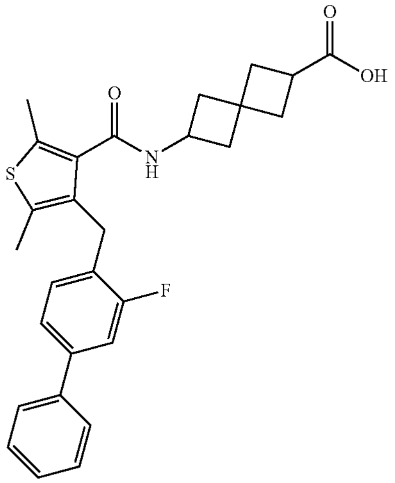

7

To a solution of methyl 6-(4-((3-fluoro-[1,1'-biphenyl]-4-yl)methyl)-2,5-dimethylthiophene-3-carboxamido)spiro [3.3] heptane-2-carboxylate (12 mg, 0.02 mmol) in $H_2O$/THF/MeOH (0.3 M, 0.1 mL), LiOH·$H_2O$ (3.0 mg, 0.06 mmol) was added and stirred for 4 hours. The reaction mixture was acidified by addition of 1 N HCl aqueous solution and extracted with EA (3×5 mL). The organic layer was dried over $MgSO_4$, filtered, concentrated, and then purified by silica gel column chromatography (n-hexane and ethyl acetate) to obtain the compound of Example 7 (6.0 mg, yield 55%). $^1$H NMR (500 MHz, Chloroform-d) δ 7.55 (d, J=7.2 Hz, 2H), 7.46 (t, J=7.6 Hz, 2H), 7.38 (t, J=7.3 Hz, 1H), 7.27 (d, J=9.7 Hz, 2H), 7.08 (t, J=7.8 Hz, 1H), 5.48 (d, J=7.8 Hz, 1H), 4.34 (h, J=8.0 Hz, 1H), 3.98 (s, 2H), 3.03 (p, J=8.4 Hz, 1H), 2.50 (dt, J=11.9, 6.3 Hz, 1H), 2.46 (s, 3H), 2.41-2.36 (m, 2H), 2.35 (s, 3H), 2.34 (s, 1H), 2.23 (dd, J=11.7, 8.2 Hz, 1H), 2.08 (ddd, J=11.6, 8.6, 2.2 Hz, 1H), 1.64 (ddd, J=20.8, 11.4, 8.5 Hz, 2H). LC/MS (ESI) m/z: 478.2 $[M+H]^+$.

Example 8: 6-(4-((2-amino-[1,1'-biphenyl]-4-yl)methyl)-2,5-dimethylthiophene-3-carboxamido)spiro[3.3]heptane-2-carboxylic acid

Step 1: Synthesis of (2-amino-[1,1'-biphenyl]-4-yl)(4-bromo-2,5-dimethylthiophen-3-yl)methanone

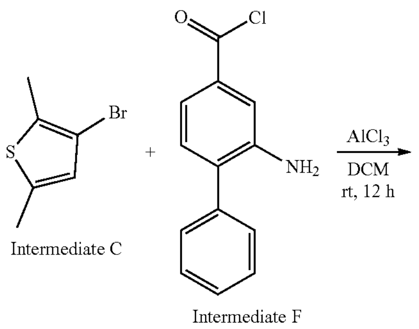

-continued

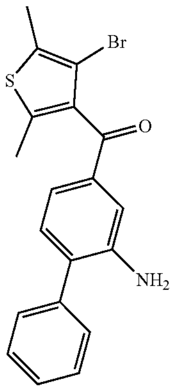

To a mixture of $AlCl_3$ (1.74 g, 13.1 mmol) and DCM (42.2 mL, 0.3 M), Intermediate C (2.5 g, 13.1 mmol) was added and stirred for 30 minutes, and then Intermediate F (2.95 g, 12.7 mmol) was added to the reaction mixture and stirred for 12 hours. The reaction mixture was poured into ice, acidified with 1 N citric acid aqueous solution, and then extracted twice with DCM. The organic layer was washed with distilled water and brine, dried over $MgSO_4$, concentrated under reduced pressure, and then purified by column chromatography to obtain (2-amino-[1,1'-biphenyl]-4-yl)(4-bromo-2,5-dimethylthiophen-3-yl)methanone (960 mg, yield 20%). $^1H$ NMR (300 MHz, chloroform-d) δ 7.50 (d, J=4.4 Hz, 4H), 7.44-7.40 (m, 1H), 7.31 (d, J=1.2 Hz, 1H), 7.26-7.22 (m, 2H), 4.02 (s, 2H), 2.41 (s, 3H), 2.37 (s, 3H).

Steps 2 to 5: Synthesis of 6-(4-((2-amino-[1,1'-biphenyl]-4-yl)methyl)-2,5-dimethylthiophene-3-carboxamido)spiro[3.3] heptane-2-carboxylic acid

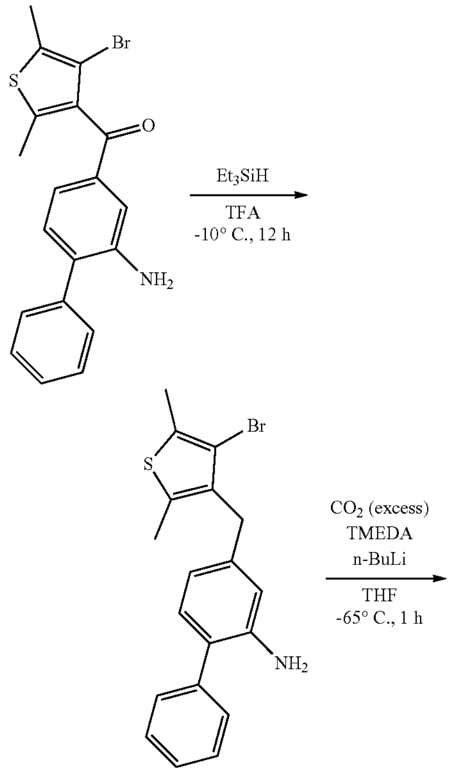

-continued

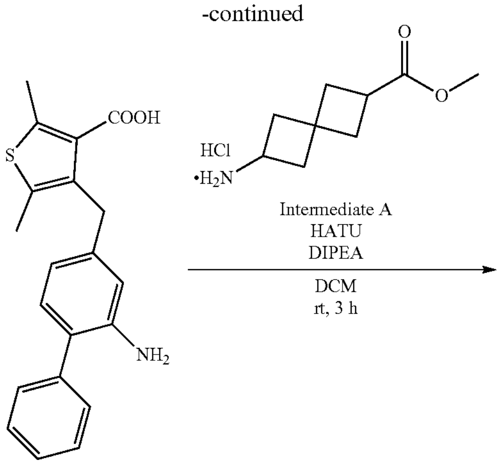

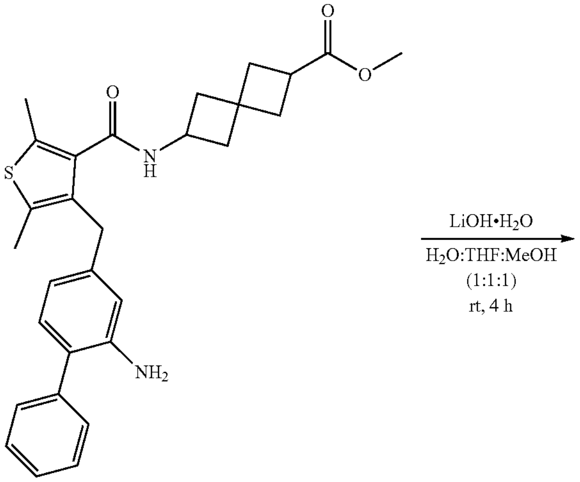

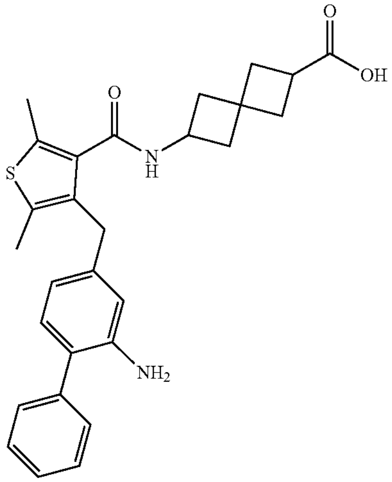

8

The compound of Example 8 was prepared by reacting (2-amino-[1,1'-biphenyl]-4-yl)(4-bromo-2,5-dimethylthiophen-3-yl)methanone obtained in Step 1 above in the same manner as in Steps 2 to 5 of Example 7. $^1H$ NMR (300 MHz, chloroform-d) δ 7.50-7.33 (m, 5H), 7.08 (d, J=7.7 Hz, 1H), 6.63 (d, J=8.7 Hz, 1H), 6.57 (s, 1H), 5.67 (d, J=8.8 Hz, 1H), 4.27 (q, J=8.0 Hz, 1H), 3.91 (s, 2H), 3.08-2.94 (m, 1H), 2.46 (s, 4H), 2.37 (s, 3H), 2.31 (d, J=8.1 Hz, 3H), 2.26-2.17 (m, 1H), 2.11-2.01 (m, 1H), 1.65-1.50 (m, 2H). LC/MS (ESI) m/z: 475.5 $[M+H]^+$.

Example 9: 6-(2,5-dimethyl-4-(4-morpholinobenzyl)thiophene-3-carboxamido)spiro[3.3]heptane-2-carboxylic acid Step 1: Synthesis of (4-bromo-2,5-dimethylthiophen-3-yl)(4-fluorophenyl)methanone

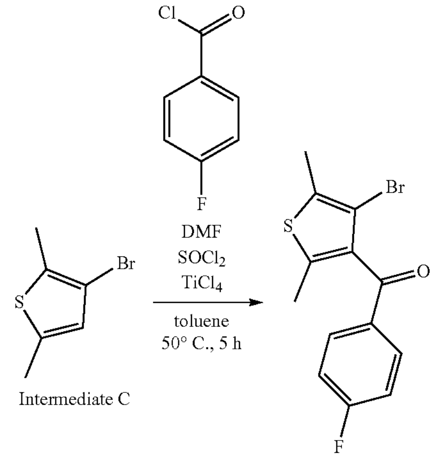

To a solution of 4-fluorobenzoic acid (3.0 g, 21.3 mmol) and DMF (about 1 mL) in toluene (24 mL, 0.8 M), $SOCl_2$ (1.8 mL, 24.6 mmol) was added at 0° C. and then stirred at 50° C. for 5 hours. 3-Bromo-2,5-dimethylthiophene (3.7 g, 19.4 mmol) was added at 50° C., and then $TiCl_4$ (2.1 mL, 19.4 mmol) solution was added. 1 N HCl aqueous solution (30 mL) was added and stirred for 5 minutes, and then the organic layer was extracted, and the aqueous layer was washed twice with heptane. The organic layer was washed with brine, dried over $MgSO_4$, filtered, and concentrated to obtain (4-bromo-2,5-dimethylthiophen-3-yl)(4-fluorophenyl)methanone (1.45 g, yield 24%).

Step 2: Synthesis of (4-bromo-2,5-dimethylthiophen-3-yl)(4-morpholinophenyl)methanone

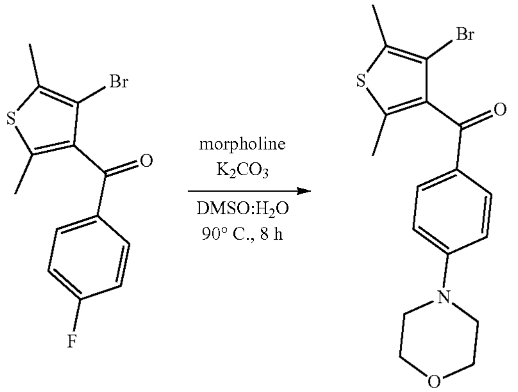 [SMILES: Cc1sc(C)c(C(=O)c2ccc(F)cc2)c1Br ; Cc1sc(C)c(C(=O)c2ccc(N3CCOCC3)cc2)c1Br]

To a solution of (4-bromo-2,5-dimethylthiophen-3-yl)(4-fluorophenyl)methanone (1.45 g, 4.62 mmol) and morpholine (1.2 mL, 13.9 mmol) in DMSO:$H_2O$ (8 mL, 0.6 M), $K_2CO_3$ (0.95 g, 6.5 mmol) was added, then heated to 90° C., and stirred for 8 hours. The reaction mixture was diluted with distilled water and extracted twice with DCM. The organic layer was washed with brine, dried over $MgSO_4$, filtered, and concentrated to obtain (4-bromo-2,5-dimethylthiophen-3-yl)(4-morpholinophenyl)methanone (1.21 g, yield 69%).

Step 3: Synthesis of 4-(4-((4-bromo-2,5-dimethylthiophen-3-yl)methyl)phenyl)morpholine

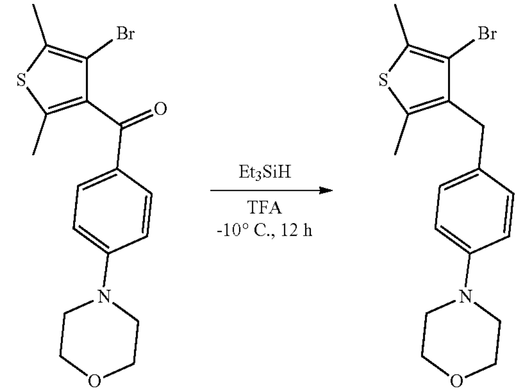 [SMILES: "Et3SiH" ; Cc1sc(C)c(C(=O)c2ccc(N3CCOCC3)cc2)c1Br ; Cc1sc(C)c(Cc2ccc(N3CCOCC3)cc2)c1Br]

To a solution of (4-bromo-2,5-dimethylthiophen-3-yl)(4-morpholinophenyl)methanone (1.21 g, 3.2 mmol) in TFA (8 mL, 0.4 M), $Et_3SiH$ (1.80 mL, 11.2 mmol) was added at −10° C. and stirred at ambient temperature for 12 hours. The reaction mixture was poured into 10 mL of ice water, extracted with ethyl acetate (3×20 mL), then washed with saturated $NaHCO_3$ aqueous solution (20 mL), distilled water (10 mL), and brine (20 mL), and dried over $Na_2SO_4$. It was concentrated under reduced pressure, and then the crude product was purified by silica gel column chromatography (ethyl acetate/hexane) to obtain 4-(4-((4-bromo-2,5-dimethylthiophen-3-yl)methyl)phenyl)morpholine (0.62 g, yield 53%). $^1$H NMR (300 MHz, Chloroform-d) δ 7.08 (d, J=8.7 Hz, 2H), 6.86 (d, J=8.3 Hz, 2H), 3.91-3.84 (m, 6H), 3.17-3.11 (m, 4H), 2.38-2.34 (m, 6H).

Step 4: Synthesis of 2,5-dimethyl-4-(4-morpholinobenzyl)thiophene-3-carboxylic acid

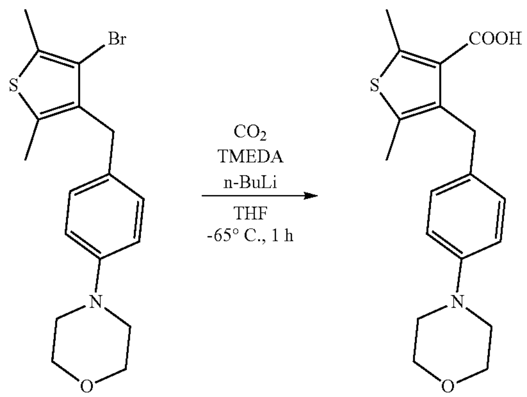 [SMILES: Cc1sc(C)c(Cc2ccc(N3CCOCC3)cc2)c1Br ; "CO2TMEDAn-BuLi" ; Cc1sc(C)c(C(=O)O)c1Cc1ccc(N2CCOCC2)cc1]

To a solution of 4-(4-((4-bromo-2,5-dimethylthiophen-3-yl)methyl)phenyl)morpholine (0.62 g, 1.69 mmol), TMEDA (48 μL, 1.86 mmol) and THF (8.5 mL, 0.2 M), n-BuLi (2.5

M in THF, 0.73 mL, 1.86 mmol) was slowly added at −65° C. and then stirred for 45 minutes. An excess of dry ice was added to the reaction mixture at −65° C. and stirred at ambient temperature for 1 hour. 1 N citric acid aqueous solution (2.0 mL) was added and stirred for 15 minutes, and the organic layer was extracted, and the aqueous layer was washed twice with EA. The organic layer was washed with brine, dried over $MgSO_4$, then filtered, and concentrated to obtain 2,5-dimethyl-4-(4-morpholinobenzyl)thiophene-3-carboxylic acid. $^1H$ NMR (500 MHz, Chloroform-d) δ 7.03 (d, J=8.6 Hz, 2H), 6.82 (d, J=8.6 Hz, 2H), 4.14 (d, J=2.7 Hz, 2H), 3.88-3.83 (m, 4H), 3.13-3.09 (m, 4H), 2.66 (s, 3H), 2.32 (s, 3H).

Step 5: Synthesis of methyl 6-(2,5-dimethyl-4-(4-morpholinobenzyl)thiophene-3-carboxamido)spiro[3.3]heptane-2-carboxylate

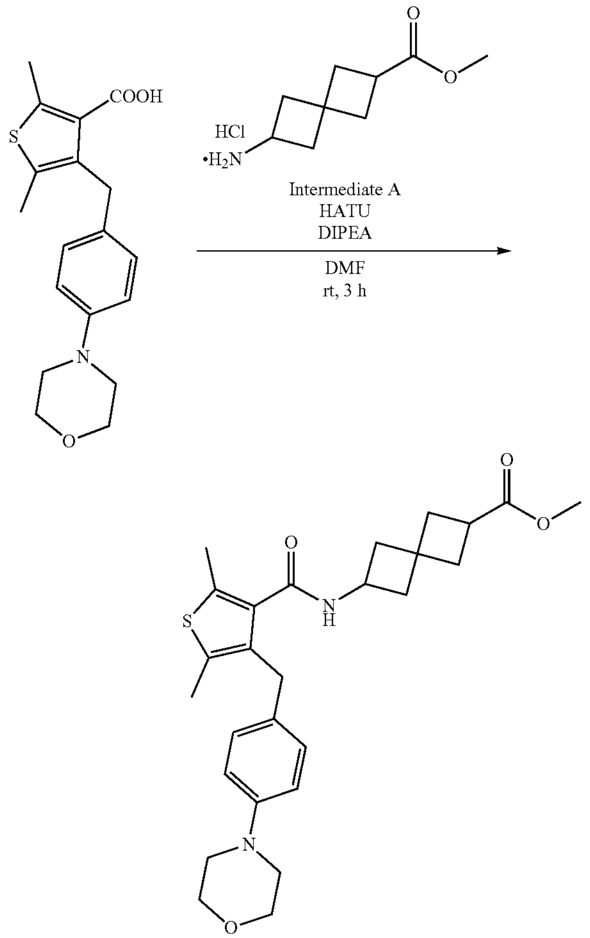

To a solution of 2,5-dimethyl-4-(4-morpholinobenzyl)thiophene-3-carboxylic acid (220 mg, 0.66 mmol), Intermediate A (148 mg, 0.72 mmol) and HATU (273 mg, 0.72 mmol) in DMF (2.2 mL, 0.3 M), DIPEA (0.4 mL, 1.98 mmol) was added and stirred for 3 hours. The reaction mixture was concentrated and diluted with 1N NaOH aqueous solution and ethyl acetate, and the aqueous layer was extracted three times with ethyl acetate. The organic layer was washed with brine, dried over $MgSO_4$, concentrated, and then purified by silica gel column chromatography using n-hexane and ethyl acetate to obtain methyl 6-(2,5-dimethyl-4-(4-morpholinobenzyl)thiophene-3-carboxamido)spiro[3.3]heptane-2-carboxylate (157 mg, yield 49%). $^1H$ NMR (500 MHz, Chloroform-d) δ 7.01 (d, J=8.6 Hz, 2H), 6.85 (d, J=8.7 Hz, 2H), 5.41 (d, J=7.7 Hz, 1H), 4.27 (h, J=7.9 Hz, 1H), 3.88 (t, J=4.8 Hz, 6H), 3.68 (s, 3H), 3.14-3.10 (m, 4H), 3.00 (p, J=8.5 Hz, 1H), 2.45 (s, 4H), 2.34 (s, 3H), 2.31 (ddd, J=12.4, 8.6, 4.9 Hz, 3H), 2.21 (dd, J=11.6, 8.4 Hz, 1H), 2.03 (ddd, J=11.6, 8.6, 2.7 Hz, 1H), 1.57 (dd, J=11.1, 8.5 Hz, 1H), 1.50 (dd, J=11.6, 8.6 Hz, 1H).

Step 6: Synthesis of 6-(2,5-dimethyl-4-(4-morpholinobenzyl)thiophene-3-carboxamido)spiro[3.3]heptane-2-carboxylic acid

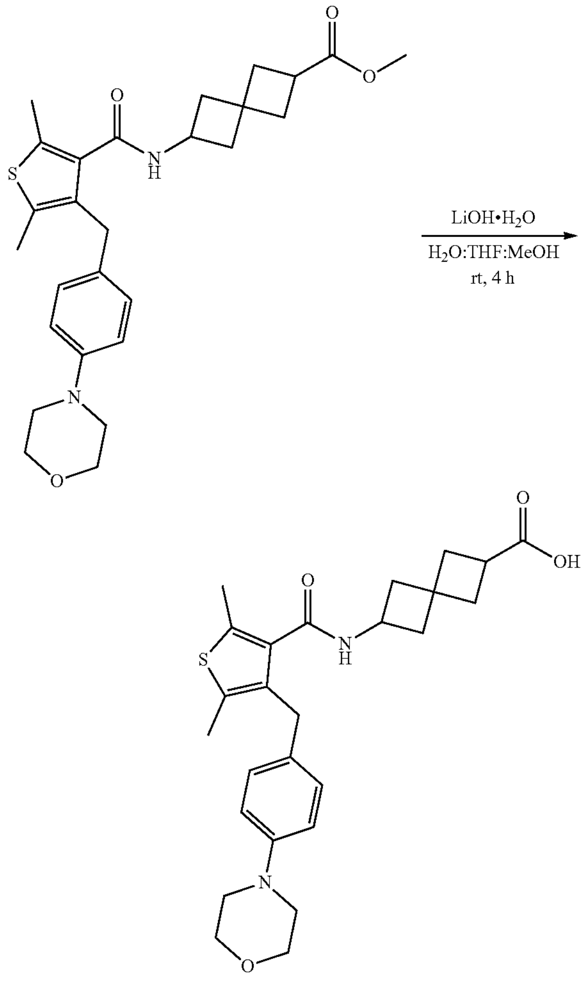

9

To a solution of methyl 6-(2,5-dimethyl-4-(4-morpholinobenzyl)thiophene-3-carboxamido)spiro[3.3]heptane-2-carboxylate (157 mg, 0.32 mmol) in $H_2O$/THF/MeOH (0.3 M, 1.1 mL), LiOH·$H_2O$ (40 mg, 0.96 mmol) was added and stirred for 4 hours. The reaction mixture was acidified by addition of 1 N citric acid aqueous solution and extracted with EA (3×5 mL). The organic layer was dried over $MgSO_4$, filtered, concentrated, and then purified by silica gel column chromatography (n-hexane and ethyl acetate) to obtain the compound of Example 9 (12 mg, yield 8%). $^1H$ NMR (500 MHz, Chloroform-d) δ 7.01 (d, J=8.6 Hz, 2H), 6.86 (d, J=8.7 Hz, 2H), 5.42 (d, J=7.7 Hz, 1H), 4.26 (h, J=7.9 Hz, 1H), 3.88 (t, J=4.8 Hz, 6H), 3.15-3.10 (m, 4H), 3.02 (p, J=8.3 Hz, 1H), 2.45 (s, 4H), 2.34 (s, 3H), 2.31 (dd, J=11.3, 8.8 Hz, 3H), 2.21 (dd, J=11.7, 8.0 Hz, 1H), 2.11-2.05 (m, 1H), 1.57 (dd, J=11.2, 8.3 Hz, 1H), 1.48 (dd, J=11.6, 8.4 Hz, 1H). LC/MS (ESI) m/z: 469.4 $[M+H]^+$.

Example 10: 6-(4-([1,1'-biphenyl]-4-carbonyl)-2,5-dimethylthiophene-3-carboxamido)spiro[3.3]heptane-2-carboxylic acid Step 1: Synthesis of 4-([1,1'-biphenyl]-4-carbonyl)-2,5-dimethylthiophene-3-carbonitrile

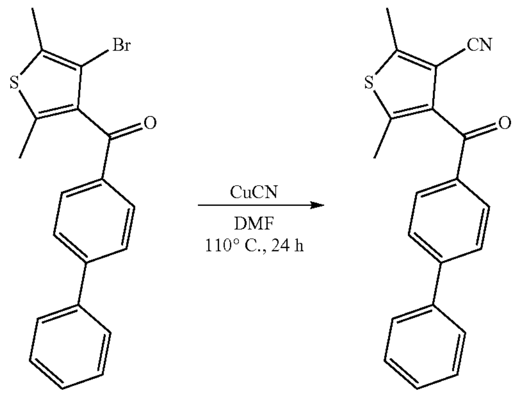 [SMILES: Cc1sc(C)c(C(=O)c2ccc(-c3ccccc3)cc2)c1Br ; "CuCN" ; Cc1sc(C)c(C(=O)c2ccc(-c3ccccc3)cc2)c1C#N]

To a solution of [1,1'-biphenyl]-4-yl(4-bromo-2,5-dimethylthiophen-3-yl)methanone (1.30 g, 3.5 mmol) obtained in Step 2 of Example 1 in DMF (58 mL, 0.06 M), CuCN (0.63 g, 7.0 mmol) was added and stirred at 110° C. for 24 hours. The reaction mixture was concentrated and diluted with 1 N HCl aqueous solution and ethyl acetate, and then the aqueous layer was extracted three times with ethyl acetate. The organic layer was washed with brine, dried over $MgSO_4$, concentrated, and then purified by silica gel column chromatography (n-hexane and ethyl acetate) to obtain 4-([1,1'-biphenyl]-4-carbonyl)-2,5-dimethylthiophene-3-carbonitrile (610 mg). $^1H$ NMR (500 MHz, Chloroform-d) δ 7.91 (d, J=8.2 Hz, 2H), 7.75 (d, J=8.2 Hz, 2H), 7.67 (d, J=7.6 Hz, 2H), 7.51 (t, J=7.6 Hz, 2H), 7.44 (t, J=7.3 Hz, 1H), 2.67 (s, 3H), 2.43 (s, 3H).

Step 2: Synthesis of 4-([1,1'-biphenyl]-4-carbonyl)-2,5-dimethylthiophene-3-carboxylic acid

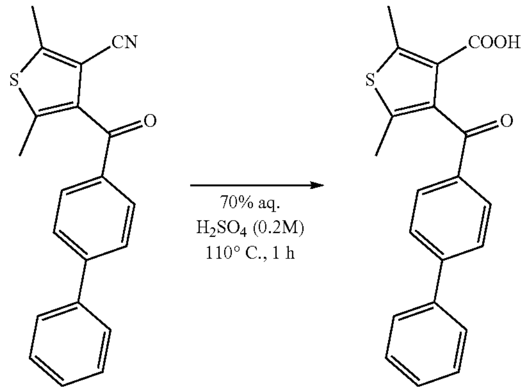 [SMILES: Cc1sc(C)c(C(=O)c2ccc(-c3ccccc3)cc2)c1C#N ; Cc1sc(C)c(C(=O)c2ccc(-c3ccccc3)cc2)c1C(=O)O]

4-([1,1'-biphenyl]-4-carbonyl)-2,5-dimethylthiophene-3-carbonitrile (340 mg, 1.07 mmol) was added to 70% $H_2SO_4$ aqueous solution (5.3 mL, 0.2 M) and then stirred under reflux at 110° C. for 1 hour. The reaction mixture was poured into ice water and extracted three times with DCM, and the organic layer was dried over $MgSO_4$, concentrated, and then purified by silica gel column chromatography (DCM and MeOH) to obtain 4-([1,1'-biphenyl]-4-carbonyl)-2,5-dimethylthiophene-3-carboxylic acid (42 mg, yield 12%). $^1H$ NMR (500 MHz, Chloroform-d) δ 7.85 (d, J=8.4 Hz, 2H), 7.66-7.61 (m, 4H), 7.48 (t, J=7.5 Hz, 2H), 7.42 (t, J=7.3 Hz, 1H), 2.68 (s, 3H), 2.27 (s, 3H).

Step 3: Synthesis of methyl 6-(4-([1,1'-biphenyl]-4-carbonyl)-2,5-dimethylthiophene-3-carboxamido) spiro[3.3]heptane-2-carboxylate

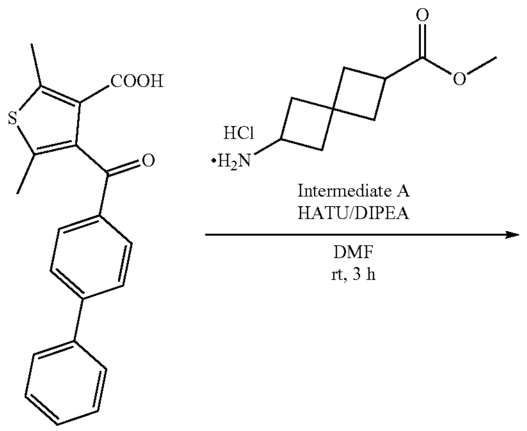

-continued

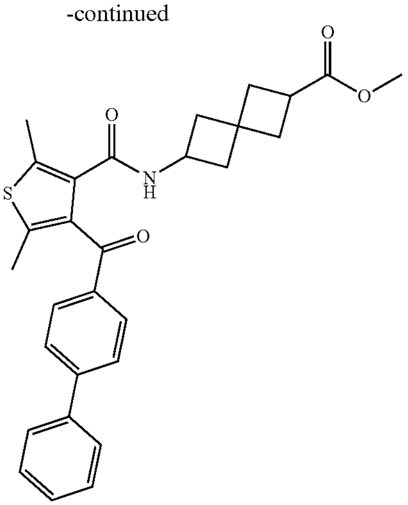

To a solution of 4-([1,1'-biphenyl]-4-carbonyl)-2,5-dimethylthiophene-3-carboxylic acid (12 mg, 0.036 mmol), Intermediate A (17 mg, 0.08 mmol) and HATU (31 mg, 0.08 mmol) in DMF (0.3 mL, 0.3 M), DIPEA (0.04 mL, 0.22 mmol) was added and stirred for 3 hours. The reaction mixture was concentrated and diluted with 1 N NaOH aqueous solution and ethyl acetate, and the aqueous layer was extracted three times with ethyl acetate. The organic layer was washed with brine, dried over $MgSO_4$, concentrated, and then purified by silica gel column chromatography (n-hexane and ethyl acetate) to obtain methyl 6-(4-([1,1'-biphenyl]-4-carbonyl)-2,5-dimethylthiophene-3-carboxamido)spiro[3.3]heptane-2-carboxylate (33 mg, yield 55%). $^1H$ NMR (500 MHz, Chloroform-d) δ 7.89 (d, J=8.4 Hz, 2H), 7.69 (d, J=8.4 Hz, 2H), 7.65 (d, J=7.2 Hz, 2H), 7.50 (t, J=7.5 Hz, 2H), 7.43 (t, J=7.3 Hz, 1H), 5.97 (d, J=7.3 Hz, 1H), 4.09 (dd, J=16.0, 7.6 Hz, 1H), 3.65 (s, 3H), 2.96 (p, J=8.5 Hz, 1H), 2.60 (s, 3H), 2.34 (s, 4H), 2.26-2.17 (m, 4H), 2.09-2.03 (m, 1H), 1.66-1.63 (m, 1H), 1.60 (d, J=9.0 Hz, 1H). LC/MS (ESI) m/z: 488.4 $[M+H]^+$ Step 4: Synthesis of 6-(4-([1,1'-biphenyl]-4-carbonyl)-2,5-dimethylthiophene-3-carboxamido)spiro[3.3]heptane-2-carboxylic acid -continued

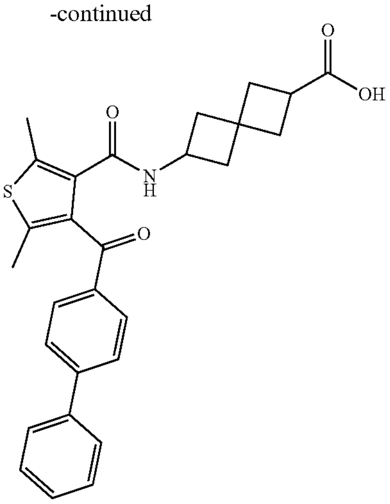

10

To a solution of methyl 6-(4-([1,1'-biphenyl]-4-carbonyl)-2,5-dimethylthiophene-3-carboxamido)spiro[3.3]heptane-2-carboxylate (33 mg, 0.07 mmol) in $H_2O$/THF/MeOH (0.3 M, 0.2 mL), $LiOH{\cdot}H_2O$ (9 mg, 0.21 mmol) was added and stirred for 4 hours. The reaction mixture was acidified by addition of 1 N HCl aqueous solution and extracted with EA (3×20 mL). The organic layer was dried over $MgSO_4$, filtered, concentrated, and then purified by silica gel column chromatography (n-hexane and ethyl acetate) to obtain the compound of Example 10 (20 mg, yield 63%). $^1H$ NMR (500 MHz, Chloroform-d) δ 7.89 (d, J=8.3 Hz, 2H), 7.69 (d, J=8.3 Hz, 2H), 7.64 (d, J=7.3 Hz, 2H), 7.50 (t, J=7.5 Hz, 2H), 7.43 (t, J=7.3 Hz, 1H), 6.03 (d, J=7.3 Hz, 1H), 4.10 (h, J=8.1 Hz, 1H), 2.99 (p, J=8.5 Hz, 1H), 2.59 (s, 3H), 2.34 (s, 4H), 2.23 (dt, J=23.0, 9.6 Hz, 4H), 2.10 (t, J=10.3 Hz, 1H), 1.66-1.59 (m, 2H). LC/MS (ESI) m/z: 474.4 $[M+H]^+$.

Example 11: 6-(4-([1,1'-biphenyl]-4-yl(hydroxy)methyl)-2,5-dimethylthiophene-3-carboxamido)spiro[3.3]heptane-2-carboxylic acid

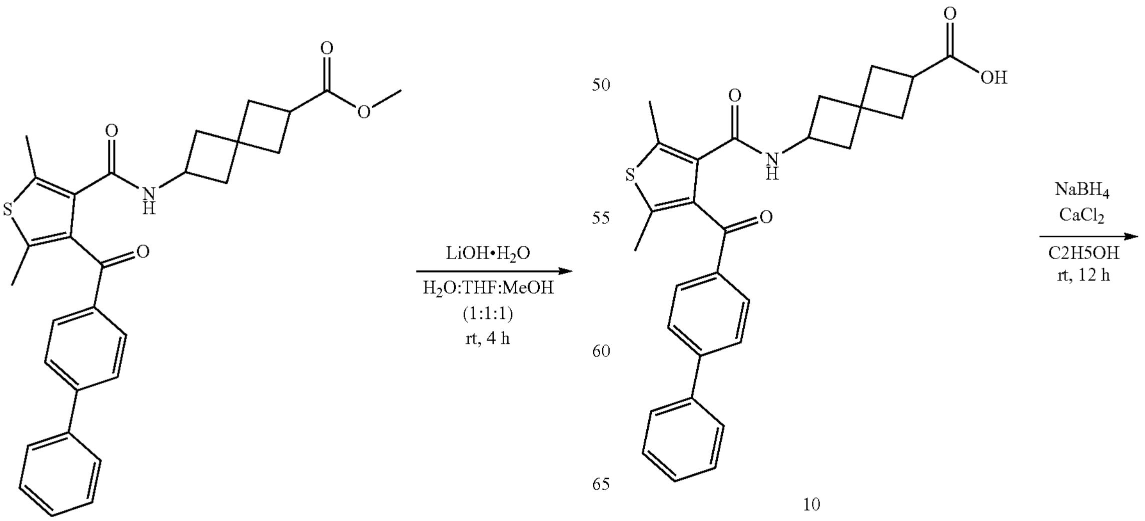

10

-continued

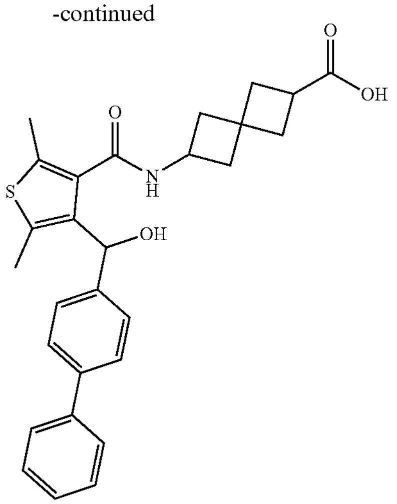

11

To a mixture of the compound of Example 10 (10 mg, 0.02 mmol) and ethanol (0.4 mL, 0.05 M), $NaBH_4$ (1.5 mg, 0.04 mmol) and $CaCl_2$ (2.0 mg, 0.02 mmol) were added and stirred for 12 hours. Distilled water and ethyl acetate were added, and then the aqueous layer was extracted with ethyl acetate (10 mL). The organic layer was dried over $MgSO_4$, concentrated, and then purified by silica gel column chromatography (DCM and MeOH) to obtain the compound of Example 11 (4.0 mg, yield 40%). $^1$H NMR (500 MHz, Methanol-$d_4$) δ 8.42 (t, J=7.8 Hz, 1H), 7.61 (t, J=7.0 Hz, 2H), 7.55 (dd, J=8.3, 6.4 Hz, 2H), 7.44 (t, J=7.5 Hz, 2H), 7.36-7.31 (m, 3H), 5.94 (d, J=3.9 Hz, 1H), 4.00-3.89 (m, 1H), 2.90 (dq, J=32.3, 8.5 Hz, 1H), 2.49 (d, J=1.9 Hz, 3H), 2.42 (d, J=2.1 Hz, 3H), 2.37-2.15 (m, 4H), 2.14-1.94 (m, 3H), 1.74 (dt, J=20.8, 10.7 Hz, 1H), 1.57-1.51 (m, 1H). LC/MS (ESI) m/z: 474.3 $[M+H]^-$.

Example 12: 6-(4-([1,1'-biphenyl]-4-yl(methoxy)methyl)-2,5-dimethylthiophene-3-carboxamido)spiro[3.3]heptane-2-carboxylic acid Step 1: Synthesis of [1,1'-biphenyl]-4-yl(4-bromo-2,5-dimethylthiophen-3-yl)methanol

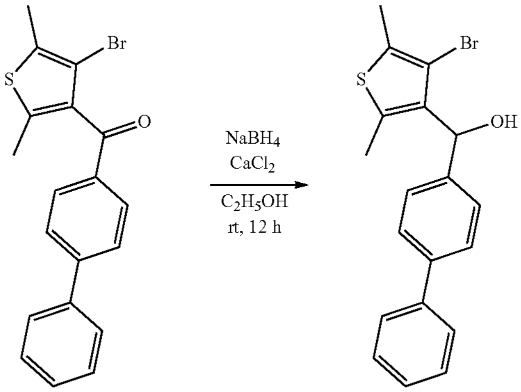 [SMILES: Cc1sc(C)c(C(=O)c2ccc(-c3ccccc3)cc2)c1Br ; "NaBH4CaCl2" ; Cc1sc(C)c(C(O)c2ccc(-c3ccccc3)cc2)c1Br]

To a mixture of [1,1'-biphenyl]-4-yl(4-bromo-2,5-dimethylthiophen-3-yl)methanone (2.0 g, 5.39 mmol) obtained in Step 2 of Example 1 and ethanol (108 mL, 0.05 M), $NaBH_4$ (0.41 g, 10.8 mmol) and $CaCl_2$ (0.60 g, 5.39 mmol) were added and stirred for 12 hours. Distilled water and ethyl acetate were added, and then the aqueous layer was extracted with ethyl acetate (50 mL). The organic layer was dried over $MgSO_4$, concentrated, and then purified by silica gel column chromatography (DCM and MeOH) to obtain [1,1'-biphenyl]-4-yl(4-bromo-2,5-dimethylthiophen-3-yl)methanol (1.3 g, yield 62%). $^1$H NMR (300 MHz, Chloroform-d) δ 7.65-7.57 (m, 4H), 7.46 (dd, J=7.9, 3.8 Hz, 4H), 7.37 (t, J=7.3 Hz, 1H), 6.13 (dd, J=10.9, 3.2 Hz, 1H), 2.42-2.35 (m, 6H).

Step 2: Synthesis of 3-([1,1'-biphenyl]-4-yl(methoxyl)methyl-4-bromo-2,5-dimethylthiophene

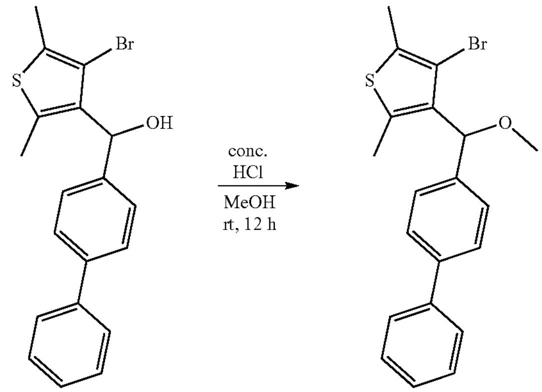 [SMILES: Cc1sc(C)c(C(O)c2ccc(-c3ccccc3)cc2)c1Br ; "conc. HCl" ; COC(c1ccc(-c2ccccc2)cc1)c1c(C)sc(C)c1Br]

To a solution of [1,1'-biphenyl]-4-yl(4-bromo-2,5-dimethylthiophen-3-yl)methanol (900 mg, 2.41 mmol) in methanol (80 mL, 0.03 M), HCl (35% in $H_2O$, 19 mL, 214 mmol) was added and stirred for 12 hours. The reaction mixture was concentrated, basified with sodium bicarbonate aqueous solution, and extracted with EA. The organic layer was dried over $MgSO_4$, concentrated, and then purified by silica gel column chromatography (0-5% MeOH in DCM) to obtain 3-([1,1'-biphenyl]-4-yl(methoxy)methyl)-4-bromo-2,5-dimethylthiophene (680 mg, yield 50%). $^1$H NMR (300 MHz, Chloroform-d) δ 7.63-7.54 (m, 4H), 7.49-7.41 (m, 4H), 7.35 (t, J=7.3 Hz, 1H), 5.68 (s, 1H), 3.45 (s, 3H), 2.41-2.35 (m, 6H).

Step 3: Synthesis of 4-([1,1'-biphenyl]-4-yl(methoxy)methyl)-2,5-dimethylthiophene-3-carboxylic acid

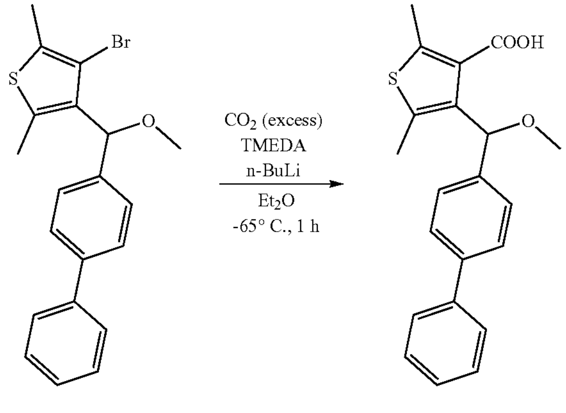 [SMILES: COC(c1ccc(-c2ccccc2)cc1)c1c(C)sc(C)c1Br ; "CO2 (excess)TMEDAn-BuLi" ; COC(c1ccc(-c2ccccc2)cc1)c1c(C)sc(C)c1C(=O)O]

To a solution of 3-([1,1'-biphenyl]-4-yl(methoxy)methyl)-4-bromo-2,5-dimethylthiophene (517 mg, 1.33 mmol), TMEDA (0.22 mL, 1.46 mmol) and $Et_2O$ (6.7 mL, 0.2 M), n-BuLi (2.5 M in THF, 0.70 mL, 1.73 mmol) was slowly added at −65° C. and stirred for 45 minutes, and then an excess of dry ice was added. 1 N HCl aqueous solution (10 mL) was added and stirred for 15 minutes, and then the organic layer was extracted, and the aqueous layer was washed twice with EA. The organic layer was washed with brine, dried over $MgSO_4$, then filtered, and concentrated to obtain 4-([1,1'-biphenyl]-4-yl(methoxy)methyl)-2,5-dimethylthiophene-3-carboxylic acid (151 mg, yield 32%). $^1H$ NMR (300 MHz, DMSO-d6) δ 12.88 (s, 1H), 7.67-7.58 (m, 4H), 7.45 (t, J=7.5 Hz, 2H), 7.36 (d, J=8.1 Hz, 3H), 6.11 (s, 1H), 3.31 (s, 3H), 2.54 (s, 3H), 2.23 (s, 3H).

Step 4: Synthesis of methyl 6-(4-([1,1'-biphenyl]-4-yl(methoxy)methyl)-2,5-dimethylthiophene-3-carboxamido)spiro[3.3] heptane-2-carboxylate

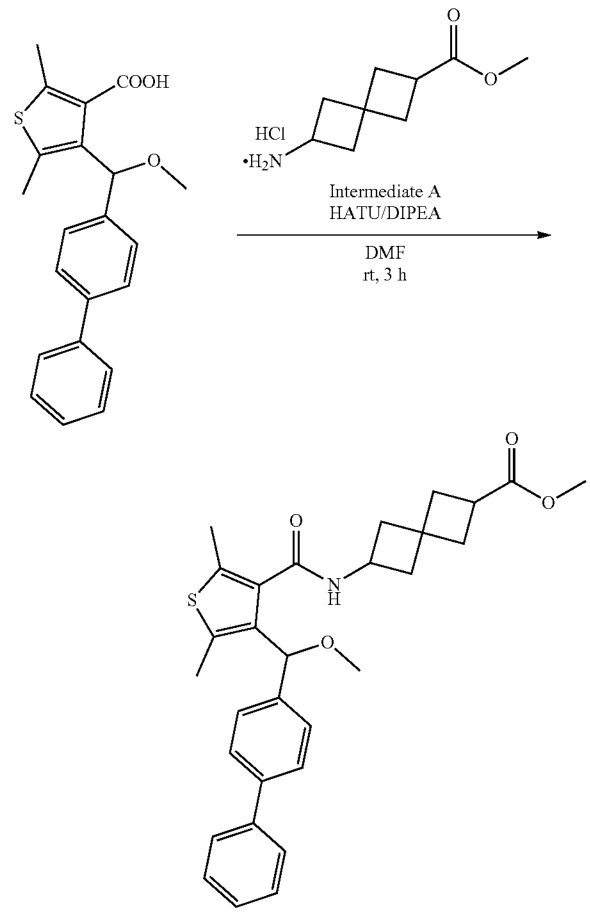

To a solution of 4-([1,1'-biphenyl]-4-yl(methoxy)methyl)-2,5-dimethylthiophene-3-carboxylic acid (151 mg, 0.43 mmol), Intermediate A (96 mg, 0.47 mmol) and HATU (179 mg, 0.47 mmol) in DMF (1.4 mL, 0.3 M), DIPEA (0.22 mL, 1.3 mmol) was added and stirred for 3 hours. The reaction mixture was concentrated and diluted with 1 N NaOH aqueous solution and ethyl acetate, and the aqueous layer was extracted three times with ethyl acetate. The organic layer was washed with brine, dried over $MgSO_4$, concentrated, and then purified by silica gel column chromatography (n-hexane and ethyl acetate) to obtain methyl 6-(4-([1,1'-biphenyl]-4-yl(methoxy)methyl)-2,5-dimethylthiophene-3-carboxamido)spiro[3.3] heptane-2-carboxylate (138 mg, yield 64%). $^1H$ NMR (300 MHz, Chloroform-d) S 7.55 (dt, J=9.7, 7.2 Hz, 4H), 7.45 (t, J=7.6 Hz, 2H), 7.35 (td, J=7.6, 3.6 Hz, 3H), 5.63 (s, 1H), 3.97 (h, J=8.3 Hz, 1H), 3.65 (d, J=4.9 Hz, 3H), 3.52 (d, J=0.9 Hz, 3H), 2.95 (dt, J=15.0, 8.6 Hz, 1H), 2.58 (d, J=2.6 Hz, 3H), 2.47 (s, 3H), 2.44-2.35 (m, 1H), 2.29-2.11 (m, 4H), 2.08-1.91 (m, 1H), 1.78-1.65 (m, 1H), 1.23-1.10 (m, 1H).

Step 5: Synthesis of 6-(4-([1,1'-biphenyl]-4-yl (methoxy)methyl)-2,5-dimethylthiophene-3-carboxamido)spiro[3.3] heptane-2-carboxylic acid

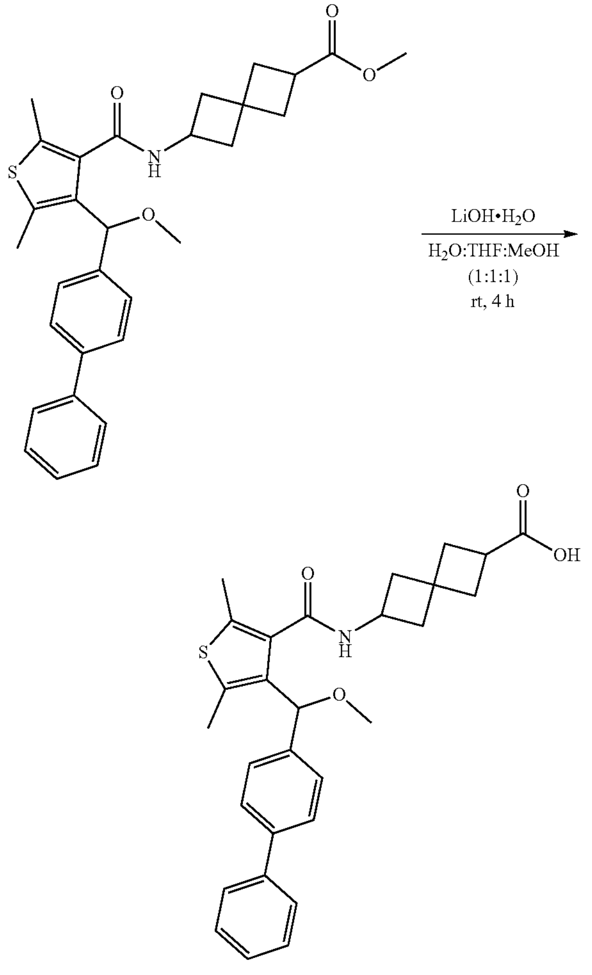

12

To a solution of methyl 6-(4-([1,1'-biphenyl]-4-yl (methoxy)methyl)-2,5-dimethylthiophene-3-carboxamido) spiro[3.3] heptane-2-carboxylate (138 mg, 0.27 mmol) in $H_2O$/THF/MeOH (0.3 M, 0.9 mL), LiOH·$H_2O$ (34 mg, 0.81 mmol) was added and stirred for 12 hours. The reaction mixture was acidified by addition of 1 N HCl aqueous solution and extracted with EA (20 mL×3). The organic layer was dried over $MgSO_4$, filtered, concentrated, and purified by silica gel column chromatography (n-hexane and ethyl acetate) to obtain 6-(4-([1,1'-biphenyl]-4-yl(methoxy) methyl)-2,5-dimethylthiophene-3-carboxamido)spiro[3.3] heptane-2-carboxylic acid (121 mg, yield 90%). $^1$H NMR (300 MHz, DMSO-d6) δ 12.02 (s, 1H), 8.41 (d, J=7.3 Hz, 1H), 7.62 (dd, J=13.7, 7.8 Hz, 4H), 7.41 (tt, J=15.5, 7.2 Hz, 5H), 5.51 (s, 1H), 4.17 (h, J=8.0 Hz, 1H), 3.30 (s, 3H), 2.92 (p, J=8.5 Hz, 1H), 2.45-2.30 (m, 4H), 2.28-2.14 (m, 6H), 2.12-2.03 (m, 2H), 1.91 (tt, J=19.4, 8.9 Hz, 2H). LC/MS (ESI) m/z: 488.3 [M+H]$^-$.

Example 13: 6-(4-([1,1'-biphenyl]-4-ylmethyl)thiophene-3-carboxamido)spiro[3.3]heptane-2-carboxylic acid

Step 1: Synthesis of 2-([1,1'-biphenyl]-4-ylmethyl)-4,4,5,5-tetramethyl-1,3,2-dioxaborolane

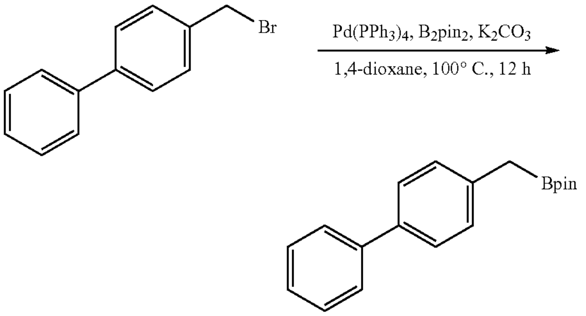

A solution of 4-bromomethyl-biphenyl (600 mg, 2.44 mmol), $K_2CO_3$ (1.0 g, 7.28 mmol), (pinacolato)diboron (740 mg, 2.92 mmol) and $Pd(PPh_3)_4$ (140 mg, 0.12 mmol) in 1,4-dioxane (12 mL) was stirred at 100° C. for 12 hours. Ethyl acetate (20 mL) was added, and the precipitate was removed by Celite filtration, and then the organic layer was concentrated under reduced pressure, and the crude product was purified by flash column chromatography (0 to 100% Hexane/EtOAc) to obtain 2-([1,1'-biphenyl]-4-ylmethyl)-4,4,5,5-tetramethyl-1,3,2-dioxaborolane (61 mg, yield 86%) as a white solid. $^1$H NMR (300 MHz, Chloroform-d) δ 7.60-7.54 (m, 2H), 7.49-7.45 (m, 2H), 7.44-7.37 (m, 2H), 7.33-7.29 (m, 1H), 7.27-7.24 (m, 2H), 2.34 (s, 2H), 1.25 (s, 12H).

Step 2: Synthesis of methyl 4-([1,1'-biphenyl]-4-ylmethyl)thiophene-3-carboxylate

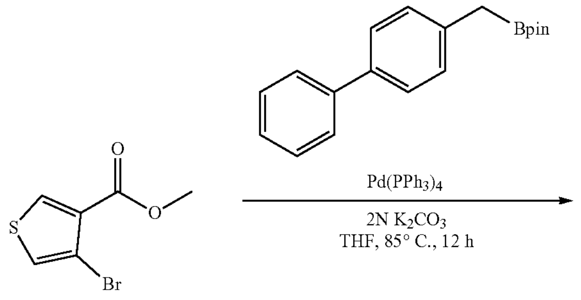

-continued

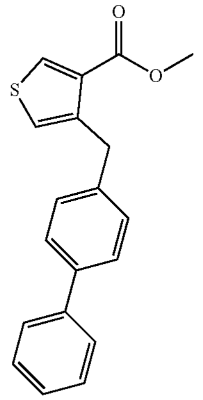

Under $N_2$, a solution of methyl 3-bromobenzo[b]thiophene-2-carboxylate (300 mg, 1.32 mmol), 2-(biphenyl-4-ylmethyl)-4,4,5,5-tetramethyl-1,3,2-dioxaborolane (192 mg, 0.528 mmol) and $Pd(PPh_3)_4$ (60 mg) in THF (18 mL) and 2 N $K_2CO_3$ aqueous solution was placed in a flask and stirred at 85° C. for 12 hours. The reaction mixture was cooled to ambient temperature and then extracted with distilled water and EtOAc. The organic layer was washed with brine, then dried over $MgSO_4$, filtered, and then concentrated under reduced pressure, and purified by silica gel column chromatography to obtain methyl 4-([1,1'-biphenyl]-4-ylmethyl) thiophene-3-carboxylate (306 mg, yield 75%) as a pale yellow oil. $^1$H NMR (400 MHz, chloroform-d) δ 10.07 (s, 1H), 8.12 (d, J=3.6 Hz, 1H), 7.99-7.94 (m, 1H), 7.78-7.73 (m, 1H), 7.67-7.62 (m, 1H), 7.61-7.53 (m, 1H), 7.52-7.46 (m, 2H), 7.45-7.41 (m, 1H), 7.41-7.36 (m, 1H), 7.32 (d, J=3.7 Hz, 1H), 3.91-3.87 (m, 5H).

Step 3: Synthesis of 4-([1,1'-biphenyl]-4-ylmethyl) thiophene-3-carboxylic acid

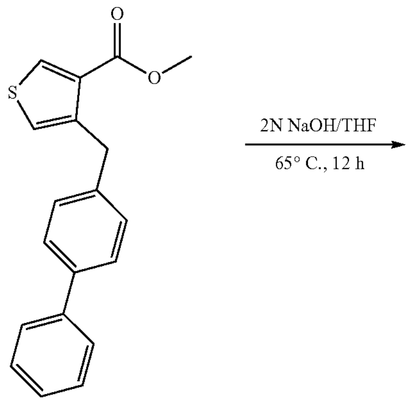

-continued

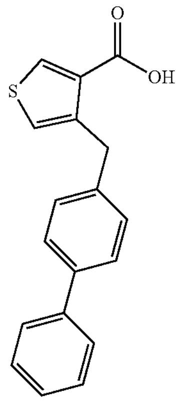

To a solution of methyl 4-([1,1'-biphenyl]-4-ylmethyl) thiophene-3-carboxylate (121 mg, 0.39 mmol) in THF (0.18 mL), 2 N NaOH aqueous solution (0.2 mL) was added and stirred at 65° C. for 12 hours. The reaction mixture was cooled to ambient temperature, and then 2 N HCl aqueous solution was added to adjust the pH to 2, stirred for 2 hours, and then extracted with EtOAc. The organic layer was washed with brine, then dried over $MgSO_4$, filtered, then concentrated under reduced pressure, and purified by column chromatography to obtain 4-([1,1'-biphenyl]-4-ylmethyl)thiophene-3-carboxylic acid (51 mg, yield 42%) as a white solid. $^1H$ NMR (500 MHz, chloroform-d) δ 8.28 (d, J=3.6 Hz, 1H), 7.59-7.57 (m, 2H), 7.54 (d, J=7.9 Hz, 2H), 7.47-7.44 (m, 2H), 7.33 (s, 1H), 7.32-7.28 (m, 2H), 6.83 (dd, J=2.8, 1.7 Hz, 1H), 4.31 (s, 2H).

Step 4: Synthesis of methyl 6-(4-([1,1'-biphenyl]-4-ylmethyl)thiophene-3-carboxamido)spiro[3.3]heptane-2-carboxylate

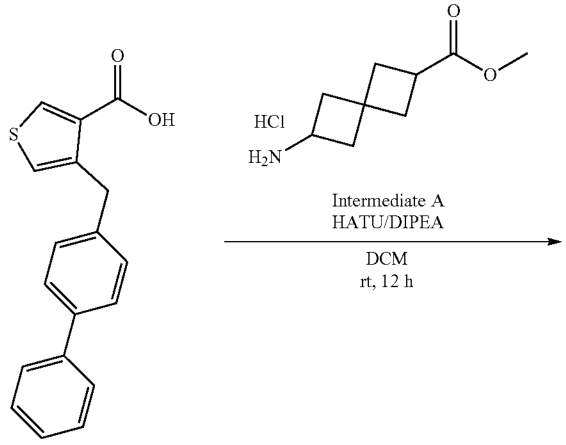

-continued

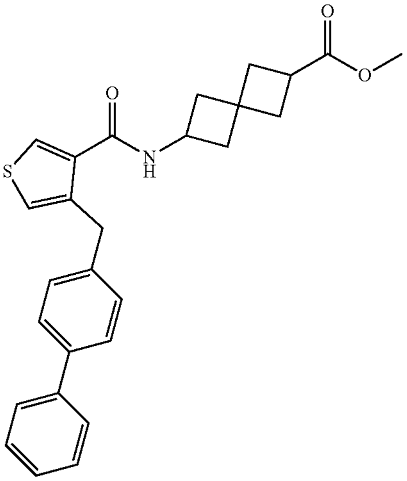

To a solution of methyl 4-([1,1'-biphenyl]-4-ylmethyl) thiophene-3-carboxylic acid (30 mg, 0.1 mmol) in DCM (1 mL), Intermediate A (20 mg, 0.12 mmol), HATU (36 mg, 0.12 mmol), and DIPEA (0.03 mL, 0.4 mmol) were added and stirred for 12 hours. EtOAc and brine were added to the reaction mixture, and the organic layer was dried over $MgSO_4$ and then concentrated under reduced pressure. The crude product was purified by silica gel column chromatography to obtain methyl 6-(4-([1,1'-biphenyl]-4-ylmethyl) thiophene-3-carboxamido)spiro[3.3]heptane-2-carboxylate (26 mg, yield 59%) as a white solid. $^1H$ NMR (300 MHz, chloroform-d) o 7.63 (d, J=3.2 Hz, 1H), 7.61-7.51 (m, 4H), 7.45 (ddd, J=7.6, 6.8, 1.3 Hz, 2H), 7.38-7.32 (m, 1H), 7.30 (s, 1H), 7.27 (s, 1H), 6.97 (dt, J=3.2, 0.9 Hz, 1H), 5.82 (d, J=7.7 Hz, 1H), 4.39-4.27 (m, 1H), 4.23 (s, 2H), 3.68 (s, 3H), 3.02 (p, J=8.4 Hz, 1H), 2.54 (tt, J=7.5, 5.2 Hz, 1H), 2.46-2.38 (m, 1H).

Step 5: Synthesis of 6-(4-([1,1'-biphenyl]-4-ylmethyl)thiophene-3-carboxamido)spiro[3.3]heptane-2-carboxylic acid

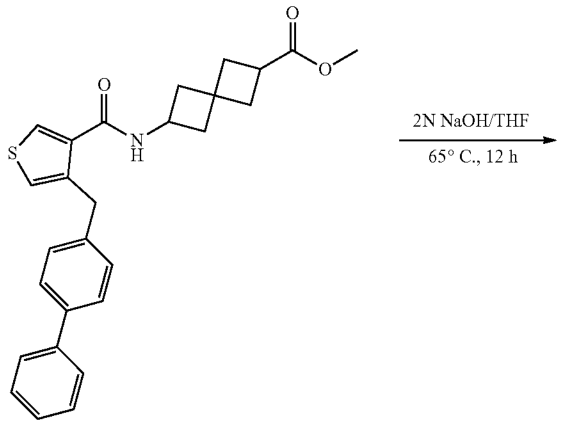

-continued

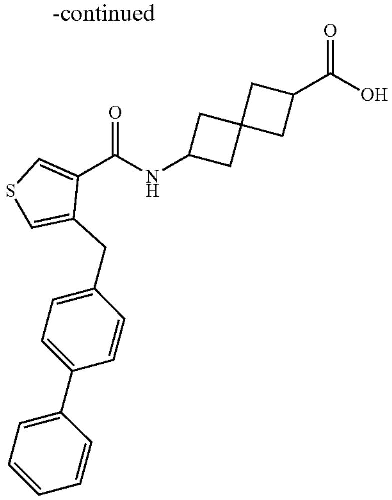

13

-continued

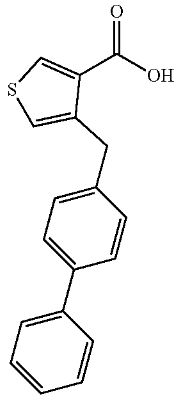

To a solution of methyl 6-(4-([1,1'-biphenyl]-4-ylmethyl)thiophene-3-carboxamido)spiro[3.3]heptane-2-carboxylate (20 mg, 0.04 mmol) in THF, 2 N NaOH aqueous solution was added and stirred at 65° C. for 12 hours. The reaction mixture was cooled to ambient temperature, and then 2 N HCl aqueous solution was added to adjust the pH to 2, stirred for 2 hours, and then extracted with EtOAc. The organic layer was washed with brine, then dried over $MgSO_4$, filtered, then concentrated under reduced pressure, and purified by column chromatography to obtain the compound of Example 13 (3.2 mg, yield 19%) as a white solid. $^1H$ NMR (500 MHz, chloroform-d) δ 7.61 (d, J=3.2 Hz, 1H), 7.58-7.55 (m, 2H), 7.54-7.50 (m, 2H), 7.45-7.40 (m, 2H), 7.36-7.31 (m, 1H), 7.27 (s, 2H), 6.95 (dt, J=3.3, 0.9 Hz, 1H), 5.80 (d, J=7.6 Hz, 1H), 4.33 (h, J=8.0 Hz, 1H), 4.21 (s, 2H), 3.04 (p, J=8.5 Hz, 1H), 2.55-2.49 (m, 1H), 2.44-2.38 (m, 1H), 2.35 (dd, J=8.5, 2.6 Hz, 2H), 2.26 (dd, J=11.8, 8.2 Hz, 1H), 2.12-2.08 (m, 1H), 1.78-1.71 (m, 2H). LC/MS (ESI) m/z: 432.3 $[M+H]^+$.

Example 14: 6-(4-([1,1'-biphenyl]-4-ylmethyl)-2-methylthiophene-3-carboxamido)spiro[3.3]heptane-2-carboxylic acid

Step 1: Synthesis of 4-([1,1'-biphenyl]-4-ylmethyl)thiophene-3-carboxylic acid

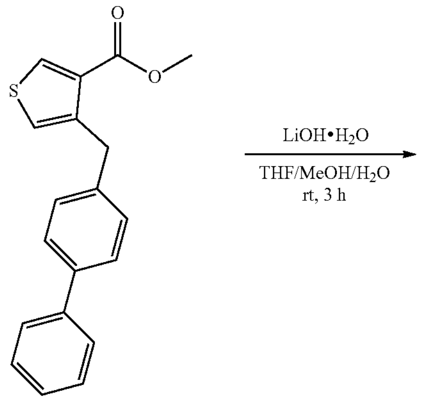

To a solution of methyl 4-([1,1'-biphenyl]-4-ylmethyl)thiophene-3-carboxylate (120 mg, 0.4 mmol) obtained in Step 2 of Example 13 in THF/MeOH/$H_2O$ (2/1/2 mL), $LiOH{\cdot}H_2O$ (51 mg, 1.20 mmol, 3.0 equiv) was added and stirred for 3 hours. The reaction mixture was partially concentrated and acidified with 1 N HCl, and then the aqueous layer was extracted with EtOAc. The organic layer was dried over $MgSO_4$ and then concentrated under reduced pressure. The crude product was purified by silica gel column chromatography (15% EtOAc/hexane) to obtain 4-([1,1'-biphenyl]-4-ylmethyl)thiophene-3-carboxylic acid (101 mg, yield 86%) as a white solid. $^1H$ NMR (400 MHz, Chloroform-d) δ 10.02 (s, 1H), 8.23 (dd, J=3.1, 1.2 Hz, 1H), 7.60-7.52 (m, 6H), 7.44-7.40 (m, 1H), 7.35-7.28 (m, 2H), 6.82 (d, J=3.3 Hz, 1H), 4.31 (s, 2H).

Step 2: Synthesis of 4-([1,1'-biphenyl]-4-ylmethyl-2-methylthiophene-3-carboxylic acid

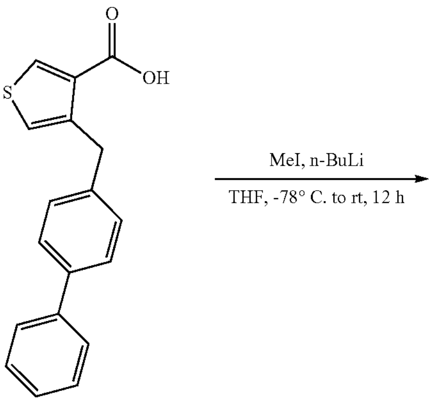

-continued

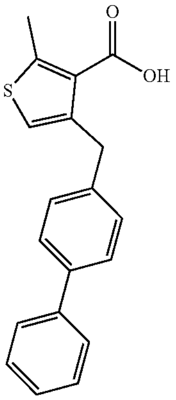

To a solution of methyl 4-([1,1'-biphenyl]-4-ylmethyl)thiophene-3-carboxylic acid (70 mg, 0.12 mmol) in THF (1 mL) cooled to −78° C., n-BuLi (2.5 M in THF, 125 μL, 0.27 mmol) was added and stirred for 30 minutes. Iodomethane (18 μL, 0.31 mmol) was slowly added at −78° C., and the mixture was stirred at ambient temperature for 12 hours. The reaction mixture was quenched with distilled water (15 mL) and EtOAc, and then purified by silica gel column chromatography to obtain 4-([1,1'-biphenyl]-4-ylmethyl)-2-methylthiophene-3-carboxylic acid (32 mg, yield 45%) as a white solid. $^1$H NMR (300 MHz, Chloroform-d) δ 7.60-7.51 (m, 3H), 7.48-7.38 (m, 3H), 7.35-7.26 (m, 2H), 7.00 (d, J=5.4 Hz, 1H), 6.50 (d, J=1.2 Hz, 1H), 4.24 (s, 2H), 2.77 (s, 3H).

Step 3: Synthesis of methyl 6-(4-([1,1'-biphenyl]-4-ylmethyl)-2-methylthiophene-3-carboxamido)spiro[3.3]heptane-2-carboxylate -continued

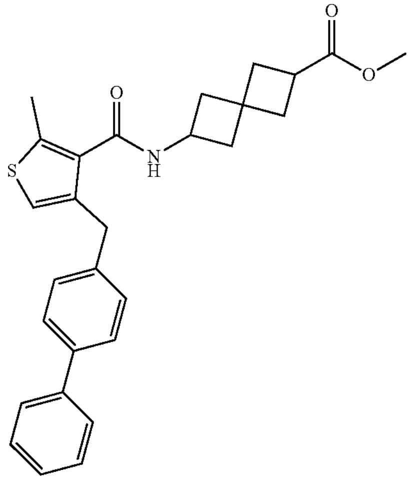

To a solution of 4-([1,1'-biphenyl]-4-ylmethyl)-2-methylthiophene-3-carboxylic acid (30 mg, 0.096 mmol) in MeCN (0.6 mL), 4-(4,6-dimethoxy-[1,3,5]triazin-2-yl)-4-methylmorpholin-4-ium chloride (DMT-MM) (27 mg, 0.105 mmol) was added and stirred for 1 hour. Intermediate A (15 mg, 0.105 mmol) and N-methylpyrrolidone (25.8 μL) were added to the reaction mixture and stirred for 12 hours, and then the reaction was quenched with distilled water and EtOAc. The crude product was purified by column chromatography (hexane:EA (35%)) to obtain methyl 6-(4-([1,1'-biphenyl]-4-ylmethyl)-2-methylthiophene-3-carboxamido)spiro[3.3]heptane-2-carboxylate (18 mg, yield 40%). $^1$H NMR (500 MHz, Chloroform-d) δ 7.57-7.54 (m, 2H), 7.52-7.49 (m, 2H), 7.43 (dd, J=8.5, 6.9 Hz, 2H), 7.36-7.32 (m, 1H), 7.25-7.21 (m, 2H), 6.74 (s, 1H), 5.46 (d, J=7.7 Hz, 1H), 4.35-4.27 (m, 1H), 4.02 (s, 2H), 3.65 (s, 3H), 2.96 (q, J=8.5 Hz, 1H), 2.50 (s, 3H), 2.48-2.44 (m, 1H), 2.37-2.33 (m, 1H), 2.29 (dd, J=8.5, 4.0 Hz, 2H), 2.20 (dd, J=11.7, 8.4 Hz, 1H), 2.02 (ddd, J=11.6, 8.6, 2.7 Hz, 1H), 1.66-1.61 (m, 2H).

Step 4: Synthesis of 6-(4-([1,1'-biphenyl]-4-ylmethyl)-2-methylthiophene-3-carboxamido)spiro[3.3]heptane-2-carboxylic acid

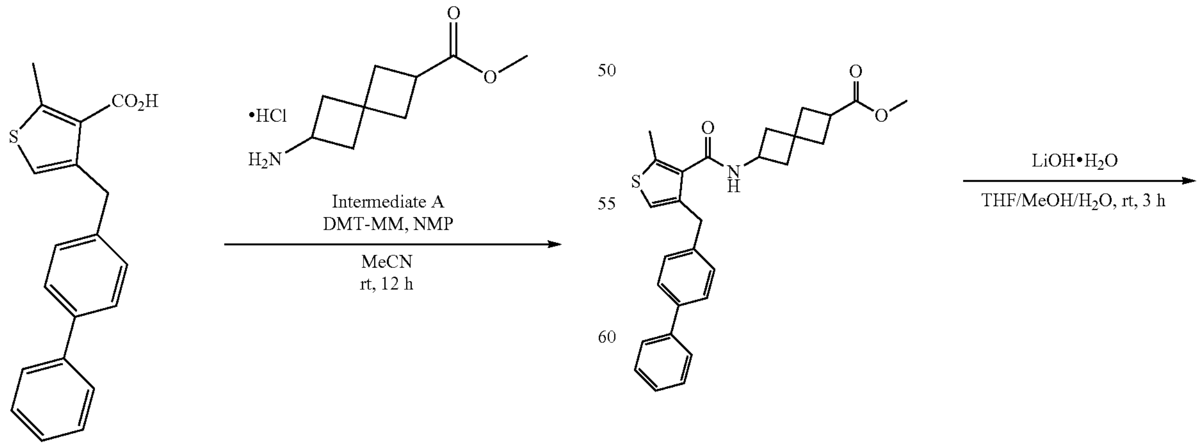

-continued

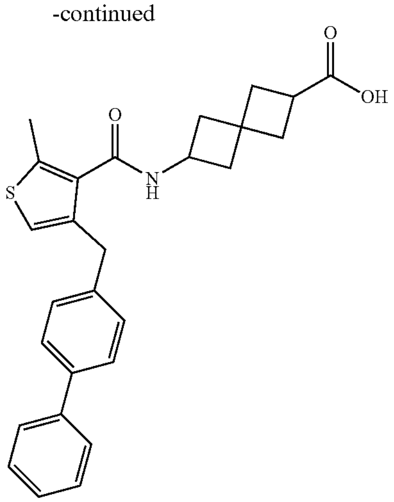

14

To a solution of methyl 6-(4-([1,1'-biphenyl]-4-ylmethyl)-2-methylthiophene-3-carboxamido)spiro[3.3]heptane-2-carboxylate (10 mg) in THF/MeOH/$H_2O$ (2/1/2 mL), LiOH·$H_2O$ (2 mg, 3.0 equiv) was added and stirred for 3 hours. The mixture was partially concentrated and then acidified with 1 N HCl aqueous solution. The aqueous layer was extracted with EtOAc, and the organic layer was dried over $MgSO_4$ and then concentrated under reduced pressure. The crude product was purified by column chromatography (hexane:EA (60%)) to obtain the compound of Example 14 (2.3 mg, yield 24%). $^1H$ NMR (500 MHz, Methanol-d4) δ 7.61-7.58 (m, 2H), 7.53-7.50 (m, 2H), 7.43 (td, J=7.9, 2.1 Hz, 2H), 7.32 (td, J=7.2, 1.4 Hz, 1H), 7.24 (t, J=8.4 Hz, 2H), 6.89 (s, 1H), 4.21-4.16 (m, 1H), 4.01 (s, 2H), 2.96 (q, J=8.5 Hz, 1H), 2.44 (s, 3H), 2.43-2.37 (m, 1H), 2.35-2.26 (m, 3H), 2.16 (dd, J=11.8, 8.4 Hz, 1H), 2.10-2.05 (m, 1H), 1.86-1.79 (m, 2H). LC/MS (ESI) m/z: 446.58 $[M+H]^+$, 444.42 $[M+H]^-$.

Example 15: 6-(4-([1,1'-biphenyl]-4-ylmethyl)-5-bromothiophene-3-carboxamido)spiro[3.3]heptane-2-carboxylic acid

Step 1: Synthesis of 4-([1,1'-biphenyl]-4-ylmethyl)thiophene-3-carboxylic acid

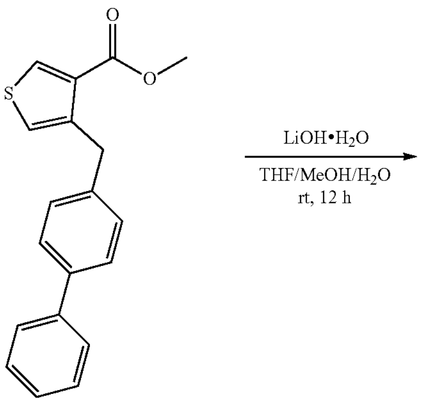

-continued

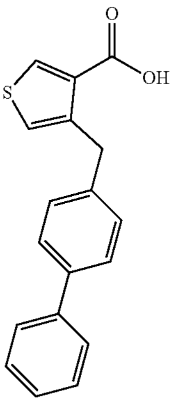

To a solution of methyl 4-([1,1'-biphenyl]-4-ylmethyl)thiophene-3-carboxylate (1.3 g, 4.215 mmol) obtained in Step 2 of Example 13 in THF/MeOH/$H_2O$ (2/1/2 mL), LiOH·$H_2O$ (530 mg, 12.645 mmol, 3.0 equiv) was added and stirred for 12 hours. The reaction mixture was partially concentrated and then acidified with 1 N HCl aqueous solution, and the aqueous layer was extracted with EtOAc. The organic layer was dried over $MgSO_4$ and concentrated under reduced pressure, and then the crude product was purified by silica gel column to obtain 4-([1,1'-biphenyl]-4-ylmethyl)thiophene-3-carboxylic acid (350 mg, yield 28%) as an ivory solid. $^1H$ NMR (400 MHz, Chloroform-d) δ 8.32-8.28 (m, 1H), 7.64-7.60 (m, 2H), 7.60-7.55 (m, 2H), 7.48-7.43 (m, 2H), 7.37-7.32 (m, 3H), 6.89-6.82 (m, 1H), 4.34 (s, 2H).

Step 2: Synthesis of 4-([1,1'-biphenyl]-4-ylmethyl)-5-bromothiophene-3-carboxylic acid

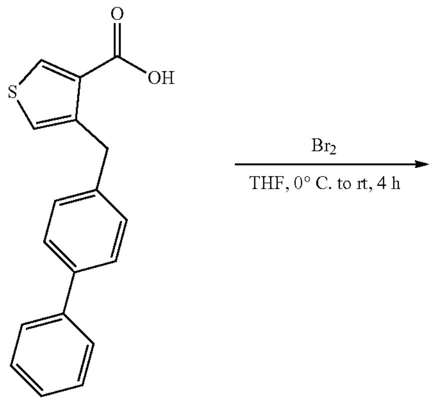

-continued

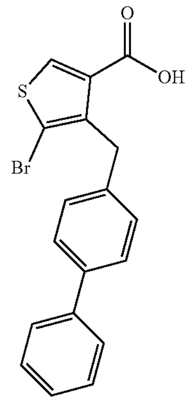

To a solution of 4-([1,1'-biphenyl]-4-ylmethyl)thiophene-3-carboxylic acid (200 mg, 0.66 mmol) in THF (1 mL), $Br_2$ (0.04 mL, 0.69 mmol) was added at 0° C. and stirred for 4 hours. The reaction mixture was acidified with 1 N HCl aqueous solution, and the aqueous layer was extracted with ether, and then the organic layer was washed with distilled water, dried over $MgSO_4$, and concentrated under reduced pressure. The crude product was purified by silica gel flash column chromatography to obtain 4-([1,1'-biphenyl]-4-ylmethyl)-5-bromothiophene-3-carboxylic acid (132 mg, yield 28%) as a brown solid. $^1H$ NMR (500 MHz, Chloroform-d) δ 8.29 (s, 1H), 7.59-7.54 (m, 2H), 7.52-7.48 (m, 2H), 7.44-7.40 (m, 2H), 7.36-7.31 (m, 1H), 7.30-7.29 (m, 1H), 7.29-7.27 (m, 1H), 4.41-4.36 (m, 2H).

Step 3: Synthesis of methyl 6-(4-([1,1'-biphenyl]-4-ylmethyl)-5-bromothiophene-3-carboxamido)spiro[3.3]heptane-2-carboxylate

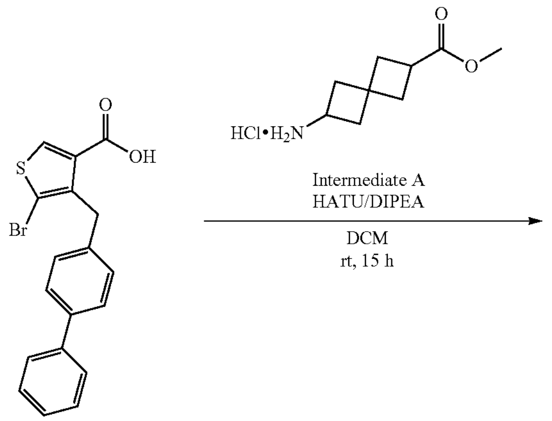

-continued

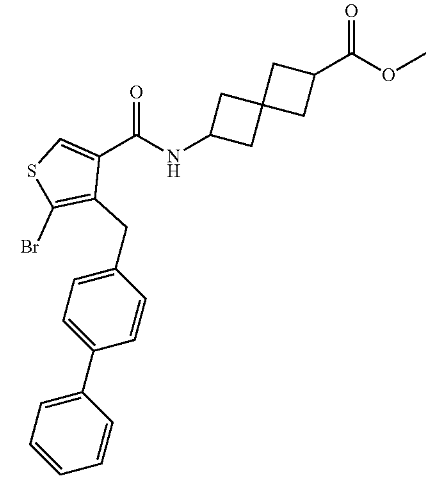

To a solution of 4-([1,1'-biphenyl]-4-ylmethyl)-5-bromothiophene-3-carboxylic acid (50 mg, 0.134 mmol) and HATU (56 mg, 0.147 mmol) in DMF (1 mL), DIPEA (0.070 mL, 0.402 mmol) was added, and Intermediate A (17 mg, 0.120 mmol) was added to the reaction mixture and stirred for 15 hours. The reaction mixture was diluted with ethyl acetate and washed with distilled water and brine solution. The organic layer was dried over $Na_2SO_4$ and concentrated under reduced pressure. The crude product was purified by column chromatography (20% ethyl acetate in hexane) to obtain methyl 6-(4-([1,1'-biphenyl]-4-ylmethyl)-5-bromothiophene-3-carboxamido)spiro[3.3]heptane-2-carboxylate (44.9 mg, yield 64%) as an ivory solid. $^1H$ NMR (500 MHz, Chloroform-d) δ 7.56-7.53 (m, 3H), 7.50-7.48 (m, 2H), 7.44-7.39 (m, 2H), 7.35-7.31 (m, 1H), 7.26-7.22 (m, 2H), 5.82-5.76 (m, 1H), 4.28-4.23 (m, 1H), 4.22 (s, 2H), 3.63 (s, 3H), 3.02-2.91 (m, 1H), 2.48-2.41 (m, 1H), 2.35-2.31 (m, 1H), 2.30-2.25 (m, 2H), 2.22-2.16 (m, 1H), 2.04-1.96 (m, 1H), 1.68-1.59 (m, 2H).

Step 4: Synthesis of 6-(4-([1,1'-biphenyl]-4-ylmethyl)-5-bromothiophene-3-carboxamido)spiro[3.3]heptane-2-carboxylic acid

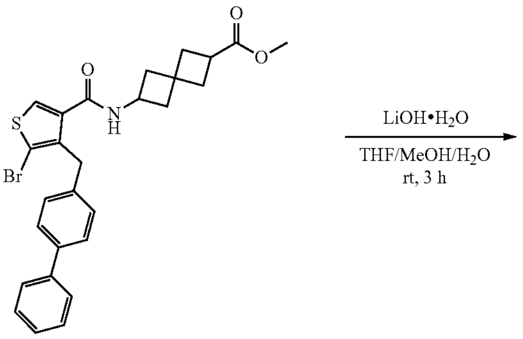

-continued

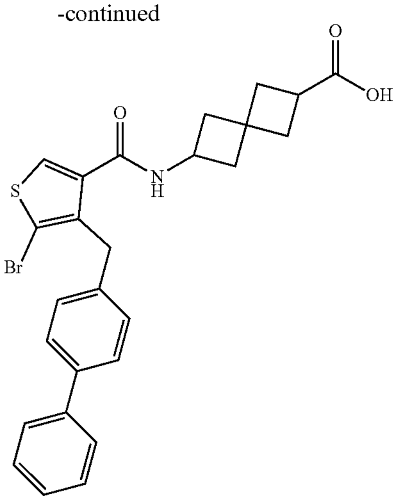

15

To a solution of methyl 6-(4-([1,1'-biphenyl]-4-ylmethyl)-5-bromothiophene-3-carboxamido)spiro[3.3]heptane-2-carboxylate (20 mg, 0.038 mmol) in THF/MeOH/$H_2O$ (2/1/2 mL), LiOH·$H_2O$ (5 mg, 0.114 mmol, 3.0 equiv) was added and stirred for 3 hours. The mixture was partially concentrated and then acidified with 1 N HCl, and then the aqueous layer was extracted with EtOAc. The organic layer was dried over $MgSO_4$ and then concentrated under reduced pressure. The crude product was purified by silica gel column to obtain the compound of Example 15 (15 mg, yield 77%) as an ivory solid. $^1$H NMR (400 MHz, Chloroform-d) δ 7.58 (s, 1H), 7.56-7.52 (m, 2H), 7.51-7.47 (m, 2H), 7.45-7.40 (m, 2H), 7.36-7.30 (m, 1H), 7.25-7.21 (m, 2H), 5.74-5.68 (m, 1H), 4.33-4.26 (m, 1H), 4.23 (s, 2H), 3.05-2.94 (m, 1H), 2.50-2.41 (m, 1H), 2.39-2.35 (m, 1H), 2.34-2.29 (m, 2H), 2.24-2.16 (m, 1H), 2.07-1.99 (m, 1H), 1.68-1.58 (m, 2H). LC/MS (ESI) m/z: 510.51 $[M+H]^+$, 508.35 $[M-H]^-$.

Example 16: 6-(4-([1,1'-biphenyl]-4-ylmethyl)-2,5-dibromothiophene-3-carboxamido)spiro[3.3]heptane-2-carboxylic acid

Step 1: Synthesis of methyl 4-([1,1'-biphenyl]-4-ylmethyl)-2,5-dibromothiophene-3-carboxylate

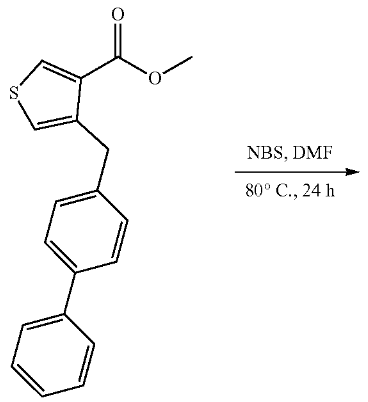

-continued

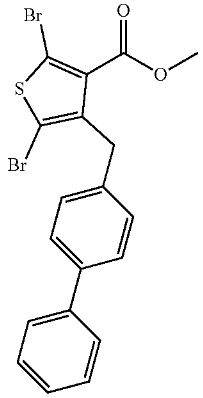

To a solution of methyl 4-([1,1'-biphenyl]-4-ylmethyl) thiophene-3-carboxylate (100 mg, 0.324 mmol) obtained in Step 2 of Example 13 in DMF (3 mL), NBS (287 mg, 1.622 mmol) was added and stirred at 80° C. for 24 hours. 10% sodium bicarbonate aqueous solution and EA were added to the reaction mixture, and the organic layer was dried over $MgSO_4$ and concentrated to obtain methyl 4-([1,1'-biphenyl]-4-ylmethyl)-2,5-dibromothiophene-3-carboxylate (76 mg, yield 50%) as a white solid. $^1$H NMR (300 MHz, $CDCl_3$) δ 7.59-7.53 (m, 2H), 7.51-7.46 (m, 2H), 7.44-7.39 (m, 2H), 7.30-7.33 (m, 1H), 7.18 (d, J=8.2 Hz, 2H), 4.23 (s, 2H), 3.76 (s, 3H).

Step 2: Synthesis of 4-([1,1'-biphenyl]-4-ylmethyl)-2,5-dibromothiophene-3-carboxylic acid

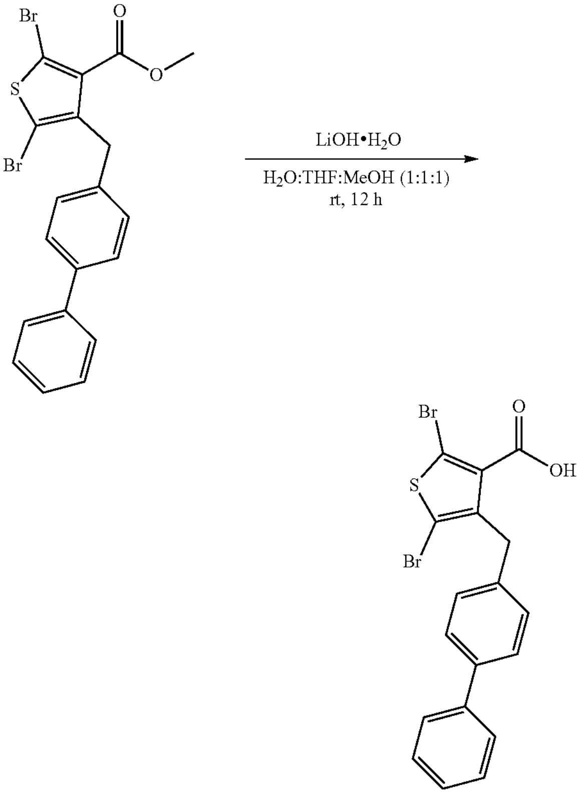

To a solution of methyl 4-([1,1'-biphenyl]-4-ylmethyl)-2,5-dibromothiophene-3-carboxylate (76 mg, 0.163 mmol) in THF/MeOH/$H_2O$ (1/1/1 mL), LiOH·$H_2O$ (21 mg, 0.489 mmol) was added and stirred for 12 hours. The reaction mixture was partially concentrated and then acidified with 1 N HCl aqueous solution, and the aqueous layer was extracted with EtOAc. The organic layer was dried over $MgSO_4$ and then concentrated to obtain 4-([1,1'-biphenyl]-4-ylmethyl)-2,5-dibromothiophene-3-carboxylic acid (35.5 mg, yield 47%) as a white solid. $^1H$ NMR (300 MHz, $CDCl_3$) δ 7.50-7.56 (m, 2H), 7.47 (d, J=8.2 Hz, 2H), 7.45-7.40 (m, 2H), 7.35-7.32 (m, 1H), 7.19 (d, J=8.2 Hz, 2H), 4.29 (s, 2H).

Step 3: Synthesis of methyl 6-(4-([1,1'-biphenyl]-4-ylmethyl)-2,5-dibromothiophene-3-carboxamido)spiro[3.3]heptane-2-carboxylate

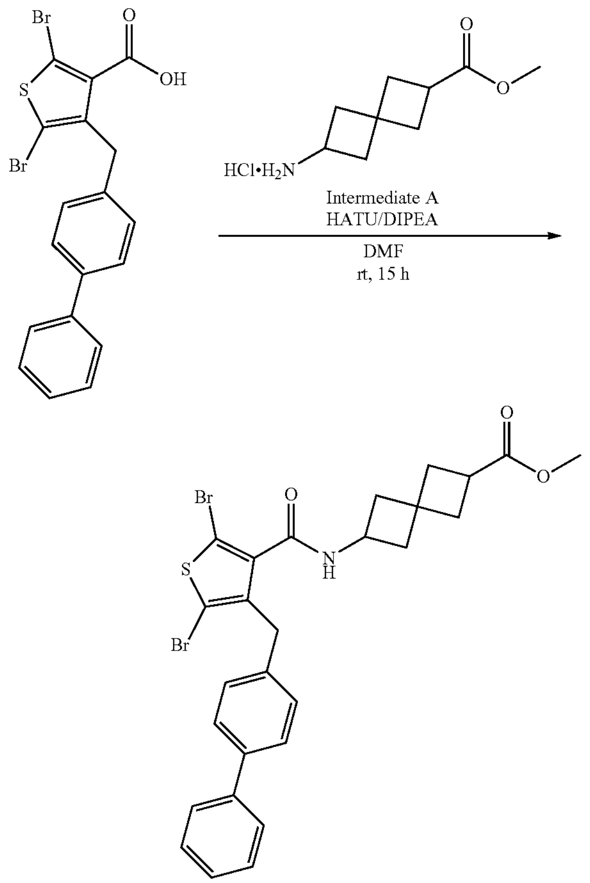

To a solution of 4-([1,1'-biphenyl]-4-ylmethyl)-2,5-dibromothiophene-3-carboxylic acid (35.5 mg, 0.079 mmol) and HATU (33 mg, 0.086 mmol) in DMF (1 mL), DIPEA (0.041 mL, 0.237 mmol) was added, and then Intermediate A (18 mg, 0.086 mmol) was added and stirred for 15 hours. The reaction mixture was diluted with ethyl acetate and washed with distilled water and brine solution. The organic layer was dried over $Na_2SO_4$ and concentrated under reduced pressure. The crude product was purified by column chromatography to obtain methyl 6-(4-([1,1'-biphenyl]-4-ylmethyl)-2,5-dibromothiophene-3-carboxamido)spiro[3.3]heptane-2-carboxylate (43.8 mg, yield 92%) as a white solid. $^1H$ NMR (300 MHz, $CDCl_3$) δ 7.57-7.51 (m, 2H), 7.50-7.40 (m, 4H), 7.37-7.30 (m, 1H), 7.20 (s, 2H), 5.58 (d, J=7.9 Hz, 1H), 4.32-4.24 (m, 1H), 4.11 (s, 2H), 3.65 (s, 3H), 3.02-2.91 (m, 1H), 2.50-2.42 (m, 1H), 2.25-2.40 (m, 3H), 2.20-2.17 (m, 1H), 2.06-1.99 (m, 1H), 1.73-1.63 (m, 2H).

Step 4: Synthesis of 6-(4-([1,1'-biphenyl]-4-ylmethyl)-2,5-dibromothiophene-3-carboxamido)spiro[3.3]heptane-2-carboxylic acid

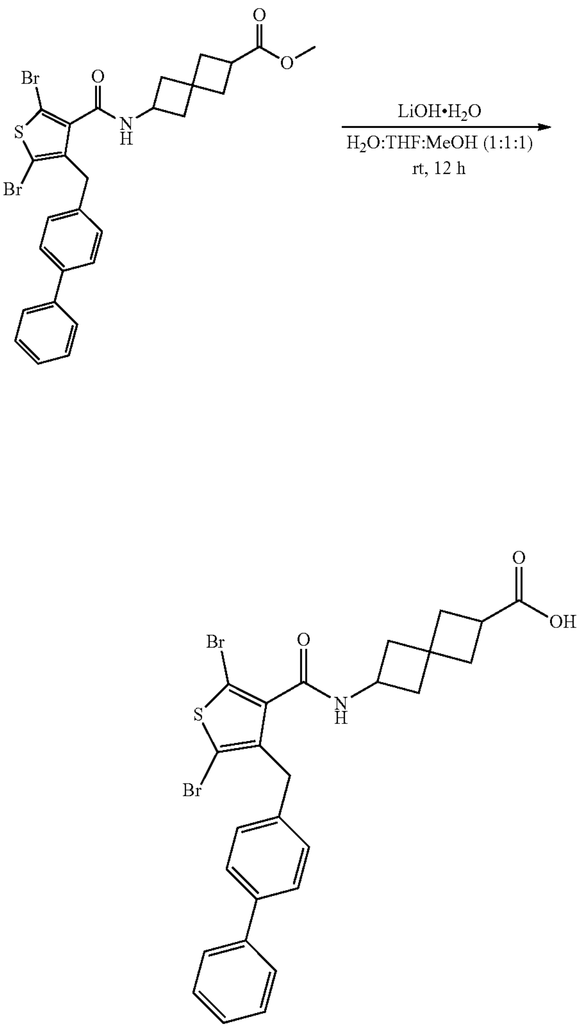

16

To a solution of methyl 6-(4-([1,1'-biphenyl]-4-ylmethyl)-2,5-dibromothiophene-3-carboxamido)spiro[3.3]heptane-2-carboxylate (42 mg, 0.070 mmol) in THF/MeOH/$H_2O$ (1/1/1 mL), LiOH·$H_2O$ (9 mg, 0.209 mmol) was added and stirred for 12 hours. The reaction mixture was partially concentrated, then acidified with 1 N HCl aqueous solution, and filtered to obtain the compound of Example 16 (4 mg, yield 4%) as a white solid. $^1H$ NMR (300 MHz, $CDCl_3$) δ 7.56-7.51 (m, 2H), 7.50-7.39 (m, 4H), 7.36-7.33 (m, 1H), 7.21 (d, J=8.2 Hz, 2H), 5.58 (d, J=7.7 Hz, 1H), 4.32-4.24 (m, 1H), 4.11 (s, 2H), 3.06-2.95 (m, 1H), 2.51-2.29 (m, 4H), 2.25-2.17 (m, 1H), 2.14-2.04 (m, 1H), 1.77-1.63 (m, 2H). LC/MS (ESI) m/z: 590.4 $[M+H]^+$.

Example 17: 6-(4-([1,1'-biphenyl]-4-ylmethyl)-2,5-dichlorothiophene-3-carboxamido)spiro[3.3]heptane-2-carboxylic acid Step 1: Synthesis of 4-([1,1'-biphenyl]-4-ylmethyl)-2,5-dichlorothiophene-3-carboxylic acid

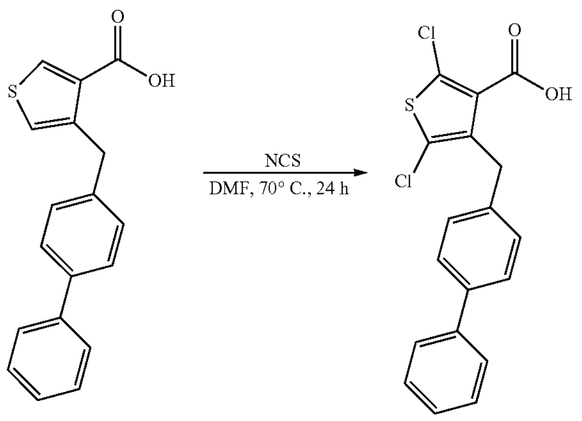 [SMILES: O=C(O)c1cscc1Cc1ccc(-c2ccccc2)cc1 ; "NCS" ; O=C(O)c1c(Cl)sc(Cl)c1Cc1ccc(-c2ccccc2)cc1]

To a solution of 4-([1,1'-biphenyl]-4-ylmethyl)thiophene-3-carboxylic acid (110 mg, 0.374 mmol) obtained in Step 3 of Example 13 in DMF (3.6 mL), NCS (250 mg, 1.869 mmol) was added, heated to 70° C., and stirred for 24 hours. The reaction mixture was quenched with 10% sodium bicarbonate aqueous solution, and after 15 minutes, extracted with EA and distilled water, dried over $MgSO_4$, and concentrated to obtain a crude product of 4-([1,1'-biphenyl]-4-ylmethyl)-2,5-dichlorothiophene-3-carboxylic acid (34.4 mg, yield 25%). $^1H$ NMR (300 MHz, $CDCl_3$) δ 7.58-7.52 (m, 2H), 7.52-7.46 (m, 2H), 7.42 (td, J=8.2, 1.8 Hz, 3H), 7.36 (s, 1H), 7.23 (d, J=8.2 Hz, 2H), 4.29 (s, 2H).

Steps 2 and 3: Synthesis of 6-(4-([1,1'-biphenyl]-4-ylmethyl)-2,5-dichlorothiophene-3-carboxamido)spiro[3.3]heptane-2-carboxylic acid

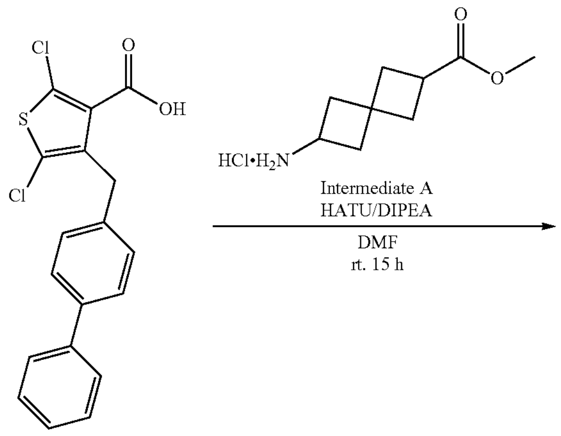

-continued

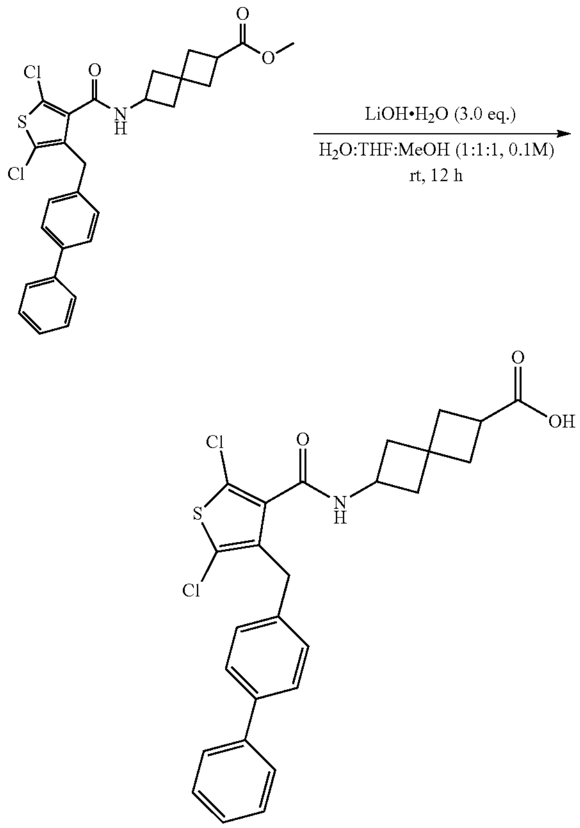

17

The compound of Example 17 was obtained by reacting 4-([1,1'-biphenyl]-4-ylmethyl)-2,5-dichlorothiophene-3-carboxylic acid obtained in Step 1 above in the same manner as in Steps 3 and 4 of Example 16. $^1H$ NMR (300 MHz, $CDCl_3$) δ 7.57-7.51 (m, 2H), 7.50-7.39 (m, 4H), 7.34-7.31 (m, 1H), 7.22 (d, J=8.2 Hz, 2H), 5.68 (d, J=7.6 Hz, 1H), 4.33-4.25 (m, 1H), 4.11 (s, 2H), 3.07-2.95 (m, 1H), 2.53-2.30 (m, 4H), 2.27-2.03 (m, 2H), 1.75-1.66 (m, 2H). LC/MS (ESI) m/z: 500.3 $[M+H]^+$.

Example 18: 6-(3-([1,1'-biphenyl]-4-ylmethyl)thiophene-2-carboxamido)spiro[3.3]heptane-2-carboxylic acid Step 1: Synthesis of 3-([1,1'-biphenyl]-4-ylmethyl)thiophene-2-carboxylic acid

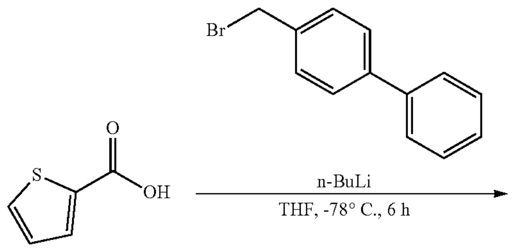

-continued

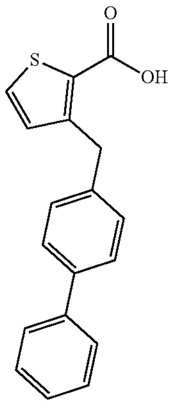

To a solution of thiophene-2-carboxylic acid (200 mg, 1.561 mmol) in THF (15 mL), n-BuLi (10 M in THF, 0.324 ml, 3.434 mmol) was slowly added at −78° C. for 0.5 hours, and then 4-(bromomethyl)-1,1'-biphenyl (772 mg, 3.122 mmol) was added. The reaction mixture was stirred for 6 hours, and then quenched with 1 N HCl aqueous solution, and extracted with EA and distilled water. The organic layer was dried over $MgSO_4$ and then concentrated under reduced pressure. The crude product was purified by flash column chromatography to obtain 3-([1,1'-biphenyl]-4-ylmethyl) thiophene-2-carboxylic acid as a white solid (28 mg, yield 6%). $^1$H NMR (300 MHz, $CDCl_3$) δ 7.60-7.55 (m, 2H), 7.55-7.48 (m, 3H), 7.45-7.40 (m, 2H), 7.35-7.28 (m, 3H), 6.93 (d, J=5.1 Hz, 1H), 4.45 (s, 2H).

Step 2: Synthesis of methyl 6-(3-([1,1'-biphenyl]-4-ylmethyl)thiophene-2-carboxamido)spiro[3.3]heptane-2-carboxylate -continued

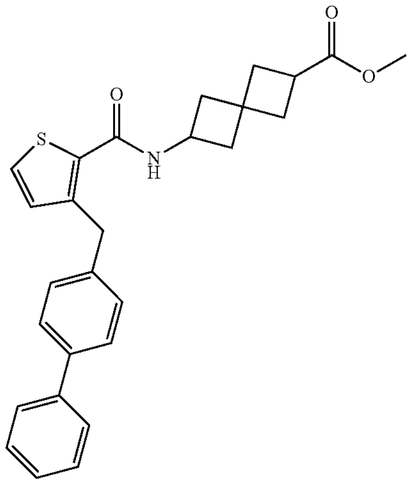

To a solution of 3-([1,1'-biphenyl]-4-ylmethyl)thiophene-2-carboxylic acid (26 mg, 0.088 mmol) and HATU (20 mg, 0.097 mmol) in DCM (1 mL), DIPEA (0.046 mL, 0.264 mmol) was added and stirred for 10 minutes. Intermediate A (20 mg, 0.097 mmol) was added to the reaction mixture and stirred for 15 hours. The reaction mixture was diluted with ethyl acetate and washed with distilled water and brine solution. The organic layer was dried over $Na_2SO_4$ and concentrated under reduced pressure. The crude product was purified by column chromatography (20% EtOAc in Hexane) to obtain methyl 6-(3-([1,1'-biphenyl]-4-ylmethyl) thiophene-2-carboxamido)spiro[3.3]heptane-2-carboxylate (32 mg, yield 82%) as a white solid. $^1$H NMR (300 MHz, $CDCl_3$) δ 7.59-7.50 (m, 4H), 7.42 (t, J=7.3 Hz, 2H), 7.34 (d, J=7.3 Hz, 1H), 7.32-7.27 (m, 3H), 6.92 (d, J=5.0 Hz, 1H), 5.84 (d, J=7.5 Hz, 1H), 4.50-4.34 (m, 3H), 3.66 (s, 3H), 3.07-2.96 (m, 1H), 2.59-2.51 (m, 1H), 2.46-2.40 (m, 1H), 2.35-2.22 (m, 3H), 2.14-2.07 (m, 1H), 1.87-1.76 (m, 2H).

Step 3: Synthesis of 6-(3-([1,1'-biphenyl]-4-ylmethyl)thiophene-2-carboxamido)spiro[3.3]heptane-2-carboxylic acid

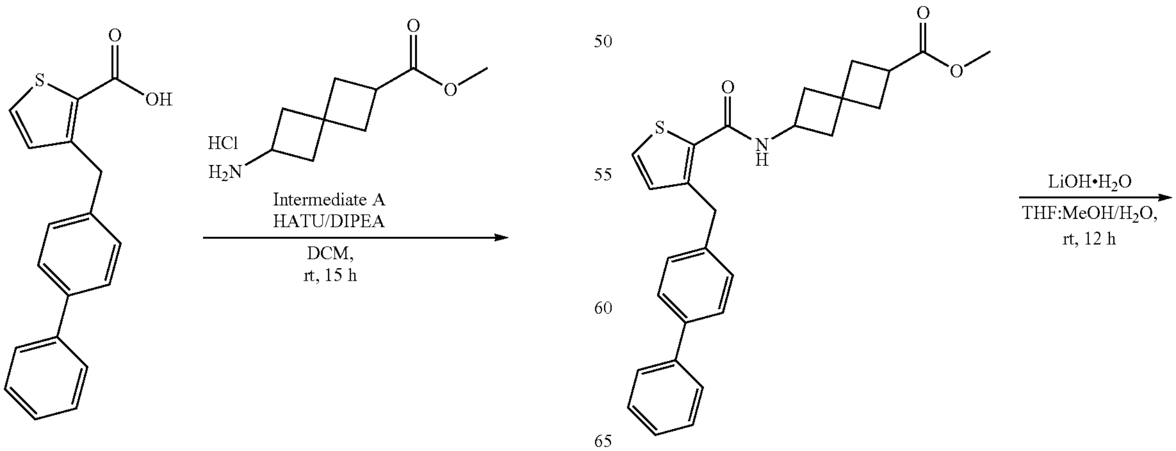

-continued

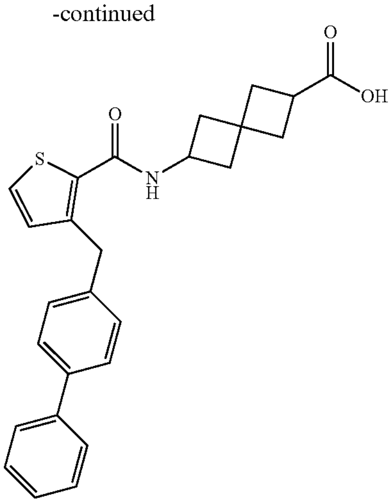

18

To a solution of methyl 6-(3-([1,1'-biphenyl]-4-ylmethyl)thiophene-2-carboxamido)spiro[3.3]heptane-2-carboxylate (32 mg, 0.072 mmol) in THF/MeOH/$H_2O$ (1/1/1), LiOH·$H_2O$ (9 mg, 0.209 mmol) was added and stirred for 12 hours. The reaction mixture was partially concentrated, then acidified with 1 N HCl aqueous solution, and filtered to obtain the compound of Example 18 (30.7 mg, yield 99%) as a pale yellow solid. $^1$H NMR (300 MHz, $CDCl_3$) δ 7.59-7.50 (m, 4H), 7.42 (t, J=7.4 Hz, 2H), 7.34 (d, J=7.4 Hz, 1H), 7.31-7.26 (m, 3H), 6.92 (d, J=5.0 Hz, 1H), 5.85 (d, J=7.5 Hz, 1H), 4.47-4.29 (m, 3H), 3.11-2.99 (m, 1H), 2.60-2.52 (m, 1H), 2.46-2.40 (m, 1H), 2.38-2.36 (m, 2H), 2.30-2.26 (m, 1H), 2.18-2.14 (m, 1H), 1.87-1.77 (m, 2H). LC/MS (ESI) m/z: 432.4 $[M+H]^+$.

Example 19: 6-(3-((3'-fluoro-5'-methoxy-[1,1'-biphenyl]-4-yl)methyl)thiophene-2-carboxamido)spiro[3.3]heptane-2-carboxylic acid

Steps 1 and 2: Synthesis of methyl 6-(3-(4-chlorobenzyl)thiophene-2-carboxamido)spiro[3.3]heptane-2-carboxylate

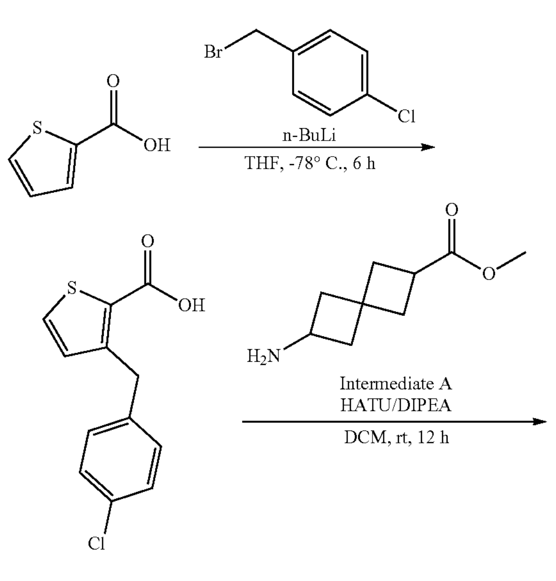

-continued

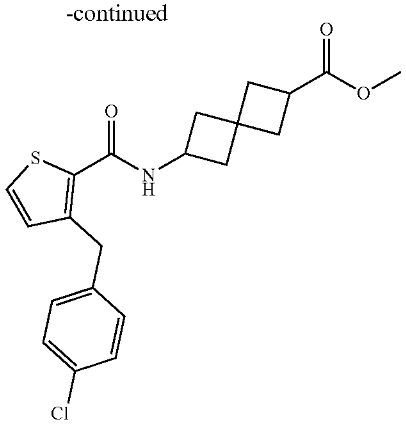

Methyl 6-(3-(4-chlorobenzyl)thiophene-2-carboxamido)spiro[3.3]heptane-2-carboxylate was obtained in the same manner as in Steps 1 and 2 of Example 18, except that 4-chlorobenzyl bromide was used instead of 4-(bromomethyl)-1,1-biphenyl in Step 1 of Example 18. $^1$H NMR (300 MHz, chloroform-d) δ 7.25-7.17 (m, 3H), 7.17-7.09 (m, 2H), 6.80 (d, J=5.0 Hz, 1H), 5.95 (d, J=7.5 Hz, 1H), 4.42-4.28 (m, 1H), 4.24 (s, 2H), 3.64 (s, 3H), 3.06-2.95 (m, 1H), 2.57-2.49 (m, 1H), 2.46-2.36 (m, 1H), 2.34-2.22 (m, 3H), 2.17-2.07 (m, 1H), 1.91-1.80 (m, 2H).

Step 3: Synthesis of methyl 6-(3-((3'-fluoro-5'-methoxy-[1,1'-biphenyl]-4-yl)methyl))thiophene-2-carboxamido)spiro[3.3]heptane-2-carboxylate

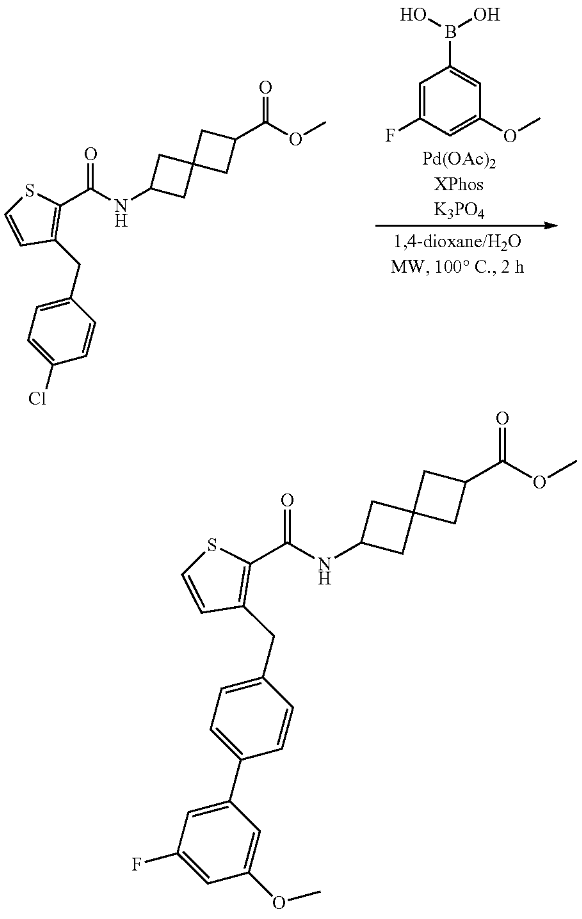

Methyl 6-(3-(4-chlorobenzyl)thiophene-2-carboxamido) spiro[3.3]heptane-2-carboxylate (286 mg, 0.7 mmol), 3-fluoro-5-methoxyphenylboronic acid (178 mg, 1.05 mmol, 1.5 equiv), $Pd(OAc)_2$ (16 mg, 0.07 mmol, 0.1 equiv), XPhos (67 mg, 0.14 mmol, 0.2 equiv) and $K_3PO_4$ (297 mg, 1.4 mmol, 2.0 equiv) were stirred in 1,4-dioxane/$H_2O$ (10/1 mL) under microwave irradiation at 100° C. for 2 hours. The reaction mixture was poured into distilled water and extracted with DCM. The organic layer was dried over $MgSO_4$ and concentrated under reduced pressure. The crude product was purified by flash column chromatography to obtain methyl 6-(3-((3'-fluoro-5'-methoxy-[1,1'-biphenyl]-4-yl)methyl)thiophene-2-carboxamido)spiro[3.3]heptane-2-carboxylate. $^1$H NMR (300 MHz, chloroform-d) δ 7.47 (d, J=8.2 Hz, 2H), 7.33-7.27 (m, 2H), 6.93-6.80 (m, 3H), 6.58 (dt, J=10.5, 2.3 Hz, 1H), 5.89 (d, J=7.5 Hz, 1H), 4.44-4.35 (m, 1H), 4.34 (s, 2H), 3.83 (s, 3H), 3.65 (s, 3H), 3.07-2.96 (m, 1H), 2.63-2.49 (m, 1H), 2.47-2.24 (m, 4H), 2.15-2.07 (m, 1H), 1.90-1.79 (m, 2H).

Step 4: Synthesis of 6-(3-((3'-fluoro-5'-methoxy-[1,1'-biphenyl]-4-yl)methyl)thiophene-2-carboxamido) spiro[3.3]heptane-2-carboxylic acid

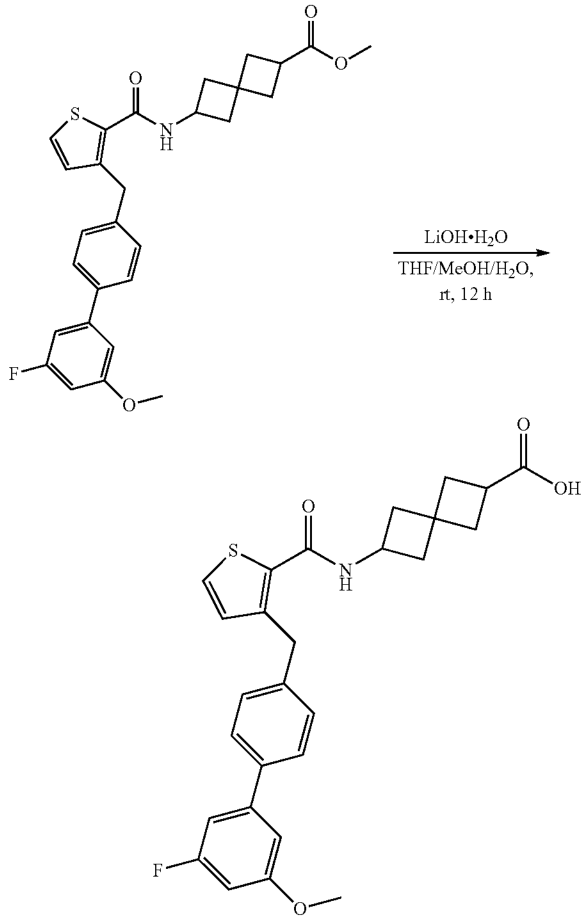

19

The compound of Example 19 was obtained by reacting methyl 6-(3-((3'-fluoro-5'-methoxy-[1,1'-biphenyl]-4-yl) methyl)thiophene-2-carboxamido)spiro[3.3]heptane-2-carboxylate obtained in Step 3 above in the same manner as in Step 3 of Example 18. $^1$H NMR (300 MHz, Methanol-$d_4$) δ 8.15 (d, J=7.2 Hz, 1H), 7.50 (d, J=8.2 Hz, 2H), 7.42 (d, J=5.0 Hz, 1H), 7.26 (d, J=8.3 Hz, 2H), 6.94 (t, J=1.9 Hz, 1H), 6.92-6.86 (m, 2H), 6.64 (dt, J=10.7, 2.3 Hz, 1H), 4.31-4.23 (m, 3H), 3.83 (s, 3H), 3.07-2.95 (m, 1H), 2.54-2.46 (m, 1H), 2.39-2.30 (m, 3H), 2.29-2.14 (m, 2H), 2.07-1.96 (m, 2H). LC/MS (ESI) m/z: 480.4 $[M+H]^+$.

Example 20: 6-(4-([1,1'-biphenyl]-4-ylmethyl)-5-methylthiophene-3-carboxamido)spiro[3.3]heptane-2-carboxylic acid

Step 1: Synthesis of methyl 4-([1,1'-biphenyl]-4-ylmethyl)-5-bromothiophene-3-carboxylate

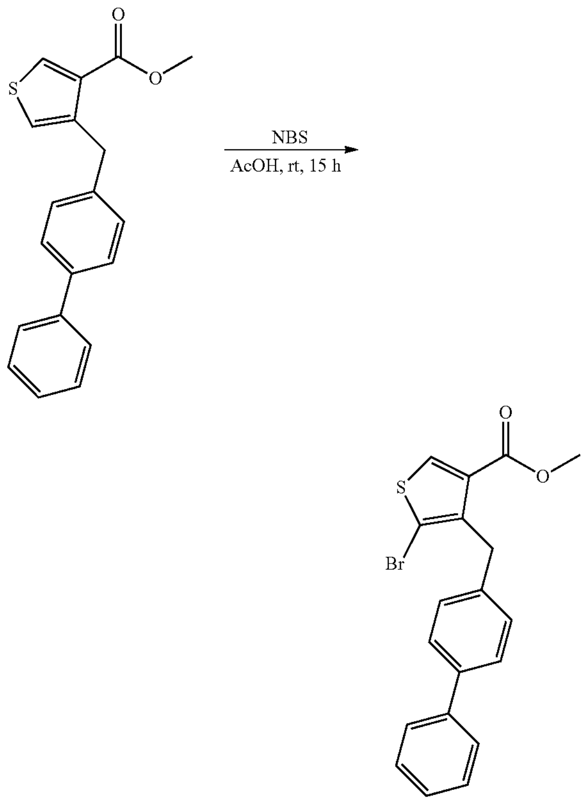

To a solution containing methyl 4-([1,1'-biphenyl]-4-ylmethyl)thiophene-3-carboxylate (200 mg, 0.649 mmol) obtained in Step 2 of Example 13 in AcOH, N-bromosuccinimide (NBS, 115 mg, 0.649 mmol) was slowly added at ambient temperature. After stirring for 15 hours, the reaction mixture was extracted with DCM and washed with sodium carbonate aqueous solution and distilled water. The organic layer was again washed twice with distilled water, dried over $MgSO_4$, then filtered, and concentrated under reduced pressure. The crude product was purified by silica gel (hexane) column chromatography to obtain methyl 4-([1,1'-biphenyl]-4-ylmethyl)-5-bromothiophene-3-carboxylate (150 mg, yield 59%) as a yellow solid. $^1$H NMR (300 MHz, Chloroform-d) δ 8.16 (s, 1H), 7.64-7.59 (m, 2H), 7.57-7.53 (m, 2H), 7.49-7.43 (m, 2H), 7.39-7.30 (m, 3H), 4.42 (s, 2H), 3.83 (s, 3H).

Step 2: Synthesis of methyl 4-([1,1'-biphenyl]-4-ylmethyl)-5-methylthiophene-3-carboxylate

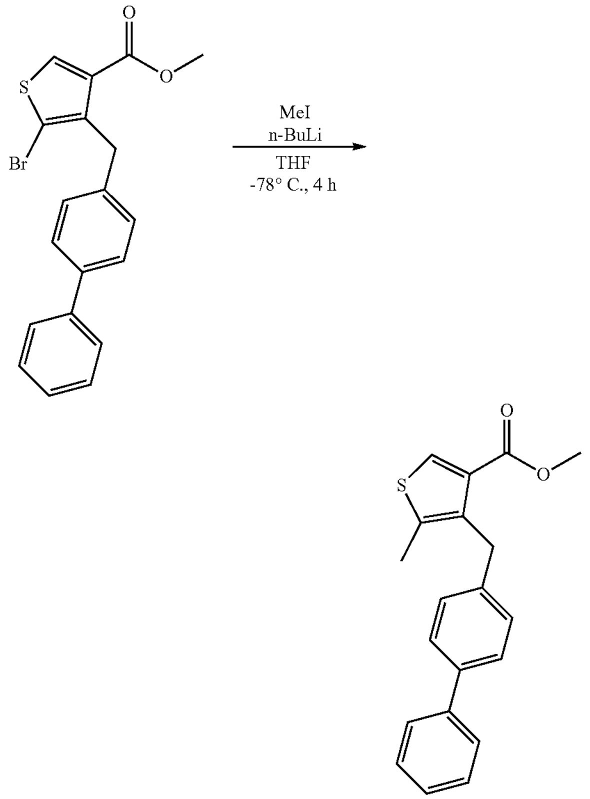

To a solution of methyl 4-([1,1'-biphenyl]-4-ylmethyl)-5-bromothiophene-3-carboxylate (200 mg, 0.516 mmol) in THF (10 mL), iodomethane (0.065 mL, 1.548 mmol, 3.0 equiv) was added and cooled to −78° C. n-BuLi (2 M in THF, 0.516 mL, 1.032 mmol) was added to the reaction mixture, stirred for 4 hours, then slowly warmed to ambient temperature, diluted with ethyl acetate, and washed with distilled water. The organic layer was dried over $Na_2SO_4$ and concentrated under reduced pressure to obtain a crude product of methyl 4-([1,1'-biphenyl]-4-ylmethyl)-5-methylthiophene-3-carboxylate (49 mg) as a yellow solid. $^1H$ NMR (400 MHz, Chloroform-d) δ 7.99 (s, 1H), 7.61-7.59 (m, 2H), 7.53-7.51 (m, 2H), 7.46-7.44 (m, 2H), 7.37-7.33 (m, 2H), 7.23-7.22 (m, 1H), 4.36 (s, 2H), 3.82 (s, 3H), 2.46 (s, 3H).

Step 3: Synthesis of 4-([1,1'-biphenyl]-4-ylmethyl)-5-methylthiophene-3-carboxylic acid

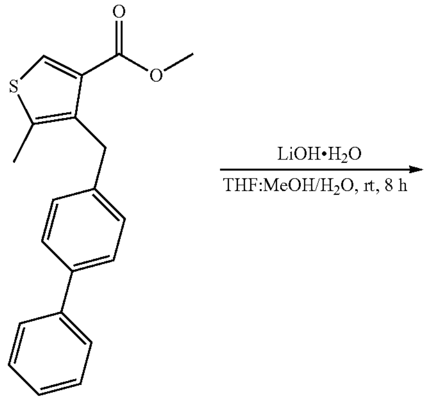

-continued

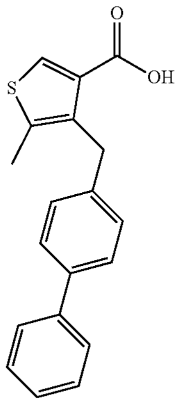

To a solution of methyl 4-([1,1'-biphenyl]-4-ylmethyl)-5-methylthiophene-3-carboxylate (20 mg, 0.062 mmol) in THF/MeOH/$H_2O$ (2/1/2), LiOH·$H_2O$ (8 mg, 0.186 mmol, 3 equiv) was added and stirred for 8 hours. The reaction mixture was partially concentrated and then acidified with 1 N HCl aqueous solution. The aqueous layer was extracted with EtOAc, and the organic layer was dried over $MgSO_4$ and then concentrated under reduced pressure. The crude product was purified by silica gel column to obtain 4-([1,1'-biphenyl]-4-ylmethyl)-5-methylthiophene-3-carboxylic acid (4.3 mg, yield 22%) as an ivory solid. $^1H$ NMR (300 MHz, chloroform-d) δ 8.10 (s, 1H), 7.59-7.54 (m, 2H), 7.50-7.47 (m, 2H), 7.45-7.39 (m, 2H), 7.36-7.31 (m, 1H), 7.22-7.16 (m, 2H), 4.34 (s, 2H), 2.44 (s, 3H).

Step 4: Synthesis of methyl 6-(4-([1,1'-biphenyl]-4-ylmethyl)-5-methylthiophene-3-carboxamido)spiro[3.3]heptane-2-carboxylate

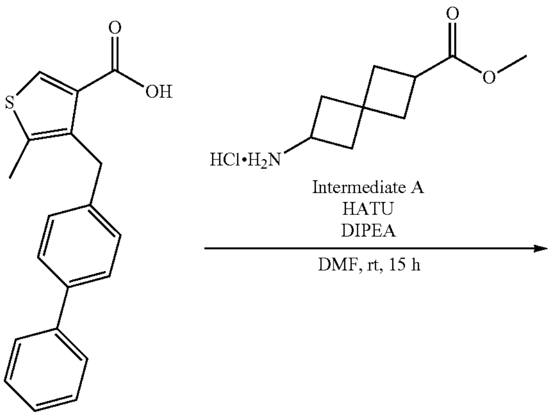

-continued

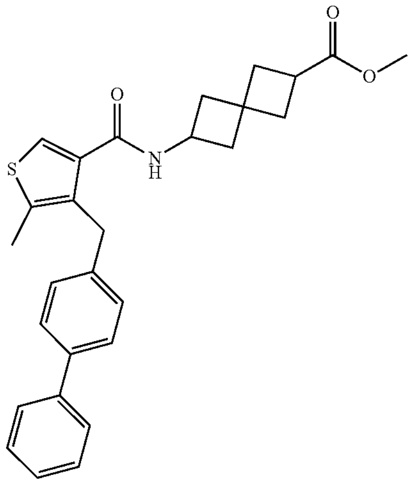

To a solution of 4-([1,1'-biphenyl]-4-ylmethyl)-5-methylthiophene-3-carboxylic acid (7.3 mg, 0.024 mmol) and HATU (10 mg, 0.026 mmol) in DMF, DIPEA (0.013 mL, 0.072 mmol) was added and stirred for 10 minutes, and then Intermediate A (4 mg, 0.026 mmol) was added and stirred for 15 hours. The reaction mixture was diluted with ethyl acetate and washed with distilled water and brine. The organic layer was dried over $Na_2SO_4$ and concentrated under reduced pressure. The crude product was purified by column chromatography (20% EtOAc in hexane) to obtain methyl 6-(4-([1,1'-biphenyl]-4-ylmethyl)-5-methylthiophene-3-carboxamido)spiro[3.3]heptane-2-carboxylate (6.9 mg, yield 63%) as a yellow solid. $^1H$ NMR (400 MHz, chloroform-d) δ 7.58-7.56 (m, 2H), 7.52-7.50 (m, 2H), 7.47-7.43 (m, 2H), 7.41 (s, 1H), 7.38-7.33 (m, 1H), 7.22-7.17 (m, 2H), 5.77-5.71 (m, 1H), 4.36-4.28 (m, 1H), 4.19 (s, 2H), 3.67 (s, 3H), 3.04-2.95 (m, 1H), 2.52-2.48 (m, 1H), 2.46 (s, 3H), 2.40-2.34 (m, 1H), 2.34-2.27 (m, 2H), 2.26-2.18 (m, 1H), 2.08-2.00 (m, 1H), 1.68-1.63 (m, 2H).

Step 5: Synthesis of 6-(4-([1,1'-biphenyl]-4-ylmethyl)-5-methylthiophene-3-carboxamido)spiro[3.3]heptane-2-carboxylic acid

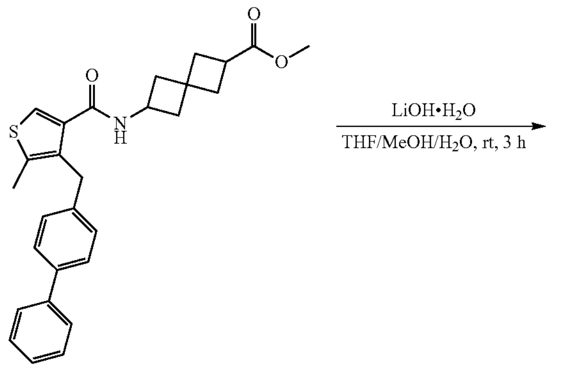

-continued

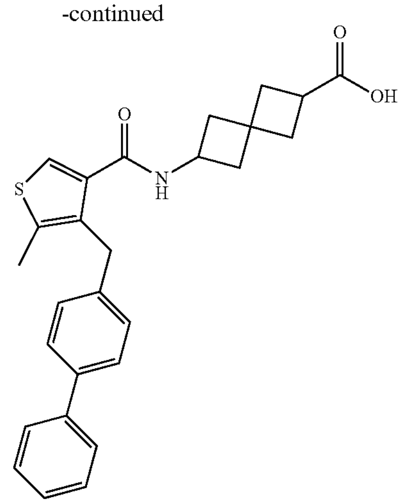

To a solution of methyl 6-(4-([1,1'-biphenyl]-4-ylmethyl)-5-methylthiophene-3-carboxamido)spiro[3.3]heptane-2-carboxylate (6.8 mg, 0.015 mmol) in $THF/MeOH/H_2O$ (2/1/2), $LiOH{\cdot}H_2O$ (2 mg, 0.044 mmol, 3.0 equiv) was added and stirred for 3 hours. The reaction mixture was partially concentrated and then acidified with 1 N HCl aqueous solution, and then the aqueous layer was extracted with EtOAc. The organic layer was dried over $MgSO_4$ and then concentrated under reduced pressure. The crude product was purified by silica gel column to obtain the compound of Example 20 (4.7 mg, yield 70%) as an ivory solid. $^1H$ NMR (500 MHz, chloroform-d) h 7.58-7.56 (xi, 2H), 7.53-7.50 (m, 2H), 7.47-7.43 (m, 3H), 7.38-7.34 (m, 1H), 7.22-7.17 (m, 2H), 5.76-5.71 (m, 1H), 4.31-4.29 (m, 1H), 4.19 (s, 2H), 3.05-2.98 (m, 1H), 2.52-2.49 (m, 1H), 2.46 (s, 3H), 2.36-2.33 (m, 3H), 2.27-2.22 (m, 1H), 2.10-2.05 (m, 1H), 1.71-1.65 (m, 2H). LC/MS (ESI) m/z: 446.11 $[M+H]^+$, 444.28 $[M-H]^-$.

The compounds of Examples 21 and 22 were prepared in the same manner as in Example 20 except for the differences in the preparation methods described below.

TABLE 3

| Example No. | Chemical structure | Name | Difference in preparation method |
|---|---|---|---|
| 21 | 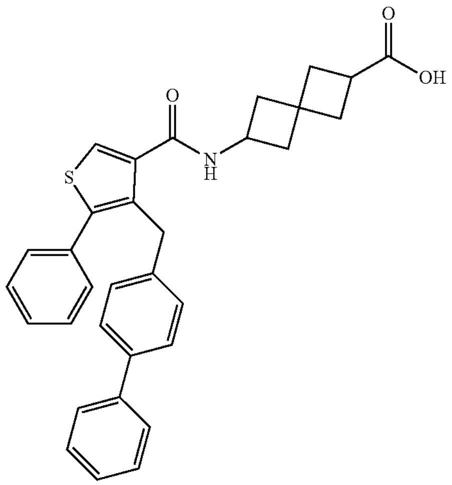 [SMILES: O=C(NC1CC2(C1)CC(C(=O)O)C2)c1csc(-c2ccccc2)c1Cc1ccc(-c2ccccc2)cc1] | 6-(4-([1,1'-biphenyl]-4-ylmethyl)-5-phenylthiophene-3-carboxamido)spiro[3.3]heptane-2-carboxylic acid | Suzuki coupling using phenylboronic acid instead of MeI in Step 2. Reaction reagents and conditions: $Na_2CO_3$ (4 equiv) and $Pd(PPh_3)_4$(12 mol %), toluene/$H_2O$ (6:1), 90° C., 12 hours |
| 22 | 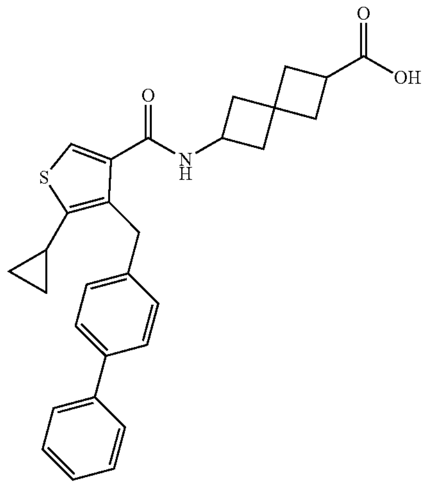 [SMILES: O=C(NC1CC2(C1)CC(C(=O)O)C2)c1csc(C2CC2)c1Cc1ccc(-c2ccccc2)cc1] | 6-(4-(1,1'-biphenyl]-4-ylmethyl)-5-cyclopropylthiophene-3-carboxamido)spiro[3.3]heptane-2-carboxylic acid | Suzuki coupling using cyclopropylboronic acid instead of MeI in Step 2. Reaction reagents and conditions were the same as in Example 21. |

TABLE 4

| Example No. | LC/MS (ESI) m/z: $[M + H]^+$ | NMR |
|---|---|---|
| 21 | n + 1 = 508.5 | $^1H$ NMR (300 MHz, DMSO) δ 12.04 (s, 1H), 8.39 (d, J = 7.4 Hz, 1H), 7.89 (s, 1H), 7.62-7.55 (m, 2H), 7.51-7.38 (m, 8H), 7.35-7.29 (m, 1H), 7.02-6.95 (m, 2H), 4.23 (s, 2H), 4.13-4.05 (m, 1H), 2.94-2.83 (m, 1H), 2.35-2.25 (m, 1H), 2.24-1.96 (m, 5H), 1.92-1.81 (m, 2H). |
| 22 | n + 1 = 472.4 | $^1H$ NMR (300 MHz, DMSO-d6) δ 12.05 (s, 1H), 8.32 (d, J = 7.5 Hz, 1H), 7.64-7.58 (m, 2H), 7.54 (s, 1H), 7.51 (d, J = 8.2 Hz, 2H), 7.44 (t, J = 7.5 Hz, 2H), 7.36-7.31 (m, 1H), 7.22 (d, J = 8.2 Hz, 2H), 4.26 (s, 2H), 4.21-4.08 (m, 1H), 2.97-2.86 (m, 1H), 2.40-2.32 (m, 1H), 2.26-2.02 (m, 6H), 1.98-1.86 (m, 2H), 1.07-0.98 (m, 2H), 0.63-0.57 (m, 2H). |

Example 23: 6-(4-(4-chlorobenzyl)-2,5-dimethylthiophene-3-carboxamido)spiro[3.3]heptane-2-carboxylic acid

Step 1: Synthesis of 3-bromo-4-(4-chlorobenzyl)-2,5-dimethylthiophene

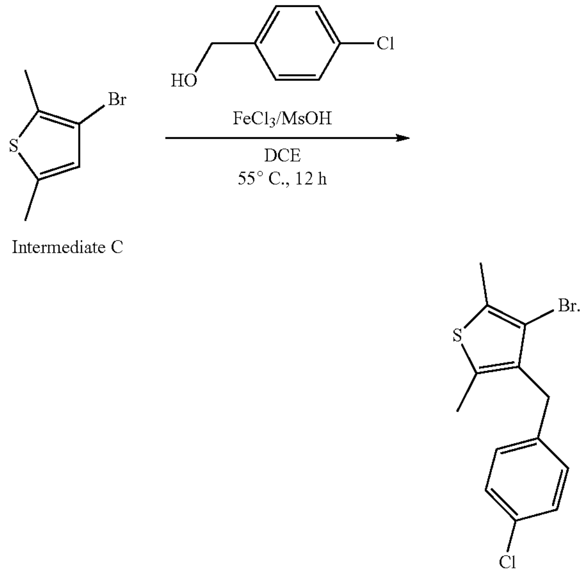

To a solution of (4-chlorophenyl)methanol (427 mg, 3.0 mmol) in DCE (3 mL), Intermediate C (1.15 g, 6.0 mmol), MsOH (78 μL, 1.20 mmol) and $FeCl_3$ (194 mg, 1.20 mmol) were added, then heated to 55° C., and stirred for 12 hours. The reaction mixture was diluted with ethyl acetate and washed with distilled water and brine solution. The organic layer was dried over $Na_2SO_4$ and then concentrated under reduced pressure. The crude product was purified by column chromatography to obtain bromo-4-(4-chlorobenzyl)-2,5-dimethylthiophene (541 mg, yield 57%) as a white solid. $^1$H NMR (300 MHz, chloroform-d) δ 7.28-7.20 (m, 2H), 7.08 (d, J=8.6 Hz, 2H), 3.91 (s, 2H), 2.37 (s, 3H), 2.35 (s, 3H).

Step 2: Synthesis of 4-(4-chlorobenzyl)-2,5-dimethylthiophene-3-carboxylic acid

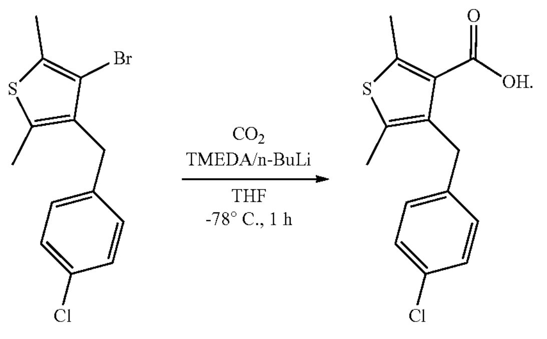 [SMILES: Cc1sc(C)c(Cc2ccc(Cl)cc2)c1Br ; Cc1sc(C)c(C(=O)O)c1Cc1ccc(Cl)cc1]

To a solution of 3-bromo-4-(4-chlorobenzyl)-2,5-dimethylthiophene (541 mg, 1.71 mmol) and TMEDA (0.3 mL, 1.88 mmol) in THF (10 mL), n-BuLi (2.5 M in THF, 0.8 mL, 2.0 mmol) was added at −78° C. and stirred for 1 hour. The reaction mixture was quenched with $CO_2$ gas at −78° C. and left at ambient temperature over 30 minutes. The reaction mixture was acidified with 1 N HCl solution, diluted with EtOAc, and then washed with distilled water. The organic layer was dried over $Na_2SO_4$ and then concentrated under reduced pressure to obtain 4-(4-chlorobenzyl)-2,5-dimethylthiophene-3-carboxylic acid (450 mg, crude product) as a pale yellow solid. LC/MS (ESI) m/z: 281.26 [M+H]$^+$.

Step 3: Synthesis of methyl 6-(4-(4-chlorobenzyl)-2,5-dimethylthiophene-3-carboxamido)spiro[3.3]heptane-2-carboxylate

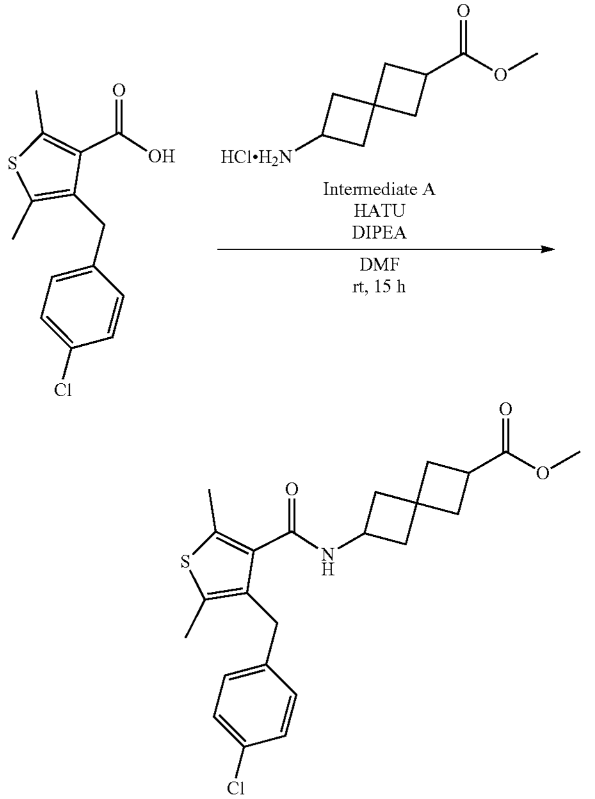

To a solution of 4-(4-chlorobenzyl)-2,5-dimethylthiophene-3-carboxylic acid (450 mg, 1.60 mmol) and HATU (670 mg, 1.76 mmol) in DMF (8 mL), DIPEA (0.8 mL, 4.81 mmol) was added and stirred for 10 minutes, and then Intermediate A (330 mg, 1.60 mmol) was added to the reaction mixture and stirred for 15 hours. The reaction mixture was diluted with EtOAc and washed with distilled water and brine solution. The organic layer was dried over $Na_2SO_4$ and then concentrated under reduced pressure. The crude product was purified by column chromatography to obtain methyl 6-(4-(4-chlorobenzyl)-2,5-dimethylthiophene-3-carboxamido)spiro[3.3]heptane-2-carboxylate (418 mg, yield 56%) as a white solid. $^1$H NMR (400 MHz, chloroform-d) δ 7.23 (d, J=8.5 Hz, 2H), 7.04 (d, J=8.4 Hz, 2H), 5.47-5.17 (m, 1H), 4.36-4.17 (m, 1H), 3.91 (s, 2H), 3.69 (s, 3H), 3.02 (t, J=8.5 Hz, 1H), 2.54-2.41 (m, 4H), 2.40-2.29 (m, 5H), 2.25 (dd, J=11.7, 8.4 Hz, 1H), 2.13-2.01 (m, 1H), 1.68-1.52 (m, 3H). LC/MS (ESI) m/z: 432.37 [M+H]$^+$.

Step 4: Synthesis of 6-(4-(4-chlorobenzyl)-2,5-dimethylthiophene-3-carboxamido)spiro[3.3]heptane-2-carb oxylic acid

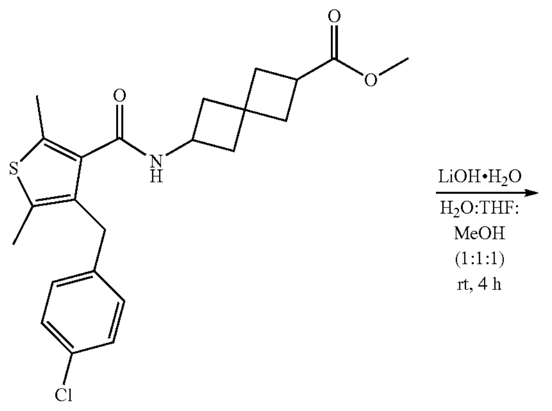

-continued

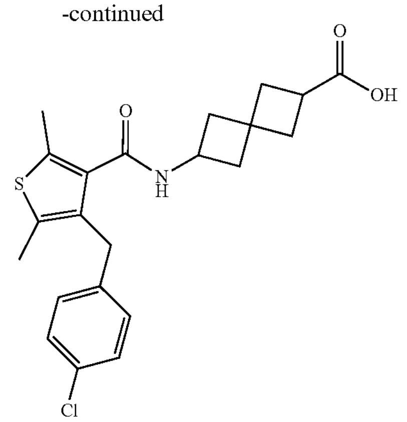

23

To a solution of methyl 6-(4-(4-chlorobenzyl)-2,5-dimethylthiophene-3-carboxamido)spiro[3.3]heptane-2-carboxylate (43 mg, 0.1 mmol) in $H_2O$:THF:MeOH (1:1:1), LiOH·$H_2O$ (13 mg, 0.3 mmol) was added and stirred for 4 hours. The reaction mixture was partially concentrated under reduced pressure, acidified by addition of 1 N HCl (pH~6), and then extracted with EtOAc. The organic layer was dried over $Na_2SO_4$ and concentrated under reduced pressure. The crude product was purified by column chromatography to obtain the compound of Example 23 (30 mg, yield 71%). $^1$H NMR (300 MHz, chloroform-d) δ 7.27-7.18 (m, 2H), 7.04 (d, J=8.5 Hz, 2H), 5.35 (d, J=7.9 Hz, 1H), 4.27 (d, J=7.8 Hz, 1H), 3.91 (s, 2H), 3.06 (t, J=8.5 Hz, 1H), 2.53-2.44 (m, 1H), 2.43 (s, 3H), 2.41-2.35 (m, 2H), 2.35-2.30 (m, 1H), 2.33 (s, 3H), 2.31-2.21 (m, 1H), 2.17-2.06 (m, 1H), 1.60 (dt, J=11.5, 7.7 Hz, 2H). LC/MS (ESI) m/z: 418.23 $[M+H]^+$.

The compounds of Examples 24 and 25 were prepared in the same manner as in Example 23 except for the differences in the preparation methods described below.

TABLE 5

| Example No. | Chemical structure | Name | Difference in preparation method |
|---|---|---|---|
| 24 | 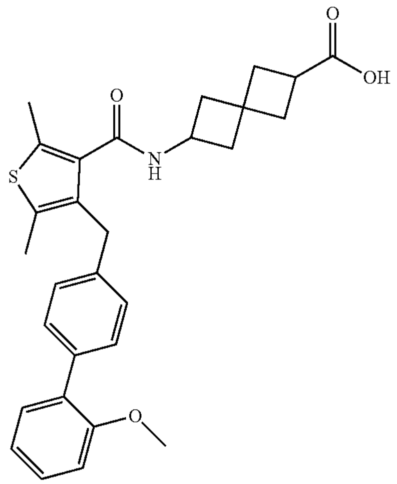 [SMILES: COc1ccccc1-c1ccc(Cc2c(C)sc(C)c2C(=O)NC2CC3(C2)CC(C(=O)O)C3)cc1] | 6-(4-((2'-methoxy-[1,1'-biphenyl]-4-yl)methyl)-2,5-dimethylthiophene-3-carboxamido)spiro[3.3]heptane-2-carboxylic acid | Intermediate G was used instead of (4-chlorophenyl)methanol in Step 1 |

TABLE 5-continued

| Example No. | Chemical structure | Name | Difference in preparation method |
|---|---|---|---|
| 25 | 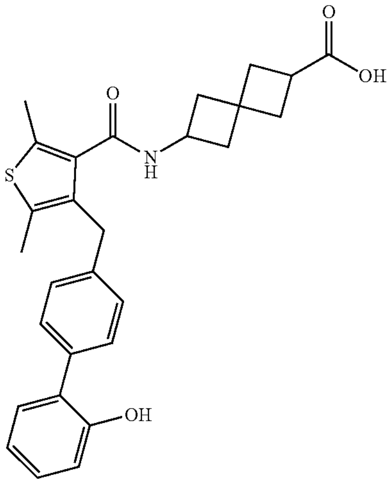 [SMILES: Cc1sc(C)c(C(=O)NC2CC3(C2)CC(C(=O)O)C3)c1Cc1ccc(-c2ccccc2O)cc1] | 6-(4-((2'-hydroxy-[1,1'-biphenyl]-4-yl)methyl)-2,5-dimethylthiophene-3-carboxamido)spiro[3.3] heptane-2-carboxylic acid | The methoxy group of the compound of Example 24 was demethylated. Reaction conditions and reagents: $BBr_3$, DCM (0.01M), rt, 1.5 h |

TABLE 6

| Example No. | LC/MS (ESI) m/z: $[M + H]^+$ | NMR |
|---|---|---|
| 24 | ES + 490.12 | $^1$H NMR (500 MHz, $CDCl_3$) δ 7.42 (d, J = 8.2 Hz, 2H), 7.29 (td, J = 7.8, 1.8 Hz, 1H), 7.25-7.22 (m, 3H), 7.09 (d, J = 7.9 Hz, 2H), 7.00 (td, J = 7.5, 1.1 Hz, 1H), 6.96 (d, J = 8.2 Hz, 1H), 5.36 (d, J = 7.9 Hz, 1H), 4.23 (h, J = 7.9 Hz, 1H), 3.86 (d, J = 83.4 Hz, 5H), 2.96 (p, J = 8.5 Hz, 1H), 2.42 (s, 3H), 2.34 (s, 3H), 2.27 (dd, J = 8.6, 2.4 Hz, 3H), 2.15 (dd, J = 11.8, 8.2 Hz, 1H), 1.48 (ddd, J = 17.8, 11.4, 8.5 Hz, 2H). |
| 25 | ES + 476.15 | $^1$H NMR (500 MHz, $CDCl_3$) δ 7.38 (d, J = 7. 8Hz, 2H), 7.24 (s, 1H), 7.20 (d, J = 7.8 Hz, 3H), 6.99-6.94 (m, 2H), 5.41 (d, J = 7.8 Hz, 1H), 4.28 (d, J = 8.0 Hz, 1H), 3.98 (s, 2H), 3.03-2.99 (m, 1H), 2.44 (s, 3H), 2.36 (s, 3H), 2.31 (d, J = 8.5 Hz, 2H), 1.56 (dt, J = 20.7, 10.1 Hz, 8H). |

Example 26: 6-(2,5-dimethyl-4-(4-(pyridin-4-yl)benzyl)thiophene-3-carboxamido)spiro[3.3]heptane-2-carboxylic acid

Step 1: Synthesis of methyl 6-(2,5-dimethyl-4-(4-(pyridin-4-yl)benzyl)thiophene-3-carboxamido)spiro[3.3]heptane-2-carboxylate

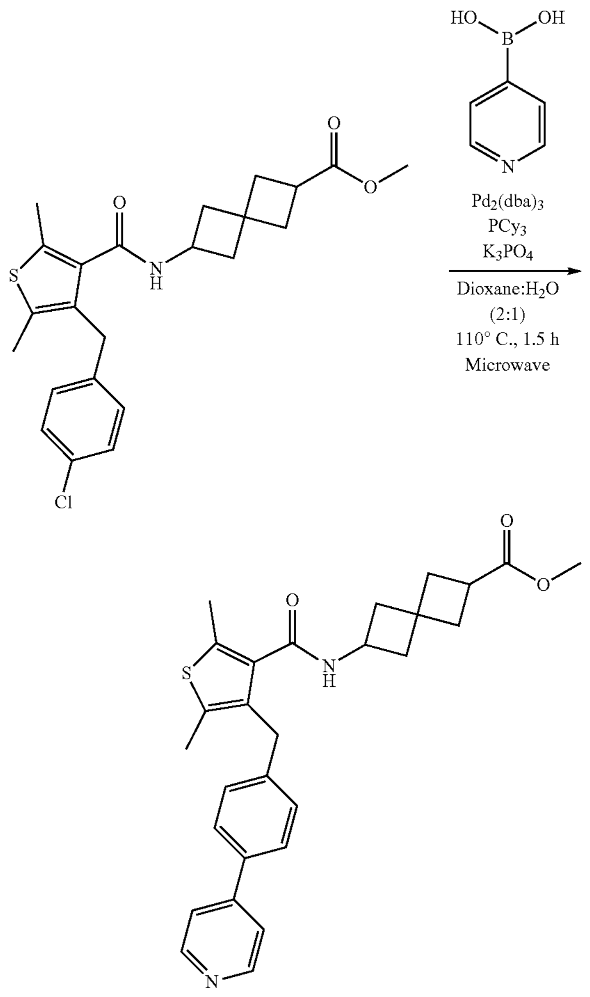

A solution of methyl 6-(4-(4-chlorobenzyl)-2,5-dimethyl-thiophene-3-carboxamido)spiro[3.3]heptane-carboxylate (27 mg, 0.06 mmol) obtained in Step 3 of Example 23, pyridin-4-ylboronic acid (9 mg, 0.075 mmol) and $K_3PO_4$ (13 mg, 0.063 mmol) in 1,4-dioxane:$H_2O$ (2:1) was substituted under $N_2$ atmosphere, and then $Pd_2(dba)_3$ (6 mg, 6.2 μmol) and $PCy_3$ (3 mg, 9.4 μmol) were added. The reaction mixture was irradiated with microwave at 110° C. for 1.5 hours, then filtered through Celite, and concentrated under reduced pressure to obtain methyl 6-(2,5-dimethyl-4-(4-(pyridin-4-yl)benzyl)thiophene-3-carboxamido)spiro[3.3]heptane-2-carboxylate. LC/MS (ESI) m/z: 476.28 $[M+2]^+$.

Step 2: Synthesis of 6-(2,5-dimethyl-4-(4-(pyridin-4-yl)benzyl)thiophene-3-carboxamido)spiro[3.3]heptane-2-carboxylic acid

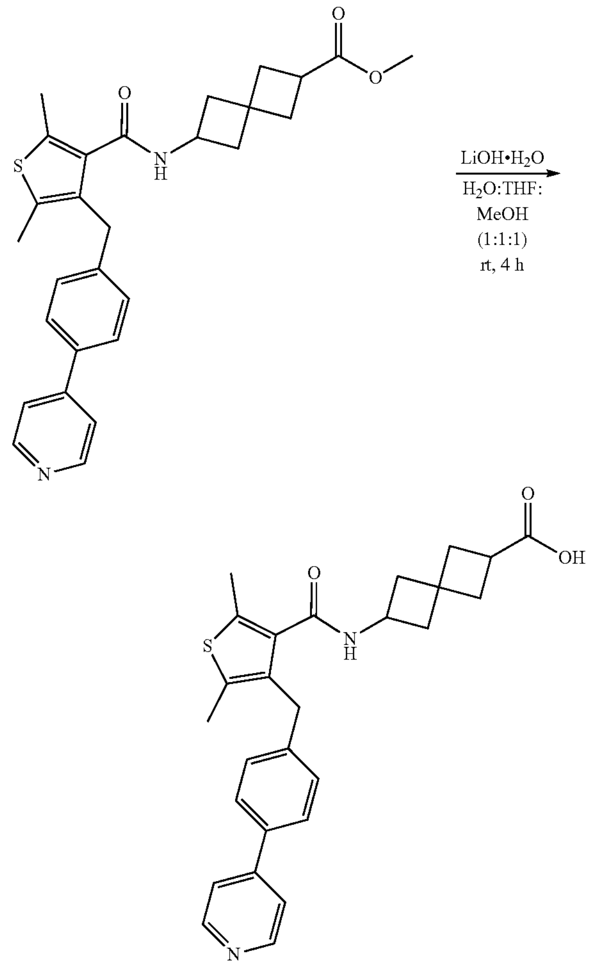

26

To a solution of methyl 6-(2,5-dimethyl-4-(4-(pyridin-4-yl)benzyl)thiophene-3-carboxamido)spiro[3.3]heptane-2-carboxylate (crude product, 0.06 mmol) in $H_2O$:THF:MeOH (1:1:1), LiOH·$H_2O$ (9 mg, 0.18 mmol) was added and stirred for 4 hours. The reaction mixture was concentrated under reduced pressure, diluted with distilled water, then acidified with 1 N HCl (pH~6), and extracted with EtOAc. The organic layer was dried over $Na_2SO_4$ and concentrated under reduced pressure. The crude product was purified by column chromatography to obtain the compound of Example 26 (12 mg, yield 42%) as a white solid. $^1H$ NMR (300 MHz, methanol-$d_4$) δ 8.92-8.31 (m, 2H), 7.68 (dd, J=14.7, 7.0 Hz, 4H), 7.25 (d, J=8.1 Hz, 2H), 4.34-3.95 (m, 1H), 4.00 (s, 2H), 3.07-2.82 (m, 1H), 2.38 (s, 6H), 2.34-2.19 (m, 3H), 2.20-1.93 (m, 3H), 1.91-1.60 (m, 2H). LC/MS (ESI) m/z: 462.31 $[M+2]^+$.

Example 27: 6-(2,5-dimethyl-4-(4-(pyridin-3-yl)benzyl)thiophene-3-carboxamido)spiro[3.3]heptane-2-carboxylic acid

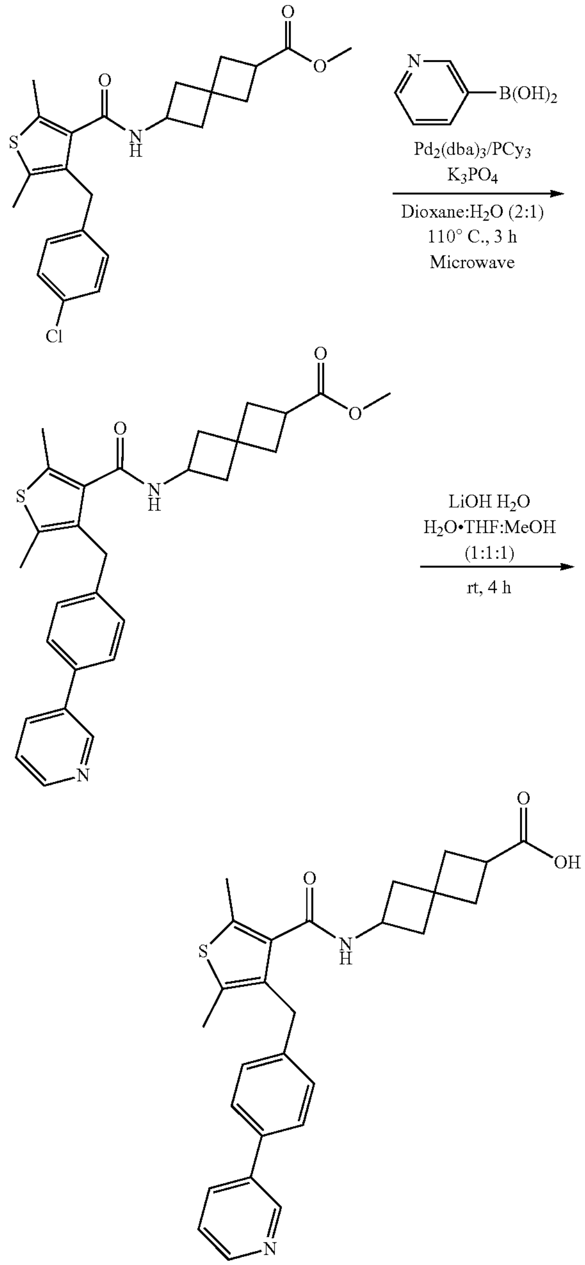

27

The compound of Example 27 was obtained as a white solid in the same manner as in Example 26, except that pyridin-3-ylboronic acid was used instead of pyridin-4-ylboronic acid in Step 1 of Example 26. $^1H$ NMR (500 MHz, methanol-$d_4$) δ 8.78 (s, 1H), 8.51 (d, J=4.2 Hz, 1H), 8.08 (d, J=8.0 Hz, 1H), 7.62-7.49 (m, 3H), 7.24 (d, J=8.2 Hz, 2H), 4.26-4.08 (m, 1H), 4.00 (s, 2H), 3.03-2.87 (m, 1H), 2.45-2.37 (m, 1H), 2.38 (s, 6H), 2.35-2.21 (m, 3H), 2.13 (dd, J=8.2 Hz, 1H), 2.10-2.00 (m, 1H), 1.79 (ddd, J=24.7, 11.0, 8.9 Hz, 2H). LC/MS (ESI) m/z: 462.24 $[M+2]^+$.

Example 28: 6-(4-((3',4'-dimethyl-[1,1'-biphenyl]-4-yl)methyl)-2,5-dimethylthiophene-3-carboxamido)spiro[3.3]heptane-2-carboxylic acid Step 1: Synthesis of methyl 6-(4-((3',4'-dimethyl-[1,1'-biphenyl]-4-yl)methyl)-2,5-dimethylthiophene-3-carboxamido)spiro[3.3]heptane-2-carboxylate

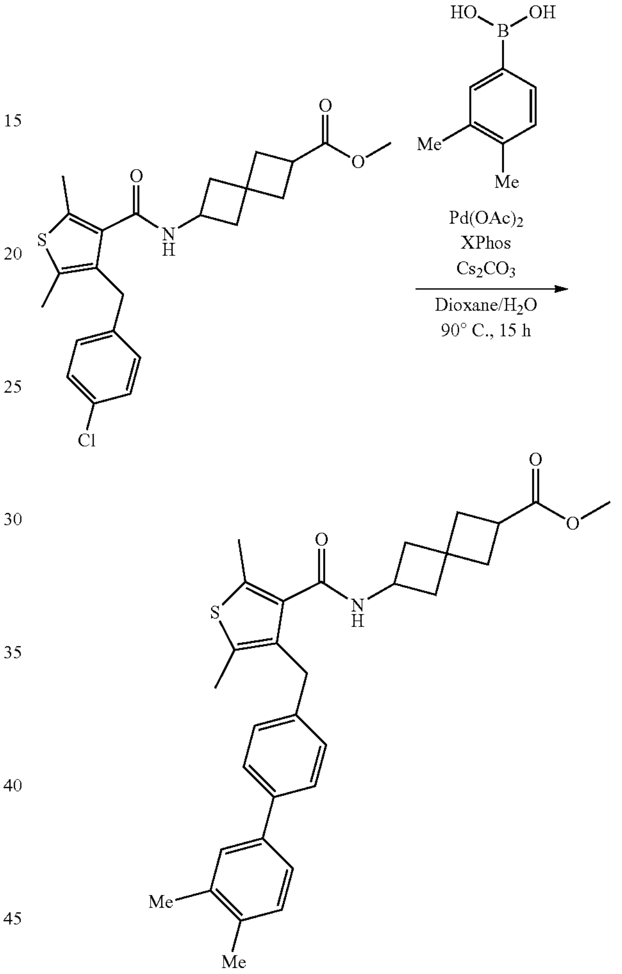

A solution of methyl 6-(4-(4-chlorobenzyl)-2,5-dimethylthiophene-3-carboxamido)spiro[3.3]heptane-carboxylate (50 mg, 0.023 mmol) obtained in Step 3 of Example 23 and 3,4-dimethylphenylboronic acid (4.1 mg, 0.027 mmol) in 1,4-dioxane (0.2 mL) was placed in a sealed tube, and distilled water (0.01 mL) and $Cs_2CO_3$ (8 mg, 0.046 mmol) were added. $Pd(OAc)_2$ (0.5 mg) and Xphos (13 mg, 0.023 mmol) were added under $N_2$ atmosphere, and then the reaction mixture was stirred at 90° C. for 15 hours. The reaction mixture was diluted with ethyl acetate, washed with distilled water, then dried over $Na_2SO_4$, filtered, and concentrated. The crude product was purified using a silica column (6% MeOH in $CHCl_3$) to obtain methyl 6-(4-((3',4'-dimethyl-[1,1'-biphenyl]-4-yl)methyl)-2,5-dimethylthiophene-3-carboxamido)spiro[3.3]heptane-2-carboxylate (20 mg, mixture). $^1H$ NMR (500 MHz, Chloroform-d) δ 7.48-7.45 (m, 2H), 7.32 (d, J=2.0 Hz, 1H), 7.28 (dd, J=7.8, 2.1 Hz, 1H), 7.19 (d, J=8.1 Hz, 1H), 7.13 (d, J=8.2 Hz, 2H), 5.38 (d, J=7.8 Hz, 1H), 4.24 (h, J=7.9 Hz, 1H), 3.96 (s, 2H), 3.63

(s, 3H), 2.96-2.90 (m, 1H), 2.43 (s, 2H), 2.42-2.39 (m, 2H), 2.35 (s, 3H), 2.32 (s, 3H), 2.30 (s, 3H), 2.27-2.23 (m, 2H), 2.15 (dd, J=11.7, 8.5 Hz, 1H), 1.96 (ddd, J=11.7, 8.6, 2.9 Hz, 1H), 1.49 (ddd, J=14.9, 11.4, 8.5 Hz, 2H).

Step 2: Synthesis of 6-(4-((3',4'-dimethyl-[1,1'-biphenyl]-4-yl)methyl)-2,5-dimethylthiophene-3-carboxamido)spiro[3.3]heptane-2-carboxylic acid

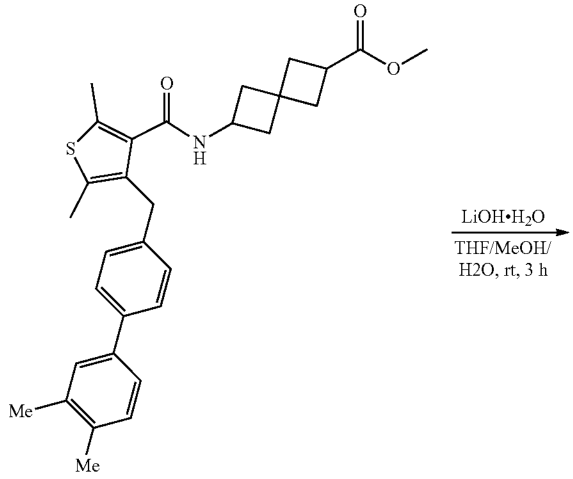

-continued

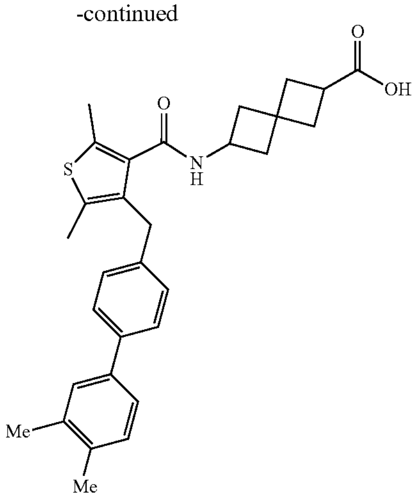

28

To a solution of methyl 6-(4-((3',4'-dimethyl-[1,1'-biphenyl]-4-yl)methyl)-2,5-dimethylthiophene-3-carboxamido)spiro[3.3]heptane-2-carboxylate (20 mg) in THF/MeOH/$H_2O$ (2/1/2), LiOH·$H_2O$ (4 mg, 0.084 mmol, 3.0 equiv) was added and stirred for 3 hours. The reaction mixture was partially concentrated and then acidified with 1 N HCl aqueous solution, and the aqueous layer was extracted with EtOAc. The organic layer was dried over $MgSO_4$ and then concentrated under reduced pressure. The crude product was purified by preparative TLC to obtain the compound of Example 28 (3.4 mg, yield 30%). $^1$H NMR (500 MHz, chloroform-d) δ 7.49-7.45 (m, 2H), 7.32 (d, J=2.0 Hz, 1H), 7.28 (dd, J=7.8, 2.1 Hz, 1H), 7.19 (d, J=7.8 Hz, 1H), 7.14-7.11 (m, 2H), 5.35 (d, J=7.8 Hz, 1H), 4.24 (h, J=8.0 Hz, 1H), 3.96 (s, 2H), 2.97 (p, J=8.5 Hz, 1H), 2.43 (s, 3H), 2.42-2.36 (m, 2H), 2.36 (s, 3H), 2.32 (s, 3H), 2.30 (s, 3H), 2.28 (t, J=4.1 Hz, 2H), 2.17 (dd, J=11.7, 8.3 Hz, 1H), 1.99 (ddd, J=11.6, 8.7, 2.4 Hz, 1H), 1.49 (dt, J=11.7, 9.1 Hz, 2H). LC/MS (ESI) m/z: 488.43 [M+H]$^+$.

The compounds of Examples 29 to 66 were prepared in the same manner as in Example 28 except for the differences in the preparation methods described below.

TABLE 7

| Example No. | Chemical structure | Name | Difference in preparation method |
|---|---|---|---|
| 29 | 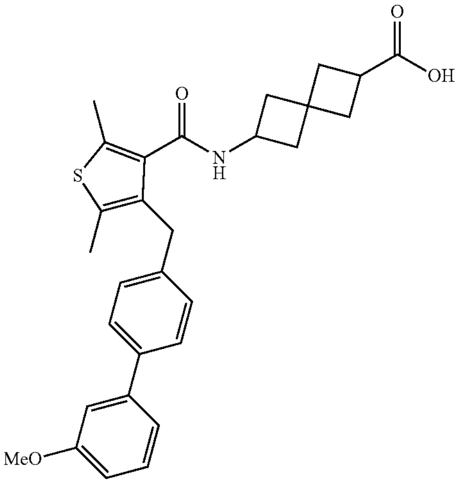 [SMILES: COc1cccc(-c2ccc(Cc3c(C)sc(C)c3C(=O)NC3CC4(C3)CC(C(=O)O)C4)cc2)c1] | 6-(4-((3'-methoxy-[1,1'-biphenyl]-4-yl)methyl)-2,5-dimethylthiophene-3-carboxamido)spiro[3.3]heptane-2-carboxylic acid | 3-methoxyphenylboronic acid was used instead of 3,4-dimethylphenylboronic acid in Step 1 |

TABLE 7-continued

| Example No. | Chemical structure | Name | Difference in preparation method |
|---|---|---|---|
| 30 | 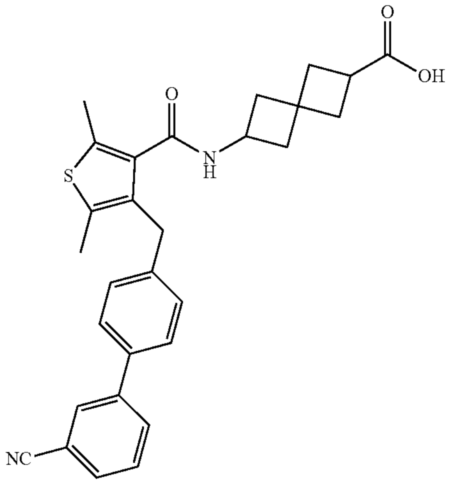 [SMILES: Cc1sc(C)c(C(=O)NC2CC3(C2)CC(C(=O)O)C3)c1Cc1ccc(-c2cccc(C#N)c2)cc1] | 6-(4-(3'-cyano-[1,1'-biphenyl]-4-yl)methyl)-2,5-dimethylthiophene-3-carboxamido)spiro[3.3]heptane-2-carboxylic acid | 3-(cyanophenyl)boronic acid was used instead of 3,4-dimethylphenylboronic acid in Step 1 |
| 31 | 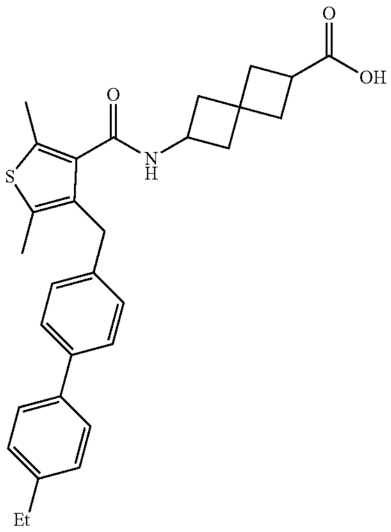 [SMILES: CCc1ccc(-c2ccc(Cc3c(C)sc(C)c3C(=O)NC3CC4(C3)CC(C(=O)O)C4)cc2)cc1] | 6-(4-((4'-ethyl-[1,1'-biphenyl]-4-yl)methyl)-2,5-dimethylthiophene-3-carboxamido)spiro[3.3]heptane-2-carboxylic acid | 4-ethylphenylboronic acid was used instead of 3,4-dimethylphenylboronic acid in Step 1 |
| 32 | 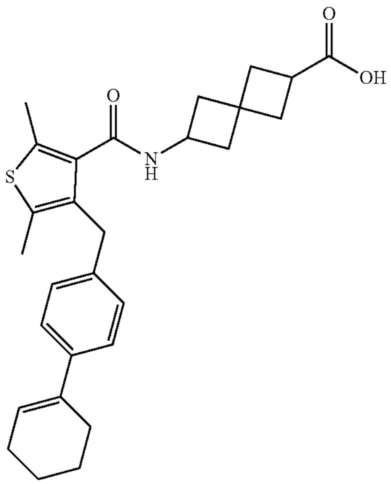 [SMILES: Cc1sc(C)c(C(=O)NC2CC3(C2)CC(C(=O)O)C3)c1Cc1ccc(C2=CCCCC2)cc1] | 6-(2,5-dimethyl-4-((2',3',4',5'_tetrahydro-[1,1'-biphenyl]-4-yl)methyl)thiophene-3-carboxamido)spiro[3.3]heptane-2-carboxylic acid | 2-(cyclohex-1-en-1-yl)-4,4,5,5-tetramethyl-1,3,2-dioxaborolane was used instead of 3,4-dimethylphenylboronic acid in Step 1 |

TABLE 7-continued

| Example No. | Chemical structure | Name | Difference in preparation method |
|---|---|---|---|
| 33 | 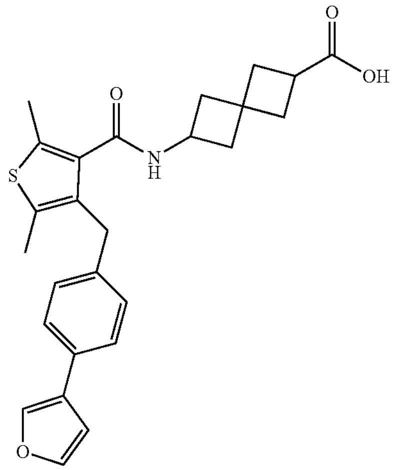 [SMILES: Cc1sc(C)c(C(=O)NC2CC3(C2)CC(C(=O)O)C3)c1Cc1ccc(-c2ccoc2)cc1] | 6-(4-(4-(furan-3-yl)benzyl)-2,5-dimethylthiophene-3-carboxamido)spiro[3.3]heptane-2-carboxylic acid | 3-furylboronic acid was used instead of 3,4-dimethylphenylboronic acid in Step 1 |
| 34 | 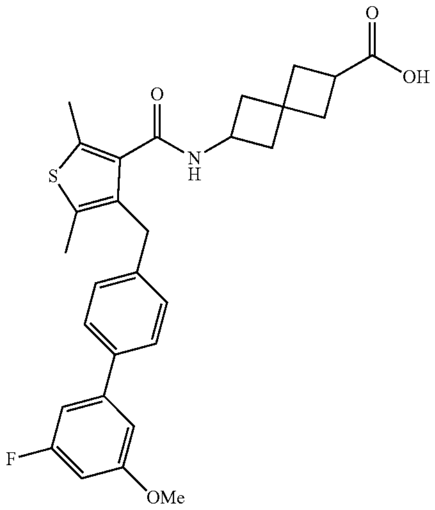 [SMILES: COc1cc(F)cc(-c2ccc(Cc3c(C)sc(C)c3C(=O)NC3CC4(C3)CC(C(=O)O)C4)cc2)c1] | 6-(4-((3'-fluoro-5'-methoxy-[1,1'-biphenyl]-4-yl)methyl)-2,5-dimethylthiophene-3-carboxamido)spiro[3.3]heptane-2-carboxylic acid | 3-fluoro-5-methoxyphenylboronic acid was used instead of 3,4-dimethylphenylboronic acid in Step 1 |
| 35 | 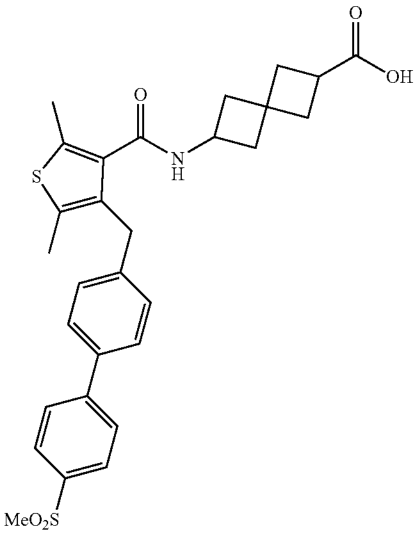 [SMILES: Cc1sc(C)c(C(=O)NC2CC3(C2)CC(C(=O)O)C3)c1Cc1ccc(-c2ccc(S(C)(=O)=O)cc2)cc1] | 6-(2,5-dimethyl-4-((4'-(methylsulfonyl)-[1,1'-biphenyl]-4-yl)methyl)thiophene-3-carboxamido)spiro[3.3]heptane-2-carboxylic acid | 4-(methanesulfonyl)phenylboronic acid was used instead of 3,4-dimethylphenylboronic acid in Step 1 |

TABLE 7-continued

| Example No. | Chemical structure | Name | Difference in preparation method |
|---|---|---|---|
| 36 | 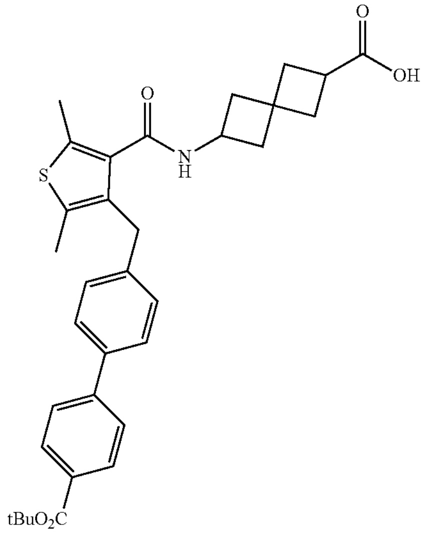 [SMILES: Cc1sc(C)c(C(=O)NC2CC3(C2)CC(C(=O)O)C3)c1Cc1ccc(-c2ccc(C(=O)OC(C)(C)C)cc2)cc1] | 6-(4-((4'-(tert-butoxycarbonyl)-[1,1'-biphenyl]-4-yl)methyl)-2,5-dimethylthiophene-3-carboxamido)spiro[3.3]heptane-2-carboxylic acid | 4-tert-butoxycarbonylphenylboronic acid was used instead of 3,4-dimethylphenylboronic acid in Step 1 |
| 37 | 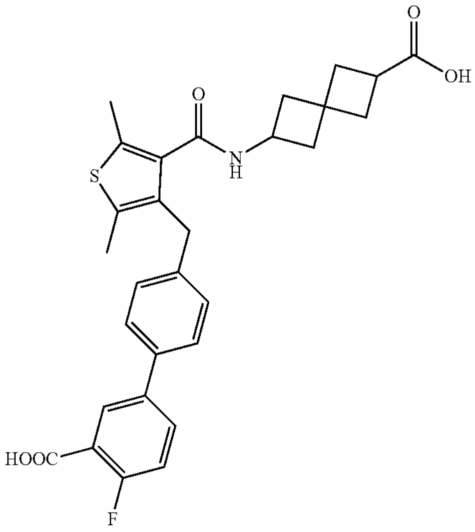 [SMILES: Cc1sc(C)c(C(=O)NC2CC3(C2)CC(C(=O)O)C3)c1Cc1ccc(-c2ccc(F)c(C(=O)O)c2)cc1] | 6-(4-((3'-carboxy-4'-fluoro-[1,1'-biphenyl]-4-yl)methyl)-2,5-dimethylthiophene-3-carboxamido)spiro[3.3]heptane-2-carboxylic acid | 4-fluoro-3-methoxycarbonylphenylboronic acid was used instead of 3,4-dimethylphenylboronic acid in Step 1 |
| 38 | 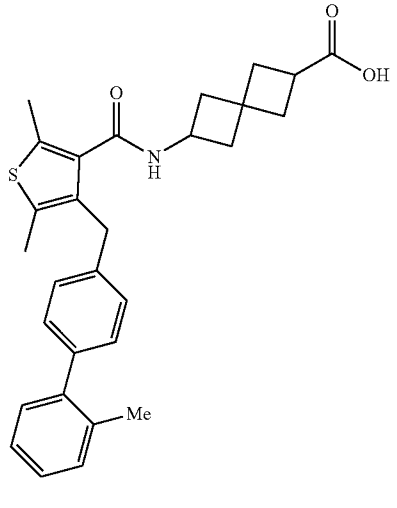 [SMILES: Cc1ccccc1-c1ccc(Cc2c(C)sc(C)c2C(=O)NC2CC3(C2)CC(C(=O)O)C3)cc1] | 6-(2,5-dimethyl-4-((2'-methyl-[1,1'-biphenyl]-4-yl)methyl)thiophene-3-carboxamido)spiro[3.3]heptane-2-carboxylic acid | 2-methylphenylboronic acid was used instead of 3,4-dimethylphenylboronic acid in Step 1 |

TABLE 7-continued

| Example No. | Chemical structure | Name | Difference in preparation method |
| --- | --- | --- | --- |
| 39 | 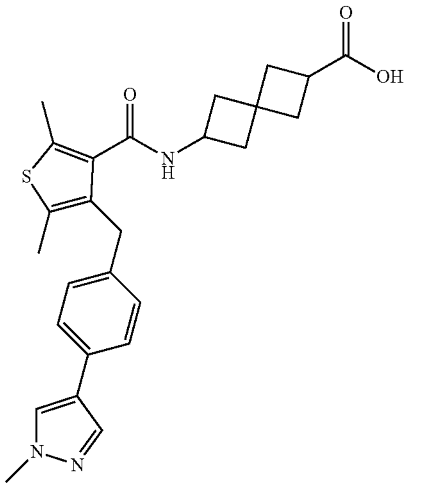 [SMILES: Cc1sc(C)c(C(=O)NC2CC3(C2)CC(C(=O)O)C3)c1Cc1ccc(-c2cnn(C)c2)cc1] | 6-(2,5-dimethyl-4-(4-(1-methyl-1H-pyrazol-4-yl)benzyl)thiophene-3-carboxamido)spiro[3.3]heptane-2-carboxylic acid | 1-methyl-4-(4,4,5,5-tetramethyl-1,3,2-dioxaborolan-2-yl)-1H-pyrazole was used instead of 3,4-dimethylphenylboronic acid in Step 1 |
| 40 | 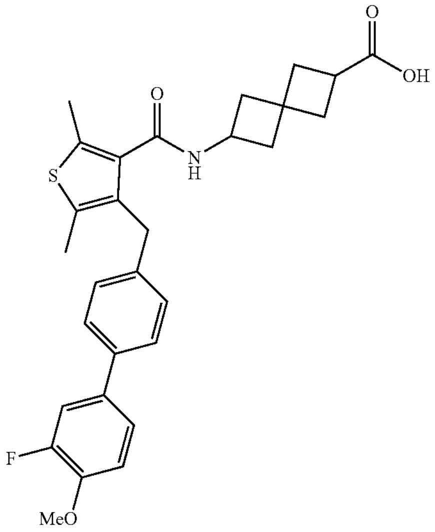 [SMILES: COc1ccc(-c2ccc(Cc3c(C)sc(C)c3C(=O)NC3CC4(C3)CC(C(=O)O)C4)cc2)cc1F] | 6-(4-((3'-fluoro-4'-methoxy-[1,1'-biphenyl]-4-yl)methyl)-2,5-dimethylthiophene-3-carboxamido)spiro[3.3]heptane-2-carboxylic acid | (3-fluoro-4-methoxyphenyl)boronic acid was used instead of 3,4-dimethylphenylboronic acid in Step 1 |
| 41 | 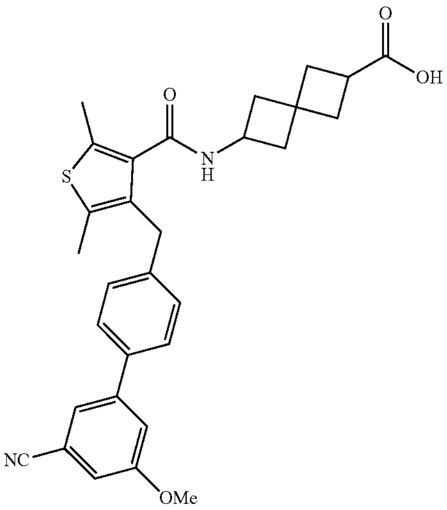 [SMILES: COc1cc(C#N)cc(-c2ccc(Cc3c(C)sc(C)c3C(=O)NC3CC4(C3)CC(C(=O)O)C4)cc2)c1] | 6-(4-((3'-cyano-5'-methoxy-[1,1'-biphenyl]-4-yl)methyl)-2,5-dimethylthiophene-3-carboxamido)spiro[3.3]heptane-2-carboxylic acid | 3-cyano-5-methoxyphenylboronic acid pinacol ester was used instead of 3,4-dimethylphenylboronic acid in Step 1 |

TABLE 8

| Example No. | LC/MS (ESI) m/z: $[M + H]^+$ | NMR |
|---|---|---|
| 29 | — | $^1H$ NMR (500 MHz, Chloroform-d) δ 7.51-7.46 (m, 2H), 7.34 (t, J = 7.9 Hz, 1H), 7.17-7.11 (m, 3H), 7.08 (dd, J = 2.6, 1.6 Hz, 1H), 6.88 (ddd, J = 8.2, 2.6, 1.0 Hz, 1H), 5.37 (d, J = 7.8 Hz, 1H), 4.29-4.21 (m, 1H), 3.97 (s, 2H), 3.85 (s, 3H), 3.01-2.94 (m, 1H), 2.45-[2.42 (m, 3H), 2.41-2.37 (m, 1H), 2.36 (s, 3H), 2.33-2.27 (m, 3H), 2.16 (dd, J = 11.8, 8.2 Hz, 1H), 2.03-1.99 (m, 1H), 1.54-1.47 (m, 2H). |
| 30 | $[M + H]^+$: 485.33, $[M + H]^-$: 483.51 | $^1H$ NMR (500 MHz, Chloroform-d) δ 7.81 (t, J = 1.8 Hz, 1H), 7.76 (dt, J = 7.9, 1.5 Hz, 1H), 7.60 (dt, J = 7.7, 1.4 Hz, 1H), 7.53 (t. J = 7.8 Hz, 1H), 7.47-7.42 (m, 2H), 7.20 (d, J = 8.1 Hz, 2H), 5.46 (d, J = 7.8 Hz, 1H), 4.32-4.24 (m, 1H), 3.98 (s, 2H), 2.98 (p, J = 8.4 Hz, 1H), 2.47-2.42 (m, 4H), 2.37-2.32 (m, 4H), 2.30 (d, J = 8.3 Hz, 2H), 2.18 (dd, J = 11.8, 8.1 Hz, 1H), 2.05-2.00 (m, 1H), 1.63-1.53 (m, 2H). |
| 31 | $[M + H]^+$: 488.64, $[M + H]^-$: 486.54 | $^1H$ NMR (300 MHz, Chloroform-d) δ 7.49 (dd, J = 4.2, 1.9 Hz, 2H), 7.46 (d, J = 4.1 Hz, 2H), 7.28 (s, 2H), 7.14 (d, J = 8.1 Hz, 2H), 5.35 (d, J = 7.9 Hz, 1H), 4.32-4.18 (m, 1H), 3.97 (s, 2H), 2.98 (p, J = 8.5 Hz, 1H), 2.69 (q, J = 7.6 Hz, 2H), 2.43 (s, 3H), 2.39 (d, J = 4.8 Hz, 1H), 2.36 (s, 3H), 2.29 (d, J = 8.4 Hz, 3H), 2.17 (dd, J = 11.7, 8.2 Hz, 1H), 2.04-1.95 (m, 1H), 1.52-1.44 (m, 2H), 1.28 (d, J = 7.6 Hz, 3H). |
| 32 | $[M + H]^+$: 464.40, $[M + H]^-$: 462.58 | $^1H$ NMR (500 MHz, Methanol-$d_4$) δ 7.24 (d, J = 8.3 Hz, 2H), 7.00 (d, J = 8.1 Hz, 2H), 6.06 (tt, J = 3.9, 1.8 Hz, 1H), 4.16-4.06 (m, 1H), 3.89 (s, 2H), 2.97 (p, J = 8.4 Hz, 1H), 2.40-2.37 (m, 3H), 2.35 (d, J = 5.5 Hz, 6H), 2.31-2.25 (m, 2H), 2.24-2.19 (m, 3H), 2.18-2.14 (m, 1H), 2.09-2.07 (m, 1H), 1.81-1.73 (m, 4H), 1.69-1.66 (m, 2H). |
| 33 | $[M + H]^+$: 450.6, $[M + H]^-$: 448.6 | $^1H$ NMR (400 MHz, Chloroform-d) δ 7.72-7.66 (m, 1H), 7.49-7.43 (m, 1H), 7.41-7.34 (m, 2H), 7.12-7.04 (m, 2H), 6.71-6.63 (m, 1H), 5.42-5.32 (m, 1H), 4.29-4.18 (m, 1H), 3.93 (s, 2H), 3.05-2.93 (m, 1H), 2.42 (s, 3H), 2.43-2.37 (m, 1H), 2.34 (s, 3H), 2.34-2.25 (m, 3H), 2.21-2.12 (m, 1H), 2.06-1.96 (m, 1H), 1.57-1.48 (m, 2H) |
| 34 | $[M + H]^+$: 508.42, $[M + H]^-$: 506.53 | $^1H$ NMR (500 MHz, Chloroform-d) δ 7.50-7.45 (m, 2H), 7.21-7.18 (m, 2H), 6.91-6.86 (m, 2H), 6.64-6.59 (m, 1H), 5.40-5.35 (m, 1H), 4.34-4.26 (m, 1H), 4.00 (s, 2H), 3.87 (s, 3H), 3.08-2.97 (m, 1H), 2.45 (s, 3H), 2.38 (s, 3H), 2.36-2.31 (m, 3H), 2.23-2.17 (m, 1H), 2.08-2.03 (m, 1H), 1.57-1.52 (m, 3H). |
| 35 | $[M + H]^+$: 538.4, $[M + H]^-$: 536.5 | $^1H$ NMR (400 MHz, Chloroform-d) δ 8.02-7.96 (m, 2H), 7.75-7.69 (m, 2H), 7.53-7.49 (m, 2H), 7.24-7.19 (m, 2H), 5.43-5.38 (m, 1H), 4.32-4.21 (m, 1H), 3.99 (s, 2H), 3.09 (s, 3H), 3.02-2.94 (m, 1H), 2.48-2.46 (m, 1H), 2.43 (s, 3H), 2.35 (s, 3H), 2.32-2.28 (m, 3H), 2.19-2.13 (m, 1H), 2.05-1.99 (m, 1H), 1.65-1.58 (m, 1H), 1.55-1.48 (m, 1H). |
| 36 | $[M + H]^+$: 560.4, $[M + H]^-$: 558.4 | $^1H$ NMR (400 MHz, Chloroform-d) δ 8.08-8.01 (m, 2H), 7.67-7.60 (m, 2H), 7.55-7.51 (m, 2H), 7.23-7.17 (m, 2H), 5.49-5.43 (m, 1H), 4.35-4.22 (m, 1H), 4.00 (s, 2H), 3.07-2.94 (m, 1H), 2.44 (s, 3H), 2.43-2.39 (m, 1H), 2.37 (s, 3H), 2.36-2.29 (m, 3H), 2.19-2.15 (m, 1H), 2.07-1.99 (m, 1H), 1.63 (s, 9H), 1.61-1.53 (m, 2H). |
| 37 | $[M + H]^+$: 522.5, $[M + H]^-$: 520.6 | $^1H$ NMR (400 MHz, DMSO-$d_6$) δ 7.96-7.81 (m, 2H), 7.58-7.52 (m, 1H), 7.47-7.41 (m, 2H), 7.18-7.13 (m, 1H), 7.13-7.08 (m, 2H), 4.11-4.07 (m, 1H), 4.04-3.96 (m, 1H), 3.89 (s, 2H), 3.20-3.16 (m, 2H), 2.81-2.73 (m, 1H), 2.42 (s, 3H), 2.26 (s, 3H), 2.22-2.17 (m, 2H), 2.05-1.97 (m, 2H), 1.86-1.79 (m, 1H), 1.66-1.60 (m, 1H), 1.54-1.47 (m, 1H). |
| 38 | $[M + H]^+$: 474.5, $[M + H]^-$: 472.5 | $^1H$ NMR (500 MHz, Chloroform-d) δ 7.26-7.23 (m, 5H), 7.19-7.14 (m, 1H), 7.14-7.11 (m, 2H), 5.42-5.36 (m, 1H), 4.32-4.24 (m, 1H), 3.98 (s, 2H), 3.04-2.96 (m, 1H), 2.45 (s, 3H), 2.43-2.40 (m, 1H), 2.36 (s, 3H), 2.32-2.29 (m, 3H), 2.26 (s, 3H), 2.22-2.17 (m, 1H), 2.06-2.01 (m, 1H), 1.56-1.54 (m, 2H). |
| 39 | $[M + H]^+$: 464.33, $[M + H]^-$: 462.44 | $^1H$ NMR (300 MHz, Chloroform-d) δ 7.72 (s, 1H), 7.57 (s, 1H), 7.38-7.31 (m, 2H), 7.11-7.04 (m, 2H), 5.40 (d, J = 7.7 Hz, 1H), 4.30-4.17 (m, 1H), 3.93 (s, 3H), 3.92 (s, 2H), 2.97 (p, J = 8.4 Hz, 1H), 2.42 (s, 4H), 2.34 (s, 3H), 2.32-2.23 (m, 3H), 2.15 (dd, J = 11.7, 8.0 Hz, 1H), 2.03-1.95 (m, 1H), 1.57-1.44 (m, 2H). |
| 40 | $[M + H]^+$: 508.35, $[M + H]^-$: 506.46 | $^1H$ NMR (500 MHz, Chloroform-d) δ 7.44-7.40 (m, 2H), 7.30-7.27 (m, 1H), 7.26-7.23 (m, 1H), 7.16-7.10 (m, 2H), 7.04-6.99 (m, 1H), 5.41-5.39 (m, 1H), 4.30-4.22 (m, 1H), 3.96 (s, 2H), 3.92 (s, 3H), 3.04-2.94 (m, 1H), 2.42 (s, 3H), 2.41-2.38 (m, 1H), 2.35 (s, 3H), 2.33-2.28 (m, 3H), 2.19-2.14 (m, 1H), 2.02-1.97 (m, 1H), 1.57-1.48 (m, 2H). |
| 41 | $[M + H]^+$: 515.44, $[M + H]^-$: 513.48 | $^1H$ NMR (500 MHz, Chloroform-d) δ 7.47-7.39 (m, 3H), 7.28-7.27 (m, 1H), 7.20-7.15 (m, 2H), 7.11-7.09 (m, 1H), 5.43-5.38 (m, 1H), 4.31-4.24 (m, 1H), 3.98 (s, 3H), 3.88 (s, 2H), 3.03-2.93 (m, 1H), 2.47-2.44 (m, 1H), 2.42 (s, 3H), 2.34 (s, 3H), 2.33-2.28 (m, 3H), 2.22-2.15 (m, 1H), 2.06-2.00 (m, 1H), 1.62-1.53 (m, 2H). |

TABLE 9

| Example No. | Chemical structure | Name | Difference in preparation method |
|---|---|---|---|
| 42 | 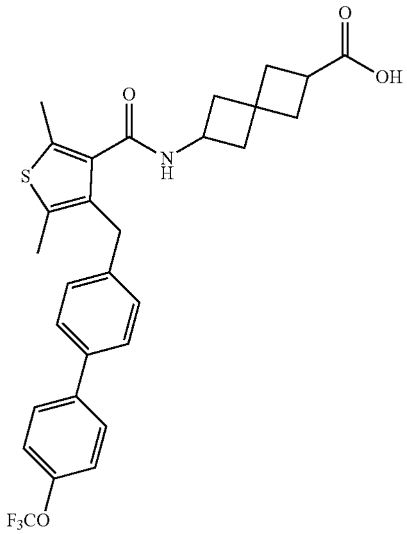 [SMILES: Cc1sc(C)c(C(=O)NC2CC3(C2)CC(C(=O)O)C3)c1Cc1ccc(-c2ccc(OC(F)(F)F)cc2)cc1] | 6-(2,5-dimethyl-4-((4'-(trifluoromethoxy)-[1,1'-biphenyl]-4-yl)methyl)thiophene-3-carboxamido)spiro[3.3]heptane-2-carboxylic acid | 4-(trifluoromethoxy)phenylboronic acid was used instead of 3,4-dimethylphenylboronic acid in Step 1 |
| 43 | 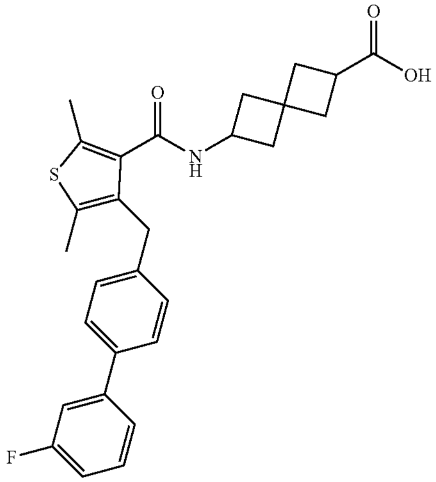 [SMILES: Cc1sc(C)c(C(=O)NC2CC3(C2)CC(C(=O)O)C3)c1Cc1ccc(-c2cccc(F)c2)cc1] | 6-(4-((3'-fluoro-[1,1'-biphenyl]-4-yl)methyl)-2,5-dimethylthiophene-3-carboxamido)spiro[3.3]heptane-2-carboxylic acid | 3-fluorophenylboronic acid was used instead of 3,4-dimethylphenylboronic acid in Step 1 |
| 44 | 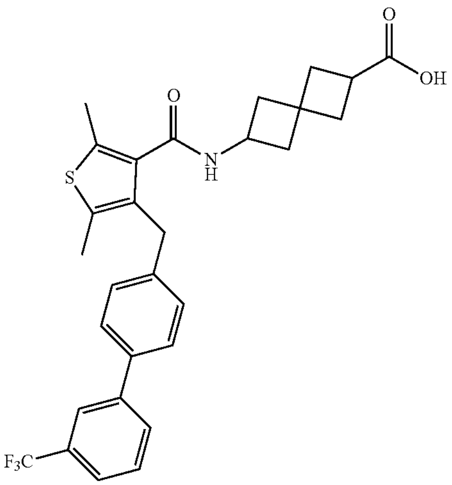 [SMILES: Cc1sc(C)c(C(=O)NC2CC3(C2)CC(C(=O)O)C3)c1Cc1ccc(-c2cccc(C(F)(F)F)c2)cc1] | 6-(2,5-dimethyl-4-((3'-(trifluoromethyl)-[1,1'-biphenyl]-4-yl)methyl)thiophene-3-carboxamido)spiro[3.3]heptane-2-carboxylic acid | 3-(trifluoromethyl) phenylboronic acid was used instead of 3,4-dimethylphenylboronic acid in Step 1 |

TABLE 9-continued

| Example No. | Chemical structure | Name | Difference in preparation method |
|---|---|---|---|
| 45 | 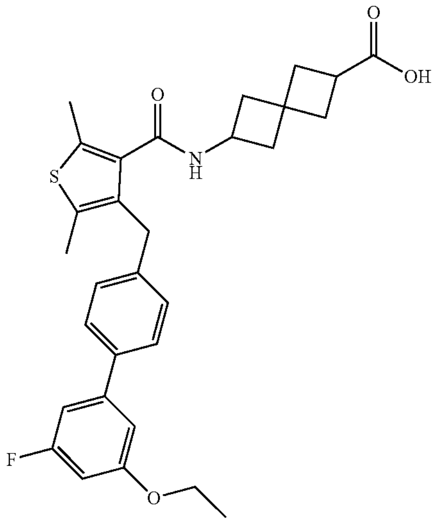 [SMILES: CCOc1cc(F)cc(-c2ccc(Cc3c(C)sc(C)c3C(=O)NC3CC4(C3)CC(C(=O)O)C4)cc2)c1] | 6-(4-((3'-ethoxy-5'-fluoro-[1,1'-biphenyl]-4-yl)methyl)-2,5-dimethylthiophene-3-carboxamido)spiro[3.3]heptane-2-carboxylic acid | 3-fluoro-5-ethoxyphenylboronic acid was used instead of 3,4-dimethylphenylboronic acid in Step 1 |
| 46 | 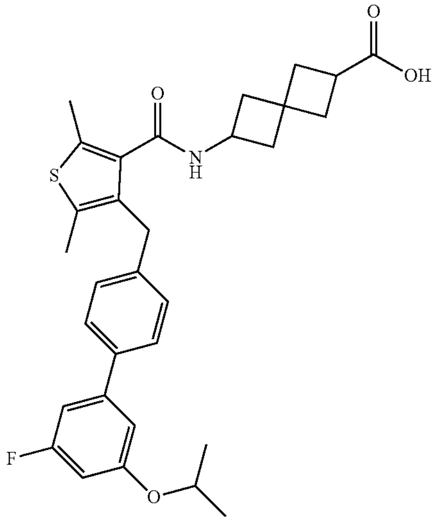 [SMILES: Cc1sc(C)c(C(=O)NC2CC3(C2)CC(C(=O)O)C3)c1Cc1ccc(-c2cc(F)cc(OC(C)C)c2)cc1] | 6-(4-((3'-fluoro-5'-isopropoxy-[1,1'-biphenyl]-4-yl)methyl)-2,5-dimethylthiophene-3-carboxamido)spiro[3.3]heptane-2-carboxylic acid | 3-fluoro-5-isopropoxyphenylboronic acid was used instead of 3,4-dimethylphenylboronic acid in Step 1 |
| 47 | 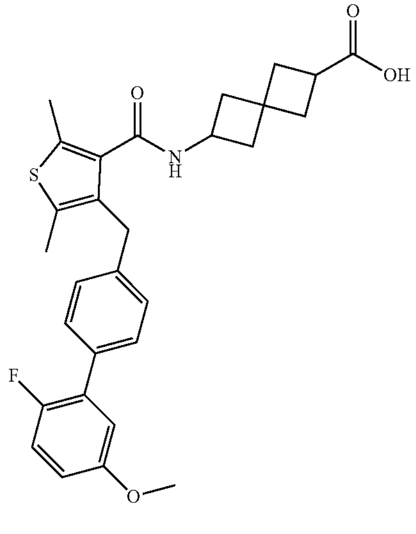 [SMILES: COc1ccc(F)c(-c2ccc(Cc3c(C)sc(C)c3C(=O)NC3CC4(C3)CC(C(=O)O)C4)cc2)c1] | 6-(4-((2'-fluoro-5'-methoxy-[1,1'-biphenyl]-4-yl)methyl)-2,5-dimethylthiophene-3-carboxamido)spiro[3.3]heptane-2-carboxylic acid | (2-fluoro-5-methoxyphenyl)boronic acid was used instead of 3,4-dimethylphenylboronic acid, and $K_3PO_4$ was used instead of $Cs_2CO_3$ in Step 1 |

TABLE 9-continued

| Example No. | Chemical structure | Name | Difference in preparation method |
|---|---|---|---|
| 48 | 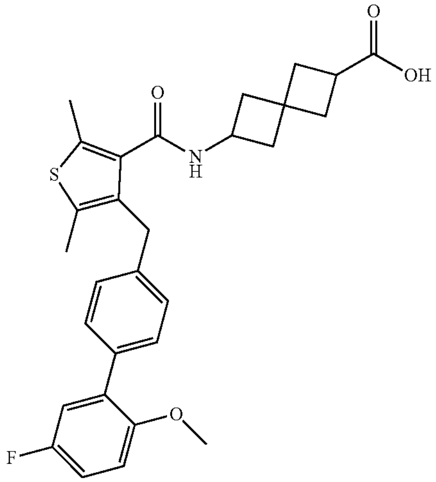 [SMILES: COc1ccc(F)cc1-c1ccc(Cc2c(C)sc(C)c2C(=O)NC2CC3(C2)CC(C(=O)O)C3)cc1] | 6-(4-((5'-fluoro-2'-methoxy-[1,1'-biphenyl]-4-yl)methyl)-2,5-dimethylthiophene-3-carboxamido)spiro[3.3]heptane-2-carboxylic acid | 5-fluoro-2-methoxyphenylboronic acid was used instead of 3,4-dimethylphenylboronic acid, and $K_3PO_4$ was used instead of $Cs_2CO_3$ in Step 1 |
| 49 | 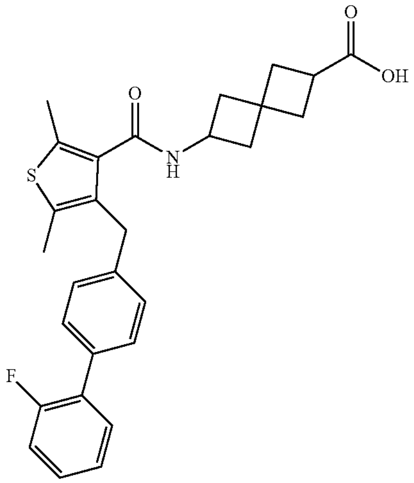 [SMILES: Cc1sc(C)c(C(=O)NC2CC3(C2)CC(C(=O)O)C3)c1Cc1ccc(-c2ccccc2F)cc1] | 6-(4-((2'-fluoro-[1,1'-biphenyl]-4-yl)methyl)-2,5-dimethylthiophene-3-carboxamido)spiro[3.3]heptane-2-carboxylic acid | 2-fluorophenylboronic acid was used instead of 3,4-dimethylphenylboronic acid, and $K_3PO_4$ was used instead of $Cs_2CO_3$ in Step 1 |
| 50 | 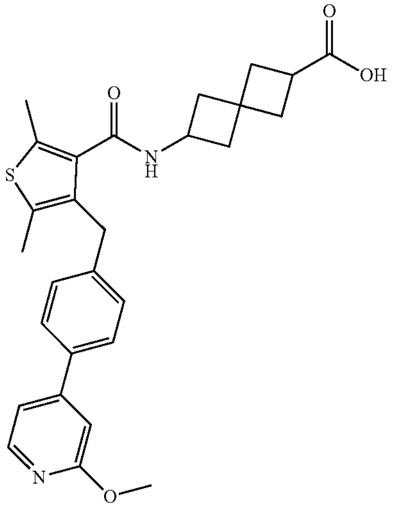 [SMILES: COc1cc(-c2ccc(Cc3c(C)sc(C)c3C(=O)NC3CC4(C3)CC(C(=O)O)C4)cc2)ccn1] | 6-(4-(4-(2-methoxypyridin-4-yl)benzyl)-2,5-dimethylthiophene-3-carboxamido)spiro[3.3]heptane-2-carboxylic acid | (2-methoxypyridin-4-yl)boronic acid was used instead of 3,4-dimethylphenylboronic acid, and $K_3PO_4$ was used instead of $Cs_2CO_3$ in Step 1 |

TABLE 9-continued

| Example No. | Chemical structure | Name | Difference in preparation method |
|---|---|---|---|
| 51 | 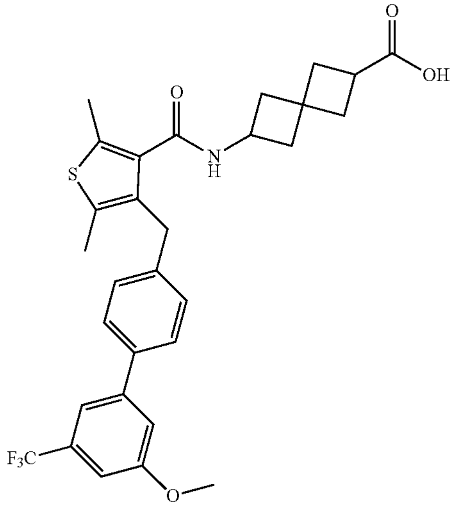 [SMILES: COc1cc(-c2ccc(Cc3c(C)sc(C)c3C(=O)NC3CC4(C3)CC(C(=O)O)C4)cc2)cc(C(F)(F)F)c1] | 6-(4-((3'-methoxy-5'-(trifluoromethyl)-[1,1'-biphenyl]-4-yl)methyl)-2,5-dimethylthiophene-3-carboxamido)spiro[3.3]heptane-2-carboxylic acid | (3-methoxy-5-trifluoromethyl)phenylboronic acid was used instead of 3,4-dimethylphenylboronic acid in Step 1 |

TABLE 10

| Example No. | LC/MS (ESI) m/z: $[M + H]^+$ | NMR |
|---|---|---|
| 42 | $[M + H]^+$: 544.33, $[M + H]^-$: 542.44 | $^1$H NMR (400 MHz, Chloroform-d) δ 7.58-7.53 (m, 2H), 7.46 (s, 2H), 7.29-7.26 (m, 2H), 7.21-7.15 (m, 2H), 5.43-5.36 (m, 1H), 4.31-4.23 (m, 1H), 3.97 (s, 2H), 3.03-2.95 (m, 1H), 2.43 (s, 3H), 2.41-2.39 (m, 1H), 2.35 (s, 3H), 2.34-2.28 (m, 4H), 2.20-2.14 (m, 1H), 1.60-1.50 (m, 2H). |
| 43 | 478.4 | $^1$H NMR (500 MHz, Chloroform-d) δ 7,49 (d, J = 8.1 Hz, 2H), 7.43-7.38 (m, 1H), 7.34 (d, J = 7.8 Hz, 1H), 7.26 (dt, J = 10.2, 1.9 Hz, 1H), 7.19 (d, J = 8.1 Hz, 2H), 7.04 (td, J = 8.3, 2.2 Hz, 1H), 5.44 (d, J = 7.7 Hz, 1H), 4.28 (h, J = 8.0 Hz, 1H), 4.00 (s, 2H), 3.00 (p, J = 8.4 Hz, 1H), 2.47-2.41 (m, 4H), 2.37 (s, 3H), 2.33 (td, J = 7.8, 4.2 Hz, 3H), 2.19 (dd, J = 11.7, 8.2 Hz, 1H), 2.03 (ddd, J = 11.5, 8.8, 2.1 Hz, 1H), 1.56 (ddd, J = 16.2, 11.3, 8.6 Hz, 2H). |
| 44 | 528.3 | $^1$H NMR (500 MHz, Chloroform-d) δ 7.80 (s, 1H), 7.74 (d, J = 7.6 Hz, 1H), 7.58 (dt, J = 15.3, 7.7 Hz, 2H), 7.51 (d, J = 8.1 Hz, 2H), 7.22 (d, J = 8.1 Hz, 2H), 5.42 (d, J = 7.8 Hz, 1H), 4.30 (h, J = 8.0 Hz, 1H), 4.01 (s, 2H), 3.00 (p, J = 8.5 Hz, 1H), 2.45 (s, 4H), 2.38 (s, 3H), 2.33 (t, J = 7.6 Hz, 3H), 2.20 (dd, J = 11.7, 8.2 Hz, 1H), 2.04 (q, J = 9.4, 8.7 Hz, 1H), 1.58 (ddd, J = 16.6, 11.3, 8.7 Hz, 2H). |
| 45 | $[M + H]^+$: 522.19, $[M + H]^-$: 520.36 | $^1$H NMR (300 MHz, Chloroform-d) δ 7.47-7.42 (m, 2H), 7.18-7.13 (m, 2H), 6.88-6.79 (m, 2H), 6.62-6.54 (m, 1H), 5.42-5.33 (m, 1H), 4.33-4.16 (m, 1H), 4.11-4.02 (m, 2H), 3.96 (s, 2H), 3.04-2.91 (m, 1H), 2.45-2.38 (m, 4H), 2.35 (s, 3H), 2.32-2.26 (m, 3H), 2.21-2.14 (m, 1H), 2.08-1.99 (m, 1H), 1.59-1.47 (m, 2H), 1.46-1.40 (m, 3H). |
| 46 | $[M + H]^+$: 536.30, $[M + H]^-$: 534.47 | $^1$H NMR (400 MHz, Chloroform-d) δ 7.46-7.42 (m, 2H), 7.17-7.13 (m, 2H), 6.84-6.79 (m, 2H), 6.60-6.54 (m, 1H), 5.41-5.35 (m, 1H), 4.61-4.52 (m, 1H), 4.30-4.20 (m, 1H), 3.96 (s, 2H), 3.04-2.93 (m, 1H), 2.45-2.40 (m, 4H), 2.35 (s, 3H), 2.32-2.28 (m, 3H), 2.22-2.15 (m, 1H), 2.06-2.00 (m, 1H), 1.58-1.48 (m, 2H), 1.37-1.34 (m, 6H). |
| 47 | 508.28 | $^1$H NMR (500 MHz, $CDCl_3$) δ 7.46 (d, J = 7.7 Hz, 2H), 7.18 (d, J = 7.9 Hz, 2H), 7.08 (t, J = 9.4 Hz, 1H), 6.92 (dd, J = 6.3, 3.2 Hz, 1H), 6.84 (dt, J = 9.0, 3.4 Hz, 1H), 5.37 (d, J = 7.8 Hz, 1H), 4.27 (d, J = 8.0 Hz, 1H), 4.00 (s, 2H), 3.84 (s, 3H), 3.01 (t, J = 8.5 Hz, 1H), 2.45 (s, 3H), 2.31 (d, J = 8.7 Hz, 3H), 2.18 (d, J = 8.5 Hz, 3H), 2.05 (t, J = 10.3 Hz, 1H), 1.56-1.51 (m, 2H), 1.29 (d, J = 15.5 Hz, 3H) |
| 48 | 509.43 | $^1$H NMR (500 MHz, $CDCl_3$) δ 7.44 (d, J = 8.0 Hz, 2H), 7.15 (d, J = 7.9 Hz, 2H), 7.03-6.98 (m, 2H), 6.92 (dd, J = 9.8, 4.5 Hz, 1H), 5.40 (d, J = 7.9 Hz, 1H), 4.29 (q, J = 8.1 Hz, 1H), 3.99 (s, 2H), 3.80 (s, 3H), 3.02 (p, J = 8.4 Hz, 1H), 2.46 (s, 3H), 2.38 (s, 3H), 2.33 (d, J = 8.5 Hz, 4H), 2.20 (dd, J = 11.9, 8.1 Hz, 2H), 2.12-2.02 (m, 2H). |
| 49 | 478.24 | $^1$H NMR (500 MHz, $CDCl_3$) δ 7.50-7.45 (m, 2H), 7.41 (td, J = 7.8, 1.8 Hz, 1H), 7.37-7.29 (m, 1H), 7.25-7.21 (m, 1H), 7.20-7.11 (m, 3H), 5.37 (d, J = 7.9 Hz, 1H), 4.27 (h, J = 8.0 Hz, 1H), 4.00 (s, 2H), 3.12-2.91 (m, 1H), 2.50-2.40 (m, 1H), 2.45 (s, 3H), 2.39 (s, 3H), 2.34-2.29 (m, 3H), 2.24-2.16 (m, 1H), 2.08-2.00 (m, 1H), 1.58-1.48 (m, 2H). |

TABLE 10-continued

| Example No. | LC/MS (ESI) m/z: [M + H]+ | NMR |
|---|---|---|
| 50 | 491.27 | $^1$H NMR (400 MHz, MeOD) δ 8.16 (d, J = 5.5 Hz, 1H), 7.63-7.55 (m, 2H), 7.25-7.18 (m, 3H), 7.02 (d, J = 1.5 Hz, 1H), 4.14 (p, J = 8.1 Hz, 1H), 3.99 (s, 2H), 3.96 (s, 3H), 2.93 (p, J = 8.5 Hz, 1H), 2.38 (s, 7H), 2.34-2.18 (m, 3H), 2.18-2.09 (m, 1H), 2.08-1.97 (m, 1H), 1.84-1.70 (m, 2H). |
| 51 | [M + H]+: 558.6, [M + H]−: 556.5 | $^1$H NMR (400 MHz, chloroform-d) δ 7.51-7.44 (m, 2H), 7.36 (s, 1H), 7.23-7.21 (m, 1H), 7.19-7.16 (m, 2H), 7.10-7.07 (m, 1H), 5.44-5.34 (m, 1H), 4.34-4.20 (m, 1H), 3.98 (s, 2H), 3.89 (s, 3H), 3.03-2.91 (m, 1H), 2.42 (s, 3H) ), 2.40-2.38 (m, 1H), 2.35 (s, 3H), 2.33-2.27 (m, 3H), 2.20-2.14 (m, 1H), 2.05-1.98 (m, 1H), 1.60-1.50 (m, 2H). |

TABLE 11

| Example No. | Chemical structure | Name | Difference in preparation method |
|---|---|---|---|
| 52 | 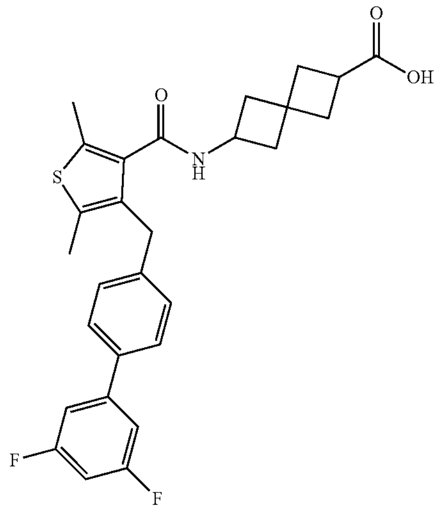 [SMILES: Cc1sc(C)c(C(=O)NC2CC3(C2)CC(C(=O)O)C3)c1Cc1ccc(-c2cc(F)cc(F)c2)cc1] | 6-(4-((3',5'-difluoro-[1,1'-biphenyl]-4-yl)methyl)-2,5-dimethylthiophene-3-carboxamido)spiro[3.3]heptane-2-carboxylic acid | 3,5-difluorophenylboronic acid was used instead of 3,4-dimethylphenylboronic acid, and $K_3PO_4$ was used instead of $Cs_2CO_3$ in Step 1 |
| 53 | 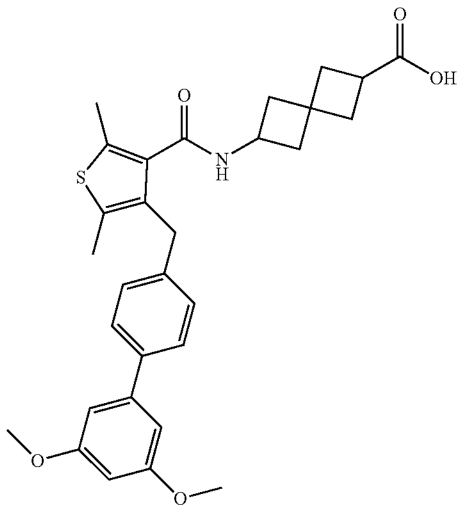 [SMILES: COc1cc(OC)cc(-c2ccc(Cc3c(C)sc(C)c3C(=O)NC3CC4(C3)CC(C(=O)O)C4)cc2)c1] | 6-(4-((3',5'-dimethoxy-[1,1'-biphenyl]-4-yl)methyl)-2,5-dimethylthiophene-3-carboxamido)spiro[3.3]heptane-2-carboxylic acid | 3,5-dimethoxyphenylboronic acid was used instead of 3,4-dimethylphenylboronic acid, and $K_3PO_4$ was used instead of $Cs_2CO_3$ in Step 1 |

TABLE 11-continued

| Example No. | Chemical structure | Name | Difference in preparation method |
|---|---|---|---|
| 54 | 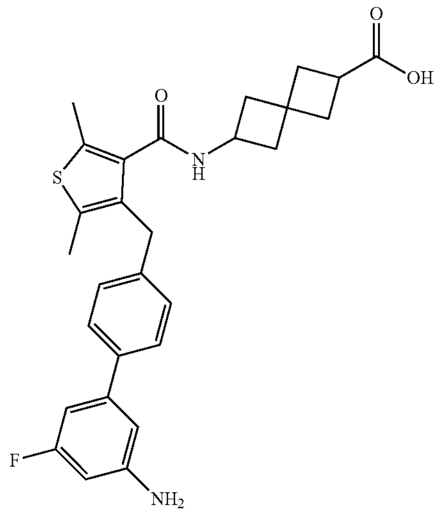 [SMILES: Cc1sc(C)c(C(=O)NC2CC3(C2)CC(C(=O)O)C3)c1Cc1ccc(-c2cc(N)cc(F)c2)cc1] | 6-(4-((3'-amino-5'-fluoro-[1,1'-biphenyl]-4-yl)methyl)-2,5-dimethylthiophene-3-carboxamido)spiro[3.3]heptane-2-carboxylic acid | Intermediate H was used instead of 3,4-dimethylphenylboronic acid in Step 1 |
| 55 | 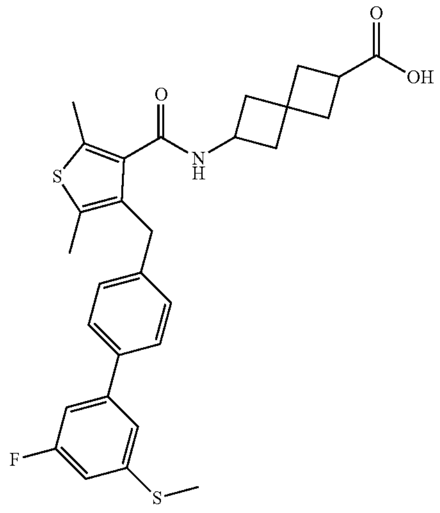 [SMILES: CSc1cc(F)cc(-c2ccc(Cc3c(C)sc(C)c3C(=O)NC3CC4(C3)CC(C(=O)O)C4)cc2)c1] | 6-(4-((3'-fluoro-5'-(methylthio)-[1,1'-biphenyl]-4-yl)methyl)-2,5-dimethylthiophene-3-carboxamido)spiro[3.3]heptane-2-carboxylic acid | Intermediate I was used instead of 3,4-dimethylphenylboronic acid in Step 1 |
| 56 | 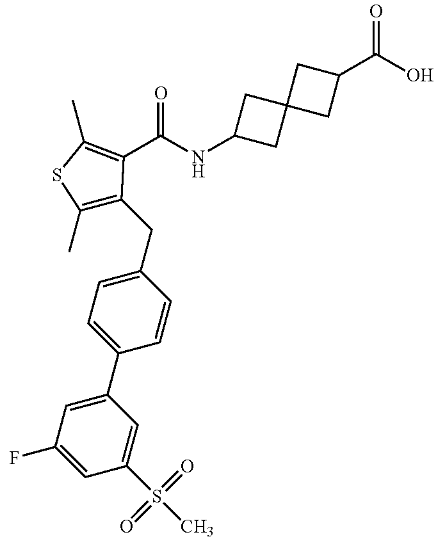 [SMILES: Cc1sc(C)c(C(=O)NC2CC3(C2)CC(C(=O)O)C3)c1Cc1ccc(-c2cc(F)cc(S(C)(=O)=O)c2)cc1] | 6-(4-((3'-fluoro-5'-(methylsulfonyl)-[1,1'-biphenyl]-4-yl)methyl)-2,5-dimethylthiophene-3-carboxamido)spiro[3.3]heptane-2-carboxylic acid | The methylthio group of methyl 6-(4-((3'-fluoro-5'-(methylthio)-[1,1'-biphenyl]-4-yl)methyl)-2,5-dimethylthiophene-3-carboxamido)spiro[3.3]heptane-2-carboxylate obtained in Step 1 of Example 55 was oxidated, and then Step 2 was performed. Oxidation reaction conditions and reagents: oxone, $MeOH/H_2O$, 0° C. to room temperature, 5 hours |

TABLE 11-continued

| Example No. | Chemical structure | Name | Difference in preparation method |
|---|---|---|---|
| 57 | 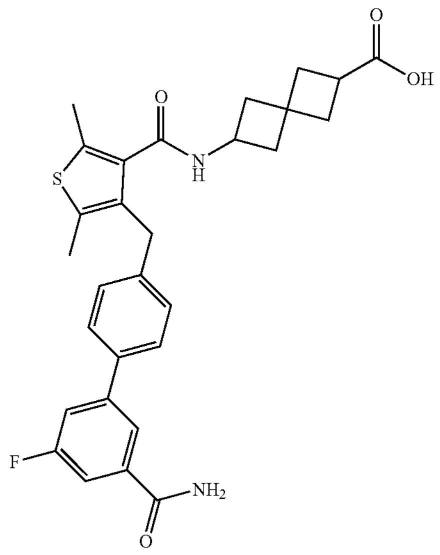 [SMILES: Cc1sc(C)c(C(=O)NC2CC3(C2)CC(C(=O)O)C3)c1Cc1ccc(-c2cc(F)cc(C(N)=O)c2)cc1] | 6-(4-((3'-carbamoyl-5'-fluoro-[1,1'-biphenyl]-4-yl)methyl)-2,5-dimethylthiophene-3-carboxamido)spiro[3.3]heptane-2-carboxylic acid | Intermediate J was used instead of 3,4-dimethylphenylboronic acid in Step 1 |
| 58 | 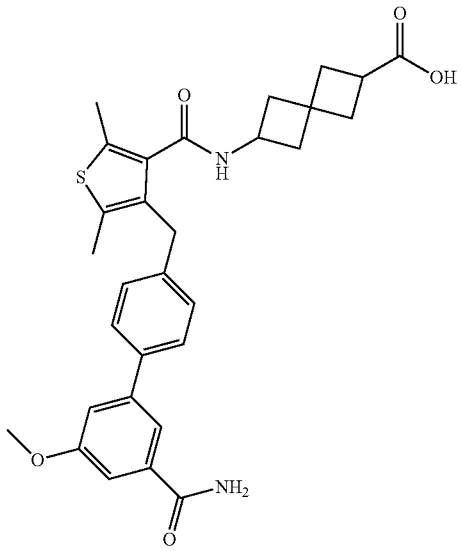 [SMILES: COc1cc(C(N)=O)cc(-c2ccc(Cc3c(C)sc(C)c3C(=O)NC3CC4(C3)CC(C(=O)O)C4)cc2)c1] | 6-(4-((3'-carbamoyl-5'-methoxy-[1,1'-biphenyl]-4-yl)methyl)-2,5-dimethylthiophene-3-carboxamido)spiro[3.3]heptane-2-carboxylic acid | Intermediate K was used instead of 3,4-dimethylphenylboronic acid in Step 1 |

TABLE 11-continued

| Example No. | Chemical structure | Name | Difference in preparation method |
|---|---|---|---|
| 59 | 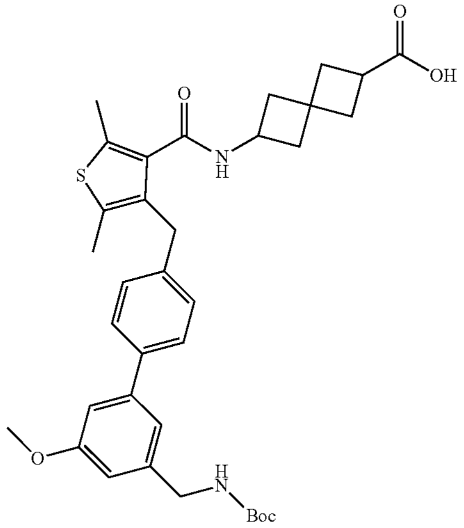 [SMILES: COc1cc(CNC(=O)OC(C)(C)C)cc(-c2ccc(Cc3c(C)sc(C)c3C(=O)NC3CC4(C3)CC(C(=O)O)C4)cc2)c1] | 6-(4-((3'-(((tert-butoxycarbonyl)amino)methyl)-5'-methoxy-[1,1'-biphenyl]-4-yl)methyl)-2,5-dimethylthiophene-3-carboxamido)spiro[3.3]heptane-2-carboxylic acid | Intermediate L was used instead of 3,4-dimethylphenylboronic acid in Step 1 |
| 60 | 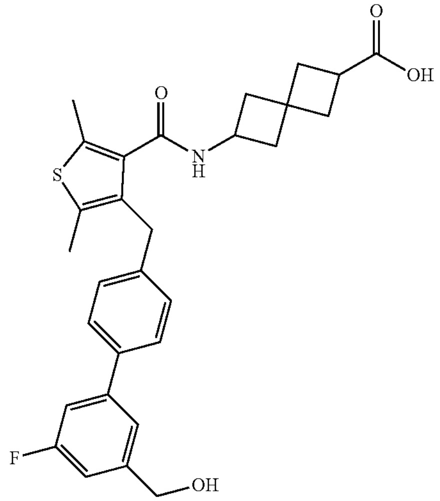 [SMILES: Cc1sc(C)c(C(=O)NC2CC3(C2)CC(C(=O)O)C3)c1Cc1ccc(-c2cc(F)cc(CO)c2)cc1] | 6-(4-((3'-fluoro-5'-(hydroxymethyl)-[1,1'-biphenyl]-4-yl)methyl)-2,5-dimethylthiophene-3-carboxamido)spiro[3.3]heptane-2-carboxylic acid | Intermediate M was used instead of 3,4-dimethylphenylboronic acid in Step 1 |
| 61 | 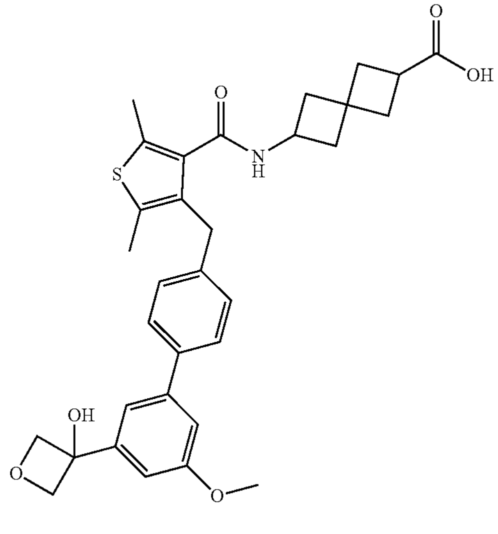 [SMILES: COc1cc(-c2ccc(Cc3c(C)sc(C)c3C(=O)NC3CC4(C3)CC(C(=O)O)C4)cc2)cc(C2(O)COC2)c1] | 6-(4-((3'-(3-hydroxyoxetane-3-yl)-5'-methoxy-[1,1'-biphenyl]-4-yl)methyl)-2,5-dimethylthiophene-3-carboxamido)spiro[3.3]heptane-2-carboxylic acid | Intermediate N was used instead of 3,4-dimethylphenylboronic acid, and $K_3PO_4$ was used instead of $Cs_2CO_3$ in Step 1 |

TABLE 11-continued

| Example No. | Chemical structure | Name | Difference in preparation method |
|---|---|---|---|
| 62 | 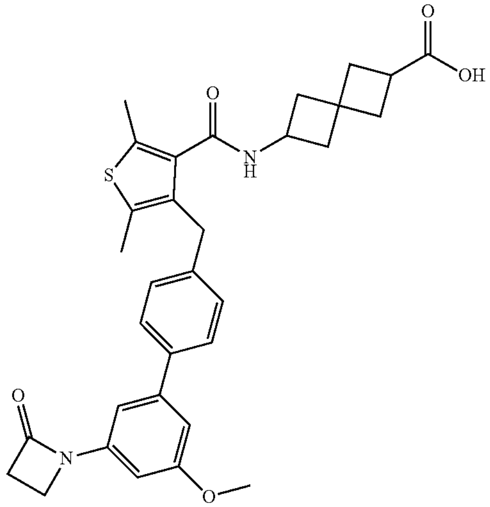 [SMILES: COc1cc(-c2ccc(Cc3c(C)sc(C)c3C(=O)NC3CC4(C3)CC(C(=O)O)C4)cc2)cc(N2CCC2=O)c1] | 6-(4-((3'-methoxy-5'-(2-oxoazetidin-1-yl)-[1,1'-biphenyl]-4-yl)methyl)-2,5-dimethylthiophene-3-carboxamido)spiro[3.3]heptane-2-carboxylic acid | Intermediate O was used instead of 3,4-dimethylphenylboronic acid, and $K_3PO_4$ was used instead of $Cs_2CO_3$ in Step 1 |
| 63 | 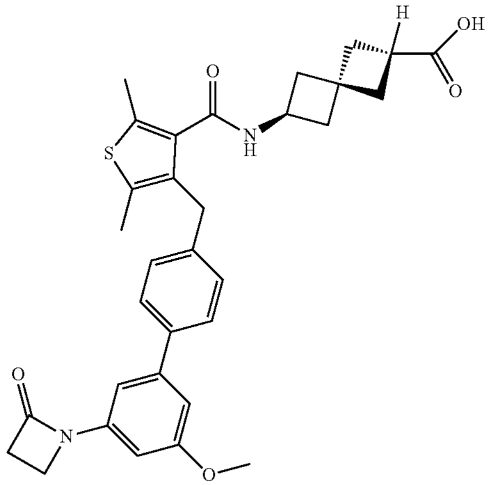 | (2R,4R,6R)-6-(4-((3'-methoxy-5'-(2-oxoazetidin-1-yl)-[1,1'-biphenyl]-4-yl)methyl)-2,5-dimethylthiophene-3-carboxamido)spiro[3.3]heptane-2-carboxylic acid | Intermediate O was used instead of 3,4-dimethylphenylboronic acid, and $K_3PO_4$ was used instead of $Cs_2CO_3$ in Step 1. In addition, (2R,4R,6R)-methyl 6-(4-4-chlorobenzyl-2,5-dimethylthiophene-3-carboxamido)spiro[3.3]heptane-carboxylate, which was obtained using Intermediate Z instead of Intermediate A in Step 3 of Example 23, was used in Step 1. |
| 64 | 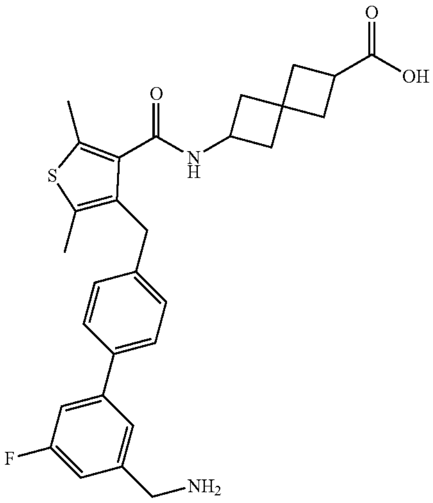 [SMILES: Cc1sc(C)c(C(=O)NC2CC3(C2)CC(C(=O)O)C3)c1Cc1ccc(-c2cc(F)cc(CN)c2)cc1] | 6-(4-((3'-(aminomethyl)-5'-fluoro-[1,1'-biphenyl]-4-yl)methyl)-2,5-dimethylthiophene-3-carboxamido)spiro[3.3]heptane-2-carboxylic acid | 6-(4-((3'-(((tert-butoxycarbonyl)amino)methyl)-5'-fluoro-[1,1'-biphenyl]-4-yl)methyl)-2,5-dimethylthiophene-3-carboxamido)spiro[3.3]heptane-2-carboxylic acid was obtained in the same manner as in Example 28, except that Intermediate P was used instead of 3,4-dimethylphenylboronic acid in Step 1. Thereafter, Boc deprotection was performed to obtain the hydrochloride salt of the compound of Example 64.<br>Boc deprotection reaction reagents and<br>conditions: 4N HCl in dioxane (1M), DCM, room temperature, 15 hours |

TABLE 11-continued

| Example No. | Chemical structure | Name | Difference in preparation method |
|---|---|---|---|
| 65 | 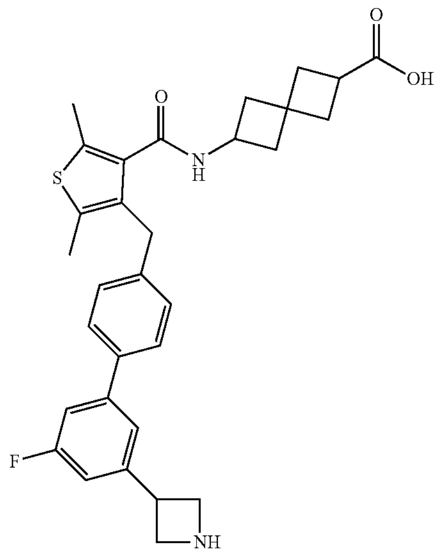 [SMILES: Cc1sc(C)c(C(=O)NC2CC3(C2)CC(C(=O)O)C3)c1Cc1ccc(-c2cc(F)cc(C3CNC3)c2)cc1] | 6-(4-((3'-(azetidin-3-yl)-5'-fluoro-[1,1'-biphenyl]-4-yl)methyl)-2,5-dimethylthiophene-3-carboxamido)spiro[3.3]heptane-2-carboxylic acid | The hydrochloride salt of the compound of Example 65 was obtained in the same manner as in Example 64, except that Intermediate Q was used instead of 3,4-dimethylphenylboronic acid, and $K_3PO_4$ was used instead of $Cs_2CO_3$ in Step 1 |
| 66 | 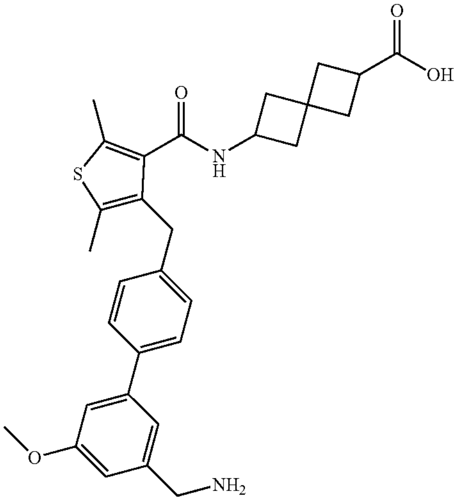 [SMILES: COc1cc(CN)cc(-c2ccc(Cc3c(C)sc(C)c3C(=O)NC3CC4(C3)CC(C(=O)O)C4)cc2)c1] | 6-(4-((3'-(aminomethyl)-5'-methoxy-[1,1'-biphenyl]-4-yl)methyl)-2,5-dimethylthiophene-3-carboxamido)spiro[3.3]heptane-2-carboxylic acid | The hydrochloride salt of the compound of Example 66 was obtained in the same manner as in Example 64, except that Intermediate L was used instead of 3,4-dimethylphenylboronic acid in Step 1. |

TABLE 12

| Example No. | LC/MS (ESI) m/z: $[M + H]^+$ | NMR |
|---|---|---|
| 52 | 496.5 | $^1$H NMR (300 MHz, DMSO-$d_6$) δ 12.01 (s, 1H), 8.28 (d, J = 7.5 Hz, 1H), 7.64-7.56 (m, 2H), 7.38 (dt, J = 7.6, 2.2 Hz, 2H), 7.23-7.14 (m, 3H), 4.18-4.10 (m, 1H), 3.90 (s, 2H), 2.95-2.84 (m, 1H), 2.38-2.27 (m, 7H), 2.26-2.13 (m, 3H), 2.10-1.98 (m, 2H), 1.85 (ddd, J = 15.9, 11.0, 8.5 Hz, 2H). |
| 53 | 520.5 | $^1$H NMR (300 MHz, Methanol-$d_4$) δ 7.44 (d, J = 8.2 Hz, 2H), 7.12 (d, J = 8.2 Hz, 2H), 6.69 (d, J = 2.3 Hz, 2H), 6.45 (t. J = 2.2 Hz, 1H), 4.18-4.06 (m, 1H), 3.94 (s, 2H), 3.81 (s, 6H), 2.97-2.88 (m, 1H), 2.41-2.33 (m, 7H), 2.31-2.17 (m, 3H), 2.16-2.10 (m, 1H), 2.06-1.98 (m, 1H), 1.79-1.71 (m, 2H). |
| 54 | 493.5 | $^1$H NMR (400 MHz, $CDCl_3$) δ 7.44 (d, J = 8.1 Hz, 2H), 7.15 (d, J = 7.9 Hz, 2H), 6.71-6.60 (m, 2H), 6.40 (dt, J = 10.3, 2.2 Hz, 1H), 5.33 (d, J = 8.0 Hz, 1H), 4.26 (h, J = 8.1 Hz, 1H), 3.98 (s, 2H), 2.99 (p, J = 8.0 Hz, 1H), 2.44 (s, 3H), 2.44-2.38 (m, 1H), 2.38 (s, 3H), 2.37-2.24 (m, 3H), 2.17-2.01 (m, 2H), 1.55 (dd, J = 11.4, 8.3 Hz, 1H), 1.39 (dd, J = 11.7, 8.4 Hz, 1H). |

TABLE 12-continued

| Example No. | LC/MS (ESI) m/z: $[M + H]^+$ | NMR |
|---|---|---|
| 55 | — | $^1$H NMR (500 MHz, Chloroform-d) δ 7.49-7.45 (m, 2H), 7.20-7.17 (m, 3H), 7.03-6.99 (m, 1H), 6.94-6.91 (m, 1H), 5.44-5.42 (m, 1H), 4.33-4.26 (m, 1H), 4.00 (s, 2H), 3.05-2.97 (m, 1H), 2.55-2.53 (m, 3H), 2.48-2.46 (m, 1H), 2.45 (s, 3H), 2.45-2.42 (m, 1H), 2.37 (s, 3H), 2.35-2.30 (m, 3H), 2.23-2.18 (m, 1H), 1.61-1.54 (m, 2H). |
| 56 | $[M + H]^+$: 556.28, $[M - H]^-$: 554.39 | $^1$H NMR (300 MHz, Chloroform-d) δ 7.96-7.94 (m, 1H), 7.64-7.63 (m, 1H), 7.54-7.51 (m, 3H), 7.26-7.24 (m, 2H), 6.07-6.05 (m, 1H), 4.32-4.29 (m, 1H), 3.51 (s, 2H), 3.15 (s, 3H), 3.06-3.04 (m, 1H), 2.57-2.55 (m, 1H), 2.53-2.51 (m, 3H), 2.46-2.46 (m, 1H), 2.43 (s, 3H), 2.38-2.37 (m, 3H), 2.22-2.22 (m, 1H), 1.70-1.67 (m, 2H). |
| 57 | 521.5 | $^1$H NMR (300 MHz, Methanol-$d_4$) δ 8.23 (d, J = 7.3 Hz, 1H), 7.95 (t. J = 1.5 Hz, 1H), 7.60-7.50 (m, 4H), 7.20 (d, J = 8.2 Hz, 2H), 4.18-4.07 (m, 1H), 3.97 (s, 2H), 2.99-2.88 (m, 1H), 2.37 (s, 3H), 2.37 (s, 3H), 2.36 (s, 3H), 2.32-2.18 (m, 3H), 2.16-1.96 (m, 3H), 1.84-1.70 (m, 2H). |
| 58 | 533.6 | $^1$H NMR (300 MHz, DMSO-$d_6$) δ 8.28 (d, J = 7.5 Hz, 1H), 8.07 (s, 1H), 7.69 (s, 1H), 7.57 (d, J = 8.2 Hz, 2H), 7.42 (s, 1H), 7.38 (s, 1H), 7.26 (s, 1H), 7.19 (d, J = 8.2 Hz, 2H), 4.26-4.08 (m, 1H), 3.90 (s,] 2H), 3.85 (s, 3H), 2.95-2.79 (m, 1H), 2.31 (s, 6H), 2.23-2.12 (m, 3H), 2.09-1.97 (m, 2H), 1.94-1.78 (m, 2H), 1.68-1.55 (m, 1H). |
| 59 | 619.5 | $^1$H NMR (300 MHz, Methanol-$d_6$) δ 7.46 (d, J = 8.2 Hz, 2H), 7.13 (d, J = 8.2 Hz, 2H), 7.07 (s, 1H), 6.97 (s, 1H), 6.81 (s, 1H), 4.63 (s, 1H), 4.25 (s, 2H), 4.18-4.03 (m, 1H), 3.95 (s, 2H), 3.83 (s, 3H), 3.01-2.84 (m, 1H), 2.36 (s, 6H), 2.32-2.17 (m, 3H), 2.17-2.08 (m, 1H), 2.08-1.97 (m, 1H), 1.82-1.68 (m, 2H), 1.47 (s, 9H). |
| 60 | 508.08 | $^1$H NMR (400 MHz, $CDCl_3$) δ 7.50 (d, J = 8.0 Hz, 2H), 7.38 (s, 1H), 7.23-7.15 (m, 3H), 7.07-7.00 (m, 1H), 5.34 (d, J = 8.0 Hz, 1H), 4.78 (s, 2H), 4.23 (h, J = 7.7, 7.2 Hz, 1H), 4.00 (s, 2H), 2.95 (p, J = 8.0 Hz, 1H), 2.47-2.41 (m, 1H), 2.44 (s, 3H), 2.39 (s, 3H), 2.35-2.25 (m, 3H), 2.13-1.97 (m, 2H), 1.58 (dd, J = 11.6, 7.8 Hz, 1H), 1.36 (dd, J = 11.8, 7.9 Hz, 1H). |
| 61 | ES + 562.08 | $^1$H NMR (500 MHz, $CDCl_3$) δ 7.48 (d, J = 8.0 Hz, 2H), 7.35 (s, 1H), 7.16-7.09 (m, 3H), 7.02 (s, 1H), 5.30 (d, J = 8.0 Hz, 1H), 5.05-4.85 (m, 4H), 4.19 (q, J = 7.8 Hz, 1H), 3.96 (s, 2H), 3.86 (s, 3H), 2.91 (p, J = 8.1 Hz, 1H), 2.40 (s, 3H), 2.40-2.35 (m, 1H), 2.35 (s, 3H), 2.25 (dd, J = 13.0, 7.6 Hz, 3H), 2.01 (t. J = 8.8 Hz, 2H), 1.54 (dd, J = 11.6, 7.7 Hz, 1H), 1.32 (dd, J = 12.0, 8.0 Hz, 1H). |
| 62 | ES + 559.32 | $^1$H NMR (500 MHz, $CDCl_3$) δ 7.45 (d, J = 7.9 Hz, 2H), 7.15-7.11 (m, 3H), 6.86 (t, J = 2.1 Hz, 1H), 6.79 (t, J = 1.9 Hz, 1H), 5.33 (d, J = 7.8 Hz, 1H), 4.22 (h, J = 8.0 Hz, 1H), 3.95 (s, 2H), 3.84 (s, 3H), 3.64 (t, J = 4.5 Hz, 2H), 3.10 (t, J = 4.5 Hz, 2H), 2.95 (p, J = 8.4 Hz, 1H), 2,40 (s, 3H), 2.39-2.34 (m, 1H), 2.34 (s, 3H), 2.30-2.23 (m, 3H), 2.11 (dd, J = 11.8, 8.0 Hz, 1H), 2.06-1.97 (m, 1H), 1.48 (ddd, J = 16.7, 11.6, 8.3 Hz, 2H). |
| 63 | ES + 559.32 | $^1$H NMR (500 MHz, $CDCl_3$) δ 7.45 (d, J = 7.9 Hz, 2H), 7.15-7.11 (m, 3H), 6.86 (t. J = 2.1 Hz, 1H), 6.79 (t, J = 1.9 Hz, 1H), 5.33 (d, J = 7.8 Hz, 1H), 4.22 (h. J = 8.0 Hz, 1H), 3.95 (s, 2H), 3.84 (s, 3H), 3.64 (t, J = 4.5 Hz, 2H), 3.10 (t, J = 4.5 Hz, 2H), 2.95 (p, J = 8.4 Hz, 1H), 2.40 (s, 3H), 2.39-2.34 (m, 1H), 2.34 (s, 3H), 2.30-2.23 (m, 3H), 2.11 (dd, J = 11.8, 8.0 Hz, 1H), 2.06-1.97 (m, 1H), 1.48 (ddd, J = 16.7, 11.6, 8.3 Hz, 2H). |
| 64 | n + 1 = 507.5 | $^1$H NMR (300 MHz, DMSO-$d_6$) δ 8.30 (d, J = 7.5 Hz, 1H), 7.65 (d, J = 1.5 Hz, 1H), 7.58 (d, J = 8.2 Hz, 2H), 7.52-7.47 (m, 1H), 7.33-7.29 (m, 1H), 7.21 (d, J = 8.2 Hz, 2H), 4.22-4.06 (m, 3H), 3.90 (s, 2H), 2.96-2.85 (m, 1H), 2.39-2.28 (m, 7H), 2.27-2.10 (m, 3H), 2.09-2.02 (m, 2H), 1.90-1.81 (m, 2H). |
| 65 | 533.3 | $^1$H NMR (300 MHz, Methanol-$d_4$) δ 7.55 (d, J = 8.2 Hz, 2H), 7.46 (s, 1H), 7.32 (dt, J =9,9, 2.0 Hz, 1H), 7.23-7.15 (m, 3H), 4.48-4.27 (m, 5H), 4.14 (p, J = 8.0 Hz, 1H), 3.98 (s, 2H), 3.01-2.87 (m, 1H), 2.38 (d, J = 4.4 Hz, 7H), 2.31-2.18 (m, 3H), 2.17-1.99 (m, 2H), 1.87-1.70 (m, 2H). |
| 66 | 519.5 | $^1$H NMR (300 MHz, DMSO-$d_6$) δ 8.31 (d, J = 7.5 Hz, 1H), 7.54 (d, J = 8.0 Hz, 2H), 7.33 (s, 1H), 7.19 (d, J = 8.0 Hz, 2H), 7.13 (s, 1H), 7.07 (s, 1H), 4.24-4.09 (m, 1H), 4.05 (s, 2H), 3.89 (s, 2H), 3.83 (s, 3H), 2.98-2.83 (m, 1H), 2.31 (d, J = 1.4 Hz, 6H), 2.27-2.10 (m, 4H), 2.10-1.97 (m, 2H), 1.95-1.77 (m, 2H). |

Example 67: 6-(4-(4-cyclohexylbenzyl)-2,5-dimethylthiophene-3-carboxamido)spiro[3.3]heptane-2-carboxylic acid

Step 1: Synthesis of methyl 6-(2,5-dimethyl-4-((2',3',4',5'-tetrahydro-[1,1'-biphenyl]-4-yl)methyl)thiophene-3-carboxamido)spiro[3.3]heptane-2-carboxylate

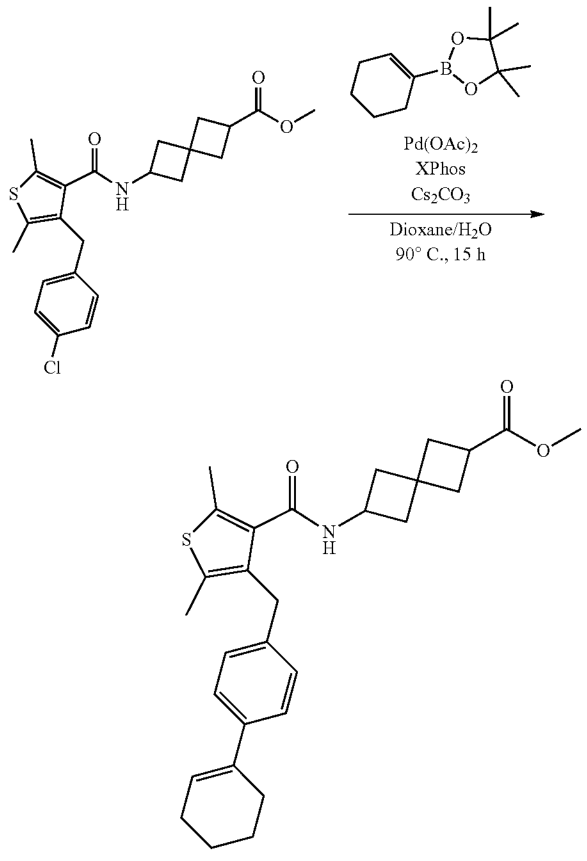

A solution of methyl 6-(4-(4-chlorobenzyl)-2,5-dimethylthiophene-3-carboxamido)spiro[3.3]heptane-2-carboxylate (50 mg, 0.11 mmol) obtained in Step 3 of Example 23 and 2-(cyclohex-1-en-1-yl)-4,4,5,5-tetramethyl-1,3,2-dioxaborolane (27 mg, 0.13 mmol) in 1,4-dioxane (1 mL) was placed in a sealed tube, and $H_2O$ (0.05 mL) and $Cs_2CO_3$ (40 mg, 0.22 mmol) were added. $Pd(OAc)_2$ (2.5 mg) and Xphos (65 mg, 0.115 mmol) were added under $N_2$ atmosphere and stirred at 90° C. for 15 hours. The reaction mixture was diluted with ethyl acetate, washed with distilled water, then dried over $MgSO_4$, filtered, and concentrated. The crude product was purified by silica gel column chromatography (30% EtOAc in hexane) to obtain methyl 6-(2,5-dimethyl-4-((2',3',4',5'-tetrahydro-[1,1'-biphenyl]-4-yl)methyl)thiophene-3-carboxamido)spiro[3.3]heptane-2-carboxylate (59 mg, mixture). $^1H$ NMR (400 MHz, Methanol-$d_4$) δ 7.28-7.22 (m, 2H), 7.00 (d, J=8.3 Hz, 2H), 6.07 (tt, J=3.9, 1.7 Hz, 1H), 4.13-4.09 (m, 1H), 3.90 (s, 2H), 3.66 (s, 3H), 3.02 (p, J=8.5 Hz, 1H), 2.50-2.42 (m, 1H), 2.41-2.37 (m, 2H), 2.35 (d, J=5.5 Hz, 6H), 2.32-2.25 (m, 2H), 2.24-2.13 (m, 4H), 2.10-2.05 (m, 1H), 1.81-1.75 (m, 4H), 1.71-1.67 (m, 2H).

Step 2: Synthesis of methyl 6-(4-(4-cyclohexylbenzyl)-2,5-dimethylthiophene-3-carboxamido)spiro[3.3]heptane-2-ca late

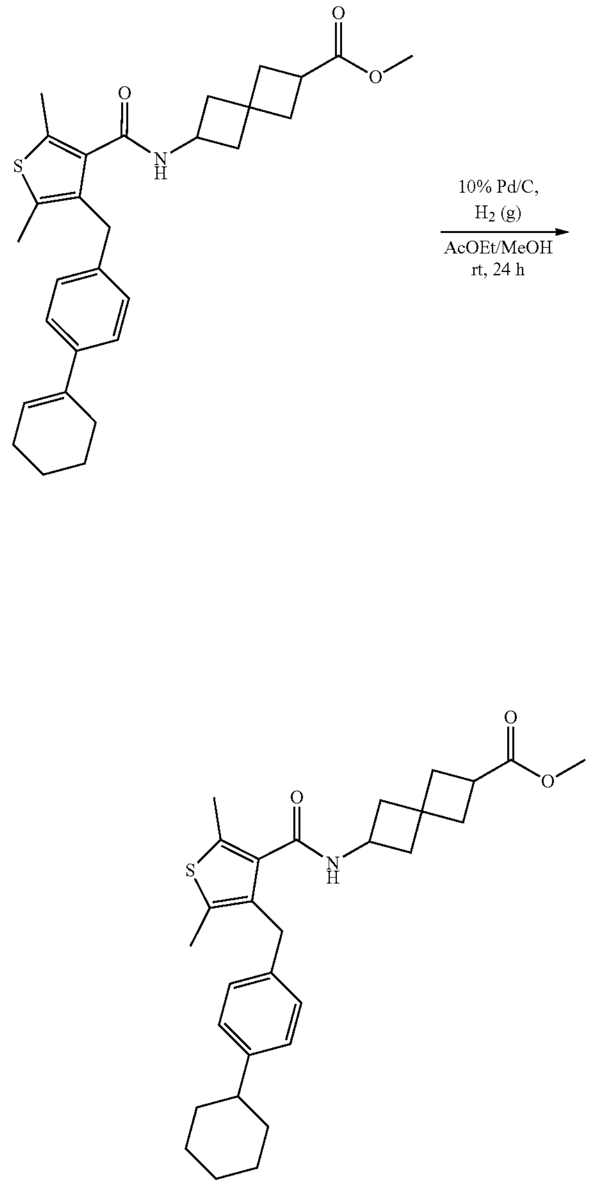

To a solution of methyl 6-(2,5-dimethyl-4-((2',3',4',5'-tetrahydro-[1,1'-biphenyl]-4-yl) methyl)thiophene-3-carboxamido)spiro[3.3]heptane-2-carboxylate (20 mg, 0.042 mmol) in ethyl acetate/methanol (8/2, 0.2 mL), 10% Pd/C (2.2 mg) was added. The reaction mixture was stirred under hydrogen gas for 24 hours and filtered through Celite using ethyl acetate to obtain methyl 6-(4-(4-cyclohexylbenzyl)-2,5-dimethylthiophene-3-carboxamido)spiro[3.3]heptane-2-carboxylate (12 mg). $^1H$ NMR (400 MHz, Chloroform-d) δ 7.16-7.10 (m, 2H), 7.02 (s, 2H), 5.32 (d, J=7.9 Hz, 1H), 4.31-4.13 (m, 1H), 3.91 (s, 2H), 3.68 (s, 3H), 3.03-2.95 (m, 1H), 2.52-2.46 (m, 1H), 2.45 (s, 3H), 2.40-2.36 (m, 1H), 2.35 (s, 3H), 2.30-2.26 (m, 2H), 2.26-2.23 (m, 1H), 2.22-2.16 (m, 1H), 2.02-1.96 (m, 1H), 1.87-1.83 (m, 4H), 1.69-1.65 (m, 2H), 1.48-1.43 (m, 2H), 1.40-1.32 (m, 5H).

Step 3: Synthesis of 6-(4-(4-cyclohexylbenzyl)-2,5-dimethylthiophene-3-carboxamido)spiro[3.3]heptane-2-carboxylic acid

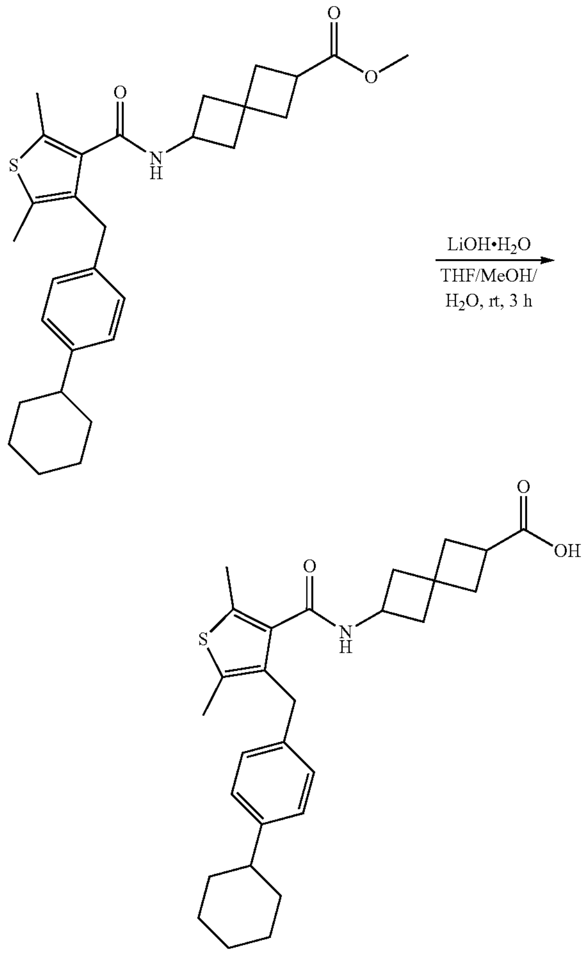

67

To a solution of methyl 6-(4-(4-cyclohexylbenzyl)-2,5-dimethylthiophene-3-carboxamido)spiro[3.3]heptane-2-carboxylate (12 mg) in THF/MeOH/$H_2O$ (2/1/2), LiOH·$H_2O$ (3 mg, 0.075 mmol, 3.0 equiv) was added and stirred for 3 hours. The reaction mixture was partially concentrated and then acidified with 1 N HCl aqueous solution, and the aqueous layer was extracted with EtOAc. The organic layer was dried over $MgSO_4$ and then concentrated under reduced pressure, and the crude product was purified by silica gel column chromatography to obtain the compound of Example 67 (3.7 mg, yield 32%). $^1H$ NMR (300 MHz, Chloroform-d) δ 7.14-7.08 (m, 2H), 6.99 (d, J=8.1 Hz, 2H), 5.30 (d, J=7.8 Hz, 1H), 4.29-4.12 (m, 1H), 3.89 (s, 2H), 3.00 (p, J=8.5 Hz, 1H), 2.52-2.45 (m, 1H), 2.42 (s, 3H), 2.40-2.35 (m, 1H), 2.33 (s, 3H), 2.31-2.27 (m, 2H), 2.26-2.21 (m, 1H), 2.18 (dd, J=10.6, 7.2 Hz, 1H), 2.06-1.96 (m, 1H), 1.82 (d, J=8.1 Hz, 3H), 1.74 (d, J=13.0 Hz, 2H), 1.47-1.31 (m, 6H), 1.30-1.22 (m, 1H). LC/MS (ESI) m/z: 466.43 $[M+H]^+$, 464.54 $[M+H]^-$.

Example 68: 6-(2,5-dimethyl-4-(4-(piperidin-4-yl)benzyl)thiophene-3-carboxamido)spiro[3.3]heptane-2-carboxylic acid Steps 1 to 3: Synthesis of 6-(4-(4-(1-(tert-butoxycarbonyl)piperidin-4-yl)benzyl)-2,5-dimethylthiophene-3-carboxamido)spiro[3.3]heptane-2-carboxylic acid

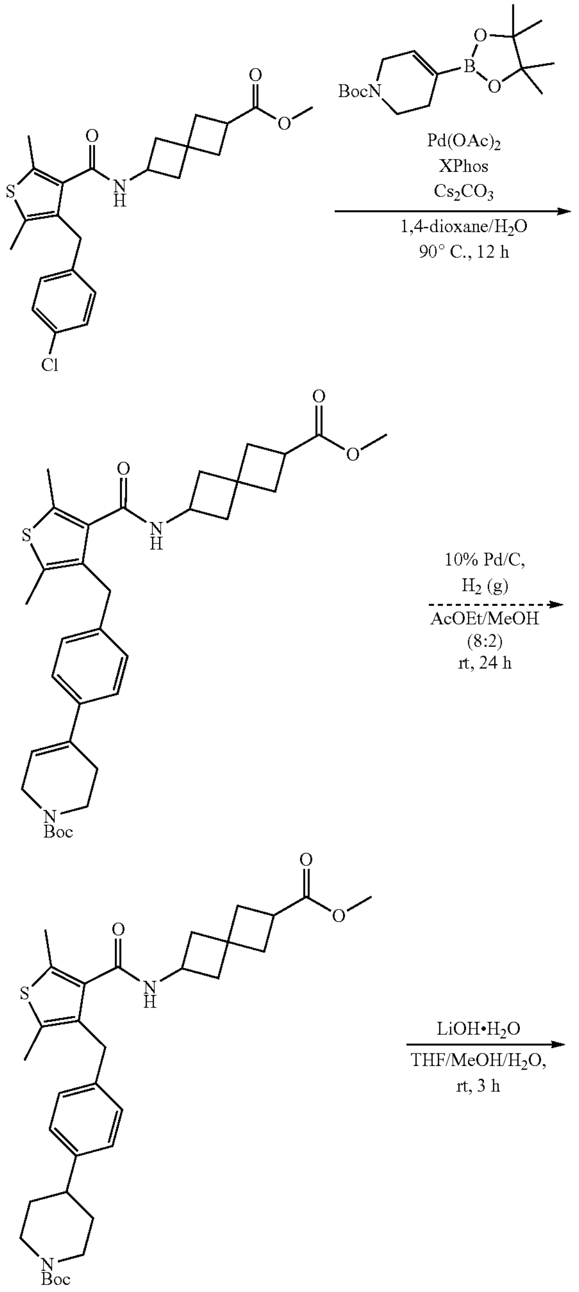

-continued

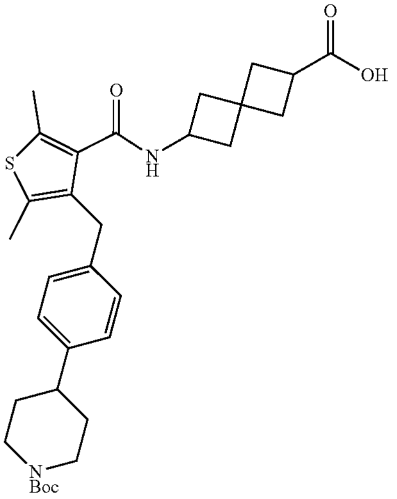

6-(4-(4-(1-(tert-butoxycarbonyl)piperidin-4-yl)benzyl)-2,5-dimethylthiophene-3-carboxamido)spiro[3.3]heptane-2-carboxylic acid was obtained as an ivory solid in the same manner as in Example 67, except that tert-butyl 4-(4,4,5,5-tetramethyl-1,3,2-dioxaborolan-2-yl)-3,6-dihydropyridine-1(2H)-carboxylat e was used instead of 2-(cyclohex-1-en-1-yl)-4,4,5,5-tetramethyl-1,3,2-dioxaborolane in Step 1 of Example 67. $^{1}$H NMR (400 MHz, Chloroform-d) δ 7.13 (s, 2H), 7.06-7.01 (m, 2H), 5.34-5.29 (m, 1H), 4.30-4.20 (m, 3H), 3.91 (s, 2H), 3.05-2.96 (m, 1H), 2.86-2.74 (m, 2H), 2.69-2.59 (m, 1H), 2.43 (s, 3H), 2.41-2.38 (m, 1H), 2.35 (s, 3H), 2.33-2.27 (m, 4H), 2.15-2.09 (m, 1H), 1.82-1.76 (m, 2H), 1.67-1.54 (m, 4H), 1.50 (s, 9H).

Step 4: Synthesis of 6-(2,5-dimethyl-4-(4-(piperidin-4-yl)benzyl)thiophene-3-carboxamido)spiro[3.3]heptane-2-carboxylic acid

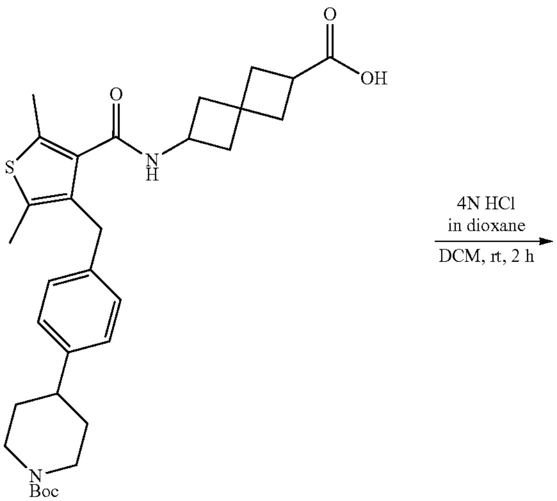

-continued

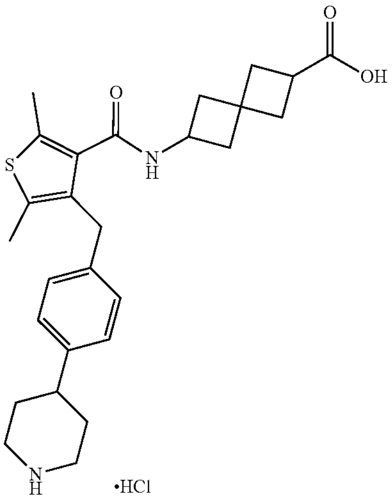

68

A solution of 6-(4-(4-(1-(tert-butoxycarbonyl)piperidin-4-yl)benzyl)-2,5-dimethyl thiophene-3-carboxamido)spiro[3.3]heptane-2-carboxylic acid (14 mg, 0.024 mmol) and 4 N HCl in dioxane (0.5 mL) was stirred for 2 hours. The reaction mixture was poured into ether and concentrated under reduced pressure to obtain the hydrochloride salt of the compound of Example 68 (4 mg, 33%) as an ivory solid. $^{1}$H NMR (500 MHz, Methanol-$d_4$) δ 7.15-7.08 (m, 2H), 7.04-6.98 (m, 2H), 4.16-4.09 (m, 1H), 3.86 (s, 2H), 3.49-3.44 (m, 2H), 3.16-3.08 (m, 2H), 3.03-2.97 (m, 1H), 2.86-2.79 (m, 1H), 2.41-2.35 (m, 2H), 2.33 (s, 3H), 2.30 (s, 3H), 2.26-2.20 (m, 2H), 2.17-2.12 (m, 1H), 2.12-2.06 (m, 1H), 2.03-1.98 (m, 2H), 1.93-1.81 (m, 3H), 1.77-1.70 (m, 1H). LC/MS (ESI) m/z: 465.7 $[M-H]^-$.

Example 69: 6-(4-((4'-fluoro-[1,1'-biphenyl]-4-yl)methyl)-2,5-dimethylthiophene-3-carboxamido)spiro[3.3]heptane-2-carboxylic acid

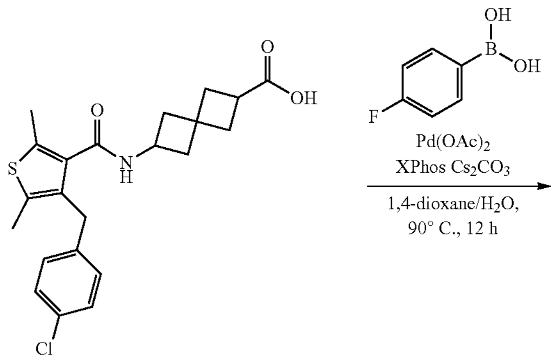

23

-continued

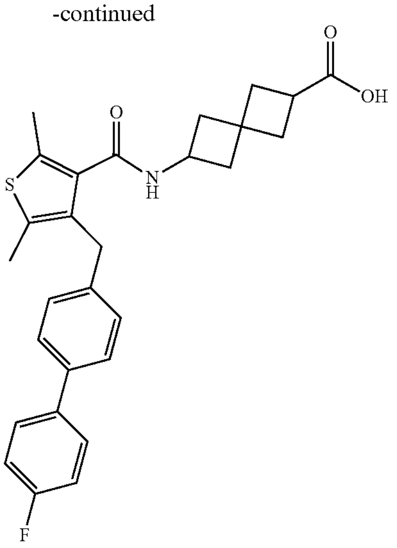

69

A solution of the compound of Example 23 (30 mg, 0.069 mmol) and 4-fluoroboronic acid (12 mg, 0.083 mmol) in 1,4-dioxane (0.2 mL) was placed in a sealed tube, and $H_2O$ (0.01 mL) and $Cs_2CO_3$ (45 mg, 0.138 mmol) were added. $Pd(OAc)_2$ (2 mg, 0.007 mmol) and Xphos (33 mg, 0.069 mmol) were added under $N_2$ atmosphere and stirred at 90° C. for 12 hours. The reaction mixture was diluted with ethyl acetate, washed with distilled water, dried over $Na_2SO_4$, then filtered, and concentrated. The crude product was purified using a silica column (hexane:ethyl acetate=1:1) to obtain the compound of Example 69 (3 mg, yield 12%) as an ivory solid. $^1H$ NMR (500 MHz, Chloroform-d) δ 7.55-7.49 (m, 2H), 7.48-7.45 (m, 2H), 7.19-7.17 (m, 2H), 7.17-7.12 (m, 2H), 5.46-5.35 (m, 1H), 4.33-4.25 (m, 1H), 3.99 (s, 2H), 3.04-2.96 (m, 1H), 2.46 (s, 3H), 2.44-2.41 (m, OH), 2.38 (s, 3H), 2.36-2.30 (m, 4H), 2.22-2.15 (m, 1H), 2.06-1.98 (m, 1H), 1.62-1.49 (m, 3H). LC/MS (ESI) m/z: 478.6 $[M+H]^+$, 476.6 $[M-H]^-$.

Example 70: 6-(4-((3'-cyano-5'-fluoro-[1,1'-biphenyl]-4-yl)methyl)-2,5-dimethylthiophene-3-carboxamido)spiro[3.3]heptane-2-carboxylic acid

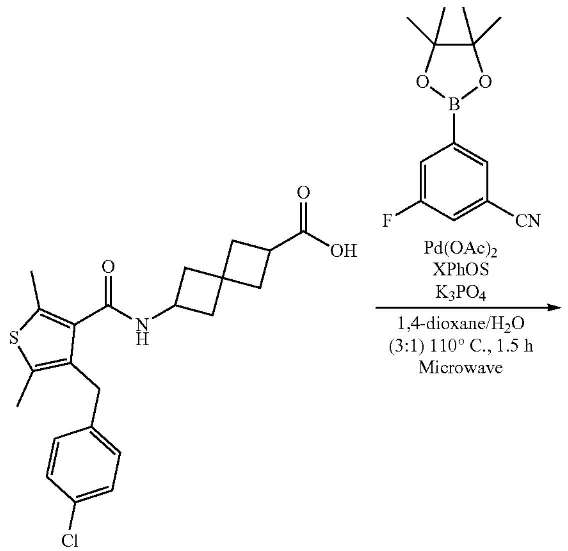

23

-continued

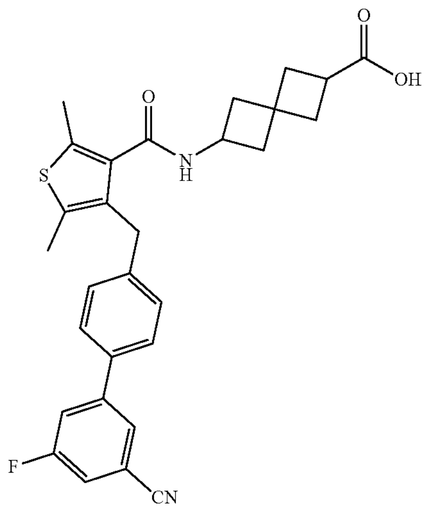

70

The compound of Example 70 was obtained in the same manner as in Example 69, except that 3-fluoro-5-(4,4,5,5-tetramethyl-1,3,2-dioxaborolan-2-yl)benzonitrile was used instead of 4-fluoroboronic acid, and $K_3PO_4$ was used instead of $Cs_2CO_3$ in Example 69. $^1H$ NMR (300 MHz, MeOD) δ 8.28 (d, J=7.5 Hz, 1H), 7.85 (t, J=1.5 Hz, 1H), 7.73 (ddd, J=10.1, 2.5, 1.6 Hz, 1H), 7.63-7.54 (m, 2H), 7.52 (ddd, J=8.1, 2.5, 1.3 Hz, 1H), 7.23 (d, J=8.2 Hz, 2H), 4.22-4.08 (m, 1H), 3.99 (s, 2H), 2.95 (p, J=8.4 Hz, 1H), 2.49-2.38 (m, 1H), 2.39 (s, 3H), 2.37 (s, 3H), 2.35-2.20 (m, 3H), 2.19-2.10 (m, 1H), 2.09-1.99 (m, 1H), 1.87-1.70 (m, 2H). LC/MS (ESI) m/z: 503.02 $[M+H]^+$.

Example 71: 6-(4-((3'-fluoro-5'-hydroxy-[1,1'-biphenyl]-4-yl)methyl)-2,5-dimethylthiophene-3-carboxamido)spiro[3.3]heptane-2-carboxylic acid Step 1: Synthesis of methyl 6-(4-((3'-fluoro-5'-methoxy-[1,1'-biphenyl]-4-yl)methyl-2,5-dimethylthiophene-3-carboxamido)spiro[3.3]heptane-2-carboxylate

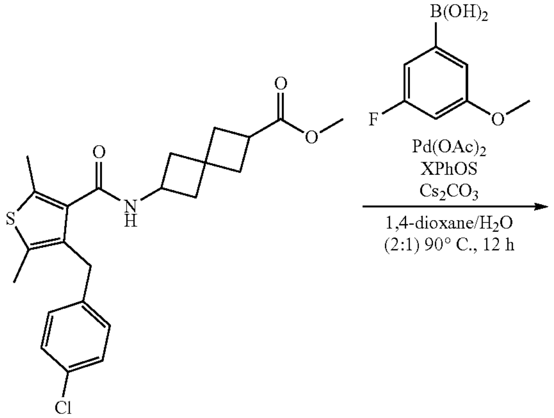

-continued

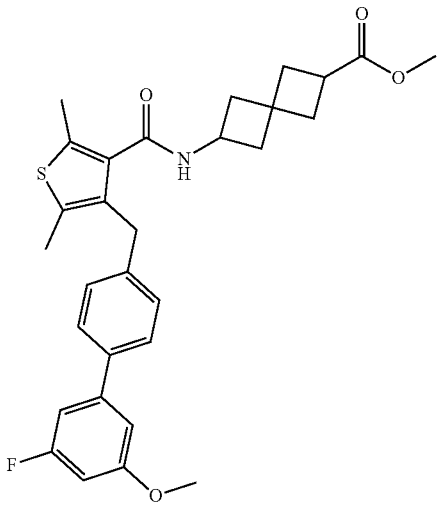

Methyl 6-(4-((3'-fluoro-5'-methoxy-[1,1'-biphenyl]-4-yl)methyl)-2,5-dimethylthiophene-3-carboxamido)spiro[3.3]heptane-2-carboxylate was obtained in the same manner as in Step 1 of Example 67, except that (3-fluoro-5-methoxyphenyl)boronic acid was used instead of 2-(cyclohex-1-en-1-yl)-4,4,5,5-tetramethyl-1,3,2-dioxaborolane in Step 1 of Example 67. $^1$H NMR (400 MHz, $CDCl_3$) δ 7.50-7.46 (m, 2H), 7.18 (d, J=8.2 Hz, 2H), 7.01 (d, J=5.4 Hz, 1H), 6.89 (q, J=2.1, 1.7 Hz, 1H), 6.62 (dt, J=10.5, 2.3 Hz, 1H), 5.39 (d, J=7.8 Hz, 1H), 4.28 (q, J=8.1 Hz, 1H), 3.99 (s, 2H), 3.87 (s, 3H), 3.66 (s, 3H), 3.03-2.95 (m, 1H), 2.45 (s, 3H), 2.37 (s, 3H), 2.30 (dq, J=8.6, 4.2, 3.4 Hz, 3H), 2.18 (dd, J=11.7, 8.4 Hz, 1H), 2.02-1.97 (m, 1H), 1.58-1.51 (m, 2H).

Step 2: Synthesis of 6-(4-((3'-fluoro-5'-hydroxy-[1,1'-biphenyl]-4-yl)methyl)-2,5-dimethylthiophene-3-carboxamido)spiro[3.3]heptane-2-carboxylic acid

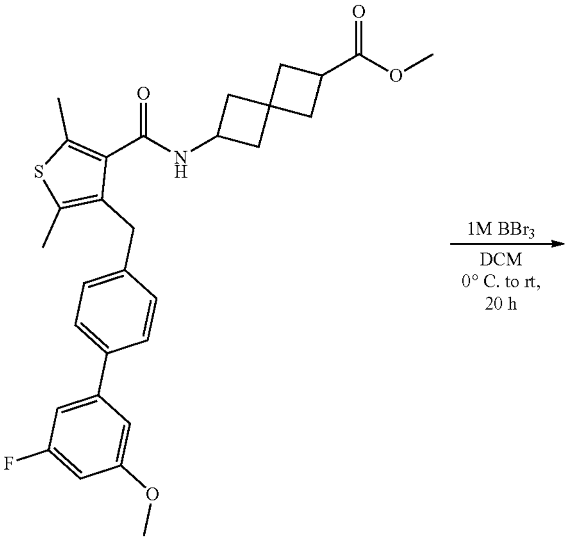

-continued

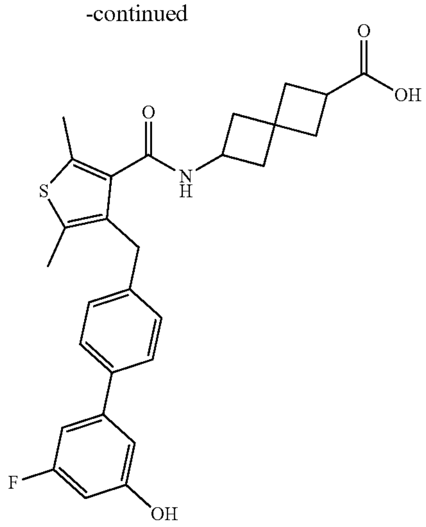

71

To a solution of methyl 6-(4-((3'-fluoro-5'-methoxy-[1,1'-biphenyl]-4-yl)methyl)-2,5-dimethylthiophene-3-carboxamido)spiro[3.3]heptane-2-carboxylate (94 mg, 0.18 mmol) in DCM (0.1 M), $BBr_3$ (0.7 mL, 0.72 mmol) was added at 0° C. and stirred at ambient temperature for 5 hours. The reaction mixture was quenched with distilled water, further stirred for 15 hours, then extracted with ethyl acetate (2×20 mL), and washed with brine. The organic layer was dried over $Na_2SO_4$, filtered, and then concentrated under reduced pressure. The crude product was purified by column chromatography (5% MeOH in DCM) to obtain the compound of Example 71 (22 mg, yield 25%) as an off-white solid. $^1$H NMR (500 MHz, $CDCl_3$)$^1$H NMR (400 MHz, Chloroform-d) δ 7.41 (d, J=7.8 Hz, 2H), 7.14 (d, J=8.0 Hz, 2H), 6.88 (t, J=1.9 Hz, 1H), 6.83-6.75 (m, 1H), 6.62-6.54 (m, 1H), 5.40-5.26 (m, 1H), 4.24 (h, J=8.1 Hz, 1H), 3.98 (s, 2H), 3.02 (p, J=7.5 Hz, 1H), 2.49-2.27 (m, 3H), 2.41 (s, 3H), 2.40 (s, 3H), 2.17-2.08 (m, 2H), 1.60 (dd, J=12.1, 8.1 Hz, 1H), 1.38-1.22 (m, 2H). LC/MS (ESI) m/z: 494.1 $[M+H]^+$.

Example 72: 6-(4-(4-(2-hydroxypyridin-4-yl)benzyl)-2,5-dimethylthiophene-3-carboxamido)spiro[3.3]heptane-2-carboxylic acid Steps 1 and 2: Synthesis of methyl 6-(4-(4-(2-hydroxypyridin-4-yl)benzyl)-2,5-dimethylthiophene-3-carboxamido)spiro[3,3]heptane-2-carboxylate

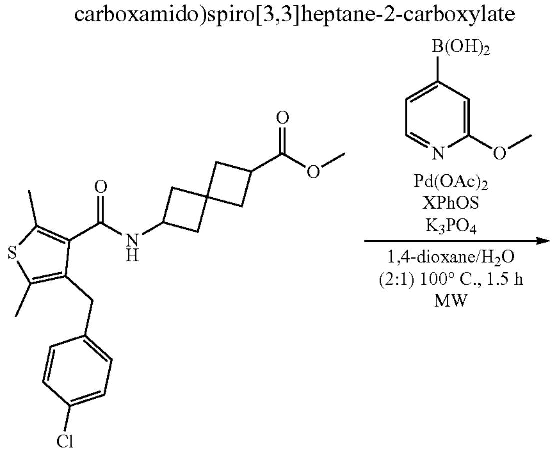

-continued

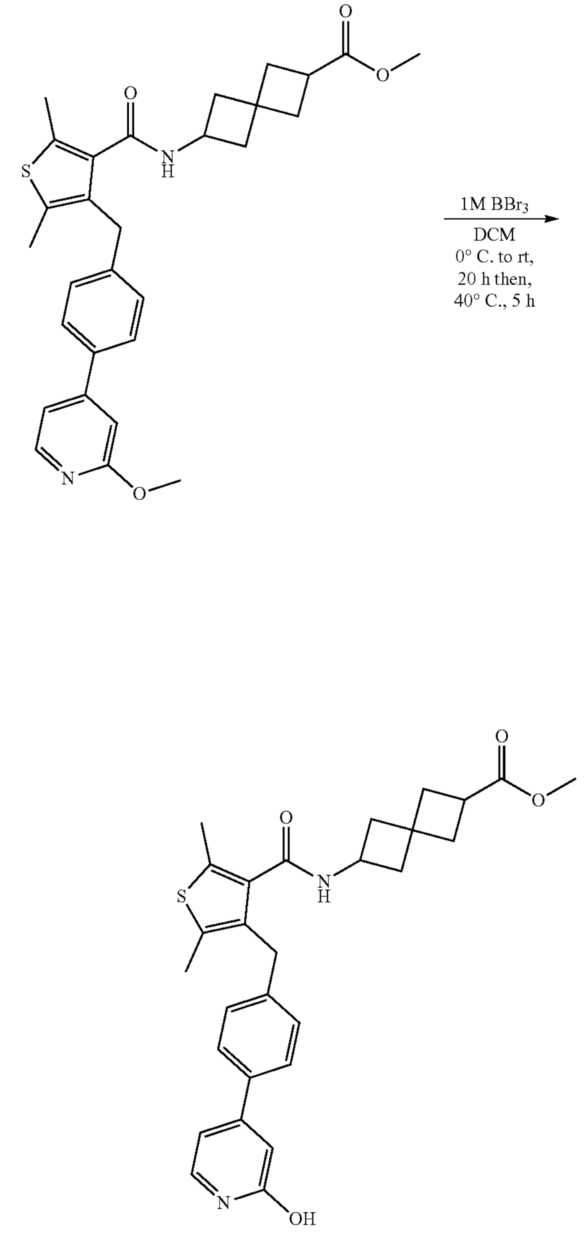

Methyl 6-(4-(4-(2-hydroxypyridin-4-yl)benzyl)-2,5-dimethylthiophene-3-carboxamido) spiro[3.3]heptane-2-carboxylate was obtained in the same manner as in Example 71, except that (2-methoxypyridin-4-yl)boronic acid was used instead of (3-fluoro-5-methoxyphenyl)boronic acid, and $K_3PO_4$ was used instead of $Cs_2CO_3$ in Step 1 of Example 71.

Step 3: Synthesis of 6-(4-(4-(2-hydroxypyridin-4-yl)benzyl)-2,5-dimethylthiophene-3-carboxamido) spiro[3,3]heptane-2-carboxylic acid

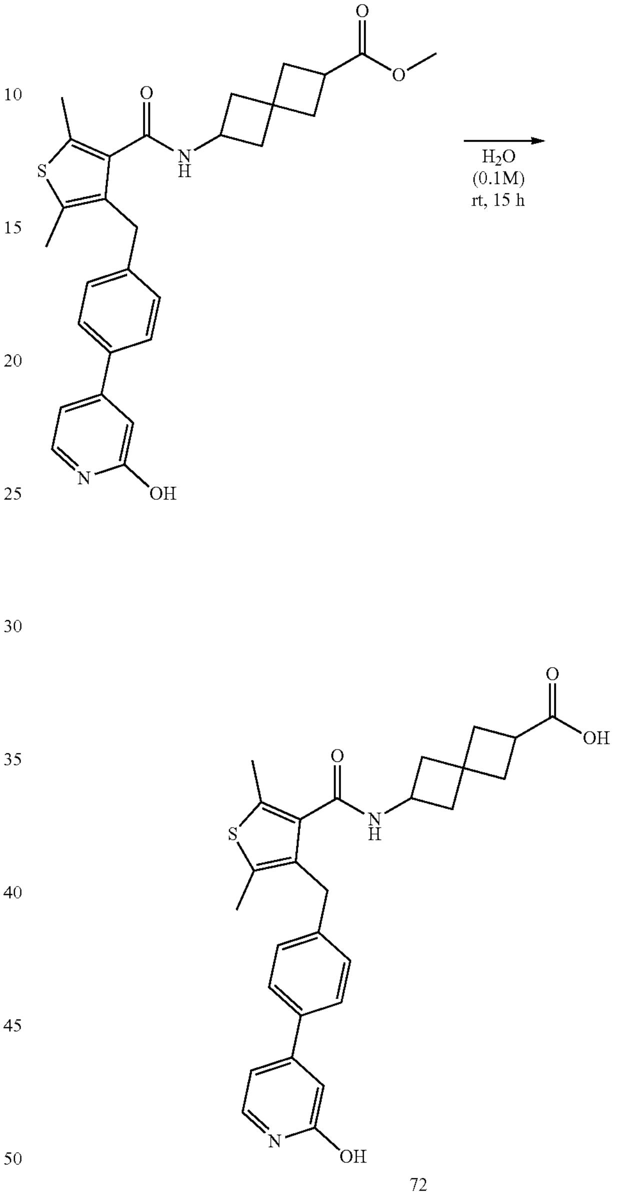

72

A solution of methyl 6-(4-(4-(2-hydroxypyridin-4-yl)benzyl)-2,5-dimethylthiophene-3-carboxamido)spiro[3,3]heptane-2-carboxylate in $H_2O$ (0.1 M) was stirred for 15 hours. The precipitated solid was filtered and dried to obtain the crude product, which was then purified by column chromatography (15% MeOH in DCM) to obtain the compound of Example 72 as an off-white solid. $^1H$ NMR (300 MHz, MeOD) δ 8.25 (d, J=7.4 Hz, 1H), 7.61-7.54 (m, 2H), 7.51 (d, J=7.6 Hz, 1H), 7.22 (d, J=8.2 Hz, 2H), 6.78-6.69 (m, 2H), 4.21-4.08 (m, 1H), 3.99 (s, 2H), 2.96 (p, J=8.4 Hz, 1H), 2.38 (s, 6H), 2.32-1.98 (m, 6H), 1.76 (ddd, J=17.0, 11.4, 8.6 Hz, 2H); LC/MS (ESI) m/z: 477.16 $[M+H]^+$.

Example 73: 6-(4-([1,1'-biphenyl]-4-ylmethyl)-N,2,5-trimethylthiophene-3-carboxamido)spiro[3.3]heptane-2-carboxylic acid Step 1: Synthesis of 3-([1,1'-biphenyl]-4-ylmethyl)-4-bromo-2,5-dimethylthiophene

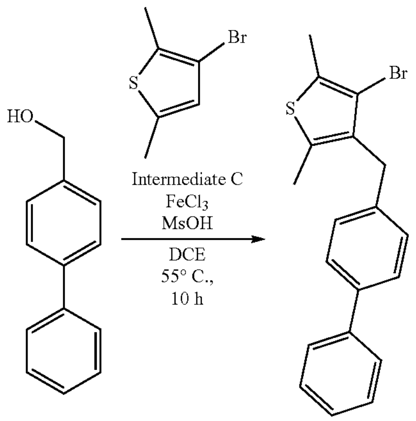

To a solution of [1,1'-biphenyl]-4-ylmethanol (553 mg, 3.0 mmol) in DCE (0.5 M), 3-bromo-2,5-dimethylthiophene (918 mg, 4.80 mmol), $FeCl_3$ (195 mg, 1.20 mmol) and MsOH (78 µL, 1.20 mmol) were added and stirred at 55° C. for 10 hours. Ethyl acetate was added to the reaction mixture and washed with distilled water and brine, and then the organic layer was dried over $Na_2SO_4$ and concentrated under reduced pressure. The crude product was purified by column chromatography (hexane) to obtain 3-([1,1'-biphenyl]-4-ylmethyl)-4-bromo-2,5-dimethylthiophene (466 mg, yield 43%) as a white solid. $^1$H NMR (500 MHz, chloroform-d) δ 7.61-7.57 (m, 2H), 7.52 (m, 2H), 7.44 (t, J=7.7 Hz, 2H), 7.39-7.31 (m, 1H), 7.24 (d, J=7.9 Hz, 2H), 4.00 (s, 2H), 2.41 (s, 3H), 2.40 (s, 3H).

Step 2: Synthesis of 4-([1,1'-biphenyl]-4-ylmethyl)-2,5-dimethylthiophene-3-carboxylic acid

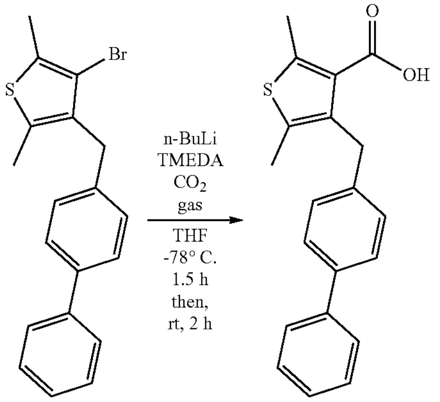 [SMILES: Cc1sc(C)c(Cc2ccc(-c3ccccc3)cc2)c1Br ; Cc1sc(C)c(C(=O)O)c1Cc1ccc(-c2ccccc2)cc1]

To a solution of 3-([1,1'-biphenyl]-4-ylmethyl)-4-bromo-2,5-dimethylthiophene (169 mg, 0.47 mmol) and TMEDA (78 µL, 0.52 mmol) in THF (0.1 M), n-BuLi (0.228 mL, 0.57 mmol) was added at −78° C. and stirred for 1.5 hours. The reaction mixture was quenched with $CO_2$ gas at −78° C. and then slowly warmed to room temperature over 2 hours. It was acidified with 1 N HCl solution, extracted with ethyl acetate, and washed with water. The organic layer was dried over $Na_2SO_4$ and concentrated under reduced pressure. The crude product was purified by column chromatography (hexane) to obtain 4-([1,1'-biphenyl]-4-ylmethyl)-2,5-dimethylthiophene-3-carboxylic acid (56 mg, yield 37%) as a white solid.

Step 3: Synthesis of methyl 6-(4-([1,1'-biphenyl]-4-ylmethyl)-N,2,5-trimethylthiophene-3-carboxamido) spiro[3.3]heptane-2-carboxylate

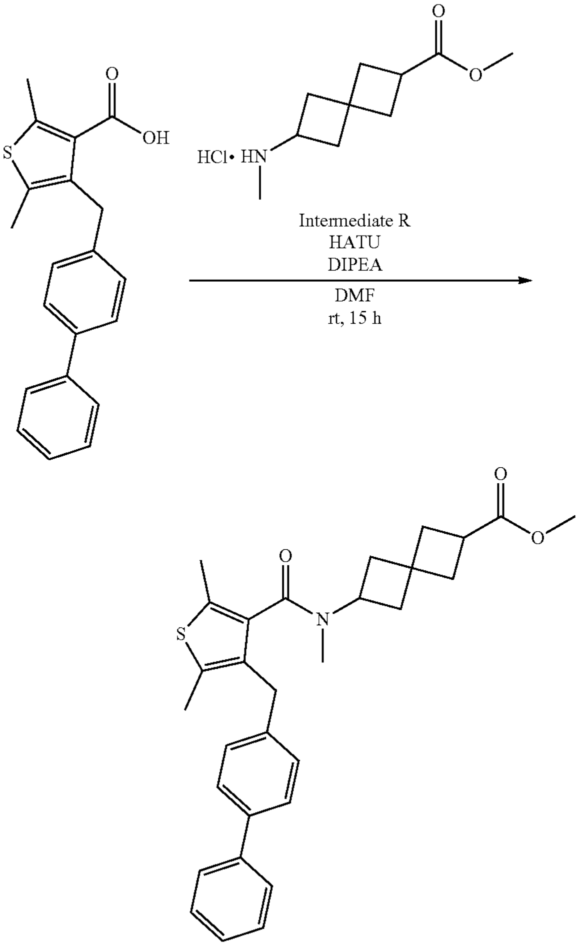

To a solution of 4-([1,1'-biphenyl]-4-ylmethyl)-2,5-dimethylthiophene-3-carboxylic acid (52 mg, 0.16 mmol) and HATU (68 mg, 0.18 mmol) in DMF (0.05 M), DIPEA (84 µL, 0.48 mmol) was added and stirred for 10 minutes, and Intermediate R (39 mg, 0.18 mmol) was added and stirred for 15 hours. The reaction mixture was diluted with ethyl acetate and washed with distilled water and brine. The organic layer was dried over $Na_2SO_4$, concentrated under reduced pressure, and then purified by column chromatography (20% EtOAc in hexane) to obtain methyl 6-(4-([1,1'-biphenyl]-4-ylmethyl)-N,2,5-trimethylthiophene-3-carboxamido)spiro[3.3]heptane-2-carboxylate (47 mg, yield 59%) as a white solid.

Step 4: Synthesis of 6-(4-([1,1'-biphenyl]-4-ylmethyl)-N,2,5-trimethylthiophene-3-carboxamido) spiro[3.3]heptane-2-carboxylic acid

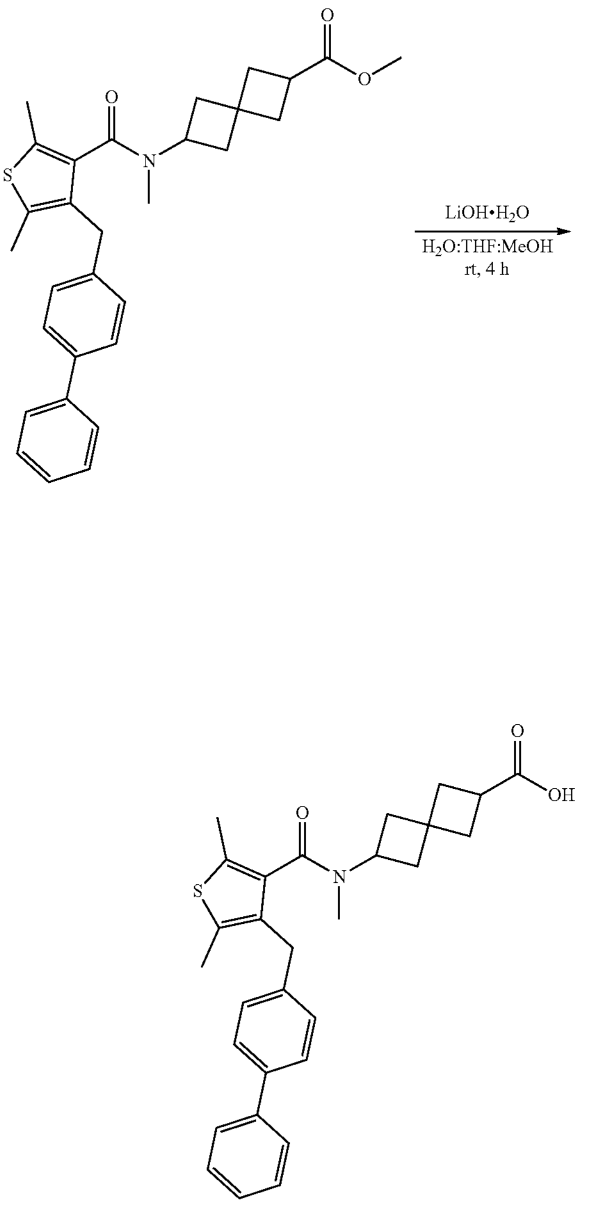

73

To a stirred solution of methyl 6-(4-([1,1'-biphenyl]-4-ylmethyl)-N,2,5-trimethylthiophene-3-carboxamido)spiro[3.3]heptane-2-carboxylate (47 mg, 0.1 mmol) in $H_2O$:THF:MeOH (0.1 M), $LiOH \cdot H_2O$ (12 mg, 0.3 mmol) was added and stirred for 4 hours. The reaction mixture was partially concentrated under reduced pressure, acidified with 2 N HCl aqueous solution (pH ~6), and extracted with ethyl acetate (2×30 mL). The organic layer was dried over $Na_2SO_4$, concentrated under reduced pressure, and then purified by column chromatography (70% EtOAc in hexane) to obtain the compound of Example 73 (36 mg, yield 79%) as a white solid. LC/MS (ESI) m/z: 474.25 $[M+H]^+$.

Example 74: 6-(4-([1,1'-biphenyl]-4-yloxy)-2,5-dimethylthiophene-3-carboxamido)spiro[3.3]heptane-2-carboxylic acid Step 1: Synthesis of methyl 4-([1,1'-biphenyl]-4-yloxy)-2,5-dimethylthiophene-3-carboxylate

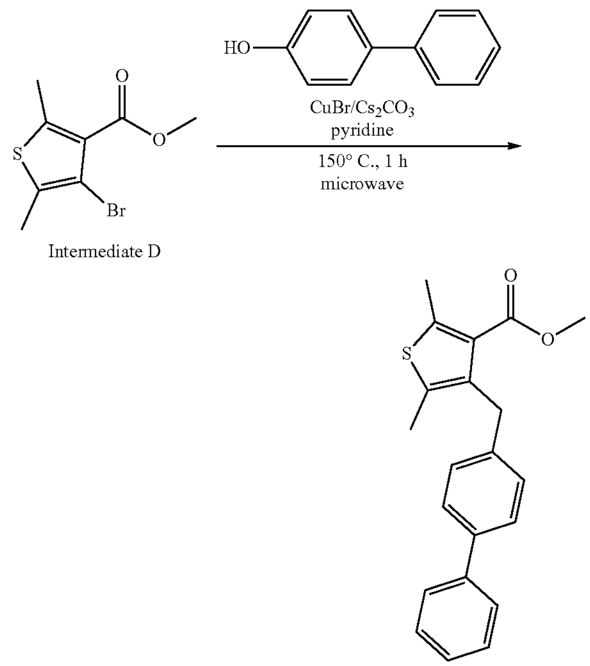

A solution of Intermediate D (996 mg, 4.0 mmol), 4-phenylphenol (817 mg, 4.8 mmol, 1.2 equiv), CuBr (115 mg, 0.8 mmol, 0.2 equiv) and $Cs_2CO_3$ (3.9 g, 12.0 mmol, 3.0 equiv) in pyridine (8 mL) was irradiated with microwave and stirred at 150° C. for 1 hour. The reaction mixture was filtered through Celite, added to distilled water, and extracted with EtOAc, and then the organic layer was dried over $MgSO_4$ and then concentrated under reduced pressure. The crude product was purified by column chromatography to obtain methyl 4-([1,1'-biphenyl]-4-yloxy)-2,5-dimethylthiophene-3-carboxylate (550 mg, 40% yield).

Step 2: Synthesis of 4-([1,1'-biphenyl]-4-yloxy)-2,5-dimethylthiophene-3-carboxylic acid

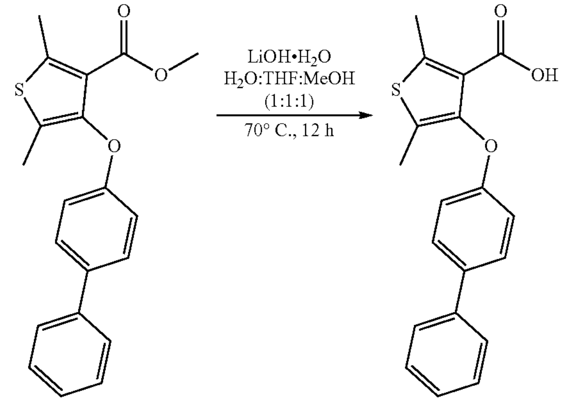 [SMILES: COC(=O)c1c(C)sc(C)c1Oc1ccc(-c2ccccc2)cc1 ; "LiOH·H2OH2O:THF:MeOH(1:1:1)" ; Cc1sc(C)c(C(=O)O)c1Oc1ccc(-c2ccccc2)cc1]

To a solution of methyl 4-([1,1'-biphenyl]-4-yloxy)-2,5-dimethylthiophene-3-carboxylate (550 mg, 1.62 mmol) in THF/MeOH/$H_2O$ (1:1:1), LiOH·$H_2O$ (340 mg, 8.12 mmol, 5.0 equiv) was added, and the reaction mixture was stirred at 70° C. for 12 hours. The reaction mixture was partially concentrated and then acidified with 1 N HCl, and then the aqueous layer was extracted with DCM. The organic layer was dried over $MgSO_4$, then concentrated under reduced pressure, and purified by column chromatography to obtain 4-([1,1'-biphenyl]-4-yloxy)-2,5-dimethylthiophene-3-carboxylic acid (100 mg, yield 19%).

Step 3: Synthesis of methyl 6-(4-([1,1'-biphenyl]-4-yloxy)-2,5-dimethylthiophene-3-carboxamido)spiro[3.3]heptane-2-carboxylate

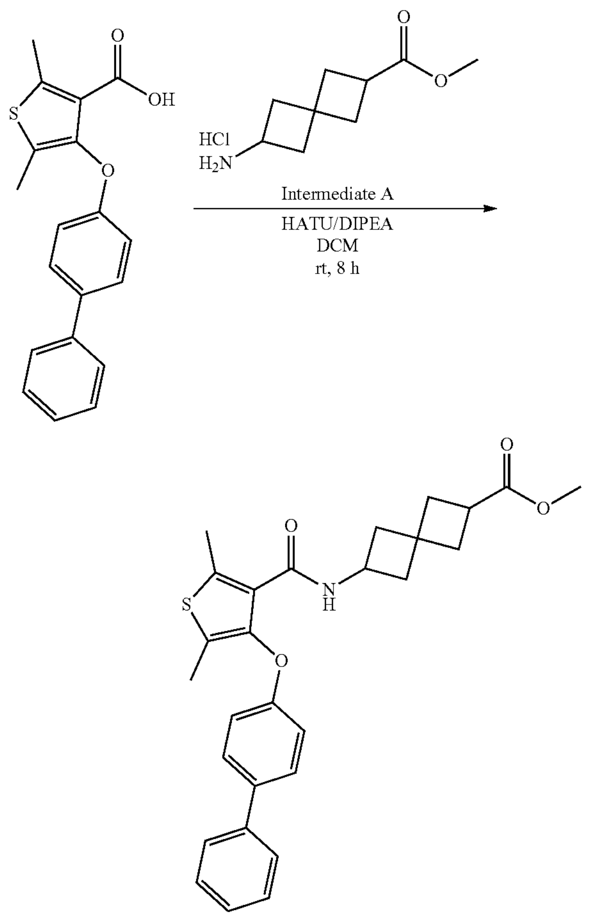

To a solution of 4-([1,1'-biphenyl]-4-yloxy)-2,5-dimethylthiophene-3-carboxylic acid (100 mg, 0.3 mmol) and HATU (137 mg, 0.36 mmol, 1.2 equiv) in DCM (2 mL), DIPEA (80 μL, 0.45 mmol, 1.5 equiv) was added at 0° C. and stirred for 15 minutes. A solution of Intermediate A (68 mg, 0.33 mmol, 1.1 equiv) in DCM (1 mL) was added to the reaction mixture and then stirred for 8 hours. The reaction mixture was added to distilled water and extracted with DCM. The organic layer was dried over $MgSO_4$ and then concentrated under reduced pressure. The crude product was purified by column chromatography to obtain methyl 6-(4-([1,1'-biphenyl]-4-yloxy)-2,5-dimethylthiophene-3-carboxamido)spiro[3.3]heptane-2-carboxylate (50 mg, 34% yield).

Step 4: Synthesis of 6-(4-([1,1'-biphenyl]-4-yloxy)-2,5-dimethylthiophene-3-carboxamido)spiro[3.3]heptane-2-carboxylic acid

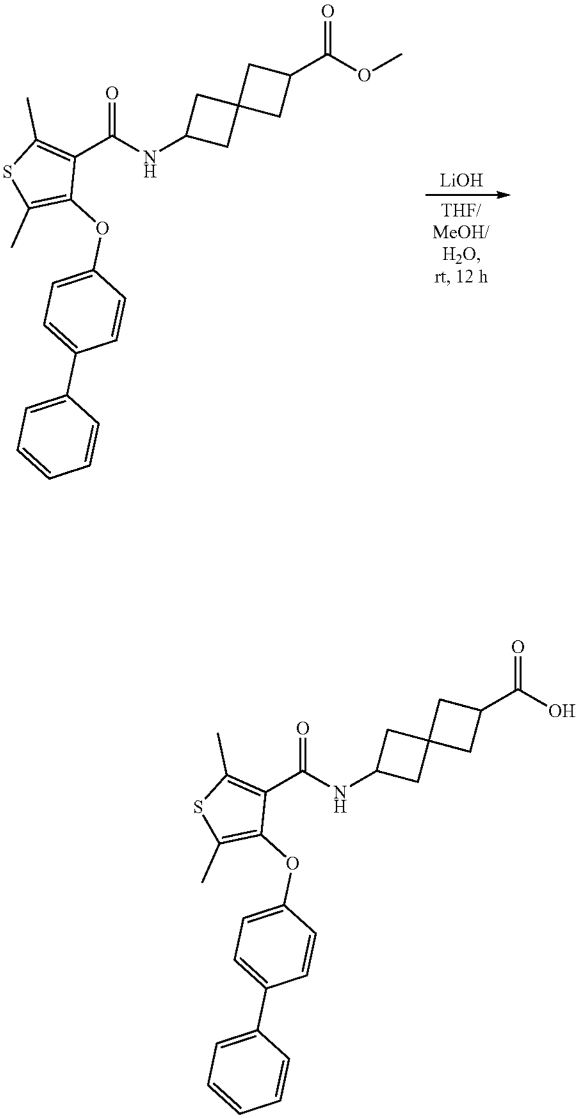

74

To a solution of methyl 6-(4-([1,1'-biphenyl]-4-yloxy)-2,5-dimethylthiophene-3-carboxamido)spiro[3.3]heptane-2-carboxylate (50 mg, 0.5 mmol) in THF/MeOH/$H_2O$ (1:1:1), LiOH·$H_2O$ (13 mg, 0.3 mmol, 3.0 equiv) was added and stirred for 12 hours. The reaction mixture was partially concentrated, then acidified with 1 N HCl, and extracted with EtOAc. The organic layer was dried over $MgSO_4$ and then concentrated under reduced pressure. The crude product was purified by column chromatography to obtain the compound of Example 74 (22 mg, yield 47%). $^1H$ NMR (300 MHz, methanol-$d_4$) δ 7.60-7.49 (m, 4H), 7.46-7.34 (m, 2H), 7.34-7.23 (m, 1H), 6.98-6.87 (m, 2H), 4.12-3.96 (m, 1H), 2.96-2.85 (m, 1H), 2.52 (s, 3H), 2.36-2.28 (m, 1H), 2.25-2.18 (m, 5H), 2.18-1.95 (m, 3H), 1.75-1.65 (m, 2H). LC/MS (ESI) m/z: 462.5 $[M+H]^+$.

Example 75: 6-(4-([1,1'-biphenyl]-4-ylamino)-2,5-dimethylthiophene-3-carboxamido)spiro[3.3]heptane-2-carboxylic acid Step 1: Synthesis of methyl 4-amino-2,5-dimethylthiophene-3-carboxylate

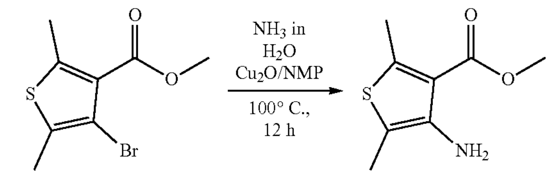

Intermediate D

To a solution of Intermediate D (1.25 g, 5.0 mmol, 1.0 equiv) and $Cu_2O$ (715 mg, 5.0 mmol, 1.0 equiv) in NMP (10 mL), $NH_3$ in $H_2O$ (5 mL) was added, heated to 100° C., and stirred for 12 hours. The reaction mixture was added to distilled water and extracted with DCM. The organic layer was dried over $MgSO_4$ and then concentrated under reduced pressure. The crude product was purified by column chromatography to obtain methyl 4-amino-2,5-dimethylthiophene-3-carboxylate (182 mg, yield 19%).

Step 2: Synthesis of methyl 4-([1,1'-biphenyl]-4-ylamino)-2,5-dimethylthiophene-3-carboxylate

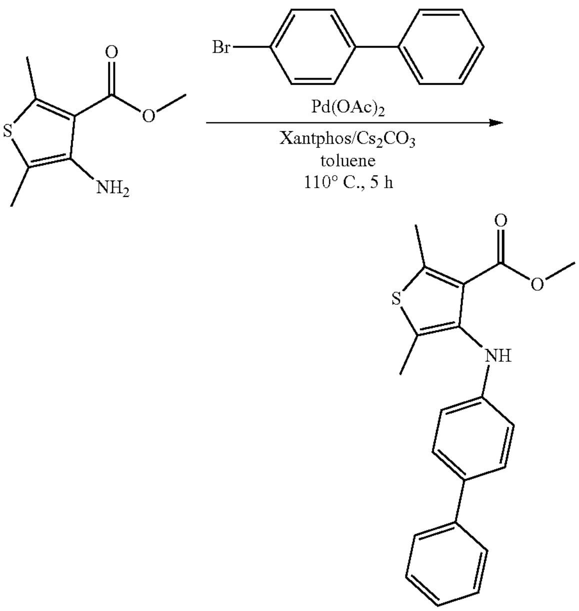

A solution of methyl 4-amino-2,5-dimethylthiophene-3-carboxylate (182 mg, 0.98 mmol), 4-bromobiphenyl (274 mg, 1.18 mmol, 1.2 equiv), $Pd(OAc)_2$ (22 mg, 0.098 mmol, 0.1 equiv), Xantphos (114 mg, 0.196 mmol, 0.2 equiv) and $Cs_2CO_3$ (639 mg, 1.96 mol, 2.0 equiv) in toluene (7 mL) was stirred at 110° C. for 5 hours. The reaction mixture was added to distilled water and extracted with DCM. The organic layer was dried over $MgSO_4$ and then concentrated under reduced pressure. The crude product was purified by column chromatography to obtain methyl 4-([1,1'-biphenyl]-4-ylamino)-2,5-dimethylthiophene-3-carboxylate (147 mg, 44% yield).

Step 3: Synthesis of 4-([1,1'-biphenyl]-4-ylamino)-2,5-dimethylthiophene-3-carboxylic acid

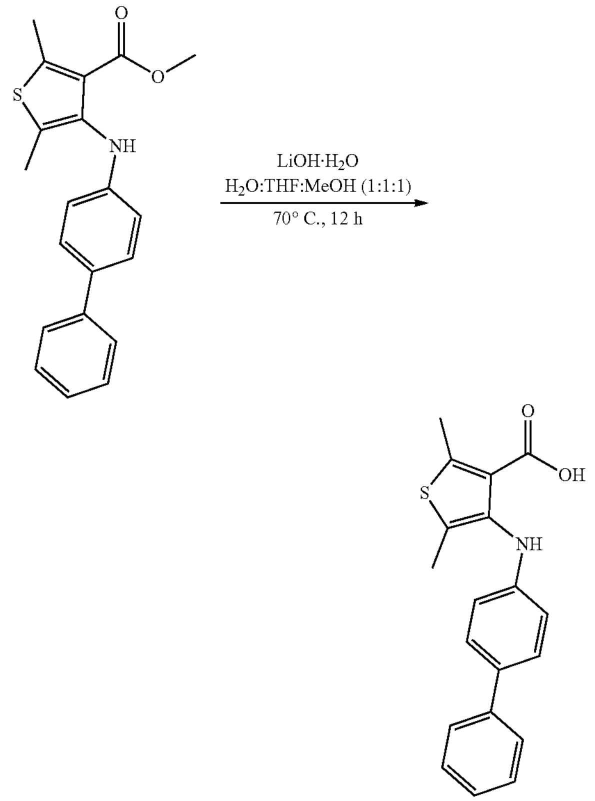

To a solution of methyl 4-([1,1'-biphenyl]-4-ylamino)-2,5-dimethylthiophene-3-carboxylate (142 mg, 0.42 mmol) in THF/MeOH/$H_2O$ (1:1:1), LiOH·$H_2O$ (53 mg, 1.26 mmol, 3.0 equiv) was added and stirred at 70° C. for 12 hours. The reaction mixture was partially concentrated and then acidified with 1 N HCl. The precipitated solid was removed by filtration, washed with distilled water, and then dried to obtain 4-([1,1'-biphenyl]-4-ylamino)-2,5-dimethylthiophene-3-carboxylic acid (135 mg, yield 99%).

Step 4: Synthesis of methyl 6-(4-([1,1'-biphenyl]-4-ylamino)-2,5-dimethylthiophene-3-carboxamido)spiro[3.3]heptane-2-carboxylate

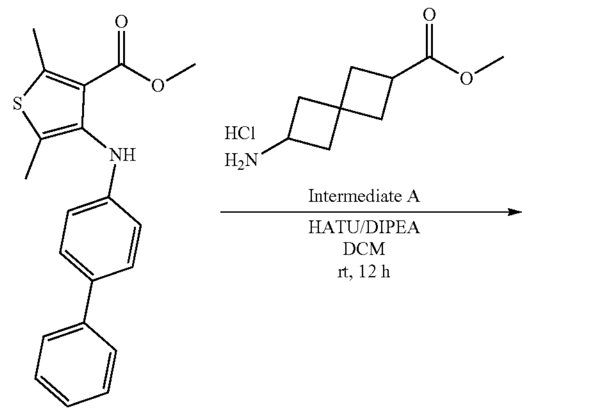

-continued

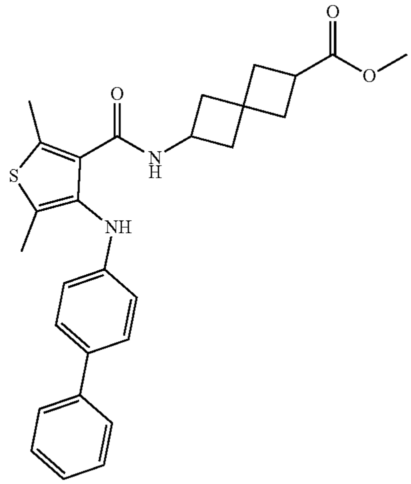

To a solution of 4-([1,1'-biphenyl]-4-ylamino)-2,5-dimethylthiophene-3-carboxylic acid (135 mg, 0.41 mmol) and HATU (186 mg, 0.49 mmol, 1.2 equiv) in DCM (2 mL), DIPEA (110 μL, 0.62 mmol, 1.5 equiv) was added at 0° C. and stirred for 15 minutes. A solution of Intermediate A (93 mg, 0.45 mmol, 1.1 equiv) in DCM (1 mL) was added to the reaction mixture and stirred for 12 hours. The reaction mixture was added to distilled water and extracted with DCM. The organic layer was dried over $MgSO_4$ and then concentrated under reduced pressure. The crude product was purified by column chromatography to obtain methyl 6-(4-([1,1'-biphenyl]-4-ylamino)-2,5-dimethylthiophene-3-carboxamido)spiro[3.3]heptane-2-carboxylate (126 mg, 65% yield).

Step 5: Synthesis of 6-(4-([1,1'-biphenyl]-4-ylamino)-2,5-dimethylthiophene-3-carboxamido) spiro[3.3]heptane-2-carboxylic acid

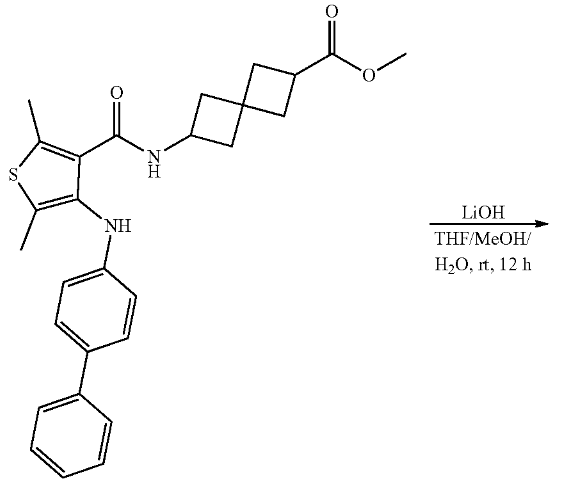

-continued

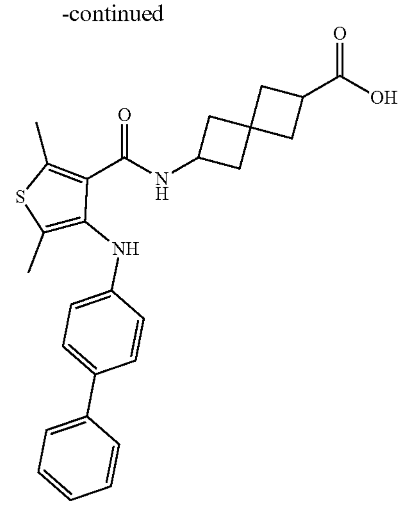

75

To a solution of methyl 6-(4-([1,1'-biphenyl]-4-ylamino)-2,5-dimethylthiophene-3-carboxamido)spiro[3.3]heptane-2-carboxylate (50 mg, 0.1 mmol) in THF/MeOH/$H_2O$ (1:1:1), $LiOH \cdot H_2O$ (13 mg, 0.3 mmol, 3.0 equiv) was added and stirred for 12 hours. The reaction mixture was partially concentrated, then acidified with 1 N HCl, and extracted with EtOAc. The organic layer was dried over $MgSO_4$ and then concentrated under reduced pressure. The crude product was purified by flash column chromatography to obtain the compound of Example 75 (20 mg, 43% yield). $^1H$ NMR (300 MHz, Methanol-$d_4$) δ 7.56-7.47 (m, 2H), 7.47-7.30 (m, 4H), 7.28-7.16 (m, 1H), 6.67 (d, J=8.6 Hz, 2H), 4.16-3.99 (m, 1H), 2.92-2.80 (m, 1H), 2.57 (s, 3H), 2.35-2.27 (m, 1H), 2.23 (s, 3H), 2.22-2.11 (m, 3H), 2.08-2.02 (m, 1H), 1.98-1.90 (m, 1H), 1.63-1.54 (m, 2H). LC/MS (ESI) m/z: 461.6 $[M+1]^+$.

Example 76: 6-(4-([1,1'-biphenyl]-4-yl(methyl)amino)-2,5-dimethylthiophene-3-carboxamido)spiro[3.3]heptane-2-carboxylic acid Step 1: Synthesis of methyl 6-(4-([1,1'-biphenyl]-4-yl(methyl)amino)-2,5-dimethylthiophene-3-carboxamido)spiro[3.3]heptane-2-carboxylate

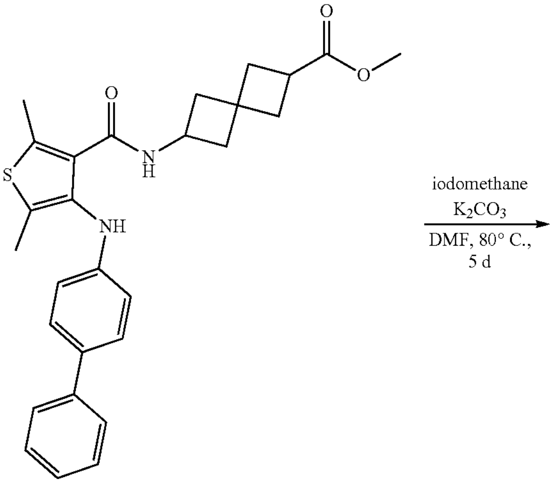

-continued

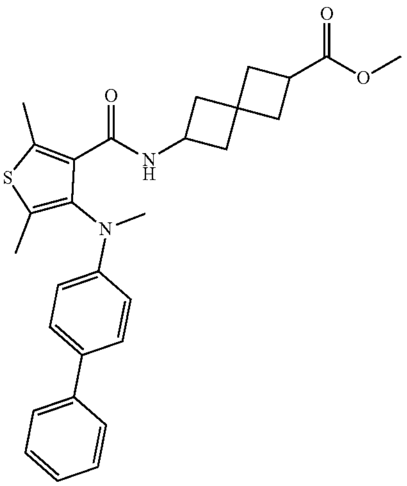

To a solution of methyl 6-(4-([1,1'-biphenyl]-4-ylamino)-2,5-dimethylthiophene-3-carboxamido)spiro[3.3]heptane-2-carboxylate (120 mg, 0.25 mmol, 1.0 equiv) obtained in Step 4 of Example 75 and $K_2CO_3$ (104 mg, 0.75 mmol, 3.0 equiv) in DMF (3 mL), iodomethane (80 μL, 1.25 mmol, 5.0 equiv) was added and stirred at 80° C. for 5 days. The reaction mixture was added to distilled water and extracted with DCM. The organic layer was dried over $MgSO_4$ and then concentrated under reduced pressure. The crude product was purified by flash column chromatography to obtain methyl 6-(4-([1,1'-biphenyl]-4-yl(methyl)amino)-2,5-dimethylthiophene-3-carboxamido)spiro[3.3]heptane-2-carboxylate (18 mg). $^1$H NMR (300 MHz, Chloroform-d) δ 7.58-7.46 (m, 4H), 7.40 (dd, J=8.4, 6.8 Hz, 2H), 7.32-7.26 (m, 1H), 6.72-6.67 (m, 2H), 4.27-4.19 (m, 1H), 3.60 (s, 3H), 3.20 (s, 3H), 2.96-2.84 (m, 1H), 2.69-2.63 (m, 3H), 2.44-2.33 (m, 1H), 2.32-2.16 (m, 3H), 2.14-2.10 (m, 3H), 2.10-2.03 (m, 1H), 1.94-1.86 (m, 1H), 1.48-1.38 (m, 2H).

Step 2: Synthesis of 6-(4-([1,1'-biphenyl]-4-yl(methyl)amino)-2,5-dimethylthiophene-3-carboxamido)spiro[3.3]heptane-2-carboxylic acid

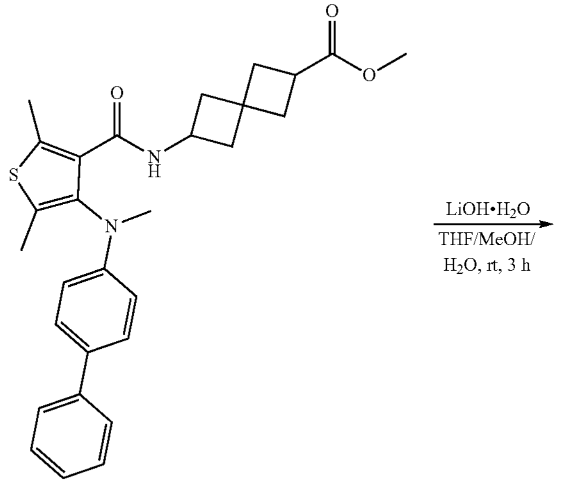

-continued

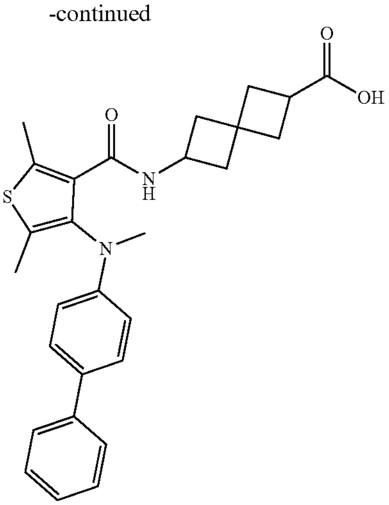

76

To a solution of methyl 6-(4-([1,1'-biphenyl]-4-yl(methyl)amino)-2,5-dimethylthiophene-3-carboxamido)spiro[3.3]heptane-2-carboxylate (18 mg, 0.036 mmol) in THF/MeOH/$H_2O$ (3/2/3 mL), $LiOH \cdot H_2O$ (5 mg, 0.108 mmol, 3.0 equiv) was added and stirred for 3 hours. The reaction mixture was partially concentrated and then acidified with 1 N HCl. The precipitated solid was filtered, washed with $H_2O$, and then dried to obtain the compound of Example 76 (12 mg). $^1$H NMR (500 MHz, Methanol-$d_4$) δ7.76 (d, J=7.2 Hz, 1H), 7.56-7.51 (m, 2H), 7.47 (d, J=8.8 Hz, 2H), 7.36 (t, J=7.8 Hz, 2H), 7.22 (t, J=7.4 Hz, 1H), 6.69 (d, J=8.7 Hz, 2H), 4.06-4.01 (m, 1H), 3.23 (s, 3H), 2.88-2.81 (m, 1H), 2.48 (s, 3H), 2.30 (dt, J=12.1, 6.1 Hz, 1H), 2.21-2.18 (m, 2H), 2.18 (s, 3H), 2.17-2.12 (m, 1H), 2.06-2.02 (m, 1H), 1.96-1.90 (m, 1H), 1.60-1.54 (m, 2H. LC/MS (ESI) m/z: 475.7 $[M+H]^+$.

Example 77: 6-(2,5-dimethyl-4-((4-phenylpiperazin-1-yl)methyl)thiophene-3-carboxamido)spiro[3.3]heptane-2-carboxylic acid

Step 1: Synthesis of 4-bromo-2,5-dimethylthiophene-3-carboxylic acid

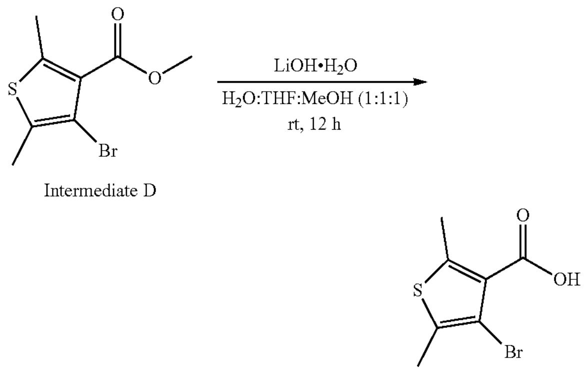

Intermediate D

To a solution of Intermediate D (2.25 g, 9.03 mmol) in $H_2O$/THF/MeOH (0.3 M, 30 mL), $LiOH \cdot H_2O$ (1.1 g, 27.1 mmol) was added and stirred for 12 hours. The reaction mixture was acidified by addition of 1 N HCl solution and extracted with EA (3×30 mL). The organic layer was dried over $MgSO_4$, filtered, concentrated, and then purified by silica gel column chromatography (n-hexane and ethyl acetate) to obtain 4-bromo-2,5-dimethylthiophene-3-carboxylic acid (1.97 g, yield 93%). $^1H$ NMR (500 MHz, DMSO-$d_6$) δ 13.06 (s, 1H), 2.55 (s, 3H), 2.32 (s, 3H).

Step 2: Synthesis of (4-bromo-2,5-dimethylthiophen-3-yl)(4-phenylpiperazin-1-yl)methanone

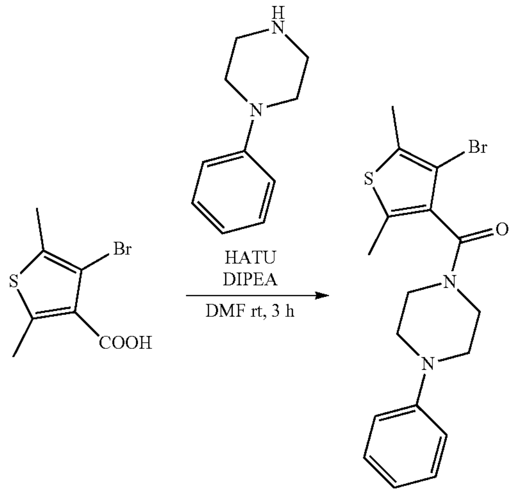 [SMILES: Cc1sc(C)c(C(=O)O)c1Br ; c1ccc(N2CCNCC2)cc1 ; Cc1sc(C)c(C(=O)N2CCN(c3ccccc3)CC2)c1Br]

To a solution of 4-bromo-2,5-dimethylthiophene-3-carboxylic acid (1.97 g, 8.4 mmol), 1-phenylpiperazine (1.4 mL, 9.24 mmol) and HATU (3.5 g, 9.24 mmol) in DMF (28 mL, 0.3 M), DIPEA (4.3 mL, 25.2 mmol) was added and stirred for 3 hours. The reaction mixture was concentrated and diluted with 1 N NaOH aqueous solution and ethyl acetate, and the aqueous layer was extracted three times with ethyl acetate. The organic layer was washed with brine, dried over $MgSO_4$, concentrated, and then purified by silica gel column chromatography (n-hexane and ethyl acetate) to obtain (4-bromo-2,5-dimethylthiophen-3-yl)(4-phenylpiperazin-1-yl)methanone (2.92 g, yield 92%). $^1H$ NMR (500 MHz, Chloroform-d) δ 7.34-7.29 (m, 2H), 6.95 (dd, J=13.9, 7.6 Hz, 3H), 4.07 (dt, J=13.0, 5.0 Hz, 1H), 3.92 (dt, J=13.0, 5.3 Hz, 1H), 3.54 (ddd, J=13.0, 6.6, 3.3 Hz, 1H), 3.45 (ddd, J=13.0, 7.2, 3.3 Hz, 1H), 3.29 (t, J=5.2 Hz, 2H), 3.24 (ddd, J=10.7, 7.2, 3.4 Hz, 1H), 3.15-3.09 (m, 1H), 2.41 (s, 3H), 2.37 (s, 3H).

Step 3: Synthesis of 1-((4-bromo-2,5-dimethylthiophen-3-yl)methyl)-5-phenylpiperazine

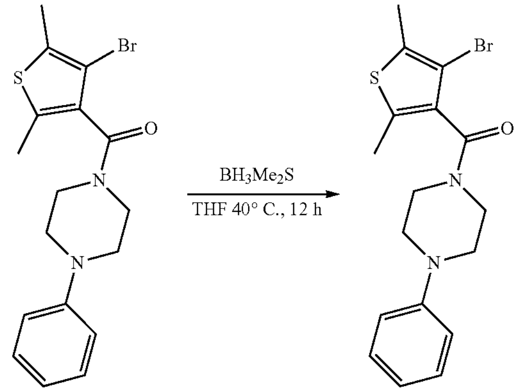 [SMILES: Cc1sc(C)c(C(=O)N2CCN(c3ccccc3)CC2)c1Br ; Cc1sc(C)c(C(=O)N2CCN(c3ccccc3)CC2)c1Br]

To a stirred solution of (4-bromo-2,5-dimethylthiophen-3-yl)(4-phenylpiperazin-1-yl)methanone (2.87 g, 7.6 mmol) and THF (19 mL, 0.4 M), $BH_3$-$Me_2S$ (19.5 mL, 39 mmol) was added and stirred at 40° C. for 12 hours. The reaction mixture was cooled to ambient temperature and extracted with $NaHCO_3$ aqueous solution (70 mL) and EA. The organic layer was dried over $Na_2SO_4$ and filtered, and then the crude product was purified by silica gel column chromatography (ethyl acetate/hexane) to obtain 1-((4-bromo-2,5-dimethylthiophen-3-yl)methyl)-5-phenylpiperazine (1.4 g, yield 51%). $^1H$ NMR (500 MHz, Chloroform-d) δ 7.30-7.26 (m, 2H), 6.94 (d, J=7.8 Hz, 2H), 6.87 (t, J=7.3 Hz, 1H), 3.49 (s, 2H), 3.21-3.16 (m, 4H), 2.67-2.63 (m, 4H), 2.46 (s, 3H), 2.38 (s, 3H).

Step 4: Synthesis of 2,5-dimethyl-4-((4-phenylpiperazin-1-yl)methyl)thiophene-3-carboxylic acid

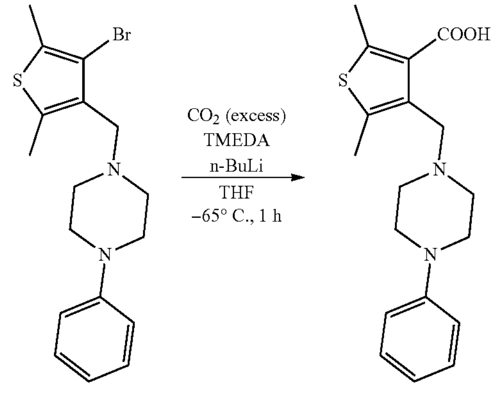 [SMILES: Cc1sc(C)c(CN2CCN(c3ccccc3)CC2)c1Br ; Cc1sc(C)c(C(=O)O)c1CN1CCN(c2ccccc2)CC1]

To a stirred solution of 1-((4-bromo-2,5-dimethylthiophen-3-yl)methyl)-5-phenylpiperazine (500 mg, 1.37 mmol), tetramethylenediamine (0.23 mL, 1.51 mmol) and THF (7.0 mL, 0.2 M), n-BuLi (2.5 M in THF, 0.72 mL, 1.8 mmol) was slowly added at −65° C. and stirred for 1 hour, and then an excess of dry ice was added. It was acidified with 1 N HCl and extracted with EtOAc. The organic layer was dried over $MgSO_4$, filtered, and concentrated to obtain 2,5-dimethyl-4-((4-phenylpiperazin-1-yl)methyl)thiophene-3-carboxylic acid (502 mg).

Step 5: Synthesis of methyl 6-(2,5-dimethyl-4-((4-phenylpiperazin-1-yl)methyl)thiophene-3-carboxamido)spiro[3.3]heptane-2-carboxylate

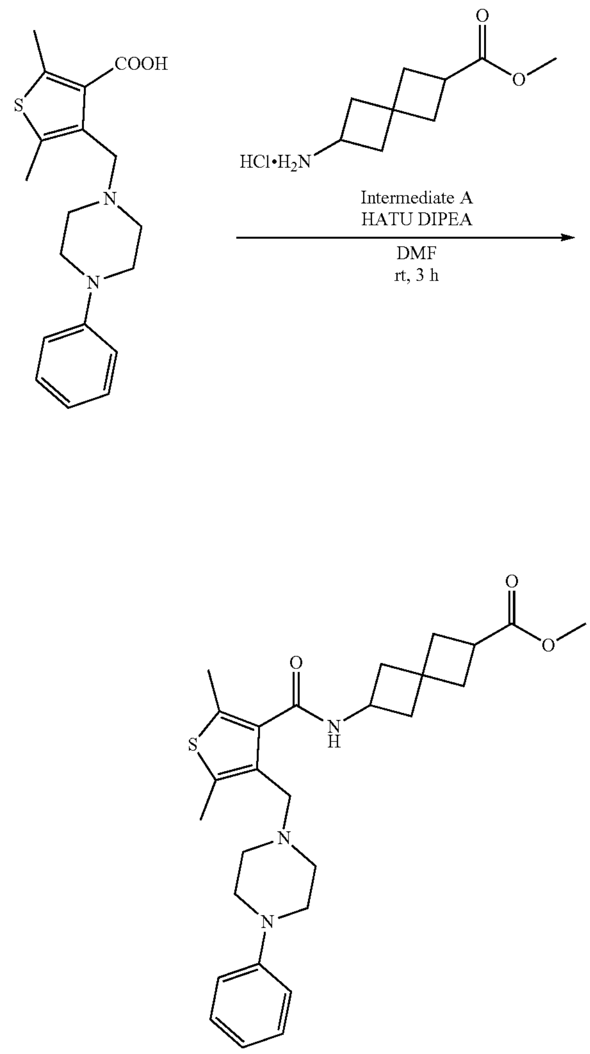

To a solution of 2,5-dimethyl-4-((4-phenylpiperazin-1-yl)methyl)thiophene-3-carboxylic acid (576 mg, 1.52 mmol), Intermediate A (0.34 g, 1.67 mmol), and HATU (0.63 g, 1.67 mmol) in DMF (5.1 mL, 0.3 M), DIPEA (0.80 mL) was added and stirred for 3 hours. The reaction mixture was concentrated and diluted with 1 N NaOH aqueous solution and ethyl acetate, and the aqueous layer was extracted three times with ethyl acetate. The organic layer was washed with brine, dried over $MgSO_4$, concentrated, and then purified by silica gel chromatography (n-hexane and ethyl acetate) to obtain methyl 6-(2,5-dimethyl-4-((4-phenylpiperazin-1-yl)methyl)thiophene-3-carboxamido)spiro[3.3]heptane-2-carboxylate (102 mg, yield 14%). $^1$H NMR (500 MHz, Chloroform-d) δ 9.73 (d, J=7.0 Hz, 1H), 7.32 (t, J=7.9 Hz, 2H), 6.94 (dd, J=17.1, 7.9 Hz, 3H), 4.45 (h, J=8.2, 7.7 Hz, 1H), 3.68 (s, 3H), 3.44 (s, 2H), 3.23 (s, 4H), 3.05 (p, J=8.5 Hz, 1H), 2.72 (s, 4H), 2.62 (s, 4H), 2.47 (dt, J=12.5, 6.5 Hz, 1H), 2.38 (d, J=7.0 Hz, 5H), 2.31 (dd, J=11.6, 8.5 Hz, 1H), 2.16-2.10 (m, 1H), 1.91 (dt, J=23.8, 10.4 Hz, 2H).

Step 6: Synthesis of 6-(2,5-dimethyl-4-((4-phenylpiperazin-1-yl)methyl)thiophene-3-carboxamido)spiro[3.3]heptane-2-carboxylic acid

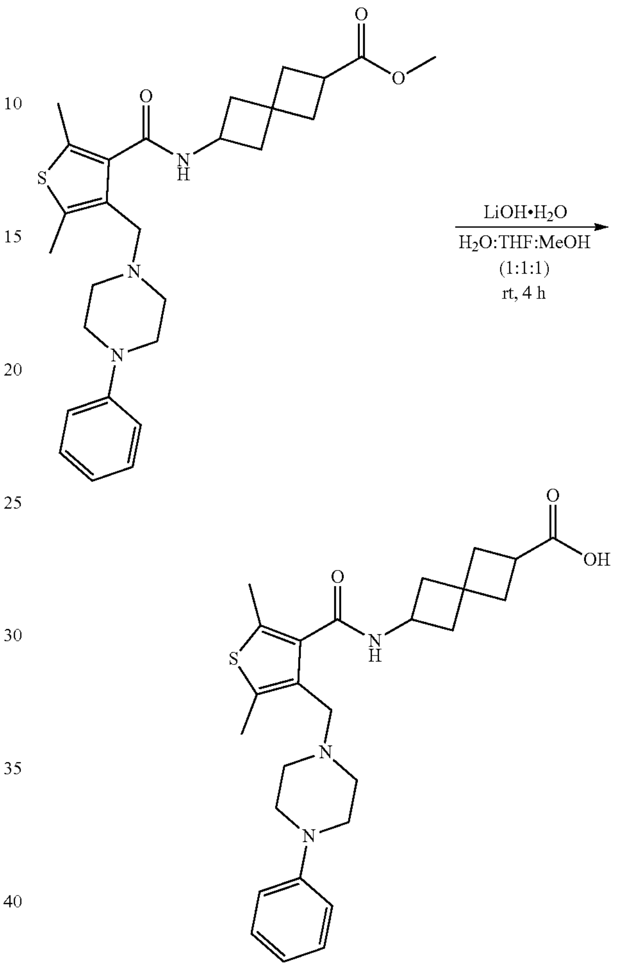

77

To a solution of methyl 6-(2,5-dimethyl-4-((4-phenylpiperazin-1-yl)methyl)thiophene-3-carboxamido)spiro[3.3]heptane-2-carboxylate (163 mg, 0.34 mmol) in $H_2O$/THF/MeOH (0.3 M, 1.1 mL), $LiOH{\cdot}H_2O$ (43 mg, 1.02 mmol) was added and stirred for 12 hours. The reaction mixture was acidified by addition of 1 N HCl solution and extracted with EA (3×20 mL). The organic layer was dried over $MgSO_4$, filtered, concentrated, and then purified by silica gel column chromatography (n-hexane and ethyl acetate) to obtain the compound of Example 77 (12 mg, yield 8%). $^1$H NMR (500 MHz, Methanol-$d_4$) δ 7.27 (t, J=7.8 Hz, 2H), 7.00 (d, J=8.3 Hz, 2H), 6.88 (t, J=7.3 Hz, 1H), 4.37 (p, J=8.2 Hz, 1H), 3.64 (s, 2H), 3.24 (s, 4H), 3.01 (p, J=8.4 Hz, 1H), 2.83 (s, 4H), 2.59 (dt, J=11.7, 6.6 Hz, 1H), 2.53 (s, 3H), 2.41 (s, 4H), 2.39-2.31 (m, 2H), 2.28-2.23 (m, 1H), 2.16 (t, J=10.1 Hz, 1H), 2.04 (dt, J=28.7, 9.7 Hz, 2H). LC/MS (ESI) m/z: 468.3 $[M+H]^+$.

Example 78: 6-(4-([1,1'-biphenyl]-4-ylmethyl)-N,2,5-trimethylthiophene-3-carboxamido)spiro[3.3]heptane-2-carboxylic acid Step 1: Synthesis of methyl 6-(4-(((tert-butyldimethylsilyl)oxy)methyl)-2,5-dimethylthiophene-3-carboxamido)spiro[3.3]heptane-2-carboxylate

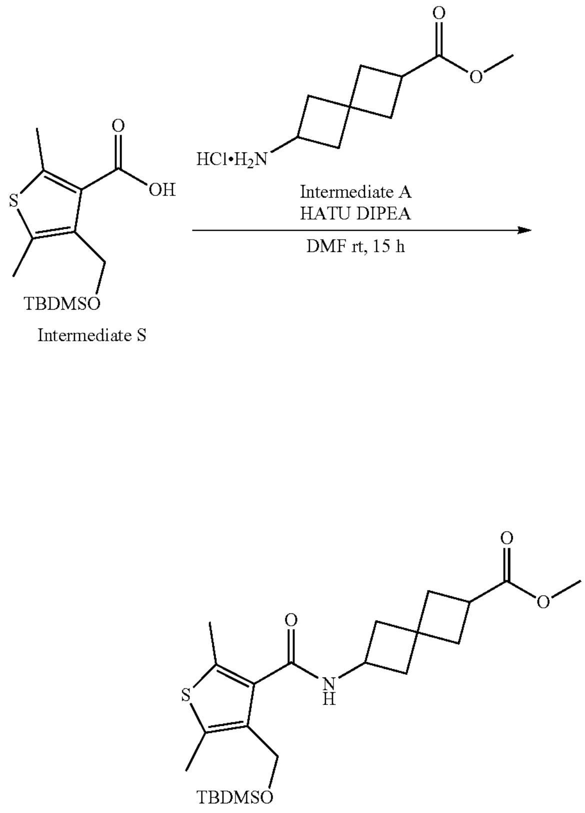

To a solution of Intermediate S (300 mg, 1.0 mmol) and HATU (456 mg, 1.20 mmol) in DMF (0.1 M), DIPEA (0.5 mL, 3.0 mmol) was added and stirred for 10 minutes, and Intermediate A (169 mg, 1.0 mmol) was added and stirred for 15 hours. The reaction mixture was diluted with ethyl acetate and washed with distilled water (3×25 mL) and brine. The organic layer was dried over $Na_2SO_4$, concentrated under reduced pressure, and purified by column chromatography (40% EtOAc in hexane) to obtain methyl 6-(4-(((tert-butyldimethylsilyl)oxy)methyl)-2,5-dimethylthiophene-3-carboxamido)spiro[3.3]heptane-2-carboxylate (260 mg, yield 83%) as a yellow liquid. $^1$H NMR (300 MHz, chloroform-d) δ 7.85 (d, J=7.6 Hz, 1H), 4.58 (s, 2H), 4.55-4.32 (m, 1H), 3.69 (s, 3H), 3.06 (p, J=8.6 Hz, 1H), 2.68-2.59 (m, 1H), 2.58 (s, 3H), 2.52-2.41 (m, 1H), 2.41-2.25 (m, 6H), 2.20-2.09 (m, 1H), 2.04-1.85 (m, 2H), 0.94 (s, 9H), 0.16 (s, 6H).

Step 2: Synthesis of methyl 6-(4-(hydroxymethyl)-2,5-dimethylthiophene-3-carboxamido)spiro[3.3]heptane-2-carb oxy

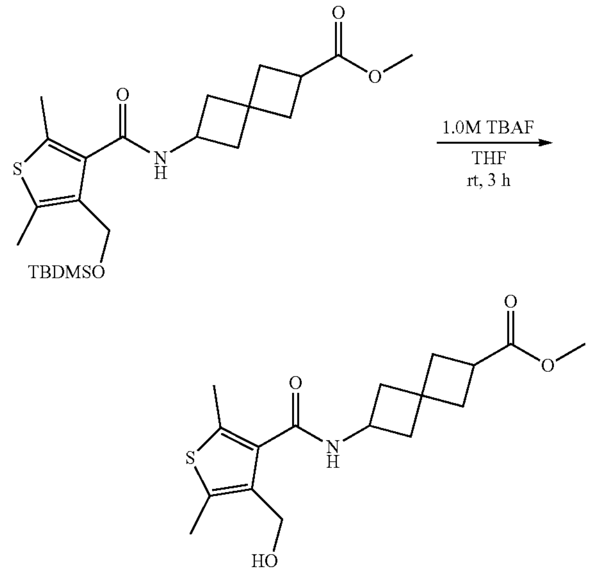

To a solution of methyl 6-(4-(((tert-butyldimethylsilyl)oxy)methyl)-2,5-methylthiophene-3-carboxamido)spiro[3.3]heptane-2-carboxylate (226 mg, 0.50 mmol) in THF (0.1 M), tetra-n-butylammonium fluoride (TBAF) (1.0 M in THF, 0.75 mL, 0.75 mmol) was added and stirred for 15 hours. The reaction mixture was diluted with ethyl acetate and washed with distilled water (3×25 mL) and brine. The organic layer was dried over $Na_2SO_4$, concentrated under reduced pressure, and purified by column chromatography (30% EtOAc in hexane) to obtain methyl 6-(4-(hydroxymethyl)-2,5-dimethylthiophene-3-carboxamido)spiro[3.3]heptane-2-carboxylate (171 mg) as a yellow liquid. $^1$H NMR (300 MHz, chloroform-d) δ 6.49 (d, J=7.9 Hz, 1H), 4.53-4.37 (m, 3H), 3.69 (s, 3H), 3.05 (q, J=8.5 Hz, 1H), 2.71-2.58 (m, 1H), 2.54 (s, 3H), 2.53-2.44 (m, 1H), 2.40 (s, 3H), 2.38-2.27 (m, 3H), 2.24-2.14 (m, 1H), 2.07-1.86 (m, 2H).

Step 3: Synthesis of methyl 6-(4-(bromomethyl)-2,5-dimethylthiophene-3-carboxamido)spiro[3.3]heptane-2-carboxylate

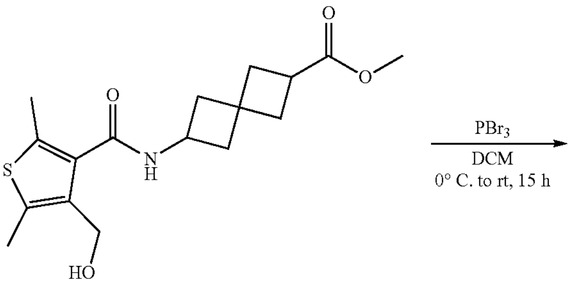

-continued

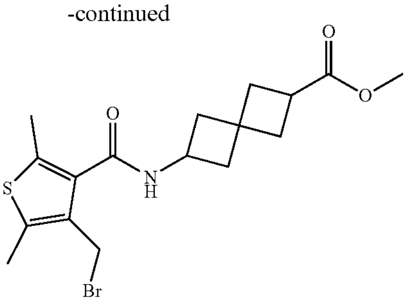

To a stirred solution of methyl 6-(4-(hydroxymethyl)-2,5-dimethylthiophene-3-carboxamido)spiro[3.3]heptane-2-carboxylate (82 mg, 0.24 mmol) in DCM (0.1 M), $PBr_3$ (92 μL, 2.03 mmol) was added at 0° C. and stirred for 15 hours. The reaction mixture was diluted with ethyl acetate and washed with bicarbonate solution and distilled water. The organic layer was dried over $Na_2SO_4$, filtered, concentrated under reduced pressure, and purified by column chromatography (25% EtOAc in hexane) to obtain methyl 6-(4-(bromomethyl)-2,5-dimethylthiophene-3-carboxamido)spiro[3.3]heptane-2-carboxylate (49 mg, yield 50%) as a white solid. $^1H$ NMR (300 MHz, chloroform-d) δ 6.18 (d, J=7.0 Hz, 1H), 4.53 (s, 2H), 4.53-4.39 (m, 1H), 3.69 (s, 3H), 3.05 (q, J=8.5 Hz, 1H), 2.74-2.59 (m, 1H), 2.57-2.51 (m, 1H), 2.47 (s, 3H), 2.42-2.35 (m, 1H), 2.38 (s, 3H), 2.38-2.28 (m, 2H), 2.25-2.15 (m, 1H), 2.11-1.91 (m, 2H).

Step 4: Synthesis of methyl 6-(2,5-dimethyl-4-((4-phenyl-1H-pyrazol-1-yl)methyl)thiophene-3-carboxamido)spiro[3.3]heptane-2-carboxylate

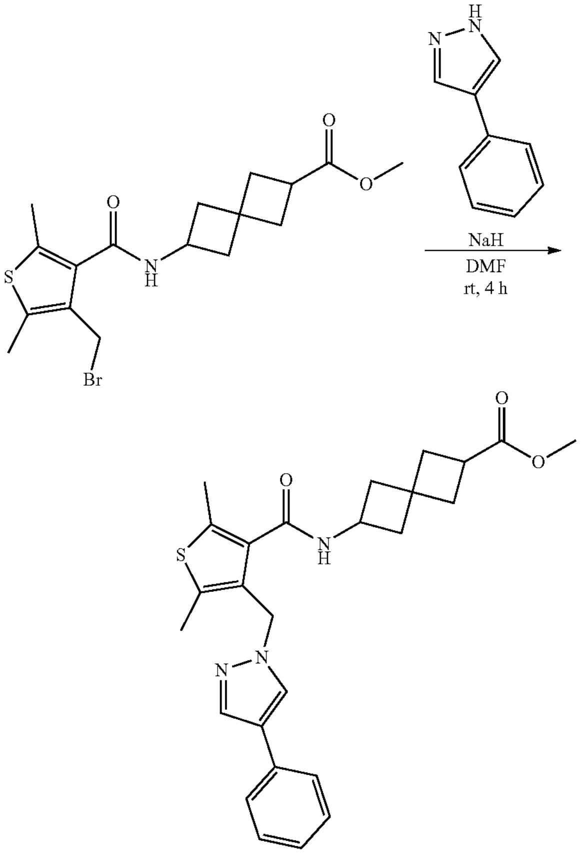

To a solution of 4-phenyl-1H-pyrazole (12 mg, 0.08 mmol) in DMF (0.1 M), NaH (5 mg, 0.12 mmol) was added and stirred for 15 minutes. Methyl 6-(4-(bromomethyl)-2,5-dimethylthiophene-3-carboxamido)spiro[3.3]heptane-2-carboxylate (32 mg, 0.08 mmol) was added and stirred for 4 hours. The reaction mixture was diluted with ethyl acetate (10 mL) and washed with distilled water (2×10 mL). The organic layer was dried over $Na_2SO_4$, filtered, concentrated under reduced pressure, and purified by column chromatography (40% EtOAc in hexane) to obtain methyl 6-(2,5-dimethyl-4-((4-phenyl-1H-pyrazol-1-yl)methyl)thiophene-3-carboxamido)spiro[3.3]heptane-2-carboxylate (16 mg, yield 43%) as a white solid.

Step 5: Synthesis of 6-(2,5-dimethyl-4-((4-phenyl-1H-pyrazol-1-yl)methyl)thiophene-3-carboxamido)spiro[3.3]heptane-2-carboxylic acid

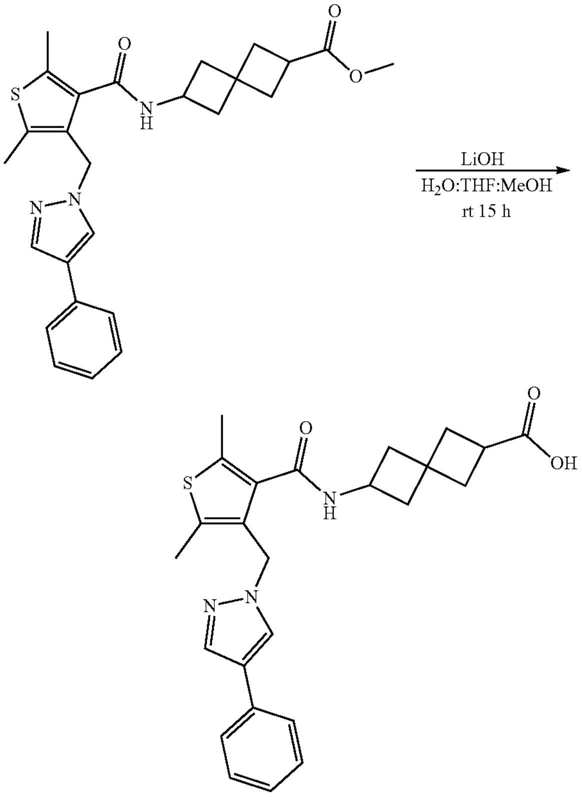

78

To a solution of methyl 6-(2,5-dimethyl-4-((4-phenyl-1H-pyrazol-1-yl)methyl)thiophene-3-carboxamido)spiro[3.3]heptane-2-carboxylate (16 mg, 0.03 mmol) in $H_2O$:THF:MeOH (1:1:1, 0.1 M), $LiOH \cdot H_2O$ (3 mg, 0.1 mmol) was added and stirred for 15 hours. The reaction mixture was partially concentrated, acidified with 1 N HCl solution (pH~4), and extracted with ethyl acetate (2×10 mL). The organic layer was dried over $Na_2SO_4$, filtered, concentrated under reduced pressure, and then purified by column chromatography (5% MeOH in DCM) to obtain the compound of Example 78 (5 mg, yield 32%) as a white solid. $^1H$ NMR (400 MHz, MeOD) δ 7.85 (s, 1H), 7.81 (s, 1H), 7.57-7.50 (m, 2H), 7.36 (t, J=7.7 Hz, 2H), 7.26-7.17 (m, 1H), 5.28 (s, 2H), 4.20 (p, J=8.1 Hz, 1H), 2.91 (p, J=8.5 Hz, 1H), 2.46 (s, 3H), 2.43-2.32 (m, 1H), 2.40 (s, 3H), 2.31-2.19 (m, 3H), 2.17-2.07 (m, 1H), 2.01 (ddd, J=11.4, 8.7, 2.7 Hz, 1H), 1.93-1.80 (m, 2H). LC/MS (ESI) m/z: 450.09 [M+H]$^+$.

Example 79: 6-(4-([1,1'-biphenyl]-4-ylmethyl)-4H-thieno[3,2-b]pyrrole-3-carboxamido)spiro[3.3]heptane-2-carboxylic acid Step 1: Synthesis of methyl 4-([1,1'-biphenyl]-4-ylmethyl)-3-bromo-4H-thieno[3,2-b]pyrrole-5-carboxylate

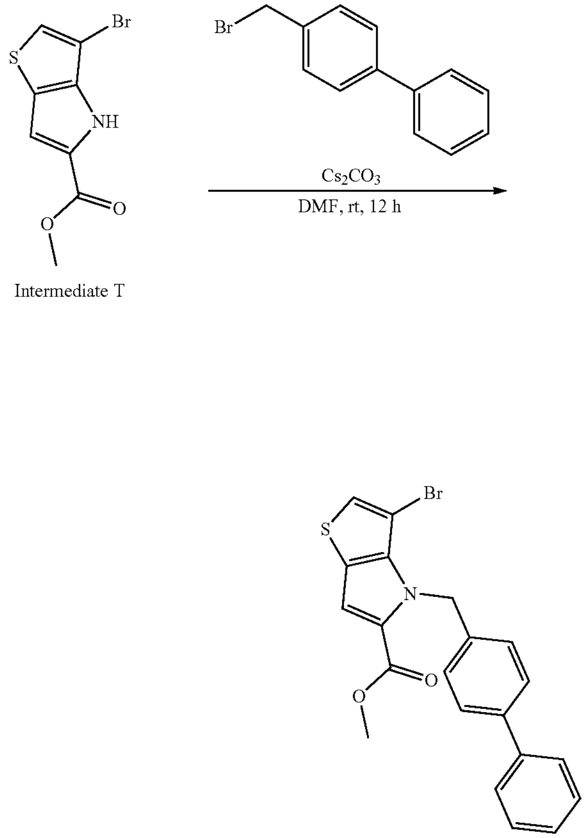

Intermediate T

To a solution of Intermediate T (780 mg, 3.0 mmol, 1.0 equiv) and $Cs_2CO_3$ (2.44 g, 7.5 mmol, 2.5 equiv) in DMF (10 mL), 4-bromomethyl-biphenyl (890 mg, 3.6 mmol, 1.2 equiv) was added and stirred for 12 hours. The reaction mixture was poured into distilled water and extracted with DCM, and then the organic layer was dried over $MgSO_4$ and then concentrated under reduced pressure. The crude product was purified by flash column chromatography to obtain methyl 4-([1,1'-biphenyl]-4-ylmethyl)-3-bromo-4H-thieno[3,2-b]pyrrole-5-carboxylate (940 mg, yield 73%). $^1$H NMR (300 MHz, chloroform-d) δ 7.57-7.48 (m, 4H), 7.44-7.37 (m, 2H), 7.36-7.29 (m, 1H), 7.26 (s, 1H), 7.25 (s, 1H), 7.11 (d, J=8.1 Hz, 2H), 6.14 (s, 2H), 3.82 (s, 3H).

Step 2: Synthesis of 4-([1,1'-biphenyl]-4-ylmethyl)-3-bromo-4H-thieno[3,2-b]pyrrole-5-carboxylic acid

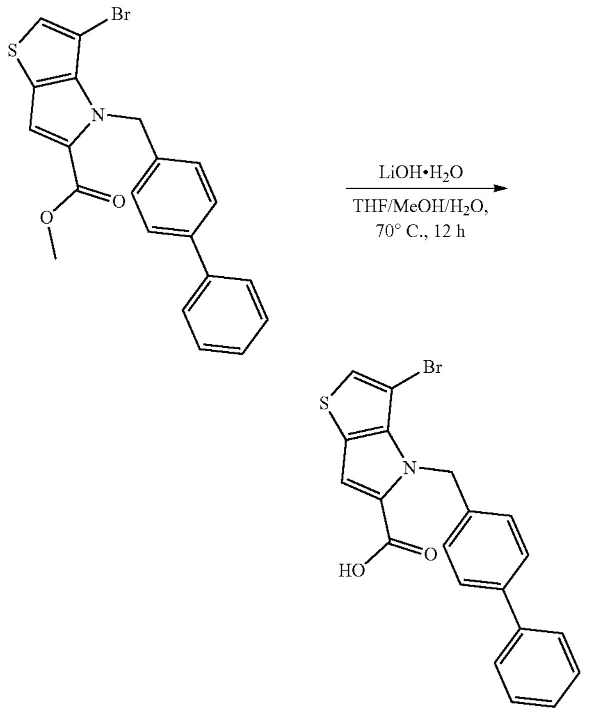

To a solution of methyl 4-([1,1'-biphenyl]-4-ylmethyl)-3-bromo-4H-thieno[3,2-b]pyrrole-5-carboxylate (940 mg, 2.2 mmol) in $THF/MeOH/H_2O$ (20/10/10 mL), $LiOH·H_2O$ (277 mg, 6.6 mmol, 3.0 equiv) was added and stirred at 70° C. for 12 hours. The reaction mixture was partially concentrated and then acidified with 1 N HCl solution. The precipitated solid was filtered, then washed with distilled water, and dried to obtain 4-([1,1'-biphenyl]-4-ylmethyl)-3-bromo-4H-thieno[3,2-b]pyrrole-5-carboxylic acid (815 mg, yield 90%). $^1$H NMR (300 MHz, chloroform-d) δ 7.58-7.36 (m, 3H), 7.43-7.36 (m, 2H), 7.32 (d, J=6.8 Hz, 2H), 7.11 (d, J=8.1 Hz, 2H), 6.12 (s, 2H).

Step 3: Synthesis of 4-([1,1'-biphenyl]-4-ylmethyl)-3-bromo-2-methyl-4H-thieno[3,2-b]pyrrole

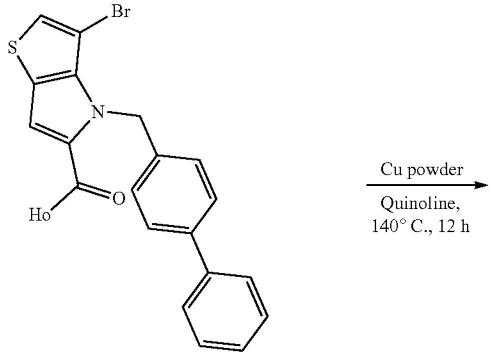

-continued

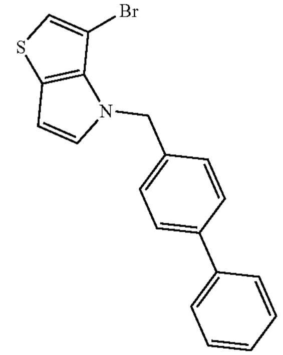

A solution of 4-([1,1'-biphenyl]-4-ylmethyl)-3-bromo-4H-thieno[3,2-b]pyrrole-5-carboxylic acid (815 mg, 1.97 mmol) and Cu powder (82 mg, 10 wt %) in quinoline (10 mL) was stirred at 140° C. for 12 hours. The reaction mixture was cooled, acidified with 6 N HCl solution, and then extracted with $Et_2O$. The organic layer was dried over $MgSO_4$ and then concentrated under reduced pressure, and the crude product was purified by flash column chromatography to obtain 4-([1,1'-biphenyl]-4-ylmethyl)-3-bromo-2-methyl-4H-thieno[3,2-b]pyrrole (170 mg, yield 23%).

Step 4: Synthesis of 4-([1,1'-biphenyl]-4-ylmethyl)-4H-thieno[3,2-b]pyrrole-3-carboxylic acid

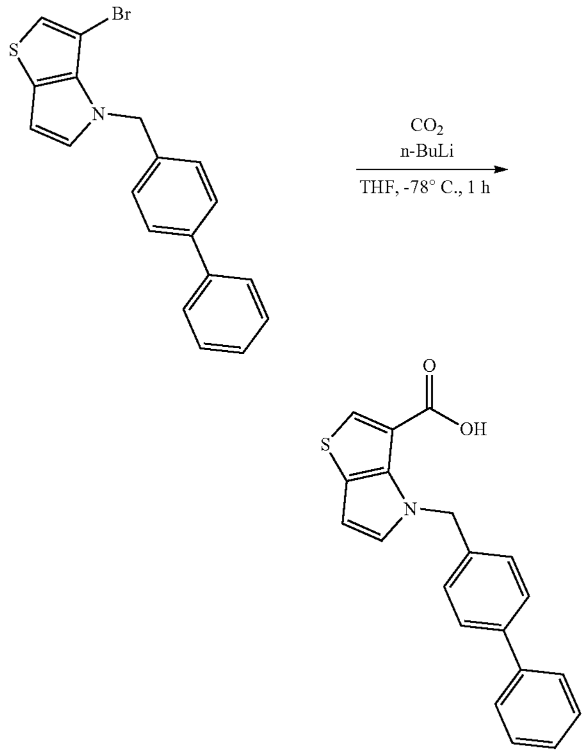

To a solution of 4-([1,1'-biphenyl]-4-ylmethyl)-3-bromo-2-methyl-4H-thieno[3,2-b]pyrrole (170 mg, 0.46 mmol, 1.0 equiv) in THF (5 mL), n-BuLi (2.0 M in cyclohexane, 0.3 mL, 1.2 equiv) was added at −78° C. and stirred for 10 minutes. Dry ice was added to the reaction mixture, stirred for 1 hour at ambient temperature, then acidified with 1 N HCl solution, and extracted with EtOAc. The organic layer was dried over $MgSO_4$ and then concentrated under reduced pressure, and the crude product was purified by flash column chromatography to obtain 4-([1,1'-biphenyl]-4-ylmethyl)-4H-thieno[3,2-b]pyrrole-3-carboxylic acid (100 mg, mixture).

Step 5: Synthesis of methyl 6-(4-([1,1'-biphenyl]-4-ylmethyl)-4H-thieno[3,2-b]pyrrole-3-carboxamido)spiro[3.3]heptane-2-carboxylate

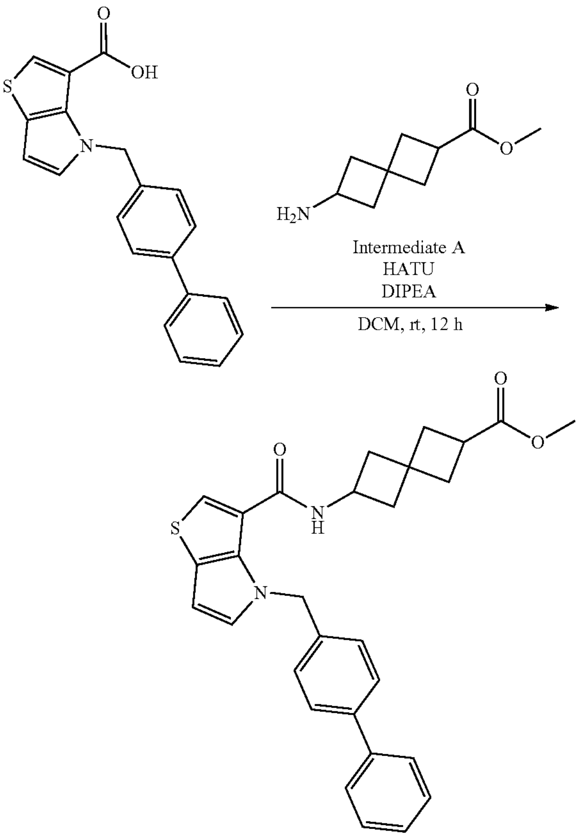

To a solution of 4-([1,1'-biphenyl]-4-ylmethyl)-4H-thieno[3,2-b]pyrrole-3-carboxylic acid (100 mg, 0.3 mmol) and HATU (137 mg, 0.36 mmol, 1.2 equiv) in DCM (2 mL), DIPEA (80 μL, 0.45 mmol, 1.5 equiv) was added at 0° C. and stirred for 15 minutes. Intermediate A (68 mg, 0.33 mmol, 1.1 equiv) was added to the reaction mixture and stirred for 12 hours. The reaction mixture was poured into distilled water and extracted with DCM, and the organic layer was dried over $MgSO_4$ and then concentrated under reduced pressure. The crude product was purified by flash column chromatography to obtain methyl 6-(4-([1,1'-biphenyl]-4-ylmethyl)-4H-thieno[3,2-b]pyrrole-3-carboxamido)spiro[3.3]heptane-2-carboxylate (40 mg, yield 30%). $^1H$ NMR (300 MHz, chloroform-d) δ 7.56-7.50 (m, 2H), 7.50-7.39 (m, 4H), 7.36-7.29 (m, 1H), 7.11 (d, J=8.3 Hz, 2H), 7.00 (dd, J=2.9, 1.3 Hz, 1H), 6.44 (d, J=2.9 Hz, 1H), 5.99 (d, J=7.8 Hz, 1H), 5.60 (s, 2H), 4.36-4.28 (m, 1H), 3.66 (s, 3H), 3.05-2.94 (m, 1H), 2.54-2.46 (m, 1H), 2.42-2.36 (m, 1H), 2.33-2.30 (m, 2H), 2.27-2.20 (m, 1H), 2.09-2.01 (m, 1H), 1.80-1.71 (m, 2H).

Step 6: Synthesis of 6-(4-([1,1'-biphenyl]-4-ylmethyl)-4H-thieno[3,2-b]pyrrole-3-carboxamido)spiro[3.3]heptane-2-carboxylic acid

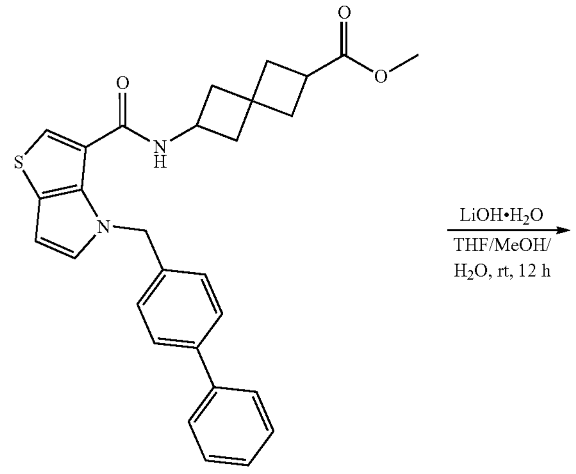

-continued

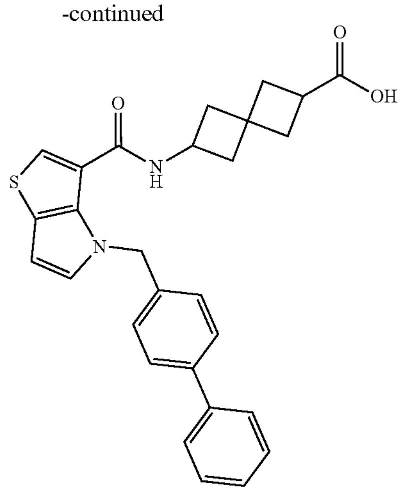

79

To a solution of methyl 6-(4-([1,1'-biphenyl]-4-ylmethyl)-4H-thieno[3,2-b]pyrrole-3-carboxamido)spiro[3.3]heptane-2-carboxylate (40 mg, 0.08 mmol) in THF/MeOH/$H_2O$ (1:1:1, 9 mL), LiOH·$H_2O$ (10 mg, 0.24 mmol, 3.0 equiv) was added and stirred for 12 hours. The reaction mixture was partially concentrated and then acidified with 1 N HCl solution. The precipitated solid was filtered, washed with distilled water, and dried, and then the crude product was purified by flash column chromatography to obtain the compound of Example 79 (15 mg, yield 40%). $^1$H NMR (300 MHz, methanol-$d_4$) δ 8.34 (d, J=7.3 Hz, 1H), 7.58-7.52 (m, 2H), 7.50-7.44 (m, 2H), 7.44-7.35 (m, 3H), 7.33-7.26 (m, 1H), 7.15 (dd, J=3.0, 1.3 Hz, 1H), 7.02 (d, J=8.3 Hz, 2H), 6.43 (d, J=3.0 Hz, 1H), 5.56 (s, 2H), 4.25-4.11 (m, 1H), 3.02-2.90 (m, 1H), 2.46-2.38 (m, 1H), 2.35-2.23 (m, 3H), 2.22-2.01 (m, 2H), 1.91-1.81 (m, 2H). LC/MS (ESI) m/z: 471.4 $[M+H]^+$.

The compounds of Examples 80 to 89 were prepared in the same manner as in Example 79 except for the differences in the preparation methods described below.

TABLE 13

| Example No. | Chemical structure | Name | Difference in preparation method |
|---|---|---|---|
| 80 | 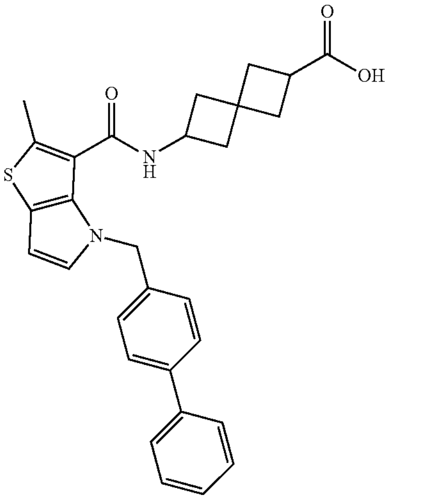 [SMILES: Cc1sc2ccn(Cc3ccc(-c4ccccc4)cc3)c2c1C(=O)NC1CC2(C1)CC(C(=O)O)C2] | 6-(4-([1,1'-biphenyl]-4-ylmethyl)-2-methyl-4H-thieno[3,2-b]pyrrole-3-carboxamido)spiro[3.3]heptane-2-carboxylic acid | Intermediate U was used instead of Intermediate T in Step 1 |

TABLE 13-continued

| Example No. | Chemical structure | Name | Difference in preparation method |
|---|---|---|---|
| 81 | 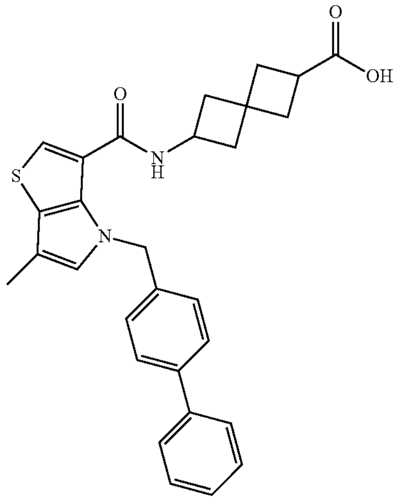 [SMILES: Cc1cn(Cc2ccc(-c3ccccc3)cc2)c2c(C(=O)NC3CC4(C3)CC(C(=O)O)C4)csc12] | 6-(4-([1,1'-biphenyl]-4-ylmethyl)-6-methyl-4H-thieno[3,2-b]pyrrole-3-carboxamido)spiro[3.3]heptane-2-carboxylic acid | Intermediate V was used instead of Intermediate T in Step 1 |
| 82 | 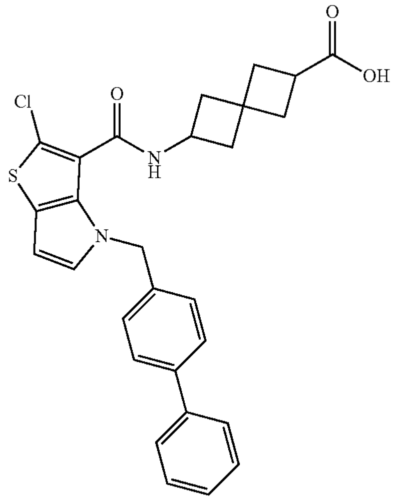 [SMILES: O=C(NC1CC2(C1)CC(C(=O)O)C2)c1c(Cl)sc2ccn(Cc3ccc(-c4ccccc4)cc3)c12] | 6-(4-([1,1'-biphenyl]-4-ylmethyl)-2-chloro-4H-thieno[3,2-b]pyrrole-3-carboxamido)spiro[3.3]heptane-2-carboxylic acid | Intermediate W was used instead of Intermediate T in Step 1 |
| 83 | 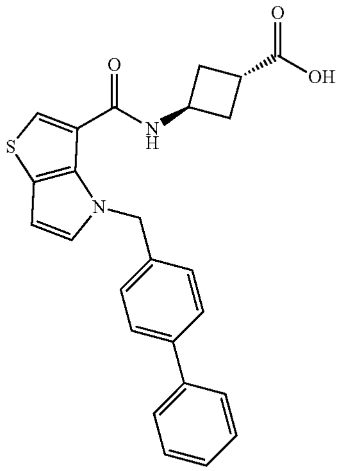 [SMILES: O=C(N[C@H]1C[C@H](C(=O)O)C1)c1csc2ccn(Cc3ccc(-c4ccccc4)cc3)c12] | (1R,3R)-3-(4-([1,1'-biphenyl]-4-ylmethyl)-4H-thieno[3,2-b]pyrrole-3-carboxamido)cyclobutane-1-carboxylic acid | Methyl (1R,3R)-3-aminocyclobutane-1-carboxylate hydrochloride having the following structure was used instead of Intermediate A in Step 5: 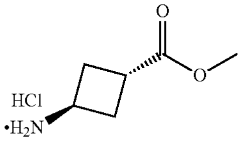 |

TABLE 13-continued

| Example No. | Chemical structure | Name | Difference in preparation method |
|---|---|---|---|
| 84 | 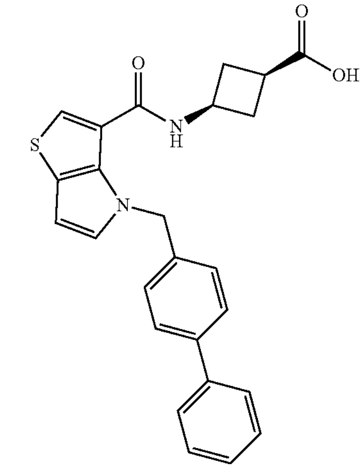 [SMILES: O=C(N[C@H]1C[C@@H](C(=O)O)C1)c1csc2ccn(Cc3ccc(-c4ccccc4)cc3)c12] | (1S,3S)-3-(4-([1,1'-biphenyl]-4-ylmethyl)-4H-thieno[3,2-b]pyrrole-3-carboxamido)cyclobutane-1-carboxylic acid | Methyl (1S,3S)-3-aminocyclobutane-1-carboxylate hydrochloride having the following structure was used instead of Intermediate A in Step 5: 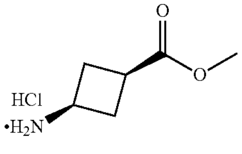 |
| 85 | 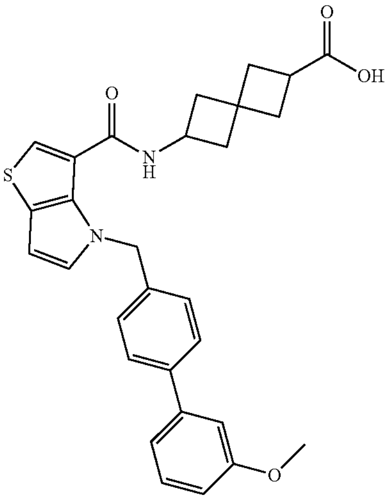 [SMILES: COc1cccc(-c2ccc(Cn3ccc4scc(C(=O)NC5CC6(C5)CC(C(=O)O)C6)c43)cc2)c1] | 6-(4-((3'-methoxy-[1,1'-biphenyl]-4-yl)methyl)-4H-thieno[3,2-b]pyrrole-3-carboxamido)spiro[3.3]heptane-2-carboxylic acid | Intermediate X was used instead of 4'-bromomethylbiphenyl in Step 1 |
| 86 | 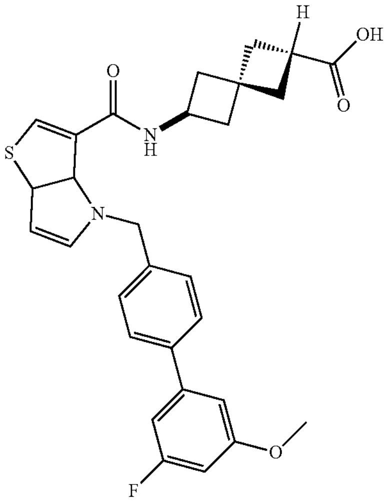 | (2R,4R,6R)-6-(4-((3'-fluoro-5'-methoxy-[1,1'-biphenyl]-4-yl)methyl)-4H-thieno[3,2-b]pyrrole-3-carboxamido)spiro[3.3]heptane-2-carboxylic acid | Intermediate Y was used instead of 4'-bromomethylbiphenyl in Step 1, and Intermediate Z was used instead of Intermediate A in Step 5 |

TABLE 13-continued

| Example No. | Chemical structure | Name | Difference in preparation method |
|---|---|---|---|
| 87 | 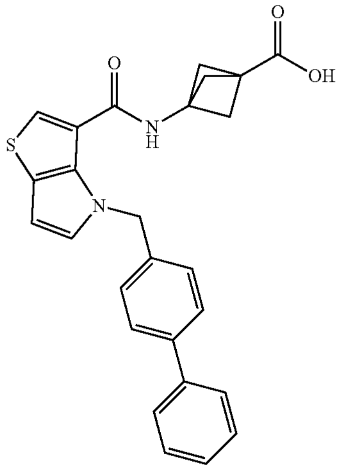 [SMILES: O=C(NC12CC(C(=O)O)(C1)C2)c1csc2ccn(Cc3ccc(-c4ccccc4)cc3)c12] | 3-(4-([1,1'-biphenyl]-4-ylmethyl)-4H-thieno[3,2-b]pyrrole-3-carboxamido)bicyclo[1.1.1]pentane-1-carboxylic acid | Methyl 3-aminobicyclo[1.1.1]pentane-1-carboxylate hydrochloride having the following structure was used instead of Intermediate A in Step 5: 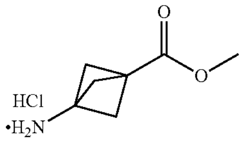 |
| 88 | 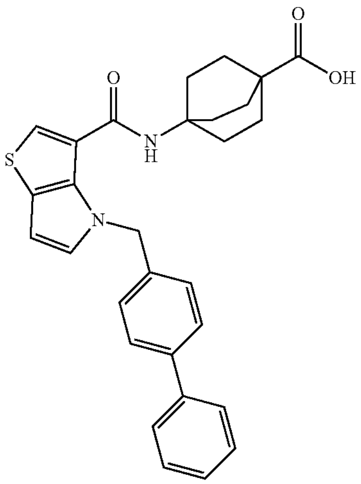 [SMILES: O=C(NC12CCC(C(=O)O)(CC1)CC2)c1csc2ccn(Cc3ccc(-c4ccccc4)cc3)c12] | 4-(4-([1,1'-biphenyl]-4-ylmethyl)-4H-thieno[3,2-b]pyrrole-3-carboxamido)bicyclo[2.2.2]octane-1-carboxylic acid | Methyl 4-aminobicyclo[1.1.1]octane-1-carboxylate hydrochloride having the following structure was used instead of Intermediate A in Step 5: 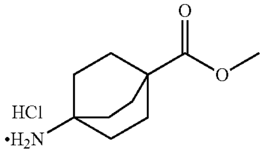 |
| 89 | 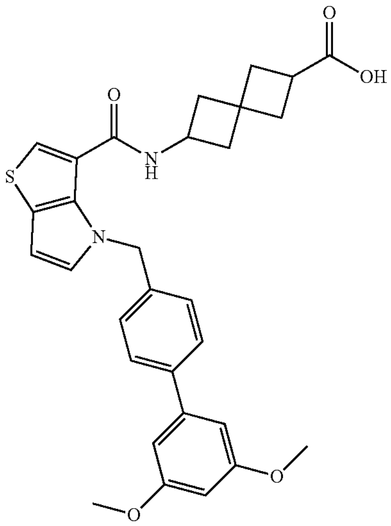 [SMILES: COc1cc(OC)cc(-c2ccc(Cn3ccc4scc(C(=O)NC5CC6(C5)CC(C(=O)O)C6)c43)cc2)c1] | 6-(4-((3',5'-dimethoxy-[1,1'-biphenyl]-4-yl)methyl)-4H-thieno[3,2-b]pyrrole-3-carboxamido)spiro[3.3]heptane-2-carboxylic acid | Intermediate AA was used instead of 4'-bromomethylbiphenyl in Step 1 |

TABLE 14

| Example No. | LC/MS (ESI) m/z: $[M + H]^+$ | NMR |
|---|---|---|
| 80 | 485.26 | $^1$H NMR (400 MHz, Chloroform-d) δ 7.60-7.52 (m, 2H), 7.52-7.47 (m, 2H), 7.45 (t, J = 7.7 Hz, 2H), 7.40-7.32 (m, 1H), 7.07 (d, J = 8.0 Hz, 2H), 6.92 (d, J = 3.0 Hz, 1H), 6.39 (d, J = 2.9 Hz, 1H), 5.57 (d, J = 7.9 Hz, 1H), 5.42 (s, 2H), 4.33 (d, J = 8.1 Hz, 1H), 3.03 (m, 1H), 2.56 (s, 3H), 2.52-2.43 (m, 1H), 2.36 (d, J = 8.3 Hz, 3H), 2.28-2.16 (m, 1H), 2.08 (m, 1H), 1.65 (d, J = 10.0 Hz, 2H). |
| 81 | 485.4 | $^1$H NMR (300 MHz, DMSO-$d_6$) δ 12.03 (s, 1H), 8.48 (d, J = 7.4 Hz, 1H), 7.62-7.55 (m, 3H), 7.55-7.50 (m, 2H), 7.45-7.40 (m,2H), 7.35-7.30 (m, 1H), 7.14 (d, J = 8.1 Hz, 2H), 7.05 (s, 1H), 5.53 (s, 2H), 4.24-4.16 (m, 1H), 2.97-2.86 (m, 1H), 2.43-2.35 (m, 1H), 2.31-2.16 (m, 3H), 2.14 (s, 3H), 2.11-1.86 (m, 4H). |
| 82 | 505.4 | $^1$H NMR (300 MHz, DMSO-$d_6$) δ 12.03 (s, 1H), 8.73 (d, J = 7.5 Hz, 1H), 7.65-7.51 (m, 4H), 7.45 (t, J = 7.6 Hz, 2H), 7.39-7.32 (m, 2H), 7.14 (d, J = 8.2 Hz, 2H), 6.43 (d, J = 3.0 Hz, 1H), 5.33 (s, 2H), 4.24-4.14 (m, 1H), 2.95-2.83 (m, 1H), 2.41-2.31 (m, 1H), 2.31-2.14 (m, 3H), 2.10-1.93 (m, 2H), 1.93-1.77 (m, 2H). |
| 83 | 431.4 | $^1$H NMR (300 MHz, DMSO-$d_6$) δ 8.61 (d, J = 7.7 Hz, 1H), 7.63-7.56 (m, 3H), 7.53 (d, J = 8.2 Hz, 2H), 7.43 (t, J = 7.4 Hz, 2H), 7.34 (t. J = 5.0 Hz, 2H), 7.15 (d, J = 8.2 Hz, 2H), 6.46 (d, J = 2.9 Hz, 1H), 5.62 (s, 2H), 4.51 (h. J = 7.7 Hz, 1H), 2.89-2.78 (m, 1H), 2.47-2.36 (m, 2H), 2.19 (td, J = 12.2, 11.0, 6.0 Hz, 2H). |
| 84 | 431.1 | $^1$H NMR (300 MHz, DMSO-$d_6$) δ 12.13 (s, 1H), 8.61 (d, J = 7.7 Hz, 1H), 7.64-7.56 (m, 3H), 7.53 (d, J = 8.2 Hz, 2H), 7.43 (t, J = 7.4 Hz, 2H), 7.37-7.29 (m, 2H), 7.15 (d, J = 8.2 Hz, 2H), 6.46 (d, J = 2.9 Hz, 1H), 5.63 (s, 2H), 4.31 (h, J = 7.9 Hz, 1H), 2.84-2.69 (m, 1H), 2.44 (td, J = 8.3, 2.8 Hz, 2H), 2.16 (qd, J = 9.5, 2.5 Hz, 2H). |
| 85 | [M + 1] = 501.4 | $^1$H NMR (300 MHz, DMSO-$d_6$) δ 12.03 (s, 1H), 8.48 (d, J = 7.5 Hz, 1H), 7.57 (d, J = 1.3 Hz, 1H), 7.53 (d, J = 8.3 Hz, 2H), 7.40-7.27 (m, 2H), 7.18-7.05 (m, 4H), 6.94-6.82 (m, 1H), 6.44 (d, J = 2.9 Hz, 1H), 5.61 (s, 2H), 4.21 (h, J = 8.1 Hz, 1H), 3.79 (s, 3H), 2.92 (p, J = 8.4 Hz, 1H), 2.46-2.35 (m, 1H), 2.30-2.18 (m, 3H), 2.13-1.85 (m, 4H). |
| 86 | 519.3 | $^1$H NMR (300 MHz, DMSO-$d_6$) δ 12.03 (s, 1H), 8.49 (d, J = 7.5 Hz, 1H), 7.57 (d, J = 8.4 Hz, 3H), 7.31 (dd, J = 2.9, 1.1 Hz, 1H), 7.13 (d, J = 8.2 Hz, 2H), 7.02 (dt, J = 12.2, 1.9 Hz, 2H), 6.81 (dt, J = 10.9, 2.2 Hz, 1H), 6.45 (d, J = 2.9 Hz, 1H), 5.62 (s, 2H), 4.22 (p, J = 8.2 Hz, 1H), 3.81 (s, 3H), 2.93 (p, J = 8.4 Hz, 1H), 2.40 (dt, J = 11,7, 6.5 Hz, 1H), 2.24 (dtd, J = 24.3, 13,7, 12.5, 3.8 Hz, 3H), 2.13-2.03 (m, 2H), 2.01-1.88 (m, 2H). |
| 87 | — | $^1$H NMR (300 MHz, DMSO-$d_6$) δ 12.45 (s, 1H), 8.97 (s, 1H), 7.58 (dd, J = 16.3, 8.0 Hz, 5H), 7.44 (t, J = 7.5 Hz, 2H), 7.37-7.31 (m, 2H), 7.18 (d, J = 8.2 Hz, 2H), 6.46 (d, J = 2.9 Hz, 1H), 5.62 (s, 2H), 2.28 (s, 6H). |
| 88 | 485.3 | $^1$H NMR (300 MHz, DMSO-$d_6$) δ 12.05 (s, 1H), 7.78 (s, 1H), 7.63-7.51 (m, 5H), 7.44 (t, J = 7.4 Hz, 2H), 7.37-7.28 (m, 2H), 7.18 (d, J = 8.2 Hz, 2H), 6.44 (d, J = 2.9 Hz, 1H), 5.60 (s, 2H), 1.90 (dd, J = (10.7, 4.4 Hz, 6H), 1.77 (dd, J = 10.3, 4.5 Hz, 6H). |
| 89 | 531.5 | $^1$H NMR (300 MHz, DMSO-$d_6$) δ 12.04 (s, 1H), 8.48 (d, J = 7.5 Hz, 1H), 7.58 (d, J = 1.3 Hz, 1H), 7.52 (d, J = 8.2 Hz, 2H), 7.30 (dd, J = 3.0, 1.3 Hz, 1H), 7.11 (d, J = 8.2 Hz, 2H), 6.70-6.69 (m, 2H), 6.47 (t, J = 2.2 Hz, 1H), 6.44 (d, J = 2.9 Hz, 1H), 5.61 (s, 2H), 4.34-4.09 (m, 1H), 3.77 (s, 6H), 2.98-2.85 (m, 1H), 2.45-2.35 (m, 1H), 2.32-2.18 (m, 3H), 2.12-2.02 (m, 2H), 2.01-1.86 (m, 2H), |

Example 90: 6-(4-(4-(trifluoromethyl)benzyl)-4H-thieno[3,2-b]pyrrole-3-carboxamido)spiro[3.3]heptane-2-carboxylic acid Steps 1 to 3: Synthesis of 3-bromo-4-(4-(trifluoromethyl)benzyl)-4H-thieno[3,2-b]pyrrole

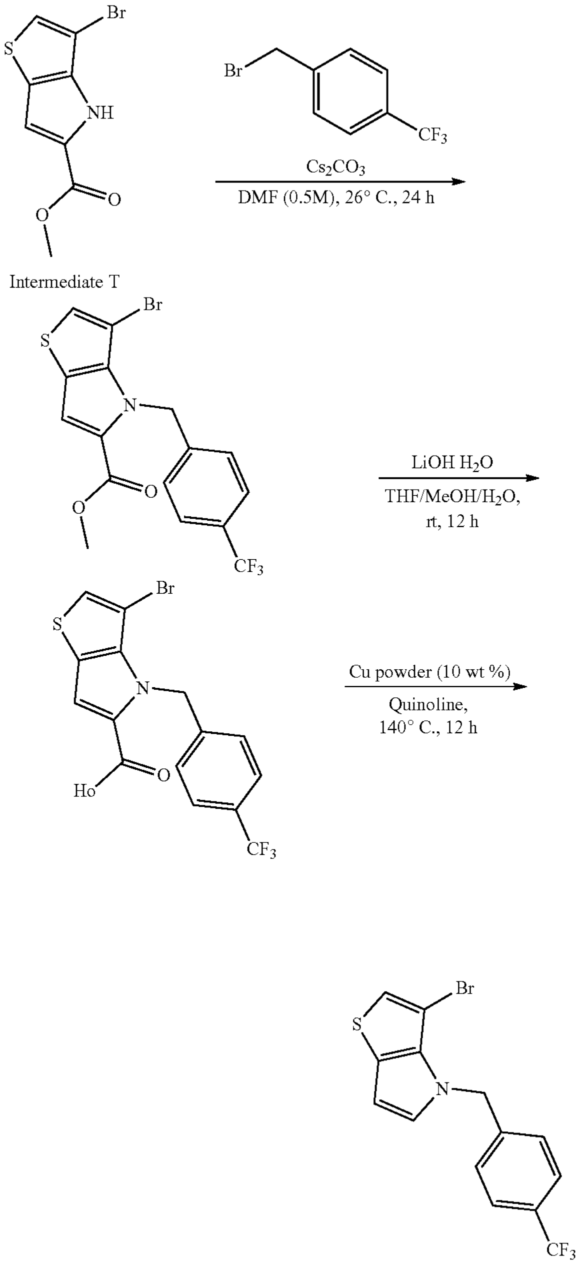

3-Bromo-4-(4-(trifluoromethyl)benzyl)-4H-thieno[3,2-b]pyrrole was obtained as a yellow liquid in the same manner as in Steps 1 to 3 of Example 79, except that 1-bromomethyl)benzene was used instead of 4-bromo methylbiphenyl in Step 1 of Example 79. $^1$H NMR (300 MHz, chloroform-d) δ 7.60-7.55 (m, 2H), 7.23-7.17 (m, 2H), 7.03-6.98 (m, 1H), 6.88-6.85 (m, 1H), 6.44 (d, J=3.0 Hz, 1H), 5.57 (d, J=9.4 Hz, 2H).

Step 4: Synthesis of 4-(4-(trifluoromethyl)benzyl)-4H-thieno[3,2-b]pyrrole-3-carboxylic acid

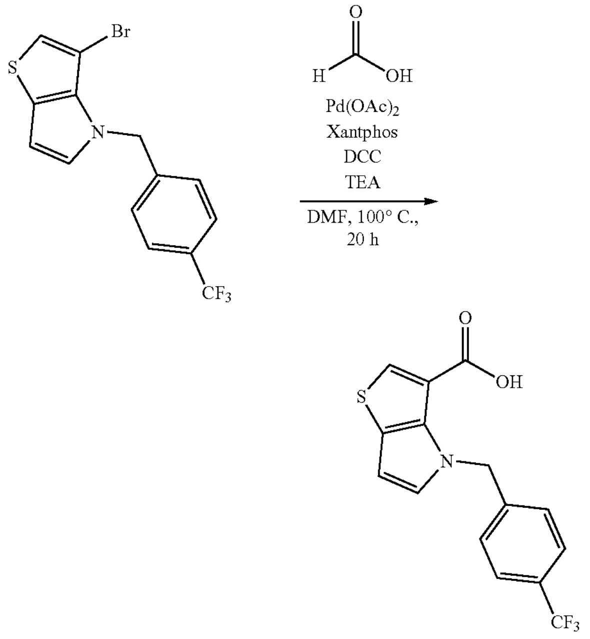

$Pd(OAc)_2$ (3 mol %) and Xantphos (3 mol %) were placed in an oven-dried tube under vacuum and substituted three times with argon, and then a solution of formic acid (0.24 mL, 6.258 mmol) and 3-bromo-4-(4-(trifluoromethyl)benzyl)-4H-thieno[3,2-b]pyrrole (322 mg, 0.894 mmol) in DMF (3.0 mL) was added. DCC (37 mg, 0.179 mmol) and $Et_3N$ (0.25 mL, 1.788 mmol) were added, and then the tube was sealed, and the mixture was stirred at 100° C. for 20 hours. The reaction mixture was filtered and concentrated under reduced pressure, and then the crude product was purified by silica gel column chromatography to obtain 4-(4-(trifluoromethyl)benzyl)-4H-thieno[3,2-b]pyrrole-3-carboxylic acid (124 mg, yield 43%) as a white solid. $^1$H NMR (300 MHz, chloroform-d) δ 8.09 (d, J=1.3 Hz, 1H), 7.51 (d, J=8.1 Hz, 2H), 7.11 (d, J=8.1 Hz, 2H), 6.95 (dd, J=3.1, 1.3 Hz, 1H), 6.51 (d, J=3.1 Hz, 1H), 5.81 (s, 2H).

Steps 5 and 6: Synthesis of 6-(4-(4-(trifluoromethyl)benzyl)-4H-thieno[3,2-b]pyrrole-3-carboxamido)spiro[3.3]heptane-2-carboxylic acid

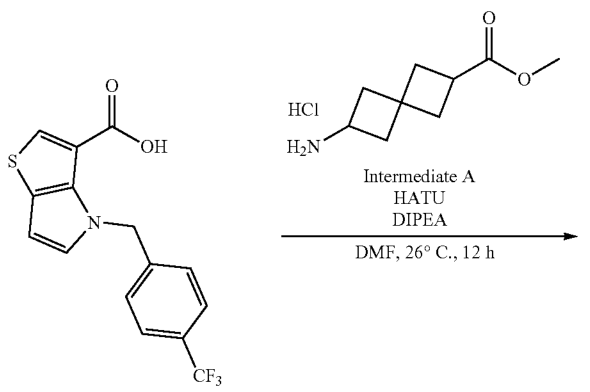

-continued

-continued

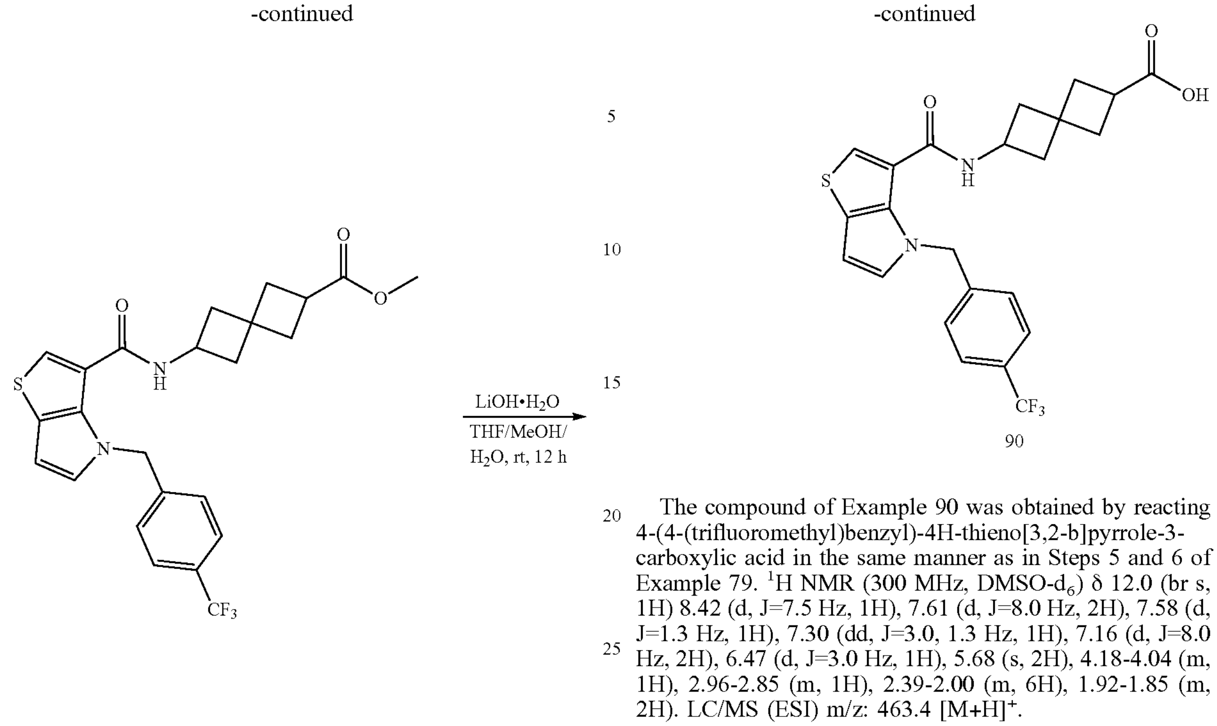

90

The compound of Example 90 was obtained by reacting 4-(4-(trifluoromethyl)benzyl)-4H-thieno[3,2-b]pyrrole-3-carboxylic acid in the same manner as in Steps 5 and 6 of Example 79. $^1$H NMR (300 MHz, DMSO-$d_6$) δ 12.0 (br s, 1H) 8.42 (d, J=7.5 Hz, 1H), 7.61 (d, J=8.0 Hz, 2H), 7.58 (d, J=1.3 Hz, 1H), 7.30 (dd, J=3.0, 1.3 Hz, 1H), 7.16 (d, J=8.0 Hz, 2H), 6.47 (d, J=3.0 Hz, 1H), 5.68 (s, 2H), 4.18-4.04 (m, 1H), 2.96-2.85 (m, 1H), 2.39-2.00 (m, 6H), 1.92-1.85 (m, 2H). LC/MS (ESI) m/z: 463.4 $[M+H]^+$.

The compounds of Examples 91 to 94 were prepared in the same manner as in Example 90 except for the differences in the preparation methods described below.

TABLE 15

| Example No. | Chemical structure | Name | Difference in preparation method |
|---|---|---|---|
| 91 | 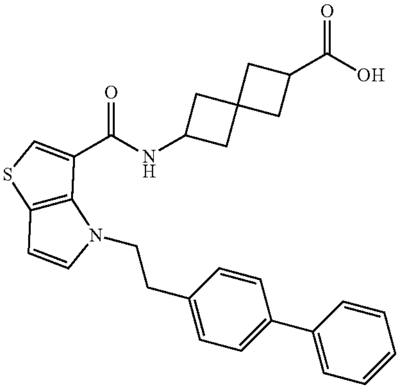 [SMILES: O=C(NC1CC2(C1)CC(C(=O)O)C2)c1csc2ccn(CCc3ccc(-c4ccccc4)cc3)c12] | 6-(4-(2-([1,1'-biphenyl]-4-yl)ethyl)-4H-thieno[3,2-b]pyrrole-3-carboxamido)spiro[3.3]heptane-2-carboxylic acid | Intermediate BB was used instead of 1-(bromomethyl)-4-(trifluoromethyl)benzene in Step 1 |

TABLE 15-continued

| Example No. | Chemical structure | Name | Difference in preparation method |
|---|---|---|---|
| 92 | 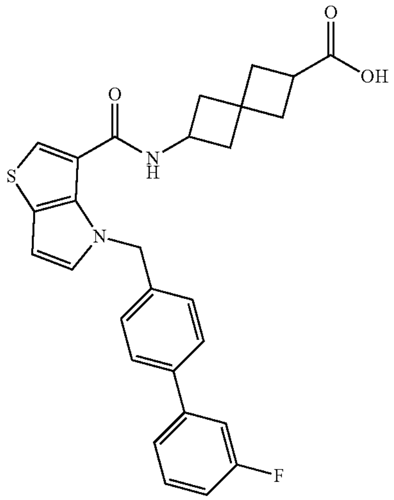 [SMILES: O=C(NC1CC2(C1)CC(C(=O)O)C2)c1csc2ccn(Cc3ccc(-c4cccc(F)c4)cc3)c12] | 6-(4-((3'-fluoro-[1,1'-biphenyl]-4-yl)methyl)-4H-thieno[3,2-b]pyrrole-3-carboxamido)spiro[3.3]heptane-2-carboxylic acid | Intermediate CC was used instead of 1-(bromomethyl)-4-(trifluoromethyl)benzene in Step 1 |
| 93 | 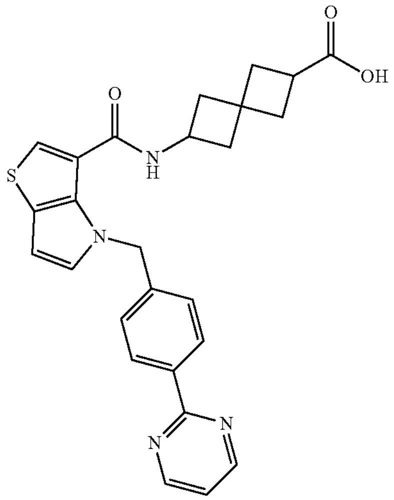 [SMILES: O=C(NC1CC2(C1)CC(C(=O)O)C2)c1csc2ccn(Cc3ccc(-c4ncccn4)cc3)c12] | 6-(4-(4-(pyrimidin-2-yl)benzyl)-4H-thieno[3,2-b]pyrrole-3-carboxamido)spiro[3.3]heptane-2-carboxylic acid | Intermediate DD was used instead of 1-(bromomethyl)-4-(trifluoromethyl)benzene in Step 1 |
| 94 | 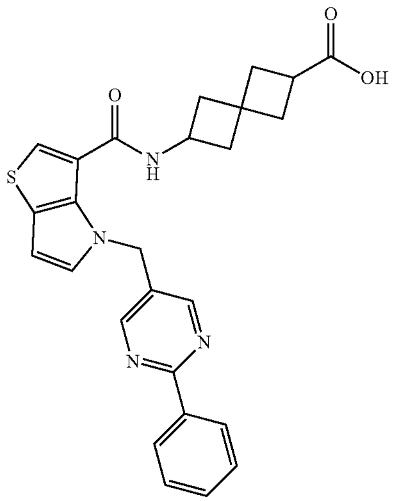 | 6-(4-((2-phenylpyrimidin-5-yl)methyl)-4H-thieno[3,2-b]pyrrole-3-carboxamido)spiro[3.3]heptane-2-carboxylic acid | Intermediate EE was used instead of 1-(bromomethyl)-4-(trifluoromethyl)benzene in Step 1 |

TABLE 16

| Example No. | LC/MS (ESI) m/z: [M + H]$^+$ | NMR |
|---|---|---|
| 91 | [M + H]$^+$ = 485.4, [M + K]$^+$ = 522.4, [M + H + DMSO]$^+$ = 563.4 | $^1$H NMR (300 MHz, DMSO-d$_6$) δ 8.69-8.59 (m, 1H), 7.74 (d, J = 1.2 Hz, 1H), 7.70-7.62 (m, 2H), 7.60-7.56 (m, 2H), 7.48-7.43 (m, 2H), 7.37-7.32 (m, 1H), 7.31-7.21 (m, 3H), 4.57-4.52 (m, 2H), 4.31-4.24 (m, 1H), 2.99-2.87 (m, 3H), 2.48-2.38 (m, 1H), 2.32-2.21 (m, 3H), 2.15-1.99 (m, 4H). |
| 92 | 489.4 | $^1$H NMR (300 MHz, DMSO-d$_6$) δ 12.06 (s, 1H), 8.48 (d, J = 7.5 Hz, 1H), 7.64-7.53 (m, 3H), 7.52-7.45 (m, 3H), 7.31 (dd, J = 3.0, 1.3 Hz, 1H), 7.20-7.14 (m, 1H), 7.16-7.11 (m, 2H), 6.45 (d, J = 2.9 Hz, 1H), 5.62 (s, 2H), 4.24-4.16 (m, 1H), 2.97-2.86 (m, 1H), 2.43-2.35 (m, 1H), 2.10-1.90 (m, 7H). |
| 93 | 473.5 | $^1$H NMR (300 MHz, DMSO-d$_6$) δ 12.01 (s, 1H), 8.91-8.83 (m, 2H), 8.47 (d, J = 7.4 Hz, 1H), 8.26 (d, J = 7.8 Hz, 2H), 7.57 (s, 1H), 7.43-7.40 (m, 1H), 7.32 (s, 1H), 7.17 (d, J = 7.9 Hz, 2H), 6.46 (s, 1H), 5.65 (s, 2H), 4.22-4.14 (m, 1H), 2.96-2.85 (m, 1H), 2.42-2.32 (m, 1H), 2.29-2.15 (m, 3H), 2.12-1.83 (m, 4H). |
| 94 | 473.3 | $^1$H NMR (300 MHz, DMSO-d$_6$) δ 12.02 (s, 1H), 8.53 (s, 2H), 8.34-8.30 (m, 2H), 7.64 (s, 1H), 7.54-7.48 (m, 3H), 7.40-7.36 (m, 1H), 6.50 (d, J = 3.0 Hz, 1H), 5.68 (s, 2H), 5.57 (d, J = 8.0 Hz, 1H), 4.24-4.10 (m, 1H), 2.98-2.83 (m, 1H), 2.42-2.32 (m, 1H), 2.30-2.14 (m, 3H), 2.12-1.98 (m, 2H), 1.96-1.83 (m, 2H). |

Example 95: 6-(4-(3'-fluoro-5'-methoxy-[1,1'-biphenyl]-4-yl)methyl)-2-methyl-4H-thieno[3,2-b]pyrrole-3-carboxamido)spiro[3.3]heptane-2-carboxylic acid

Steps 1 to 3: Synthesis of 3-bromo-4-((3'-fluoro-5'-methoxy-[1,1'-biphenyl]-4-yl)methyl)-2-methyl-4H-thieno[3,2-b]pyrrole

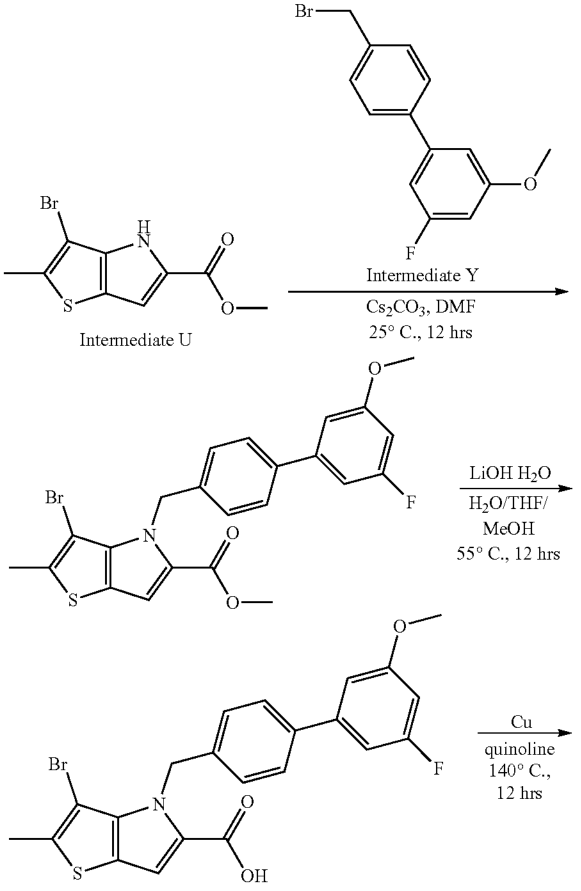

-continued

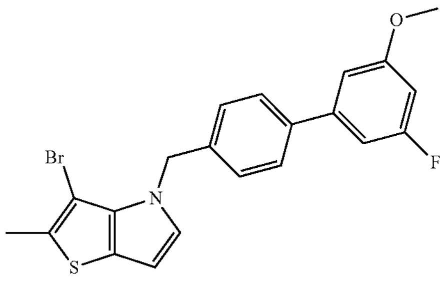

3-Bromo-4-((3'-fluoro-5'-methoxy-[1,1'-biphenyl]-4-yl)methyl)2-methyl-4H-thieno[3,2-b]pyrrole was obtained by using Intermediate U and Intermediate Y as starting materials in the same manner as in Steps 1 to 3 of Example 79. $^1$H NMR (400 MHz, $CDCl_3$) δ 7.50 (d, J=8.3 Hz, 2H), 7.18 (d, J=8.1 Hz, 2H), 6.92-6.79 (m, 3H), 6.60 (td, J=2.3, 10.5 Hz, 1H), 6.37 (d, J=2.9 Hz, 1H), 5.57 (s, 2H), 3.84 (s, 3H), 2.44 (s, 3H). LC/MS (ESI) m/z: 430.2 [M+1].

Step 4: Synthesis of methyl 4-((3'-fluoro-5'-methoxy-[1,1'-biphenyl]-4-yl)methyl)-2-methyl-4H-thieno[3,2-b]pyrrole-3-carboxylate

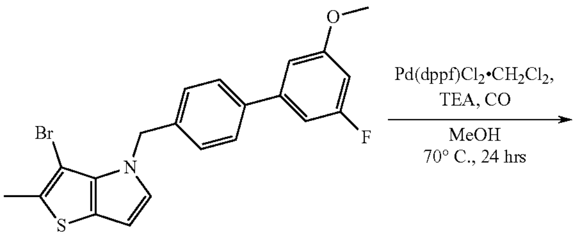

-continued

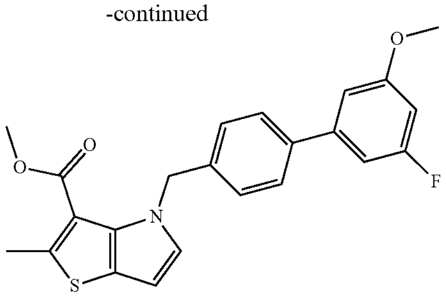

To a solution of 3-bromo-4-((3'-fluoro-5'-methoxy-[1,1'-biphenyl]-4-yl)methyl)2-methyl-4H-thieno[3,2-b]pyrrole (410 mg, 953 umol, 1.00 equiv) in MeOH (4 mL), Pd(dppf) $Cl_2 \cdot CH_2Cl_2$ (156 mg, 191 umol, 0.2 equiv) and TEA (289 mg, 2.86 mmol, 398 uL, 3.0 equiv) were added under $N_2$ atmosphere. The reaction mixture was substituted three times under CO atmosphere and then stirred under CO (50 Psi) at 70° C. for 24 hours. The reaction mixture was cooled, filtered, and concentrated, and then the crude product was purified by silica gel column chromatography (petroleum ether/ethyl acetate=50/1 to 20/1) to obtain methyl 4-((3'-fluoro-5'-methoxy-[1,1'-biphenyl]-4-yl)methyl)-2-methyl-4H-thieno[3,2-b]pyrrole-3-carboxylate (280 mg, yield 71.7%) as a yellow oil. $^1$H NMR (400 MHz, DMSO) δ 7.46 (d, J=8.40 Hz, 2H), 7.07 (d, J=8.40 Hz, 2H), 6.93-6.82 (m, 3H), 6.59 (td, J=2.40, 10.4 Hz, 1H), 6.40 (d, J=3.00 Hz, 1H), 5.64 (s, 2H), 3.84 (s, 3H), 3.76 (s, 3H), 2.69 (s, 3H).

Step 5: Synthesis of 4-((3'-fluoro-5'-methoxy-[1,1'-biphenyl]-4-yl)methyl)-2-methyl-4H-thieno[3,2-b]pyrrole-3-carboxylic acid

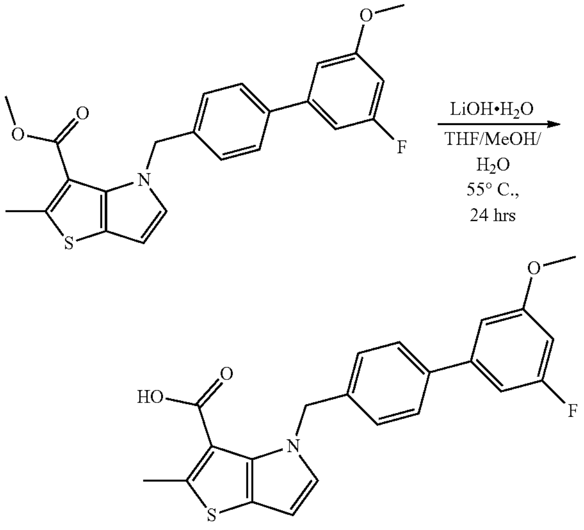

To a solution of methyl 4-((3'-fluoro-5'-methoxy-[1,1'-biphenyl]-4-yl)methyl)-2-methyl-4H-thieno[3,2-b]pyrrole-3-carboxylate (250 mg, 611 umol, 1.00 equiv) in MeOH (1 mL) and THF (1 mL), $LiOH \cdot H_2O$ (1 M, 3.66 mL, 6.00 equiv) was added and stirred at 55° C. for 24 hours. The reaction mixture was partially concentrated and then acidified with 1 N HCl solution (pH=3), and the aqueous layer was extracted with EtOAc (50 mL×2). The organic layer was washed with brine (50 mL×1), dried over $Na_2SO_4$, then filtered, and concentrated under reduced pressure to obtain 4-((3'-fluoro-5'-methoxy-[1,1'-biphenyl]-4-yl)methyl)-2-methyl-4H-thieno[3,2-b]pyrrole-3-carboxylic acid (220 mg, yield 91.1%) as a yellow solid. $^1$H NMR (400 MHz, DMSO) δ 13.29-12.68 (m, 1H), 7.60 (d, J=8.40 Hz, 2H), 7.21 (d, J=3.00 Hz, 1H), 7.09-6.98 (m, 4H), 6.80 (td, J=2.20, 11.2 Hz, 1H), 6.41 (d, J=3.00 Hz, 1H), 5.66 (s, 2H), 3.81 (s, 3H), 2.61 (s, 3H).

Steps 6 and 7: Synthesis of 6-(4-((3'-fluoro-5'-methoxy-[1,1'-biphenyl]-4-yl)methyl)-2-methyl-4H-thieno[3,2-b]pyrrole-3-carboxamido)spiro[3.3]heptane-2-carboxylic acid

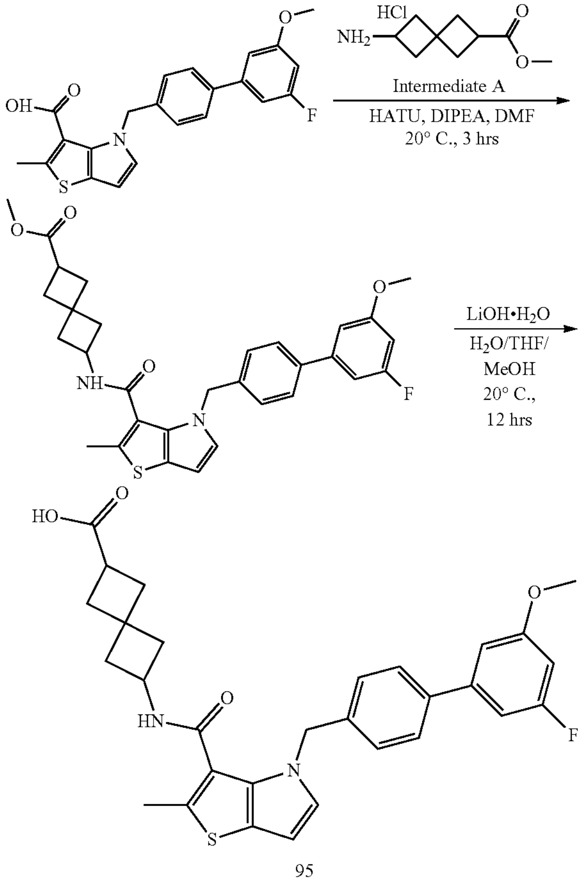

95

The compound of Example 95 was obtained by reacting 4-((3'-fluoro-5'-methoxy-[1,1'-biphenyl]-4-yl)methyl)-2-methyl-4H-thieno[3,2-b]pyrrole-3-carboxylic acid in the same manner as in Steps 5 and 6 of Example 79. $^1$H NMR (400 MHz, DMSO) δ 12.26-11.69 (m, 1H), 8.40 (d, J=7.60 Hz, 1H), 7.57 (d, J=8.20 Hz, 2H), 7.19 (d, J=3.00 Hz, 1H), 7.10 (d, J=8.20 Hz, 2H), 7.06-6.96 (m, 2H), 6.86-6.77 (m, 1H), 6.35 (d, J=2.80 Hz, 1H), 5.35 (s, 2H), 4.30-4.14 (m, 1H), 3.82 (s, 3H), 2.98-2.83 (m, 1H), 2.42 (s, 3H), 2.39-2.16 (m, 4H), 2.10-1.95 (m, 2H), 1.91-1.77 (m, 2H). LC/MS (ESI) m/z: 533.1 [M+1].

Example 96: 6-(2-methyl-4-(3-phenylprop-2-yn-1-yl)-4H-thieno[3,2-b]pyrrole-3-carboxamido)spiro [3.3]heptane-2-carboxylic acid Step 1: Synthesis of 3-bromo-2-methyl-4H-thieno [3,2-b]pyrrole-5-carboxylic acid

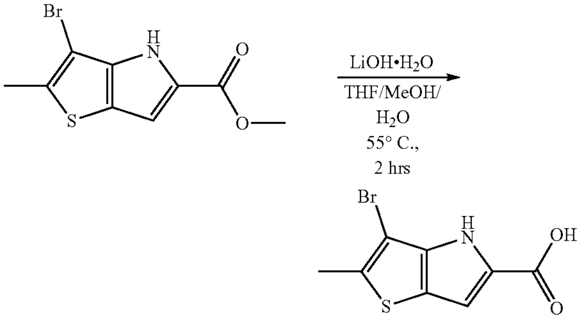

To a solution of Intermediate U (3.00 g, 10.9 mmol, 1.00 equiv) in THF (15 mL) and MeOH (15 mL), LiOH·$H_2O$ (1 M, 32.8 mL, 3.00 equiv) was added and stirred at 55° C. for 2 hours. The reaction mixture was partially concentrated and acidified with 1 N HCl solution (pH=3), and then the aqueous layer was extracted with EtOAc (50 mL×2). The organic layer was filtered and concentrated under reduced pressure to obtain 3-bromo-2-methyl-4H-thieno[3,2-b]pyrrole-5-carboxylic acid (2.70 g, 10.38 mmol, yield 94.8%) as a yellow solid. $^1H$ NMR (400 MHz, $CDCl_3$) δ 7.09 (d, J=8.60 Hz, 2H), 6.91-6.82 (m, 2H), 6.77 (d, J=3.00 Hz, 1H), 6.32 (d, J=3.00 Hz, 1H), 5.47 (s, 2H), 3.79 (s, 3H), 2.44 (s, 3H).

Step 2: Synthesis of 3-bromo-2-methyl-4H-thieno[3,2-b]pyrrole

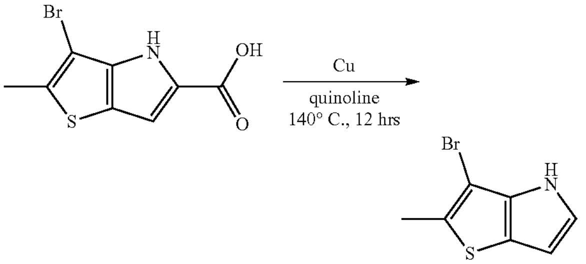

To a solution of 3-bromo-2-methyl-4H-thieno[3,2-b]pyrrole-5-carboxylic acid (2.00 g, 7.69 mmol, 1.00 equiv) in quinoline (20 mL), Cu powder (210 mg, 3.32 mmol) was added and stirred at 140° C. for 12 hours. The reaction mixture was washed with 1 N HCl (1×150 mL) and brine (1×50 mL). The organic layer was dried over $Na_2SO_4$, then filtered, and concentrated under reduced pressure. The crude product was purified by prep-HPLC (FA condition) to obtain 3-bromo-2-methyl-4H-thieno[3,2-b]pyrrole (810 mg, 3.75 mmol, yield 48.7%) as a gray solid. $^1H$ NMR (400 MHz, $CDCl_3$) δ 8.17 (br s, 1H), 6.96 (t, J=2.60 Hz, 1H), 6.44 (dd, J=2.00, 3.00 Hz, 1H), 2.47 (s, 3H).

Step 3: Synthesis of 3-bromo-2-methyl-4-(3-phenylprop-2-yn-1-yl)-4H-thieno[3,2-b]pyrrole

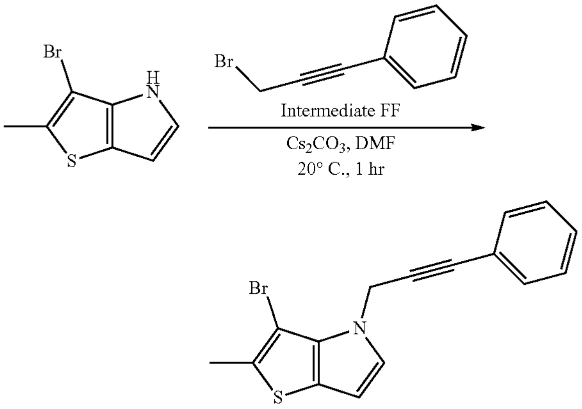

To a solution of 3-bromo-2-methyl-4H-thieno[3,2-b]pyrrole (300 mg, 1.39 mmol, 1.00 equiv) and Intermediate FF (406 mg, 2.08 mmol, 1.50 equiv) in DMF (3 mL), $Cs_2CO_3$ (1.13 g, 3.47 mmol, 2.50 equiv) was added and stirred at 20° C. for 1 hour. The reaction mixture was partially concentrated and extracted with 50 mL of distilled water and EA (2×50 mL). The organic layer was washed with brine (3×20 mL), dried over $Na_2SO_4$, then filtered, and concentrated under reduced pressure. The crude product was purified by prep-HPLC (FA condition) to obtain 3-bromo-2-methyl-4-(3-phenylprop-2-yn-1-yl)-4H-thieno[3,2-b]pyrrole (180 mg, yield 39.2%) as a yellow solid. $^1H$ NMR (400 MHz, $CDCl_3$) δ 7.52-7.43 (m, 2H), 7.39-7.28 (m, 3H), 7.04 (d, J=2.80 Hz, 1H), 6.40-6.32 (m, 1H), 5.35 (s, 2H), 2.46 (s, 3H).

Steps 4 to 7: Synthesis of 6-(2-methyl-4-(3-phenylprop-2-yn-1-yl)-4H-thieno[3,2-b]pyrrole-3-carboxamido)spiro [3.3]heptane-2-carboxylic acid

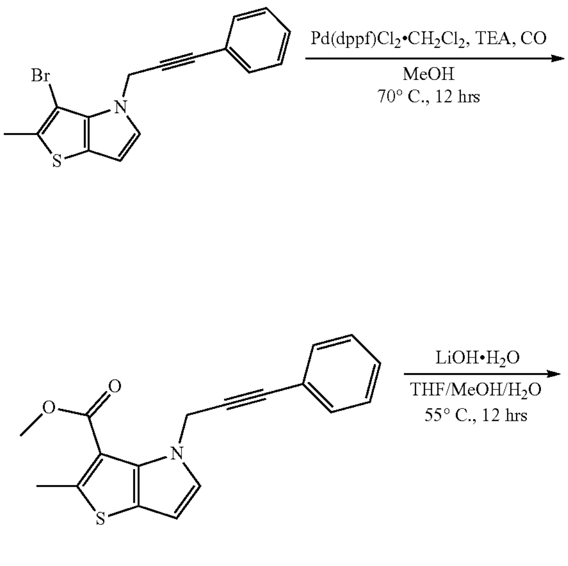

-continued

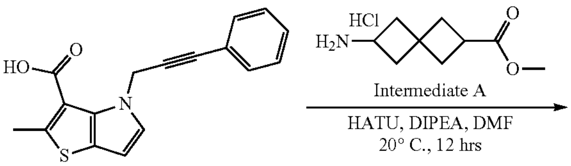

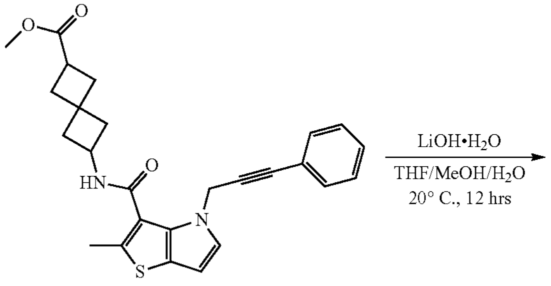

-continued

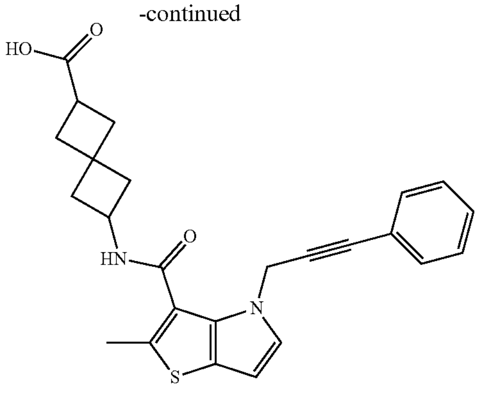

96

The compound of Example 96 was obtained as an off-white solid by reacting 3-bromo-2-methyl-4-(3-phenylprop-2-yn-1-yl)-4H-thieno[3,2-b]pyrrole in the same manner as in Steps 4 to 7 of Example 95. $^{1}$H NMR (400 M Hz, $CDCl_3$) δ 7.42-7.35 (m, 2H), 7.35-7.29 (m, 3H), 6.98 (d, J=3.00 Hz, 1H), 6.34 (d, J=3.00 Hz, 1H), 5.92 (br d, J=7.60 Hz, 1H), 5.16 (s, 2H), 4.54-4.40 (m, 1H), 3.09-2.99 (m, 1H), 2.64-2.59 (m, 3H), 2.59-2.53 (m, 1H), 2.49-2.34 (m, 3H), 2.31-2.22 (m, 1H), 2.15-2.06 (m, 1H), 1.92 (ddd, J=8.60, 11.2, 16.0 Hz, 2H). LC/MS (ESI) m/z: 433.2 [M+1].

The compounds of Examples 97 and 98 were prepared in the same manner as in Example 96 except for the differences in the preparation methods described below.

TABLE 17

| Example No. | Chemical structure | Name | Difference in preparation method |
|---|---|---|---|
| 97 | 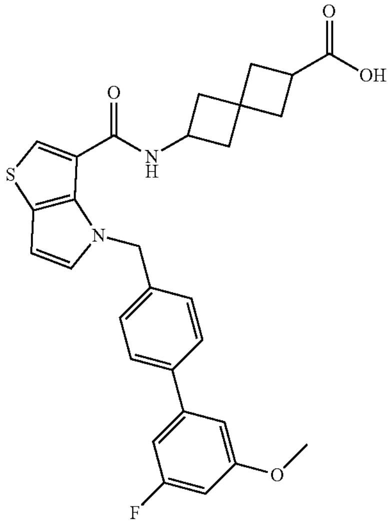 [SMILES: COc1cc(F)cc(-c2ccc(Cn3ccc4scc(C(=O)NC5CC6(C5)CC(C(=O)O)C6)c43)cc2)c1] | 6-4-((3'-fluoro-5'-methoxy[1,1'-biphenyl-4-yl)methyl)-4H-thieno[3,2-b]pyrrole-3-carboxamido)spiro[3.3]heptane-2-carboxylic acid | Intermediate T was used instead of Intermediate U in Step 1, and Intermediate Y was used instead of Intermediate FF in Step 3 |

TABLE 17-continued

| Example No. | Chemical structure | Name | Difference in preparation method |
|---|---|---|---|
| 98 | 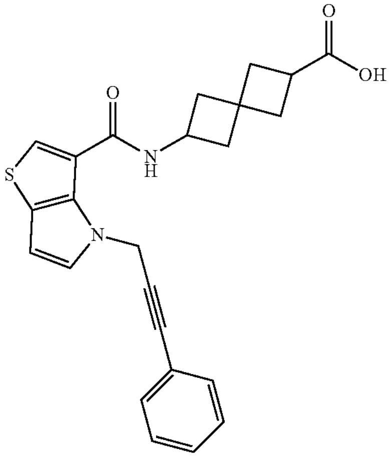 [SMILES: O=C(NC1CC2(C1)CC(C(=O)O)C2)c1csc2ccn(CC#Cc3ccccc3)c12] | 6-(2-4-(3-phenylprop-2-yn-1-yl)-4H-thieno[3,2-b]pyrrole-3-carboxamido)spiro[3.3]heptane-2-carboxylic acid | Intermediate T was used instead of Intermediate U in Step 1 |

TABLE 18

| Example No. | LC/MS (ESI) m/z: $[M + H]^+$ | NMR |
|---|---|---|
| 97 | 519.0 | $^1$H NMR (400 MHz, CHLOROFORM-d) δ 7.35 (d, J = 8.20 Hz, 2H), 7.19 (d, J = 3.20 Hz, 1H), 7.03 (d, J = 8.20 Hz, 2H), 6.92 (d, J = 1.80 Hz, 1H), 6.80-6.71 (m, 2H), 6.51 (td, J = 2.20, 10.4 Hz, 1H), 6.37 (d, J = 3.00 Hz, 1H), 5.86 (br d, J =7.60 Hz, 1H), 5.54 (s, 2H), 4.32-4.18 (m, 1H), 3.75 (s, 3H), 2.96 (quin, J = 8.40 Hz, 1H), 2.48-2.39 (m, 1H), 2.38-2.32 (m, 1H), 2.29 (br d, J = 8.20 Hz, 2H), 2.19 (dd, J = 8.2, 11.6 Hz, 1H), 2.09-2.00 (m, 1H), 1.75-1.64 (m, 2H). |
| 98 | 418.9 | $^1$H NMR (400 MHz, METHANOL-$d_4$) δ 7.46 (d, J = 1.20 Hz, 1H), 7.26-7.22 (m, 2H), 7.22-7.17 (m, 3H), 7.02 (dd, J = 1.20, 3.00 Hz, 1H), 6.30 (d, J = 3.00 Hz, 1H), 5.26 (s, 2H), 4.19 (q, J = 8.20 Hz, 1H), 2.79 (br t, J = 8.20 Hz, 1H), 2.39-2.33 (m, 1H), 2.19 (br d, J = 8.20 Hz, 3H), 2.10-2.04 (m, 1H), 1.97-1.92 (m, 2H), 1.90-1.85 (m, 1H). |

Example 99: 6-(4-(4-(pyridin-3-yl)benzyl)-4H-thieno[3,2-b]pyrrole-3-carboxamido)spiro[3.3]heptane-2-carboxylic acid

Step 1: Synthesis of methyl 3-bromo-4-(4-(pyridin-3-yl)benzyl)-4H-thieno[3,2-b]pyrrole-5-carboxylate

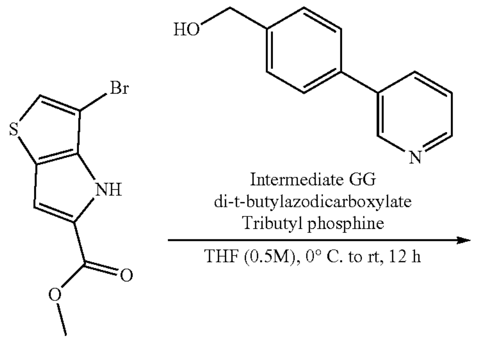

Intermediate T

-continued

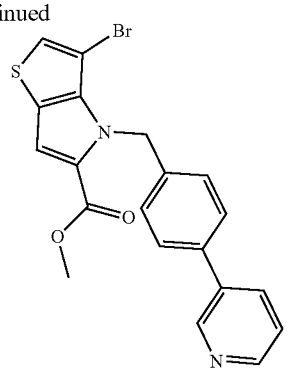

Intermediate GG (392 mg, 2.1145 mmol) was dissolved in THF and cooled to 0° C., and then Intermediate T (500 mg, 1.9223 mmol) and tributylphosphine (0.62 mL, 2.499 mmol) were added. Di-tert-butylazodicarboxylate (0.49 mL, 2.499 mmol) was slowly added and stirred at 50° C. for 12 hours. Saturated $NaHCO_3$ aqueous solution was added and the mixture was stirred for 10 minutes and then extracted with EtOAc. The organic layer was washed with brine, dried over $Na_2SO_4$, and concentrated under reduced pressure, and then the crude product was purified by silica gel chromatography (petroleum ether:EtOAc 80:20→50:50) to obtain methyl 3-bromo-4-(4-(pyridin-3-yl)benzyl)-4H-thieno[3,2-b]pyrrole-5-carboxylate (639 mg, yield 78%). $^1$H NMR (300 MHz, Chloroform-d) δ 8.90-8.81 (m, 1H), 8.62 (dd, J=5.1, 1.5 Hz, 1H), 8.17 (dt, J=8.1, 1.9 Hz, 1H), 7.64 (dd, J=8.1, 5.1 Hz, 1H), 7.51 (d, J=8.3 Hz, 2H), 7.27 (d, J=3.7 Hz, 1H), 7.19 (d, J=8.3 Hz, 2H), 6.16 (s, 2H), 3.82 (s, 3H).

Step 2: Synthesis of 3-bromo-4-(4-(pyridin-3-yl)benzyl)-4H-thieno[3,2-b]pyrrole-5-carboxylic acid

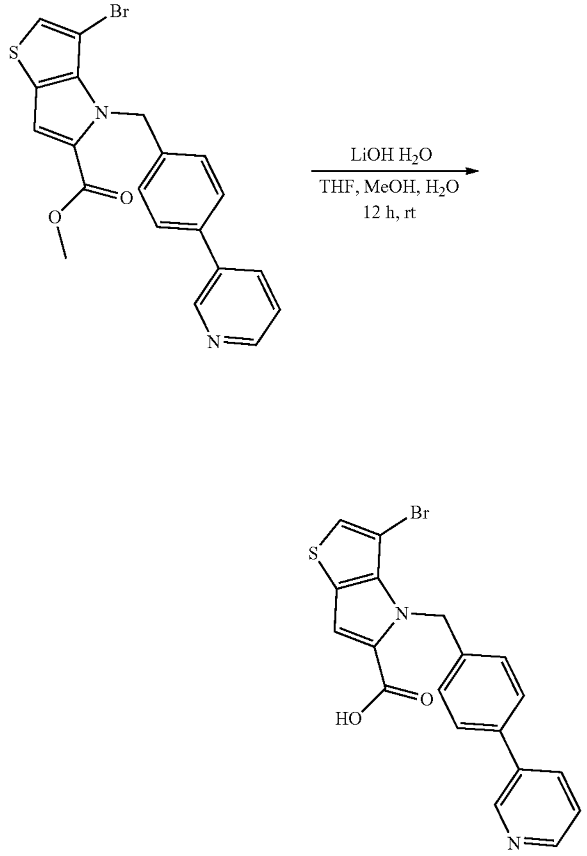

To a solution of methyl 3-bromo-4-(4-(pyridin-3-yl)benzyl)-4H-thieno[3,2-b]pyrrole-5-carboxylate (639 mg, 1.4954 mmol) in THF/MeOH/$H_2O$ (1/1/1), LiOH·$H_2O$ (188 mg, 4.4862 mmol) was added and stirred for 12 hours. The reaction mixture was partially concentrated, then acidified with 1 N HCl solution, and washed with distilled water to obtain 3-bromo-4-(4-(pyridin-3-yl)benzyl)-4H-thieno[3,2-b]pyrrole-5-carboxylic acid (609 mg, yield 98%) as a white solid. $^1$H NMR (300 MHz, DMSO-d6) δ 12.82 (s, 1H), 8.93 (d, J=2.3 Hz, 1H), 8.62 (dd, J=5.0, 1.5 Hz, 1H), 8.21 (dt, J=8.2, 1.9 Hz, 1H), 7.73 (s, 1H), 7.72-7.67 (m, 2H), 7.61 (dd, J=8.0, 5.0 Hz, 1H), 7.35 (s, 1H), 7.06 (d, J=8.2 Hz, 2H), 6.11 (s, 2H).

Step 3: Synthesis of 3-bromo-4-(4-(pyridin-3-yl)benzyl)-4H-thieno[3,2-b]pyrrole

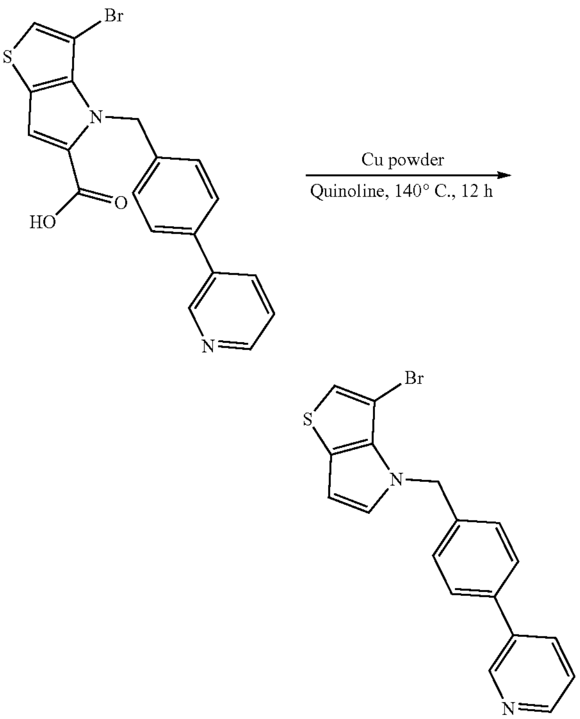

A solution of 3-bromo-4-(4-(pyridin-3-yl)benzyl)-4H-thieno[3,2-b]pyrrole-5-carboxylic acid (759 mg, 1.8365 mmol) and Cu powder (76 mg, 10 wt %) in quinoline (20 mL) was stirred at 140° C. for 12 hours. The reaction mixture was cooled, acidified with 6 N HCl solution, and then extracted with $Et_2O$. The organic layer was dried over $MgSO_4$ and then concentrated under reduced pressure, and the crude product was purified by flash column chromatography to obtain 3-bromo-4-(4-(pyridin-3-yl)benzyl)-4H-thieno[3,2-b]pyrrole (crude product).

Step 4: Synthesis of 4-(4-(pyridin-3-yl)benzyl)-4H-thieno[3,2-b]pyrrole-3-carboxylic acid

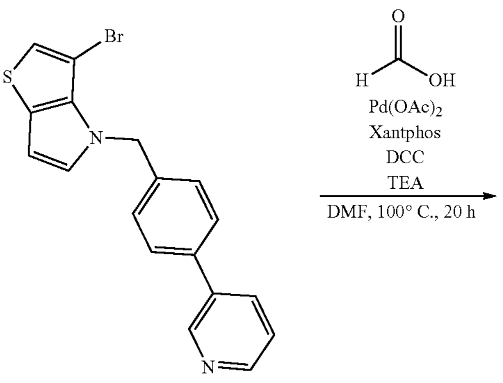

-continued

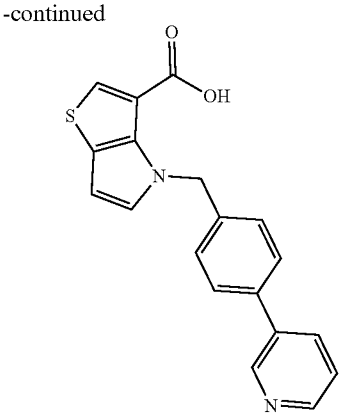

$Pd(OAc)_2$ (3 mol %) and Xantphos (3 mol %) were added to an oven-dried tube under $N_2$ atmosphere and then refilled three times with argon. A solution of formic acid (0.4 mL, 10.5966 mmol) and 3-bromo-4-(4-(pyridin-3-yl)benzyl)-4H-thieno[3,2-b]pyrrole (559 mg, 1.5138 mmol) in DMF (3.0 mL) was added. DCC (62 mg, 0.3028 mmol) and $Et_3N$ (0.42 mL, 3.0276 mmol) were added, and then the tube was sealed, and the mixture was stirred at 100° C. for 20 hours. The reaction mixture was filtered and concentrated under reduced pressure, and then the crude product was purified by silica gel column chromatography to obtain 4-(4-(pyridin-3-yl)benzyl)-4H-thieno[3,2-b]pyrrole-3-carboxylic acid (crude product).

Step 5: Synthesis of methyl 6-(4-(4-(pyridin-3-yl)benzyl)-4H-thieno[3,2-b]pyrrole-3-carboxamido)spiro[3.3]heptane-2-carboxylate

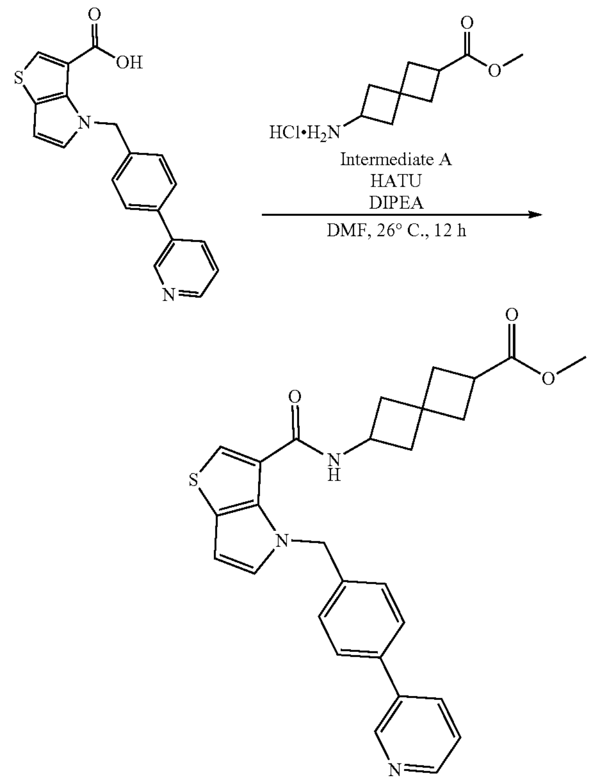

To a solution of 4-(4-(pyridin-3-yl)benzyl)-4H-thieno[3,2-b]pyrrole-3-carboxylic acid (512 mg) and HATU (582 mg, 1.531 mmol) in DMF (4 mL), DIPEA (0.8 mL, 4.593 mmol) was added and stirred for 10 minutes, and then Intermediate A (315 mg, 1.531 mmol) was added and stirred for 12 hours. The reaction mixture was diluted with ethyl acetate and washed with distilled water and brine. The organic layer was dried over $Na_2SO_4$ and concentrated under reduced pressure, and then the crude product was purified by column chromatography to obtain methyl 6-(4-(4-(pyridin-3-yl)benzyl)-4H-thieno[3,2-b]pyrrole-3-carboxamido)spiro[3.3]heptane-2-carboxylate (147 mg, yield 16%). $^1H$ NMR (300 MHz, Chloroform-d) δ 8.87 (d, J=2.1 Hz, 1H), 8.64 (d, J=5.5 Hz, 1H), 8.46 (d, J=8.1 Hz, 1H), 7.90 (dd, J=8.1, 5.5 Hz, 1H), 7.48 (d, J=8.2 Hz, 2H), 7.36-7.32 (m, 1H), 7.27 (s, 1H), 7.24 (s, 1H), 6.98 (dd, J=3.0, 1.3 Hz, 1H), 6.47 (d, J=3.0 Hz, 1H), 6.06 (d, J=7.7 Hz, 1H), 5.71 (d, J=5.9 Hz, 2H), 4.37-4.29 (m, 1H), 3.66 (s, 3H), 3.07-2.95 (m, 1H), 2.62-2.47 (m, 1H), 2.47-2.22 (m, 4H), 2.19-2.07 (m, 1H), 1.92-1.75 (m, 2H).

Step 6: Synthesis of 6-(4-(4-(pyridin-3-yl)benzyl)-4H-thieno[3,2-b]pyrrole-3-carboxamido)spiro[3.3]heptane-2-carboxylic acid

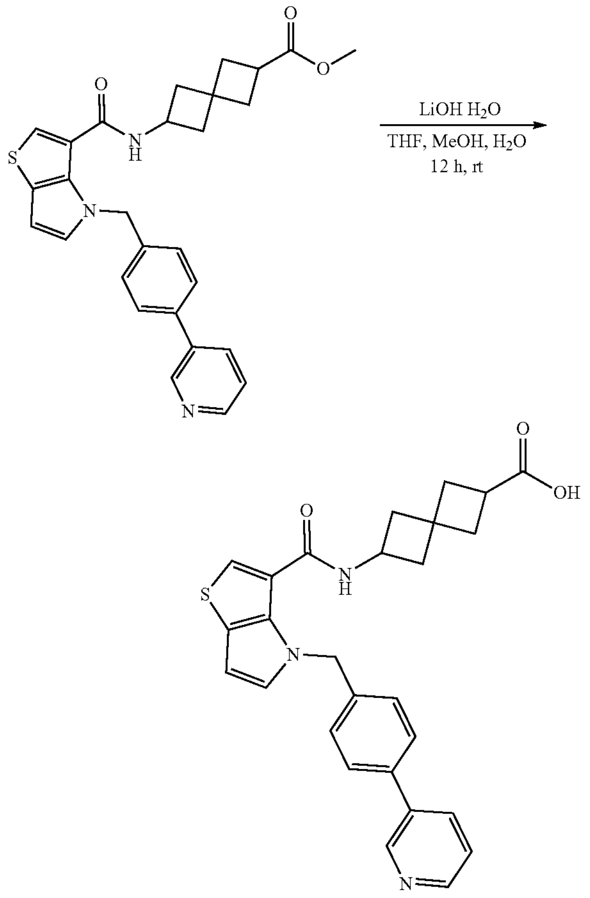

99

To a solution of methyl 6-(4-(4-(pyridin-3-yl)benzyl)-4H-thieno[3,2-b]pyrrole-3-carboxamido)spiro[3.3]heptane-2-carboxylate (147 mg, 0.3027 mmol) in THF/MeOH/$H_2O$ (1/1/1), $LiOH{\cdot}H_2O$ (38 mg, 0.9081 mmol) was added and stirred for 12 hours. The reaction mixture was partially concentrated and then acidified with 1 N HCl solution, and the aqueous layer was extracted with EtOAc. The organic layer was dried over $MgSO_4$ and then concentrated under reduced pressure to obtain the compound of Example 99 (92 mg, yield 64%). $^1$H NMR (300 MHz, DMSO-$d_6$) δ 12.04 (s, 1H), 8.83 (s, 1H), 8.54 (d, J=4.6 Hz, 1H), 8.48 (d, J=7.5 Hz, 1H), 8.01 (d, J=8.0 Hz, 1H), 7.63-7.59 (m, 2H), 7.58 (d, J=1.3 Hz, 1H), 7.46 (t, J=6.3 Hz, 1H), 7.31 (dd, J=3.0, 1.3 Hz, 1H), 7.16 (d, J=8.2 Hz, 2H), 6.45 (d, J=3.0 Hz, 1H), 5.63 (s, 2H), 4.24-4.16 (m, 1H), 2.99-2.85 (m, 1H), 2.43-2.35 (m, 1H), 2.32-1.85 (m, 7H). LC/MS (ESI) m/z: 472.4 [M+H]$^+$.

The compounds of Examples 100 to 113 were prepared in the same manner as in Example 99 except for the differences in the preparation methods described below.

TABLE 19

| Example No. | Chemical structure | Name | Difference in preparation method |
|---|---|---|---|
| 100 | 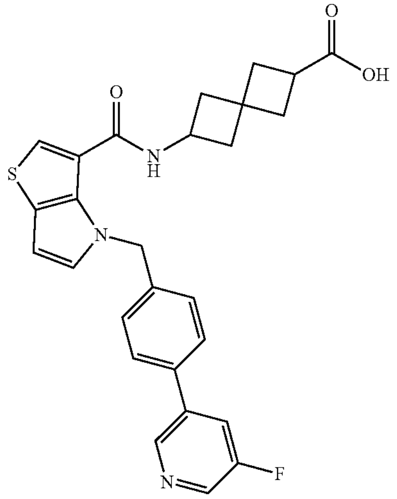 [SMILES: O=C(NC1CC2(C1)CC(C(=O)O)C2)c1csc2ccn(Cc3ccc(-c4cncc(F)c4)cc3)c12] | 6-(4-(4-(5-fluoropyridin-3-yl)benzyl)-4H-thieno[3,2-b]pyrrole-3-carboxamido)spiro[3.3]heptane-2-carboxylic acid | Intermediate HH was used instead of Intermediate GG in Step 1 |
| 101 | 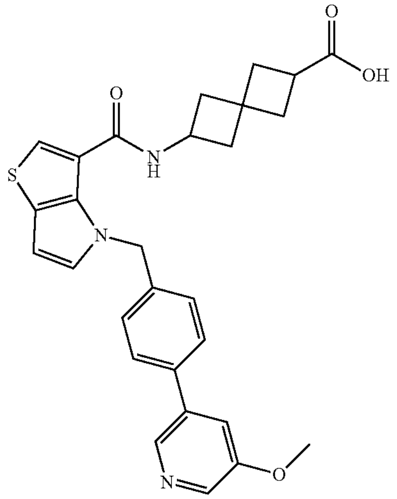 [SMILES: COc1cncc(-c2ccc(Cn3ccc4scc(C(=O)NC5CC6(C5)CC(C(=O)O)C6)c43)cc2)c1] | 6-(4-(4-(5-methoxypyridin-3-yl)benzyl)-4H-thieno[3,2-b]pyrrole-3-carboxamido)spiro[3.3]heptane-2-carboxylic acid | Intermediate II was used instead of Intermediate GG in Step 1 |

TABLE 19-continued

| Example No. | Chemical structure | Name | Difference in preparation method |
|---|---|---|---|
| 102 | 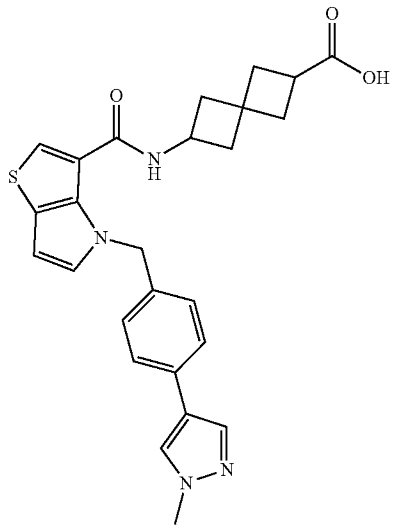 [SMILES: Cn1cc(-c2ccc(Cn3ccc4scc(C(=O)NC5CC6(C5)CC(C(=O)O)C6)c43)cc2)cn1] | 6-(4-(4-(1-methyl-1H-pyrazol-4-yl)benzyl)-4H-thieno[3,2-b]pyrrole-3-carboxamido)spiro[3.3]heptane-2-carboxylic acid | Intermediate JJ was used instead of Intermediate GG in Step 1 |
| 103 | 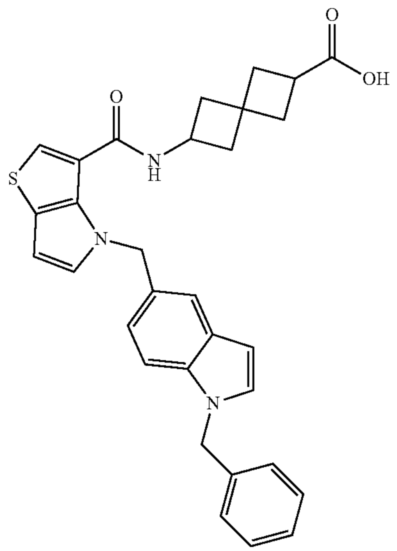 [SMILES: O=C(NC1CC2(C1)CC(C(=O)O)C2)c1csc2ccn(Cc3ccc4c(ccn4Cc4ccccc4)c3)c12] | 6-(4-((1-benzyl-IH-indol-5-yl)methyl)-4H-thieno[3,2-b]pyrrole-3-carboxamido)spiro[3.3]heptane-2-carboxylic acid | Intermediate KK was used instead of Intermediate GG in Step 1. |
| 104 | 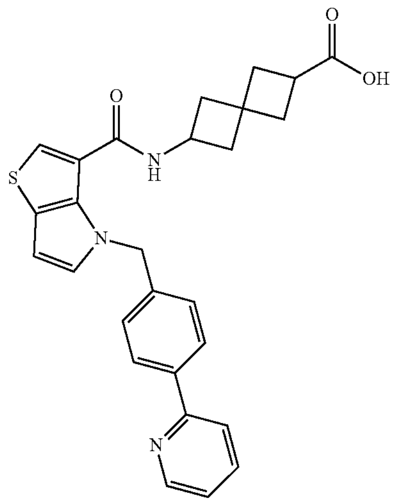 [SMILES: O=C(NC1CC2(C1)CC(C(=O)O)C2)c1csc2ccn(Cc3ccc(-c4ccccn4)cc3)c12] | 6-(4-(4-(pyridin-2-yl)benzyl)-4H-thieno[3,2-b]pyrrole-3-carboxamido)spiro[3.3]heptane-2-carboxylic acid | Intermediate LL was used instead of Intermediate GG in Step 1 |

TABLE 19-continued

| Example No. | Chemical structure | Name | Difference in preparation method |
|---|---|---|---|
| 105 | 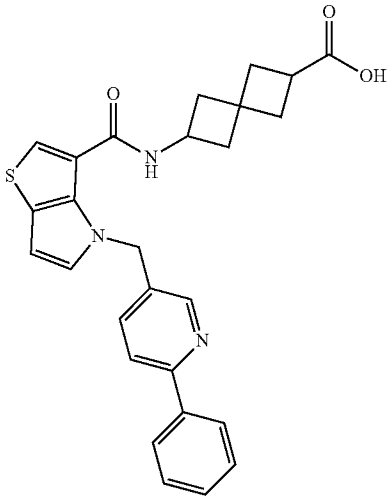 [SMILES: O=C(NC1CC2(C1)CC(C(=O)O)C2)c1csc2ccn(Cc3ccc(-c4ccccc4)nc3)c12] | 6-(4-((6-phenylpyridin-3-yl)methyl)-4H-thieno[3,2-b]pyrrole-3-carboxamido)spiro[3.3]heptane-2-carboxylic acid | Intermediate MM was used instead of Intermediate GG in Step 1 |
| 106 | 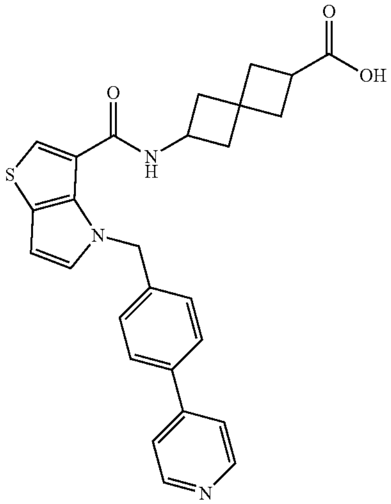 [SMILES: O=C(NC1CC2(C1)CC(C(=O)O)C2)c1csc2ccn(Cc3ccc(-c4ccncc4)cc3)c12] | 6-(4-(4-(pyridin-4-yl)benzyl)-4H-thieno[3,2-b]pyrrole-3-carboxamido)spiro[3.3]heptane-2-carboxylic acid | Intermediate NN was used instead of Intermediate GG in Step 1 |
| 107 | 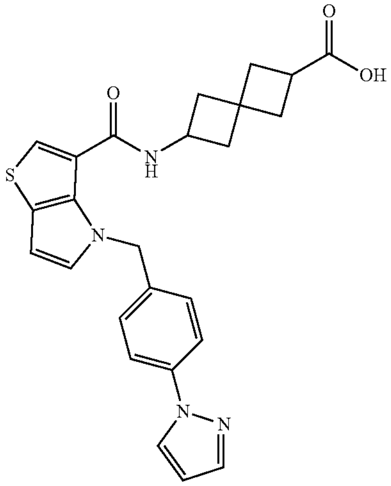 [SMILES: O=C(NC1CC2(C1)CC(C(=O)O)C2)c1csc2ccn(Cc3ccc(-n4cccn4)cc3)c12] | 6-(4-(4-(1H-pyrazol-1-yl)benzyl)-4H-thieno[3,2-b]pyrrole-3-carboxamido)spiro[3.3]heptane-2-carboxylic acid | (4-pyrazol-1-ylphenyl)methanol was used instead of Intermediate GG in Step 1 |

TABLE 19-continued

| Example No. | Chemical structure | Name | Difference in preparation method |
|---|---|---|---|
| 108 | 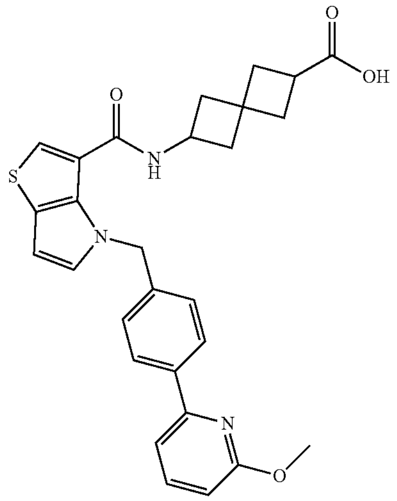 [SMILES: COc1cccc(-c2ccc(Cn3ccc4scc(C(=O)NC5CC6(C5)CC(C(=O)O)C6)c43)cc2)n1] | 6-(4-(4-(6-methoxypyridin-2-yl)benzyl)-4H-thieno[3,2-b]pyrrole-3-carboxamido)spiro[3.3]heptane-2-carboxylic acid | Intermediate OO was used instead of Intermediate GG in Step 1 |
| 109 | 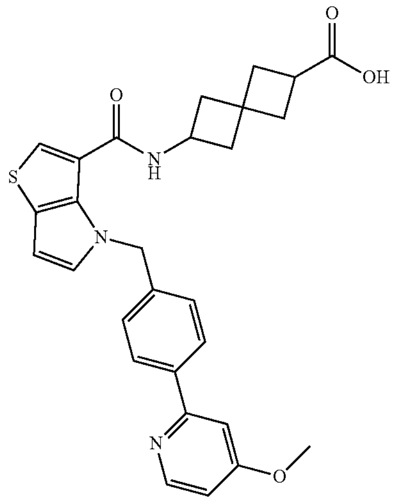 [SMILES: COc1ccnc(-c2ccc(Cn3ccc4scc(C(=O)NC5CC6(C5)CC(C(=O)O)C6)c43)cc2)c1] | 6-(4-(4-(4-methoxypyridin-2-yl)benzyl)-4H-thieno[3,2-b]pyrrole-3-carboxamido)spiro[3.3]heptane-2-carboxylic acid | Intermediate PP was used instead of Intermediate GG in Step 1 |
| 110 | 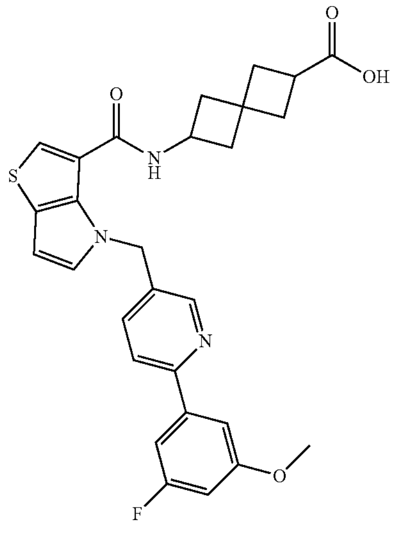 [SMILES: COc1cc(F)cc(-c2ccc(Cn3ccc4scc(C(=O)NC5CC6(C5)CC(C(=O)O)C6)c43)cn2)c1] | 6-(4-((6-(3-fluoro-5-methoxyphenyl)pyridin-3-yl)methyl)-4H-thieno[3,2-b]pyrrole-3-carboxamido)spiro[3.3]heptane-2-carboxylic acid | Intermediate QQ was used instead of Intermediate GG in Step 1 |

TABLE 19-continued

| Example No. | Chemical structure | Name | Difference in preparation method |
|---|---|---|---|
| 111 | 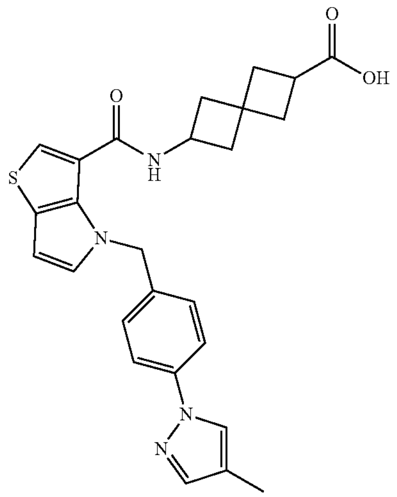 [SMILES: Cc1cnn(-c2ccc(Cn3ccc4scc(C(=O)NC5CC6(C5)CC(C(=O)O)C6)c43)cc2)c1] | 6-(4-(4-(4-methyl-1H-pyrazol-1-yl)benzyl)-4H-thieno[3,2-b]pyrrole-3-carboxamido)spiro[3.3]heptane-2-carboxylic acid | Intermediate RR was used instead of Intermediate GG in Step 1 |
| 112 | 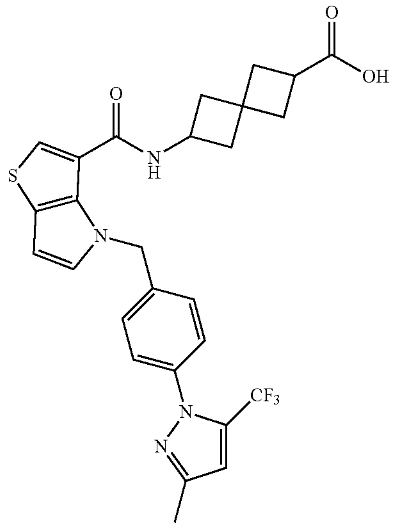 [SMILES: Cc1cc(C(F)(F)F)n(-c2ccc(Cn3ccc4scc(C(=O)NC5CC6(C5)CC(C(=O)O)C6)c43)cc2)n1] | 6-(4-(4-(3-methyl-5-(trifluoromethyl)-IH-pyrazol-1-yl)benzyl)-4H-thieno[3,2-b]pyrrole-3-carboxamido)spiro[3.3]heptane-2-carboxylic acid | Intermediate SS was used instead of Intermediate GG in Step 1 |
| 113 | 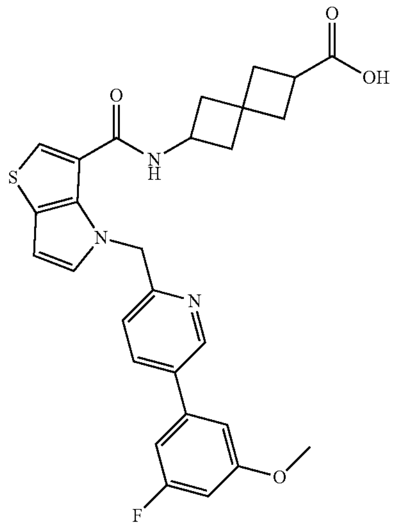 [SMILES: COc1cc(F)cc(-c2ccc(Cn3ccc4scc(C(=O)NC5CC6(C5)CC(C(=O)O)C6)c43)nc2)c1] | 6-(4-((5-(3-fluoro-5-methoxyphenyl)pyridin-2-yl)methyl)-4H-thieno[3,2-b]pyrrole-3-carboxamido)spiro[3.3]heptane-2-carboxylic acid | Intermediate TT was used instead of Intermediate GG in Step 1, and the carbonylation condition in Step 4 was modified as follows: $CO_2$ (excess), TMEDA, n-BuLi, THF, −65° C., 1 h |

TABLE 20

| Example No. | LC/MS (ESI) m/z: [M + H]$^+$ | NMR |
|---|---|---|
| 100 | 490.5 | $^1$H NMR (300 MHz, DMSO-$d_6$) δ 8.75 (s, 1H), 8.55 (d, J = 2.7 Hz, 1H), 8.48 (d, J = 7.4 Hz, 1H), 8.00 (dt. J = 10.4, 2.3 Hz, 1H), 7.67 (d, J = 8.2 Hz, 2H), 7.60 (d, J = 1.3 Hz, 1H), 7.31 (dd, J =2.9, 1.3 Hz, 1H), 7.16 (d, J = 8.2 Hz, 2H), 6.45 (d, J = 2.9 Hz, 1H), 5.64 (s, 2H), 4.26-4.15 (m, 1H), 2.95-2.84 (m, 1H), 2.45-2.33 (m, 1H), 2.30-2.11 (m, 3H), 2.11-1.87 (m, 4H). |
| 101 | 502.5 | $^1$H NMR (300 MHz, DMSO-$d_6$) δ 8.48 (d, J = 8.0 Hz, 2H), 8.34 (d, J = 2.6 Hz, 1H), 7.71 (t, J = 2.3 Hz, 1H), 7.66 (d, J = 8.2 Hz, 2H), 7.60 (d, J = 1.3 Hz, 1H), 7.31 (dd, J = 3.0, 1.3 Hz, 1H), 7.17 (d, J = 8.2 Hz, 2H), 6.45 (d, J = 3.0 Hz, 1H), 5.65 (s, 2H), 4.20 (q, J = 8.0 Hz, 1H), 3.91 (s, 3H), 2.97-2.86 (m, 1H), 2.43-2.35 (m, 1H), 2.32-2.17 (m, 3H), 2.12-1.87 (m, 4H). |
| 102 | 475.4 | $^1$H NMR (300 MHz, DMSO-$d_6$) δ 8.50 (d, J = 7.5 Hz, 1H), 8.06 (s, 1H), 7.79 (s, 1H), 7.56 (d, J = 1.3 Hz, 1H), 7.41 (d, J = 8.1 Hz, 2H), 7.28 (dd, J = 3.0, 1.3 Hz, 1H), 7.04 (d, J = 8.1 Hz, 2H), 6.42 (d, J = 3.0 Hz, 1H), 5.53 (s, 2H), 4.30-4.13 (m, 1H), 3.83 (s, 3H), 3.00- 2.87 (m, 1H), 2.47-2.35 (m, 1H), 2.34-2.16 (m, 3H), 2.13-1.88 (m, 4H). |
| 103 | 524.3 | $^1$H NMR (300 MHz, DMSO-$d_6$) δ 8.48 (d, J = 7.5 Hz, 1H), 7.49 (d, J = 1.3 Hz, 1H), 7.47 (d, J = 3.1 Hz, 1H), 7.34-7.29 (m, 3H), 7.29-7.21 (m, 3H), 7.20-7.14 (m, 2H), 6.93 (dd, J = 8.4, 1.7 Hz, 1H), 6.38 (dd, J = 3.2, 2.0 Hz 2H), 5.56 (s, 2H), 5.36 (s, 2H), 4.33-4.17 (m, 1H), 3.61 (s, 3H), 3.14-2.99 (m, 1H), 2.47-2.36 (m, 1H), 2.34-2.17 (m, 3H), 2.18-2.07 (m, 2H), 2.05-1.89 (m, 2H). |
| 104 | 472.3 | $^1$H NMR (300 MHz, DMSO-$d_6$) δ 12.0 (s, 1H), 8.64 (dt, J = 4.8, 1.3 Hz, 1H), 8.49 (d, J = 7.4 Hz, 1H), 7.96 (d, J = 8.3 Hz, 2H), 7.92-7.81 (m, 2H), 7.58 (d, J = 1.3 Hz, 1H), 7.34-7.30 (m, 2H), 7,16 (d, J = 8.3 Hz, 2H), 6.46 (d, J = 3.0 Hz, 1H), 5.63 (s, 2H), 4.27-4.14 (m, 1H), 2.97-2.86 (m, 1H) 2.43-2.35 (m, 1H), 2.34-2.13 (m, 3H), 2.13-1.86 (m, 4H). |
| 105 | ES + 472.30 | $^1$H NMR (500 MHz, MeOD) δ 8.35 (d, J = 7.2 Hz, 1H), 8.22 (s, 1H), 7.88 (d, J = 7.0 Hz, 2H), 7.72 (d, J = 8.2 Hz, 1H), 7.54-7.43 (m, 5H), 7.42 (d, J = [7.1 Hz, 1H), 7.22 (dd, J = 3.1, 1.3 Hz, 2H), 6.47 (d, J = 3.0 Hz, 1H), 5.66 (d, J = 3.1 Hz, 2H), 4.33-4.13 (m, 1H), 2.96 (p, J = 8.4 Hz, 1H), 2.43 (dt, J = 11.9, 6.6 Hz, 1H), 2.37-2.23 (m, 3H), 2.21-2.11 (m, 1H), 2.05 (ddd, J = 11.6, 8.6, 3.1 Hz, 1H), 1.94-1.82 (m, 2H). |
| 106 | 472.4 | $^1$H NMR (300 MHz, DMSO-$d_6$) δ 12.0 (s, 1H), 8.60 (s, 2H), 8.47 (d, J = 7.4 Hz, 1H), 7.68 (d, J = 8.3 Hz, 2H), 7.64 (d, J = 4.9 Hz, 2H), 7.59 (d, J = 1.3 Hz, 1H), 7.31 (dd, J = 3.0, 1.3 Hz, 1H), 7.16 (d, J = 8.3 Hz, 2H), 6.45 (d, J = 3.0 Hz, 1H), 5.64 (s, 2H), 4.22-4.12 (m, 1H), 2.97-2.86 (m, 1H), 2.43-2.31 (m, 1H), 2.31-2.13 (m, 3H), 2.12-2.01 (m, 2H), 2.01-1.87 (m, 2H). |
| 107 | 461.3 | $^1$H NMR (300 MHz, DMSO-$d_6$) δ 12.03 (s, 1H), 8.49 (d, J = 7.5 Hz, 1H), 8.42 (d, J = 2.5 Hz, 1H), 7.75-7.69 (m, 3H), 7.57 (d, J = 1.3 Hz, 1H), 7.32-7.30 (m, 1H), 7.16 (d, J = 8.6 Hz, 2H), 6.51 (t, J = 2.2 Hz, 1H), 6.44 (d, J = 2.9 Hz, 1H), 5.59 (s, 2H), 4.25-4.17 (m, 1H), 2.96-2.87 (m, 1H), 2.46-2.34 (m, 1H), 2.33-2.16 (m, 3H), 2.16-2.02 (m, 2H), 1.97-1.89 (m, 2H). |
| 108 | 502.3 | $^1$H NMR (300 MHz, DMSO-$d_6$) δ 12.02 (s, 1H), 8.48 (d, J = 7.4 Hz, 1H),] 7.96 (d, J = 8.3 Hz, 2H), 7.79-7.71 (m, 1H), 7.56 (d, J = 1.1 Hz, 1H), 7.49 (d, J = 7.4 Hz, 1H), 7.32 (dd, J = 2.9, 1.1 Hz, 1H), 7.14 (d, J = 8.3 Hz, 2H), 6.75 (d, J = 8.1 Hz, 1H), 6.46 (d, J = 2.9 Hz, 1H), 5.62 (s, 2H), 4.21 (h, J = 8.0 Hz, 1H), 3.93 (s, 3H), 2.92 (p, J = 8.4 Hz, 1H), 2.41 (ddd, J = 11.1, 7.4, 4.9 Hz, 1H), 2.25 (ddd, J = 14.1, 9.6, 6.6 Hz, 3H), 2.14-1.88 (m, 4H). |
| 109 | 502.4 | $^1$H NMR (300 MHz, DMSO-$d_6$) δ 8.48 (d, J = 7.5 Hz, 1H), 8.44 (d, J = 5.7 Hz, 1H), 7.94 (d, J = 8.2 Hz, 2H), 7.57 (d, J = 1.3 Hz, 1H), 7.40 (d, J = 2.4 Hz, 1H), 7.31 (dd, J = 3.0, 1.3 Hz, 1H), 7.13 (d, J = 8.2 Hz, 2H), 6.92 (dd, J = 5.7, 2.4 Hz, 1H), 6.45 (d, J = 2.9 Hz, 1H), 5.62 (s, 2H), 4.23-4.12 (m, 1H), 3.88 (s, 3H), 2.96- 2.85 (m, 1H), 2.42 -2.35 (m, 1H), 2.29-2.16 (m, 3H), 2.13-2.01 (m, 2H), 2.01-1.91 (m, 2H). |
| 110 | 520.5 | $^1$H NMR (300 MHz, DMSO-$d_6$) δ 12.01 (s, 1H), 8.50 (d, J = 7.4 Hz, 1H), 8.36 (d, J = 1.9 Hz, 1H), 7.91 (d, J = 8.2 Hz, 1H), 7.62 (s, 1H), 7.50-7.34 (m, 4H), 6.89 (dt, J = 10.8, 2.3 Hz, 1H), 6.48 (d, J = 3.0 Hz, 1H), 5.67 (s, 2H). 4.18 (q, J = 7.9 Hz, 1H), 3.83 (s, 3H), 2.92 (p, J = 8.4 Hz, 1H), 2.40 (ddt, J = 11.4. 7.9, 4.0 Hz, 1H), 2.26 (ddd, J = 22.1, 12.5, 5.6 Hz, 3H), 2.14-2.01 (m, 2H), 1.93 (q, J = 9.1 Hz, 2H). |
| 111 | 475.4 | $^1$H NMR (300 MHz, DMSO-$d_6$) δ 11.22 (s, 1H), 8.49 (d, J = 7.5 Hz, 1H), 8.18 (s, 1H), 7.63 (d, J = 8.6 Hz, 2H), 7.56 (d, J = 1.3 Hz, 1H), 7.51 (s, 1H), 7.30 (dd, J = 3.0, 1.3 Hz, 1H), 7.13 (d, J = 8.6 Hz, 2H), 6.44 (d, J = 3.0 Hz, 1H), 5.57 (s, 2H), 4.20 (m, 1H), 2.92 (m, 1H), 2.40 (m, 1H), 2.32-2.15 (m, 3H), 2.13-2.02 (m, 5H), 2.01-1.86 (m, 2H). |
| 112 | 543.4 | $^1$H NMR (300 MHz, DMSO-$d_6$) δ 8.48 (d, J = 7.5 Hz, 1H), 7.59 (d, J = 1.3 Hz, 1H), 7.45 (d, J = 8.4 Hz, 2H), 7.32 (dd, J = 3.0, 1.3 Hz, 1H), 7.17 (d, J = 8.4 Hz, 2H), 6.73 (s, 1H), 6.47 (d, J = 3.0 Hz, 1H), 5.67 (s, 2H), 4.23-4.09 (m, 1H), 2.96-2.85 (m, 1H), 2.41-2.33 (m, 1H), 2.29 (s, 3H), 2.28-2.12 (m, 3H), 2.12-1.85 (m, 4H). |

TABLE 20-continued

| Example No. | LC/MS (ESI) m/z: [M + H]+ | NMR |
|---|---|---|
| 113 | 520.3 | $^1$H NMR (300 MHz, DMSO-$d_6$) δ 11.99 (s, 1H), 8.81 (d, J = 2.1 Hz, 1H), 8.44 (d, J = 7.4 Hz, 1H), 8.00 (dd, J = 8.2, 2.4 Hz, 1H), 7.63 (d, J = 1.1 Hz, 1H), 7.23 (dd, J = 2.9, 1.2 Hz, 1H), 7.16-7.07 (m, 2H), 6.87 (dt, J = 11.0, 2.2 Hz, 1H), 6.80 (d, J = 8.1 Hz, 1H), 6.47 (d, J = 3.0 Hz, 1H), 5.75 (s, 2H), 4.19-4.05 (m, 1H), 3.83 (s, 3H), 2.89 (p, J = 8.4 Hz, 1H), 2.37-2.26 (m, 1H), 2.25-2.15 (m, 2H), 2.10 (q, J = 5.2, 4.8 Hz, 2H), 2.05-1.95 (m, 1H), 1.93-1.82 (m,] 2H). |

Preparation of Isomers

Examples 1a and 1b: (2S,4S,6S)-6-(4-([1,1'-biphenyl]-4-ylmethyl)-2,5-dimethylthiophene-3-carboxamido)spiro[3.3]heptane-2-carboxylic acid (1a) and (2R,4R,6R)-6-(4-([1,1'-biphenyl]-4-ylmethyl)-2,5-dimethylthiophene-3-carboxamido)spiro[3.3]heptane-2-carboxylic acid (1b)

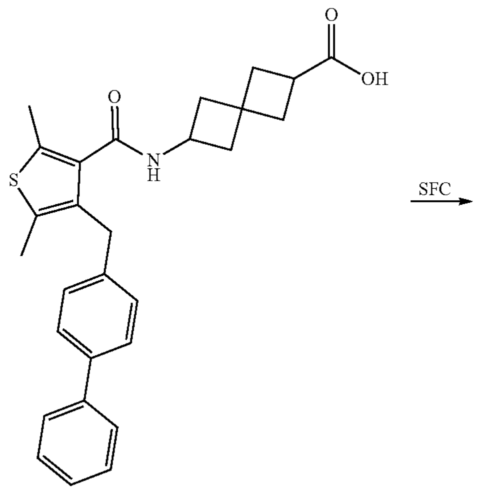

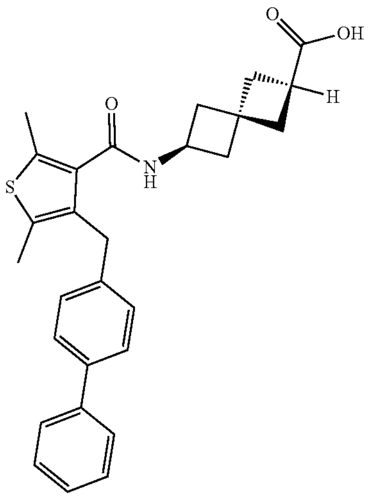

1a

-continued

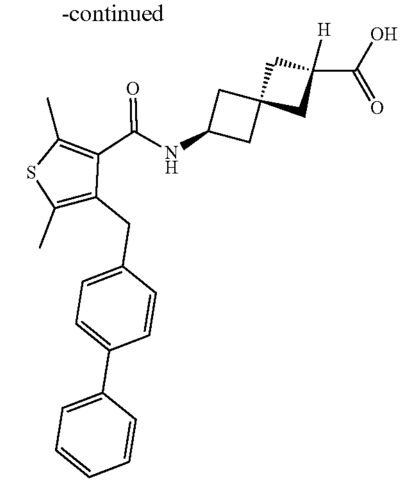

1b

The compound of Example 1 (106 g, 231 mmol, 1.00 equiv) was purified by supercritical fluid chromatography (SFC) under the following conditions to separate Example 1a (66.06 g, 143 mmol, yield 61.9%, purity 99.3%) and Example 1b (16.02 g, 34.4 mmol, yield 14.9%, purity 98.6%) as a white solid, respectively.

Column: DAICEL CHIRALCEL OJ column (250 mm×50 mm, 10 um)

Mobile phase: [Neu-MeOH]; B %: 30%-30%, 4.6; 1860 minutes.

Example 1a: $^1$H NMR (400 MHz, DMSO) δ 12.00 (br s, 1H), 8.26 (br d, J=7.60 Hz, 1H), 7.60 (br d, J=7.20 Hz, 2H), 7.51 (d, J=8.40 Hz, 2H), 7.45 (t, J=7.60 Hz, 2H), 7.37-7.31 (m, 1H), 7.18 (d, J=8.00 Hz, 2H), 4.22-4.11 (m, 1H), 3.90 (s, 2H), 2.91 (m, 1H), 2.38 (br s, 1H), 2.33 (br d, J=7.60 Hz, 6H), 2.29-2.14 (m, 3H), 2.12-1.98 (m, 2H), 1.94-1.80 (m, 2H). LC/MS (ESI) m/z=460.2 $[M+H]^+$.

Example 1b: $^1$H NMR (400 MHz, DMSO) δ 11.99 (br s, 1H), 8.26 (d, J=7.60 Hz, 1H), 7.65-7.57 (m, 2H), 7.51 (d, J=8.00 Hz, 2H), 7.45 (t, J=7.60 Hz, 2H), 7.37-7.31 (m, 1H), 7.19 (d, J=8.00 Hz, 2H), 4.16 (m, 1H), 3.90 (s, 2H), 2.91 (m, 1H), 2.40-2.35 (m, 1H), 2.33 (d, J=7.20 Hz, 6H), 2.29-2.14 (m, 3H), 2.12-1.99 (m, 2H), 1.93-1.80 (m, 2H). LC/MS (ESI) m/z=460.2 $[M+H]^+$.

Examples 34a and 34b: (2S,4S,6S)-6-(4-((3'-fluoro-5'-methoxy-[1,1'-biphenyl]-4-yl)methyl)-2,5-dimethylthiophene-3-carboxamido)spiro[3.3]heptane-2-carboxylic acid (34a) and (2R,4R,6R)-6-(4-((3'-fluoro-5'-methoxy-[1,1'-biphenyl]-4-yl)methyl)-2,5-dimethylthiophene-3-carboxamido)spiro[3.3]heptane-2-carboxylic acid (34b)

Step 1: Separation of methyl (2S,4S,6S)-6-(4-((3'-fluoro-5'-methoxy-[1,1'-biphenyl]-4-yl)methyl)-2,5-dimethylthiophene-3-carboxamido)spiro[3.3]heptane-2-carboxylate (34a') and methyl (2R,4R,6R)-6-(4-((3'-fluoro-5'-methoxy-[1,1'-biphenyl]-4-yl)methyl)-2,5-dimethylthiophene-3-carboxamido)spiro[3.3]heptane-2-carboxylate (34b')

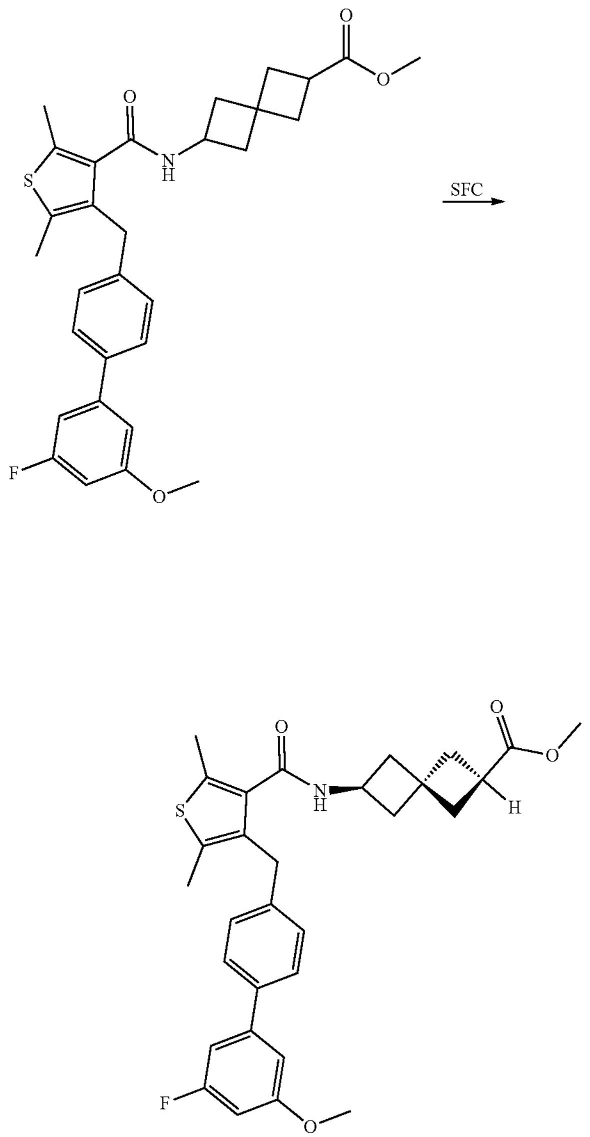

34a'

-continued

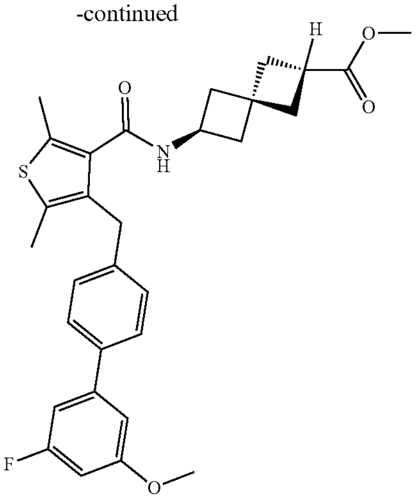

34b'

Methyl 6-(4-((3'-fluoro-5'-methoxy-[1,1'-biphenyl]-4-yl)methyl)-2,5-dimethylthiophene-3-carboxamido)spiro[3.3]heptane-2-carboxylate (91.0 g, 174 mmol, 1.00 equiv) obtained in Step 1 of Example 34 was purified by supercritical fluid chromatography (SFC) under the following conditions to obtain Intermediate 34a' (62.2 g, 119 mmol, yield 68.3%) and Intermediate 34b' (24.2 g, 46.4 mmol, yield 26.5%) as a gray solid and as an off-white solid, respectively.

Neutral condition: DAICEL CHIRALPAK AD column (250 mm×50 mm, 10 um)

Mobile phase: [Neu-ETOH]; B %: 50%-50%, 6.0; 1200 minutes

Intermediate 34a': $^1$H NMR (400 MHz, $CDCl_3$) δ 7.46 (d, J=8.3 Hz. 2H). 7.17 (d, J=8.3 Hz, 2H), 6.91-6.80 (m, 2H), 6.60 (td, J=2.2, 10.6 Hz, 1H), 5.37 (br d, J=7.7 Hz, 1H), 4.27 (q, J=8.2 Hz, 1H), 3.98 (s, 2H), 3.85 (s, 3H), 3.65 (s, 3H), 3.02-2.90 (m, 1H), 2.44 (s, 4H), 2.38-2.24 (m, 6H), 2.17 (dd, J=8.3, 11.6 Hz, 1H), 1.98 (ddd, J=2.5, 8.7, 11.5 Hz, 1H), 1.54 (dt, J=8.6, 12.3 Hz, 2H). LC/MS (ESI) m/z: 522.1 $[M+H]^+$.

Intermediate 34b': $^1$H NMR (400 MHz, $CDCl_3$) δ 7.45 (d, J=8.2 Hz, 2H), 7.16 (d, J=8.0 Hz, 2H), 6.90-6.81 (m, 2H), 6.60 (td, J=2.2, 10.5 Hz, 1H), 5.40 (br d, J=7.8 Hz, 1H), 4.34-4.20 (m, 1H), 3.97 (s, 2H), 3.85 (s, 3H), 3.64 (s, 3H), 2.96 (quin, J=8.5 Hz, 1H), 2.43 (s, 4H), 2.38-2.24 (m, 6H), 2.17 (dd, J=8.4, 11.7 Hz, 1H), 2.05-1.92 (m, 1H), 1.54 (dt, J=8.6, 12.3 Hz, 2H). LC/MS (ESI) m/z: 522.1 $[M+H]^+$.

Step 2a: Preparation of (2S,4S,6S)-6-(4-((3'-fluoro-5'-methoxy-[1,1'-biphenyl]-4-yl)methyl)-2,5-dimethylthiophene-3-carboxamido)spiro[3.3]heptane-2-carboxylic acid (34a)

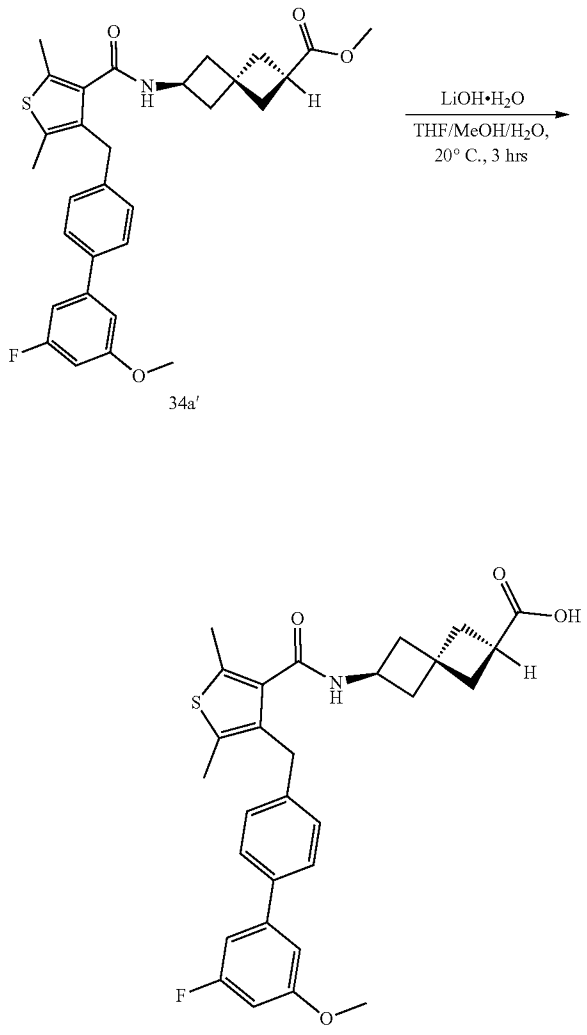

34a'

34a

To a solution of Intermediate 34a' (62.2 g, 119 mmol, 1.00 equiv) in THF/MeOH/$H_2O$ (200 mL, 100 mL, 200 mL), LiOH·$H_2O$ (15.0 g, 358 mmol, 3.00 equiv) was added and stirred at 20° C. for 3 hours. The mixture was partially concentrated, then diluted with $H_2O$ (2.00 L), and acidified with 1N HCl solution (pH 3). The aqueous layer was extracted with EtOAc (1.50 L×2), and the organic layer was washed with brine (2×1.00 L), dried over $Na_2SO_4$, filtered, and concentrated under reduced pressure. The crude product was triturated with MTBE (300 mL) at 20° C. for 12 hours and then triturated with MTBE (100 mL) at 25° C. for 30 minutes to obtain the compound of Example 34a (30.0 g, 59.1 mmol, yield 49.7%) as a white solid. $^1H$ NMR (400 MHz, DMSO) δ 12.01 (brd, J=2.5 Hz, 1H), 8.27 (d, J=7.5 Hz, 1H), 7.54 (d, J=8.2 Hz, 2H), 7.17 (d, J=8.2 Hz, 2H), 7.07-6.96 (m, 2H), 6.80 (td, J=2.1, 11.0 Hz, 1H), 4.23-4.10 (m, 1H), 3.89 (s, 2H), 3.82 (s, 3H), 2.97-2.84 (m, 1H), 2.40-2.33 (m, 1H), 2.31 (d, J=3.3 Hz, 6H), 2.28-2.13 (m, 3H), 2.12-1.97 (m, 2H), 1.92-1.79 (m, 2H). LC/MS (ESI) m/z=508.1 $[M+H]^+$.

Step 2b: Preparation of (2R,4R,6R)-6-(4-((3'-fluoro-5'-methoxy-[1,1'-biphenyl]-4-yl)methyl)-2,5-dimethylthiophene-3-carboxamido)spiro[3.3]heptane-2-carboxylic acid (34b)

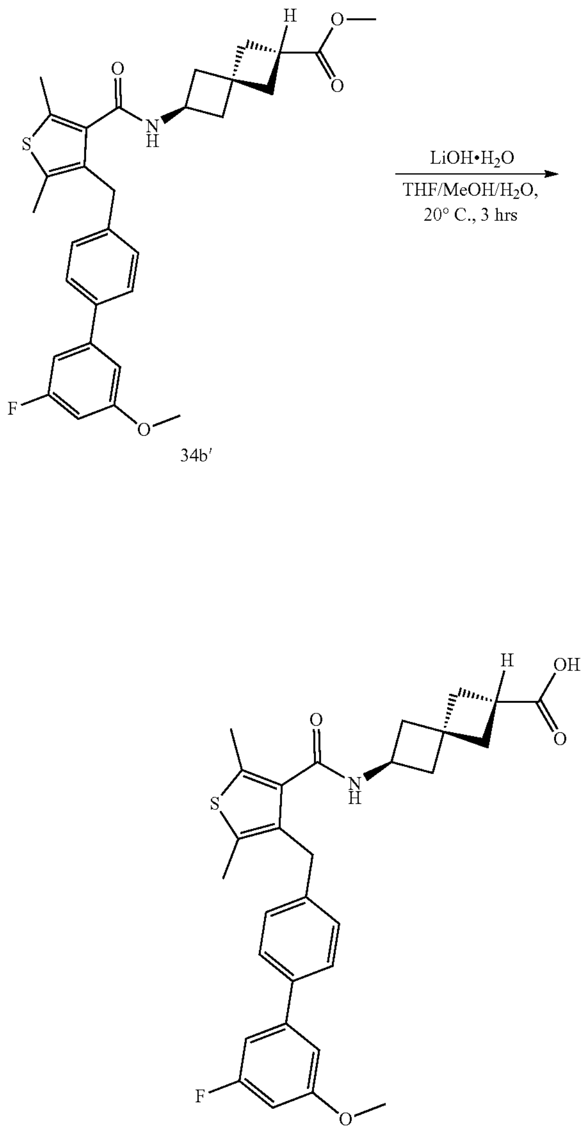

34b'

34b

The compound of Example 34b (10.0 g, 19.7 mmol, yield 42.4%) was obtained as an off-white solid by using Intermediate 34b' in the same manner as in Step 2a. $^1H$ NMR (400 MHz, DMSO) δ 12.00 (brs, 1H), 8.27 (d, J=7.5 Hz, 1H), 7.54 (d, J=8.2 Hz, 2H), 7.17 (d, J=8.2 Hz, 2H), 7.06-6.96 (m, 2H), 6.80 (td, J=2.2, 10.9 Hz, 1H), 4.21-4.09 (m, 1H), 3.89 (s, 2H), 3.82 (s, 3H), 2.90 (quin, J=8.5 Hz, 1H), 2.39-2.33 (m, 1H), 2.31 (d, J=3.3 Hz, 6H), 2.28-2.13 (m, 3H), 2.11-1.95 (m, 2H), 1.93-1.78 (m, 2H). LC/MS (ESI) m/z: 508.3 $[M+H]^+$.

Examples 79a and 79b: (2S,4S,6S)-6-(4-([1,1'-biphenyl]-4-ylmethyl)-4H-thieno[3,2-b]pyrrole-3-carboxamido)spiro[3.3]heptane-2-carboxylic acid (79a) and (2R,4R,6R)-6-(4-([1,1'-biphenyl]-4-ylmethyl)-4H-thieno[3,2-b]pyrrole-3-carboxamido)spiro[3.3]heptane-2-carboxylic acid (79b)

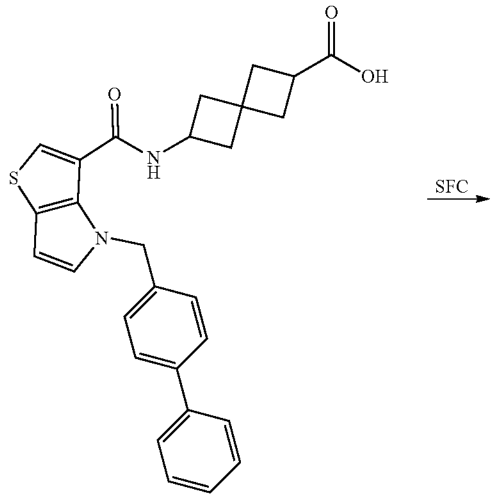

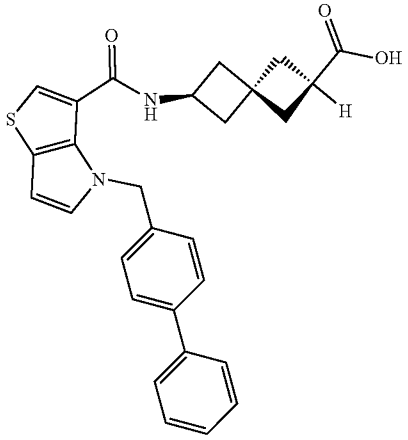

79a

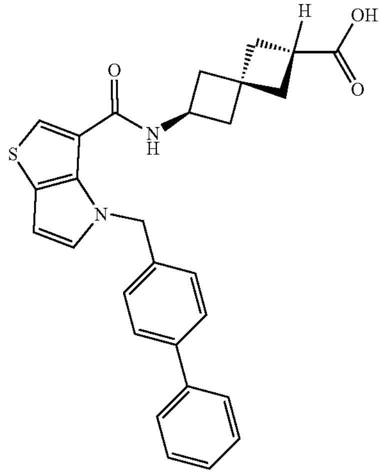

79b

The compound of Example 79 was purified by supercritical fluid chromatography (SFC) under the following conditions.

Column: Daicel ChiralPak IG column (250 mm×30 mm, 10 um)

Mobile phase: [0.1% $NH_3H_2O$ ETOH]; B %/50%-50%, 4.4 minutes; 70 minutes

The eluate was concentrated, and the residue was added to distilled water (10 mL) and acidified with HCl aqueous solution (1 M) (pH 1 to 2). The suspension was filtered, and the white solid of the filter cake was concentrated to separate the compound of Example 79a (171 mg, 356 umol, yield 55.9%, purity 98.0%) and the compound of Example 79b (36 mg, yield 11.7%, purity 98%), respectively.

Example 79a: $^1H$ NMR (400 MHz, DMSO) δ 12.71-11.10 (m, 1H), 8.50 (br d, J=7.60 Hz, 1H), 7.64-7.56 (m, 3H), 7.54 (d, J=8.20 Hz, 2H), 7.44 (t, J=7.60 Hz, 2H), 7.39-7.29 (m, 2H), 7.15 (d, J=8.20 Hz, 2H), 6.46 (d, J=2.80 Hz, 1H), 5.62 (s, 2H), 4.23 (sxt, J=8.20 Hz, 1H), 2.94 (quin, J=8.20 Hz, 1H), 2.45-2.37 (m, 1H), 2.33-2.19 (m, 3H), 2.16-2.03 (m, 2H), 2.02-1.89 (m, 2H). LC/MS (ESI) m/z: 470.9 $[M+H]^+$.

Example 79b: $^1H$ NMR (400 MHz, DMSO) δ 12.02 (br s, 1H), 8.49 (d, J=7.60 Hz, 1H), 7.63-7.56 (m, 3H), 7.53 (d, J=8.20 Hz, 2H), 7.43 (t, J=7.60 Hz, 2H), 7.36-7.29 (m, 2H), 7.14 (d, J=8.20 Hz, 2H), 6.45 (d, J=3.00 Hz, 1H), 5.62 (s, 2H), 4.30-4.13 (m, 1H), 2.99-2.90 (m, 1H), 2.44-2.36 (m, 1H), 2.32-2.18 (m, 3H), 2.16-2.02 (m, 2H), 2.01-1.86 (m, 2H). LC/MS (ESI) m/z: 471.0 $[M+H]^+$.

Examples 80a and 80b: (2S,4S,6S)-6-(4-([1,1'-biphenyl]-4-ylmethyl)-2-methyl-4H-thieno[3,2-b]pyrrole-3-carboxamido)spiro[3.3]heptane-2-carboxylic acid (80a) and (2R,4R,6R)-6-(4-([1,1'-biphenyl]-4-ylmethyl)-2-methyl-4H-thieno[3,2-b]pyrrole-3-carboxamido)spiro[3.3]heptane-2-carboxylic acid (80b)

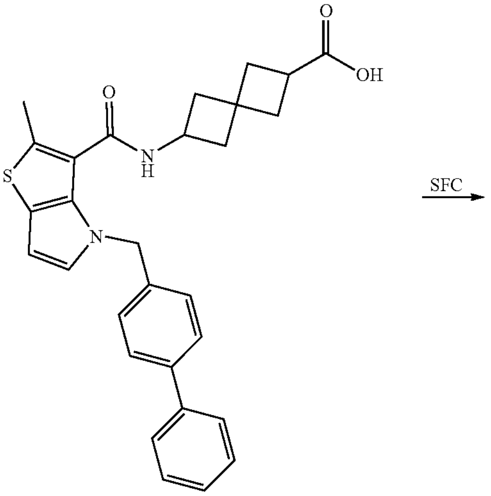

-continued

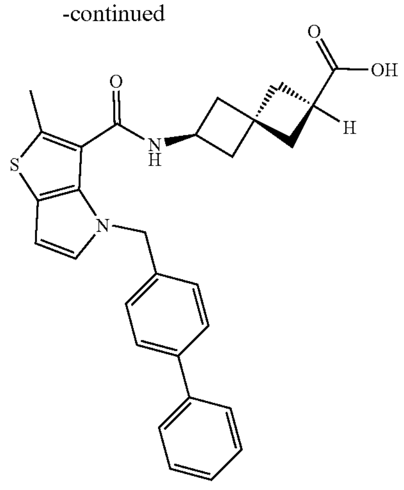

80a

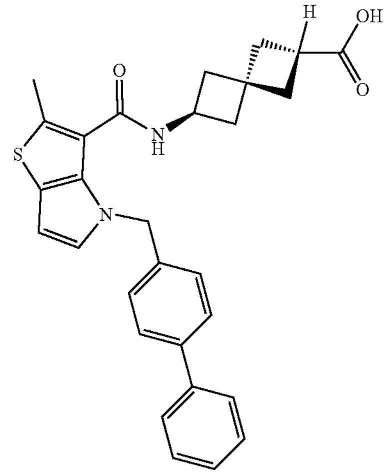

80b

The compound of Example 80 (80.0 g, 165 mmol, 1.00 eqiv) was purified by supercritical fluid chromatography (SFC) under the following conditions to separate the compound of Example 80a (30.0 g, 61.9 mmol, yield 37.5%) and the compound of Example 80b (10.0 g, 20.6 mmol, yield 12.5%) as a white solid and as an off-white solid, respectively.

Column: DAICEL CHIRALPAK AD column (250 mm×50 mm, 10 um)

Mobile phase: [Neu-ETOH]; B %: 40%-40%, 14.2; 870 minutes

Example 80a: $^1$H NMR (400 MHz, DMSO) δ 11.74-12.27 (m, 1H) 8.43 (d, J=7.58 Hz, 1H) 7.60 (d, J=7.58 Hz, 2H) 7.54 (d, J=8.19 Hz, 2H) 7.45 (t, J=7.64 Hz, 2H) 7.32-7.38 (m, 1H) 7.20 (d, J=2.81 Hz, 1H) 7.16 (d, J=8.19 Hz, 2H) 6.36 (d, J=2.81 Hz, 1H) 5.35 (s, 2H) 4.18-4.29 (m, 1H) 2.86-2.95 (m, 1H) 2.43 (s, 3H) 2.33-2.40 (m, 1H) 2.16-2.31 (m, 3H) 1.96-2.11 (m, 2H) 1.79-1.93 (m, 2H). LC/MS (ESI) m/z=485.1 $[M+H]^+$.

Example 80b: $^1$H NMR (400 MHz, DMSO) δ 11.44-12.66 (m, 1H) 8.42 (d, J=7.58 Hz, 1H) 7.60 (d, J=7.46 Hz, 2H) 7.54 (d, J=8.19 Hz, 2H) 7.45 (t, J=7.64 Hz, 2H) 7.32-7.37 (m, 1H) 7.20 (d, J=2.81 Hz, 1H) 7.13 (d, J=8.19 Hz, 2H) 6.35 (d, J=2.93 Hz, 1H) 5.35 (s, 2H) 4.19-4.29 (m, 1H) 2.90 (quin, J=8.47 Hz, 1H) 2.43 (s, 3H) 2.34-2.39 (m, 1H)

2.17-2.28 (m, 3H) 1.96-2.10 (m, 2H) 1.79-1.91 (m, 2H). LC/MS (ESI) m/z=485.1 $[M+H]^+$.

Experimental Example: Evaluation of Inhibitory Activity on EP2 and/or EP4

1. hEP2 cAMP Assay

HEK293 cells overexpressing hEP2 were cultured in growth medium (GM: MEM (Gibco™, 11095080)/10% HI FBS (Gibco™, 10082147)/1% penicillin/streptomycin). Before the experiment, the growth medium was removed, and starvation medium (HBSS (Gibco™, 14025076)/10% GM) was added. Thereafter, the cells were incubated for 4 hours. The HEK293 cells harboring hEP2 were detached from the culture dish with a non-enzymatic cell dissociation buffer (Gibco™, 15040066). The cells were resuspended in assay buffer (AB: HBSS, 0.1% BSA stabilizer, 0.5 mM IBMX, 5 mM HEPES).

1,000 cells in 5 μL of AB were seeded per well in a 384 well plate (Corning™, 3570), and stock solutions of test compounds were prepared at a concentration of 1 mM in DMSO and serially diluted in DMSO to the concentration required for the inhibition dose response curve (test concentration range of 10 μM-0.001 nM). $PGE_2$ (Sigma, P0409, stock solution: 1 μM) was used as an agonist at a final concentration of 400 pM corresponding to $EC_{50-80}$. 2.5 μL of the diluted compound and 2.5 μL of $PGE_2$ (400 pM final concentration) were transferred to the assay plate, and then the plate was incubated at room temperature for 12 minutes.

5 μL of each donor (Eu-cAMP tracer) and acceptor (ULight-anti-cAMP) was added, and the plate was incubated in the dark for 1 hour at room temperature, and then a Varioskan LUX multimode microplate reader was used to obtain the results (excitation: 334 nm, emission: 615 and 665 nm). The resulting FRET fluorescence value (665 nm/615 nm*10000) was converted and then calculated as a percentage of cAMP relative to the DMSO control value. $IC_{50}$ values and curves were generated with GraphPad Prism software using log (inhibitor) versus response-variable slopes (4 parameters), and the median of multiple experiments was taken as the experiment result.

2. hEP4 cAMP Assay

HEK293 cells overexpressing hEP4 were cultured in growth medium (GM: MEM (Gibco™, 11095080)/10% HI FBS (Gibco™, 10082147)/1% penicillin/streptomycin). Before the experiment, the growth medium was removed, and starvation medium (HBSS (Gibco™ 14025076)/10% GM) was added. Thereafter, the cells were incubated for 4 hours. HEK293 cells harboring hEP4 were detached from the culture dish with a non-enzymatic cell dissociation buffer (Gibco™, 15040066). The cells were resuspended in assay buffer (AB: HBSS, 0.1% BSA stabilizer, 0.5 mM IBMX, 5 mM HEPES).

1,000 cells in 5 μL of AB were seeded per well in a 384 well plate (Corning®, 3570), and stock solutions of test compounds were prepared at a concentration of 1 mM in DMSO and serially diluted in DMSO to the concentration required for the inhibition dose response curve (test concentration range of 10 μM-0.001 nM). $PGE_2$ (Sigma, P0409, stock solution: 100 μM) was used as an agonist at a final concentration of 20 nM corresponding to $EC_{50-80}$. 2.5 μL of the diluted compound and 2.5 μL of $PGE_2$ (20 nM final concentration) were transferred to the assay plate, and then the plate was incubated at room temperature for 18.5 minutes.

5 μL of each donor (Eu-cAMP tracer) and acceptor (ULight-anti-cAMP) was added, and the plate was incubated in the dark for 1 hour at room temperature, and then a Varioskan LUX multimode microplate reader was used to obtain the results (excitation: 334 nm, emission: 615 and 665 nm). The resulting FRET fluorescence value (665 nm/615 nm*10000) was converted and then calculated as a percentage of cAMP compared to the DMSO control value. $IC_{50}$ values and curves were generated with GraphPad Prism software using log (inhibitor) versus response-variable slope (4 parameters), and the median of multiple experiments was taken as the experiment result.

3. Experimental Results

The inhibitory activity on EP2 and EP4 of the compounds of Examples 1 to 113 measured by the above experimental method was evaluated based on the criteria of Table 21 below, and the results are shown in Tables 22 to 25.

TABLE 21

| $IC_{50}$ range | <500 nM | 500 nM < $IC_{50}$ ≤ 5.000 nM | 5,000 nM < $IC_{50}$ ≤ 10,000 | >10,000 nM |
|---|---|---|---|---|
| Grade | A | B | C | D |

TABLE 22

| | $IC_{50}$ (nM) | |
|---|---|---|
| Example | EP2 cAMP | EP4 cAMP |
| 1 | B | A |
| 1a | D | D |
| 1b | B | A |
| 2 | D | D |
| 3 | D | C |
| 4 | D | D |
| 5 | D | C |
| 6 | D | D |
| 7 | B | A |
| 8 | D | B |
| 9 | D | D |
| 10 | D | B |
| 11 | D | A |
| 12 | D | D |
| 13 | B | B |
| 14 | B | B |
| 15 | A | A |
| 16 | D | B |
| 17 | C | A |
| 18 | B | B |
| 19 | B | A |
| 20 | B | A |
| 21 | D | D |
| 22 | B | B |
| 23 | D | D |
| 24 | D | B |
| 25 | D | C |
| 26 | D | B |
| 27 | D | B |
| 28 | B | A |
| 29 | B | A |
| 30 | D | A |

TABLE 23

| | $IC_{50}$ (nM) | |
|---|---|---|
| Example | EP2 cAMP | EP4 cAMP |
| 31 | C | A |
| 32 | D | B |
| 33 | B | A |
| 34 | B | A |
| 34a | C | B |
| 34b | A | A |
| 35 | D | C |
| 36 | C | A |
| 37 | D | C |
| 38 | D | B |
| 39 | D | B |
| 40 | C | A |
| 41 | B | A |
| 42 | D | B |
| 43 | B | A |
| 44 | B | A |
| 45 | B | A |
| 46 | B | B |
| 47 | D | B |
| 48 | D | A |
| 49 | D | D |
| 50 | D | A |
| 51 | B | A |
| 52 | C | A |
| 53 | B | A |
| 54 | B | A |
| 55 | B | A |
| 56 | D | C |
| 57 | B | A |
| 58 | B | A |
| 59 | D | B |
| 60 | C | A |

TABLE 24

| | $IC_{50}$ (nM) | |
|---|---|---|
| Example | EP2 cAMP | EP4 cAMP |
| 61 | D | B |
| 62 | B | A |
| 63 | A | A |
| 64 | D | B |
| 65 | D | B |
| 66 | D | B |
| 67 | D | C |
| 68 | D | D |
| 69 | B | A |
| 70 | C | A |
| 71 | B | A |
| 72 | D | D |
| 73 | D | D |
| 74 | D | D |
| 75 | D | D |
| 76 | D | B |
| 77 | D | D |
| 78 | D | C |
| 79 | A | A |
| 79a | B | B |
| 79b | A | A |
| 80 | B | A |
| 80a | B | D |
| 80b | B | A |
| 81 | B | D |
| 82 | B | A |
| 83 | B | D |
| 84 | D | D |
| 85 | A | A |
| 86 | A | A |
| 87 | D | D |
| 88 | B | C |
| 89 | A | A |
| 90 | B | B |

TABLE 25

| | $IC_{50}$ (nM) | |
|---|---|---|
| Example | EP2 cAMP | EP4 cAMP |
| 91 | D | D |
| 92 | A | A |
| 93 | C | B |
| 94 | B | A |
| 95 | B | A |
| 96 | D | B |
| 97 | A | A |
| 98 | D | B |
| 99 | D | A |
| 100 | B | A |
| 101 | B | A |
| 102 | D | A |
| 103 | D | A |
| 104 | C | A |
| 105 | B | A |
| 106 | C | A |
| 107 | D | B |
| 108 | B | A |
| 109 | B | A |
| 110 | A | A |
| 111 | D | A |
| 112 | D | B |
| 113 | B | A |

As shown in Tables 22 to 25 above, the compounds of Examples 1 to 113 exhibited excellent inhibitory activity on EP2 and EP4.

The invention claimed is:

1. A compound of formula IA-3, or a solvate, stereoisomer or pharmaceutically acceptable salt thereof:

[Formula IA-3]

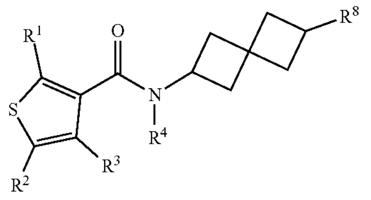

in which, $R^1$ is selected from the group consisting of hydrogen, halogen, hydroxy, $C_1$-$C_6$ alkyl, $C_1$-$C_6$ alkoxy, $C_1$-$C_6$ haloalkyl, and $C_1$-$C_6$ haloalkoxy;

$R^2$ is selected from the group consisting of hydrogen, halogen, hydroxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and phenyl; and $R^3$ is

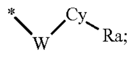

W is —$(CH_2)_o$—, —$(CH_2)_o$—C≡C—, —C(O)—, —O—, —NH—, or —N($C_1$-$C_6$ alkyl)-, wherein H of said $CH_2$ may be optionally substituted with one or more halogen, hydroxy, or $C_1$-$C_6$ alkoxy;

Cy is selected from the group consisting of $C_6$-$C_{10}$ aryl, 45- to 10-membered monocyclic or bicyclic heteroaryl containing 1 or 2 nitrogen atoms, and 4- to 7-membered heterocycloalkyl containing 1 or 2 nitrogen atoms, the heterocycloalkyl being a monocyclic or bicyclic, saturated or partially unsaturated ring system which may be spiro, bridged or fused, and Cy may be optionally substituted with one or more R';

$R_a$ is hydrogen, halogen, $C_1$-$C_6$ alkyl, $C_1$-$C_6$ haloalkyl, or —V-$Cy_2$, wherein V is absent, —$CH_2$—, or —O—, $Cy_2$ is selected from the group consisting of $C_6$-$C_{10}$ aryl, 45- to 10-membered monocyclic or bicyclic heteroaryl containing 1 or 2 heteroatoms selected from N or O, 4- to 7-membered heterocycloalkyl containing 1 or 2 heteroatoms selected from N or O, $C_3$-$C_8$ cycloalkyl and $C_3$-$C_8$ cycloalkenyl, the heterocycloalkyl being a monocyclic or bicyclic, saturated or partially unsaturated ring system which may be spiro, bridged or fused, and $Cy_2$ may be optionally substituted with one or more R";

R' is each independently selected from the group consisting of halogen, amino, $C_1$-$C_6$ alkyl, and $C_1$-$C_6$ haloalkyl;

R" is selected from the group consisting of halogen, hydroxy, cyano, amino, oxo, $C_1$-$C_6$ alkyl, $C_1$-$C_6$ alkoxy, —S—($C_1$-$C_6$ alkyl), —$SO_2$—($C_1$-$C_6$ alkyl), —CO—($C_1$-$C_6$ alkyl), —C(O)H, —COO—($C_1$-$C_6$ alkyl), —COOH, —$CONH_2$, —CONH—($C_1$-$C_6$ alkyl), —CON($C_1$-$C_6$ alkyl)$_2$, —$(CH_2)_p$—$NH_2$, —$(CH_2)_p$—NH—($C_1$-$C_6$ alkyl), —$(CH_2)_p$—N($C_1$-$C_6$ alkyl)$_2$, —$(CH_2)_p$—NH—CO—($C_1$-$C_6$ alkyl), —$(CH_2)_p$—NH—COO—($C_1$-$C_6$ alkyl), —$(CH_2)_p$—OH, 3- to 7-membered heterocycloalkyl containing 1 heteroatom selected from N, O and S, $C_3$-$C_8$ cycloalkyl, and —$(CH_2)_p$—($C_3$-$C_8$ cycloalkyl), the heterocycloalkyl being a monocyclic or bicyclic, saturated or partially unsaturated ring system which may be spiro, bridged or fused, wherein said $C_1$-$C_6$ alkyl and $C_1$-$C_6$ alkoxy may be optionally substituted with one or more halogen, hydroxy, cyano or amino, and said 3- to 7-membered heterocycloalkyl and $C_3$-$C_8$ cycloalkyl may be optionally substituted with one or more halogen, hydroxy, cyano, oxo or amino;

$R^4$ is hydrogen, or $C_1$-$C_6$ alkyl;

$R^8$ is —C(═O)$R^{8'}$ and $R^{8'}$ is hydroxy or $C_1$-$C_6$ alkoxy;

o is an integer of 1 or 2; and p is an integer of 0, 1 or 2.

2. The compound of formula IA-3 or solvate, stereoisomer or pharmaceutically acceptable salt thereof according to claim 1, wherein $R^1$ is hydrogen, halogen, or $C_1$-$C_3$ alkyl, wherein said $C_1$-$C_3$ alkyl may be optionally substituted with one or more halogen; and $R^2$ is hydrogen, halogen, $C_1$-$C_3$ haloalkyl, cyclopropyl, cyclobutyl or phenyl.

3. The compound of formula IA-3 or solvate, stereoisomer or pharmaceutically acceptable salt thereof according to claim 1, wherein Cy is phenyl, pyridinyl, pyrimidinyl, indolyl, or piperazinyl; and $Cy_2$ is phenyl, furanyl, pyrazolyl, pyridinyl, pyrimidinyl, piperidinyl, morpholinyl, cyclohexyl, or cyclohexenyl.

4. The compound of formula IA-3 or solvate, stereoisomer or pharmaceutically acceptable salt thereof according to claim 1, wherein $R_a$ is —V-$Cy_2$, and

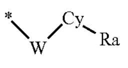

has a structure selected from the group consisting of:
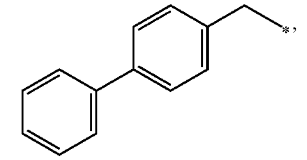
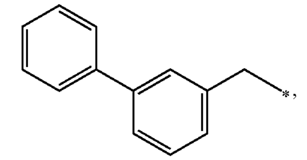
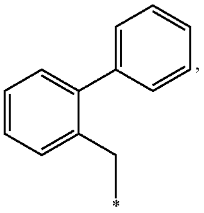
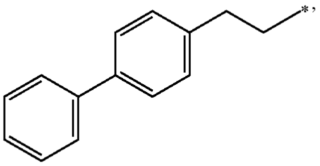
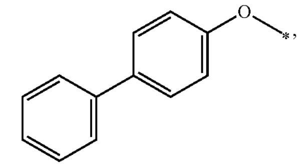
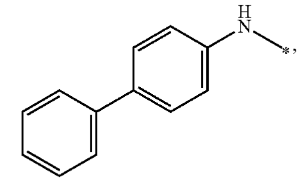
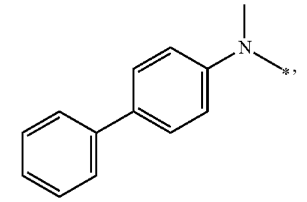
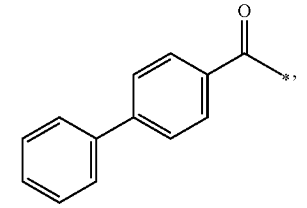
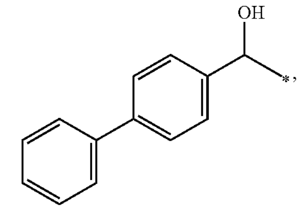
-continued
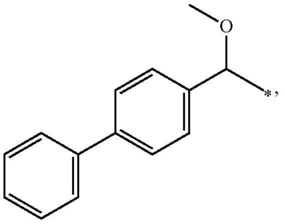
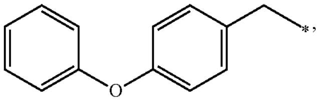
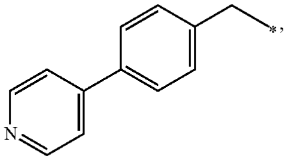
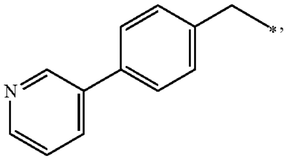
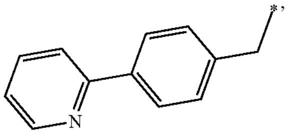
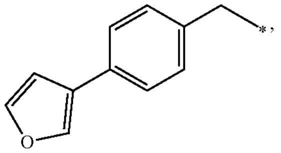
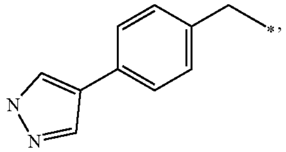
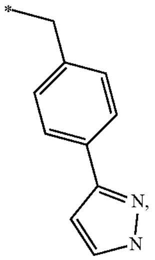
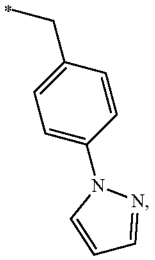

-continued

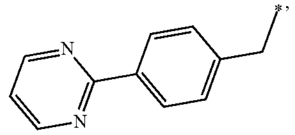,

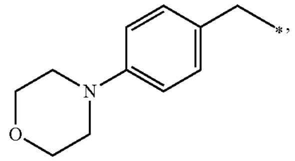,

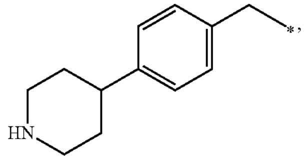,

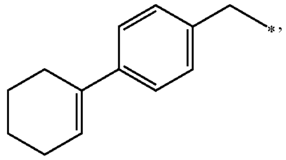,

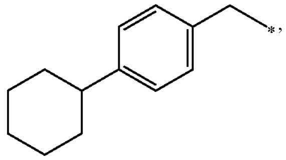,

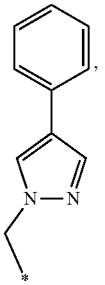,

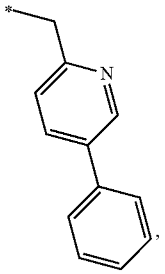,

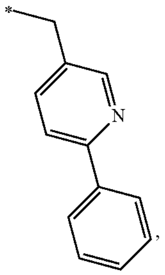,

-continued

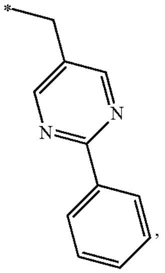,

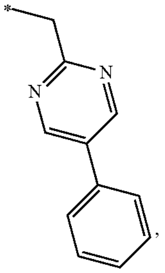,

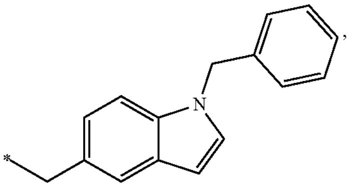,

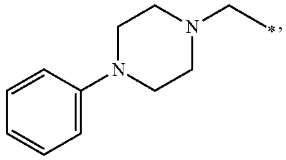, and

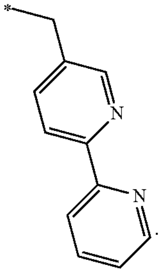.

wherein Cy and $Cy_2$ may be each optionally substituted with R' and R'', respectively.

5. The compound of formula IA-3 or solvate, stereoisomer or pharmaceutically acceptable salt thereof according to claim 1, wherein $R^8$ is C(═O)$R^{8'}$, and $R^{8'}$ is hydroxy.

6. The compound of formula IA-3 or solvate, stereoisomer or pharmaceutically acceptable salt thereof according to claim 1, wherein $R^1$ is hydrogen, halogen, hydroxy, $C_1$-$C_3$ alkyl, $C_1$-$C_3$ alkoxy, $C_1$-$C_3$ haloalkyl, or $C_1$-$C_3$ haloalkoxy;

$R^2$ is hydrogen, halogen, hydroxy, $C_1$-$C_3$ alkyl, $C_1$-$C_3$ alkoxy, $C_1$-$C_3$ haloalkyl, $C_1$-$C_3$ haloalkoxy, $C_3$-$C_6$ cycloalkyl or phenyl;

$R^3$ is

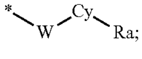;

W is —$(CH_2)_o$—, —C(O)—, —O—, —NH—, or —N($C_1$-$C_6$ alkyl)-, wherein H of said $CH_2$ may be optionally substituted with one or more halogen, hydroxy or $C_1$-$C_6$ alkoxy;

Cy is selected from the group consisting of $C_6$-$C_{10}$ aryl, 5- to 10-membered monocyclic or bicyclic heteroaryl containing 1 or 2 nitrogen atoms, and 4- to 7-membered heterocycloalkyl containing 1 or 2 nitrogen atoms, the heterocycloalkyl being a monocyclic or bicyclic, saturated or partially unsaturated ring system which may be spiro, bridged or fused, and Cy may be optionally substituted with one or more R';

$R_a$ is hydrogen, halogen, $C_1$-$C_3$ alkyl, $C_1$-$C_3$ haloalkyl or —V-$Cy_2$, wherein V is absent or —O—, and $Cy_2$ is selected from the group consisting of $C_6$-$C_{10}$ aryl, 5- to 10-membered monocyclic or bicyclic heteroaryl containing 1 or 2 heteroatoms selected from N or O, and 4- to 7-membered heterocycloalkyl containing 1 or 2 heteroatoms selected from N or O, $C_3$-$C_8$ cycloalkyl, and $C_3$-$C_8$ cycloalkenyl, the heterocycloalkyl being a monocyclic or bicyclic, saturated or partially unsaturated ring system which may be spiro, bridged or fused, and $Cy_2$ may be optionally substituted with one or more R", R' is each independently halogen, amino, $C_1$-$C_3$ alkyl, or $C_1$-$C_3$ haloalkyl;

R" is selected from the group consisting of halogen, hydroxy, cyano, amino, oxo, $C_1$-$C_6$ alkyl, $C_1$-$C_6$ alkoxy, —S—($C_1$-$C_6$ alkyl), —$SO_2$—($C_1$-$C_6$ alkyl), —COO—($C_1$-$C_6$ alkyl), —COOH, —$CONH_2$, —$(CH_2)_p$—$NH_2$, —$(CH_2)_p$—NH—($C_1$-$C_6$ alkyl), —$(CH_2)_p$—N($C_1$-$C_6$ alkyl$)_2$, —$(CH_2)_p$—NH—COO—($C_1$-$C_6$ alkyl), —$(CH_2)_p$—OH, 3- to 5-membered heterocycloalkyl containing 1 heteroatom selected from N, O and S, $C_3$-$C_5$ cycloalkyl, and —$(CH_2)_p$—($C_3$-$C_5$ cycloalkyl), the heterocycloalkyl being a monocyclic, saturated or partially unsaturated ring system which may be spiro, bridged or fused, wherein said $C_1$-$C_6$ alkyl and $C_1$-$C_6$ alkoxy may be optionally substituted with one or more halogen, hydroxy, cyano or amino, and said 3- to 5-membered heterocycloalkyl and $C_3$-$C_5$ cycloalkyl may be optionally substituted with one or more halogen, hydroxy, cyano, oxo or amino;

$R^4$ is hydrogen or $C_1$-$C_3$ alkyl;

$R^8$ is —C(═O)$R^{8'}$, and $R^{8'}$ is hydroxy or $C_1$-$C_6$ alkoxy;

o is 1 or 2; and p is an integer of 0, 1 or 2.

7. The compound of formula IA-3 or solvate, stereoisomer or pharmaceutically acceptable salt thereof according to claim 6, wherein $R^1$ is hydrogen, halogen, hydroxy, $C_1$-$C_3$ alkyl, $C_1$-$C_3$ alkoxy, $C_1$-$C_3$ haloalkyl, or $C_1$-$C_3$ haloalkoxy;

$R^2$ is hydrogen, halogen, $C_1$-$C_3$ alkyl, $C_1$-$C_3$ haloalkyl, cyclopropyl, cyclobutyl, or phenyl;

Cy is phenyl, 5- to 10-membered monocyclic or bicyclic heteroaryl containing 1 or 2 nitrogen atoms, or 4- to 7-membered heterocycloalkyl containing 1 or 2 nitrogen atoms, the heterocycloalkyl being a monocyclic or bicyclic, saturated or partially unsaturated ring system which may be spiro, bridged or fused, and Cy may be optionally substituted with one or more R';

$R_a$ is hydrogen, halogen, $C_1$-$C_3$ alkyl, $C_1$-$C_3$ haloalkyl or —V-$Cy_2$, wherein V is absent or —O—, and $Cy_2$ is phenyl, 5- to 10-membered monocyclic or bicyclic heteroaryl containing 1 or 2 heteroatoms selected from N or O, or 4- or 7-membered heterocycloalkyl containing 1 or 2 heteroatoms selected from N or O, $C_4$-$C_7$ cycloalkyl and $C_4$-$C_7$ cycloalkenyl, the heterocycloalkyl being a monocyclic or bicyclic, saturated or partially unsaturated ring system which may be spiro, bridged or fused, and $Cy_2$ may be optionally substituted with one or more R";

R' is each independently halogen, amino, $C_1$-$C_3$ alkyl or $C_1$-$C_3$ haloalkyl; and R" is selected from the group consisting of halogen, hydroxy, cyano, amino, oxo, $C_1$-$C_6$ alkyl, $C_1$-$C_6$ haloalkyl, $C_1$-$C_6$ alkoxy, $C_1$-$C_6$ haloalkoxy, —S—($C_1$-$C_6$ alkyl), —$SO_2$—($C_1$-$C_6$ alkyl), —COO—($C_1$-$C_6$ alkyl), —COOH, —$CONH_2$, —$(CH_2)_p$—$NH_2$, —$(CH_2)_p$—NH—($C_1$-$C_6$ alkyl), —$(CH_2)_p$—N($C_1$-$C_6$ alkyl$)_2$, —$(CH_2)_p$—NH—COO—($C_1$-$C_6$ alkyl), —$(CH_2)_p$—OH; azetidinyl or oxetanyl, optionally substituted with hydroxy or oxo; and cyclopropyl or cyclopropylmethyl, optionally substituted with hydroxy or oxo.

8. The compound of formula IA-3 or solvate, stereoisomer or pharmaceutically acceptable salt thereof according to claim 7, wherein Cy is phenyl, pyrazolyl, or piperazinyl; and $Cy_2$ is phenyl, furanyl, pyrazolyl, pyridinyl, morpholinyl, piperidinyl, cyclohexyl, or cyclohexenyl.

9. The compound of formula IA-3 or solvate, stereoisomer or pharmaceutically acceptable salt thereof according to claim 1, wherein the compound is selected from the group consisting of the following compounds:

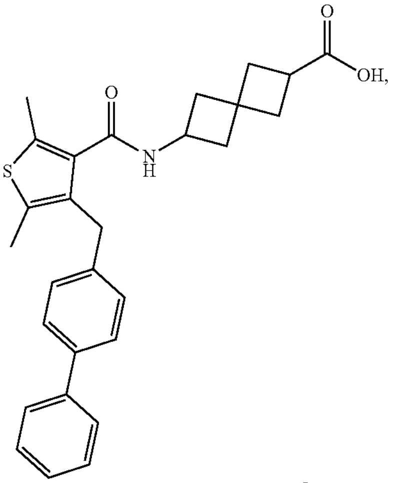

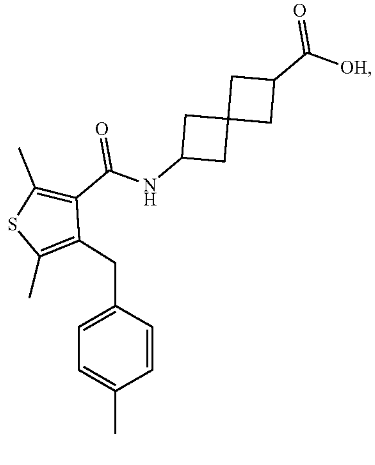

-continued
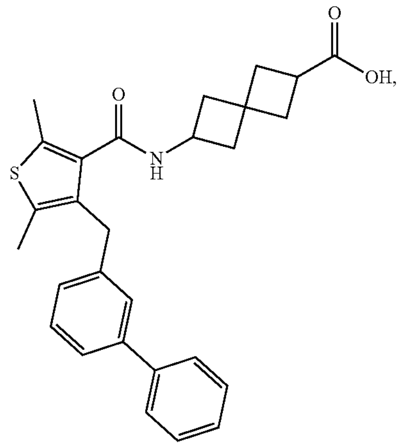
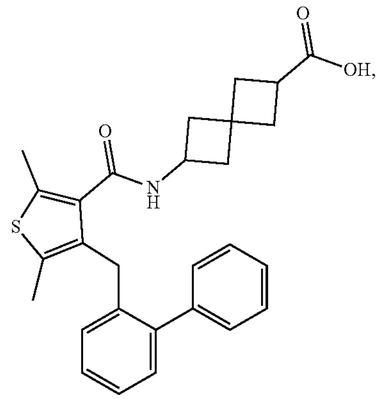
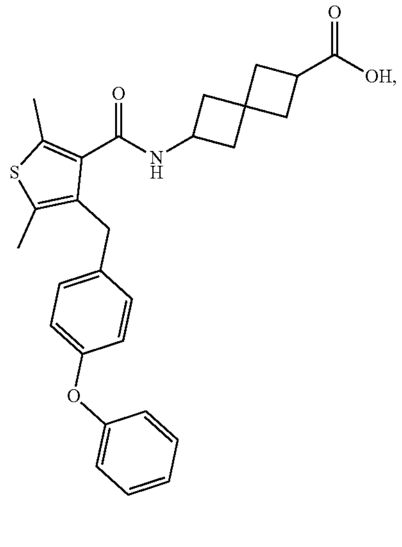
-continued
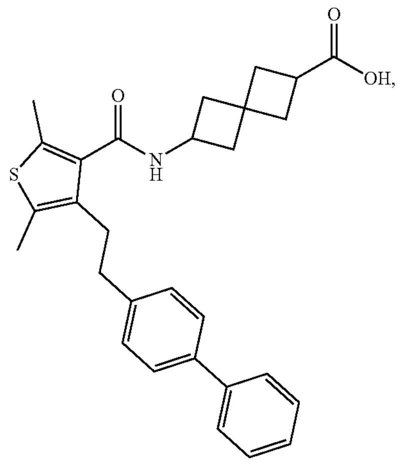
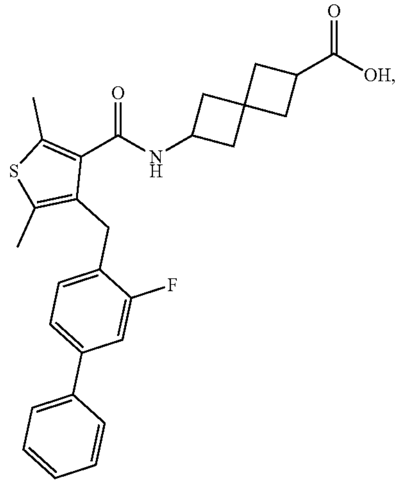
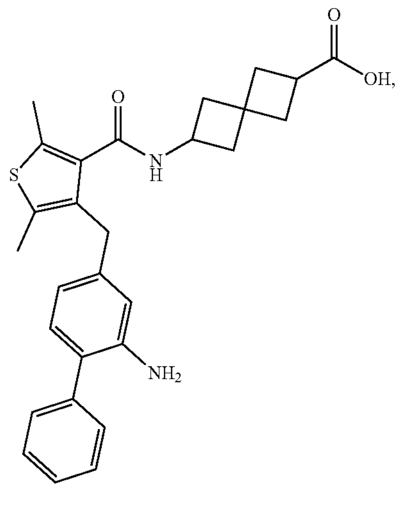

-continued
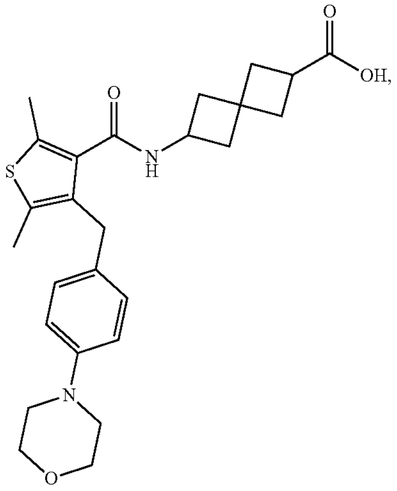
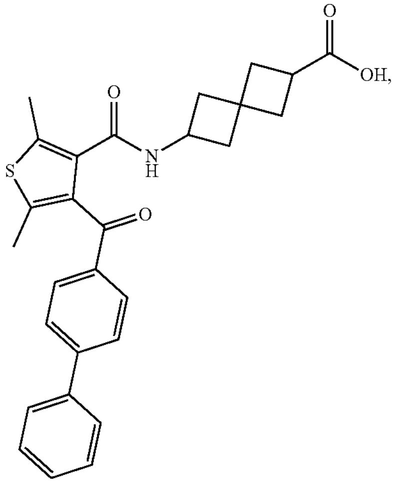
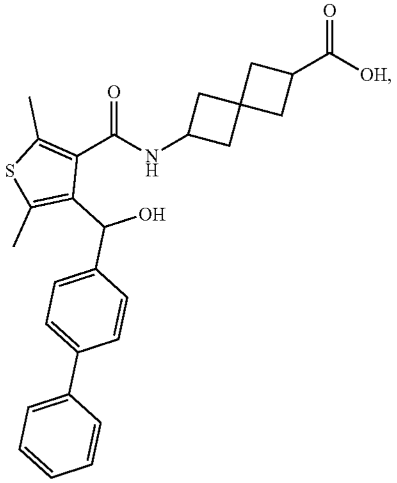
-continued
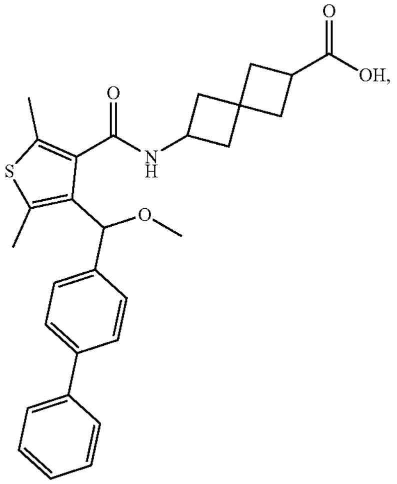
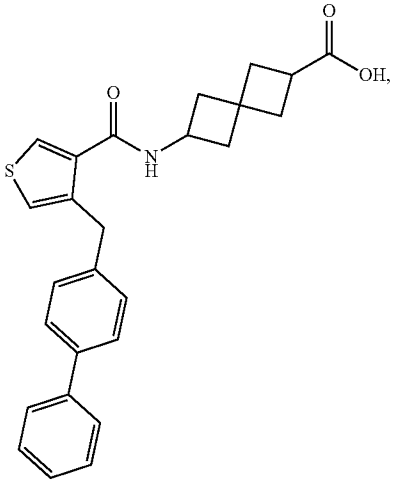
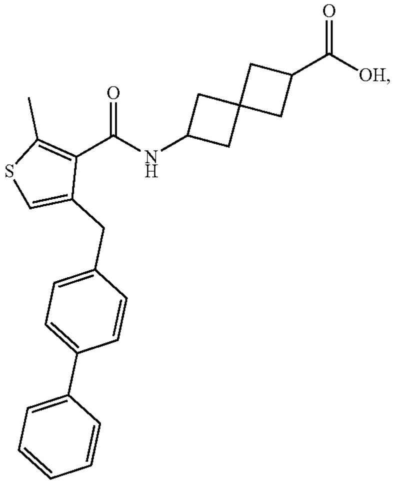

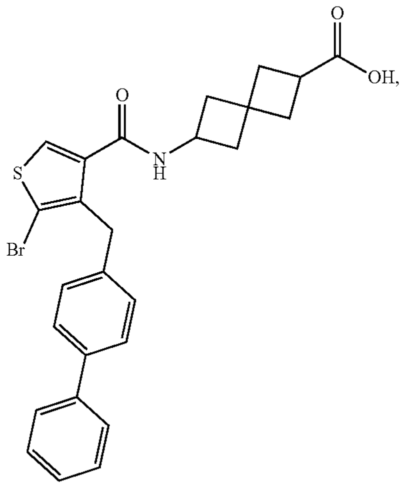
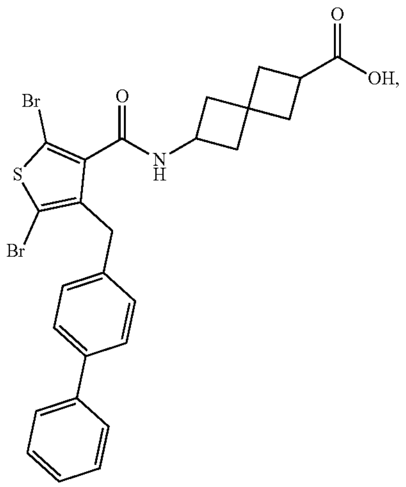
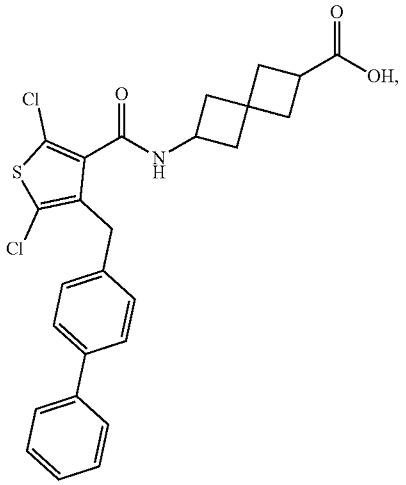 [SMILES: O=C(NC1CC2(C1)CC(C(=O)O)C2)c1c(Cl)sc(Cl)c1Cc1ccc(-c2ccccc2)cc1]
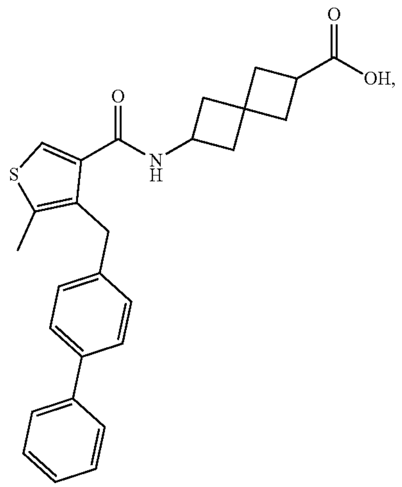
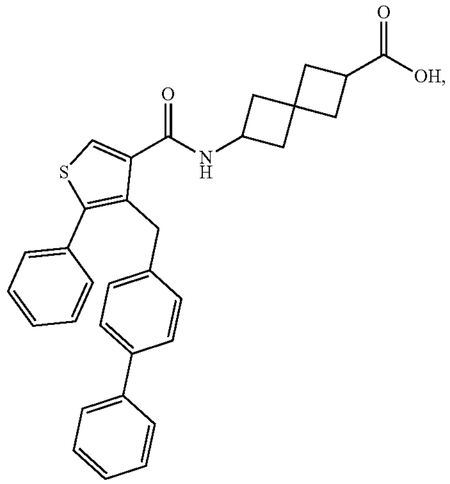
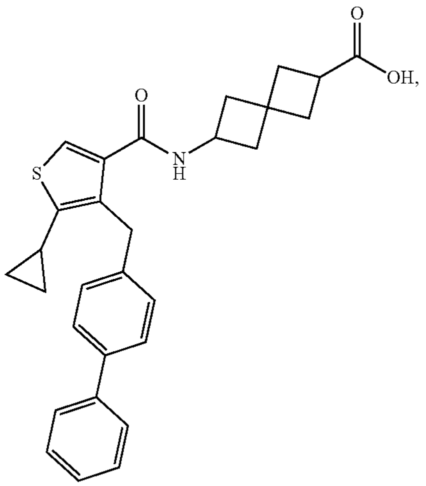

-continued
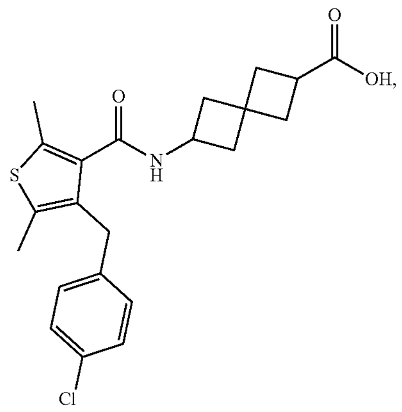
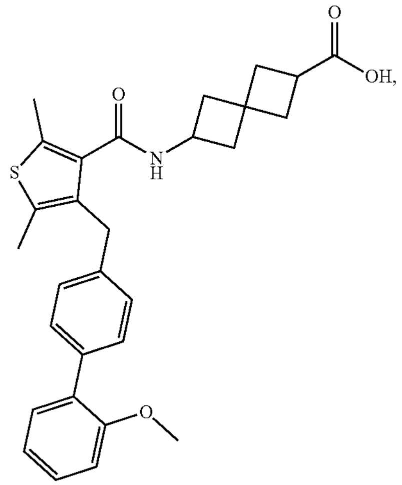
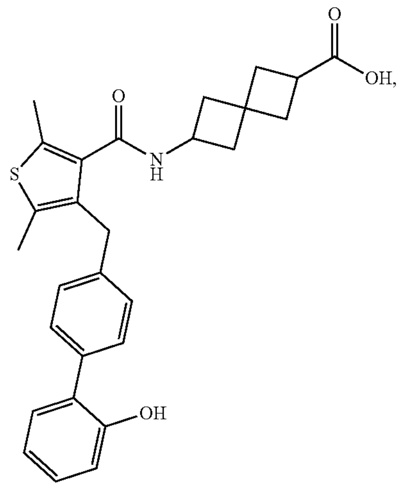
-continued
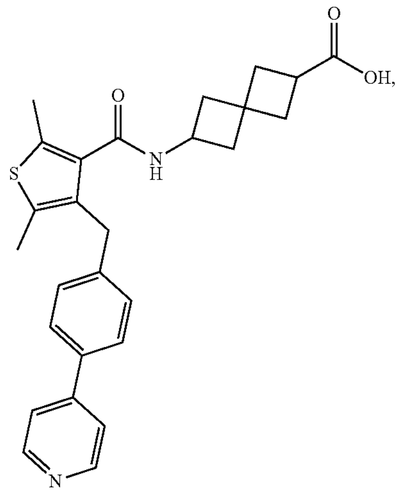
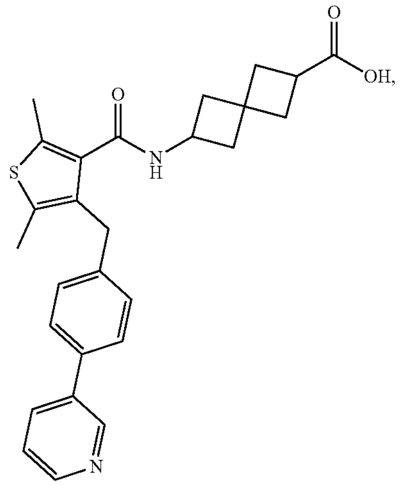
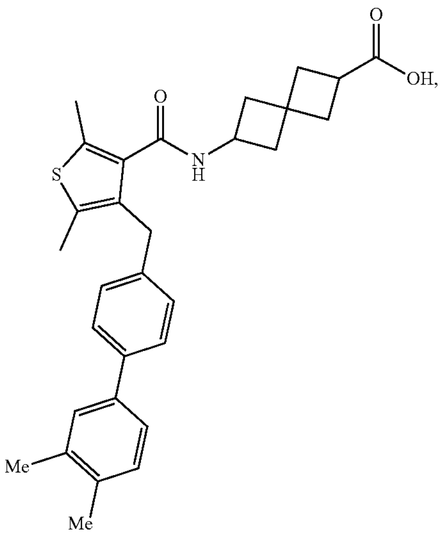

-continued
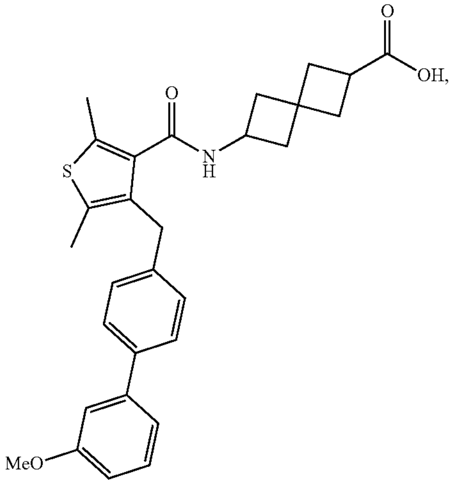
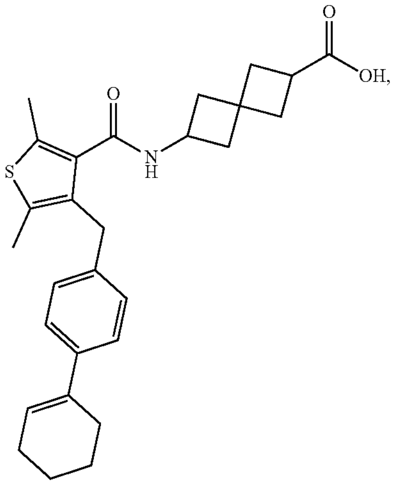
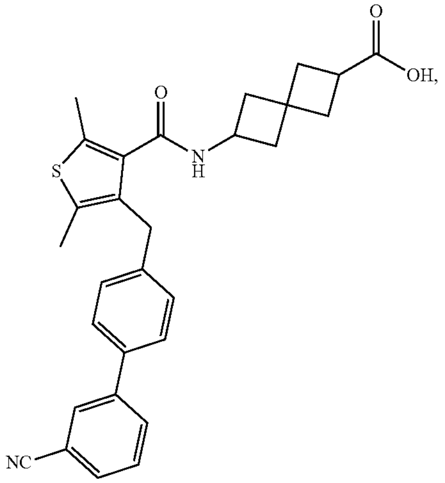
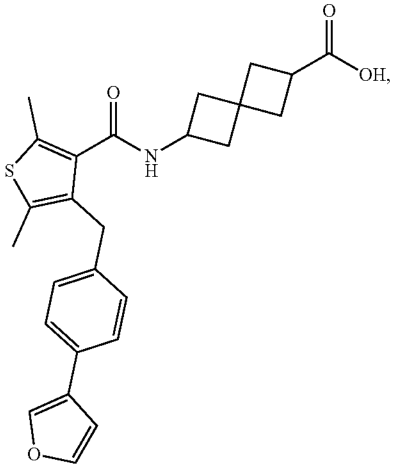
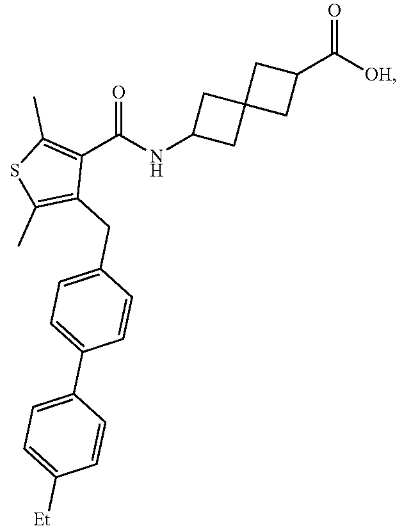
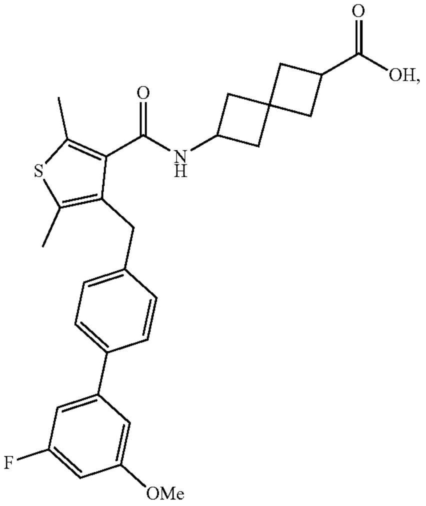

-continued
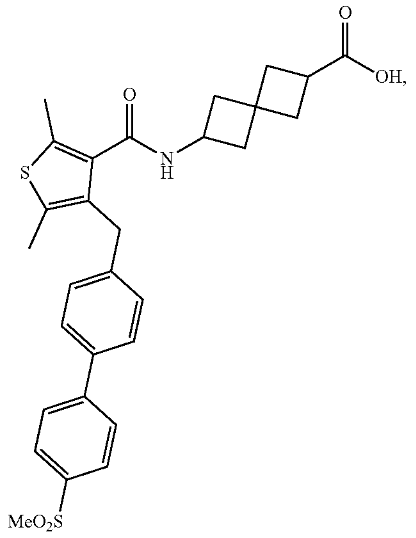
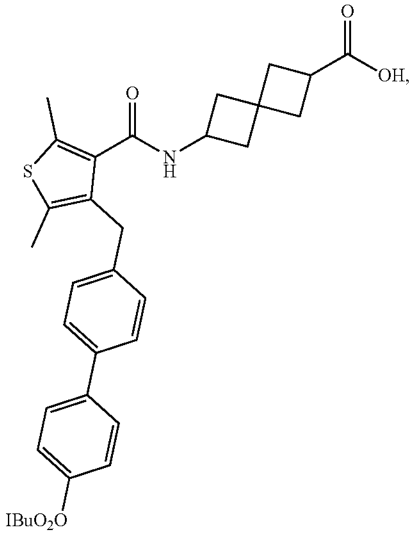
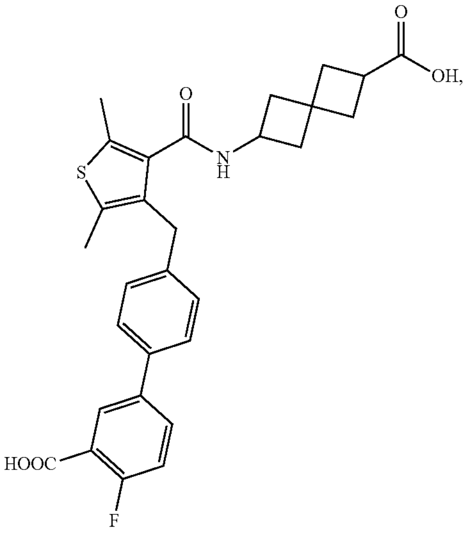
-continued
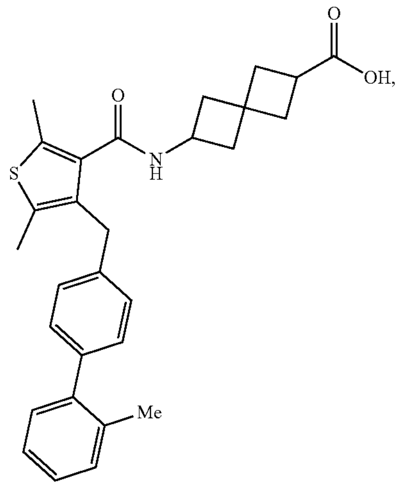
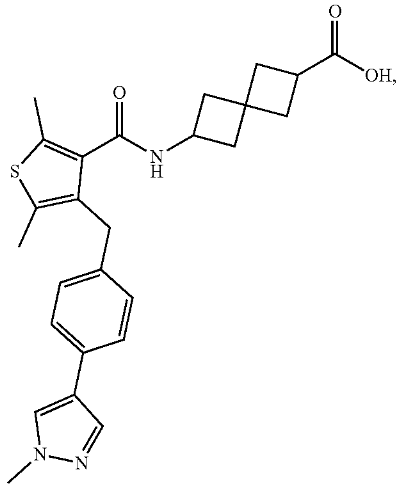
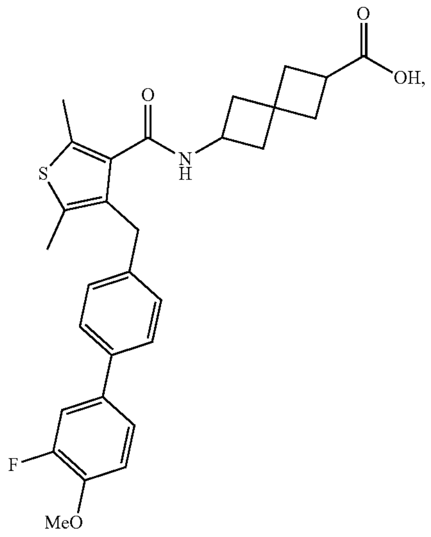

-continued
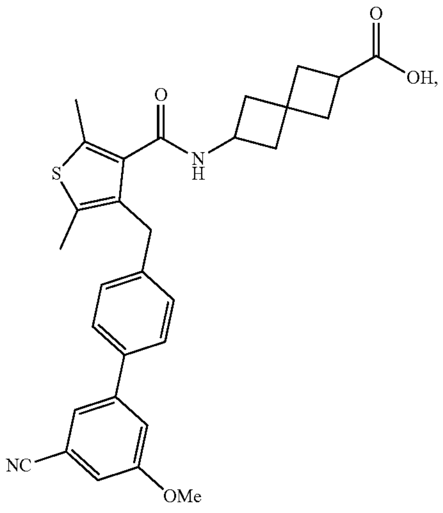
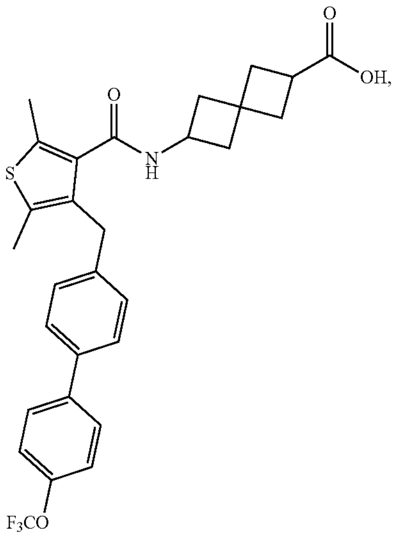
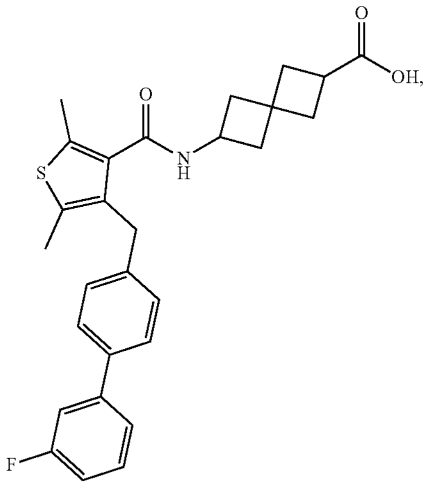
-continued
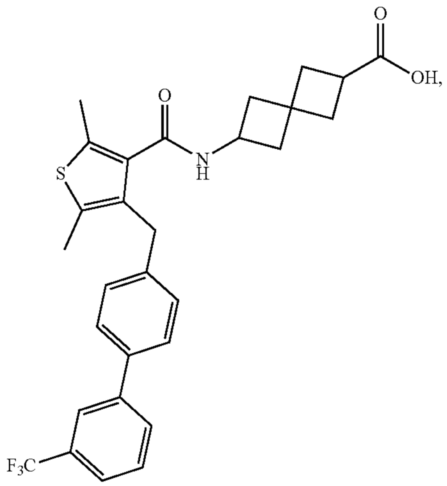
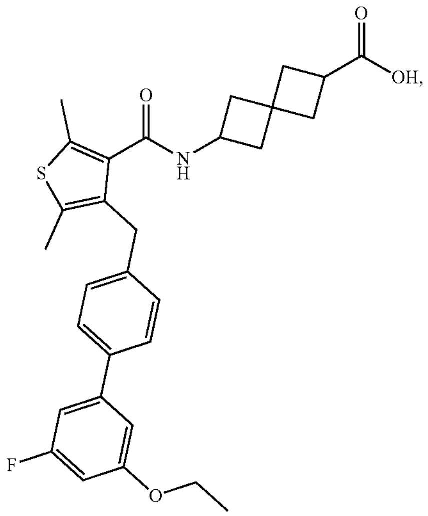
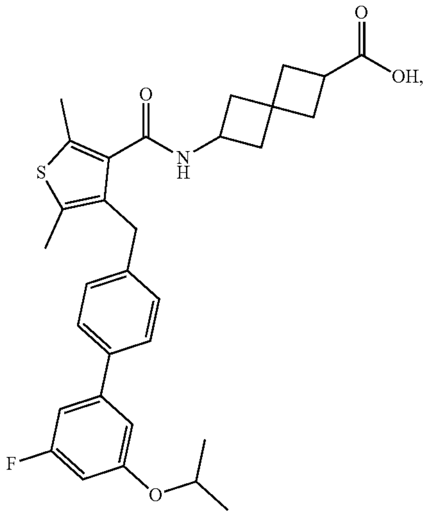

-continued
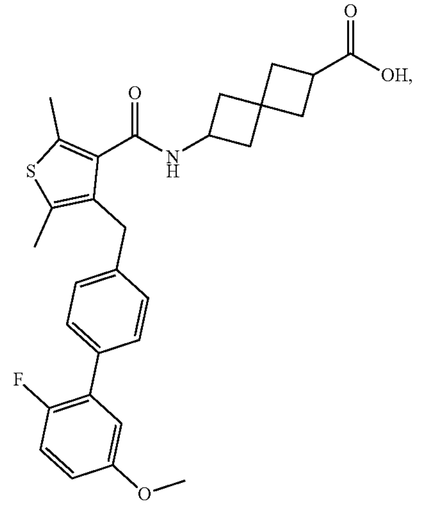
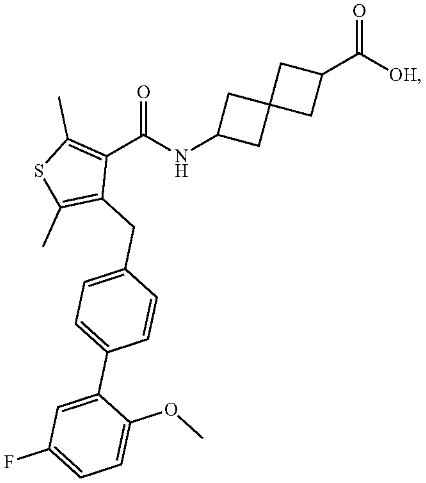
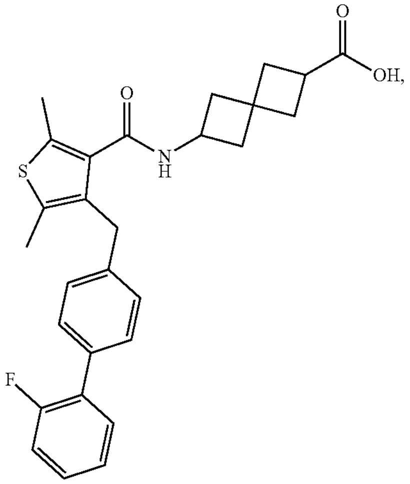
-continued
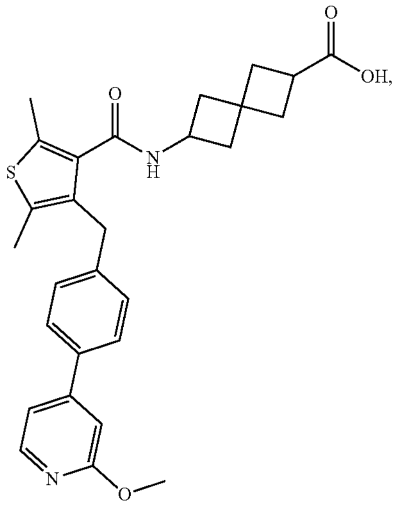
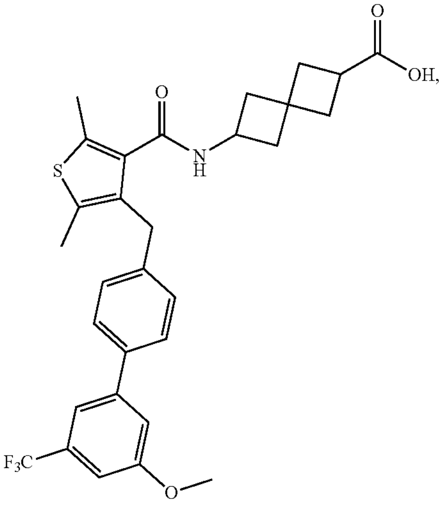
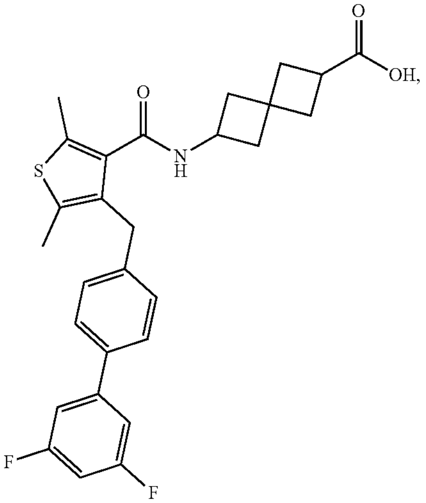

-continued
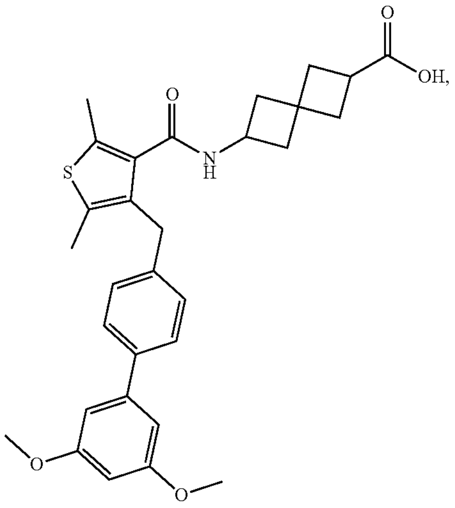
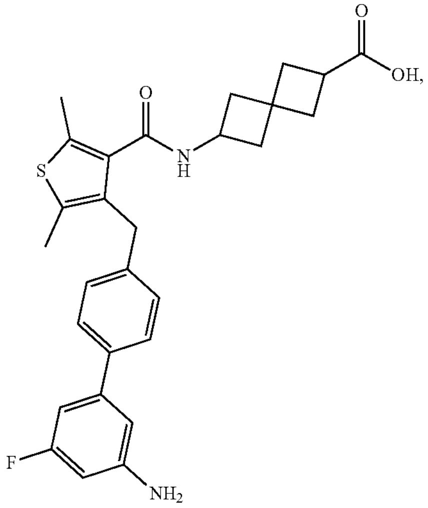
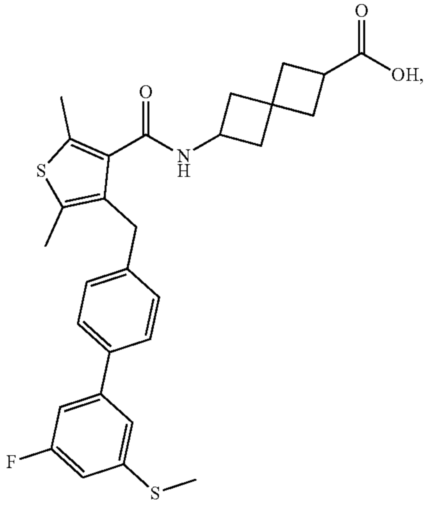
-continued
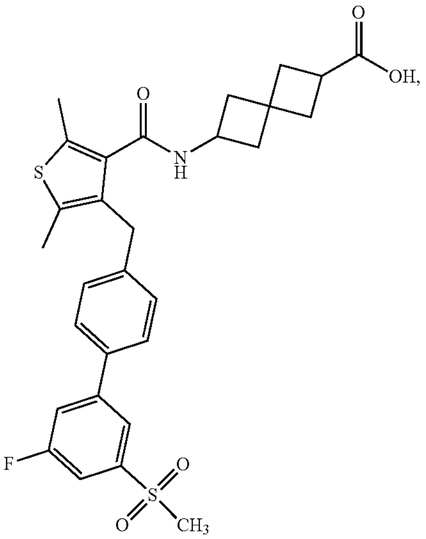
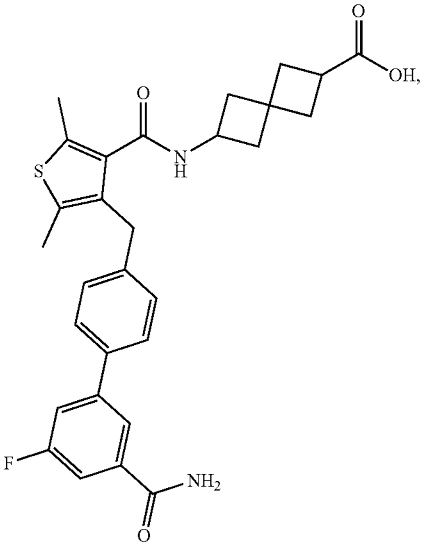
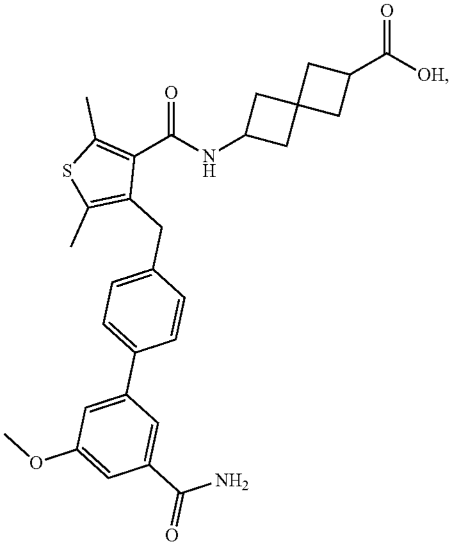

-continued
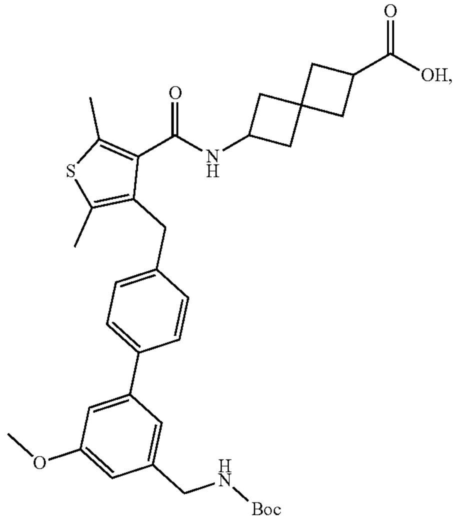
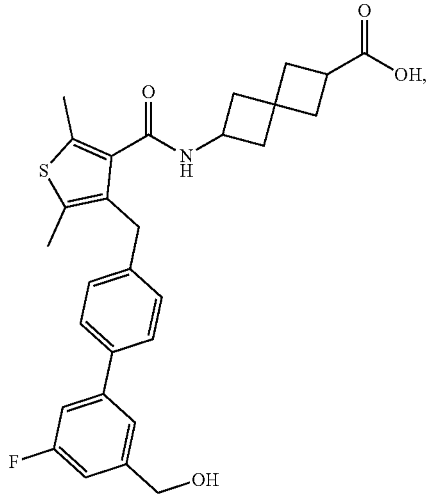
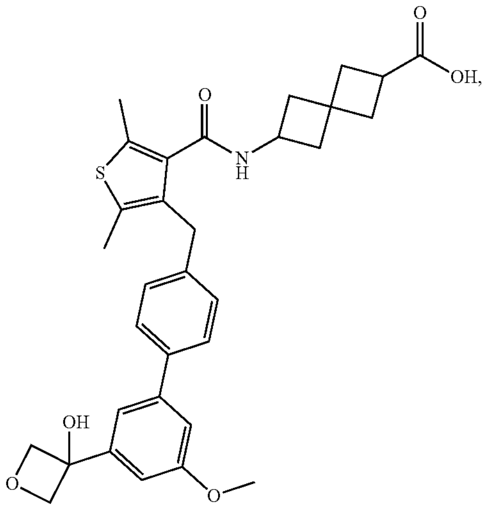
-continued
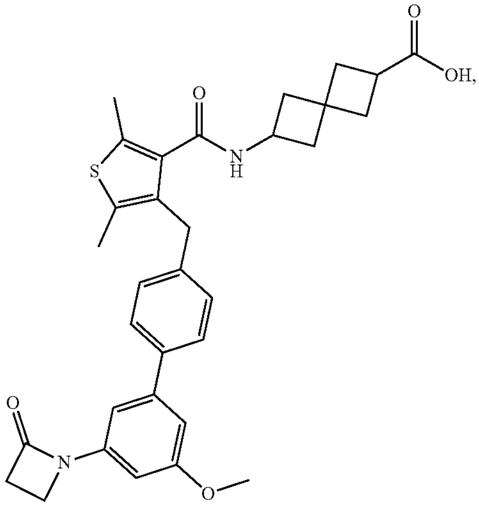
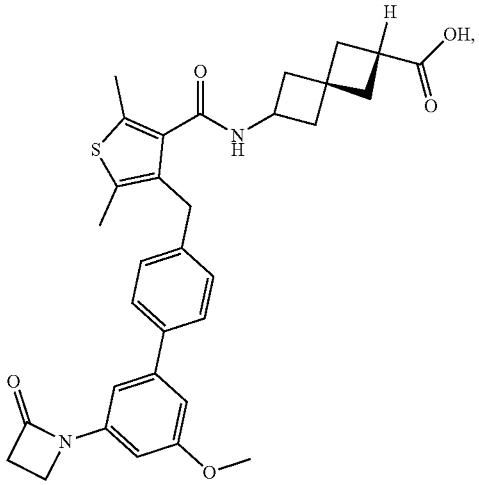
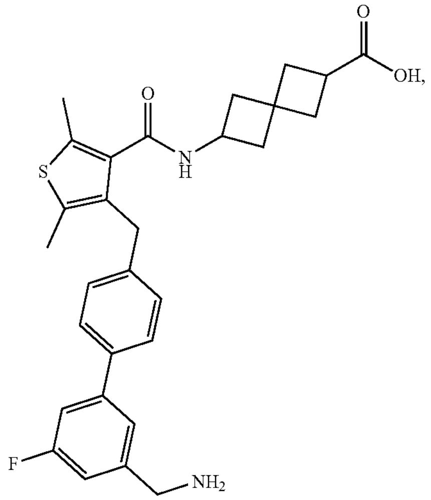

-continued
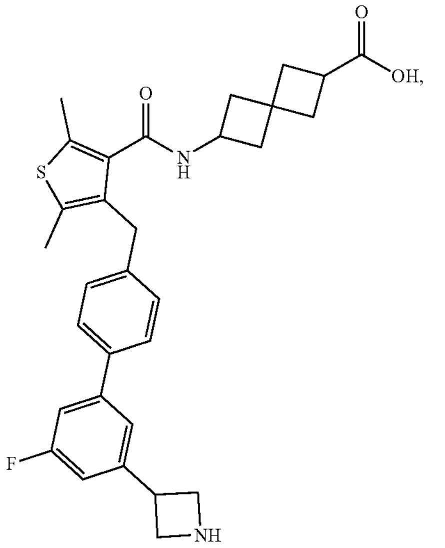
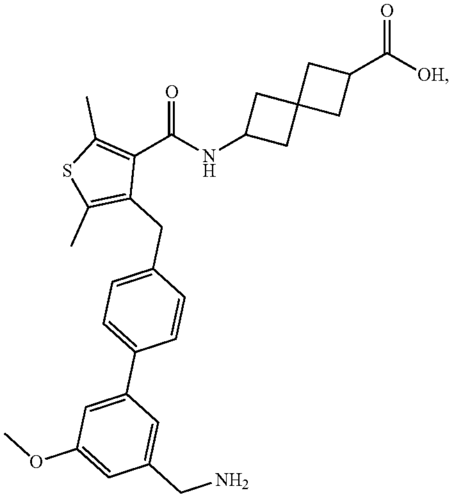
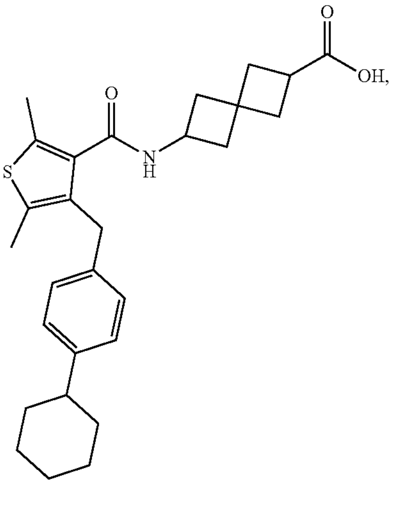
-continued
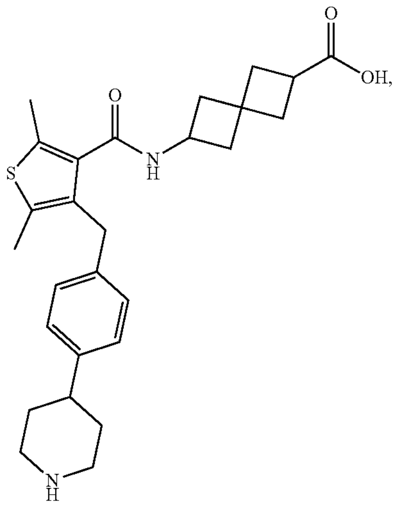
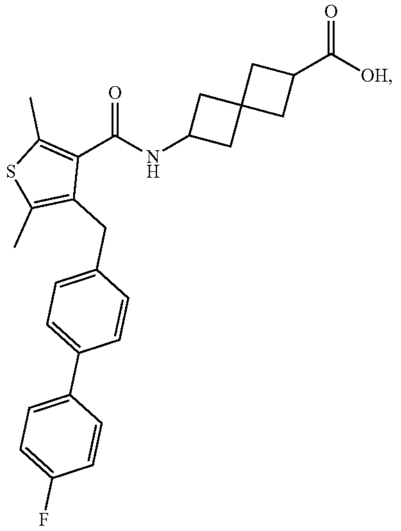
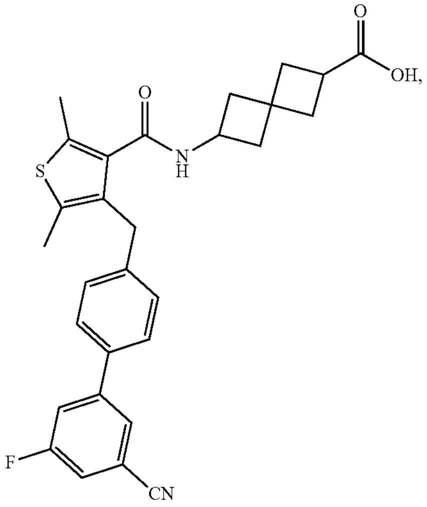

-continued
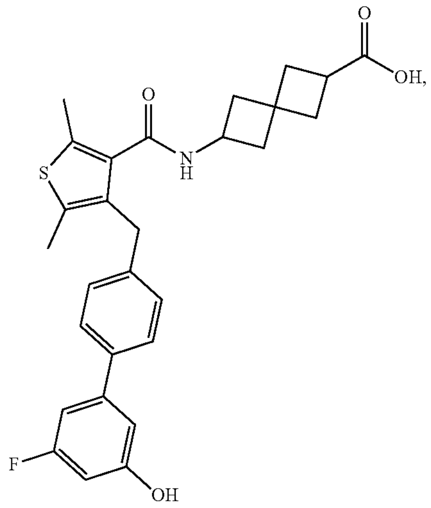
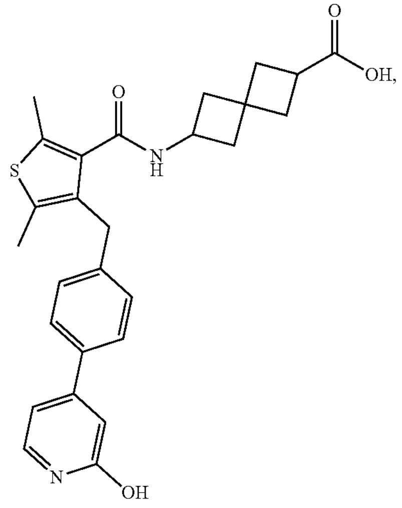
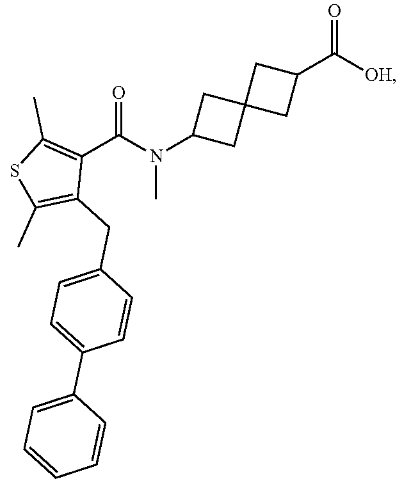
-continued
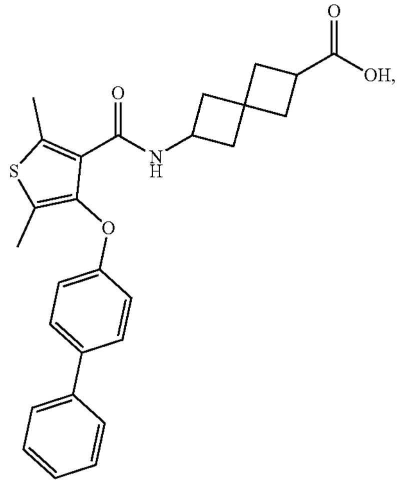
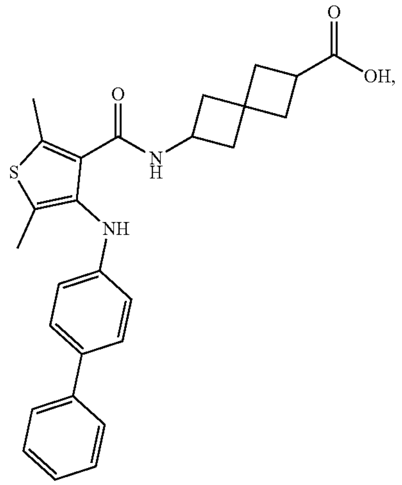
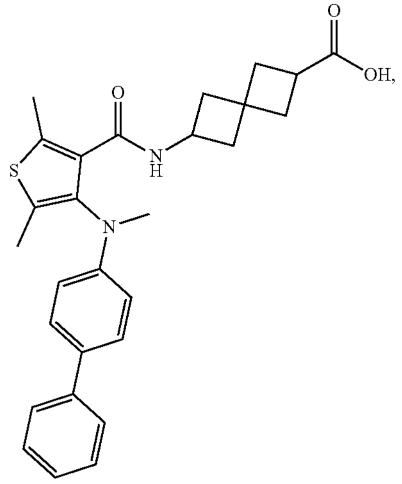

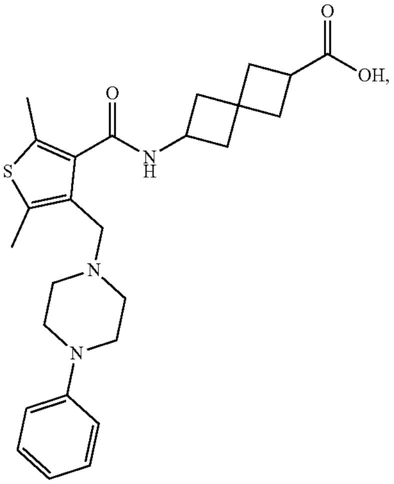

and

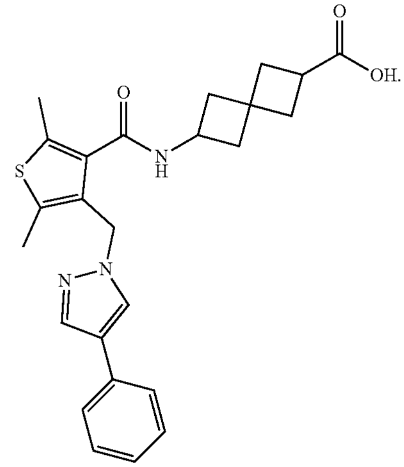

10. The compound of formula IA-3 or solvate, stereoisomer or pharmaceutically acceptable salt thereof according to claim 9, wherein the compound is selected from the group consisting of the following compounds:

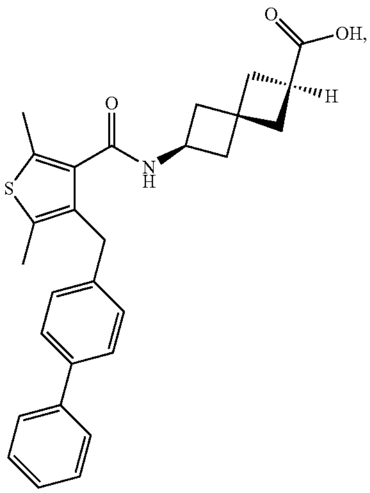

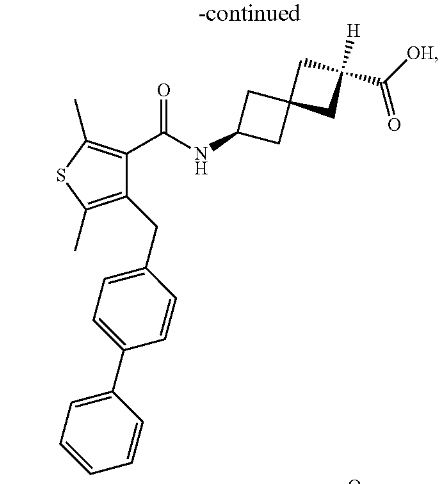

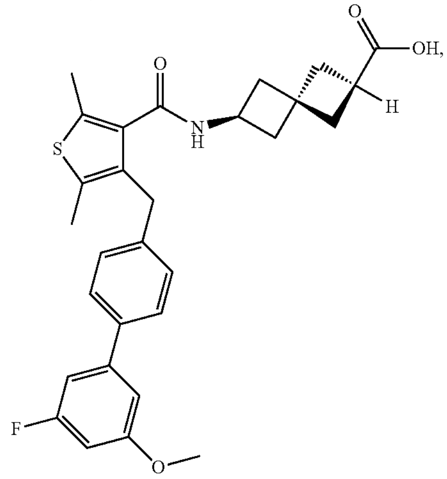

and

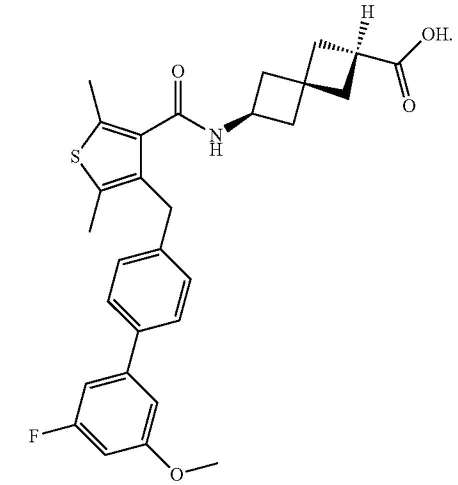

11. A pharmaceutical composition comprising the compound, solvate, stereoisomer or pharmaceutically acceptable salt thereof according to claim 1 as an active ingredient.

* * * * *